United States Patent
White et al.

(10) Patent No.: US 9,885,711 B2
(45) Date of Patent: Feb. 6, 2018

(54) SCREENING METHODS

(75) Inventors: Mark L. White, Antioch, CA (US); Marina Roell, Concord, CA (US); John Corbin, Orinda, CA (US); Robert Bauer, Pleasant Hill, CA (US); Daniel Bedinger, Vacaville, CA (US)

(73) Assignee: XOMA Technology Ltd., Berkeley, CA (US)

( * ) Notice: Subject to any disclaimer, the term of this patent is extended or adjusted under 35 U.S.C. 154(b) by 1122 days.

(21) Appl. No.: 12/890,590

(22) Filed: Sep. 24, 2010

(65) Prior Publication Data

US 2011/0274692 A1 Nov. 10, 2011

Related U.S. Application Data

(60) Provisional application No. 61/246,079, filed on Sep. 25, 2009, provisional application No. 61/306,324, filed on Feb. 19, 2010.

(51) Int. Cl.
G01N 33/53 (2006.01)
G01N 33/557 (2006.01)
G01N 33/68 (2006.01)

(52) U.S. Cl.
CPC ....... *G01N 33/557* (2013.01); *G01N 33/6854* (2013.01); *G01N 2500/02* (2013.01); *G01N 2500/20* (2013.01)

(58) Field of Classification Search
None
See application file for complete search history.

(56) References Cited

U.S. PATENT DOCUMENTS

| | | | |
|---|---|---|---|
| 4,708,871 A | 11/1987 | Geysen | |
| 4,727,022 A | 2/1988 | Skold et al. | |
| 4,761,371 A | 8/1988 | Bell et al. | |
| 4,816,567 A | 3/1989 | Cabilly et al. | |
| 4,833,092 A | 5/1989 | Geysen | |
| 5,164,295 A | 11/1992 | Kisilevsky et al. | |
| 5,223,409 A | 6/1993 | Ladner et al. | |
| 5,348,867 A | 9/1994 | Georgiou et al. | |
| 5,403,484 A | 4/1995 | Ladner et al. | |
| 5,427,908 A | 6/1995 | Dower et al. | |
| 5,432,018 A | 7/1995 | Dower et al. | |
| 5,498,530 A | 3/1996 | Schatz et al. | |
| 5,556,762 A | 9/1996 | Pinilla et al. | |
| 5,565,332 A | 10/1996 | Hoogenboom et al. | |
| 5,571,689 A | 11/1996 | Heuckeroth et al. | |
| 5,573,905 A | 11/1996 | Lerner et al. | |
| 5,580,717 A | 12/1996 | Dower et al. | |
| 5,643,768 A | 7/1997 | Kawasaki | |
| 5,658,754 A | 8/1997 | Kawasaki | |
| 5,663,143 A | 9/1997 | Ley et al. | |
| 5,698,426 A | 12/1997 | Huse | |
| 5,723,286 A | 3/1998 | Dower et al. | |
| 5,723,287 A | 3/1998 | Russell et al. | |
| 5,723,323 A | 3/1998 | Kauffman et al. | |
| 5,734,018 A | 3/1998 | Rutter et al. | |
| 5,750,373 A | 5/1998 | Garrard et al. | |
| 5,763,192 A | 6/1998 | Kauffman et al. | |
| 5,766,886 A | 6/1998 | Studnicka et al. | |
| 5,766,905 A | 6/1998 | Studier et al. | |
| 5,770,434 A | 6/1998 | Huse | |
| 5,877,293 A | 3/1999 | Adair et al. | |
| 5,969,108 A | 10/1999 | McCafferty et al. | |
| 6,054,287 A | 4/2000 | Gao et al. | |
| 6,342,358 B1 | 1/2002 | Collins et al. | |
| 6,699,658 B1 | 3/2004 | Wittrup et al. | |
| 7,888,042 B2 | 2/2011 | Chen | |
| 2002/0004215 A1 | 1/2002 | Osbourn et al. | |
| 2003/0044772 A1 | 3/2003 | Watkins et al. | |
| 2003/0190317 A1 | 10/2003 | Baca et al. | |
| 2003/0236190 A1 | 12/2003 | Pillutla et al. | |
| 2004/0101904 A1 | 5/2004 | Pardridge et al. | |
| 2006/0275288 A1 | 12/2006 | Grihalde et al. | |
| 2008/0044414 A1* | 2/2008 | Masat et al. | 424/136.1 |

FOREIGN PATENT DOCUMENTS

| | | | |
|---|---|---|---|
| EP | 1514930 A1 | 3/2005 | |
| EP | 2036574 A1 | 3/2009 | |
| JP | 2004-101509 A | 4/2004 | |
| JP | 2007-523169 A | 8/2007 | |
| JP | 2007-524566 A | 8/2007 | |
| JP | 2008-543340 A | 12/2008 | |
| JP | 2011-514527 A | 5/2011 | |
| WO | WO-84/03506 A1 | 9/1984 | |

(Continued)

OTHER PUBLICATIONS

Amstutz et al., In vitro display technologies: novel developments and applications, Curr. Opin. Biotechnol., 12:400-5 (2001).

Arulmozhi et al., Metabolic effects of various antidiabetic and hypolipidaemic agents on a high-fat diet and multiple low-dose streptozocin (MLDS) mouse model of diabetes, J. Pharm. Pharmacol., 60:1167-73 (2008).

Barbas et al., Assembly of combinatorial antibody libraries on phage surfaces: the gene III site, Proc. Natl. Acad. Sci. USA, 88:7978-82 (1991).

Bayer et al., The biotin transport system in yeast, Methods Enzymol., 62:371-8 (1979).

Beals et al., CD18 activation epitopes induced by leukocyte activation, J. Immunol., 167:6113-22 (2001).

Beattie et al., Effects of complexation with in vivo enhancing monoclonal antibodies on activity of growth hormone in two responsive cell culture systems, J. Mol. Endocrinol., 23:307-13 (1999).

(Continued)

*Primary Examiner* — Michael Pak

(74) *Attorney, Agent, or Firm* — Marshall, Gerstein & Borun LLP

(57) ABSTRACT

The present invention provides polypeptide binding agents, e.g. antibodies, that exhibit the ability to kinetically modulate the binding and signaling of biological signaling complexes, e.g., receptor-ligand complexes; methods of identifying such polypeptide binding agents, methods of making such polypeptide binding agents, compositions comprising such polypeptide binding agents, and methods of using such polypeptide binding agents.

77 Claims, 21 Drawing Sheets

(56) References Cited

FOREIGN PATENT DOCUMENTS

| WO | WO-84/03564 A1 | 9/1984 |
|---|---|---|
| WO | WO-92/01047 A1 | 1/1992 |
| WO | WO-92/09690 A2 | 6/1992 |
| WO | WO-92/15679 A1 | 9/1992 |
| WO | WO-92/18619 A1 | 10/1992 |
| WO | WO-92/20791 A1 | 11/1992 |
| WO | WO-93/01288 A1 | 1/1993 |
| WO | WO-98/22509 A1 | 5/1998 |
| WO | WO-99/10494 A2 | 3/1999 |
| WO | WO-99/54728 A2 | 10/1999 |
| WO | WO-99/58572 A1 | 11/1999 |
| WO | WO-00/47626 A1 | 8/2000 |
| WO | WO-02/072778 A2 | 9/2002 |
| WO | WO-02/094194 | 11/2002 |
| WO | WO-03/008930 | 1/2003 |
| WO | WO-03/099199 | 12/2003 |
| WO | WO-2004/050016 A2 | 6/2004 |
| WO | WO-2004/085618 A2 | 10/2004 |
| WO | WO-2005/068501 A1 | 7/2005 |
| WO | WO-2005/116077 A2 | 12/2005 |
| WO | WO 2007/002261 * | 6/2007 |
| WO | WO-2007/147213 A1 | 12/2007 |
| WO | WO-2008/022295 A2 | 2/2008 |
| WO | WO-2008/065384 A2 | 6/2008 |
| WO | WO-2009/017833 A2 | 2/2009 |
| WO | WO-2009/087173 A2 | 7/2009 |
| WO | WO-2011/038302 A2 | 3/2011 |

OTHER PUBLICATIONS

Blackard et al., Effect of Anti-Insulin Receptor Antibody on Insulin Dissociation from IM-9 lymphocytes, Horm. Metab. Res., 13:480-3 (1981).
Boado et al., Humanization of anti-human insulin receptor antibody for drug targeting across the human blood-brain barrier, Biotechnol. Bioeng., 96:381-91 (2007).
Brindle et al., Anti-(insulin receptor) monoclonal antibody-stimulated tyrosine phosphorylation in cells transfected with human insulin receptor cDNA, Biochem. J., 268:615-20 (1990).
Brunetti et al., Monoclonal antibodies to the human insulin receptor mimic a spectrum of biological effects in transfected 3T3/HIR fibroblasts without activating receptor kinase, Biochem. Biophys. Res. Commun., 165:212-8 (1989).
Burton et al., Human antibodies from combinatorial libraries, Adv. Immunol., 57:191-280 (1994).
Clackson et al., In vitro selection from protein and peptide libraries, Trends Biotechnol., 12:173-84 (1994).
Clackson et al., Making antibody fragments using phage display libraries, Nature, 352:624-8 (1991).
Colwell et al., Allosteric effects of a monoclonal antibody against thrombin exosite II, Biochem., 37(43):15057-65 (1998).
Cosgrove, The Type I IGF receptor and the insulin receptor, Technical Bulletin No. 7, 2 pages (Sep. 2004).
Cwirla et al., Peptides on phage: a vast library of peptides for identifying ligands, Proc. Natl. Acad. Sci. USA, 87:6378-82 (1990).
Dayer et al., Lack of TNFR2 expression by CD4(+) T cells exacerbates experimental colitis, Eur. J. Immunol., 39:1743-53 (2009).
De Luca et al., Inflammation and insulin resistance, FEBS Lett., 582:97-105 (2008).
De Meyts et al., Structural biology of insulin and IGF1 receptors: implications for drug design, Nat. Rev. Drug Discov., 1:769-83 (2002).
De Meyts et al., Timing-dependent modulation of insulin mitogenic versus metabolic signalling, Novartis Found. Symp., 227:46-57 (2000).
De Meyts, Insulin and its receptor: structure, function and evolution, Bioessays, 26:1351-62 (2004).
Dinarello, The many worlds of reducing interleukin-1, Arthritis Rheum., 52:1960-7 (2005).
Dove et al., Cell signaling branches out, Nat. Methods, 3:223-9 (2006).
Forsayeth et al., Effect of monoclonal antibodies on human insulin receptor autophosphorylation, negative cooperativity, and down-regulation, J. Biol. Chem., 262:4134-40 (1987).
Forsayeth et al., Monoclonal antibodies to the human insulin receptor that activate glucose transport but not insulin receptor kinase activity, Proc. Natl. Acad. Sci. USA, 84:3448-51 (1987).
Fuchs et al., Targeting recombinant antibodies to the surface of *Escherichia coli*: fusion to a peptidoglycan associated lipoprotein, Bio/Technology, 9:1370-2 (1991).
Ganderton et al., A monoclonal anti-peptide antibody reacting with the insulin receptor beta-subunit. Characterization of the antibody and its epitope and use in immunoaffinity purification of intact receptors, Biochem. J., 288:195-205 (1992).
Gao et al., Two-state selection of conformation-specific antibodies. Proc Natl Acad Sci 106(9): 3071-6 (2009).
Garrard et al., Fab assembly and enrichment in a monovalent phage display system, Biotechnology (N.Y.), 9:1373-7 (1991).
Gasparini et al., Allosteric modulators for mGlu receptors, Curr. Neuropharmacol., 5:187-94 (2007).
Geysen et al., Small peptides induce antibodies with a sequence and structural requirement for binding antigen comparable to antibodies raised against the native protein, Proc. Natl. Acad. Sci. USA, 82:178-82 (1985).
Geysen et al., Strategies for epitope analysis using peptide synthesis, J. Immunol. Methods, 102:259-74 (1987).
Geysen et al., The delineation of peptides able to mimic assembled epitopes, Synthetic Peptides in Antigens, Ciba Foundation Symposium 119, pp. 130-149 (1986).
Geysen et al., Use of peptide synthesis to probe viral antigens for epitopes to a resolution of a single amino acid, Proc. Natl. Acad. Sci. USA, 81:3998-4002 (1984).
Goodman et al., Antibody binding to the juxtamembrane region of the insulin receptor alters receptor affinity, J. Recept. Res., 14:381-98 (1994).
Gram et al., In vitro selection and affinity maturation of antibodies from a naive combinatorial immunoglobulin library, Proc. Natl. Acad. Sci. USA, 89:3576-80 (1992).
Gregory et al., Allosteric modulation of muscarinic acetylcholine receptors, Curr. Neuropharmacol., 5:157-67 (2007).
Grell et al., TR60 and TR80 Tumor Necrosis Factor (TNF)-Receptors Can Independently Mediate Cytolysis, Lymphokine and Cytokine Res., 12: 143-8 (1993).
Griffiths et al., Human anti-self antibodies with high specificity from phage display libraries, EMBO J., 12:725-34 (1993).
Groebe, In search of negative allosteric modulators of biological targets, Drug Discovery Today, 14(1/2 ):41-9 (2009).
Groebe, Screening for positive allosteric modulators of biological targets, Drug Discovery Today, 11 (13/14): 632:9 (2006).
Gu et al., Reversal of insulin-induced negative cooperativity by monoclonal antibodies that stabilize the slowly dissociating ("Ksuper") state of the insulin receptor, Biochem. Biophys. Res. Commun., 150:694-701 (1988).
Hanes et al., In vitro selection and evolution of functional proteins by using ribosome display, Proc. Natl. Acad. Sci. USA, 94:4937-42 (1997).
Hansen et al., Sustained signalling from the insulin receptor after stimulation with insulin analogues exhibiting increased mitogenic potency, Biochem. J., 315:271-9 (1996).
Hawkins et al., Selection of phage antibodies by binding affinity. Mimicking affinity maturation, J. Mol. Biol., 226:889-96 (1992).
Hawley et al., Insulin receptor monoclonal antibodies that mimic insulin action without activating tyrosine kinase, J. Biol. Chem., 264:2438-44 (1989).
Hay et al., Bacteriophage cloning and *Escherichia coli* expression of a human IgM Fab, Hum Antibodies Hybridomas, 3:81-5 (1992).
Heffetz et al., Receptor aggregation is necessary for activation of the soluble insulin receptor kinase, J. Biol. Chem., 261 :889-94 (1986).
Herrera et al., Antibodies to deduced sequences of the insulin receptor distinguish conserved and nonconserved regions in the IGF-I receptor, J. Biol. Chem., 261 :2489-91 (1986).

(56) References Cited

OTHER PUBLICATIONS

Hoogenboom et al., Multi-subunit proteins on the surface of filamentous phage: methodologies for displaying antibody (Fab) heavy and light chains, Nucleic Acids Res., 19:4133-7 (1991).
Hoogenboom et al., By-passing immunisation: human antibodies from synthetic repertoires of germline VH gene segments rearranged in vitro, J. Mol. Biol., 227:381-8 (1991).
Huse et al., Generation of a large combinatorial library of the immunoglobulin repertoire in phage lambda, Science, 246:1275-81 (1989).
International Search Report and Written Opinion for International application No. PCT/US2010/050312, dated May 26, 2011.
International Search Report and Written Opinion from International application No. PCT/US2010/050313, dated Jun. 27, 2011.
Jacobs et al., Antibodies to purified insulin receptor have insulin-like activity, Science, 200:1283-4 (1978).
Jacobs et al., Insulin receptors and insulin receptor antibodies: structure-function relationships, Ciba Found. Symp., 90:82-90 (1982).
Jahns et al., Modulation of beta1-adrenoceptor activity by domain-specific antibodies and heart failure-associated autoantibodies, J. Am. Coll. Cardiol., 36:1280-7 (2000).
Janas et al., Rituxan (anti-CD20 antibody)-induced translocation of CD20 into lipid rafts is crucial for calcium influx and apoptosis, Clin. Exp. Immunol., 139:439-46 (2005).
Jensen et al., Allosteric modulation of the calcium-sensing receptor, Curr. Neuropharmacol., 5:180-6 (2007).
Jensen et al., Molecular mechanisms of differential intracellular signaling from the insulin receptor, Vitam. Horm., 80:51-75 (2009).
Jiang et al., Display of a PorA peptide from Neisseria meningitidis on the bacteriophage T4 capsid surface, Chemical Abstracts,128(5):44380q (1997).
Johnson et al., Allosteric modulators of metabotropic glutamate receptors: lessons learnt from mGlu1, mGlu2 and mGlu5 potentiators and antagonists, Biochemical Society Transactions, 32 (5): 881-7 (2004).
Kahn et al.,Direct demonstration that receptor crosslinking or aggregation is important in insulin action, Proc. Natl. Acad. Sci. USA, 75:4209-13 (1978).
Kang et al., Linkage of recognition and replication functions by assembling combinatorial antibody Fab libraries along phage surfaces, Proc. Natl. Acad. Sci. USA, 88:4363-6 (1991).
Kenakin, Allosteric agonist modulators, J. Recept. Signal Transduct. Res., 27:247-59 (2007).
Kenakin, Allosteric theory: Taking therapeutic advantage of the malleable nature of GPCRs, Curr. Neuropharmacol., 5:149-56 (2007).
Kull et al., Monoclonal antibodies to receptors for insulin and somatomedin-C, J. Biol. Chem., 258:6561-6 (1983).
Kurtzhals et al., Correlations of receptor binding and metabolic and mitogenic potencies of insulin analogs designed for clinical use, Diabetes, 49:999-1005 (2000).
Langmead, Screening for positive allosteric modulators: assessment of modulator concentration-response curves as a screening paradigm, J. Biomolecular Screening, 12(5): 668-76 (2007).
Lebrun et al., Antibodies to the extracellular receptor domain restore the hormone-insensitive kinase and conformation of the mutant insulin receptor valine 382, J. Biol. Chem., 268:11272-7 (1993).
Lee et al., Microbial cell-surface display, Trends Biotechnol., 21:45-52 (2003).
Li et al., Small molecule insulin receptor activators potentiate insulin action in insulin-resistant cells, Diabetes, 50:2323-8 (2001).
Liu et al., Development of a novel GLUT4 translocation assay for identifying potential novel therapeutic targets for insulin sensitization, Biochem. J., 418:413-20 (2009).
Lou et al., The first three domains of the insulin receptor differ structurally from the insulin-like growth factor 1 receptor in the regions governing ligand specificity, Proc. Natl. Acad. Sci. USA, 103:12429-34 (2006).
Lowman et al., Selecting high-affinity binding proteins by monovalent phage display, Biochem., 30:10832-8 (1991).
Malmqvist et al., Kinetic analysis of engineered antibody-antigen interactions, J. Mol. Recognit., 7:1-7 (1994).
Manchem et al., A novel small molecule that directly sensitizes the insulin receptor in vitro and in vivo, Diabetes, 50:824-30 (2001).
Marks et al., By-passing immunization. Human antibodies from V-gene libraries displayed on phage, J. Mol. Biol., 222:581-97 (1991).
Marks et al., By-passing immunization: building high affinity human antibodies by chain shuffling, Biotechnology (N.Y.), 10:799-83 (1992).
Massart et al., Monoclonal antibodies to bovine growth hormone potentiate hormonal activity in vivo by enhancing growth hormone binding to hepatic somatogenic receptors, J. Endocrinol., 139:383-93 (1993).
May et al., Allosteric modulation of G protein-coupled receptors, Annu. Rev. Pharmacol. Toxicol., 47:1-51 (2007).
McKern et al., Structure of the insulin receptor ectodomain reveals a folded-over conformation, Nature, 443:218-21 (2006).
McPherson et al., The nuclear transcription factor CREB: involvement in addiction, deletion models and looking forward, Curr. Neuropharmacol., 5:202-12 (2007).
McCafferty et al., Phage antibodies: filamentous phage displaying antibody variable domains, Nature, 348:552-4 (1990).
Moller, New drug targets for type 2 diabetes and the metabolic syndrome, Nature, 414:821-7 (2001).
Morgan et al., Insulin action is blocked by a monoclonal antibody that inhibits the insulin receptor kinase, Proc. Natl. Acad. Sci. USA, 83:328-32 (1986).
Mottola et al., Functional selectivity of dopamine receptor agonists. I. Selective activation of postsynaptic dopamine D2 receptors linked to adenylate cyclase, J. Pharmacol. Exp. Ther., 301(3):1166-78 (2002).
Mould et al., The inhibitory anti-beta1 integrin monoclonal antibody 13 recognizes an epitope that is attenuated by ligand occupancy, J. Biol. Chem., 271(34):20365-74 (1996).
Mukai et al., Fast binding kinetics and conserved 3D structure underlie the antagonistic activity of mutant TNF: useful information for designing artificial proteo-antagonists, J. Biochem., 146:167-72 (2009).
Mutel et al., Editorial: The pros of not being competitive, Curr. Neuropharmacol., 5: 148 (2007).
O'Brien et al., Monoclonal antibodies for the human insulin receptor stimulate intrinsic receptor-kinase activity, Biochemical Society Transactions, 14:1021-3 (1986).
Orgad et al., Single chain antibody against the common epitope of mutant p53 restores wild-type activity to mutant p53 protein, FEBS Lett., 579:5609-15 (2005).
Ortlepp et al., Antibodies that activate β2 integrins can generate different ligand binding states, Eur. J. Immunol., 25:637-43 (1995).
Pender et al., Regulation of insulin receptor function by a small molecule insulin receptor activator, J. Biol. Chem., 277:43565-71 (2002).
Peter et al., Modulation of the M2 muscarinic acetylcholine receptor activity with monoclonal anti-M2 receptor antibody fragments, J. Biol. Chem., 279(53):55697-706 (2004).
Petruzzelli et al., Activation of lymphocyte function-associated molecule-1 (CD11a/CD18) and Mac-1 (CD11b/CD18) mimicked by an antibody directed against CD18, J. Immunol., 155:854-66 (1995).
Pin et al., Allosteric modulators of GABAB receptors: mechanism of action and therapeutic perspective, Curr. Neuropharmacol., 5:195-201 (2007).
Ponzio et al., Insulin and rabbit anti-insulin receptor antibodies stimulate additively the intrinsic receptor kinase activity, EMBO J., 6:333-40 (1987).
Ponzio et al.,Use of an anti-insulin receptor antibody to discriminate between metabolic and mitogenic effects of insulin: correlation with receptor autophosphorylation, The EMBO J., 7:4111-7 (1988).
Pradillo et al., TNFR1 upregulation mediates tolerance after brain ischemic reconditioning, J. Cereb. Blood Flow Metab., 25:193-203 (2005).

(56) References Cited

OTHER PUBLICATIONS

Prigent et al., Identification of epitopes on the human insulin receptor reacting with rabbit polyclonal antisera and mouse monoclonal antibodies, J. Biol. Chem., 265:9970-7 (1990).
Qureshi et al., Activation of insulin signal transduction pathway and anti-diabetic activity of small molecule insulin receptor activators, J. Biol. Chem., 275:36590-5 (2000).
Rakatzi et al., A novel insulin analog with unique properties: LysB3,GluB29 insulin induces prominent activation of insulin receptor substrate 2, but marginal phosphorylation of insulin receptor substrate 1, Diabetes, 52:2227-38 (2003).
Reverter et al., Inhibition of platelet-mediated, tissue factor-induced thrombin generation by the mouse/human chimeric 7E3 antibody. Potential implications for the effect of c7E3 Fab treatment on acute thrombosis and "clinical restenosis", J. Clin. Invest., 98(3):863-74 (1996).
Roell et al., Kinetic approach to pathway attenuation using XOMA052, a regulatory therapeutic antibody that modulates interleukin-1beta activity, J. Biol. Chem., 2285(27):20607-14 (Date).
Roth et al., Monoclonal antibodies to the human insulin receptor block insulin binding and inhibit insulin action, Proc. Natl. Acad. Sci. USA, 79:7312-6 (1982).
Roth et al., Monoclonal antibodies to the insulin receptor, Pharmacol. Ther., 28:1-16 (1985).
Roth et al., Regulation of the insulin receptor by a monoclonal anti-receptor antibody. Evidence that receptor down regulation can be independent of insulin action., J. Biol. Chem., 258:12094-7 (1983).
Saxena et al., Allosteric control of acetylcholinesterase activity by monoclonal antibodies, Biochem., 37:145-54 (1998).
Schaffer et al., A novel high-affinity peptide antagonist to the insulin receptor, Biochem. Biophys. Res. Commun., 376:380-3 (2008).
Schaffer et al., Assembly of high-affinity insulin receptor agonists and antagonists from peptide building blocks, Proc. Natl. Acad. Sci. USA, 100:4435-9 (2003).
Schoofs et al., Epitopes of an influenza viral peptide recognized by antibody at single amino acid resolution, J. Immunol., 140:611-6 (1988).
Sergeeva et al., Display technologies: application for the discovery of drug and gene delivery agents, Adv. Drug Deliv. Rev., 58:1622-54 (2006).
Silverstein et al., Care of children and adolescents with type 1 diabetes: a statement of the American Diabetes Association, Diabetes Care, 28:186-212 (2005).
Smith, Surface presentation of protein epitopes using bacteriophage expression systems, Curr. Opin. Biotechnol., 2:668-73 (1991).
Sojar et al., A chemical method for the deglycosylation of proteins, Arch. Biochem. Biophys., 259:52-7 (1987).
Soos et al., Monoclonal antibodies reacting with multiple epitopes on the human insulin receptor, Biochem. J., 235:199-208 (1986).
Soti et al., Molecular chaperones as regulatory elements of cellular networks, Curr. Opin. Cell Biol., 17:210-5 (2005).
Spasov et al., Study of antidiabetic activity of a new ultralow-dose antibody preparation on the model of streptozotocin diabetes in rats, Bull. Exp. Biol. Med., 144:46-8 (2007).
Steele-Perkins et al., Insulin-mimetic anti-insulin receptor monoclonal antibodies stimulate receptor kinase activity in intact cells, J. Biol. Chem., 265:9458-63 (1990).
Strowski et al., Small-molecule insulin mimetic reduces hyperglycemia and obesity in a nongenetic mouse model of type 2 diabetes, Endocrinology, 145:5259-68 (2004).
Taylor et al., Insulin-like and insulin-inhibitory effects of monoclonal antibodies for different epitopes on the human insulin receptor, Biochem. J., 242:123-9 (1987).
Towbin et al., Neoepitope immunoassay: an assay for human interleukin 1 beta based on an antibody induced conformational change, 17:353-69 (1996).
Tulloch et al., Single-molecule imaging of human insulin receptor ectodomain and its Fab complexes, J. Struct. Biol., 125:11-8 (1999).
Valente et al., Monoclonal antibodies to the thyrotropin receptor: Stimulating and blocking antibodies derived from the lymphocytes of patients with Graves disease, Proc. Natl. Acad. Sci. USA, 79: 6680-4 (1982).
Walshe et al., Induction of cytosolic calcium flux by CD20 is dependent upon B Cell antigen receptor signaling, J. Biol Chem., 283:16971-84 (2008).
Ward et al., Ligand-induced activation of the insulin receptor: a multi-step process involving structural changes in both the ligand and the receptor, Bioessays, 31:422-34 (2009).
Ward et al., Structural insights into ligand-induced activation of the insulin receptor, Acta Physiol. (Oxf.), 192:3-9 (2008).
Watkins, Screening of phage-expressed antibody libraries by capture lift, Methods Mol. Biol., 178:187-93 (2002).
Wickstrom, Effects of nicotine during pregnancy: human and experimental evidence, Curr. Neuropharmacol., 5:213-22 (2007).
Winter et al., Making antibodies by phage display technology, Annu. Rev. Immunol., 12:433-55 (1994).
Wittrup, Protein engineering by cell-surface display, Curr. Opin. Biotechnol., 12:395-9 (2001).
Zhang et al., A region of the insulin receptor important for ligand binding (residues 450-601) is recognized by patients' autoimmune antibodies and inhibitory monoclonal antibodies, Proc. Natl. Acad. Sci. USA, 88:9858-62 (1991).
Zhang et al., Discovery of a small molecule insulin mimetic with antidiabetic activity in mice, Science, 284:974-7 (1999).
Goldfine et al., Monoclonal antibodies to the insulin receptor as probes of insulin receptor structure and function, Horiz Biochem Biophys, 8:471-502 (1986).
Siddle et al., Monoclonal antibodies as probes of the structure and function of insulin receptors, Biochem Soc Trans, 15:47-51 (1987).
Le Marchand-Brustel et al., Anti-insulin receptor antibodies inhibit insulin binding and stimulate glucose metabolism in skeletal muscle, Diabetologia, 14:311-7 (1978).
De Pirro et al., Characterization of the serum from a patient with insulin resistance and hypoglycemia. Evidence for multiple populations of insulin receptor antibodies with different receptor binding and insulin-mimicking activities, Diabetes, 33:301-4 (1984).
Zick et al., The role of antireceptor antibodies in stimulating phosphorylation of the insulin receptor, J Biol Chem, 259:4396-400 (1984).
Taylor et al., Hypoglycemia associated with antibodies to the insulin receptor, N Engl J Med 307:1422-6 (1982).
Doern et al., Characterization of inhibitory anti-insulin-like growth factor receptor antibodies with different epitope specificity and ligand-blocking properties, J. Biol. Chem., 284(15):10254-7 (2009).

\* cited by examiner

Figure 4. Simulated data from an equilibrium solution affinity measurement method to detect modulation of a protein-protein interaction. This shows the amount of free or unbound receptor on the y-axis against ligand concentration on the x-axis.
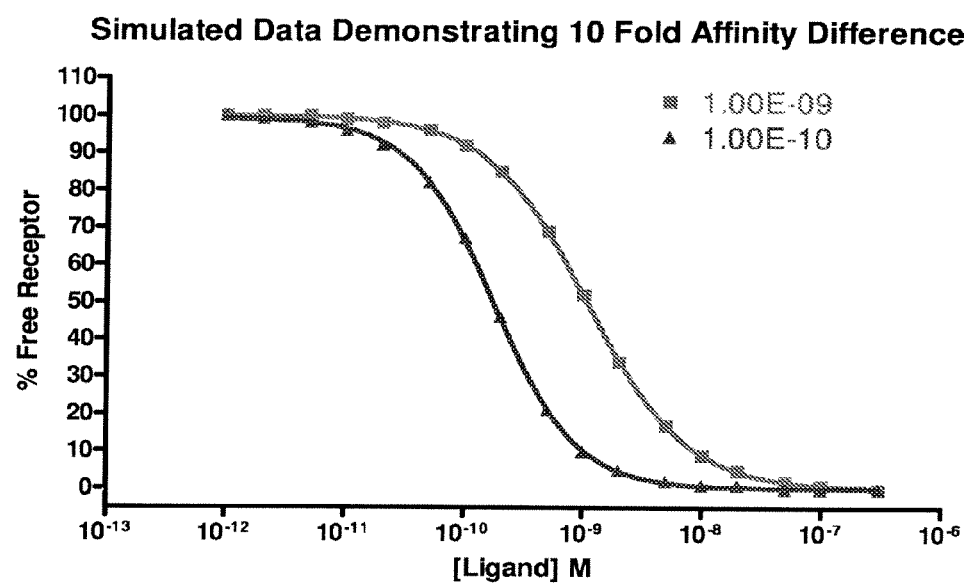

Figure 7. IL-1β clears more rapidly when bound to XOMA 052 than when bound to a blocking antibody.
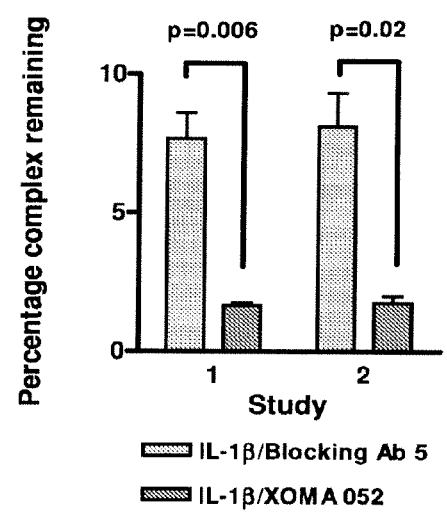

Figure 8. Illustration of the regulation of IL-1β activity by different drug types in T2D
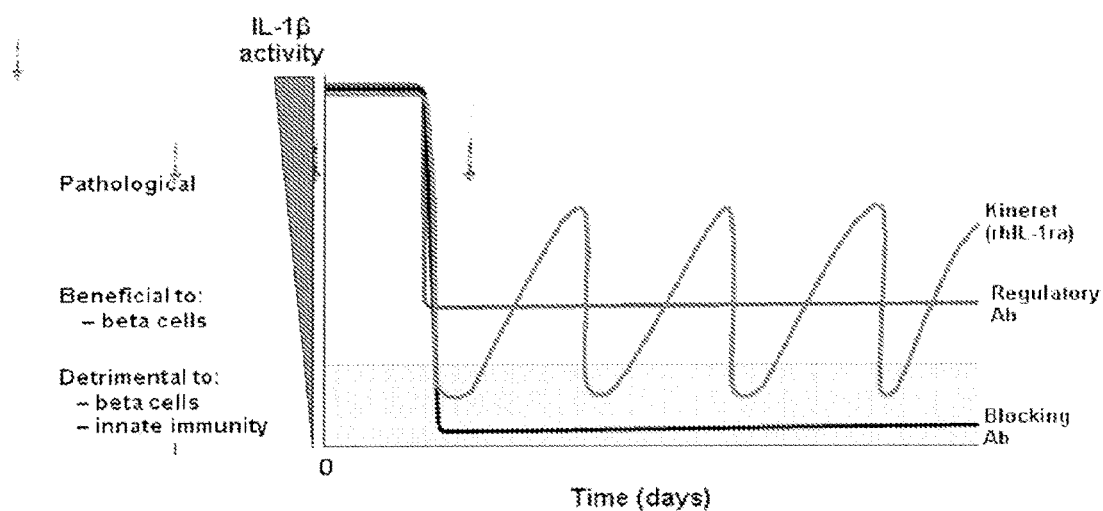

Single point assay (fixed concentration of antibody and ligand)

Ligand Titration

Antibody Titration

POSITIVE CONTROL (83.7 mAb)

BINDS EXCLUSIVELY TO INS/INSR COMPLEX

PREFERENTIALLY BINDS INS/INSR COMPLEX

PREFERENTIALLY BINDS INSR

BINDS EQUALLY TO INSR AND INS/INSR COMPLEX

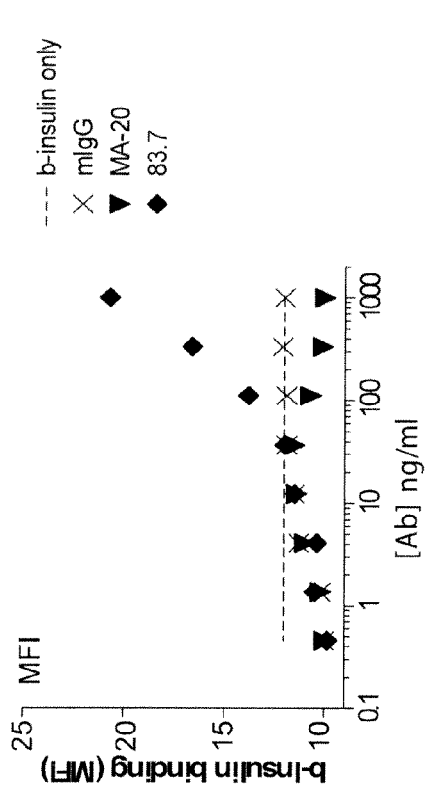
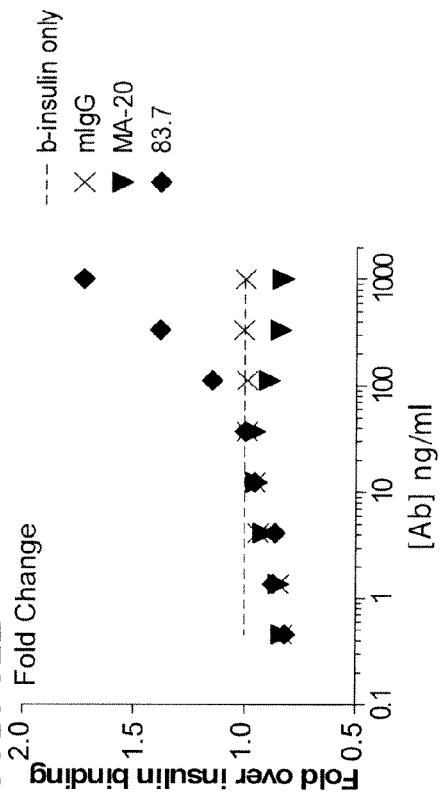
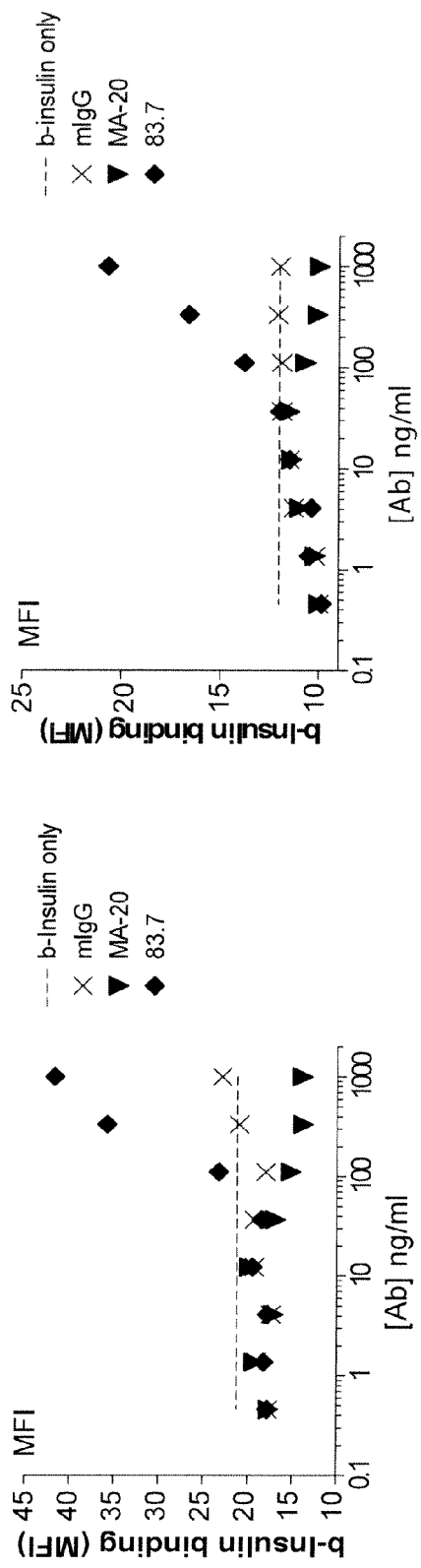
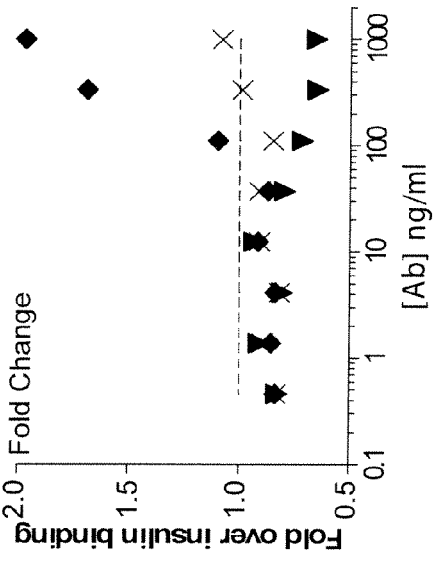

Figure 13. Example results from assay measuring the ability of test antibodies to stimulate pIRS-1 phosphorylation
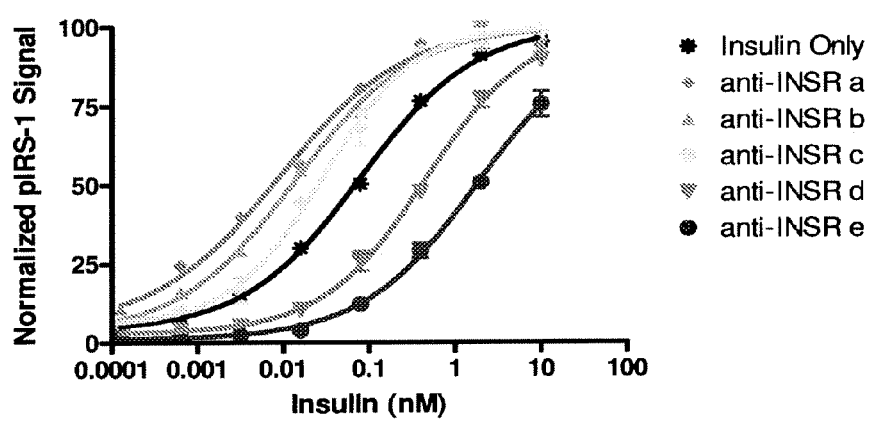

Figure 14. Table of insulin EC50 values from the pIRS-1 assay ranked according to EC50 ratio +Ab/-Ab

| Anti-INSR Ab | Ab type | [Ab] (ug/ml) | Insulin EC50 (nM) | | Fold change in insulin EC50 | | | Ab property |
|---|---|---|---|---|---|---|---|---|
| | | | insulin alone | Insulin + antibody | -Ab EC50/+Ab EC50 | +Ab EC50/-Ab EC50 | absolute change | |
| Ab001 | IgG2 | 5.00 | 0.11 | 0.0048 | 23.32 | 0.04 | 23.32 | Abs with significant positive modulation |
| Ab002 | IgG2 | 2.50 | 0.12 | 0.0166 | 7.32 | 0.14 | 7.32 | |
| Ab003 | IgG2 | 2.25 | 0.12 | 0.0171 | 7.11 | 0.14 | 7.11 | |
| Ab004 | IgG2 | 5.00 | 0.13 | 0.0239 | 5.34 | 0.19 | 5.34 | |
| Ab005 | Fab | 2.50 | 0.08 | 0.0188 | 4.48 | 0.22 | 4.48 | |
| Ab006 | IgG2 | 1.25 | 0.13 | 0.0367 | 3.47 | 0.29 | 3.47 | |
| Ab007 | IgG2 | 5.00 | 0.11 | 0.0346 | 3.22 | 0.31 | 3.22 | |
| Ab008 | Fab | 0.63 | 0.08 | 0.0270 | 3.11 | 0.32 | 3.11 | |
| Ab009 | IgG2 | 5.00 | 0.13 | 0.0461 | 2.77 | 0.36 | 2.77 | |
| Ab010 | IgG2 | 2.50 | 0.12 | 0.0463 | 2.62 | 0.38 | 2.62 | |
| Ab011 | IgG2 | 2.50 | 0.13 | 0.0719 | 1.78 | 0.56 | 1.78 | |
| Ab012 | IgG2 | 2.50 | 0.08 | 0.0504 | 1.67 | 0.60 | 1.67 | |
| Ab013 | IgG2 | 1.25 | 0.08 | 0.0540 | 1.56 | 0.64 | 1.56 | |
| Ab014 | IgG2 | 5.00 | 0.11 | 0.0984 | 1.13 | 0.88 | 1.13 | |
| Ab015 | IgG2 | 1.25 | 0.20 | 0.2450 | 0.82 | 1.23 | 1.23 | Abs without significant modulation |
| Ab016 | IgG2 | 1.25 | 0.20 | 0.2714 | 0.74 | 1.36 | 1.36 | |
| Ab017 | IgG2 | 2.50 | 0.20 | 0.2747 | 0.73 | 1.37 | 1.37 | |
| Ab018 | IgG2 | 5.00 | 0.09 | 0.2969 | 0.29 | 3.48 | 3.48 | Abs with significant negative modulation |

* $p < 0.01$ (one-tailed) ND/isotope compared to HFD/isotope

* $p \leq 0.01$ (two-tailed) compared to HFD/isotope

** $p < 0.001$ (two-tailed) compared to HFD/isotope

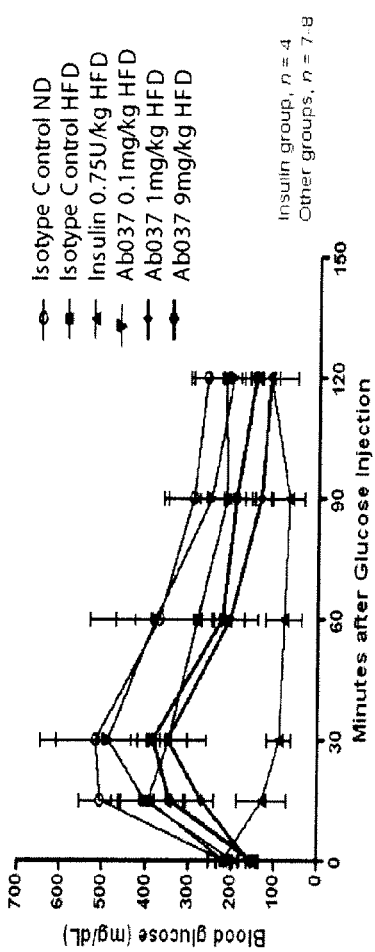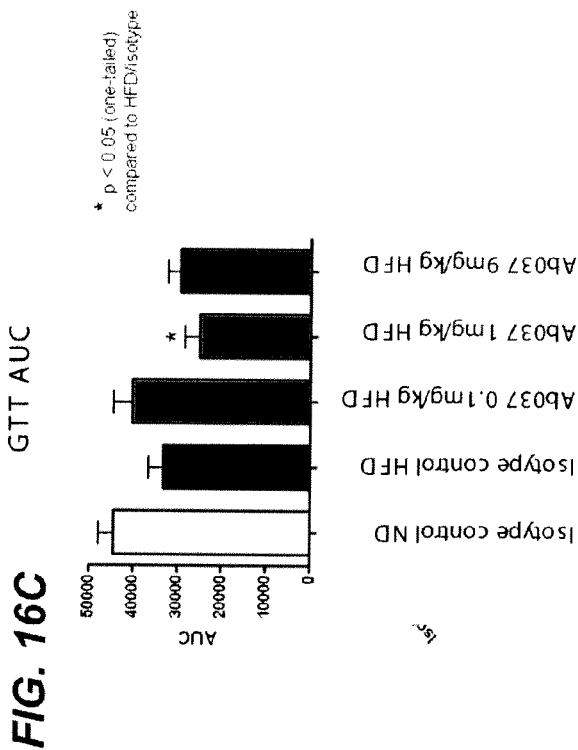
FIG. 16A
FIG. 16B
FIG. 16C

Fasted

GTT AUC

Figure 21

| Engineered insulin receptor cell line used in the assay | Assay parameter determined from sigmoidal dose-response curve fit | Human Insulin | Ab037 | Ab030 | Ab040 | Ab018 |
|---|---|---|---|---|---|---|
| Human INSR CHO-K1 | Relative maximum activation of pAkt by insulin or antibody alone | 100% | 44% | 47% | 19% | 36% |
| | $EC_{50}$ (nM) of insulin or antibody alone | 0.6 | 0.8 | 12 | 4 | 1 |
| | Hill coefficient of insulin or antibody alone | 0.8 | 0.9 | 1.8 | 1.4 | 1.4 |
| Mouse INSR CHO-K1 | Relative maximum activation of pAkt by insulin or antibody alone | 100% | 29% | 37% | 25% | 26% |
| | $EC_{50}$ (nM) of insulin or antibody alone | 3.4 | 1.4 | 11 | 4 | 3 |
| | Hill coefficient of insulin or antibody alone | 0.7 | 1 | 1.7 | 1.3 | 1 |

Figure 22

| Engineered insulin receptor cell line used in the assay | Assay parameter determined from sigmoidal dose-response curve fit | Assay 1 | | Assay 2 | |
|---|---|---|---|---|---|
| | | Hu Insulin with 10 ug/ml control antibody | Hu Insulin with 10 ug/ml Ab037 | Hu Insulin with 10 ug/ml control antibody | Hu Insulin with 10 ug/ml Ab040 |
| Human INSR CHO-K1 | Relative maximum activation of pAkt in the presence of 10 ug/ml antibody | 100 ± 5% | 93 ± 2% | 100 ± 3% | 85 ± 1% |
| | EC50 of insulin in the presence of 10 ug/ml antibody (nM) | 0.7 ± 0.3 | 1 ± 0.3 | 0.8 ± 0.2 | 0.3 ± 0.1 |
| Mouse INSR CHO-K1 | Relative maximum activation of pAkt in the presence of 10 ug/ml antibody | 100 ± 2% | 99 ± 1% | 100 ± 3% | 98 ± 1% |
| | EC50 of insulin in the presence of 10 ug/ml antibody (nM) | 3.3 ± 0.6 | 2.1 ± 0.4 | 3 ± 1 | 0.6 ± 0.2 |

SCREENING METHODS

CROSS REFERENCE TO RELATED APPLICATIONS

The present application claims the priority benefit of U.S. Provisional Patent Application No. 61/246,079, filed Sep. 25, 2009 and U.S. Provisional Patent Application No. 61/306,324, filed Feb. 19, 2010, each of which is incorporated by reference in its entirety.

FIELD

The present invention relates to methods of screening for polypeptide binding agents, e.g. antibodies, that exhibit the ability to kinetically modulate the binding and signaling of biological signaling complexes, e.g., receptor-ligand complexes. The invention also relates to specific polypeptide binding agents characterized by desired kinetic modulating properties.

INCORPORATION OF APPENDIX

This application includes a table, Appendix A, "41726_SecretedProteins.txt", 255 KB in size, created 25 Sep. 2009, submitted with this application. The material included in this ASCII text file is hereby incorporated by reference in its entirety pursuant to 37 C.F.R. §1.52(e)(5).

TABLES

The patent contains table(s) that have been included at the end of the specification.

BACKGROUND

Most antibody drugs are conventionally identified by screening for antibodies that bind to either a cell-surface receptor or its cognate ligand, and identifying antibodies that specifically block or stimulate the receptor signaling activity. Many antibody drugs block signaling pathways by binding to either the ligand or receptor, thereby eliminating the ability of the ligand to bind to and activate the receptor. Such blocking antibodies mediate their effect stoichiometrically by preventing the formation of receptor-ligand complex. Conversely, some antibody drugs bind to and activate signaling of a receptor. Such agonist antibodies may mediate their effects by mimicking the natural activity of the ligand and thus do not require the presence of ligand to activate signaling.

SUMMARY

The invention provides novel categories of polypeptide binding agents, designated "kinetic modulating drugs" or "kinetic modulators," that have desirable properties for modulating, either positively or negatively, cellular pathway activity involving a target and its signaling partner. The target and/or its signaling partner may be an endogenous or exogenous compound, either proteinaceous or non-proteinaceous in nature, but which optionally may exclude ions and salts. The invention also provides novel methods of identifying such kinetic modulators, based on their effect on binding kinetics between the target and its signaling partner, or based on differential binding of the kinetic modulator for the target (and/or its signaling partner) in complexed form versus uncomplexed form. The polypeptide binding agent may bind the target, its signaling partner and/or a complex comprising the target and its signaling partner. This discovery allows biophysical screening assays to be designed which can identify modulators of cellular pathway activity suitable for therapeutic use.

In some aspects, assays are provided to identify polypeptide binding agents which modulate the binding kinetics between a target and its signaling partner. Nonlimiting examples of targets include, e.g. a secreted protein of any of the Accession nos. as set forth in Appendix A (or SEQ ID NOS: 1-88). These secreted proteins include a number of secreted membrane-bound receptors. Appendix A herewith lists human secreted proteins as compiled by the Swissprot/EMBL database (see e.g., Boeckmann et al. "The SWISS-PROT protein knowledgebase and its supplement TrEMBL in 2003", Nucleic Acids Res. 31:365-370 (2003). Appendix A sets out the Swissprot accession number for the amino acid sequence of the secreted protein, the name of the protein (and all acronyms or related names) and the length of the amino acid sequence in the database. As used herein, a "signaling partner" is a binding partner of a target that, when bound to the target, forms a signaling complex or is part of a signaling complex that activates or inhibits a cellular pathway. The presence of such kinetic modulator polypeptide binding agents alters (strengthens or weakens) the apparent binding affinity of the target for its signaling partner, thus altering the dose-response of the target for activating the cellular pathway. Alternatively, a kinetic modulator polypeptide binding agent that alters (increases or decreases) the on-rate or alters (decreases or increases) the off-rate of the target for its signaling partner can also change (increase or decrease) the residency time of the target complexed with the signaling partner, change the rate of receptor internalization and/or change the degree of phosphorylation of signaling proteins that are activated or deactivated by the signaling partner complex. Such changes could significantly alter the relative activation of different signaling pathways by the complexation of target and signaling partner and thus alter the dose-response of the target for activating the cellular pathway. Such kinetic modulators are expected to have advantages over conventional therapeutic drugs, including improved safety profiles, altered clearance rates, broader therapeutic windows and less frequent dosing. Where the target is an exogenous compound that is being administered to the patient, administration of the kinetic modulator as an adjunct therapy with the target can alter (e.g., decrease) the total amount (daily, weekly or monthly) and/or the frequency of dosing of the target.

The invention provides methods of identifying candidate kinetic modulating drugs that are polypeptide binding agents, excluding traditional small molecule drugs such as non-polymeric organic chemical compounds having a molecular weight of about 1000 daltons or less. Examples of specifically contemplated polypeptide binding agents include antibodies, including antigen-binding fragments thereof, peptibodies, polypeptides and peptides, optionally conjugated to other peptide moieties or non-peptidic moieties. Examples of antibodies include monoclonal antibodies, tetrameric immunoglobulins comprising two heavy chains and two light chains, single chain antibodies, single domain antibodies, antibody fragments, scFv, Fab, CDRs, rodent antibodies, mammalian antibodies, human antibodies, chimeric antibodies and humanized antibodies.

The invention provides methods of identifying a candidate polypeptide binding agent, e.g. an antibody, that modulates binding between first and second components of a signaling complex (the target and signaling partner, or vice versa). Examples of such first and/or second components include any of the secreted proteins of Appendix A (or SEQ ID NOS: 1-88) and endogenous or exogenous signaling partners of such secreted proteins, or any of the ligands or receptors or transmembrane proteins described herein. In some embodiments, the first and second components are polypeptides. In exemplary specific embodiments, the first and second components are endogenous.

In one aspect, the methods of identifying a candidate kinetic modulating drug include (a) measuring a binding affinity or binding rate parameter of said first component for said second component, in the presence of a test polypeptide binding agent, e.g. antibody, (b) measuring a binding affinity or binding rate parameter of said first component for said second component in the absence of said test polypeptide binding agent; and (c) identifying said test polypeptide binding agent as a candidate kinetic modulating drug when said test polypeptide binding agent exhibits at least a 1.5-fold difference in a binding affinity or binding rate parameter measured in steps (a) and (b). FIG. 1 shows a schematic diagram illustrating some exemplary embodiments. In some embodiments, the difference in binding affinity or binding rate parameter ranges from about 1.5-fold (i.e., 50%) to, optionally, about 1000-fold, or about 1.5-fold to about 100-fold, or about 2-fold to 25-fold, or about 2-fold to 50-fold, or about 1.5-fold to about 25-fold, or about 1.5-fold to about 50-fold, e.g. at least 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 500-fold, or up to 200-fold, or up to 150-fold, or up to 100-fold, or up to 90-fold, or up to 80-fold, or up to 70-fold, or up to 60-fold, or up to 50-fold, or up to 40-fold, or up to 30-fold. In some embodiments, the test polypeptide binding agent is identified as a candidate positive modulator if the test polypeptide agent strengthens a binding affinity or binding rate parameter between said first component and said second component (e.g., reduced $K_D$, or increased $K_A$, or reduced ratio of off-rate/on-rate, or increased ratio of on-rate/off-rate, or increased on-rate, or decreased off-rate). In other embodiments, the test polypeptide agent is identified as a candidate negative modulator if the test polypeptide agent weakens a binding affinity or binding rate parameter between said first component and said second component (e.g., increased $K_D$, or decreased $K_A$, or increased ratio of off-rate/on-rate, or decreased ratio of on-rate/off-rate, or decreased on-rate, or increased off-rate).

In some alternative embodiments, where a stronger binding rate parameter (e.g., increased association or residency time, via increased on-rate or decreased off-rate) results in increased relative activation of the desired signaling pathway, even when binding affinity is not detectably changed, the test polypeptide binding agent is identified as a candidate positive modulator by identifying the desired-fold strengthening in binding rate parameter. Where a weaker binding rate parameter (e.g., decreased association or residency time, via decreased on-rate or increased off-rate) results in increased relative activation of the desired signaling pathway, even when binding affinity is not detectably changed, the test polypeptide binding agent is identified as a candidate positive modulator by identifying the desired-fold weakening in binding rate parameter. Similarly, where a stronger binding rate parameter (e.g., increased association or residency time, via increased on-rate or decreased off-rate) results in decreased relative activation of the desired signaling pathway, even when binding affinity is not detectably changed, the test polypeptide binding agent is identified as a candidate negative modulator by identifying the desired-fold strengthening in binding rate parameter. Where a weaker binding rate parameter (e.g., decreased association or residency time, via decreased on-rate or increased off-rate) results in decreased relative activation of the desired signaling pathway, even when binding affinity is not detectably changed, the test polypeptide binding agent is identified as a candidate negative modulator by identifying the desired-fold weakening in binding rate parameter.

In another aspect, the methods of identifying a candidate kinetic modulating drug include (a) (i) measuring a binding affinity or binding rate parameter of a test polypeptide binding agent, e.g. antibody, for said first component in the presence of said second component, or (ii) measuring a binding affinity or binding rate parameter of a test polypeptide binding agent for said second component in the presence of said first component; and (b) (i) measuring a binding affinity or binding rate parameter of said test polypeptide binding agent for said first component in the absence of said second component, or (ii) measuring a binding affinity or binding rate parameter of said test polypeptide binding agent for said second component in the absence of said first component; and (c) identifying said test polypeptide binding agent as a candidate kinetic modulating drug when said test polypeptide binding agent exhibits a 1.5-fold to 100-fold difference in the binding affinity or binding rate parameter measured in steps (a) and (b). FIG. 2 shows a schematic diagram illustrating some exemplary embodiments, in which interaction is measured in the presence and absence of the second component.

In some embodiments, the difference in binding affinity or binding rate parameter measured in steps (a) and (b) ranges from about 1.5-fold (i.e., 50%) to, optionally, about 1000-fold, or about 1.5-fold to about 100-fold, or about 2-fold to 25-fold, or about 2-fold to about 50-fold, or about 1.5-fold to about 25-fold, or about 1.5-fold to about 50-fold, e.g. at least 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 500-fold, or up to 200-fold, or up to 150-fold, or up to 100-fold, or up to 90-fold, or up to 80-fold, or up to 70-fold, or up to 60-fold, or up to 50-fold, or up to 40-fold, or up to 30-fold. In some embodiments, the test polypeptide binding agent is identified as a candidate positive modulator if the binding affinity or binding rate parameter measured in step (a) is stronger than the binding affinity or binding rate parameter measured in step (b). In other embodiments, the test polypeptide binding agent is identified as a candidate negative modulator if the binding affinity or binding rate parameter measured in step (b) is stronger than the binding affinity or binding rate parameter measured in step (a).

Any of the foregoing methods can be carried out as high throughput assays, in which multiple polypeptide binding agents (e.g., at least 5, 10, 15, 20, 25, 30, 35, 40, 50, 100, 150, 200, 500, 1,000, 10,000, or 25,000) are screened simultaneously or sequentially. In some embodiments, the methods further involve assaying a plurality of test polypeptide binding agents, e.g. antibodies, for binding affinity to any one of (a) the first component, (b) the second component, or (c) a complex comprising the first component and second component, optionally prior to measuring differences in binding affinity or binding rate parameter. Such prescreening of libraries can also be carried out as high throughput assays, in which multiple polypeptide binding agents (e.g., at least 5, 10, 15, 20, 25, 30, 35, 40, 50, 100, 150, 200, 500 or 1000) are screened simultaneously or sequentially. In some embodiments, the plurality of test polypeptide binding agents screened are variants of a parent polypeptide binding agent made by introducing one or more different mutations into a parent polypeptide binding agent.

In further embodiments, the polypeptide binding agents may be screened for selectivity of effect for the first or second component, compared to a different binding partner such as a decoy receptor, clearance receptor, or alternate signal pathway component. Such methods may involve identifying a polypeptide binding agent that does not significantly change the binding affinity or binding rate parameter of the first or second component for a different binding partner, such binding partner being neither the first nor second component.

Any of the preceding measurements of binding affinity or binding rate parameter may be carried out in assays where one or more of the first component, second component and polypeptide binding agent are in solution, or in assays where one or more of the first component, second component and polypeptide binding agent are linked to a solid phase (covalently or noncovalently), or in assays where one or more of the first component, second component and polypeptide binding agent are expressed on a cell surface. The first and/or second components may each themselves be complexes of multiple compounds. The first and/or second components (e.g., target or signaling partner or vice versa) may be soluble or membrane-bound ligands or receptors, including but not limited to 7-transmembrane receptors, G-protein coupled receptors (GPCRs), adrenergic receptors, neurotransmitter receptors, olfactory receptors, opioid receptors, chemokine receptors, rhodopsin, receptor tyrosine kinases, growth factor receptors, integrins, and toll-like receptors, enzymes, or substrates.

Any of the preceding methods may further include recloning and expressing, or synthesizing and expressing, or synthesizing, the candidate kinetic modulating polypeptide binding agent; purifying and/or sequencing the kinetic modulator; adding or replacing an Fc region or fragment thereof; formulating the kinetic modulator or a variant, e.g. an antibody comprising at least three or six of the same CDRs of the parent antibody, in a sterile composition with a sterile pharmaceutically acceptable diluent; and/or administering the kinetic modulator or a variant to an animal.

Any of the preceding methods may further include measuring the level of signaling mediated by the signaling complex in the presence and absence of the test polypeptide binding agent, and determining whether the test polypeptide binding agent is additionally an agonist, partial agonist, antagonist or partial antagonist. In certain embodiments, the agonist or partial agonist is an allosteric agonist.

In related aspects, the invention provides a polypeptide binding agent, e.g. an antibody, identified by any of the preceding methods or any of the methods described elsewhere herein.

In a separate aspect, the invention also provides polypeptide binding agents with desired characteristics. In some embodiments, the invention provides a positive modulator that (a) binds to the target, e.g., a secreted protein of any of Appendix A (or SEQ ID NOS: 1-88) with an equilibrium dissociation constant $K_D$ of about $10^{-5}$M or less, e.g., $10^{-6}$M or less, or $10^{-7}$M or less, or $10^{-8}$M or less (wherein a lower number indicates higher binding affinity), and (b) is capable of improving the binding affinity $K_D$ between said target and its signaling partner by about 1.5-fold (i.e., 50%) to, optionally, about 1000-fold, or about 1.5-fold to about 100-fold, or about 2-fold to 25-fold, or about 2-fold to about 50-fold, or about 1.5-fold to about 25-fold, or about 1.5-fold to about 50-fold, e.g. at least 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 500-fold, or up to 200-fold, or up to 150-fold, or up to 100-fold, or up to 90-fold, or up to 80-fold, or up to 70-fold, or up to 60-fold, or up to 50-fold, or up to 40-fold, or up to 30-fold. In other embodiments, the invention provides a negative modulator that (a) binds to the target, e.g., secreted protein of any of Appendix A (or SEQ ID NOS: 1-88) with an equilibrium dissociation constant $K_D$ of about $10^{-5}$M or less, e.g., $10^{-6}$M or less, or $10^{-7}$M or less, or $10^{-8}$M or less, and (b) is capable of reducing the binding affinity $K_D$ between said target and its signaling partner by about 1.5-fold (i.e., 50%) to, optionally, about 1000-fold, or about 1.5-fold to about 100-fold, or about 2-fold to 25-fold, or about 2-fold to about 50-fold, or about 1.5-fold to about 25-fold, or about 1.5-fold to about 50-fold, e.g. at least 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 500-fold, or up to 200-fold, or up to 150-fold, or up to 100-fold, or up to 90-fold, or up to 80-fold, or up to 70-fold, or up to 60-fold, or up to 50-fold, or up to 40-fold, or up to 30-fold.

Any of such polypeptide binding agents may be further subject to purification, to obtain a substantially homogeneous composition, e.g. at least about 90%, 95%, 97%, 98%, 99% or 99.5% pure.

The invention further provides methods of preparing a sterile pharmaceutical composition comprising adding a sterile pharmaceutically acceptable diluent to such polypeptide binding agents, sterile compositions of such polypeptide binding agents, e.g., in a therapeutically effective amount, and methods of administering such sterile compositions, e.g. to modulate (increase or decrease) signaling of a complex comprising the secreted protein.

It is understood that each feature or embodiment, or combination, described herein is a non-limiting, illustrative example of any of the aspects of the invention and, as such, is meant to be combinable with any other feature or embodiment, or combination, described herein. For example, where features are described with language such as "one embodiment", "some embodiments", "further embodiment", "specific exemplary embodiments", and/or "another embodiment", each of these types of embodiments is a non-limiting example of a feature that is intended to be combined with any other feature, or combination of features, described herein without having to list every possible combination. Such features or combinations of features apply to any of the aspects of the invention. Similarly, where a method describes identifying polypeptide binding agents, such as antibodies, characterized by certain features, polypeptide binding agents characterized by those features are also contemplated by the invention. Where examples of values falling within ranges are disclosed, any of these examples are contemplated as possible endpoints of a range, any and all numeric values between such endpoints are contemplated, and any and all combinations of upper and lower endpoints are envisioned.

Numerous additional aspects and advantages of the invention will become apparent to those skilled in the art upon consideration of the following detailed description of the invention which describes presently preferred embodiments thereof. All U.S. patents, U.S. patent application publications, U.S. patent applications, foreign patents, foreign patent applications, and non-patent publications referred to in this application, are incorporated herein by reference, in their entireties.

BRIEF DESCRIPTION OF THE FIGURES

(FIG. 3B) varying modulator concentrations (non-agonist antibody); and (FIG. 3C) varying modulator concentrations (agonist antibody).

FIG. 4 shows simulated data from an equilibrium solution affinity measurement method to detect modulation of a protein-protein interaction.

FIG. 7 shows the amount of total IL-1β remaining in circulation 48 hours following injection of antibody/IL-1β complexes.

FIG. 8 is an illustration of the regulation of IL-1β activity by different drug types in T2D.

FIGS. 11A-E represent example results from receptor occupancy screen showing test antibody binding to IM-9 cells in the presence and absence of insulin.

FIGS. 12A-D show sample results from a cell-based affinity measurement assay to measure modulation of the hINS-INSR binding interaction by test antibodies. FIGS. 12A-D represent example results from biotinylated ligand screen showing the effects of test antibodies on insulin binding to insulin receptor.

FIG. 13 shows example results from an assay measuring the ability of test anti-INSR antibodies to stimulate pIRS-1 phosphorylation.

FIG. 14 is a table showing insulin EC50 values from the pIRS-1 assay in the presence or absence of fixed concentrations of various test antibodies.

FIG. 15A. Line graph of glucose levels. FIG. 15B. Bar chart of glucose levels showing statistically significant reduction in blood glucose after injection of partial agonist anti-INSR antibody.

FIGS. 16A-C illustrate that administration of a partial agonist anti-INSR antibody improves glycemic control in DIO mice: FIG. 16A. Glucose tolerance test timecourse; FIG. 16B. Fasting blood glucose levels; FIG. 16C. Glucose tolerance test; area under curve (AUC).

FIG. 17A. Insulin tolerance test timecourse; FIG. 17B. Fasting blood glucose levels; FIG. 17C. Insulin tolerance test; area under curve (AUC).

FIG. 18A. Glucose tolerance test timecourse; FIG. 18B. Fasting blood glucose levels; FIG. 18C. Glucose tolerance test; area under curve (AUC).

FIG. 21 illustrates the activation parameters for a set of partial allosteric agonists alone relative to the endogenous ligand insulin. Data obtained from measurements of percent Akt phosphorylation at Ser473.

FIG. 22 illustrates the activation properties of insulin in the presence of 10 ug/ml partial allosteric agonist antibodies relative to the maximal response to the endogenous ligand in the presence of a negative control antibody. Data obtained from measurements of percent Akt phosphorylation at Ser473.

DETAILED DESCRIPTION

Figure 1A:
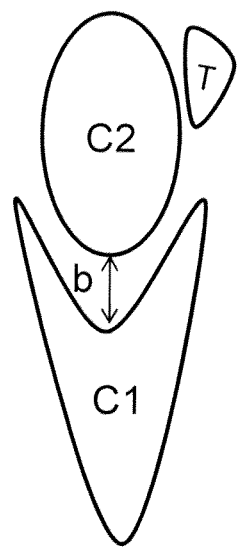
FIGS. 1A-1F are schematic diagrams to illustrate binding assay configurations for measurement of binding performed in the presence or absence of test polypeptide binding agent.
Figure 1C:
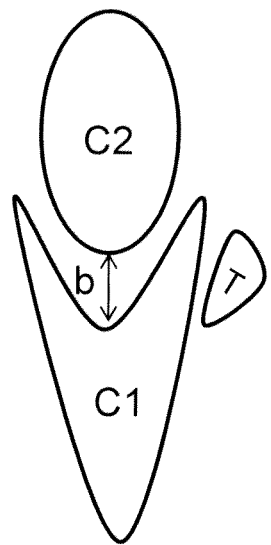
Figure 1E:
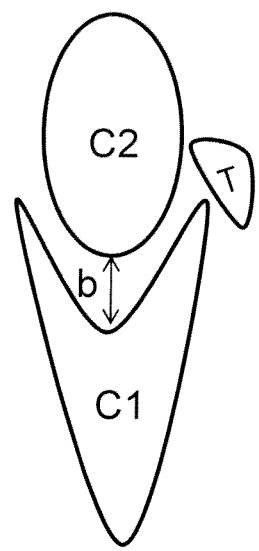
Figure 1B:
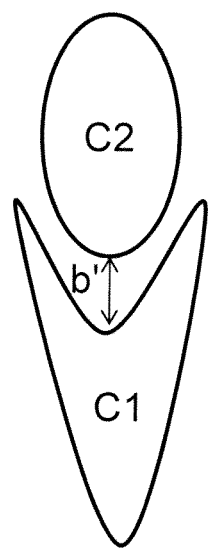
Figure 1D:
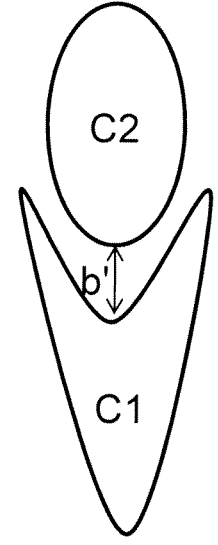
Figure 1F:
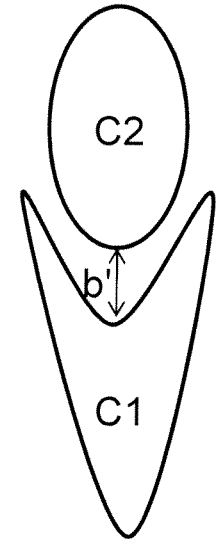
Figure 2A:
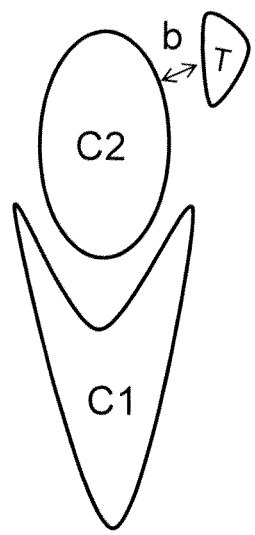
FIGS. 2A-2F are schematic diagrams to illustrate binding assay configurations for measurement of binding performed in the presence or absence of a second complex component.
Figure 2C:
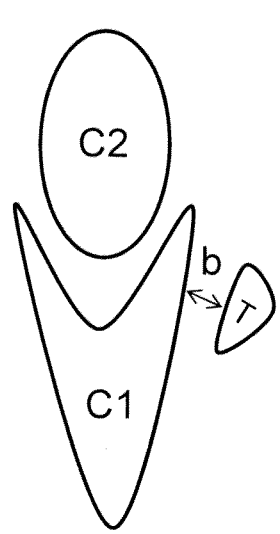
Figure 2E:
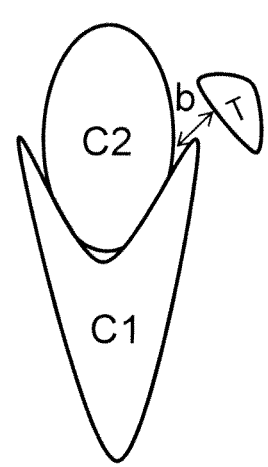
Figure 2B:
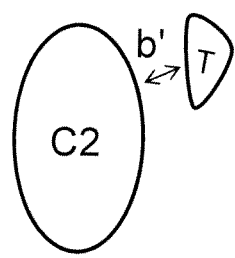
Figure 2D:
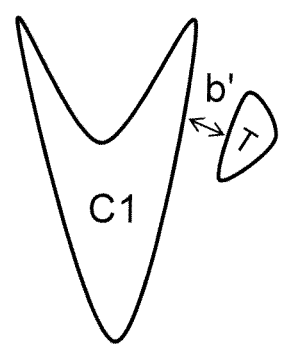
Figure 2F:
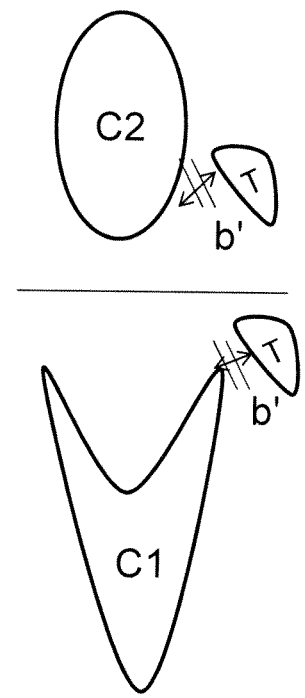

The invention provides kinetic modulating drugs that are polypeptide binding agents, uses thereof, and various methods of identifying kinetic modulating drugs. These kinetic modulators can induce either a positive or negative effect on the cellular response by altering the kinetic rate constants for assembly and dissociation of signaling complex components or by other mechanisms including altering the structural state of the signaling complex, e.g., by binding to a transition state and accelerating the activation of signaling.

Modulation of a signaling complex can result in an increase or decrease in sensitivity to signal input and concomitant increases or decreases in signal transduction. Administration of these kinetic modulators increases or decreases the sensitivity of the cellular pathway and/or absolute levels of the cellular response. The kinetic modulators of the invention, depending on their properties, can function as a modulator, potentiator, regulator, effector or sensitizer.

Many antibody drugs act to block signaling pathways by binding to either a cell-surface receptor or its cognate ligand and eliminating the ability of the ligand to bind to and activate the receptor. Such blocking drugs mediate their effect stoichiometrically by preventing the formation of receptor-ligand complex. However, most pathways that have been linked to disease when abnormally activated also have normal developmental or homeostatic roles in normal biology. This observation is particularly true for the immune system, where highly potent cytokines such as TNF-α and IL-6 drive inflammation in pathological contexts but also have important beneficial roles in the control of infections. Successful treatment of some diseases may therefore require attenuation rather than complete inhibition of signaling pathways to restore a normal physiological state with acceptable side-effect profiles. The kinetic modulators provided by the invention are expected to provide such advantages.

Other therapeutic drugs affect cellular signaling pathways by binding to a cell-surface receptor and altering the activity of the receptor. Such direct agonist drugs may mediate their effects by mimicking the natural activity of the ligand and thus have inherent activity i.e. they do not require the presence of ligand to mediate their effects. Further therapeutic drugs affect cellular signaling pathways by binding to a ligand. Such indirect agonist drugs may mediate their effects by altering ligand stability or valency.

Biological processes are generally regulated in a continuous rather than binary manner, and thus in many cases modulation of pathway activity may be a more appropriate therapeutic strategy than complete pathway blockade or stimulation. Performing functional, cell-based screens for modulation of pathway activity, rather than for complete pathway blockade or stimulation, is laborious and may not readily be readily performed in a high throughput manner, since such screens generally require a known concentration of test compound and may be sensitive to any impurities in the test compound preparation. In particular, the ability to perform high throughput functional, cell-based screens for modulation of pathway activity is restricted for cell-impermeable molecules which are unable to enter the intracellular environment, and especially for recombinant biological molecules which may have different expression levels, degrees of purity and stability in the production system used. In addition, some binding interactions may have no signaling output to measure in a functional screen (e.g. in the case of decoy receptors, decoy substrates, or inactive forms of a target) making it difficult to identify agents that perturb these interactions.

The present invention overcomes these disadvantages and provides a means for identifying positive and negative kinetic modulators of the desired activity and desired potency in a high throughput manner.

Definitions

The term "compound" refers to any chemical compound, organic or inorganic, endogenous or exogenous, including, without limitation, polypeptides, proteins, peptides, small molecules, nucleic acids (e.g. DNA and RNA), carbohydrates, lipids, fatty acids, steroids, purines, pyrimidines, peptidomimetics, polyketides and derivatives, structural analogs or combinations thereof. "Endogenous" means naturally occurring in a mammal, while "exogenous" means not naturally occurring in the mammal, e.g. an administered foreign compound.

The term "polypeptide binding agent" refers to a polypeptide that is capable of specifically binding an antigen, e.g. a target or its signaling partner, or that is capable of binding an antigen with a measurable binding affinity. Examples of polypeptide binding agents include antibodies, peptibodies, polypeptides and peptides, optionally conjugated to other peptide moieties or non-peptidic moieties. Antigens to which a polypeptide binding agent may bind include any proteinaceous or non-proteinaceous molecule that is capable of eliciting an antibody response, or that is capable of binding to a polypeptide binding agent with detectable binding affinity greater than non-specific binding. The antigen to which a kinetic modulating polypeptide binding agent binds may include a target, a signaling partner of a target, and/or a complex comprising the target and its signaling partner.

The term "antibody" is used in the broadest sense and includes fully assembled antibodies, tetrameric antibodies, monoclonal antibodies, polyclonal antibodies, multispecific antibodies (e.g., bispecific antibodies), antibody fragments that can bind an antigen (e.g., Fab', F'(ab)2, Fv, single chain antibodies, diabodies), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as one, two, three, four, five, or six CDR sequences, as long as the antibody retains the desired biological activity.

"Monoclonal antibody" refers to an antibody obtained from a population of substantially homogeneous antibodies, i.e., the individual antibodies comprising the population are identical except for possible naturally occurring mutations that may be present in minor amounts.

"Antibody variant" as used herein refers to an antibody polypeptide sequence that contains at least one amino acid substitution, deletion, or insertion in the variable region of the natural antibody variable region domains. Variants may be substantially homologous or substantially identical to the unmodified antibody.

A "chimeric antibody," as used herein, refers to an antibody containing sequence derived from two different antibodies (see, e.g., U.S. Pat. No. 4,816,567) which typically originate from different species. Most typically, chimeric antibodies comprise human and rodent antibody fragments, generally human constant and mouse variable regions.

A "neutralizing antibody" is an antibody molecule which is able to eliminate or significantly reduce a biological function of an antigen to which it binds. Accordingly, a "neutralizing" antibody is capable of eliminating or significantly reducing a biological function, such as enzyme activity, ligand binding, or intracellular signaling.

An "isolated" antibody is one that has been identified and separated and recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, an antibody that "specifically binds" is "antigen specific", is "specific for" antigen or is "immunoreactive" with an antigen refers to an antibody or polypeptide binding agent of the invention that binds an antigen with greater affinity than other antigens of similar sequence. In one aspect, the polypeptide binding agents of the invention, or fragments, variants, or derivatives thereof, will bind with a greater affinity to human antigen as compared to its binding affinity to similar antigens of other, i.e., non-human, species, but polypeptide binding agents that recognize and bind orthologs of the target are within the scope of the invention.

For example, a polypeptide binding agent that is an antibody or fragment thereof "specific for" its cognate antigen indicates that the variable regions of the antibodies recognize and bind the desired antigen with a detectable preference (e.g., where the desired antigen is a polypeptide, the variable regions of the antibodies are able to distinguish the antigen polypeptide from other known polypeptides of the same family, by virtue of measurable differences in binding affinity, despite the possible existence of localized sequence identity, homology, or similarity between family members). It will be understood that specific antibodies may also interact with other proteins (for example, *S. aureus* protein A or other antibodies in ELISA techniques) through interactions with sequences outside the variable region of the antibodies, and in particular, in the constant region of the molecule. Screening assays to determine binding specificity of a polypeptide binding agent, e.g. antibody, for use in the methods of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies for use in the invention can be produced using any method known in the art.

The term "epitope" refers to that portion of any molecule capable of being recognized by and bound by a selective binding agent at one or more of the antigen binding regions. Epitopes usually consist of chemically active surface groupings of molecules, such as, amino acids or carbohydrate side chains, and have specific three-dimensional structural characteristics as well as specific charge characteristics. Epitopes as used herein may be contiguous or non-contiguous.

The term "derivative" when used in connection with polypeptide binding agents and polypeptides of the invention refers to polypeptides chemically modified by such techniques as ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins. Derivatives retain the binding properties of underivatized molecules of the invention.

"Detectable moiety" or a "label" refers to a composition detectable by spectroscopic, photochemical, biochemical, immunochemical, or chemical means. For example, useful labels include 32P, 35S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to another labeled nucleic acid molecule. The detectable moiety often generates a measurable signal, such as a radioactive, chromogenic, or fluorescent signal, that can be used to quantitate the amount of bound detectable moiety in a sample.

"Peptides" or "oligopeptides" are short amino acid sequences, typically between 3 and 100 amino acid residues in length and encompass naturally occurring amino acid residues and non-naturally occurring analogs of residues which may be used singly or in combination with naturally occurring amino acid residues in order to give the peptide a particular conformational specificity or a particular biological activity, such as resistance to proteolysis. Peptides include repeats of peptide sequences and may include 2, 3, 4, 5, 6, 7, 8, 9, 10 or more copies of an amino acid sequence arranged head-to-tail or head-to-head. Peptides may be conjugated to non-peptidic moieties, e.g. [expand]. Peptides include dimers, trimers or higher order multimers, e.g. formed through conjugation to other polymeric or non-polymeric moieties, such as PEG.

"Polypeptides" are longer amino acid sequences, typically 100 or more amino acid residues in length, and encompass naturally occurring amino acid residues and non-naturally occurring analogs of residues which may be used singly or in combination with naturally occurring amino acid residues in order to give the polypeptide a particular conformational specificity or a particular biological activity, such as resistance to proteolysis.

As used herein, a "peptibody" is a fusion polypeptide comprising one or more peptides fused to all or a portion of an immunoglobulin (Ig) constant region. See, e.g., U.S. Pat. No. 6,660,843. The peptide may be any naturally occurring or recombinantly prepared or chemically synthesized peptide that binds to the antigen. The peptide may be repeated and may include 2, 3, 4, 5, 6, 7, 8, 9, 10 or more copies of an amino acid sequence arranged head-to-tail or head-to-head. The portion of the Ig constant region may include at least one constant region domain (e.g., CH1, CH2, CH3, and/or CH4), multiple domains (e.g., CH2 with CH3), multiple copies of domains (e.g., CH2-CH2), any fragment of a constant domain that retains the desired activity, e.g. the salvage receptor epitope responsible for the prolonged half-life of immunoglobulins in circulation, or any combinations thereof.

A "small" molecule or "small" organic molecule is defined herein as a non-polymeric organic chemical compound having a molecular weight of about 1000 Daltons or less.

As used herein, a "signaling complex" is an assembly of proteins and/or endogenous or exogenous compounds that mediate the transduction of a cellular signal. Examples of a signaling complex include, but are not limited to, a ligand bound to a membrane bound receptor, an enzyme bound to a substrate or any cellular molecules that associate to propagate biochemical reactions that are involved in a signal cascade. Signaling complexes can also include coreceptors, cofactors, scaffold proteins, allosteric modulators and numerous other types of proteins and molecules that are involved in cellular signal transduction. Signaling complexes can be formed transiently or can be long lived. The molecular constituents or components of a signaling complex can vary over time and can be dependent on activation state of each component and the cellular environment. Signaling complexes can undergo chemical modification and regulation that can induce a spectrum of effects on the complex including subtle changes in transduction activity, complete inactivation and constitutive activation or both positive and negative modulation. A component of a signaling complex may be a protein, e.g. a secreted protein of any of Appendix A (or SEQ ID NOS: 1-88), that can exist in association with other proteins and/or compounds in a complex ("complexed") or separately therefrom ("uncomplexed").

The term "therapeutically effective amount" is used herein to indicate the amount of kinetic modulator composition of the invention that is effective to ameliorate or lessen symptoms or signs of disease associated with abnormal (e.g. abnormally high or abnormally low) signaling of the signaling complex.

As used herein "binding" is the physical association between two or more distinct molecular entities that results from a specific network of non-covalent interactions consisting of one or more of the weak forces including hydrogen bonds, Van der Waals, ion-dipole and hydrophobic interactions and the strong force ionic bonds. The level or degree of binding may be measured in terms of affinity. Affinity, or "binding affinity", is a measure of the strength of the binding interaction between two or more distinct molecular entities that can be defined by equilibrium binding constants or kinetic binding rate parameters. Examples of suitable constants or parameters and their measurement units are well known in the art and include but are not limited to equilibrium association constant ($K_A$), e.g. about $10^5 M^{-1}$ or higher, about $10^6 M^{-1}$ or higher, about $10^7 M^{-1}$ or higher, about $10^8 M^{-1}$ or higher, about $10^9 M^{-1}$ or higher, about $10^{10} M^{-1}$ or higher, about $10^{11} M^{-1}$ or higher or about $10^{12} M^{-1}$ or higher; equilibrium dissociation constant ($K_D$), e.g., about $10^{-5} M$ or less, or about $10^{-6} M$ or less, or about $10^{-7} M$ or less, or about $10^{-8} M$ or less, or about $10^{-9} M$ or less, or about $10^{-10} M$ or less, or about $10^{-11} M$ or less, or about $10^{-12} M$ or less; on-rate (e.g., $sec^{-1}$, $mol^{-1}$) and off-rate (e.g., $sec^{-1}$)). In the case of $K_A$, higher values mean "stronger" or "strengthened" binding affinity while in the case of $K_D$, lower values mean "stronger" or "strengthened" binding affinity. As used herein, a "strengthened" binding rate parameter means increased residency time, faster association or slower dissociation. As used herein, a "weakened" binding rate parameter means decreased residency time, slower association or faster dissociation. In the case of on-rate, higher values mean faster or more frequent association and thus generally result in strengthened binding affinity. In the case of off-rate, lower values generally mean slower dissociation and thus generally result in stronger binding affinity. However, it is the ratio of the on-rate and off-rate that indicates binding affinity, as explained in further detail later.

Affinity between two compounds, e.g. between an antibody and an antigen, or between first and second components of a signaling complex, may be measured directly or indirectly. Indirect measurement of affinity may be performed using surrogate properties that are indicative of, and/or proportional to, affinity. Such surrogate properties include: the quantity or level of binding of a first component to a second component of a signaling complex, or a biophysical characteristic of the first component or the second component that is predictive of or correlated to the apparent binding affinity of the first component for the second component. Specific examples include measuring the quantity or level of binding of first component to a second component at a subsaturating, concentration of either the first or the second component. Other biophysical characteristics that can be measured include, but are not limited to, the net molecular charge, rotational activity, diffusion rate, melting temperature, electrostatic steering, or conformation of one or both of the first and second components. Yet other biophysical characteristics that can be measured include determining stability of a binding interaction to the impact of varying temperature, pH, or ionic strength.

Measured affinity is dependent on the exact conditions used to make the measurement including, among many other factors, concentration of binding components, assay setup, valence of binding components, buffer composition, pH, ionic strength and temperature as well as additional components added to the binding reaction such as allosteric modulators and regulators. Quantitative and qualitative methods may be used to measure both the absolute and relative strength of binding interactions.

Apparent affinity is a measure of the strength of the binding interaction between two or more distinct molecular entities under conditions where the affinity is altered by conditions or components in the binding reaction such as allosteric modulators, inhibitors, binding component valence etc.

As used herein a "subsaturating concentration" is a concentration of one or more components in a binding reaction that is significantly below the binding affinity $K_D$ and/or a concentration of one component in a binding reaction that is less than is required to occupy all of the binding sites of the other component(s). Under subsaturating conditions a significant percentage of one of the binding components in the binding reaction has available binding sites.

As used herein a "biophysical assay" is any method that measures, in an absolute or relative fashion, the binding, association, dissociation, binding affinity, binding level, or binding rate parameters between at least two compounds. Biophysical assays are generally performed in vitro and may be conducted with purified binding components, unpurified components, cell associated components as well as a combination of purified and cell associated components.

An agonist is a term used to describe a type of ligand or drug that binds and activates signaling of a signaling complex component. The ability to alter the activity of a signaling complex component (e.g. a receptor), also known as the agonist's efficacy, is a property that distinguishes it from antagonists, a type of receptor ligand which also binds a signaling complex component but which does not activate signaling of the signaling complex component. The efficacy of an agonist may be positive, causing an increase in the signaling complex component's activity, or negative causing a decrease in the signaling complex component's activity. Full agonists bind and activate a signaling complex component, displaying full efficacy at that signaling complex component. Partial agonists also bind and activate a given signaling complex component, but have only partial efficacy at the signaling complex component relative to a full agonist. An inverse agonist is an agent which binds to the same signaling complex component binding-site as an agonist for that signaling complex component and reverses constitutive activity of the signaling complex component. Inverse agonists exert the opposite pharmacological effect of an agonist. A co-agonist works with other co-agonists to produce the desired effect together.

In a different aspect, the agonists disclosed herein act as allosteric agonists. They bind to a portion of a receptor that is distinct from the active ligand-binding site, and do not appreciably change the binding affinity of ligand and receptor, e.g. they alter binding affinity by less than 2-fold or 3-fold. They also do not appreciably affect the EC50 of ligand activation of its receptor, e.g. they alter EC50 by less than 2-fold or 3-fold. Such allosteric agonists constitutively activate the receptor with a maximal agonist response that is 80% or less of the maximal agonist response of ligand, for example 15%-80%, 20-80%, 20-60%, 20%-40% or 15%-30%. In certain embodiments, the allosteric agonists constitutively activate the receptor with a maximal agonist response that at least about 15%, 20%, 25%, 30%, 35%, 40%; and up to 45%, 50%, 55%, 60%, 65%, 70%, 75% or 80% of the maximal agonist response of ligand. It is understood that any combination of any of these range endpoints is contemplated without having to recite each possible combination. In further embodiments, the invention provides an allosteric agonist that binds to a receptor with a $K_D$ affinity of $10^{-5}$, $10^{-6}$, $10^{-7}$, $10^{-8}$, $10^{-9}$ M or less (wherein a lower number indicates higher binding affinity). Without being bound by a theory of the invention, the weak agonist activity of allosteric agonists serves to mimic the effect of natural basal ligand activation levels, while permitting exogenously administered ligand to have its normal effect. In certain embodiments, an allosteric agonist is a partial allosteric agonist. An antagonist blocks a receptor from activation by agonists. A selective agonist is selective for one certain type of signaling complex component. It can additionally be of any of the aforementioned types. In exemplary embodiments, the invention provides an allosteric agonist polypeptide binding agent, e.g. antibody, that binds to any of the secreted proteins in Appendix A (or SEQ ID NOS: 1-88) with an affinity of at least $10^{-5}$, $10^{-6}$, $10^{-7}$, $10^{-8}$, $10^{-9}$ M or less (wherein a lower number indicates greater binding affinity), and (a) exhibits maximal agonist activity that is 20%-80% that of the native ligand's maximal agonist activity when measured in an in vitro assay, (b) when present does not alter the EC50 of ligand for receptor by more than 2-fold, and (c) when present does not alter the KD of ligand for receptor by more than 2-fold.

The potency of an agonist is usually defined by the inverse of its EC50 value. This can be calculated for a given agonist by determining the concentration of agonist needed to elicit half of the maximum biological response of the agonist. The lower the EC50, the greater the potency of the agonist.

An antagonist is a type of ligand or drug that does not provoke a biological response itself upon binding to a signaling complex component (e.g. a receptor), but blocks or dampens agonist-mediated responses. Antagonists may have affinity but no efficacy for their cognate signaling complex component, and binding will disrupt the interaction and inhibit the function of an agonist or inverse agonist at receptors. Antagonists mediate their effects by binding to the active site or to allosteric sites on signaling complex components, or they may interact at unique binding sites not normally involved in the biological regulation of the signaling complex component's activity. Antagonist activity may be reversible or irreversible depending on the longevity of the antagonist-receptor complex, which, in turn, depends on the nature of antagonist binding to signaling complex component. The majority of antagonists achieve their potency by competing with endogenous ligands or substrates at structurally-defined binding sites on receptors.

Antagonists display no efficacy to activate the signaling complex components they bind. Once bound, however, antagonists may inhibit the function of agonists, inverse agonists and partial agonists. In functional antagonist assays, a dose-response curve measures the effect of the ability of a range of concentrations of antagonists to reverse the activity of an agonist. The potency of an antagonist is usually defined by its IC50 value. This can be calculated for a given antagonist by determining the concentration of antagonist needed to elicit half inhibition of the maximum biological response of an agonist. The lower the IC50, the greater the potency of the antagonist.

Competitive antagonists reversibly bind to signaling complex components at the same binding site (active site) as the ligand or agonist, but without activating the signaling complex component, thereby competing with agonist for the same binding site on the signaling complex component. Non-competitive, or allosteric, antagonists bind to a separate binding site from the agonist, exerting their action to that signaling complex component via that separate binding site. Thus, they do not compete with agonists for binding. Uncompetitive antagonists differ from non-competitive antagonists in that they require signaling complex component activation by an agonist before they can bind to a separate allosteric binding site.

Methods of Identifying Kinetic Modulators

Without being bound by a theory of the invention, the present disclosure provides that kinetic perturbation of an interaction between two components (first component, C1 and second component, C2) of a signaling complex with a kinetic modulator (M) can be described mathematically as:

$$K'_{C1C2} = K_{C1C2} \frac{(1 + M/K_{MC1})(1 + M/K_{MC2})}{(1 + M/K_{[C1C2]M})}$$

where the change in binding equilibrium constant between the components ($K'_{C1C2}$) is a function of equilibrium constant between the components ($K_{C1C2}$), kinetic modulator concentration (M), kinetic modulator affinity for the complex ($K_{[C1C2]M}$) and kinetic modulator affinity for either the first component ($K_{MC1}$) or the second component ($K_{MC2}$).

In cases where the signaling complex is a receptor-ligand complex, and the modulator is an antibody, the kinetic perturbation of the receptor-ligand interaction with an antibody can be described mathematically as:

$$K'_{RL} = K_{RL} \frac{\left(1 + \frac{A}{K_{AR}}\right)\left(1 + \frac{A}{K_{AL}}\right)}{\left(1 + \frac{A}{K_{[RL]A}}\right)}$$

where the change in receptor-ligand binding equilibrium constant ($K'_{RL}$) is a function of receptor-ligand equilibrium constant ($K_{RL}$), antibody concentration (A), antibody affinity for the complex ($K_{[RL]A}$) and antibody affinity for either the receptor ($K_{AR}$) or ligand ($K_{AL}$).

A kinetic modulator binds the target, or its signaling partner, or a complex of the target and signaling partner, in such a manner that the binding affinity or binding rate parameter of the target for its signaling partner is weakened or strengthened. For example, where the target is either a receptor or ligand, the binding affinity or binding rate parameter of the ligand for its receptor is weakened or strengthened in the presence of the kinetic modulator. A kinetic modulator with complete blocking activity represents a boundary condition in this analysis, since when $K_{[C1C2]M}$ is sufficiently high, $K'_{C1C2}$ approaches infinity. One implication of this model is that the degree of signaling modulation is independent of kinetic modulator concentration when the concentration of kinetic modulator ([M]) is sufficiently above the equilibrium dissociation constant ($K_D$) for the kinetic modulator/antigen interaction to be saturating for binding ligand. Hence, modulation of the interaction is related to the ratio of affinities for the complex versus the components where [M]>$K_D$ for the modulator and its antigen.

Figure 3A:
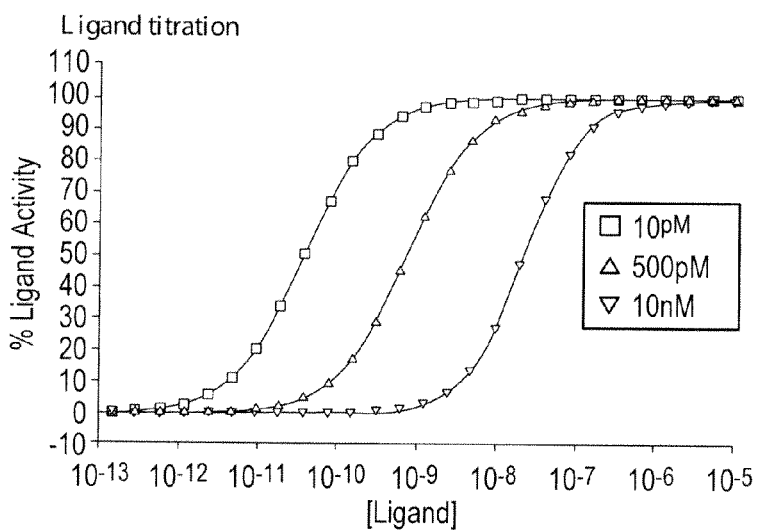
FIGS. 3A-3C show simulated data to show predicted effects of kinetic modulators on signaling activity at (FIG. 3A) varying ligand concentrations.
Figure 3B:
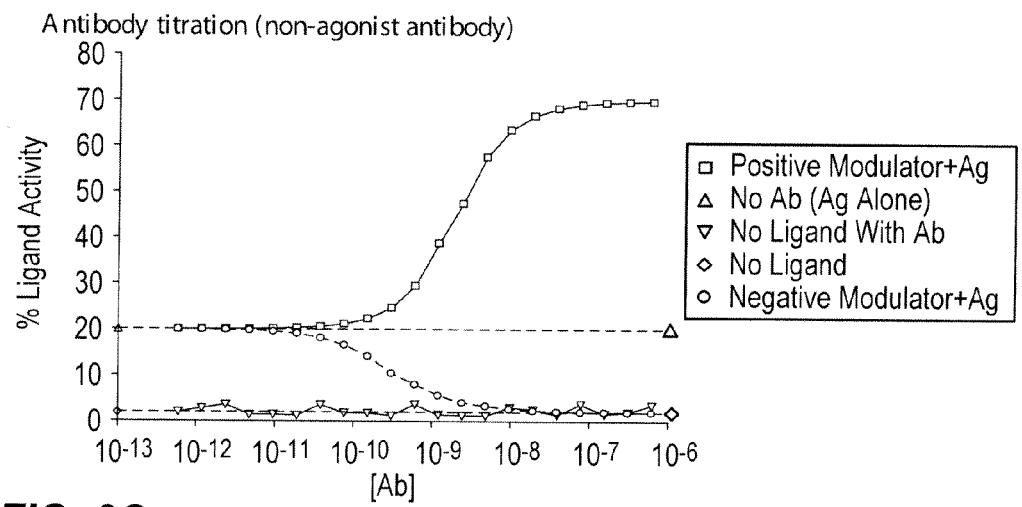
Figure 3C:
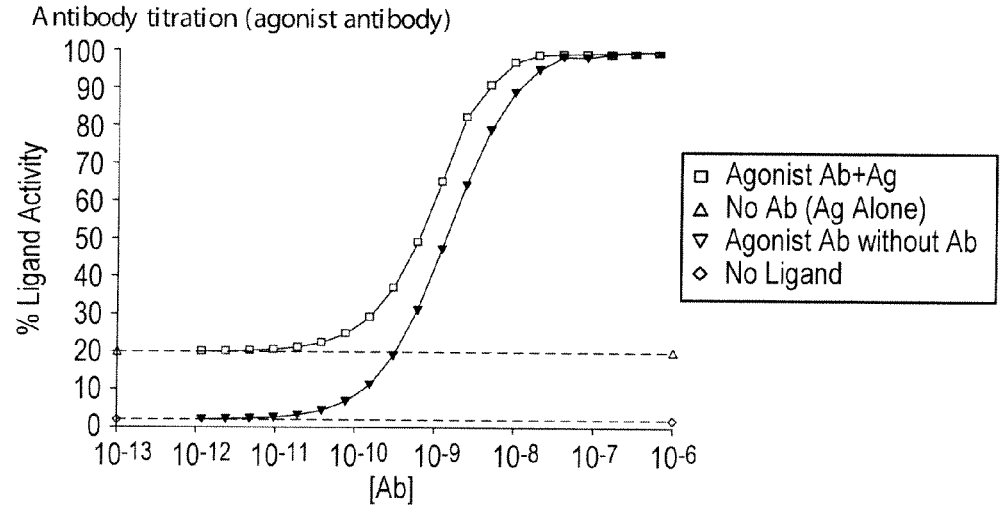

The present disclosure provides that the biophysical properties of a kinetic modulator's interactions with a target and/or its signaling partner can be used to predict the functional effect of the kinetic modulator on the target signaling pathway. Kinetic modulators which alter the signaling pathway can therefore be identified based on their relative affinity for target (and/or its signaling partner) in complexed versus uncomplexed form. The invention contemplates that kinetic perturbation of an interaction between two components (first component, C1 and second component, C2) of a signaling complex with a kinetic modulator (M) can be predicted in the following manner:

$K_{[C1C2]M}$ or $K_{[MC2]C1}$ or $K_{[MC1]C2}$<$K_{MC2}$ or $K_{MC1}$ leads to positive kinetic modulation $K_{[C1C2]M}$ or $K_{[MC2]C1}$ or $K_{[MC1]C2}$=$K_{MC2}$ or $K_{MC1}$ leads to no kinetic modulation $K_{[C1C2]M}$ or $K_{[MC2]C1}$ or $K_{[MC1]C2}$>$K_{MC2}$ or $K_{MC1}$ leads to negative kinetic modulation In cases where the signaling complex is a receptor (R)-ligand (L) complex, and the kinetic modulator is an antibody (A), the kinetic perturbation can be predicted in the Following manner:

$K_{[RL]A}$ or $K_{[AL]R}$ or $K_{[AR]L}$<$K_{AL}$ or $K_{AR}$ leads to positive kinetic modulation $K_{[RL]A}$ or $K_{[AL]R}$ or $K_{[AR]L}$=$K_{AL}$ or $K_{AR}$ leads to no kinetic modulation $K_{[RL]A}$ or $K_{[AL]R}$ or $K_{[AR]L}$>$K_{AL}$ or $K_{AR}$ leads to negative kinetic modulation In some embodiments, a kinetic modulator, such as an antibody (A) can be identified by its ability to alter a binding interaction, such as a receptor (R)-ligand (L) interaction at any given sub-saturating concentration of the first or second component (e.g. ligand (L) concentration), as depicted in FIG. 3A. The data in FIG. 3A was generated from a reversible interaction model, assuming an affinity of the receptor ligand interaction of either 10 pM, 500 pM or 10 nM. A kinetic modulator could effectively shift the affinity and the corresponding dose response of the receptor ligand interaction from the 500 pM interaction to either the 10 pM (positive modulator) or 10 nM (negative modulator) as depicted. In some embodiments the kinetic modulator will produce a higher level of R-L binding at a given ligand concentration, shifting the assay curve to the left (positive modulation). In other embodiments the kinetic modulator will produce a lower level of R-L binding at a given ligand concentration, shifting the assay curve to the right (negative modulation). In some embodiments the shift is uniform, as shown in FIG. 3A. In other embodiments the shift is non-uniform, reflecting the involvement of other factors e.g. accessory proteins in the complex, receptor internalization, etc. The data from FIG. 3A at a 500 pM affinity was used to generate FIGS. 3B and 3C in which the effects of various concentrations of non-agonist (FIG. 3B) or agonist (FIG. 3C) antibodies on signaling were depicted, assuming a fixed concentration of antigen.

The correlation of binding characteristics to functional effect is depicted in Table 1 below for an illustrative target, insulin receptor.

TABLE 1

| Target Binding Characteristics | | | | |
|---|---|---|---|---|
| R | L | R − L | KD ratios | Functional effect |
| − | − | + | $K_{[RL]A} < K_R, K_L$ | Positive modulation |
| − | + | + | $K_{[AL]R} < K_L$ | Positive modulation |
| + | − | + | $K_{[AR]L} < K_R$ | Positive modulation |
| − | + | + | $K_{[AL]R} > K_L$ | Negative modulation |
| + | − | + | $K_{[AR]L} > K_R$ | Negative modulation |

Illustrative examples of data showing the predicted effects match the binding characteristics are shown in Table 2 below.

TABLE 2

| | Target Binding Characteristics | | | | Functional effect (pAKT assay, fold-decrease in insulin $EC_{50}$ relative to isotype control Ab)[#] |
|---|---|---|---|---|---|
| Ab | R | L | R-L | KD ratios | |
| Predicted | − | − | + | $K_{[RL]A} <$ $K_R, K_L$ | Positive modulation |
| Ab078 | Out of Range* | | 3.4e-10 | | 3.3 |
| Ab085 | No Binding | | 2e-10 | | 8.9 |
| Predicted | + | − | + | $K_{[AR]L} < K_R$ | Positive modulation |
| Ab001 | 1.2e-8 | | 1.16e-10 | 103.4 | 9.7 |
| Ab079 | 9.6e-9 | | 4.96e-10 | 19.4 | 6.7 |
| Ab080 | 1.2e-8 | | 6.8e-10 | 17.6 | 8.4 |
| Ab083 | 7.6e-9 | | 3.76e-10 | 20.2 | 8.5 |
| Predicted | + | − | + | $K_{[AR]L} = K_R$ | Non-Modulators |
| Ab037 | 1.08e-10 | | 8e-11 | 1.4 | No change |
| Ab053 | 1.48e-10 | | 9.6e-11 | 1.5 | No change |
| Ab062 | 1.24e-10 | | 1.08e-10 | 1.1 | No change |

*Binding of this clone in the absence of insulin is evident, but insufficiently potent to be accurately measured in this assay.
[#]Assay run at saturating concentrations of test antibody (2-20 ug/ml). Insulin $EC_{50}$ in the presence of 10 ug/ml isotype control Ab = 0.44 nM.

Thus, the binding properties of the interaction(s) between the modulator and the target, its signaling partner and/or a complex comprising the target and its signaling partner, are generally predictive of the functional effect of the kinetic modulator on the target signaling pathway. Depending on the target being studied, certain other factors may need to be considered. These include: (1) the concentration of the kinetic modulator, the concentration of the target, and/or the concentration of its signaling partner (e.g., the prediction is optimized if the kinetic modulator concentration ([M]) is significantly greater than the $K_D$ of the binding between kinetic modulator and its antigen), (2) the structural form of the kinetic modulator used e.g. monovalent vs divalent or bivalent, (3) inter/intra target crosslinking, which may restrict the conformation of target and/or cause target activation, (4) the kinetic modulator's ability to alter assembly or docking, or to alter additional components of the signaling complex by steric or allosteric mechanisms, (5) signaling pathway specific properties such as alterations in the signal pathway due to disease that introduce a "bottleneck," (6) negative/positive feedback regulation of the signaling pathway, (7) alteration of clearance/internalization rates of the components of the signaling complex, (8) alterations in the target that uncouple or differentially alter ligand binding and activation e.g. a modulator enhances ligand binding but traps its receptor in a desensitized state, or a modulator attenuates ligand binding but induces a conformational change in its receptor that is activating.

In some aspects the invention provides methods for measuring the differential binding of a first component of a signaling complex for a second component of the signaling complex in the presence or absence of a test polypeptide agent. In these aspects, differential binding is preferably observed when there are sub-saturating concentrations of the first or second component. In some preferred embodiments the concentration of the first or second component may be reduced to provide sub-saturating conditions.

In some aspects the invention provides methods for measuring the differential binding of a test polypeptide binding agent, e.g. antibody, to target and/or its signaling partner, in complexed and uncomplexed form. In these aspects, differential binding is preferably observed when there are sub-saturating concentrations of test polypeptide binding agent. In some preferred embodiments the concentration of test polypeptide binding agent may be reduced to provide sub-saturating conditions.

In some embodiments, testing in the absence of a test polypeptide agent is performed using a control compound which is preferably a compound belonging to a similar structural class as the test polypeptide agent, but which binds to a different antigen that has no effect on the signaling complex being tested. For example, a control for a test antibody may be an isotype-matched antibody binding to an unrelated antigen, e.g. keyhole limpet hemocyanin (KLH).

For positive modulators, at a given sub-saturating concentration of C1, higher C1 affinity will be reflected in a higher signal for C1 binding to C2 in the presence of the positive modulator. Preferential binding of the kinetic modulator will be reflected in a higher signal for the complex comprising C1 and C2, compared to the signal for either C1 alone or C2 alone. In some aspects, there may be binding of the kinetic modulator to the complex of C1 and C2, but no measurable binding to either C1 alone or C2 alone.

For negative modulators, at a given sub-saturating concentration of C1, lower C1 affinity will be reflected in a lower signal for C1 binding to C2 in the presence of the modulator. Preferential binding of the kinetic modulator will be reflected in a higher signal for binding of the kinetic modulator to C1 alone, or to C2 alone, compared to the signal for binding of the kinetic modulator to the complex of C1 and C2.

The invention provides methods of identifying a candidate polypeptide binding agent, e.g. an antibody, that modulates binding between first and second components of a signaling complex. Examples of such first and/or second components include any of the secreted proteins of Appendix A (or SEQ ID NOS: 1-88) and endogenous or exogenous signaling partners of such secreted proteins, which may be proteinaceous or non-proteinaceous but which optionally may exclude ions and salts. In some embodiments, the first and second components are polypeptides. In exemplary specific embodiments, the first and second components are endogenous.

Other examples include any one of TNFα, CD3, CD4, CD20, VEGF-A, CD25, HER-2, EGFR, CD33, CD52, EPO, insulin, INSR, human growth hormone, GM-CSF, G-CSF, IL-2, TPO, neurotrophic factors (NGF, NT-3, NT-4, GDNF), IFNβ, TGFβ, TNFα, FGFR4, CETP, Leptin Receptor, IL-10, IL-10 receptor alpha, IL-10 receptor beta, Growth hormone receptor, IL-13 receptor, IL-18 receptor, IL-2 receptor alpha subunit, complement factor C5a, IL-17 receptor, IL-20 receptor, IL-3 receptor, IL-4 receptor, IL-5 receptor, IL-9 receptor, Interferon type I receptor 1 (IFNAR1), Interferon type I receptor 2 (IFNAR2), Lymphocyte function antigen-3 receptor, Monocyte chemotactic protein 1 ligand, NGF receptor, IL-6, IL-6 receptor. Their sequences are well known in the art and representative Accession Numbers and amino acid sequences from NCBI's Genbank database are set forth below. NCBI handbook [Internet]. Bethesda (MD): National Library of Medicine (US), National Center for Biotechnology Information; 2002 October Chapter 18, The Reference Sequence (RefSeq) Project. Reference to any of the proteins set forth in Appendix A or SEQ ID NOS: 1-88 herein includes reference to any naturally occurring human allelic variant thereof, such as those comprising amino acid sequences at least 90%, 91%, 92%, 93%, 94%, 95%, 96%, 97%, 98%, 99% identical to the representative sequence of any of SEQ ID NOs: 1-88, or comprising amino acid sequences encoded by nucleic acid molecules that can be obtained from human genomic DNA or cDNA libraries using nucleic acid molecules that encode any of SEQ ID NOs: 1-88 or fragments thereof that are at least about 20, 30, 40, 50 or more bases in length, e.g., under stringent hybridization conditions such as 42° C. in 50% formamide, 5×SSC, 20 mM Na.PO4, pH 6.8; and washing in 1×SSC at 55° C. for 30 minutes.

| Target | Accession Number | SEQ ID NO: |
|---|---|---|
| TNFα | NP_000585 | 1 |
| T cell receptor beta chain CD3 region; TCR CD3 | AAB27501 | 2 |
| CD3 antigen, delta subunit isoform B precursor | NP_001035741 | 3 |
| CD3 antigen, delta subunit isoform A precursor | NP_000723 | 4 |
| T-cell surface glycoprotein CD3 gamma chain | P09693 | 5 |
| T-cell surface glycoprotein CD3 gamma chain precursor | ACA05963 | 6 |
| T-cell surface glycoprotein CD3 epsilon chain | P07766 | 7 |
| T-cell surface glycoprotein CD3 delta chain | P04234 | 8 |
| T-cell surface glycoprotein CD3 delta chain precursor | ACA05962 | 9 |
| T-cell surface glycoprotein CD3 zeta chain | P20963 | 10 |
| CD4 | P01730 | 11 |
| CD4 antigen (p55), isoform CRA_a | EAW88739 | 12 |

-continued

| Target | Accession Number | SEQ ID NO: |
|---|---|---|
| CD20 | P11836 | 13 |
| | NP_068769.2 or NP_690605.1 | |
| membrane-spanning 4-domains, subfamily A, member 1 | NP_690605 | 14 |
| membrane-spanning 4-domains, subfamily A, member 3 isoform a | NP_006129 | 15 |
| membrane-spanning 4-domains, subfamily A, member 3 isoform b | NP_001026979 | 16 |
| membrane-spanning 4-domains, subfamily A, member 3 isoform c | NP_001026836 | 17 |
| VEGF-A | P15692 | 18 |
| vascular endothelial growth factor A isoform a precursor | NP_001020537 | 19 |
| vascular endothelial growth factor A isoform b precursor | NP_003367 | 20 |
| vascular endothelial growth factor A isoform c precursor | NP_001020538 | 21 |
| vascular endothelial growth factor A isoform d precursor | NP_001020539 | 22 |
| vascular endothelial growth factor A isoform e precursor | NP_001020540 | 23 |
| vascular endothelial growth factor A isoform f precursor | NP_001020541 | 24 |
| vascular endothelial growth factor A isoform g precursor | NP_001028928 | 25 |
| CD25 (interleukin 2 receptor, alpha chain precursor) | NP_000408 | 26 |
| HER-2 | AAA75493 | 27 |
| EGFR | AAH94761; | 28 |
| epidermal growth factor receptor isoform a precursor | NP_005219 or P00533 | 29 |
| epidermal growth factor receptor isoform b precursor | NP_958439 | 30 |
| epidermal growth factor receptor isoform c precursor | NP_958440 | 31 |
| epidermal growth factor receptor isoform d precursor | NP_958441 | 32 |
| CD33 antigen isoform 1 precursor | NP_001763 | 33 |
| CD33 antigen isoform 2 precursor | NP_001076087 | 34 |
| CD33 antigen (gp67), isoform CRA_a | EAW71994 | 35 |
| CD33 antigen (gp67), isoform CRA_b | EAW71995 | 36 |
| CD33 antigen (gp67), isoform CRA_c | EAW71996 | 37 |
| CD52 antigen precursor | NP_001794 | 38 |
| EPO | CAA26095 | 39 |
| insulin | AAA59172 | 40 |
| INSR | P06213 | 41 |
| insulin receptor isoform Short precursor | NP_001073285 | 42 |
| insulin receptor isoform Long precursor | NP_000199 | 43 |
| human growth hormone | AAA72260 | 44 |
| GM-CSF | AAA52578 | 45 |
| G-CSF | P09919 | 46 |
| IL-2 | AAB46883 | 47 |
| TPO | AAB33390 | 48 |
| NGF | AAH32517 | 49 |
| nerve growth factor, beta polypeptide precursor | NP_002497 | 50 |
| NT-3 | P20783 | 51 |
| neurotrophin 3 isoform 1 preproprotein | NP_001096124 | 52 |
| neurotrophin 3 isoform 2 preproprotein | NP_002518 | 53 |
| NT-4 | AAA60154 | 54 |
| Chain A, Brain Derived Neurotrophic Factor, Neurotrophin-4 | 1B8M_A | 55 |
| Chain B, Brain Derived Neurotrophic Factor, Neurotrophin-4 | 1B8M_B | 56 |
| GDNF | P39905 | 57 |
| glial cell derived neurotrophic factor isoform 1 preproprotein | NP_000505 | 58 |
| glial cell derived neurotrophic factor isoform 2 precursor | NP_954701 | 59 |
| glial cell derived neurotrophic factor isoform 3 | NP_954704 | 60 |
| IFNβ | P01574 | 61 |
| TGFβ | AAA36738 | 62 |
| FGFR4 | AAB25788 | 63 |
| fibroblast growth factor receptor 4 isoform 1 precursor | NP_998812 | 64 |
| fibroblast growth factor receptor 4 isoform 2 precursor | NP_075252 | 65 |
| CETP | P11597 | 66 |
| Leptin Receptor | P48357 | 67 |

| Target | Accession Number | SEQ ID NO: |
|---|---|---|
| IL-10 | P22301 | 68 |
| IL-10 receptor alpha | EAW67343 | 69 |
| IL-10 receptor beta | AAH01903 | 70 |
| Growth hormone receptor | P10912 | 71 |
| IL-13 receptor | CAA70021 | 72 |
| IL-18 receptor | AAH93977 | 73 |
| IL-2 receptor alpha subunit | P01589 | 74 |
| complement factor C5a | NP_001726 | 75 |
| IL-17 receptor | AAB99730 | 76 |
| IL-20 receptor | Q9UHF4 | 77 |
| IL-3 receptor | AAA59148 | 78 |
| IL-4 receptor | CAA36672 | 79 |
| IL-5 receptor | CAA01794 | 80 |
| IL-9 receptor | AAB30844 | 81 |
| Interferon type I receptor 1 (IFNAR1) | P17181 | 82 |
| Interferon type I receptor 2 (IFNAR2) | P48551 | 83 |
| Lymphocyte function antigen-3 receptor | P19256 | 84 |
| Monocyte chemotactic protein 1 ligand | P13500 or NP_002973 | 85 |
| NGF receptor | AAB59544 | 86 |
| IL-6 | NP_000591 | 87 |
| IL-6 receptor | NP_000556 | 88 |

In one aspect, the methods of identifying a candidate kinetic modulating drug include (a) measuring a binding affinity or binding rate parameter of said first component for said second component, in the presence of a test polypeptide binding agent, e.g. antibody, (b) measuring a binding affinity or binding rate parameter of said first component for said second component in the absence of said test polypeptide binding agent; and (c) identifying said test polypeptide binding agent as a candidate kinetic modulating drug when said test polypeptide binding agent exhibits at least a 1.5-fold difference in the binding affinity or binding rate parameter measured in steps (a) and (b). In some embodiments, the difference in binding affinity or binding rate parameter ranges from about 1.5-fold (i.e., 50%) to, optionally, about 1000-fold, or about 1.5-fold to about 100-fold, or about 2-fold to 25-fold, or about 2-fold to about 50-fold, or about 1.5-fold to about 25-fold, or about 1.5-fold to about 50-fold.

In some embodiments, the test polypeptide binding agent is identified as a candidate positive modulator if the test polypeptide agent strengthens the binding affinity or binding rate parameter between said first component and said second component. In other embodiments, the test polypeptide agent is identified as a candidate negative modulator if the test polypeptide agent weakens the binding affinity or binding rate parameter between said first component and said second component.

Whether a change (increase or decrease) in a particular binding affinity value or binding rate parameter value represents "strengthened" (or stronger) or "weakened" (or weaker) binding affinity or binding rate parameter depends on the value of the parameter and its units, and is well known in the art. For example, in the case of the parameter $K_A$, higher values mean "strengthened" binding affinity, such that a $K_A$ of about $10^6 M^{-1}$ is stronger than a $K_A$ of about $10^5 M^{-1}$. As another example, in the case of the parameter $K_D$, lower values mean "strengthened" binding affinity, such that a $K_D$ of about $10^{-6} M$ is stronger than a $K_D$ of about $10^{-5} M$. Conversely, in the case of $K_A$, lower values mean "weakened" binding affinity, such that a $K_A$ of about $10^5 M^{-1}$ is a weakened binding affinity compared to a $K_A$ of about $10^6 M^{-1}$. As another example, in the case of $K_D$, higher values mean "weakened" binding affinity, such that a $K_D$ of about $10^{-5} M$ is weakened binding affinity compared to a $K_D$ of about $10^{-6} M$.

As used herein, a "strengthened" binding rate parameter means increased residency time, faster association or slower dissociation. As used herein, a "weakened" binding rate parameter means decreased residency time, slower association or faster dissociation.

Binding affinity can also be determined through the ratio of the on-rate and off-rate binding rate parameters. Generally, in the case of on-rate, higher values mean faster or stronger association or increased residence time, and typically result in stronger binding affinity. Conversely, lower values for on-rate mean slower or weaker association or decreased residence time, and typically result in weaker binding affinity. Generally, in the case of off-rate, higher values mean faster dissociation or decreased residence time, and typically result in weaker binding affinity. Conversely, lower values for off-rate mean slower dissociation or increased residence time, and typically result in stronger binding affinity. This is because the ratio of off-rate to on-rate, or on-rate to off-rate, indicates binding affinity as displayed in the equations below.

$$\text{Affinity} \begin{cases} K_D = \frac{[A][L]}{[AL]} = \frac{\text{off-rate}}{\text{on-rate}} \\ K_A = \frac{[AL]}{[A][L]} = \frac{\text{on-rate}}{\text{off-rate}} \end{cases}$$

where $$A + L \underset{K_{off}}{\overset{K_{on}}{\rightleftharpoons}} AL$$

Even when binding affinity is not detectably or significantly altered, however, the change in residence time, i.e. an increased residence time via increased on-rate or decreased off-rate, or a decreased residence time via a decreased on-rate or increased off-rate, may still result in differential activation of signaling pathways. For example, in some instances where a receptor may activate two different pathways, the pathways differ in the degree of receptor activation required for a full effect. One signaling pathway can be fully activated at low levels of receptor activation or residence time, while full activation of the second pathway requires higher levels of receptor activation or residence time.

In another aspect, the methods of identifying a candidate kinetic modulating drug include (a) (i) measuring a binding affinity or binding rate parameter of a test polypeptide binding agent, e.g. antibody, for said first component in the presence of said second component, or (ii) measuring a binding affinity or binding rate parameter of a test polypeptide binding agent for said second component in the presence of said first component; and (b) (i) measuring a binding affinity or binding rate parameter of said test polypeptide binding agent for said first component in the absence of said second component, or (ii) measuring a binding affinity or binding rate parameter of said test polypeptide binding agent for said second component in the absence of said first component; and (c) identifying said test polypeptide binding agent as a candidate kinetic modulating drug when said test polypeptide binding agent exhibits at least a 1.5-fold (i.e., 50%) difference in the binding affinity or binding rate parameters measured in steps (a) and (b).

In some embodiments, the test polypeptide binding agent is identified as a candidate positive modulator if the binding affinity or binding rate parameter measured in step (a) is at least 1.5-fold (i.e., 50%) stronger than the binding affinity or binding rate parameter measured in step (b). In specific embodiments, the binding affinity or binding rate parameter measured in step (a) compared to that measured in step (b) is about 1.5-fold (i.e., 50%) to, optionally, about 1000-fold stronger for step (a) vs. step (b), or about 1.5-fold to about 100-fold, or about 2-fold to 25-fold, or about 2-fold to about 50-fold, or about 1.5-fold to about 25-fold, or about 1.5-fold to about 50-fold, e.g. at least 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 500-fold, or up to 200-fold, or up to 150-fold, or up to 100-fold, or up to 90-fold, or up to 80-fold, or up to 70-fold, or up to 60-fold, or up to 50-fold, or up to 40-fold, or up to 30-fold.

In other embodiments, the test polypeptide binding agent is identified as a candidate negative modulator if the binding affinity or binding rate parameter measured in step (b) is at least 1.5-fold (i.e., 50%) stronger than the binding affinity or binding rate parameter measured in step (a). In specific embodiments, the binding affinity or binding rate parameter measured in step (b) compared to that measured in step (a) is about 1.5-fold (i.e., 50%) to, optionally, about 1000-fold stronger for step (b) vs. step (a), or about 1.5-fold to about 100-fold, or about 2-fold to 25-fold, or about 2-fold to about 50-fold, or about 1.5-fold to about 25-fold, or about 1.5-fold to about 50-fold, e.g. at least 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 500-fold, or up to 200-fold, or up to 150-fold, or up to 100-fold, or up to 90-fold, or up to 80-fold, or up to 70-fold, or up to 60-fold, or up to 50-fold, or up to 40-fold, or up to 30-fold.

In some embodiments, the binding affinity or binding rate parameter of the test polypeptide binding agent for the first component alone is measured. In some embodiments, the binding affinity or binding rate parameter of the test polypeptide binding agent for the second component alone is measured.

In some embodiments, the test polypeptide binding agent is identified as a candidate positive modulator if one or more binding affinity or binding rate parameters selected from the group consisting of (A) the binding affinity or binding rate parameter of the test polypeptide binding agent for a complex comprising the first and second components, optionally $K_{[C1C2]M}$, (B) the binding affinity or binding rate parameter of the first component for a complex comprising the polypeptide binding agent and the second component, optionally $K_{[MC2]C1}$, or (C) the binding affinity or binding rate parameter of the second component for a complex comprising the polypeptide binding agent and the first component, optionally $K_{[MC1]C2}$, is at least about 1.5-fold stronger than one or more binding affinity or binding rate parameter selected from the group consisting of (1) the binding affinity or binding rate parameter of the test polypeptide binding agent for the second component alone, optionally $K_{MC2}$ or (2) the binding affinity or binding rate parameter of the test polypeptide binding agent for the first component alone, optionally $K_{MC1}$. In some embodiments, the specific binding affinity or binding rate parameter of any one or more of (A), (B) or (C) is about 1.5-fold (i.e., 50%) to, optionally, about 1000-fold stronger than the binding affinity or binding rate parameter of any one or more of (1) or (2); or alternatively, about 1.5-fold to about 100-fold stronger, or about 2-fold to 25-fold, or about 2-fold to about 50-fold, or about 1.5-fold to about 25-fold, or about 1.5-fold to about 50-fold, e.g. at least 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 500-fold, or up to 200-fold, or up to 150-fold, or up to 100-fold, or up to 90-fold, or up to 80-fold, or up to 70-fold, or up to 60-fold, or up to 50-fold, or up to 40-fold, or up to 30-fold. For example, in some embodiments, the binding affinity or binding rate parameter of any one or more of (A), (B) or (C) is stronger than the binding affinity or binding rate parameter of both (1) and (2). In some embodiments, the binding affinity or binding rate parameter of (1) is stronger than the binding affinity or binding rate parameter of (2). In other embodiments, the binding affinity or binding rate parameter of (2) is stronger than the binding affinity or binding rate parameter of (1). In some embodiments, two or more binding affinity or binding rate parameters are measured and compared, e.g. off-rate and on-rate, or $K_A$ and $K_D$, or any combination thereof.

In specific embodiments, wherein the binding affinity measured is the equilibrium dissociation constant $K_D$, any of $K_{[C1C2]M}$, $K_{[MC2]C1}$, or $K_{[MC1]C2}$ is lower, e.g., about 1.5-fold to, optionally, 1000-fold lower, than any of $K_{MC2}$ or $K_{MC1}$. Similarly, wherein the binding affinity measured is the off-rate, any of the off-rates between (A) [C1C2] and M, or (B) [MC2] and C1, or (C) [MC1] and C2 are lower, e.g. about 1.5-fold to, optionally, 1000-fold lower, than any of the off-rates between (1) M and C2 or (2) M and C1. In one exemplary embodiment, $K_{[C1C2]M}$ is about 1.5-fold to, optionally, 1000-fold lower than $K_{MC2}$. In another exemplary embodiment, $K_{[MC2]C1}$ is about 1.5-fold to, optionally, 1000-fold lower than $K_{MC2}$. In another exemplary embodiment, $K_{[MC1]C2}$ is about 1.5-fold to, optionally, 1000-fold lower than $K_{MC2}$. In another exemplary embodiment, $K_{[C1C2]M}$ is about 1.5-fold to, optionally, 1000-fold lower than $K_{MC1}$. In another exemplary embodiment, $K_{[MC2]C1}$ is about 1.5-fold to, optionally, 1000-fold lower than $K_{MC1}$. In yet another exemplary embodiment, $K_{[MC1]C2}$ is about 1.5-fold to, optionally, 1000-fold lower than $K_{MC1}$. Similar examples can be envisioned for each of the off-rates between (A) [C1C2] and M, or (B) [MC2] and C1, or (C) [MC1] and C2, compared to each of the off-rates between (1) M and C2 or (2) M and C1.

Conversely, where the binding affinity measured is the equilibrium association constant $K_A$, any of $K_{[C1C2]M}$, $K_{[MC2]C1}$, or $K_{[MC1]C2}$ is higher, e.g., about 1.5-fold to, optionally, 1000-fold higher, than any of $K_{MC2}$ or $K_{MC1}$. Similarly, wherein the binding affinity measured is the on-rate, any of the on-rates between (A) [C1C2] and M, or (B) [MC2] and C1, or (C) [MC1] and C2 are higher, e.g. about 1.5-fold to, optionally, 1000-fold higher, than any of the on-rates between (1) M and C2 or (2) M and C1. In one exemplary embodiment, $K_{[C1C2]M}$ is about 1.5-fold to, optionally, 1000-fold higher than $K_{MC2}$. In another exemplary embodiment, $K_{[MC2]C1}$ is about 1.5-fold to, optionally, 1000-fold higher than $K_{MC2}$. In another exemplary embodiment, $K_{[MC1]C2}$ is about 1.5-fold to, optionally, 1000-fold higher than $K_{MC2}$. In another exemplary embodiment, $K_{[C1C2]M}$ is about 1.5-fold to, optionally, 1000-fold higher than $K_{MC1}$. In another exemplary embodiment, $K_{[MC2]C1}$ is about 1.5-fold to, optionally, 1000-fold higher than $K_{MC1}$. In yet another exemplary embodiment, $K_{[MC1]C2}$ is about 1.5-fold to, optionally, 1000-fold higher than $K_{MC1}$. Similar examples can be envisioned for each of the on-rates between (A) [C1C2] and M, or (B) [MC2] and C1, or (C) [MC1] and C2, compared to each of the on-rates between (1) M and C2 or (2) M and C1.

In some embodiments, the test polypeptide binding agent is identified as a candidate negative modulator if one or more binding affinity or binding rate parameters selected from the group consisting of (1) the binding affinity or binding rate parameter of the test polypeptide binding agent for the second component alone, optionally $K_{MC2}$, or (2) the binding affinity or binding rate parameter of the test polypeptide binding agent for the first component alone, optionally $K_{MC1}$, is at least about 1.5-fold stronger than one or more binding affinity or binding rate parameter selected from the group consisting of (A) the binding affinity or binding rate parameter of the test polypeptide binding agent for a complex comprising the first and second components, optionally $K_{[C1C2]M}$, (B) the binding affinity or binding rate parameter of the first component for a complex comprising the polypeptide binding agent and the second component, optionally $K_{[MC2]C1}$, or (C) the binding affinity or binding rate parameter of the second component for a complex comprising the polypeptide binding agent and the first component, optionally $K_{[MC1]C2}$. In some embodiments, the specific binding affinity or binding rate parameter of any one or more of (1) or (2) is about 1.5-fold (i.e., 50%) to, optionally, about 1000-fold stronger than the binding affinity or binding rate parameter of any one or more of (A), (B) or (C); or alternatively, about 1.5-fold to about 100-fold stronger, or about 2-fold to 25-fold, or about 2-fold to about 50-fold, or about 1.5-fold to about 25-fold, or about 1.5-fold to about 50-fold, e.g. at least 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to 500-fold, or up to 200-fold, or up to 150-fold, or up to 100-fold, or up to 90-fold, or up to 80-fold, or up to 70-fold, or up to 60-fold, or up to 50-fold, or up to 40-fold, or up to 30-fold. In some embodiments, the binding affinity or binding rate parameter of any of (1) or (2) is stronger than the binding affinity or binding rate parameter of all of (A), (B) and (C). In some embodiments, the binding affinity or binding rate parameter of (1) is stronger than the binding affinity or binding rate parameter of (2). In other embodiments, the binding affinity or binding rate parameter of (2) is stronger than the binding affinity or binding rate parameter of (1). In some embodiments, two or more binding affinity or binding rate parameters are measured and compared, e.g. off-rate and on-rate, or $K_A$ and $K_D$, or any combination thereof.

In specific embodiments, where the binding affinity measured is the equilibrium dissociation constant $K_D$, any of $K_{MC2}$ or $K_{MC1}$ is lower, e.g., about 1.5-fold to, optionally, 1000-fold lower, than any of $K_{[C1C2]M}$, $K_{[MC2]C1}$, or $K_{[MC1]C2}$. Similarly, wherein the binding affinity measured is the off-rate, any of the off-rates between (1) M and C2 or (2) M and C1 are lower, e.g. about 1.5-fold to, optionally, 1000-fold lower, than any of the off-rates between (A) [C1C2] and M, or (B) [MC2] and C1, or (C) [MC1] and C2. In one exemplary embodiment $K_{MC2}$ is about 1.5-fold to, optionally, 1000-fold lower than $K_{[C1C2]M}$. In another exemplary embodiment, $K_{MC2}$ is about 1.5-fold to, optionally, 1000-fold lower than $K_{[MC2]C1}$. In another exemplary embodiment, $K_{MC2}$ is about 1.5-fold to, optionally, 1000-fold lower than $K_{[MC1]C2}$. In another exemplary embodiment, $K_{MC1}$ is about 1.5-fold to, optionally, 1000-fold lower than $K_{[C1C2]M}$. In another exemplary embodiment, $K_{MC1}$ is about 1.5-fold to, optionally, 1000-fold lower than $K_{[MC2]C1}$. In yet another exemplary embodiment, $K_{MC1}$ is about 1.5-fold to, optionally, 1000-fold lower than $K_{[MC1]C2}$. Similar examples can be envisioned for each of the off-rates between (1) M and C2 or (2) M and C1, compared to each of the off-rates between (A) [C1C2] and M, or (B) [MC2] and C1, or (C) [MC1] and C2.

Conversely, wherein the binding affinity is the equilibrium association constant $K_A$, any of $K_{MC2}$ or $K_{MC1}$ is higher, e.g., about 1.5-fold to, optionally, 1000-fold higher, than any of $K_{[C1C2]M}$, $K_{[MC2]C1}$, or $K_{[MC1]C2}$. Similarly, wherein the binding affinity measured is the on-rate, any of the on-rates between (1) M and C2 or (2) M and C1 are higher, e.g. about 1.5-fold to, optionally, 1000-fold higher, than any of the on-rates between (A) [C1C2] and M, or (B) [MC2] and C1, or (C) [MC1] and C2. In one exemplary embodiment $K_{MC2}$ is about 1.5-fold to, optionally, 1000-fold higher than $K_{[C1C2]M}$. In another exemplary embodiment, $K_{MC2}$ is about 1.5-fold to, optionally, 1000-fold higher than $K_{[MC2]C1}$. In another exemplary embodiment, $K_{MC2}$ is about 1.5-fold to, optionally, 1000-fold higher than $K_{[MC1]C2}$. In another exemplary embodiment, $K_{MC1}$ is about 1.5-fold to, optionally, 1000-fold higher than $K_{[C1C2]M}$. In another exemplary embodiment, $K_{MC1}$ is about 1.5-fold to, optionally, 1000-fold higher than $K_{[MC2]C1}$. In yet another exemplary embodiment, $K_{MC1}$ is about 1.5-fold to, optionally, 1000-fold higher than $K_{[MC1]C2}$. Similar examples can be envisioned for each of the on-rates between (1) M and C2 or (2) M and C1, compared to each of the on-rates between (A) [C1C2] and M, or (B) [MC2] and C1, or (C) [MC1] and C2.

In any of these embodiments, the test polypeptide binding agent and second component can be contacted with multiple different concentrations of said first component. In any of these embodiments, the test polypeptide binding agent and first component can be contacted with multiple different concentrations of said second component. In any of these embodiments, multiple different concentrations of the test polypeptide binding agent can be contacted with said first component and said second component.

When the effect of test polypeptide binding agent on the binding interaction between the first component and second component is determined, in some specific embodiments, when the antigen for the test polypeptide binding agent is the first component, e.g., ligand, the test polypeptide binding agent is at a saturating concentration compared to the concentration of the first component. Alternatively, when the antigen for the test polypeptide binding agent is the second component, e.g., receptor, the test polypeptide binding agent is at a saturating concentration compared to the concentration of the second component. In some embodiments, the concentration of the test polypeptide binding agent is greater than or equal to the $K_D$ of the test polypeptide binding agent for a complex comprising the first component and the second component. In further embodiments, the concentration of the second component is less than the $K_D$ of the test polypeptide binding agent for the first component, e.g., ligand. In yet further embodiments, the concentration of the first component, e.g., ligand, is at a subsaturating concentration for the binding of first component to second component, e.g., receptor. In some embodiments, the concentration of the first component, e.g., ligand is within the range of about $EC_{20}$ to $EC_{80}$ for the interaction of the first component with the second component. In some embodiments, one or more concentrations of the test polypeptide binding agent is contacted with multiple different concentrations of the first component, e.g., ligand, in the presence of one or more concentrations of the second component, e.g., receptor. In some embodiments, one or more concentrations of the test polypeptide binding agent is contacted with multiple different concentrations of the second component, e.g., receptor, in the presence of one or more concentrations of the first component, e.g., ligand.

When differential binding of test polypeptide binding agent to complexed vs uncomplexed target and/or signaling partner is determined in order to identify a positive modulator, in some embodiments, the test polypeptide binding agent is at a saturating concentration for a complex comprising the first component and the second component. In some embodiments, the concentration of test polypeptide binding agent is greater than or equal to the $K_D$ of the test polypeptide binding agent for a complex comprising the first component, e.g., ligand, and the second component, e.g., receptor. In further embodiments, the concentration of the second component, e.g., receptor is greater than the $K_D$ of the second component, e.g., receptor, for the first component, e.g., ligand. In further embodiments, the concentration of the first component, e.g., ligand, is a saturating concentration for the second component, e.g., receptor. In yet further embodiments, the test polypeptide binding agent is at a subsaturating concentration for a complex comprising the first component and the second component. In some embodiments, the concentration of the polypeptide binding agent is within the range of about $EC_{20}$ to $EC_{80}$ for the interaction of the first component with the second component. In some embodiments, the concentration of the second component, e.g., receptor, is greater than the $K_D$ of the second component, e.g., receptor, for the first component, e.g., ligand. In some embodiments, the concentration of the first component, e.g., ligand, is a saturating concentration for the second component, e.g., receptor.

When differential binding of test polypeptide binding agent to complexed vs uncomplexed target and/or signaling partner is determined in order to identify a negative modulator, in some embodiments, when the antigen to which the test polypeptide binding agent binds is the first component, e.g., ligand, the test polypeptide binding agent is at a subsaturating concentration for the first component. When the antigen to which the test polypeptide binding agent binds is the second component, e.g., receptor, the test polypeptide binding agent is at a subsaturating concentration for the second component. In further embodiments, the concentration of the polypeptide binding agent is within the range of about $EC_{20}$ to $EC_{80}$ for the interaction of the first component with the second component. In further embodiments, the concentration of the second component, e.g., receptor, is greater than the $K_D$ of the second component, e.g., receptor, for the first component, e.g., ligand. In further embodiments, the concentration of the first component, e.g., ligand, is a saturating concentration for the second component, e.g., receptor.

In some embodiments, the methods further involve assaying a plurality of test polypeptide binding agents, e.g. antibodies, for binding affinity to any one of (a) the first component, (b) the second component, or (c) a complex comprising the first component and second component. In some specific embodiments, the polypeptide binding agents have a binding affinity characterized, e.g., by an equilibrium dissociation constant $K_D$ of about $10^{-5}$M or less, or about $10^{-6}$M or less, or about $10^{-7}$M or less, or about $10^{-8}$M or less, where a lower $K_D$ means stronger binding affinity. In some embodiments, the plurality of test polypeptide binding agents screened are variants of a parent polypeptide binding agent made by introducing one or more different mutations into a parent polypeptide binding agent.

In further embodiments, the polypeptide binding agents may be screened for selectivity of effect for the first or second component, compared to a different binding partner such as a decoy receptor, clearance receptor, or alternate signal pathway component. Such methods may involve identifying a polypeptide binding agent that does not significantly change the binding affinity or binding rate parameter of the first or second component for a different binding partner, such binding partner being neither the first nor second component. In some embodiments, the presence of the polypeptide binding agent changes the binding affinity or binding rate parameter of the first or second component for a different binding partner no more than 5-fold, or no more than 10-fold, or no more than 20-fold, or no more than 30-fold, or no more than 40-fold, or no more than 50-fold.

Any of the preceding methods may further include measuring the level of signaling mediated by the signaling complex in the presence and absence of the test polypeptide binding agent, and determining whether the test polypeptide binding agent is additionally an agonist, partial agonist, antagonist or partial antagonist. Antagonism or agonism can be measured in any in vitro or in vivo assay known in the art, including but not limited to signaling in a phosphorylation assay, ion flux assay, molecular transport assay, or gene expression assay.

In some embodiments, the test polypeptide binding agent shifts (positively or negatively) the dose-response curve of the interaction of the first component, e.g. ligand, with the second component, e.g. receptor. The shift may manifest as an increased or decreased $EC_{50}$ by at least about 1.5-fold, e.g. about 1.5-fold to about 1000-fold. In some embodiments, the test polypeptide binding agent does not significantly change the maximal agonist response of the signal produced by interaction of the first and second components of the signaling complex. In other embodiments, the test polypeptide binding agent itself acts as an antagonist (e.g., reduces the maximal agonist response of the signaling produced by said signaling complex) or agonist (e.g. increases the maximal agonist response of the signaling produced by said signaling complex).

Where the test polypeptide binding agent acts as an antagonist or partial antagonist, the maximal agonist response may be decreased, e.g., by about 1.5-fold to about 100-fold, or about 2-fold to about 25-fold, or about 1.5-fold to about 50-fold; or, decreased by about 10%, 25%, 50% (1.5-fold), 75%, 2-fold, 3-fold, or 4-, 5-, 6-, 7-, 8-, 9- or 10-fold. Alternatively, where the test polypeptide binding agent acts as an agonist or partial agonist, the maximal agonist response may be increased, e.g. by at least about 10%, 25%, 50% (1.5-fold), 75%, 2-fold, 3-fold, or 4-, 5-, 6-, 7-, 8-, 9- or 10-fold. Moreover, when the test polypeptide binding agent acts as an antagonist or partial antagonist, the IC50 may be $1\times10^{-5}$ or less. The test polypeptide binding agent may exhibit further desirable characteristics, e.g. the test polypeptide binding agent does not significantly decrease clearance of said first component, or said second component, or said signaling complex comprising said first and second components.

In a related aspect, the invention provides an antibody identified by any of the methods described above or anywhere in the present application.

Polypeptide Binding Agents with Desired Characteristics

The invention also provides polypeptide binding agents, e.g., antibodies, that possess certain desirable characteristics. In some embodiments, the invention provides a positive modulator that (a) binds to the target, e.g., the secreted protein of any of Appendix A (or SEQ ID NOS: 1-88) or any of the ligands, receptors or components described herein, with an equilibrium dissociation constant $K_D$ of about $10^{-5}$M or less, e.g., $10^{-6}$M or less, or $10^{-7}$M or less, or $10^{-8}$M or less, and (b) is capable of improving the binding affinity $K_D$ between said target and its signaling partner by at least about 1.5-fold (i.e., 50%); or by about 1.5-fold to, optionally, about 1000-fold, or 1.5-fold to about 100-fold, or about 2-fold to 25-fold, or about 2-fold to about 50-fold, or about 1.5-fold to about 25-fold, or about 1.5-fold to about 50-fold, e.g. at least about 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to about 500-fold, or up to about 200-fold, or up to about 150-fold, or up to about 100-fold, or up to about 90-fold, or up to about 80-fold, or up to about 70-fold, or up to about 60-fold, or up to about 50-fold, or up to about 40-fold, or up to about 30-fold.

In other embodiments, the invention provides a negative modulator that (a) binds to the target, e.g. the secreted protein of any of Appendix A (or SEQ ID NOS: 1-88) or any of the ligands, receptors or components described herein, with an equilibrium dissociation constant $K_D$ of about $10^{-5}$M or less, e.g., $10^{-6}$M or less, or $10^{-7}$M or less, or $10^{-8}$M or less, and (b) is capable of reducing the binding affinity $K_D$ between said secreted protein and its signaling partner by at least about 1.5-fold (i.e., 50%); or by about 1.5-fold to, optionally, about 1000-fold, or 1.5-fold to about 100-fold, or about 2-fold to 25-fold, or about 2-fold to about 50-fold, or about 1.5-fold to about 25-fold, or about 1.5-fold to about 50-fold, e.g. at least about 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to about 500-fold, or up to about 200-fold, or up to about 150-fold, or up to about 100-fold, or up to about 90-fold, or up to about 80-fold, or up to about 70-fold, or up to about 60-fold, or up to about 50-fold, or up to about 40-fold, or up to about 30-fold.

In some embodiments, the invention provides a positive modulating antibody that strengthens the binding of a first component (C1) to a second component (C2) of a signaling complex, said antibody characterized by the following equilibrium dissociation constant $K_D$ binding properties: (i) said antibody binds with an equilibrium dissociation constant $K_D$ of about $10^{-5}$M or less, e.g., $10^{-6}$M or less, or $10^{-7}$M or less, or $10^{-8}$M or less, to any one of C1, C2, or a complex comprising C1 and C2 (C1C2); and (ii) any of $K_{[C1C2]A}$, $K_{[AC2]C1}$, or $K_{[AC1]C2}$ is at least about 50% (1.5-fold) lower than any of $K_{AC2}$ or $K_{AC1}$, wherein C1 or C2 is a target and its signaling partner, optionally the secreted protein of any of Appendix A (or SEQ ID NOS: 1-88). In some embodiments any of $K_{[C1C2]A}$, $K_{[AC2]C1}$, or $K_{[AC1]C2}$ is about 1.5-fold to, optionally, about 1000-fold lower than any of $K_{AC2}$ or $K_{AC1}$; or 1.5-fold to about 100-fold lower, or about 2-fold to 25-fold, or about 2-fold to about 50-fold, or about 1.5-fold to about 25-fold, or about 1.5-fold to about 50-fold, e.g. at least about 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to about 500-fold, or up to about 200-fold, or up to about 150-fold, or up to about 100-fold, or up to about 90-fold, or up to about 80-fold, or up to about 70-fold, or up to about 60-fold, or up to about 50-fold, or up to about 40-fold, or up to about 30-fold lower. In some embodiments, any of $K_{[C1C2]A}$, $K_{[AC2]C1}$, or $K_{[AC1]C2}$ is at least about 1.5-fold lower than both of $K_{AC2}$ or $K_{AC1}$; or 1.5-fold to, optionally, about 1000-fold lower, or 1.5-fold to about 100-fold lower, or about 2-fold to 25-fold, or about 2-fold to about 50-fold, or about 1.5-fold to about 25-fold, or about 1.5-fold to about 50-fold, e.g. at least about 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to about 500-fold, or up to about 200-fold, or up to about 150-fold, or up to about 100-fold, or up to about 90-fold, or up to about 80-fold, or up to about 70-fold, or up to about 60-fold, or up to about 50-fold, or up to about 40-fold, or up to about 30-fold lower.

In some embodiments, the invention provides a negative modulating antibody that weakens the binding of a first component (C1) to a second component (C2) of a signaling complex, said antibody characterized by the following equilibrium dissociation constant $K_D$ binding properties: (i) said antibody binds with an equilibrium dissociation constant $K_D$ of about $10^{-5}$M or less, e.g., $10^{-6}$M or less, or $10^{-7}$M or less, or $10^{-8}$M or less, to any one of C1, C2, or a complex comprising C1 and C2 (C1C2), and (ii) any of $K_{AC2}$ or $K_{AC1}$ is at least about 50% (1.5-fold) lower than any of $K_{[C1C2]A}$, $K_{[AC2]C1}$, or $K_{[AC1]C2}$, wherein C1 or C2 is a target and its signaling partner, optionally the secreted protein of any of Appendix A (or SEQ ID NOS: 1-88). In some embodiments, any of $K_{AC2}$ or $K_{AC1}$ is at least about 1.5-fold to, optionally, 1000-fold lower than any of $K_{[C1C2]A}$, $K_{[AC2]C1}$, or $K_{[AC1]C2}$, or 1.5-fold to about 100-fold lower, or about 2-fold to 25-fold, or about 2-fold to about 50-fold, or about 1.5-fold to about 25-fold, or about 1.5-fold to about 50-fold, e.g. at least about 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to about 500-fold, or up to about 200-fold, or up to about 150-fold, or up to about 100-fold, or up to about 90-fold, or up to about 80-fold, or up to about 70-fold, or up to about 60-fold, or up to about 50-fold, or up to about 40-fold, or up to about 30-fold lower. In some embodiments, any of $K_{AC2}$ or $K_{AC1}$ is at least about 1.5-fold lower than all of $K_{[C1C2]A}$, $K_{[AC2]C1}$, or $K_{[AC1]C2}$; or 1.5-fold to, optionally, about 1000-fold lower, or 1.5-fold to about 100-fold lower, or about 2-fold to 25-fold, or about 2-fold to about 50-fold, or about 1.5-fold to about 25-fold, or about 1.5-fold to about 50-fold, e.g. at least about 1.5-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold, or up to about 500-fold, or up to about 200-fold, or up to about 150-fold, or up to about 100-fold, or up to about 90-fold, or up to about 80-fold, or up to about 70-fold, or up to about 60-fold, or up to about 50-fold, or up to about 40-fold, or up to about 30-fold lower.

Any of such polypeptide binding agents are preferably purified and substantially homogeneous, e.g. at least about 90%, 95%, 97%, 98%, 99% or 99.5% pure. In some examples, the polypeptide binding agents are monoclonal antibodies.

The invention further provides methods of preparing a sterile pharmaceutical composition comprising adding a sterile pharmaceutically acceptable diluent to such polypeptide binding agents, sterile compositions of such polypeptide binding agents, e.g., in a therapeutically effective amount, and methods of administering such sterile compositions, e.g. to modulate (increase or decrease) signaling of a complex comprising the secreted protein.

Signaling Complexes

Activation of genes, alterations in metabolism, the continued proliferation and death of the cell, and the stimulation or suppression of locomotion, are some of the cellular responses to extracellular stimulation that may be mediated by signaling complexes. Gene activation leads to further cellular effects, since the protein products of many of the responding genes include enzymes and transcription factors themselves. Transcription factors produced as a result of a signal transduction cascade can, in turn, activate yet more genes. Therefore an initial stimulus can trigger the expression of an entire cohort of genes, and this, in turn, can lead to the activation of any number of complex physiological events. These events include the increased uptake of glucose from the blood stream stimulated by insulin and the migration of neutrophils to sites of infection stimulated by bacterial products.

Neurotransmitters are ligands that are capable of binding to ion channel proteins to form a complex, resulting in their opening to allow the rapid flow of a particular ion across the plasma membrane. This results in an altering of the cell's membrane potential and is important for processes such as the neural conduction of electrochemical impulses. For example, binding of the neurotransmitter acetylcholine at certain synapses opens channels that admit Na+ and initiate a nerve impulse or muscle contraction. Ligands can be freely soluble, or can be found on the surface of other cells or within the extracellular matrix. Such cell surface or extracellular matrix ligands signal between cells when they come in contact with each other, such as when a phagocytic cell presents antigens to lymphocytes, or upon adhesion to the extracellular matrix, as when integrins at the cell surface of fibroblasts engage fibronectin.

Most mammalian cells require stimulation to control not only cell division but also survival. In the absence of growth factor stimulation, programmed cell death ensues in most cells. Such requirements for extra-cellular stimulation are necessary for controlling cell behavior in the context of both unicellular and multicellular organisms. Signal transduction pathways are perceived to be central to biological processes and a large number of diseases have been attributed to their dysregulation.

Signal transduction may be mediated via receptors, which may be located intracellularly e.g. those for steroid hormones, thyroid hormone, retinoic acid, and derivatives of vitamin D3, or on the cell-surface, or may occur both at the cell-surface or intracellularly e.g. ligand-gated ion channel receptors. Signal transduction may also be mediated by transmembrane transporters that transport small molecules, e.g. glucose transporters, or ion channels such as sodium channels, potassium channels, calcium channels, or other positive ion channels, or chloride channels or bicarbonate channels or other anion channels. Many ion channels open or close in response to binding a small signaling molecule or ligand. Some ion channels are gated by extracellular ligands; some by intracellular ligands. Generally, the ligand is not the substance that is transported when the channel opens. ABC ("ATP-Binding Cassette") transporters are transmembrane proteins that expose a ligand-binding domain at one surface and a ATP-binding domain at the other surface. Some examples of these ABC transporters include cystic fibrosis transmembrane conductance regulator (CFTR); sulfonylurea receptor (SUR) TAP, the transporter associated with antigen processing; SPGP, the transporter that liver cells use to pump the salts of bile acids out into the bile; and the multidrug resistance (MDR) transporter that pumps chemotherapeutic drugs out of cancer cells thus reducing their effectiveness. Mutations of genes in this family have been linked to various diseases including: ALD gene-adrenoleukodystrophy, SUR gene-diabetes, CFTR gene-cystic fibrosis, MDR gene-multidrug resistance in cancer. A list of ABC transporters, their aliases (if any), chromosomal location, and putative function appears below (see Luckie et al., Current Genomics, 2003, 4, 109-121):

ABCA1 ABC1 9q31.1 Ubiquitous Cholesterol efflux onto HDL
ABCA2 ABC2 9q34 2 Brain Drug resistance
ABCA3 ABC3, ABCC 16p13.3 Lung
ABCA4 ABCR 1p22.1-p21 Rod photoreceptors N-retinylidiene-PE efflux
ABCA5 17q24 Muscle, heart, testes
ABCA6 17q24 Liver
ABCA7 19p13.3 Spleen, thymus
ABCA8 17q24 Ovary
ABCA9 17q24 Heart
ABCA10 17q24 Muscle, heart
ABCA12 2q34 Stomach
ABCA13 7p11-q11 Low in all tissues
ABCB1 PGY1, MDR 7p21 Adrenal, kidney, brain Multidrug resistance
ABCB2 TAP1 6p21 A11 cells Peptide transport
ABCB3 TAP2 6p21 A11 cells Peptide transport
ABCB4 PGY3 7q21.1 Liver PC transport
ABCB5 7p14 Ubiquitous
ABCB6 MTABC3 2q36 Mitochondria Iron transport
ABCB7 ABC7 Xq12-q13 Mitochondria Fe/S cluster transport
ABCB8 MABC1 7q36 Mitochondria
ABCB9 12q24 Heart, brain
ABCB10 MTABC2 1q42 Mitochondria
ABCB11 SPGP 2q24 Liver Bile salt transport
ABCC1 MRP1 16p13.1 Lung, testes, PBMC Drug resistance
ABCC2 MRP2 10q24 Liver Organic anion efflux
ABCC3 MRP3 17q21.3 Lung, intestine, liver Drug resistance
ABCC4 MRP4 13q32 Prostate Nucleoside transport
ABCC5 MRP5 3q27 Ubiquitous Nucleoside transport
ABCC6 MRP6 16p13.1 Kidney, liver
CFTR ABCC7 7q31.2 Exocrine tissues Chloride ion channel
ABCC8 SUR1 11p15.1 Pancreas Sulfonylurea receptor
ABCC9 SUR2 12p12.1 Heart, muscle
ABCC10 MRP7 6p21 Low in all tissues
ABCC11 16q11-q12 Low in all tissues
ABCC12 16q11-q12 Low in all tissues
ABCD1 ALD Xq28 Peroxisomes VLCFA transport regulation
4 Current Genomics, 2003, Vol. 4, No. 3 Luckie et al.
(Table 1) contd . . . .
Symb Alias Location Expression Function
ABCD2 ALDL1, ALDR 12q11-q12 Peroxisomes
ABCD3 PXMP1, PMP70 1p22 p21 Peroxisomes
ABCD4 PMP69, P70R 14q24.3 Peroxisomes
ABCE1 OABP, RNS4I 4q31 Ovary, testes, spleen Oligoadenylate binding protein
ABCF1 ABC50 6p21.33 Ubiquitous ABCF2 7q36 Ubiquitous
ABCF3 3q25 Ubiquitous
ABCG1 ABC8, White 21q22.3 Ubiquitous Cholesterol transport
ABCG2 ABCP, MXR, BCRP 4q22 Placenta, intestine Toxin efflux, drug resistance
ABCG4 White2 11q23 5 59 Liver
ABCG5 White3 2p21 17 Liver, intestine Sterol transport
ABCG8 2p21 17 Liver, intestine Sterol transport. Cell-surface receptors recognize the vast majority of extracellular signaling molecules. Transmembrane receptors span the plasma membrane of the cell, with one part of the receptor on the outside of the cell (the extracellular domain), and the other on the inside of the cell (the intracellular domain). Signal transduction generally occurs as a result of the binding of a ligand to its extracellular domain.

Binding of a ligand to a cell-surface receptor generally stimulates a series of events inside the cell, with different types of receptor stimulation of different intracellular responses. Receptors typically respond to only the binding of a specific ligand. Upon binding, the ligand generally initiates the transmission of a signal across the plasma membrane by inducing a change in the shape or conformation of the intracellular part of the receptor. Often, such changes in conformation either result in the activation of an enzymatic activity contained within the receptor or expose a binding site for other signaling proteins within the cell. Once these proteins bind to the receptor, they themselves may become active and propagate the signal into the cytoplasm.

In eukaryotic cells, most intracellular proteins activated by a ligand/receptor interaction generally possess an enzymatic activity. These enzymes include tyrosine kinases, heterotrimeric G proteins, small GTPases, various serine/threonine protein kinases, phosphatases, lipid kinases, and hydrolases. Some receptor-stimulated enzymes create specific second messengers including cyclic nucleotides, such as cyclic AMP (cAMP) and cyclic GMP (cGMP), phosphatidylinositol derivatives, such as phosphatidylinositol-triphosphate (PIP3), diacylglycerol (DAG) and inositol-triphosphate (IP3). Other activated proteins interact with adapter proteins. Adapter proteins facilitate interactions between other signaling proteins, and coordinate the formation of further signaling complexes necessary to produce an appropriate cellular response to a particular stimulus. Enzymes and adapter proteins are both responsive to various second messenger molecules.

There are many different classes of transmembrane receptor that recognize different extracellular signaling molecules. Examples include: G-protein coupled receptors, (GPCRs) e.g. adrenergic receptors, neurotransmitter receptors, olfactory receptors, opioid receptors, chemokine receptors, and rhodopsin; receptor tyrosine kinases, e.g., growth factor receptors; integrins; and toll-like receptors.

In some cases, a signaling complex component may be a member of more than one signaling complex, each comprising different complex components and performing different signaling functions (e.g. a ligand may bind more than one cognate receptor). In some cases a ligand may bind one or more decoy receptors. A decoy receptor is a receptor that binds a ligand, inhibiting it from binding to its normal receptor. For instance, the receptor VEGF-1 can prevent vascular endothelial growth factor (VEGF) from binding to the VEGFR-2. Differential modulation of the binding of a signaling complex component with one binding partner versus another should allow highly targeted regulation of biological signaling. In some instances a signaling complex component may be a mutant or variant form that is trapped in a particular conformational form, for example rendering the complex constitutively active or inactive. In some instances a receptor may be trapped in a specific conformation such as the ligand bound conformation. In some instances a signaling complex component may be a mutant or variant form, or a mimetic or analog, of a ligand.

Types and Sources of Test Polypeptide Binding Agents: Peptides and Polypeptides

Numerous libraries of natural or random peptides or polypeptides are available commercially or are readily synthesized. Alternatively, libraries of natural peptides or polypeptides in the form of bacterial, fungal, plant and animal extracts are available or readily produced. Additionally, natural or synthetically produced libraries and compounds are readily modified through conventional chemical, physical and biochemical means, and may be used to produce combinatorial libraries. Additional derivatization or modifications may be carried out, such as acylation, alkylation, esterification, amidification.

Libraries of protein scaffolds capable of specifically binding to an antigen are also available. These include: Adnectins, Affibodies, Anticalins, DARPins, engineered Kunitz-type inhibitors, tetranectins, A-domain proteins, lipocalins, repeat proteins such as ankyrin repeat proteins, immunity proteins, α2p8 peptide, insect defensin A, PDZ domains, charybdotoxins, PHD fingers, TEM-I β-lactamase, fibronectin type III domains, CTLA-4, T-cell receptors, knottins, neocarzinostatin, carbohydrate binding module 4-2, green fluorescent protein, thioredoxin (Gebauer & Skerra, Curr. Opin. Chem. Biol. 13:245-55 (2009); Gill & Damle, Curr. Opin. Biotech 17: 653-58 (2006); Hosse et al, Protein Sci. 15:14-27 (2006); Skerra, Curr. Opin. Biotech 18: 295-3-4 (2007)).

A number of different approaches for screening in combinatorial libraries are known in the art, including: biological libraries, spatially addressable parallel solid phase or solution phase libraries; synthetic library methods requiring deconvolution; the "one-bead one-compound" library method; and synthetic library methods using affinity chromatography selection.

Peptides that bind to a signaling complex or to a component thereof may be identified without undue experimentation using well known techniques. In this regard, it is noted that techniques for screening peptide libraries for peptides that are capable of specifically binding to an antigen are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Moth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

Peptides may be chemically synthesized using known peptide synthesis methodology or may be prepared and purified using recombinant technology. Peptides are usually at least about 3 amino acids in length, alternatively at least about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such peptides that are capable of binding, preferably specifically, to signaling complex or to a component thereof.

In this regard, bacteriophage (phage) display is one well known technique which allows one to screen large peptide libraries to identify member(s) of those libraries which are capable of specifically binding to an antigen. Phage display is a technique by which variant polypeptides are displayed as fusion proteins to the coat protein on the surface of bacteriophage particles (Scott, J. K. and Smith, G. P. (1990) Science 249: 386). The utility of phage display lies in the fact that large libraries of selectively randomized protein variants (or randomly cloned cDNAs) can be rapidly and efficiently sorted for those sequences that bind to an antigen with high affinity. Display of peptide (Cwirla, S. E. et al. (1990) Proc. Natl. Acad. Sci. USA, 87:6378) or protein (Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363) libraries on phage have been used for screening millions of polypeptides or peptides for ones with specific binding, properties (Smith, G. P. (1991) Current Opin. Biotechnol., 2:668).

Although most phage display methods have used filamentous phage, lambdoid phage display systems (WO 95/34683; U.S. Pat. No. 5,627,024), T4 phage display systems (Ren, Z J. et al. (1998) Gene 215:439; Zhu, Z. (1997) CAN 33:534; Jiang, J. et al. (1997) can 128:44380; Ren, Z J. et al. (1997) CAN 127:215644; Ren, Z-J. (1996) Protein Sci. 5:1833; Efimov, V. P. et al. (1995) Virus Genes 10:173) and T7 phage display systems (Smith, G. P. and Scott, J. K. (1993) Methods in Enzymology, 217, 228-257; U.S. Pat. No. 5,766, 905) are also known.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

Types and Sources of Test Polypeptide Binding Agents: Antibodies

The term "antibody" is used in the broadest sense and includes fully assembled antibodies, tetrameric antibodies, monoclonal antibodies, polyclonal antibodies, multispecific antibodies (e.g., bispecific antibodies), antibody fragments that can bind an antigen (e.g., Fab', F'(ab)2, Fv, single chain antibodies, diabodies), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as 1, 2, 3, 4, 5 or all 6 CDR sequences, as long as the antibody retains the desired biological activity.

In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa (κ) and lambda (λ) light chains. Heavy chains are classified as mu (μ), delta (Δ), gamma (γ), alpha (α), and epsilon (ε), and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Chothia et al., *J. Mol. Biol.* 196:901-917, 1987).

Immunoglobulin variable domains exhibit the same general structure of relatively conserved framework regions (FR) joined by three hypervariable regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk, (*J. Mol. Biol.* 196:901-917, 1987); Chothia et al., (*Nature* 342:878-883, 1989).

The hypervariable region of an antibody refers to the CDR amino acid residues of an antibody which are responsible for antigen-binding. The hypervariable region comprises amino acid residues from a CDR (residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5$^{th}$ Ed. Public Health Service, National Institutes of Health, Bethesda, Md. (1991)) and/or those residues from a hypervariable loop (residues 26-32 (L1), 50-52 (L2) and 91-96 (L3) in the light chain variable domain and 26-32 (H1), 53-55 (H2) and 96-101 (H3) in the heavy chain variable domain as described by Chothia et al., *J. Mol. Biol.* 196: 901-917 (1987).

Framework or FR residues are those variable domain residues other than the hypervariable region residues.

"Heavy chain variable region" as used herein refers to the region of the antibody molecule comprising at least one complementarity determining region (CDR) of said antibody heavy chain variable domain. The heavy chain variable region may contain one, two, or three CDRs of said antibody heavy chain.

"Light chain variable region" as used herein refers to the region of an antibody molecule, comprising at least one complementarity determining region (CDR) of said antibody light chain variable domain. The light chain variable region may contain one, two, or three CDRs of said antibody light chain, which may be either a kappa or lambda light chain depending on the antibody.

Depending on the amino acid sequence of the constant domain of their heavy chains, immunoglobulins can be assigned to different classes, IgA, IgD, IgE, IgG and IgM, which may be further divided into subclasses or isotypes, e.g. IgG1, IgG2, IgG3, IgG4, IgA1 and IgA2. The subunit structures and three-dimensional configurations of different classes of immunoglobulins are well known. Different isotypes have different effector functions; for example, IgG1 and IgG3 isotypes have ADCC activity. An antibody of the invention, if it comprises a constant domain, may be of any of these subclasses or isotypes, or a variant or consensus sequence thereof, or a hybrid of different isotypes (e.g., IgG1/IgG2 hybrid).

In exemplary embodiments, an antibody of the invention can comprise a human kappa (κ) or a human lambda (λ) light chain or an amino acid sequence derived therefrom, or a hybrid thereof, optionally together with a human heavy chain or a sequence derived therefrom, or both heavy and light chains together in a single chain, dimeric, tetrameric (e.g., two heavy chains and two light chains) or other form.

Monoclonal antibody refers to an antibody obtained from a population of substantially homogeneous antibodies. Monoclonal antibodies are, generally highly specific, and may be directed against a single antigenic site, in contrast to conventional (polyclonal) antibody preparations that typically include different antibodies directed against different determinants (epitopes). In addition to their specificity, monoclonal antibodies are advantageous in that they are synthesized by the homogeneous culture, uncontaminated by other immunoglobulins with different specificities and characteristics.

Monoclonal antibodies to be used in accordance with the present invention may be made by the hybridoma method first described by Kohler et al., (Nature, 256:495-7, 1975), or may be made by recombinant DNA methods (see, e.g., U.S. Pat. No. 4,816,567). The monoclonal antibodies may also be isolated from phage antibody libraries using the techniques described in, for example, Clackson et al., (Nature 352:624-628, 1991) and Marks et al., (J. Mol. Biol. 222:581-597, 1991).

In the hybridoma method, a mouse or other appropriate host animal, such as a hamster or macaque monkey, is immunized to elicit lymphocytes that produce or are capable of producing antibodies that will specifically bind to the protein used for immunization (Harlow & Lane; Antibodies: A Laboratory Manual, Cold Spring Harbor Laboratory Press: Cold Spring Harbor, N.Y. (1988).

Recombinant Production of Antibodies

The present invention also encompasses nucleic acid molecules encoding antibodies of the invention. In some embodiments, different nucleic acid molecules encode a heavy chain variable region and a light chain variable region of an antigen-specific antibody. In other embodiments, the same nucleic acid molecule encodes a heavy chain and a light chain variable regions of an antigen-specific antibody.

DNA encoding a monoclonal antibody of the invention may be isolated and sequenced from a hybridoma cell secreting the antibody using conventional procedures (e.g., by using oligonucleotide probes that are capable of binding specifically to genes encoding the heavy and light chains of the monoclonal antibodies). Sequence determination will generally require isolation of at least a portion of the gene or cDNA of interest. Usually this requires cloning the DNA or, preferably, mRNA (i.e., cDNA) encoding the monoclonal antibodies. Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. Nucleotide probe reactions and other nucleotide hybridization reactions are carried out at conditions enabling the identification of polynucleotides which hybridize to each other under specified conditions.

One exemplary set of conditions is as follows: stringent hybridization at 42° C. in 50% formamide, 5×SSC, 20 mM Na.PO4, pH 6.8; and washing in 1×SSC at 55° C. for 30 minutes. Formula for calculating equivalent hybridization conditions and/or selecting other conditions to achieve a desired level of stringency are well known. It is understood in the art that conditions of equivalent stringency can be achieved through variation of temperature and buffer, or salt concentration as described Ausubel, et al. (Eds.), Protocols in Molecular Biology, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51

In one embodiment, the polymerase chain reaction (PCR) is used to amplify cDNAs (or portions of full-length cDNAs) encoding an immunoglobulin gene segment of interest (e.g., a light chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest. As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined, is considered isolated. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

One source for RNA used for cloning and sequencing is a hybridoma produced by obtaining a B cell from the transgenic mouse and fusing the B cell to an immortal cell. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described further herein and is also well-known in the art. See e.g., Dower et al., WO 91/17271, McCafferty et al., WO 92/01047, and Caton and Koprowski, (*Proc. Natl. Acad. Sci.* USA, 87:6450-54 (1990)), each of which is incorporated herein by reference. In one embodiment, cDNA from an immunized transgenic mouse (e.g., total spleen cDNA) is isolated, the polymerase chain reaction is used to amplify a cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard phage display techniques such as panning.

The sequence of the amplified or cloned nucleic acid is then determined. Typically the sequence encoding an entire variable region of the immunoglobulin polypeptide is determined, however, it will sometimes by adequate to sequence only a portion of a variable region, for example, the CDR-encoding portion. Typically the portion sequenced will be at least 30 bases in length, more often based coding for at least about one-third or at least about one-half of the length of the variable region will be sequenced.

Sequencing can be carried out on clones isolated from a cDNA library, or, when PCR is used, after subcloning the amplified sequence or by direct PCR sequencing of the amplified segment. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be placed into expression vectors, which are then transfected into host cells such as *E. coli* cells, simian COS cells, human embryonic kidney 293 cells (e.g., 293E cells), Chinese hamster ovary (CHO) cells, or myeloma cells that do not otherwise produce immunoglobulin protein, to obtain the synthesis of monoclonal antibodies in the recombinant host cells. Recombinant production of antibodies is well known in the art.

Expression control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

In an alternative embodiment, the amino acid sequence of an immunoglobulin of interest may be determined by direct protein sequencing. Suitable encoding nucleotide sequences can be designed according to a universal codon table.

Amino acid sequence variants of the desired antibody may be prepared by introducing appropriate nucleotide changes into the encoding DNA, or by peptide synthesis. Such variants include, for example, deletions from, and/or insertions into and/or substitutions of, residues within the amino acid sequences of the antibodies. Any combination of deletion, insertion, and substitution is made to arrive at the final construct, provided that the final construct possesses the desired characteristics. The amino acid changes also may alter post-translational processes of the antibody, such as changing the number or position of glycosylation sites.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

The invention also provides isolated nucleic acid encoding antibodies of the invention, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium. Various systems and methods for antibody production are reviewed by Birch & Racher (Adv. Drug Deliv. Rev. 671-685 (2006)).

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more selective marker genes, an enhancer element, a promoter, and a transcription termination sequence.

Suitable host cells for cloning or expressing the DNA in the vectors herein are prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescens*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastors* (EP 183,070); *Candida*; *Trichoderma reesia* (EP 244,234); *Neu-* rospora crassa; Schwanniomyces such as Schwanniomyces occidentalis; and filamentous fungi such as, e.g., Neurospora, Penicillium, Tolypocladium, and Aspergillus hosts such as A. nidulans and A. niger.

Suitable host cells for the expression of glycosylated antibody are derived from multicellular organisms. Examples of invertebrate cells include plant and insect cells. Numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruitfly), and Bombyx mori have been identified. A variety of viral strains for transfection are publicly available, e.g., the L-1 variant of Autographa californica NPV and the Bm-5 strain of Bombyx mori NPV, and such viruses may be used as the virus herein according to the present invention, particularly for transfection of Spodoptera frugiperda cells.

Plant cell cultures of cotton, corn, potato, soybean, petunia, tomato, tobacco, lemna, and other plant cells can also be utilized as hosts.

Examples of useful mammalian host cell lines are Chinese hamster ovary cells, including CHOK1 cells (ATCC CCL61), DXB-11, DG-44, and Chinese hamster ovary cells/–DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, (Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y Acad. Sci. 383: 44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies that bind the desired antigen.

Host cells containing desired antibody nucleic acid sequences may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al (Meth. Enz. 58: 44, 1979), Barnes et al., Anal. Biochem. 102: 255 (1980), U.S. Pat. No. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. (Science 240:1041-43, 1988; ICSU Short Reports 10:105 (1990); and Proc. Natl. Acad. Sci. USA 90:457-461 (1993) describe a procedure for isolating antibodies which are secreted to the periplasmic space of E. coli. [See also, (Carter et al., Bio/Technology 10:163-167 (1992)].

The antibody composition prepared from microbial or mammalian cells can be purified using, for example, hydroxylapatite chromatography cation or avian exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62: 1-13, 1983). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H 3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Antibody Fragments

Antibody fragments comprise a portion of an intact full length antibody, preferably an antigen binding or variable region of the intact antibody. Examples of antibody fragments include Fab, Fab', F(ab')$_2$, and Fv fragments; diabodies; linear antibodies; single-chain antibody molecules (e.g., scFv); multispecific antibody fragments such as bispecific, trispecific, etc. antibodies (e.g., diabodies, triabodies, tetrabodies); minibody; chelating recombinant antibody; tribodies or bibodies; intrabodies; nanobodies; small modular immunopharmaceuticals (SMIP), binding-domain immunoglobulin fusion proteins; camelized antibodies; $V_{HH}$ containing antibodies; and other polypeptides formed from antibody fragments. See for example Holliger & Hudson (Nat. Biotech. 23 (9) 1126-36 (2005))

Papain digestion of antibodies produces two identical antigen-binding fragments, called "Fab" fragments, monovalent fragments consisting of the $V_L$, $V_H$, $C_L$ and $C_H$ domains each with a single antigen-binding site, and a residual "Fc" fragment, whose name reflects its ability to crystallize readily. Pepsin treatment yields a F(ab')$_2$ fragment, a bivalent fragment comprising two Fab fragments linked by a disulfide bridge at the hinge region, that has two "Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains that enables the Fv to form the desired structure for antigen binding, resulting in a single-chain antibody (scFv), in which a $V_L$ and $V_H$ region are paired to form a monovalent molecule via a synthetic linker that enables them to be made as a single protein chain (Bird et al., Science 242:423-426, 1988, and Huston et al., Proc. Natl. Acad. Sci. USA 85:5879-5883, 1988). For a review of sFv see Pluckthun, in The Pharmacology of Monoclonal Antibodies, vol. 113, Rosenburg and Moore eds., Springer-Verlag, New York, pp. 269-315 (1994). An Fd fragment consists of the $V_H$ and $C_H1$ domains.

Additional antibody fragments include a domain antibody (dAb) fragment (Ward et al., Nature 341:544-546, 1989) which consists of a $V_H$ domain. Diabodies are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., Proc. Natl. Acad. Sci. USA 90:6444-6448, 1993, and Poljak et al., Structure 2:1121-1123, 1994). Diabodies can be bispecific or monospecific.

Functional heavy-chain antibodies devoid of light chains are naturally occurring in nurse sharks (Greenberg et al., Nature 374:168-73, 1995), wobbegong sharks (Nuttall et al., Mol Immunol. 38:313-26, 2001) and Camelalae (Hamers-Casterman et al., Nature 363: 446-8, 1993; Nguyen et al., J. Mol. Biol. 275: 413, 1998), such as camels, dromedaries, alpacas and llamas. The antigen-binding site is reduced to a single domain, the VHH domain, in these animals. These antibodies form antigen-binding regions using only heavy chain variable region, i.e., these functional antibodies are homodimers of heavy chains only having the structure $H_2L_2$ (referred to as "heavy-chain antibodies" or "HCAbs"). Camelid $V_{HH}$ reportedly recombines with IgG2 and IgG3 constant regions that contain hinge, CH2, and CH3 domains and lack a CH1 domain (Hamers-Casterman et al., supra). For example, llama IgG1 is a conventional ($H_2L_2$) antibody isotype in which $V_H$ recombines with a constant region that contains hinge, CH1, CH2 and CH3 domains, whereas the llama IgG2 and IgG3 are heavy chain-only isotypes that lack CH1 domains and that contain no light chains. Camelid $V_{HH}$ domains have been found to bind to antigen with high affinity (Desmyter et al., J. Biol. Chem. 276:26285-90, 2001) and possess high stability in solution (Ewert et al., Biochemistry 41:3628-36, 2002). Classical $V_H$-only fragments are difficult to produce in soluble form, but improvements in solubility and specific binding can be obtained when framework residues are altered to be more $VH_H$-like. (See, e.g., Reichman, et al., J Immunol Methods 1999, 231:25-38.) Methods for generating antibodies having camelid heavy chains are described in, for example, in U.S. Patent Publication Nos. 20050136049 and 20050037421.

The variable domain of an antibody heavy-chain is has a molecular mass of 15 kDa, and is referred to as a nanobody (Cortez-Retamozo et al., Cancer Research 64:2853-57, 2004). A nanobody library may be generated from an immunized dromedary as described in Conrath et al., (Antimicrob Agents Chemother 45: 2807-12, 2001) or using recombinant methods as described in Revets et al, Expert Opin. Biol. Ther. 5 (1): 111-24 (2005).

Production of bispecific Fab-scFv ("bibody") and trispecific Fab-(scFv)(2) ("tribody") are described in Schoonjans et al., (J Immunol. 165:7050-57, 2000) and Willems et al. (J Chromatogr B Analyt Technol Biomed Life Sci. 786:161-76, 2003). For bibodies or tribodies, a scFv molecule is fused to one or both of the VL-CL (L) and VH-$CH_1$ (Fd) chains, e.g., to produce a tribody two scFvs are fused to C-term of Fab while in a bibody one scFv is fused to C-term of Fab.

A "minibody" consisting of scFv fused to CH3 via a peptide linker (hingeless) or via an IgG hinge has been described in Olafsen, et al., Protein Eng Des Sel. 2004 April; 17 (4):315-23.

Intrabodies are single chain antibodies which demonstrate intracellular expression and can manipulate intracellular protein function (Biocca, et al., EMBO J. 9:101-108, 1990; Colby et al., Proc Natl Acad Sci USA. 101:17616-21, 2004). Intrabodies, which comprise cell signal sequences which retain the antibody construct in intracellular regions, may be produced as described in Mhashilkar et al (EMBO J. 14:1542-51, 1995) and Wheeler et al., (FASEB J. 17:1733-5. 2003). Transbodies are cell-permeable antibodies in which a protein transduction domains (PTD) is fused with single chain variable fragment (scFv) antibodies Heng et al., (Med Hypotheses. 64:1105-8, 2005).

Further contemplated are antibodies that are SMIPs or binding domain immunoglobulin fusion proteins specific for an antigen. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

Thus, a variety of compositions comprising one, two, and/or three CDRs of a heavy chain variable region or a light chain variable region of an antibody may be generated by techniques known in the art.

Multispecific Antibodies

In some embodiments, it may be desirable to generate multispecific (e.g. bispecific) antibodies of the invention having binding specificities for at least two different epitopes of the same or different molecules. Exemplary bispecific antibodies may bind to two different epitopes of the antigen. Alternatively, an antigen-specific antibody arm may be combined with an arm which binds to a cell surface molecule, such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the desired antigen. Bispecific antibodies may also be used to localize cytotoxic agents to cells which express or take up the desired antigen. These antibodies possess an antigen-binding arm and an arm which binds the cytotoxic agent (e.g., saporin, anti-interferon-60, vinca alkaloid, ricin A chain, methotrexate or radioactive isotope hapten). Bispecific antibodies can be prepared as full length antibodies or antibody fragments (e.g., F(ab')2 bispecific antibodies).

According to another approach for making bispecific antibodies, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO96/27011 published Sep. 6, 1996.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., (*Science* 229:81-83, 1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. In yet a further embodiment, Fab'-SH fragments directly recovered from *E. coli* can be chemically coupled in vitro to form bispecific antibodies. (Shalaby et al., *J. Exp. Med.* 175:217-225 (1992))

Shalaby et al., J. Exp. Med. 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor antigens.

Various techniques for making and isolating bispecific antibody fragments directly from recombinant cell culture have also been described. For example, bispecific antibodies have been produced using leucine zippers. (Kostelny et al., *J. Immunol.* 148:1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al. (*Proc. Natl. Acad. Sci.* USA 90:6444-48, 1993) has provided an alternative mechanism for making bispecific antibody fragments.

The fragments comprise a heavy chain variable region ($V_H$) connected to a light-chain variable region ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.* 152: 5368 (1994).

Alternatively, the bispecific antibody may be a "linear antibody" produced as described in Zapata et al. Protein Eng. 8:1057-62 (1995). Linear antibodies comprise a pair of tandem Fd segments ($V_H$-$C_H$1-$V_H$-$C_H$1) which form a pair of antigen binding regions. Linear antibodies can be bispecific or monospecific.

In a further embodiment, the bispecific antibody may be a chelating recombinant antibody (CRAb). A chelating recombinant antibody recognizes adjacent and non-overlapping epitopes of the antigen, and is flexible enough to bind to both epitopes simultaneously (Neri et al., *J Mol. Biol.* 246:367-73, 1995).

Antibodies with more than two valencies are also contemplated. For example, trispecific antibodies can be prepared. (Tutt et al., *J. Immunol.* 147:60, 1991).

Chimeric and Humanized Antibodies

Because chimeric or humanized antibodies are less immunogenic in humans than the parental mouse monoclonal antibodies, they can be used for the treatment of humans with far less risk of anaphylaxis.

Chimeric monoclonal antibodies, in which the variable Ig domains of a mouse monoclonal antibody are fused to human constant Ig domains, can be generated using standard procedures known in the art (See Morrison et al., *Proc. Natl. Acad. Sci.* USA 81, 6841-6855 (1984); and, Boulianne et al, *Nature* 312, 643-646, (1984)). Although some chimeric monoclonal antibodies have proved less immunogenic in humans, the mouse variable Ig domains can still lead to a significant human anti-mouse response.

Humanized antibodies may be achieved by a variety of methods including, for example: (1) grafting the non-human complementarity determining regions (CDRs) onto a human framework and constant region (a process referred to in the art as humanizing through "CDR grafting") (2) transplanting the entire non-human variable domains, but "cloaking" them with a human-like surface by replacement of surface residues (a process referred to in the art as "veneering"), or, alternatively, (3) substituting human amino acids at positions determined to be unlikely to adversely effect either antigen binding or protein folding, but likely to reduce immunogenicity in a human environment (a process referred to in the art as HUMAN ENGINEERING™). In the present invention, humanized antibodies will include both "humanized", "veneered" and "HUMAN ENGINEERED™", antibodies. These methods are disclosed in, e.g., Jones et al., *Nature* 321:522 525 (1986); Morrison et al., *Proc. Natl. Acad. Sci.*, U.S.A., 81:6851-6855 (1984); Morrison and Oi, *Adv. Immunol.*, 44:65-92 (1988); Verhoeyer et al., *Science* 239:1534-1536 (1988); Padlan, *Molec. Immun.* 28:489-498 (1991); Padlan, *Molec. Immunol.* 31:169-217 (1994); Kettleborough et al., *Protein Eng.* 4:773-783 (1991); Studnicka et al. U.S. Pat. No. 5,766,886; Studnicka et al., (*Protein Eng* 7: 805-814, 1994) each of which is incorporated herein by reference.

Human Antibodies from Transgenic Animals

Human antibodies to antigen can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091,001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. See also, U.S. Pat. Nos. 6,114,598 6,657,103 and 6,833,268.

Using a transgenic animal described above, an immune response can be produced to a selected antigen, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigens including IL-6, IL-8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (*Nat. Biotechnol.* 14:845-851 (1996)), which contains gene sequences from unrearranged human antibody genes that code for the heavy and light chains of human antibodies. Immunization of a HuMAb-MOUSE® enables the production of fully human monoclonal antibodies to the antigen.

Also, Ishida et al. (*Cloning Stem Cells.* 4:91-102 (2002)) describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4). Immunization of the TCMOUSE™ with various human antigens produces antibody responses comprising human antibodies.

See also Jakobovits et al., *Proc. Natl. Acad. Sci.* USA, 90:2551 (1993); Jakobovits et al., *Nature,* 362:255-258 (1993); Bruggermann et al., *Year in Immunol.,* 7:33 (1993); and U.S. Pat. No. 5,591,669, U.S. Pat. No. 5,589,369, U.S. Pat. No. 5,545,807; and U.S Patent Publication No. 20020199213. U.S. Patent Publication No. 20030092125 describes methods for biasing the immune response of an animal to the desired epitope. Human antibodies may also be generated by in vitro activated B cells (see U.S. Pat. Nos. 5,567,610 and 5,229,275).

Human Antibodies from Display Technology

The development of technologies for making repertoires of recombinant human antibody genes, and the display of the encoded antibody fragments on the surface of filamentous bacteriophage, has provided a means for making human antibodies directly. The antibodies produced by phage technology are produced as antigen binding fragments—usually Fv or Fab fragments—in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

The invention contemplates a method for producing antigen-specific antibody or antigen-binding portion thereof comprising the steps of synthesizing a library of human antibodies on phage, screening the library with antigen or a portion thereof, isolating phage that bind antigen, and obtaining the antibody from the phage. By way of example, one method for preparing the library of antibodies for use in phage display techniques comprises the steps of immunizing a non-human animal comprising human immunoglobulin loci with antigen or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant antigen-specific antibodies of the invention may be obtained in this way. In another example, antibody producing cells can be extracted from non-immunized animals, RNA isolated from the extracted cells and reverse transcribed to produce cDNA, which is amplified using a primer, and inserted into a phage display vector such that antibodies are expressed on the phage. Phage-display processes mimic immune selection through the display of antibody repertoires on the surface of filamentous bacteriophage, and subsequent selection of phage by their binding to an antigen of choice. One such technique is described in WO 99/10494, which describes the isolation of high affinity and functional agonistic antibodies for MPL and msk receptors using such an approach. Antibodies of the invention can be isolated by screening of a recombinant combinatorial antibody library, preferably a scFv phage display library, prepared using human $V_L$ and $V_H$ cDNAs prepared from mRNA derived from human lymphocytes. Methodologies for preparing and screening such libraries are known in the art. See e.g., U.S. Pat. No. 5,969,108. There are commercially available kits for generating phage display libraries (e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum. Antibod. Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J. Mol. Biol.* 226:889-896; Clackson et al. (1991) *Nature* 352:624-628; Gram et al. (1992) *Proc. Natl. Acad. Sci.* USA 89:3576-3580; Garrad et al. (1991) *Bio/Technology* 9:1373-1377; Hoogenboom et al. (1991) *Nuc Acid Res* 19:4133-4137; and Barbas et al. (1991) *Proc. Natl. Acad. Sci.* USA 88:7978-7982.

In one embodiment, to isolate human antibodies specific for an antigen, with the desired binding characteristics, a human $V_H$ and $V_L$ library are screened to select for antibody fragments having the desired specificity. The antibody libraries used in this method are preferably scFv libraries prepared and screened as described herein and in the art (McCafferty et al., PCT Publication No. WO 92/01047, McCafferty et al., (*Nature* 348:552-554 (1990)); and Griffiths et al., (*EMBO J* 12:725-734 (1993)). The scFv antibody libraries preferably are screened using the antigen.

Alternatively, the Fd fragment ($V_H$-$C_H$1) and light chain ($V_L$-$C_L$) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. Through several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., *Bio/Technology* 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., *J. Mol. Biol.*, 227:381 (1991); Marks et al., *J. Mol. Biol*, 222:581-597 (1991); U.S. Pat. Nos. 5,565,332 and 5,573,905; Clackson, T., and Wells, J. A., *TIBTECH* 12, 173-184 (1994)). In particular, in vitro selection and evolution of antibodies derived from phage display libraries has become a powerful tool (See Burton, D. R., and Barbas III, C. F., *Adv. Immunol*. 57, 191-280 (1994); Winter, G., et al., *Annu. Rev. Immunol*. 12, 433-455 (1994); U.S. patent publication no. 20020004215 and WO 92/01047; U.S. patent publication no. 20030190317; and U.S. Pat. Nos. 6,054,287 and 5,877,293.

Watkins, "Screening of Phage-Expressed Antibody Libraries by Capture Lift," Methods in Molecular Biology, Antibody Phage Display: Methods and Protocols 178:187-193 (2002), and U.S. patent publication no. 20030044772, published Mar. 6, 2003, describe methods for screening phage-expressed antibody libraries or other binding molecules by capture lift, a method involving immobilization of the candidate binding molecules on a solid support.

Fv fragments are displayed on the surface of phage, by the association of one chain expressed as a phage protein fusion (e.g., with M13 gene III) with the complementary chain expressed as a soluble fragment. It is contemplated that the phage may be a filamentous phage such as one of the class I phages: fd, M13, f1, lf1, lke, ZJ/Z, Ff and one of the class II phages Xf, Pf1 and Pf3. The phage may be M13, or fd or a derivative thereof.

Once initial human $V_L$ and $V_H$ segments are selected, "mix and match" experiments, in which different pairs of the initially selected $V_L$ and $V_H$ segments are screened for antigen binding, may be performed to select preferred $V_L$/$V_H$ pair combinations. Additionally, to further improve the quality of the antibody, the $V_L$ and $V_H$ segments of the preferred $V_L$/$V_H$ pair(s) can be randomly mutated, preferably within the any of the CDR1, CDR2 or CDR3 region of $V_H$ and/or $V_L$, a process analogous to the in vivo somatic mutation process responsible for affinity maturation of antibodies during a natural immune response. This in vitro affinity maturation can be accomplished by amplifying $V_L$, and $V_H$ regions using PCR primers complimentary to the $V_H$ CDR1, CDR2, and CDR3, or $V_L$ CDR1, CDR2, and CDR3, respectively, which primers have been "spiked" with a random mixture of the four nucleotide bases at certain positions such that the resultant PCR products encode $V_L$ and $V_H$ segments into which random mutations have been introduced into the $V_H$ and/or $V_L$ CDR3 regions. These randomly mutated $V_L$ and $V_H$ segments can be rescreened for binding to antigen.

Following screening and isolation of an antigen-specific antibody from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention, as described below. To express a recombinant human antibody isolated by screening of a combinatorial library, the DNA encoding the antibody is cloned into a recombinant expression vector and introduced into a mammalian host cell, as described herein.

It is contemplated that the phage display method may be carried out in a mutator strain of bacteria or host cell. A mutator strain is a host cell which has a genetic defect which causes DNA replicated within it to be mutated with respect to its parent DNA. Example mutator strains are NR9046mutD5 and NR9046 mut T1.

It is also contemplated that the phage display method may be carried out using a helper phage. This is a phage which is used to infect cells containing a defective phage genome and which functions to complement the defect. The defective phage genome can be a phagemid or a phage with some function encoding gene sequences removed. Examples of helper phages are M13K07, M13K07 gene III no. 3, hyperphage; and phage displaying or encoding a binding molecule fused to a capsid protein.

Antibodies may also be generated via phage display screening methods using the hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage display techniques such as those described therein. This technique is also disclosed in Marks et al, (*Bio/Technology*, 10:779-783 (1992)).

Methods for display of polypeptides on the surface of viruses, yeast, microbial and mammalian cells have also been used to identify antigen specific antibodies. See, for example, U.S. Pat. Nos. 5,348,867; 5,723,287; 6,699,658; Wittrup, Curr Op. Biotech. 12:395-99 (2001); Lee et al, Trends in Biotech. 21 (1) 45-52 (2003); Surgeeva et al, Adv. Drug Deliv. Rev. 58: 1622-54 (2006). Antibody libraries may be attached to yeast proteins, such as agglutinin, effectively mimicking the cell surface display of antibodies by B cells in the immune system.

In addition to phage display methods, antibodies may be isolated using in vitro display methods including ribosome display and mRNA display (Amstutz et al, Curr. Op. Biotech. 12: 400-05 (2001)). Selection of polypeptide using ribosome display is described in Hanes et al., (*Proc. Natl. Acad Sci* USA, 94:4937-4942 (1997)) and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

Altered Glycosilation

Antibody variants can also be produced that have a modified glycosylation pattern relative to the parent antibody, for example, deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to an antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to an antibody by inserting or substituting one or more serine or threonine residues to the sequence of the original antibody.

Fc glycans influence the binding of IgG to Fc receptors and C1q, and are therefore important for IgG effector functions. Antibody variants with modified Fc glycans and altered effector function may be produced. For example, antibodies with modified terminal sugars such as sialic acids, core fucose, bisecting N-acetylglucosamine, and mannose residues may have altered binding to the FcγRIIIa receptor and altered ADCC activity. In a further example, antibodies with modified terminal galactose residues may have altered binding to C1q and altered CDC activity (Raju, Curr. Opin. Immunol. 20: 471-78 (2008).

Also contemplated are antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγKIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (Yamane-Ohnuki et al., *Biotechnol Bioeng*. 87:614-22 (2004)). Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors (Rothman et al., *Mol Immunol*. 26:1113-23 (1989)). Some host cell strains, e.g. Lec13 or rat hybridoma YB2/0 cell line naturally produce antibodies with lower fucosylation levels. (Shields et al., *J Biol. Chem.* 277:26733-40 (2002); Shinkawa et al., *J Biol. Chem.* 278: 3466-73 (2003)). An increase in the level of bisected carbohydrate, e.g. through recombinantly producing antibody in cells that overexpress GnTIII enzyme, has also been determined to increase ADCC activity (Umana et al., *Nat Biotechnol*. 17:176-80 (1999)). It has been predicted that the absence of only one of the two fucose residues may be sufficient to increase ADCC activity (Ferrara et al., *Biotechnol Bioeng*. 93:851-61 (2006)).

Variants with Altered Effector Function

Other modifications of the antibody are contemplated. In one aspect, it may be desirable to modify the antibody of the invention with respect to effector function, for example, to enhance the effectiveness of the antibody in treating cancer (Natsume et al, Drug Design Dev't & Ther. 3: 7-16 (2009). Exemplary effector functions include C1q binding; CDC; Fc receptor binding; ADCC; phagocytosis; down regulation of cell surface receptors (e.g. B cell receptor; BCR), etc. One method for modifying effector function teaches that cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., (*J. Exp Med.* 176: 1191-1195 (1992)) and Shopes, B. (*J. Immunol.* 148: 2918-2922 (1992)). Homodimeric antibodies with enhanced anti-tumor activity may also be prepared using heterobifunctional cross-linkers as described in Wolff et al., (*Cancer Research* 53: 2560-2565 (1993)). Alternatively, an antibody can be engineered which has dual Fc regions and may thereby have enhanced complement lysis and ADCC capabilities. See Stevenson et al., (*Anti-Cancer Drug Design* 3: 219-230 (1989)). In addition, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response. Also see Steplewski et al., (*Proc Natl Acad Sci* USA. 85:4852-56 (1998)), which described chimeric antibodies wherein a murine variable region was joined with human gamma 1, gamma 2, gamma 3, and gamma 4 constant regions.

In certain embodiments of the invention, it may be desirable to use an antibody fragment, rather than an intact antibody, to increase tumor penetration, for example. In this case, it may be desirable to modify the antibody fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, e.g., WO96/32478).

The salvage receptor binding epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the $C_L$ region or $V_L$ region, or both, of the antibody fragment. See also International applications WO 97/34631 and WO 96/32478 which describe Fc variants and their interaction with the salvage receptor.

Thus, antibodies of the invention may comprise a human Fc portion, a human consensus Fc portion, or a variant thereof that retains the ability to interact with the Fc salvage receptor, including variants in which cysteines involved in disulfide bonding are modified or removed, and/or in which the a met is added at the N-terminus and/or one or more of the N-terminal 20 amino acids are removed, and/or regions that interact with complement, such as the C1q binding site, are removed, and/or the ADCC site is removed [see, e.g., Sarmay et al., *Molec. Immunol.* 29:633-9 (1992)].

Previous studies mapped the binding site on human and murine IgG for FcR primarily to the lower hinge region composed of IgG residues 233-239. Other studies proposed additional broad segments, e.g. Gly316-Lys338 for human Fc receptor I, Lys274-Arg301 and Tyr407-Arg416 for human Fc receptor III, or found a few specific residues outside the lower hinge, e.g., Asn297 and Glu318 for murine IgG2b interacting with murine Fc receptor II. The report of the 3.2-Å crystal structure of the human IgG1 Fc fragment with human Fc receptor IIIA delineated IgG1 residues Leu234-Ser239, Asp265-Glu269, Asn297-Thr299, and Ala327-Ile332 as involved in binding to Fc receptor IIIA. It has been suggested based on crystal structure that in addition to the lower hinge (Leu234-Gly237), residues in IgG CH2 domain loops FG (residues 326-330) and BC (residues 265-271) might play a role in binding to Fc receptor IIA. See Shields et al., (*J. Biol. Chem.,* 276:6591-604 (2001)), incorporated by reference herein in its entirety. Mutation of residues within Fc receptor binding sites can result in altered effector function, such as altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different IgG subclass (e.g. replacing an IgG1 residue with a corresponding IgG2 residue at that position).

Shields et al. reported that IgG1 residues involved in binding to all human Fc receptors are located in the CH2 domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297. The additional IgG1 residues that affected binding to Fc receptor II are as follows: (largest effect) Arg255, Thr256, Glu258, Ser267, Asp270, Glu272, Asp280, Arg292, Ser298, and (less effect) His268, Asn276, His285, Asn286, Lys290, Gln295, Arg301, Thr307, Leu309, Asn315, Lys322, Lys326, Pro331, Ser337, Ala339, Ala378, and Lys414. A327Q, A3275, P329A, D265A and D270A reduced binding. In addition to the residues identified above for all FcR, additional IgG1 residues that reduced binding to Fc receptor IIIA by 40% or more are as follows: Ser239, Ser267 (Gly only), His268, Glu293, Gln295, Tyr296, Arg301, Val303, Lys338, and Asp376. Variants that improved binding to FcRIIIA include T256A, K290A, S298A, E333A, K334A, and A339T. Lys414 showed a 40% reduction in binding for FcRIIA and FcRIIB, Arg416 a 30% reduction for FcRIIA and FcRIIIA, Gln419 a 30% reduction to FcRIIA and a 40% reduction to FcRIIB, and Lys360 a 23% improvement to FcRIIIA. See also Presta et al., (*Biochem. Soc. Trans.* 30:487-490, 2001), incorporated herein by reference in its entirety, which described several positions in the Fc region of IgG1 were found which improved binding only to specific Fc gamma receptors (R) or simultaneously improved binding to one type of Fc gamma R and reduced binding to another type. Selected IgG1 variants with improved binding to Fc gamma RIIIa were then tested in an in vitro antibody-dependent cellular cytotoxicity (ADCC) assay and showed an enhancement in ADCC when either peripheral blood mononuclear cells or natural killer cells were used.

For example, U.S. Pat. No. 6,194,551, incorporated herein by reference in its entirety, describes variants with altered effector function containing mutations in the human IgG Fc region, at amino acid position 329, 331 or 322 (using Kabat numbering), some of which display reduced C1q binding or CDC activity. As another example, U.S. Pat. No. 6,737,056, incorporated herein by reference in its entirety, describes variants with altered effector or Fc-gamma-receptor binding containing mutations in the human IgG Fc region, at amino acid position 238, 239, 248, 249, 252, 254, 255, 256, 258, 265, 267, 268, 269, 270, 272, 276, 278, 280, 283, 285, 286, 289, 290, 292, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439 (using Kabat numbering), some of which display receptor binding profiles associated with reduced ADCC or CDC activity. Of these, a mutation at amino acid position 238, 265, 269, 270, 327 or 329 are stated to reduce binding to FcRI, a mutation at amino acid position 238, 265, 269, 270, 292, 294, 295, 298, 303, 324, 327, 329, 333, 335, 338, 373, 376, 414, 416, 419, 435, 438 or 439 are stated to reduce binding to FcRII, and a mutation at amino acid position 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 is stated to reduce binding to FcRIII.

U.S. Pat. No. 5,624,821, incorporated by reference herein in its entirety, reports that C1q binding activity of an murine antibody can be altered by mutating amino acid residue 318, 320 or 322 of the heavy chain and that replacing residue 297 (Asn) results in removal of lytic activity.

U.S. Patent Publication No. 20040132101, incorporated by reference herein in its entirety, describes variants with mutations at amino acid positions 240, 244, 245, 247, 262, 263, 266, 299, 313, 325, 328, or 332 (using Kabat numbering) or positions 234, 235, 239, 240, 241, 243, 244, 245, 247, 262, 263, 264, 265, 266, 267, 269, 296, 297, 298, 299, 313, 325, 327, 328, 329, 330, or 332 (using Kabat numbering), of which mutations at positions 234, 235, 239, 240, 241, 243, 244, 245, 247, 262, 263, 264, 265, 266, 267, 269, 296, 297, 298, 299, 313, 325, 327, 328, 329, 330, or 332 may reduce ADCC activity or reduce binding to an Fc gamma receptor.

Chappel et al. (*Proc Natl Acad Sci* USA. 88:9036-40 (1991)), incorporated herein by reference in its entirety, report that cytophilic activity of IgG1 is an intrinsic property of its heavy chain CH2 domain. Single point mutations at any of amino acid residues 234-237 of IgG1 significantly lowered or abolished its activity. Substitution of all of IgG1 residues 234-237 (LLGG) into IgG2 and IgG4 were required to restore full binding activity. An IgG2 antibody containing the entire ELLGGP sequence (residues 233-238) was observed to be more active than wild-type IgG1.

Isaacs et al. (*J Immunol.* 161:3862-9 (1998)), incorporated herein by reference in its entirety, report that mutations within a motif critical for Fc gammaR binding (glutamate 233 to proline, leucine/phenylalanine 234 to valine, and leucine 235 to alanine) completely prevented depletion of target cells. The mutation glutamate 318 to alanine eliminated effector function of mouse IgG2b and also reduced the potency of human IgG4.

Armour et al. (*Mol Immunol.* 40:585-93 (2003)), incorporated by reference herein in its entirety, identified IgG1 variants which react with the activating receptor, FcgammaRIIa, at least 10-fold less efficiently than wildtype IgG1 but whose binding to the inhibitory receptor, FcgammaRIIb, is only four-fold reduced. Mutations were made in the region of amino acids 233-236 and/or at amino acid positions 327, 330 and 331. See also WO 99/58572, incorporated by reference herein in its entirety.

Xu et al. (*J Biol Chem.* 269:3469-74 (1994)), incorporated by reference herein in its entirety, report that mutating IgG1 Pro331 to Ser markedly decreased C1q binding and virtually eliminated lytic activity. In contrast, the substitution of Pro for Ser331 in IgG4 bestowed partial lytic activity (40%) to the IgG4 Pro331 variant.

Schuurman et al. (*Mol Immunol.* 38:1-8 (2001)), incorporated by reference herein in its entirety, report that mutating one of the hinge cysteines involved in the inter-heavy chain bond formation, Cys226, to serine resulted in a more stable inter-heavy chain linkage. Mutating the IgG4 hinge sequence Cys-Pro-Ser-Cys to the IgG1 hinge sequence Cys-Pro-Pro-Cys also markedly stabilizes the covalent interaction between the heavy chains.

Angal et al. (*Mol Immunol.* 30:105-8 (1993)), incorporated by reference herein in its entirety, report that mutating the serine at amino acid position 241 in IgG4 to proline (found at that position in IgG1 and IgG2) led to the production of a homogeneous antibody, as well as extending serum half-life and improving tissue distribution compared to the original chimeric IgG4.

Covalent Modifications

Covalent modifications of the polypeptide binding agents of the invention, e.g., antibodies, are also included within the scope of this invention. They may be made by chemical synthesis or by enzymatic or chemical cleavage of the polypeptide binding agent, if applicable. Other types of covalent modifications of the polypeptide binding agent are introduced into the molecule by reacting targeted amino acid residues of the polypeptide binding agent with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, .alpha.-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R-N.dbd.C.dbd.N-R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the polypeptide binding agent. These procedures are advantageous in that they do not require production of the polypeptide binding agent in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 and in Aplin and Wriston, (*CRC Crit. Rev. Biochem.*, pp. 259-306 (1981)).

Removal of any carbohydrate moieties present on the polypeptide binding agent may be accomplished chemically or enzymatically. Chemical deglycosylation requires exposure of the polypeptide binding agent to the compound trifluoromethanesulfonic acid, or an equivalent compound. This treatment results in the cleavage of most or all sugars except the linking sugar (N-acetylglucosamine or N-acetylgalactosamine), while leaving the polypeptide binding agent intact. Chemical deglycosylation is described by Hakimuddin, et al., (*Arch. Biochem. Biophys.* 259: 52 (1987)) and by Edge et al., (*Anal. Biochem.* 118: 131 (1981)). Enzymatic cleavage of carbohydrate moieties on polypeptide binding agents can be achieved by the use of a variety of endo- and exo-glycosidases as described by Thotakura et al., (*Meth. Enzymol.* 138: 350 (1987)).

Another type of covalent modification of the polypeptide binding agent comprises linking the polypeptide binding agent to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

Derivatives

Derivative refers to polypeptide binding agents, including antibodies, chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine. Derivatives of the polypeptide binding agents of the invention, such as an antibody, are also useful as therapeutic agents and may be produced by the method of the invention The conjugated moiety can be incorporated in or attached to a polypeptide binding agent either covalently, or through ionic, van der Waals or hydrogen bonds, e.g., incorporation of radioactive nucleotides, or biotinylated nucleotides that are recognized by streptavadin.

Polyethylene glycol (PEG) may be attached to the polypeptide binding agents to provide a longer half-life in vivo. The PEG group may be of any convenient molecular weight and may be linear or branched. The average molecular weight of the PEG will preferably range from about 2 kiloDalton ("kD") to about 100 kDa, more preferably from about 5 kDa to about 50 kDa, most preferably from about 5 kDa to about 10 kDa. The PEG groups will generally be attached to the polypeptide binding agents of the invention via acylation or reductive alkylation through a natural or engineered reactive group on the PEG moiety (e.g., an aldehyde, amino, thiol, or ester group) to a reactive group on the polypeptide binding agent (e.g., an aldehyde, amino, or ester group). Addition of PEG moieties to polypeptide binding agents can be carried out using techniques well-known in the art. See, e.g., International Publication No. WO 96/11953 and U.S. Pat. No. 4,179,337.

Ligation of the polypeptide binding agent with PEG usually takes place in aqueous phase and can be easily monitored by reverse phase analytical HPLC. The PEGylated substances are purified by preparative HPLC and characterized by analytical HPLC, amino acid analysis and laser desorption mass spectrometry.

Antibody Conjugates

A polypeptide binding agent may be administered in its "naked" or unconjugated form, or may be conjugated directly to other therapeutic or diagnostic agents, or may be conjugated indirectly to carrier polymers comprising such other therapeutic or diagnostic agents. In some embodiments the polypeptide binding agent is conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (e.g., a radioconjugate). Suitable chemotherapeutic agents include: daunomycin, doxorubicin, methotrexate, and vindesine (Rowland et al., (1986) supra). Suitable toxins include: bacterial toxins such as diphtheria toxin; plant toxins such as ricin; small molecule toxins such as geldanamycin (Mandler et al J. Natl. Cancer Inst. 92 (19):1573-81 (2000); Mandler et al Bioorganic & Med. Chem. Letters 10:1025-1028 (2000); Mandler et al Bioconjugate Chem. 13.786-91 (2002)), maytansinoids (EP 1391213; Liu et al, Proc. Natl. Acad. Sci. USA 93:8618-23 (1996)), auristatins (Doronina et al, Nat. Biotech. 21: 778-84 (2003) and calicheamicin (Lode et al Cancer Res. 58:2928 (1998); Hinman et al Cancer Res. 53:3336-3342 (1993)).

Polypeptide binding agents can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

Conjugation of polypeptide binding agent moieties is described in U.S. Pat. No. 6,306,393. General techniques are also described in Shih et al., Int. J. Cancer 41:832-839 (1988); Shih et al., Int. J. Cancer 46:1101-1106 (1990); and Shih et al., U.S. Pat. No. 5,057,313. This general method involves reacting a polypeptide binding agent component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer may be, for example, an aminodextran or polypeptide of at least 50 amino acid residues. Various techniques for conjugating a drug or other agent to the carrier polymer are known in the art. A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and conjugate.

Alternatively, conjugated polypeptide binding agents can be prepared by directly conjugating a polypeptide binding agent component with a therapeutic agent. The general procedure is analogous to the indirect method of conjugation except that a therapeutic agent is directly attached to an oxidized polypeptide binding agent component. For example, a carbohydrate moiety of a polypeptide binding agent can be attached to polyethyleneglycol to extend half-life.

Alternatively, a therapeutic agent can be attached at the hinge region of a reduced antibody component via disulfide bond formation, or using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995). A variety of bifunctional protein coupling agents are known in the art, such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Antibody Fusion Proteins

Methods of making antibody fusion proteins are well known in the art. See, e.g., U.S. Pat. No. 6,306,393. Antibody fusion proteins comprising an interleukin-2 moiety are described by Boleti et al., Ann. Oncol. 6:945 (1995), Nicolet et al., Cancer Gene Ther. 2:161 (1995), Becker et al. Proc. Nat'l Acad. Sci. USA 93:7826 (1996), Hank et al., Clin. Cancer Res. 2:1951 (1996), and Hu et al., Cancer Res. 56:4998 (1996). In addition, Yang et al., (Hum. Antibodies Hybridomas 6:129 (1995)), describe a fusion protein that includes an F(ab')$_2$ fragment and a tumor necrosis factor alpha moiety. Further examples of antibody fusion proteins are described by Pastan et al, Nat. Reviews Cancer 6: 559-65 (2006).

Methods of making antibody-toxin fusion proteins in which a recombinant molecule comprises one or more antibody components and a toxin or chemotherapeutic agent also are known to those of skill in the art. For example, antibody-*Pseudomonas* exotoxin A fusion proteins have been described by Chaudhary et al., Nature 339:394 (1989), Brinkmann et al., Proc. Nat'l Acad. Sci. USA 88:8616 (1991), Batra et al., Proc. Nat'l Acad. Sci. USA 89:5867 (1992), Friedman et al., J. Immunol. 150:3054 (1993), Wels et al., Int. J. Can. 60:137 (1995), Fominaya et al., J. Biol. Chem. 271:10560 (1996), Kuan et al., Biochemistry 35:2872 (1996), and Schmidt et al., Int. J. Can. 65:538 (1996). Antibody-toxin fusion proteins containing a diphtheria toxin moiety have been described by Kreitman et al., Leukemia 7:553 (1993), Nicholls et al., J. Biol. Chem. 268:5302 (1993), Thompson et al, J. Biol. Chem. 270:28037 (1995), and Vallera et al., Blood 88:2342 (1996). Deonarain et al., Tumor Targeting 1:177 (1995), have described an antibody-toxin fusion protein having an RNase moiety, while Linardou et al., Cell Biophys. 24-25:243 (1994), produced an antibody-toxin fusion protein comprising a DNase I component. Gelonin was used as the toxin moiety in the antibody-toxin fusion protein of Wang et al., Abstracts of the 209th ACS National Meeting, Anaheim, Calif., Apr. 2-6, 1995, Part 1, BIOT005. As a further example, Dohlsten et al., Proc. Nat'l Acad. Sci. USA 91:8945 (1994), reported an antibody-toxin fusion protein comprising Staphylococcal enterotoxin-A.

Illustrative of toxins which are suitably employed in the preparation of such fusion proteins are ricin, abrin, ribonuclease, DNase I, Staphylococcal enterotoxin-A, pokeweed antiviral protein, gelonin, diphtherin toxin, *Pseudomonas* exotoxin, and *Pseudomonas* endotoxin. See, for example, Pastan et al., Cell 47:641 (1986), and Goldenberg, C A—A Cancer Journal for Clinicians 44:43 (1994). Other suitable toxins are known to those of skill in the art.

Antibodies of the present invention may also be used in ADEPT by conjugating the antibody to a prodrug-activating enzyme which converts a prodrug (e.g., a peptidyl chemotherapeutic agent, See WO81/01145) to an active anti-cancer drug. See, for example, WO88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the this invention include, but are not limited to: alkaline phosphatase; arylsulfatase; cytosine deaminase, 5-fluorouracil; proteases, such as *serratia* protease, thermolysin, subtilisin, carboxypeptidases and cathepsins (such as cathepsins B and L); D-alanylcarboxypeptidases; carbohydrate-cleaving enzymes such as β-galactosidase and neuraminidase; β-lactamase; and penicillin amidases, such as penicillin V amidase or penicillin G amidase. Alternatively, antibodies with enzymatic activity, also known in the art as abzymes, can be used to convert the prodrugs of the invention into free active drugs (See, e.g., Massey, Nature 328: 457-458 (1987). Antibody-abzyme conjugates can be prepared as described herein for delivery of the abzyme to a tumor cell population.

The enzymes above can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (See, e.g., Neuberger et al., Nature 312: 604-608 (1984))

Formulation of Pharmaceutical Compositions

To administer polypeptide binding agents of the invention to human or test mammals, it is preferable to formulate the polypeptide binding agent in a sterile composition comprising one or more sterile pharmaceutically acceptable carriers. The phrase "pharmaceutically or pharmacologically acceptable" refer to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

The polypeptide binding agent is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site.

Pharmaceutical compositions of the present invention containing a polypeptide binding agent of the invention as an active ingredient may contain sterile pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present invention. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers. A variety of aqueous carriers are suitable, e.g., sterile phosphate buffered saline solutions, bacteriostatic water, water, buffered water, 0.4% saline, 0.3% glycine, and the like, and may include other proteins for enhanced stability, such as albumin, lipoprotein, globulin, etc., subjected to mild chemical modifications or the like.

Therapeutic formulations of the polypeptide binding agent are prepared for storage by mixing the polypeptide binding agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, succinate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

The concentration of polypeptide binding agent in these formulations can vary widely, for example from less than about 0.5%, usually at or at least about 1% to as much as 15 or 20% by weight and will be selected primarily based on fluid volumes, viscosities, etc., in accordance with the particular mode of administration selected. Thus, a typical pharmaceutical composition for parenteral injection could be made up to contain 1 ml sterile buffered water, and 50 mg of polypeptide binding agent. A typical composition for intravenous infusion could be made up to contain 250 ml of sterile Ringer's solution, and 150 mg of polypeptide binding agent. Actual methods for preparing parenterally administrable compositions will be known or apparent to those skilled in the art and are described in more detail in, for example, Remington's Pharmaceutical Science, 15th ed., Mack Publishing Company, Easton, Pa. (1980). An effective dosage of polypeptide binding agent is within the range of 0.01 mg to 1000 mg per kg of body weight per administration.

The pharmaceutical compositions may be in the form of a sterile injectable aqueous, oleaginous suspension, dispersions or sterile powders for the extemporaneous preparation of sterile injectable solutions or dispersions. The suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. The carrier can be a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In all cases the form must be sterile and must be fluid to the extent that easy syringability exists. The proper fluidity can be maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

Compositions useful for administration may be formulated with uptake or absorption enhancers to increase their efficacy. Such enhancers include for example, salicylate, glycocholate/linoleate, glycholate, aprotinin, bacitracin, SDS, caprate and the like. See, e.g., Fix (*J. Pharm. Sci.,* 85:1282-1285 (1996)) and Oliyai and Stella (*Ann. Rev. Pharmacol. Toxicol.,* 32:521-544 (1993)).

Biophysical Assays

Complex biological events can be studied via molecular biophysical approaches which consider them as systems of interacting units which can be understood in terms of statistical mechanics, thermodynamics and chemical kinetics.

Nuclear magnetic resonance (NMR), Isothermal Titration calorimetry, dynamic light scattering, surface plasmon resonance, dual polarisation interferometry are commonly used to assess whether the compound binds effectively to the test antigen, the stoichiometry of binding, any associated conformational change and to identify promiscuous inhibitors. (See, for example, Correia J. J & Detrich H. W. (eds) "Biophysical Tools for Biologists vol. 2." Methods in Cell Biol 89 (2) (2008))

Fluorescent imaging techniques, as well as electron microscopy, x-ray crystallography, NMR spectroscopy and atomic force microscopy (AFM) are often used to visualize structures of biological significance. Conformational changes in structure can be measured using techniques such as dual polarisation interferometry and circular dichroism. Direct manipulation of molecules using optical tweezers or AFM can also be used to monitor biological events where forces and distances are at the nanoscale.

A number of techniques are available for use in biophysics, including: atomic force microscopy, biophotonics, biosensor and bioelectronics, calcium imaging, calorimetry, circular dichroism, cryobiology, dual polarisation interferometry, electrophysiology, fluorescence, microscopy, neuroimaging, neutron spin echo spectroscopy, patch clamping, nuclear magnetic resonance spectroscopy, x-ray crystallography. In certain embodiments, the assays of the present invention may employ a detectable moiety. The detectable moiety can be any one which is capable of producing, either directly or indirectly, a measurable signal, such as a radioactive, chromogenic, luminescence, or fluorescent signal, which can be used to quantitate the amount of bound detectable moiety or label in a sample. Detectable labels known in the art include radioisotopes, such as $^3$H, $^{14}$C, $^{32}$P, $^{35}$S, or $^{125}$I, electrochemiluminescent labels (such as Ruthenium (Ru)-based catalyst in conjunction with substrates, etc.), luminescent or bioluminescent labels (e.g., Europium, Vanadium), fluorescent or chemiluminescent compounds, such as fluorescein isothiocyanate, rhodamine, or luciferin, enzymes (e.g., enzyme, such as alkaline phosphatase, β-galactosidase, or horseradish peroxidase), colorimetric labels such as colloidal gold, colored glass or plastic beads (e.g., polystyrene, polypropylene, latex, etc.), paramagnetic atoms or magnetic agents, electron-dense reagents, a nano- or micro-bead containing a fluorescent dye, nanocrystals, a quantum dot, a quantum bead, a nanotag, dendrimers with a fluorescent label, a micro-transponder, an electron donor molecule or molecular structure, or a light reflecting particle. the microparticles may be nanocrystals or quantum dots. Nanocrystals are substances that absorb photons of light, then re-emit photons at a different wavelength (fluorophores). In addition, additional florescent labels, or secondary antibodies may be conjugated to the nanocrystals. Nanocrystals are commercially available from sources such as Invitrogen and Evident Technologies (Troy, N.Y.). Other labels include E)-5-[2-(methoxycarbonyl)ethenyl]cytidine, which is a nonfluorescent molecule that when subjected to ultraviolet (UV) irradiation yields a product, 3-.beta.-D-ribofuranosyl-2,7-dioxopyrido[2,3-d]pyrimidine, which displays a strong fluorescence signal. Bar code labels are described in U.S. Patent Publication No. US 20070037195.

A variety of assay methods known in the art may be employed in the present invention, such as competitive binding assays, direct and indirect sandwich assays, immunoprecipitation assays, fluorescent resonance energy transfer (FRET), electroimmunoassays surface plasmon resonance (SPR), and nanoparticle-derived techniques.

Competitive binding assays rely on the ability of a labeled standard (e.g., an antigen or a fragment thereof to which a polypeptide binding agent binds) to compete with antigen in the test sample for binding to the polypeptide binding agent. The amount of antigen in the test sample is inversely proportional to the amount of standard that becomes bound to the antibodies. To facilitate determining the amount of standard that becomes bound, the antibodies typically are insolubilized before or after the competition, so that the bound antigen may conveniently be separated from the unbound antigen. In alternative embodiments, competitive binding assays measure the ability of a labeled polypeptide binding agent to compete with unlabeled polypeptide binding agent for binding to antigen or a fragment thereof.

Sandwich assays typically involve the use of two antibodies, each capable of binding to a different immunogenic portion, or epitope, of the protein to be detected and/or quantitated. In a sandwich assay, the analyte in the test sample is typically bound by a first polypeptide binding agent which is immobilized on a solid phase, and thereafter a second polypeptide binding agent binds to the analyte, thus forming an insoluble three-part complex. See, e.g., U.S. Pat. No. 4,376,110. The second polypeptide binding agent may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme. See, for example, chapter 18, Current Protocols in Molecular Biology, Ausubel et al., eds., John Wiley & Sons, New York, N.Y. (1995).

Yet another example of an assay method involves fluorescent resonance energy transfer (FRET) emissions. For example, one compound is labeled with a FRET donor molecule and its binding partner is labeled with a FRET acceptor molecule, or vice versa. When binding occurs between the binding partners, the FRET donor and FRET acceptor molecules are brought into proximity and emit fluorescence at a certain wavelength. A narrow band pass filter can be used to block all wavelengths except that of the label. FRET molecule pairs are commercially available in the art (e.g., from Invitrogen), and may be used according to the manufacturer's protocol. FRET emissions are detected using optical imaging techniques, such as a CCD camera.

Yet another example of an assay method is bioluminescence resonance energy transfer (BRET), for example using biosensors as described in WO/06086883.

Another type of assay involves labeling with an electron donor. One molecule is labeled with an electron donor and the interacting molecule is bound to an electrical contact, or vice versa. When binding occurs between the binding partners, the label donates electrons to the electrical contact. See, for example, Ghindilis, Biochem Soc Trans. 28:84-9, (2000) and Dai et al., Cancer Detect Prev. 29:233-40 (2005), which describe methods for electro immunoassays. The electron contact would then be read by an A to D (analog to digital) converter and quantified. The higher the electron count the more interactions took place.

One embodiment of a label capable of single molecule detection is the use of plasmon-resonant particles (PRPs) as optical reporters, as described in Schultz et al., Proc. Natl. Acad. Sci. USA 97:996-1001 (2000), incorporated herein by reference. PRPs are metallic nanoparticles, e.g. 40-100 nm in diameter, which scatter light because of a collective resonance of the conduction electrons in the metal (the surface plasmon resonance). The magnitude, peak wavelength, and spectral bandwidth of the plasmon resonance associated with a nanoparticle are dependent on the particle's size, shape, and material composition, as well as the local environment. By influencing these parameters during preparation, PRPs can be formed that have scattering peak anywhere in the visible range of the spectrum. For spherical PRPs, both the peak scattering wavelength and scattering efficiency increase with larger radius, providing a means for producing differently colored labels. Populations of silver spheres, for example, can be reproducibly prepared for which the peak scattering wavelength is within a few nanometers of the targeted wavelength, by adjusting the final radius of the spheres during preparation. Because PRPs are bright, yet nanosized, they are used as indicators for single-molecule detection; that is, the presence of a bound PRP in a field of view can indicate a single binding event. An example of a surface plasmon resonance detector system is the BIAcore assay system. See, e.g., Malmquist, J Molec Recognition, 7:1-7 (1994).

Molecular interactions may also be detected using nanoparticle-derived techniques. See, for example, Ao et al., Anal Chem. 78:1104-6 (2006), which describes gold nanoparticle quenching, Tang et al., Biosens Bioelectron. 2005 Nov. 30, which describes SiO(2)/Au nanoparticle surfaces in antibody detection, and Lieu et al., J Immunol Methods. 307: 34-40 (2005), which describes silicon dioxide nanoparticles containing dibromofluorescein for use in solid substrate-room temperature phosphorescence immunoassay (SS-RTP-IA).

Any of the preceding measurements of binding affinity or binding rate parameter may be carried out in assays where one or more of the first component, second component and polypeptide binding agent are in solution, or in assays where one or more of the first component, second component and polypeptide binding agent are linked to a solid phase (covalently or noncovalently), or in assays where one or more of the first component, second component and polypeptide binding agent are expressed on a cell surface. The first and/or second components may each themselves be complexes of multiple compounds.

Solution Phase Biophysical Assays

In some embodiments, kinetic modulators can be identified using solution phase biophysical assays. By "solution phase" assay is meant an assay wherein the interaction to be measured takes place in a liquid. Solution affinity assays are useful tools to measure the equilibrium dissociation constant (also referred to as "affinity" or "$K_D$") of interactions at equilibrium. If a modulator can bind to proteins that form a complex, (e.g. a receptor/ligand interaction) and the modulator alters the affinity of that interaction, then a solution affinity assay can be used to determine the affinity of the interaction in the presence and absence of the kinetic modulator. It can also be used to measure a dose response to the modulator over a fixed concentration range of the complex components.

The present disclosure provides novel applications for equilibrium solution affinity measurements. Such assays enable the characterization and stratification of lead candidates on the basis of their ability to differentially modulate the affinity of the target-signaling partner interaction. Previous work on monitoring the reduction in affinity caused by inhibitory or steric-hindering drugs has utilized an excess of drug pre-complexed to one of the binding partners and has typically been done with surface plasmon resonance (SPR) technology or radio-ligand assay technology. In some aspects, the present disclosure allows for the use of drugs that bind epitopes that only exist when the ligand and receptor or other protein binding partners have formed their complex.

Example 1 describes methods for equilibrium solution affinity measurement using a model protein-protein complex. All reversible binding interactions could theoretically be affinity modulated by a drug and monitored in an assay very similar to the format described. The roles of the ligand and receptor in the assay format could be switched and doing so would serve as verification that the system was functioning properly. Any pair of interacting binding partners could be used, not just receptor-ligand pairs.

Such techniques serve as a highly sensitive method for the quantitation of the free (unbound) binding partner being interrogated. When this analysis is performed with a fixed concentration of one binding partner (B) and the other (A) is varied over a wide concentration range at least one log above and below the $K_D$ value of the interaction, then the amount of unbound B can be measured and the data fitted to a model that gives the $K_D$ value for the interaction. This experiment could be performed in the presence and absence of varying concentrations of the kinetic modulating drug, allowing for detailed characterization of the affinity enhancement. By measuring the free binding partner B and not the drug of interest, the monitoring of the A-B interaction affinity can be determined independently from the drug-complex interaction.

Such assays can be used to screen for drugs which modulate the affinity of binding interactions. This can have applications in the development of drug therapies and more sensitive diagnostic and analytical assays. Furthermore the assays allow the extent of the affinity modulation to be characterized in detail, even to drugs that recognize epitopes which are created only after a complex has formed. The present disclosure allows for the stratification and ranking of multiple drug candidates for their potency in affinity modulation.

Solid-Phase Biophysical Assays

In some embodiments, kinetic modulators can be identified using solid phase biophysical assays. By "solid phase" is meant a non-aqueous, inert matrix to which a test compound or complex component of the present invention can adhere. Examples of solid phases encompassed herein include those formed partially or entirely of glass (e.g., controlled pore glass), polysaccharides (e.g., agarose), polyacrylamides, polystyrene, polyvinyl alcohol, silicones metal, metal-alloy, anopol, polymers, nylon, or microarrays such as protein chips. In certain embodiments, depending on the context, the solid phase can comprise the well of an assay plate, a filter, a membrane, a chromatographic resin, or a bead. This term also includes a discontinuous solid phase of discrete particles, such as those described in U.S. Pat. No. 4,275,149.

In some embodiments, a test compound or complex component is attached or linked to a solid phase using any means known in the art, including but not limited to covalent bonding or indirect attachment through selective binding pairs (e.g., biotin with avidin, glutathione with GST, histidine tag with Ni).

A number of solid phase assay formats are known in the art, including microplates, beads, resins, chips etc. For example, the FMAT™ (fluorimetric microvolume assay technology; Applied Biosystems, Foster City, Calif.) system could use cells or receptor bound to beads with either a fluorescently labeled or biotinylated ligand. This has the potential to be run as a completely homogeneous assay format. A virtually identical format could be employed using the Luminex™ system (Luminex Corp., Austin, Tex.) where a similar bead based system is used. The main difference between the FMAT™ and Luminex™ assay formats is in the method of detection. The Luminex™ platform flows the beads through an optical flow cell to measure fluorescent emission from the beads and the FMAT™ images the fluorescence in a narrow plane very near the base of the well of the microplate. Alternatively electrochemiluminescence systems would be readily applicable to screening for affinity modulators due to their high sensitivity and homogenous capacity. These systems, such as the Tricorder™ (BioVeris Corp., Washington D.C.) use ruthenium derived electrochemiluminescent detection technologies. The assay formats that could be optimized for this system would be very similar to the other systems with the primary difference being the use of electrochemiluminescent labeling technology and detection instrumentation.

Suitable assays include microplate-based assays designed to detect modulation of the affinity of a labeled (e.g., biotinylated) target for its binding partner by an interacting modulator. The assay may be homogeneous or semi-homogeneous. A homogeneous assay is an assay where all the components are mixed together, incubated, and then analyzed. A semi-homogeneous assay is one where the majority of the reaction takes place as a complex mixture, but a washing step is required prior to the addition of a final reagent and analysis, in contrast to a typical stepwise assembly sandwich assay where each component is added then washed off before the next component is added. In some embodiments the assay is an immunoassay. In certain embodiments the assay is a semi-homogeneous Enzyme Immuno-Assay (EIA), allowing modulations of the equilibrium binding constants of binding partners to be monitored by using the amount of labeled (e.g., biotinylated) analyte captured on the EIA plate as a readout. At labeled analyte concentrations well below saturation in a equilibrium, or almost equilibrium environment, changes in equilibrium affinity constants result in more or less of the analyte being retained on the microplate.

In some embodiments, assays for kinetic modulators may be structured as follows. The binding partner for the analyte is immobilized on a microplate such as an EIA plate. The plate is then blocked with an irrelevant protein or blocking agent (e.g., bovine serum albumin, casein, ChemiBlock™ (Millipore, Billerica, Mass.), irrelevant IgG, etc or any combination of blocking agents). Following blocking, the plate is washed and added to the wells is a mixture of modulator, labeled analyte (e.g. biotinylated analyte) and secondary detection reagent (e.g. streptavidin) conjugated to a detectable moiety such as an enzyme or fluorophore. Various detectable moieties are known in the art including enzymes such as alkaline phosphatase or horseradish peroxidase, acting on a variety of colorimetric, fluorescent or luminescent substrates. Europium may be used for time resolved fluorescence detection and fluorophores may be used for direct fluorescence. Anti-ligand detection antibodies with various labels may also be employed, avoiding the need for biotinylated ligand as long as the antibodies used could detect receptor-bound ligand. In other embodiments, ligands which are directly conjugated to fluorophores or to colorimetric enzymes may be used.

The plates are generally incubated for several hours to allow the various interactions to approach equilibrium. After the incubation the plate is washed and developed immediately with a reporter substrate (e.g. colorimetric, fluorescent or luminescent substrates). The more labeled analyte captured on the plate, the higher the signal from the secondary detection reagent (e.g. streptavidin-alkaline phosphatase). If the modulator increases the affinity of the interaction, the amount of labeled (e.g. biotinylated) analyte bound to the plate will be greater than it would be in the absence of the kinetic modulator. If the modulator decreases the affinity of the interaction then the amount of labeled (e.g. biotinylated) analyte bound to the plate will be lower than it would be in the absence of the kinetic modulator.

Microplate assays may be used to monitor affinity modulation in several ways. In some embodiments a fixed polypeptide binding agent concentration is used and the labeled analyte titrated across various wells. This shows the affinity modulation effect as a shift in the titration curve versus the same analyte titration curve without the kinetic modulator present.

In some embodiments, once a titration of labeled analyte has been performed without modulator, a concentration can be selected for use in single labeled analyte concentration assay. This concentration should fall just above the bottom of the analyte's titration curve ($EC_{10-20}$). This allows for any enhancing modulations in the affinity of the ligand-receptor interaction to create an easily observable shift in the signal of the assay. Once a sensitive concentration of labeled analyte is determined, the assay can be performed in a screening mode where crude or purified modulator samples can be tested in single point analysis for affinity modulating effect. Also the assay can be performed with a titration of modulator at a fixed concentration of labeled analyte to demonstrate dose response of the modulator effect.

In some embodiments the labeling (e.g. biotinylation) of an analyte molecule may impact the binding ability or stability of that molecule. If this is the case an alternative assay format could be employed wherein unlabelled analyte is used in the experimental/equilibrium phase. When the samples are washed off before detection, a step could be added where an optimized amount of labeled analyte is added for a shorter amount of time, washed off then detected. This would allow the analyte that was bound in the equilibrium phase to act as competitor of the labeled analyte. Affinity enhancing antibodies would then yield a lower assay signal as the amount of unlabelled analyte prebound in the equilibrium step was higher, reducing the ability of the labeled analyte to bind to the plate. Other forms of semi-homogenous assays could also be developed using secondary reporter molecules or addition of tiered detection reagents to enhance the signal. These types of modifications are known to those skilled in the art. An example solid phase affinity assay is described in Example 2.

Cell-Based Biophysical Assays

In some embodiments kinetic modulators can be identified using cell-based biophysical assays. By "cell-based" is meant an assay in which at least one of the components of the signaling complex being tested is present on the surface of a cell. Such assays may be particularly advantageous for detecting modulators of binding interactions involving conformationally-sensitive proteins such as transmembrane receptors, including: G protein-coupled receptors (GPCRs; e.g. muscarinic acetylcholine receptor, adenosine receptors, adrenoreceptors, GABA receptors, angiotensin receptors, cannaboid receptors, cholecystokinin receptors, dopamine receptors, glucagons receptors, metabotropic glutamate receptors, histamine receptors, olfactory receptors, opiod receptors, rhodosin receptors, secretin receptors, serotonin receptors, somatostatin receptors, calcium-sensing receptor, chemokine receptors, sphingosine-1-phosphate (S1P) receptors); receptor tyrosine kinases (e.g. erythropoietin receptor, insulin receptor, insulin-like growth factor 1 receptor, Eph receptors); guanylyl cyclase receptors (e.g. receptors for natriuretic peptides, guanylin receptor); and ionotropic receptors (e.g. nicotinic acetylcholine receptor, glycine receptor, 5-HT$_3$ receptor, P2X receptors). A number of human plasma membrane receptors is listed at the Human Plasma Membrane Receptome database maintained by a group at Stanford University (Ben-Shlomo et al., "Signaling Receptome: A Genomic and Evolutionary Perspective of Plasma Membrane Receptors Involved in Signal Transduction" (Science Signaling STKE, Vol. 2003, Issue 187, pp. re9, 17 Jun. 2003); see also Ben-Shlomo et al., Molecular Endocrinology 21 (8): 2009-2014); each entry of the publication and database is incorporated herein by reference in its entirety. Additional databases for databases for receptor tyrosine kinase receptors (Grassot et al., 2003, "RTKdb: database of receptor tyrosine kinase" Nucleic Acids Res 31:353-358), G protein-coupled receptors (Horn et al., 2003, "GPCRDB information system for G protein-coupled receptors" Nucleic Acids Res 31:294-297), olfactory receptors (Skoufos et al., 2000, "Olfactory receptor database: a sensory chemoreceptor resource" Nucleic Acids Res 28:341-343), thyrotropin receptor mutations (Fuhrer et al., 2003 "The thyrotropin receptor mutation database: update 2003" Thyroid 13:1123-1126), nuclear receptors (Patterson et al., 1994 "The androgen receptor gene mutations database" Nucleic Acids Res 22:3560-3562; Gottlieb et al., 1998, "The androgen receptor gene mutations database" Nucleic Acids Res 26:234-238), and endocrine disruptor receptors (Nakata et al., 1999, "Development of the receptor database (RDB): application to the endocrine disruptor problem" Bioinformatics 15:544-552) are known; each entry of each of these publications and databases is incorporated herein by reference in its entirety. The Database of Ligand-Receptor Partners maintained by a group at University of California-Los Angeles (http://dip.doe-mbi.ucla.edu/dip/DLRP.cgi) contains subgroups of receptors for chemokines, TNF, fibroblast growth factor (FGF), and TGFβ ligands; each entry of the publication and database is incorporated herein by reference in its entirety. The Alliance for Cellular Signaling database contains extensive information on many signaling genes; each entry of the publication and database is incorporated herein by reference in its entirety. Likewise, the reactome database (Joshi-Tope et al., 2005 "Reactome: a knowledgebase of biological pathways" Nucleic Acids Res 33:D428-D432) and the Human Protein Reference Database (Peri et al., 2003, "Development of human protein reference database as an initial platform for approaching systems biology in humans," Genome Res 13:2363-2371) represent curated resources of protein-protein interactions for core pathways and reactions in human biology; each entry of each of these publications and databases is incorporated herein by reference in its entirety.

A variety of cell types may be used, so long as one component of the signaling complex to be modulated is present on the surface or in the membrane. The cells may express the signaling complex component from an endogenous, or an exogenous gene. Methods for introducing exogenous genes into host cells such that the host cells express the gene products are well known in the art. [See e.g. Sambrook et al., Molecular Cloning: A Laboratory Manual, 3rd Edition, Cold Spring Harbor, N.Y. (2001)]. Adherent or suspension cells may be used. Primary cell cultures, cell lines or engineered cell lines may be used. Suitable cell types may include: CHO, IM-9, HEK 293, and 3T3.

Several assay formats may be employed. In some embodiments, a receptor occupancy assay may be used. In certain embodiments cells are serum-starved to remove any bound ligand and modulator binding to the cells pre-incubated in either the presence or absence of ligand is then measured. Modulator binding may be detected using any suitable detection system. For example, the modulator may be tagged with an affinity or epitope tag and detected with a cognate binding species such as a metal ion, glutathione, anti-tag antibody. Suitable tags are well known in the art and include: c-myc, FLAG, poly-His, V5, HA, glutathione-S-transferase (GST), calmodulin-binding peptide (CBP), covalent yet dissociable NorpD peptide (CYD), strep-tag, heavy chain of protein C (HPC), and maltose-binding protein (MBP). Alternatively, the modulator may be detected with a specific antibody, e.g. a species-specific antibody or an anti-Fc antibody, conjugated to a detection agent such as a colorimetric enzyme (e.g. alkaline phosphatase, horseradish peroxidase), a fluorescent protein (e.g. phycoerythrin) a fluorescent dye (e.g. Alexa Fluor®, Invitrogen Corp., Carlsbad, Calif.) or other suitable agent. Positive kinetic modulators are expected to show higher binding affinity for the cells which were exposed to ligand than for the cells which were not. Negative kinetic modulators are expected to show lower binding affinity for the cells which were exposed to ligand than for the cells which were not. An example receptor occupancy assay is shown in Example 4.

In other embodiments, a labeled ligand assay may be used to measure differential ligand binding to cells in the presence or absence of test polypeptide binding agents. An example of a labeled ligand assay is described in Example 5.

Signaling Assays

The positive or negative modulatory activities of agents identified in the biophysical screens of the present disclosure may be confirmed by measuring the level of signaling in the presence and absence of the test polypeptide binding agent.

Signal transduction refers to any process by which a cell converts one kind of signal or stimulus into another. Intracellular signal transduction is largely carried out by second messenger molecules such as: calcium; lipophilic molecules e.g. diacylglycerol, ceramide, eicosanoids, and lysophosphatidic acid; nitric oxide. Thus a change in the level or location of second messenger may be used to measure signaling.

Examples of common signaling pathways include: the cAMP dependent pathway (in humans, cAMP works by activating protein kinase A), the MAPK/ERK pathway (a pathway that couples intracellular responses to the binding of growth factors to cell surface receptors); and the IP3/DAG pathway (phospholipase C cleaves the phospholipid phosphatidylinositol 4,5-bisphosphate (PIP2) yielding diacyl glycerol (DAG) and inositol 1,4,5-triphosphate (IP3). DAG remains bound to the membrane, and IP3 is released as a soluble structure into the cytosol. IP3 then diffuses through the cytosol to bind to IP3 receptors, particular calcium channels in the endoplasmic reticulum. These channels are specific to calcium and only allow the passage of calcium to move through. This causes the cytosolic concentration of calcium to increase, causing a cascade of intracellular changes and activity. In addition, calcium and DAG together work to activate protein kinase C, which goes on to phosphorylate other molecules, leading to altered cellular activity).

Signaling assays may, for example, detect the level, location, interactions or post-translational modification of cellular proteins. Gene expression may also be used to measure signaling.

A number of assays for measuring the level of signaling mediated by a signaling complex are available in the art. See, for example: Dove, Nat. Methods 3: 223-229 (2006);

The choice of assay will depend on the nature of the signaling pathway to be modulated. Assay kits available include: kits for assaying c-Fos, c-Jun, G Proteins, G Protein chimera clones, GPCRs, NF-kB p50, NF-kB p50/p65, NF-kB p65, and p38 MAPK; phosphoprotein assay kits such as for phosphothreonine and phosphotyrosine; kits for assaying second messengers, such as calcium, cAMP, cGMP and PIP3; kits for assaying s mall GTPase's such as Cdc42, Rac, Rap, Ras and Rho; and STAT assay kits (see e.g. www.biocompare.com). Available kits include ELISAs and phospho-specific ELISAs to detect non-phosphorylated or phosphorylated proteins of interest, isolation kits to extract subcellular components, enzymatic assays utilizing numerous detection methods, and targeted assays. Kits are available to measure signaling in pathways such as those relating to apoptosis, cytoskeleton/extracellular matrix, neuroscience, nitric oxide/cell stress, protein phosphorylation (see e.g. sigmaaldrich.com).

Effects of test compounds on signaling activity may be measured at a single ligand, or test compound concentration point. Alternatively or additionally, signaling assays may be performed using multiple ligand or test compound concentration points.

Exemplary methods for measuring signaling include, but are not limited to calcium flux assays, phosphorylation assays, gene expression assays, molecular transport assays, and other methods known to one of skill in the art.

Methods for determining changes in intracellular calcium due to cell signaling are well-known in the art. See e.g., Walsh et al. J. Biol. Chem., 283:16971-16984, 2008 and Janas et al., Clin Exp Immunol. 139:439-446, 2005. Briefly, appropriate cells are first cultured with an agent that inhibits calcium accumulation in the cell, such as indomethacin, fluorescent dyes, such as URA-2, FLUO-3, FLUO-4, Calcium-3, Calcium 4, Calcium 5 and Calcium Green-1/AM (Molecular Devices, Sunnyvale, Calif.), Rhod-4 NW (ABD Bioquest, Sunnyvale, Calif.) that report increases in intracellular calcium due to changes in fluorescence signal upon calcium binding, or biosensor photoproteins, e.g., aequorin and PHOTINA® (Perkin Elmer, Waltham, Mass.), which provide a luminescent signal in response to elevation in intracellular calcium. Cells are then contacted with a polypeptide of the invention, and the changes in intracellular calcium levels determined using such techniques as flow cytometry, Fluorometric Imaging Plate Reader (FLIPR), confocal fluorescent microscopy, calcium chip methods (e.g., Cell Kinetics, Lod, Israel) or other calcium detection methods known in the art.

Tyrosine or serine phosphorylation assays are often used to determine activation of cellular pathways involving receptor activation, and methods for detection of phosphotyrosine are readily available in the art. Sample protocols are disclosed in, e.g., Walsh et al., J. Biol. Chem., 283:16971-16984, 2008 and Ausubel et al., Current Protocols in Molecular Biology, John Wiley & Sons, New York, N.Y., Ch. 18.4.1-18.4.7, 1997. Appropriate cells are contacted with a polypeptide of the invention for a sufficient period of time to induce cell activation, for example 15 to 30 minutes, the cells are lysed and proteins resolved on an SDS-PAGE gel. The gel is then probed with an anti-phosphotyrosine or anti-phosphoserine antibody, and the level, type and protein-specific phosphorylation assessed using techniques in the art, such as chemiluminescence. Induction of phosphorylation is also measurable using antibodies specific for phosphphotyrosine or phosphoserine, as well as antibodies specific for receptors and/or other proteins in the phosphorylated state in assays such as enzyme linked immunosorbant assay (ELISA) and other microplate-based assays such as kits available from Meso Scale Discovery, Gaithersburg, Md.), or flow cytometry based assays from BD Biosciences, (San Jose, Calif.), or Millipore (Billerica, Mass.).

Methods for detecting gene expression are well-known in the art. Gene expression induced by contacting cells with a polypeptide of the invention is determined using techniques known in the art, including, but not limited to, Northern blot detection of mRNA for downstream signaling events or a transcript of interest, gene reporter assays, differential display, subtractive DNA assays and serial analysis of gene expression (SAGE) (See e.g., Ausubel et al., Current Protocols in Molecular Biology, John Wiley & Sons, New York, N.Y., Ch. 4 and 25, 1996, 2001 and 2007). Additionally, gene arrays are available, e.g., GeneChip Human Genome U133 Plus 2.0 Arrays, to determine levels of gene expression in a cell population or subject after contacting with a polypeptide of the invention.

Molecular transport induced by contact of cells with a polypeptide of the invention are assayed using techniques known in the art, including, but not limited to, lipid raft assays and pinocytosis assays. In one embodiment, cells are contacted with a polypeptide of the invention for a sufficient period of time to allow for signal induction, the cells are lysed and lipid and non-lipid material is separated by sucrose density gradient. Signaling proteins are isolatable from the different lipid raft fractions resolved in the sucrose gradient, and the ability of a polypeptide of the invention to affect signaling is determined by a change in the membrane bound protein composition of the lipid rafts isolated before and after contacting with a polypeptide of the invention. See e.g., Petrie et al., J. Immunol. 165:1220-7, 2000; Chamberlain et al., Proc Natl Acad Sci USA. 98:5619-24, 2001; Janas et al., Clin Exp Immunol. 139:439-446, 2005. Pinocytosis and transport of molecules is detectable using electron microscopy, by measuring the uptake of [$^{14}$C]sucrose (Chow et al., The FASEB Journal. 12:823-830, 1998), using flow cytometry, and other techniques known in the art.

An example of a phosphorylation assay is shown in Example 6.

In some aspects, biophysical screens are combined with functional screens to identify polypeptide binding agents with only kinetic modulating properties, i.e. without further antagonist or agonist properties, or to identify kinetic modulators that additionally have agonistic or antagonistic properties. Drugs with both kinetic modulating and agonistic properties can affect both affinity and efficacy of the endogenous target, thereby significantly expanding the repertoire of therapeutic intervention possibilities for a given target.

Methods of Producing Kinetic Modulating Drugs from Existing Compounds

Any polypeptide binding agents may be tested in the assays described herein to determine their kinetic modulating properties. In one embodiment, if a polypeptide binding agent is determined to have no kinetic modulating properties, it may be used in complex with its antigen, for immunization, panning etc, in order to obtain other polypeptide binding agents that bind to different epitopes and that may be more likely to produce kinetic modulating effects.

Variants of parental polypeptide binding agents may be produced by introducing mutations or chemical derivatization, including conjugation, using any methods known to those skilled in the art. The variants may then be screened in the assays disclosed herein, in order to identify those with desired kinetic modulating properties. The parental polypeptide binding agents may have no kinetic modulating activities, or may preferably have existing kinetic modulating properties that are desired to be increased, decreased, or altered in some other manner.

A number of methods for producing variants of parental drugs or drug candidates are available in the art.

Preparing Amino Acid Sequence Variants

It is contemplated that modified polypeptide compositions comprising one, two, three, four, five, and/or six CDRs of an antibody or polypeptide binding agent are generated, wherein a CDR or non-CDR region is altered to provide increased specificity or affinity to the antigen, or to provide increased modulation of binding affinity between the target and its signaling partner. For example, sites within antibody CDRs are typically modified in series, e.g., by substituting first with conservative choices (e.g., hydrophobic amino acid substituted for a non-identical hydrophobic amino acid) and then with more dissimilar choices (e.g., hydrophobic amino acid substituted for a charged amino acid), and then deletions or insertions may be made at the targeted site. For example, using the conserved framework sequences surrounding the CDRs, PCR primers complementary to these consensus sequences are generated to amplify the antigen-specific CDR sequence located between the primer regions. Techniques for cloning and expressing nucleotide and polypeptide sequences are well-established in the art [see e.g. Sambrook et al., Molecular Cloning: A Laboratory Manual, 2nd Edition, Cold Spring Harbor, N.Y. (1989)]. The amplified CDR sequences are ligated into an appropriate plasmid. The plasmid comprising one, two, three, four, five and/or six cloned CDRs optionally contains additional polypeptide encoding regions linked to the CDR.

Polypeptide binding agents comprising the modified CDRs are screened for binding affinity for the original antigen. Additionally, the antibody or polypeptide is further tested for its ability to neutralize the activity of its antigen. For example, antibodies of the invention may be analyzed as set out in the Examples to determine their ability to interfere with the biological activity of the target.

Modifications may be made by conservative or non-conservative amino acid substitutions described in greater detail below. "Insertions" or "deletions" are preferably in the range of about 1 to 20 amino acids, more preferably 1 to 10 amino acids. The variation may be introduced by systematically making substitutions of amino acids in an antibody polypeptide molecule using recombinant DNA techniques and assaying the resulting recombinant variants for activity. Nucleic acid alterations can be made at sites that differ in the nucleic acids from different species (variable positions) or in highly conserved regions (constant regions). Methods for altering antibody sequences and expressing antibody polypeptide compositions useful in the invention are described in greater detail below.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue or the antibody (including antibody fragment) fused to an epitope tag or a salvage receptor epitope. Other insertional variants of the antibody molecule include the fusion to a polypeptide which increases the serum half-life of the antibody, e.g. at the N-terminus or C-terminus.

The term "epitope tagged" refers to the antibody fused to an epitope tag. The epitope tag polypeptide has enough residues to provide an epitope against which an antibody there against can be made, yet is short enough such that it does not interfere with activity of the antibody. The epitope tag preferably is sufficiently unique so that the antibody there against does not substantially cross-react with other epitopes. Suitable tag polypeptides generally have at least 6 amino acid residues and usually between about 8-50 amino acid residues (preferably between about 9-30 residues). Examples include the flu hemagglutinin (HA) tag polypeptide and its antibody 12CA5 (Field et al., *Mol. Cell. Biol.* 8: 2159-2165 (1988)); the c-myc tag and the 8F9, 3C7, 6E10, G4, B7 and 9E10 antibodies thereto (Evan et al., *Mol. Cell. Biol.* 5:3610-16 (1985)); and the Herpes Simplex virus glycoprotein D (gD) tag and its antibody (Paborsky et al., *Protein Engineering* 3:547-53 (1990)). Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Another type of variant is an amino acid substitution variant. These variants have at least one amino acid residue in the antibody molecule removed and a different residue inserted in its place. Substitutional mutagenesis within any of the hypervariable or CDR regions or framework regions is contemplated. Conservative substitutions involve replacing an amino acid with another member of its class. Non-conservative substitutions involve replacing a member of one of these classes with a member of another class.

Conservative amino acid substitutions are made on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E).

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Affinity Maturation

Affinity maturation generally involves preparing and screening antibody variants that have substitutions within the CDRs of a parent antibody and selecting variants that have improved biological properties such as stronger binding affinity relative to the parent antibody. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity). See e.g., WO 92/01047, WO 93/112366, WO 95/15388 and WO 93/19172.

Current antibody affinity maturation methods belong to two mutagenesis categories: stochastic and nonstochastic. Error prone PCR, mutator bacterial strains (Low et al., *J. Mol. Biol.* 260, 359-68 (1996)), and saturation mutagenesis (Nishimiya et al., *J. Biol. Chem.* 275:12813-20 (2000); Chowdhury, P. S. *Methods Mol. Biol.* 178, 269-85 (2002)) are typical examples of stochastic mutagenesis methods (Rajpal et al., *Proc Natl Acad Sci* USA. 102:8466-71 (2005)). Nonstochastic techniques often use alanine-scanning or site-directed mutagenesis to generate limited collections of specific variants. Some methods are described in further detail below.

Affinity Maturation Via Panning Methods—

Affinity maturation of recombinant antibodies is commonly performed through several rounds of panning of candidate antibodies in the presence of decreasing amounts of antigen. Decreasing the amount of antigen per round selects the antibodies with the highest affinity to the antigen thereby yielding antibodies of high affinity from a large pool of starting material. Affinity maturation via panning is well known in the art and is described, for example, in Huls et al. (*Cancer Immunol Immunother.* 50:163-71 (2001)). Methods of affinity maturation using phage display technologies are described elsewhere herein and known in the art (see e.g., Daugherty et al., *Proc Natl Acad Sci* USA. 97:2029-34 (2000)).

Look-Through Mutagenesis—

Look through mutagenesis (LTM) (Rajpal et al., *Proc Natl Acad Sci* USA. 102:8466-71 (2005)) provides a method for rapidly mapping the antibody-binding site. For LTM, nine amino acids, representative of the major side-chain chemistries provided by the 20 natural amino acids, are selected to dissect the functional side-chain contributions to binding at every position in all six CDRs of an antibody. LTM generates a positional series of single mutations within a CDR where each "wild type" residue is systematically substituted by one of nine selected amino acids. Mutated CDRs are combined to generate combinatorial single-chain variable fragment (scFv) libraries of increasing complexity and size without becoming prohibitive to the quantitative display of all variants. After positive selection, clones with stronger binding affinity are sequenced, and beneficial mutations are mapped.

Error-Prone PCR—

Error-prone PCR involves the randomization of nucleic acids between different selection rounds. The randomization occurs at a low rate by the intrinsic error rate of the polymerase used but can be enhanced by error-prone PCR (Zaccolo et al., *J. Mol. Biol.* 285:775-783 (1999)) using a polymerase having a high intrinsic error rate during transcription (Hawkins et al., *J Mol Biol.* 226:889-96 (1992)). After the mutation cycles, clones with stronger binding affinity for the antigen are selected using routine methods in the art.

DNA Shuffling—

Nucleic acid shuffling is a method for in vitro or in vivo homologous recombination of pools of shorter or smaller polynucleotides to produce variant polynucleotides. DNA shuffling has been described in U.S. Pat. No. 6,605,449, U.S. Pat. No. 6,489,145, WO 02/092780 and Stemmer, *Proc. Natl. Acad. Sci.* USA, 91:10747-51 (1994). Generally, DNA shuffling is comprised of 3 steps: fragmentation of the genes to be shuffled with DNase I, random hybridization of fragments and reassembly or filling in of the fragmented gene by PCR in the presence of DNA polymerase (sexual PCR), and amplification of reassembled product by conventional PCR.

DNA shuffling differs from error-prone PCR in that it is an inverse chain reaction. In error-prone PCR, the number of polymerase start sites and the number of molecules grows exponentially. In contrast, in nucleic acid reassembly or shuffling of random polynucleotides the number of start sites and the number (but not size) of the random polynucleotides decreases over time.

In the case of an antibody, DNA shuffling allows the free combinatorial association of all of the CDR1s with all of the CDR2s with all of the CDR3s, for example. It is contemplated that multiple families of sequences can be shuffled in the same reaction. Further, shuffling generally conserves the relative order, such that, for example, CDR1 will not be found in the position of CDR2. Rare shufflants will contain a large number of the best (e.g. highest affinity) CDRs and these rare shufflants may be selected based on their superior affinity.

The template polynucleotide which may be used in DNA shuffling may be DNA or RNA. It may be of various lengths depending on the size of the gene or shorter or smaller polynucleotide to be recombined or reassembled. Preferably, the template polynucleotide is from 50 bp to 50 kb. The template polynucleotide often should be double-stranded.

It is contemplated that single-stranded or double-stranded nucleic acid polynucleotides having regions of identity to the template polynucleotide and regions of heterology to the template polynucleotide may be added to the template polynucleotide, during the initial step of gene selection. It is also contemplated that two different but related polynucleotide templates can be mixed during the initial step.

Alanine Scanning—

Alanine scanning mutagenesis can be performed to identify hypervariable region residues that contribute significantly to antigen binding. Cunningham and Wells, (*Science* 244:1081-1085 (1989)). A residue or group of targeted residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution.

Computer-Aided Design—

Alternatively, or in addition, it may be beneficial to analyze a crystal structure of the antigen-antibody complex to identify contact points between the antibody and antigen, or to use computer software to model such contact points. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Advantages of Kinetic Modulating Drugs

Kinetic modulating drugs are expected to provide several advantages as therapeutic agents in comparison to standard therapies such as competitive antagonists, agonists and ligand replacement. Such advantages may include those outlined below.

(1) Self-limiting activity. At saturating levels, kinetic modulating drugs have decreased potential for toxic effects due to concentration-independent limits on the activity of the drug. Modulators with limited cooperativity will have a ceiling level to their effect, irrespective of the administered dose. Unlike conventional drugs, kinetic modulators achieve saturation beyond which increases in the concentration of the modulator have no additional effect on function. The effect is limited by the extent of cooperativity (either positive or negative) between the modulator and the endogenous signaling complex component (e.g. ligand). The cooperativity-defined boundary enhances the safety profile of kinetic modulating drugs with respect to dosing regimens. Hence, kinetic modulating drugs could be given in larger more frequent doses than conventional drugs, while maintaining a favorable overall safety profile, providing increased efficacy due to the ability to maintain continuously saturating levels of drug.

(2) Complex component-dependent activation/inhibition limits side-effects. Unlike agonists or antagonists, a kinetic modulator can be inactive in the absence of the endogenous complex component (e.g. ligand) and active only when appropriate, such as when the complex component (e.g. ligand) is present. If a kinetic modulator does not possess appreciable agonism or antagonism, it can provide another powerful therapeutic advantage over conventional ligands, namely the ability to selectively tune up or down tissue responses only when the endogenous agonist is present. These properties enable kinetic modulating drugs to augment the endogenous spatial and temporal regulation of the target.

(3) Reduced off-target effects in vivo from greater target selectivity, tissue-, or subtype-, specificity. Kinetic modulating drugs may bind to sites other than the sites of interaction between the complex components. Such allosteric binding sites have not faced the same evolutionary pressure as orthosteric sites so are more diverse. Therefore, greater selectivity may be obtained by targeting allosteric sites. This is a particular advantage when there is a high degree of sequence conservation of the orthosteric site across target subtypes.

(4) Broader therapeutic window. Positive kinetic modulators can discriminate between activated and non-activated receptor states, while agonists indiscriminately activate all receptor states. Kinetic modulators that do not have appreciable agonism therefore have a broader therapeutic window than agonists. In addition, positive kinetic modulators may carry a reduced liability for receptor desensitization and/or tolerance, which can significantly expand the range of possible therapeutic applications. Negative kinetic modulators enable the reduction of signaling without completely blocking it. This may be useful, for example, where a receptor mediates pathological functions while at the same time mediating physiologically useful functions.

EXAMPLES

Example 1

Use of Equilibrium Solution Affinity Measurement Methods to Determine Receptor-Ligand Affinity in the Presence or Absence of Test Compounds
A. Model System This example describes methods for equilibrium solution affinity measurement using a model signaling complex, such as a receptor-ligand complex. The model system described here will use beads with an immobilized ligand, so the free receptor will be assayed and detected with an anti-receptor Cy5 labeled polyclonal antibody.

One of the binding partners, in this case the ligand, is immobilized to a solid phase that can be suspended by an automatic stirrer and allowed to form a small column bed. Typically the support is a bead of polymethylmethacrylate (PMMA), agarose, or other compatible material. The other binding partner, in this case the receptor, is detected in its bound state by a fluorescently-labeled, biotinylated, or otherwise-tagged molecule.

The KinExa™ instrument from Sapidyne Instruments can be used to perform the affinity analysis by kinetic exclusion assay (KinExA). In short, the interacting complex components, in this case the receptor and ligand, are mixed together in varying known concentrations in the presence or absence of test polypeptide binding agent and allowed to come to an equilibrium. The sample containing ligand, free receptor, and ligand-receptor complex is pulled rapidly through a small bead column that has been coupled or coated with one of the complex components, in this case the ligand, or an equivalent competitive binder. Free receptor is bound to ligand on the beads. Secondary label such as Cy5 fluorescently labeled secondary antibody to the receptor is then passed through the column. Labeled secondary antibody binds to the bound receptor. A buffer wash removes excess label, leaving fluorescence signal on the bead column directly proportional to the amount of free receptor in the original sample. The bead bed is positioned near a fluorescent detector to allow readout of the level of fluorescence signal.

A batch of beads with the immobilized ligand is prepared. A variety of bead types can be used, including PMMA, agarose, polystyrene etc. The coupling of the ligand to the beads can be performed using a variety of methods known to those skilled in the art. A stock of receptor is prepared at a concentration below the predicted $K_D$ of the receptor-ligand interaction. An experiment should be run with a variety of concentrations of receptor without ligand to determine the lowest concentration of receptor that can be used. By lowering the receptor concentration in the assay the affinity determinations become increasingly accurate. For a 500 pM interaction a receptor concentration of 50 pM should allow for accurate $K_D$ measurements. Enough receptor must be used to achieve an adequate signal and provide the dynamic range required.

Once an optimized receptor concentration is determined, a 2× stock of receptor is prepared (if final desired concentration is 50 pM then a 100 pM solution is made up), with and without test compound.

A serial dilution of ligand at 2× concentration is created. This dilution series should ideally contain points at least 10-fold above and below the $K_D$ values of the interaction. A 12-point titration plus a zero-ligand sample is usually sufficient to cover this type of range at a 1:2 dilution series.

Equal volumes of the ligand titration series are mixed with the receptor and receptor-plus-test compound samples and these are allowed to come to equilibrium. This can take from hours to several weeks depending on the kinetics of the interaction. If any of the kinetics of the interaction are known, they can be used to estimate time to equilibrium. The reaction approaches true equilibrium at a slow, but exponential rate, so it is likely not necessary to wait for a high affinity interaction to reach true equilibrium, since in a few days it is often >95 percent complete. It is, however, important to understand this relationship and evaluate it critically.

Once the required incubation time has been reached a dilution of the Cy5 labeled anti-receptor antibody is prepared. It is important that the labeled molecule is able to bind its antigen, in this case the receptor, when it is bound to its binding partner, in this case the ligand, or else the assay will have little to no signal. For the assay format described here, a 1 ug/mL solution of an anti-receptor Cy5 labeled polyclonal antibody is suitable.

The KinExa sample inlet tubes are placed into the sample vials. The KinExa instrument then analyzes the concentration of free receptor in every sample and plots it as percent free receptor over concentration of ligand. The curves are fitted to a model and the $K_D$ Value is determined. Example results are shown in FIG. 4 which are generated using the below equation where R is the receptor concentration and L is the ligand concentration.

$$R_{free} = \frac{(R_{tot} - L_{tot} - K_D)}{2} \pm \sqrt{\frac{(L_{tot} + R_{tot} + K_D)^2}{2} - L_{tot} \cdot R_{tot}}$$

B. IL-1β Signaling Complex

IL-1β is a highly potent cytokine that drives the acute phase inflammatory response and has an essential role in the innate immune response. While high levels of IL-1β have been implicated in inflammatory diseases such as rheumatoid arthritis, inflammatory bowel disease, acute respiratory distress syndrome, and Type 2 diabetes, low levels have beneficial effects on pancreatic beta cell function, proliferation, and survival, intestinal epithelial cell survival, and neuronal response to injury. As in many receptor-ligand systems, IL-1β signaling is complex, with multiple ligands interacting with membrane-bound and soluble forms of several receptors (Dinarello, Arthritis Rheum. 52 (7): 1960-1967, 2005). IL-1β signaling activity is mediated by a single receptor, IL-1 Receptor type I (IL-1RI) and its co-receptor IL-1 Receptor Accessory Protein (IL-1RAcP). A second IL-1 family member, IL-1α, signals through the same receptor complex but has not been implicated in inflammatory diseases. IL-1β activity is under tight physiological control, with multiple levels of negative regulation including: neutralization and endocytosis of excess IL-1β mediated by the decoy receptor IL-1 Receptor type II (IL-1RII); inhibition of circulating IL-1β mediated by multiple soluble forms of its receptors (sRI, RII, and sRAcP); and competitive inhibition by an inhibitory IL-1 homologue, IL-1 Receptor Antagonist (IL-1Ra). The complexity of this receptor-ligand system presents a challenge for the production of anti-IL-1β antibodies. It is proposed that the optimal therapeutic agent modulating this pathway would selectively reduce high-level IL-1β signaling to lower, beneficial levels while allowing neutralization of IL-1β activity by soluble receptors and clearance of IL-1β by receptor-mediated pathways without interfering with IL-1α signaling or IL-1Ra activity.

Biophysical Assay

A KinExA assay was configured to measure the concentration of free ligand (IL-1β) in samples of ligand-receptor (IL-1sRI or IL-1sRII) mixtures in the presence or absence of a test compound (anti-IL-1β antibody XOMA052, see U.S. Pat. No. 7,531,166)

Figure 5A:
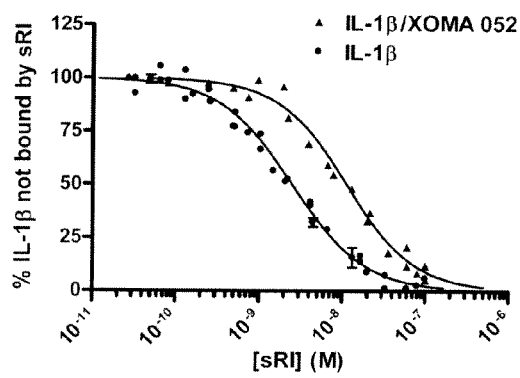
FIGS. 5A-5B show the effects of XOMA 052 on the affinity of IL-1β binding to IL-1 sRI (FIG. 5A), and to IL-1 sRII (FIG. 5B). XOMA 052 reduces the affinity of IL-1β binding to IL-1 sRI (A), but has no effect on the affinity of IL-1β binding to IL-1 sRII (B).
Figure 5B:
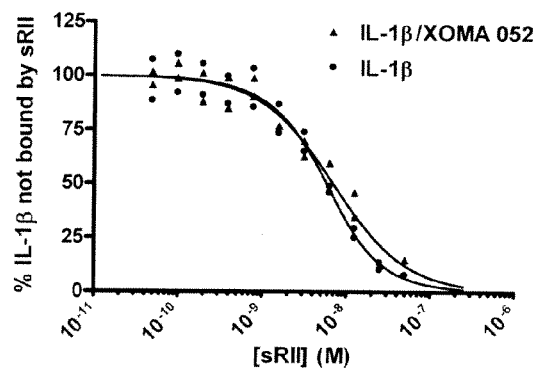

The equilibrium dissociation constants ($K_D$) of IL-1β±XOMA 052 binding to soluble IL-1 receptors (IL-1sRI: R&D Systems, cat#260-100/CF, and IL-1sRII: R&D Systems, cat#263-2R-050/CF) were determined using KinExA technology (Sapidyne, Inc). Equilibrium experiments were conducted by serially diluting soluble receptors from 150 nM to 4 pM in PBS (0.01M phosphate, pH 7.4, 0.15M NaCl, 0.02% azide) with 1% BSA sample buffer, into a constant binding site concentration (1 to 5 nM) of IL-1β alone or mixed with XOMA 052. To obtain $K_D$-controlled data, the binding site concentration was no more than two-fold above the $K_D$ (IL-1β=1 nM and IL-1β±XOMA 052=5 nM). For all experiments where XOMA 052 was present, the antibody concentration was maintained at a 100-fold molar excess over IL-1β to ensure that all of the cytokine was bound by XOMA 052. The IL-1β (±XOMA 052) plus receptor mixtures were incubated at room temperature (~22° C.) for 12-24 hours prior to assay initiation to allow complex formation to reach equilibrium. Following the incubation period, the mixtures containing receptor, IL-1β±XOMA 052, and IL-1sR/IL-1β complexes±XOMA 052, were drawn through a solid phase, consisting of receptor-blocking anti-IL-1β antibody-coupled beads, to capture IL-1β (±XOMA 052) not bound to receptor. The capture antibody was verified to completely compete with the receptor and not with XOMA 052. The captured IL-1β is directly proportional to the concentration of free IL-1β not bound by receptor remaining in the equilibrium reaction and was detected using a polyclonal anti-IL-1β antibody (R&D Systems, AB-201-NA), followed by a phycoerythrin-conjugated anti-goat IgG secondary antibody (Jackson ImmunoResearch laboratory cat #705-116-147) in the sample buffer. The bound signals were converted into relative values as a proportion of control in the absence of receptors. Two replicates of each sample were measured for all equilibrium experiments. The equilibrium titration data were fit to a 1:1 binding model using KinExA software (Version 2.4; Sapidyne Instruments). These measurements were repeated a total of five times for sRI and three times for sRII. The results show that XOMA 052 weakens the binding affinity of IL-1β binding to IL-1 sRI from 2 to 10 nM, but has no effect on the binding affinity of IL-1β binding to IL-1 sRII, which remains at 2 nM (FIG. 5). Measurements using surface plasmon resonance (SPR) were consistent with these results.

Another variation of this assay could be performed to rank potential drug candidates amongst each other. Once the full $K_D$ solution equilibrium experiment has been run, the conditions needed to generate a signal on the log linear portion of the curve are known. A ligand concentration is selected a little below the $EC_{50}$ value of the interaction without a kinetic modulating drug. Each drug candidate can then be tested at several concentrations. This allows for analysis of dose response to the drug and relative potency comparisons between potential drug candidates.

Functional Assays

Functional assays were performed to confirm the prediction that the reduction in the affinities of signal complex components will cause a shift in the cellular dose-response to IL-1β.

MRC-5 IL-6 Release Assay

MRC-5 human lung fibroblast cells (ATCC, Manassas, Va.) were seeded into a sterile 96-well tissue culture plate at 5000 cells per well in MEM complete growth medium (Invitrogen) with 10% fetal bovine serum (FBS; Hyclone). After an overnight incubation at 37° C. with 5% $CO_2$, supernatants were removed and replaced with growth medium containing recombinant human IL-1β (Peprotech, cat. 200-001B) plus either control IL-1β-blocking antibody (WO 2006/081139), anti-KLH (Keyhole Limpet Hemocyanin) isotype control antibody (IgG2; clone KLH8.G2 (XOMA)), or XOMA 052 at the concentrations indicated.

Figure 6A:
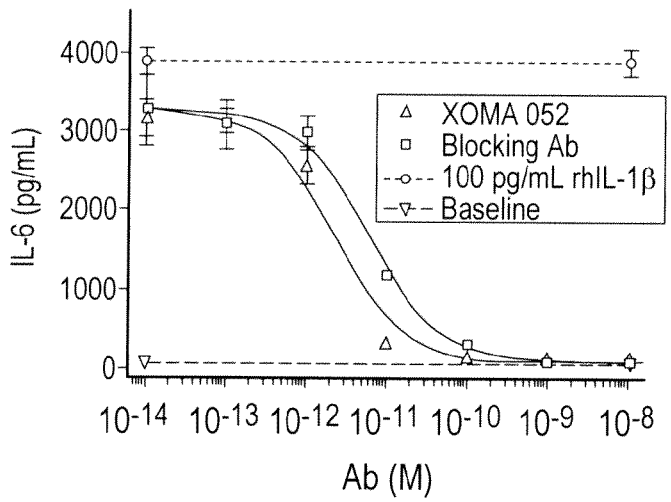
FIGS. 6A-6C show (FIG. 6A) neutralization of IL-1β activity by XOMA 052 at the EC50 of IL-1β for the cell assay, and (FIGS. 6B, 6C) that negative affinity modulation of the IL-1β to IL-1 sRI interaction results in an altered cellular dose-response to IL-1β resulting in an increase in the IC50. Negative affinity modulation of the IL-1 to IL-1 sRI interaction results in an altered cellular dose-response to IL-1.

An antibody potency assay was performed (FIG. 6A) whereby recombinant human IL-1β was pre-incubated with the indicated antibody for 1 hour at 37° C. prior to addition to the MRC-5 cells, and added at a final concentration of 100 pg/ml IL-1β.

An IL-1β dose-response assay was performed (FIG. 6B) using increasing amounts of IL-β pre-incubated overnight at room temperature with a 100-fold molar excess of antibody prior to addition to the MRC-5 cells.

Following a 20 hour incubation at 37° C. with 5% $CO_2$, cell supernatants were removed and diluted according to estimated IL-6 concentration and assayed for human IL-6 by ELISA (Quantikine™ human IL-6 ELISA, R&D Systems, cat# D6050) according to the manufacturer's instructions. All samples were set up and assayed in duplicate or triplicate.

Whole Blood IL-8 Induction Assay

Figure 6B:
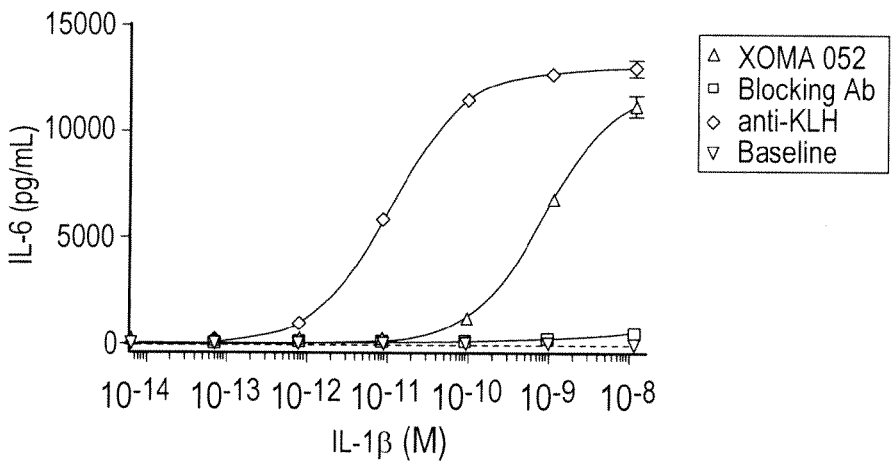
Figure 6C:
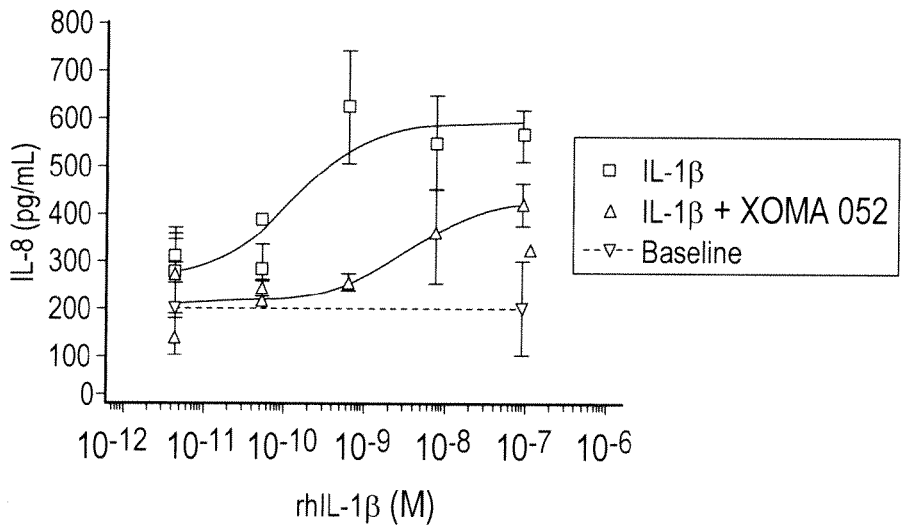

Normal human blood was collected by venipuncture into collection tubes containing heparin sulfate. An IL-1β dose-response assay was performed using increasing amounts of IL-β preincubated with a 10-fold molar excess of XOMA 052 for 1 hour at 37° C. in RPMI (Invitrogen) with 10% FBS prior to addition to whole blood. Samples were incubated for 6 hours at 37° C. in 96-well round bottom plates (Corning Costar, cat#3799) then lysed with Triton X-100 at a final concentration of 0.5% for 10 minutes. Lysates were centrifuged for 5 minutes at 2000 rpm to remove debris and transferred to a clean plate. After repeating the centrifugation step, lysates were transferred to a −80° C. freezer for overnight storage. The following morning lysates were thawed and tested for human IL-8 by ELISA (Quantikine human IL-8 ELISA, R&D Systems, cat# D8000C) according to manufacturer's instructions. All samples were set up and assayed in duplicate or triplicate. Results are shown in FIG. 6C.

Results

While XOMA 052 binding to IL-1β does not abrogate signal complex formation at high concentrations of IL-1β, it nonetheless is a potent inhibitor of IL-1β activity at physiological and pathologically relevant concentrations. XOMA 052 completely neutralizes 100 pg/mL of IL-1β in an MRC-5 cytokine release assay with an observed $IC_{50}$ in the low pM range. This is comparable to neutralization observed with a control blocking antibody (FIG. 6A), and around 10-fold more potent than recombinant IL-1ra.

The kinetic perturbation model predicts that the reduction in the affinities of signal complex components will cause a shift in the cellular dose-response to IL-1β. When XOMA 052 is in molar excess of the concentration of IL-1β, the antibody increases the $EC_{50}$ of the IL-1β dose response curve up to 60-fold in the MRC-5 cell IL-6 release assay relative to that of IL-1β in the presence of an isotype control antibody ($EC_{50}$ values of 815 pM versus 12 pM). Under the same conditions an IL-1β blocking antibody almost completely ablates cellular response across a broad range of IL-1β concentrations (FIG. 6B).

Similar dose-response shifts with XOMA 052 are seen in stimulation of IL-8 expression in whole blood (FIG. 6C), cinq1 in rat NRKE cells, and IL-8 in PBMCs, demonstrating that this effect is not unique to a particular assay system. Thus, under physiological conditions where high levels of IL-1β cause pathology (in pancreatic beta-cells, for instance), XOMA 052 will neutralize excess IL-1β while potentially allowing continued low-level beneficial signaling. Furthermore, XOMA 052 may allow for better responsiveness of the innate immune system to infection as compared to a complete blockade of IL-1β activity. The degree of signaling attenuation mediated by XOMA 052 is independent of the concentration of antibody when its concentration is sufficiently high to bind all available IL-1β. In those conditions the concomitant signaling output depends only on the concentration of ligand.

While reducing IL-1β affinity for IL-1RI causes attenuation of signaling, maintenance of efficient binding to IL-1RII is important because IL-1RII functions as a decoy receptor on responding cells to attenuate sensitivity to IL-1β. In addition, IL-1RII mediated internalization of IL-1β is an important pathway for clearance of IL-1β. When binding of a therapeutic antibody to its antigen of interest interrupts physiological clearance pathways, the prolonged half-life and high affinity of the antibody can cause the accumulation of antibody/antigen complexes. While such complexes are typically inactive, it may be necessary to maintain excess levels of antibody in order to ensure that any antigen that dissociates from the antibody is rapidly rebound by free antibody.

We have demonstrated that while XOMA 052 weakens the affinity of IL-1β binding to IL-1RI, it does not similarly weaken its binding to IL-1RII. Furthermore, XOMA 052 does not block binding of sRAcP to IL-1β/sRII complex. The ability of the IL-1β/XOMA 052 complex to bind IL-1RII and RAcP may allow clearance and neutralization of the cytokine by normal physiological mechanisms and thus reduce accumulation of long-lived complexes. In addition, retention of binding of the neutralizing soluble receptors to the XOMA 052/IL-1β complex should allow these molecules to regulate activity and thus avoid potential systemic activity by complexes before their clearance.

To test whether the ability of IL-1β/XOMA 052 complexes to bind IL-1 receptors affects clearance rates, we injected mice with recombinant human IL-1β, either free (incubated with a non-binding isotype control antibody) or pre-complexed with either XOMA 052 or a control blocking anti-IL-1β antibody (BM5), and measured the amount of total measurable IL-1β remaining in circulation after 48 hours by ELISA (BD OptEIA™ human IL-1β ELISA set, BD Biosciences, San Jose, Calif., cat#557953) as per kit instructions. In two separate experiments, C57B/6 mice were injected (n=4 per group) intravenously with 100 μl each of antibody pre-complexed with human IL-1β (1 mg/kg antibody with 20 ng IL-1β per mouse). Data for the circulating levels of BM5-IL-1β and XOMA 052-IL-1β-complexed antibodies after 48 hrs are shown in FIG. 7. In study 1, by 48 hours post injection, 7.7% of the IL-1β-complexed to BM5 remained in circulation; however, over the same time period, only 1.7% of the XOMA 052-IL-1β complex remained (p=0.006). In study 2, by 48 hours post injection, 8.1% of the IL-1β-complexed to BM5 remained in circulation while only 1.8% of the XOMA 052-IL-1β complex remained (p=0.02). While IL-1β complexed with either antibody cleared more slowly from circulation than free IL-1β, IL-1β bound to XOMA 052 cleared more rapidly than IL-1β bound to a blocking antibody. After 48 hours, an average of 4.6-fold less IL-1β bound to XOMA 052 was detected in the serum as compared to IL-1β bound to a blocking antibody. At the same time, concentrations of the total antibodies did not differ from each other, indicating that the difference did not result from differential clearance of the different antibodies.

The approach we outline here to attenuate rather than block IL-1β may yield important insights into the optimal reduction of IL-1β signaling required for disease modification in Type 2 diabetes, which is increasingly regarded as an inflammatory disease. There is evidence that high levels of IL-1β underlie the pathology of this disease by causing beta-cell dysfunction and apoptosis. However, low levels of IL-1β activity are required for maximum levels of stimulated insulin release and beta-cell proliferation and survival. Treatment of patients with ANAKINRA® (rhu IL-1ra) improves insulin secretion and glucose control but requires frequent dosing due to the rapid clearance of drug. A blocking antibody that completely neutralizes IL-1β activity will not allow low level signaling of IL-1β. A kinetic modulating (or regulatory) antibody such as XOMA 052 should reduce IL-1β activity, allowing a lower level of signaling at higher concentrations of IL-1β, thus regulating IL-1β activity within a beneficial range in T2D patients (see FIG. 8).

We have described here a recombinant antibody that differentially tunes the affinity of a ligand for binding to multiple receptors, allowing for context-dependent attenuation of ligand activity. There is increasing appreciation that many receptor-ligand systems are comprised of multiple ligands and receptors that generate complicated and context-dependent cellular effects. For some receptor systems these effects are beneficial at low levels and pathological at high levels, and have been difficult to approach mechanistically with monoclonal antibody therapeutics. The ability to use antibodies therapeutically as "rheostats" rather than "binary switches" introduces an additional level of subtlety and sophistication in therapeutic antibody design for regulating the activity of disease-relevant targets.

Example 2

Identification of Kinetic Modulators Using a Solid Phase Affinity Measurement Method The assay described here could be utilized for any two interacting binders of which one can be labeled (e.g. biotinylated) and the other immobilized on an EIA plate. This example uses granulocyte colony stimulating factor (GCSF) binding to its receptor (GCSFR) as a model system. The procedure used for this system is described below. Various conditions that may need to be optimized if different systems were to be utilized would include; plate coating conditions (both time, temperature, concentration, and buffer), analyte labeling conditions, and concentration of labeled (e.g. biotinylated) analyte.

Antibody modulators of the GCSF-GCSFR binding interaction were identified using the assay described below.

Purified GCSF (R&D Systems Minneapolis, Minn.) was biotinylated through activated NHS chemistry using $PEG_4$ Biotin (Pierce Protein Research Products cat#21329, Rockford, Ill.). GCSFR (R&D Systems Minneapolis, Minn.) was coated on an EIA plate (Nune, Rochester, N.Y.) in PBS at 2 ug/mL, 100 uL/well at 37° C. for 1 hour on a shaker. The plate was then blocked with a bovine serum albumin (BSA) and ChemiBlock™ (Millipore Billerica, Mass.) blocking solution for at least ½ hour at room temperature on a shaker. Any blocking solution that does not interfere with the reactants and sufficiently blocks nonspecific binding on the EIA plate could be used for the assay.

Samples were prepared on a dilution plate. Fab antibody fragments from an Omniclonal™ phage display library generated from mice immunized with GCSF/GCSFR complex (Biosite Inc., San Diego, Calif.) were screened as periplasmic extracts (PPE). For the single point assay, PPE samples were mixed 1:1 with biotinylated GCSF prepared at 0.15 ug/mL in blocking buffer and 50 uL of this solution was loaded onto the EIA plate. Potential hits from the single point assay (FIG. 9A) were purified and further tested at 1.8 ug/mL Fab concentration using titrations of ligand (FIG. 9B), or tested at various titrations at a fixed ligand concentration of 0.075 ug/mL (FIG. 9C). 50 uL/well of this antibody-GCSF-biotin solution was added to the blocked EIA plate and incubated at room temperature for >1 hour on a shaker. Negative controls of PBS and blocking buffer alone were included in the single point assay to establish a background signal level of roughly 0.83 OD405 nm. The purified Fab F5 was also included as 5 ug/mL as positive control and was selected from earlier rounds of screening. 50 uL of streptavidin labeled alkaline phosphatase (Zymed South San Francisco, Calif.) at 5 ug/mL in blocking buffer was then added to all the wells. The biotinylated analyte and antibody mixture remained in the well and was not removed or washed out. The plate was then incubated at room temperature on a shaker for an additional >1 hour (total reaction time of 3-4 hours was used in most assays; however longer incubations allow slower interactions to achieve equilibrium). The plate was then thoroughly washed and the developed with 100 uL/well p-NitroPhenyl Phosphate (PNPP; Pierce Protein Research Products Rockford, Ill.). After allowing the plate to develop for 5 to 15 minutes the reaction was stopped, using 100 uL/well of 1M NaOH. The absorbance was read on a microplate reader at 405 nm.

Figure 9A:
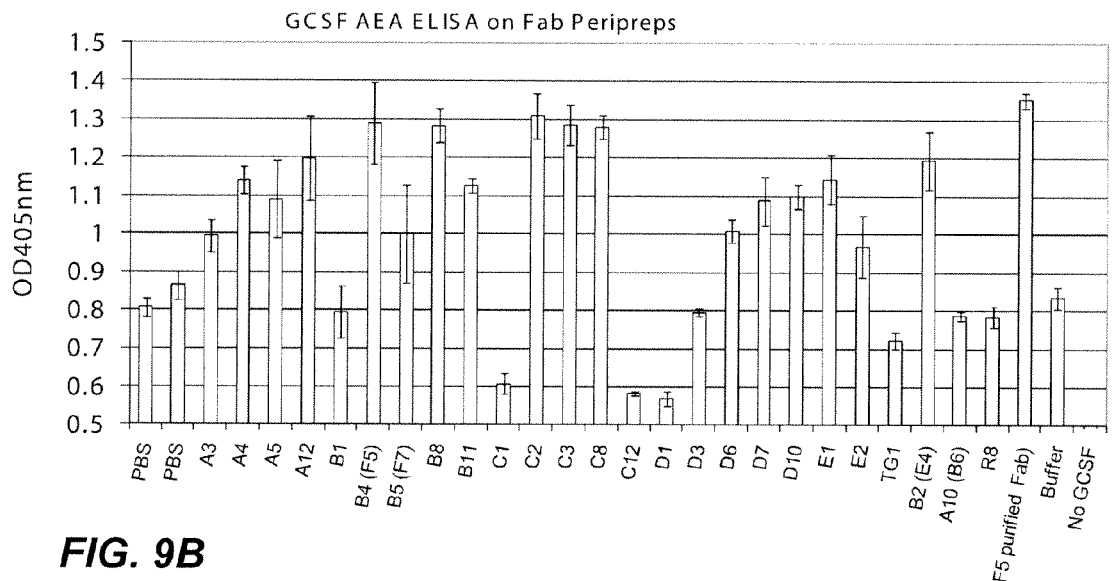
FIGS. 9A-9C show results from solid phase affinity measurement assays to identify antibodies which modulate the GCSF-GCSFR binding interaction as described in Example 2.
Figure 9B:
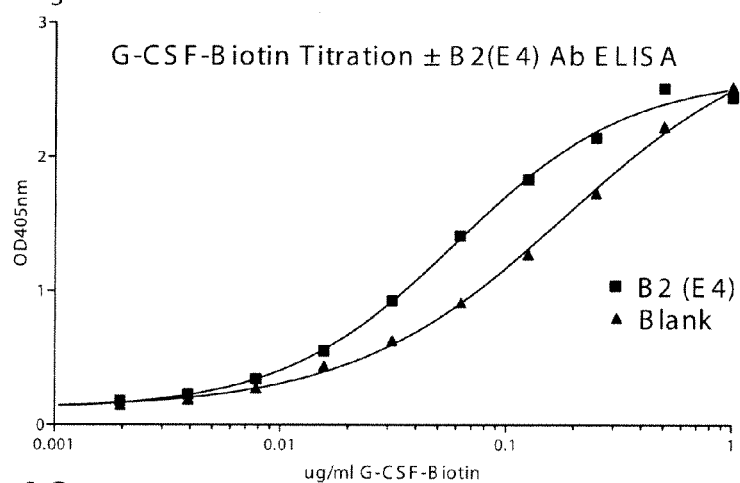
Figure 9C:
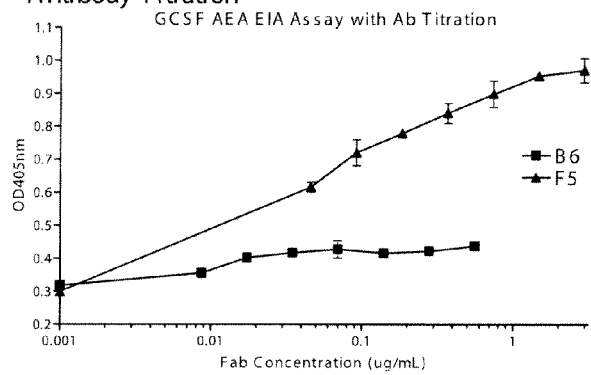

FIG. 9A shows the results of the single point in triplicate screening assay of the anti-GCSF/GCSFR Fab PPEs. Enhancement or inhibition of biotinylated GSCF binding to GCSFR compared to control was observed in the presence of several of the Fab clones tested at a fixed concentration of biotinylated GCSF:Fab mixture indicating the identification of both positive and negative modulating antibodies by the screen. FIG. 9B shows the results from a titration of GCSF-biotin in the presence and absence of one of the positive modulating Fabs, B2(E4). The biotinylated GCSF binding curve was left shifted in the presence of antibody B2(E4). This suggests enhanced affinity of the ligand receptor interaction in the presence of the antibody. FIG. 9C shows the results from titration of a further positive modulating Fab, B4(F5) as well as a weakly or non-modulating Fab B6(A10), against a fixed concentration of biotinylated GCSF. The B4(F5) Fab enhances binding of biotinylated GCSF to the plate-bound receptor in an antibody dose dependent manner.

Example 3

Identification of Kinetic Modulators of GCSF-GCSFR Binding Using a Cell Binding Measurement Method This example describes the use of FACS based assays to measure differential test compound (e.g. antibody) binding to GCSFR-transfected cells in the presence or absence of ligand (recombinant human GCSF (rhGCSF), R&D Systems, Minneapolis, Minn.). Anti-GCSF/GCSFR antibodies from phage display libraries (see example 2) were screened in ELISA assays to identify antibodies specific for binding to GCSF-GCSFR complexes. Because these antibodies are complex-specific, the mathematical model predicts that they will, modulate the kinetics of GCSF binding to GCSFR.

BaF3 is a murine lymphocytic cell line that does not respond to human GCSF but does respond to other cytokines in the family. This cell line is maintained in RPMI (Gibco/Invitrogen)/10% FBS (Hyclone/Thermo Scientific, Waltham, Mass.)/+2 ng/mL murine IL-3 (R&D Systems). The human GCSFR gene (Origene, Rockville, Md.) was stably transfected into the BaF3 cell line (Alexion AAC 621) using electroporation followed by G418 (Invitrogen, Carlsbad, Calif.) selection. Expression was confirmed by FACS analysis using a phycoerythrin-conjugated anti-GCSFRα (CD114) antibody [554538 (LMM741) BD Biosciences, San Jose, Calif.]. Stimulation of the transfected cells with human GCSF resulted in a proliferative response indicating a functional ligand/receptor interaction.

Figure 10A:
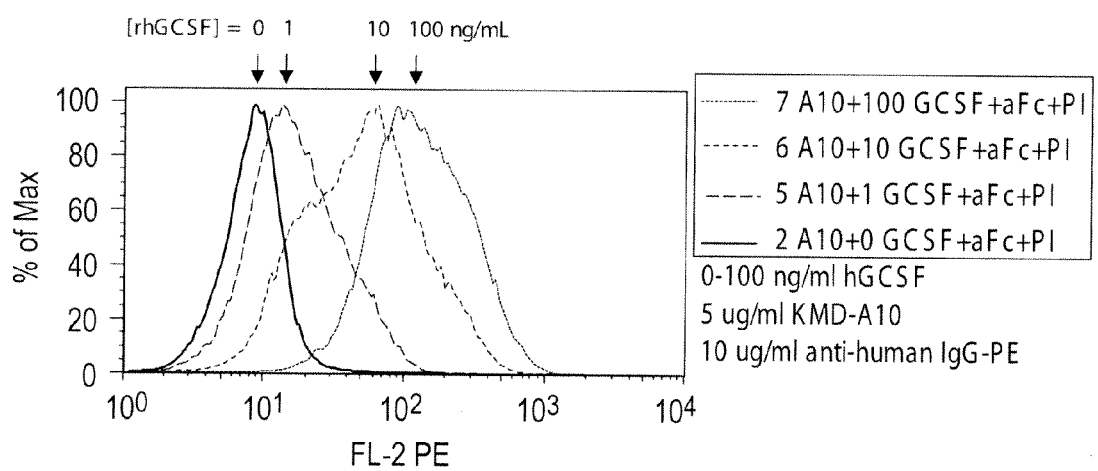
FIGS. 10A-10B show GCSF-dependent binding of A10 (B6) antibody to GCSFR-transfected BAF3 cells.
Figure 10B:
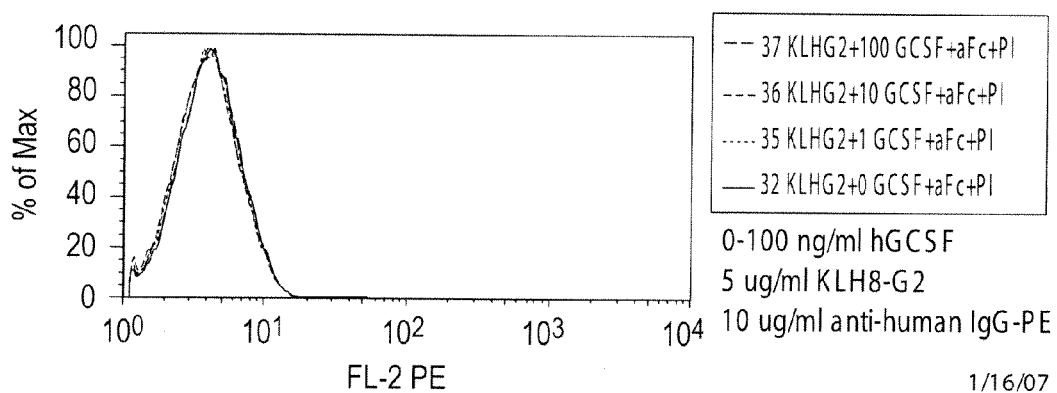
Figure 11A:
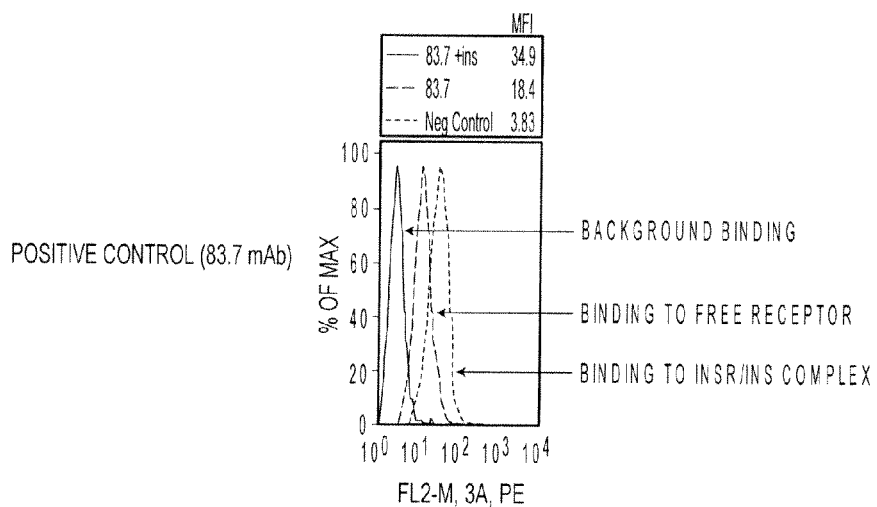
FIGS. 11A-E show sample results from a cell-based affinity measurement assay to identify antibodies which modulate the hINS-INSR binding interaction.
Figure 11B:
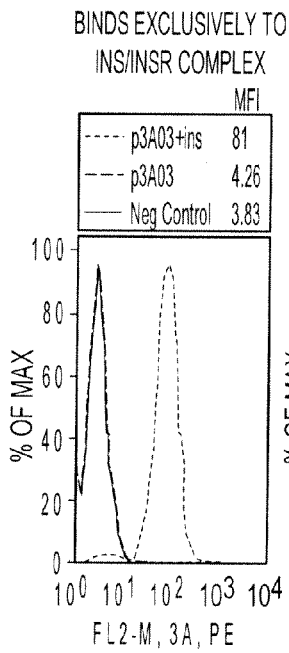
Figure 11C:
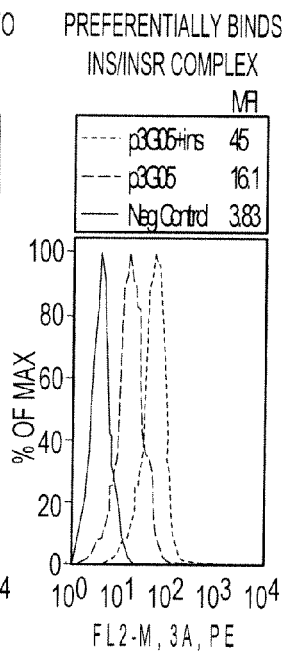
Figure 11D:
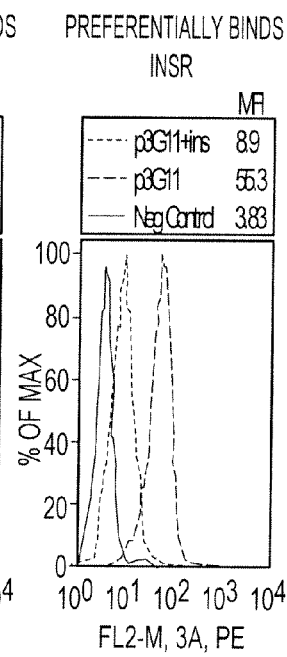
Figure 11E:
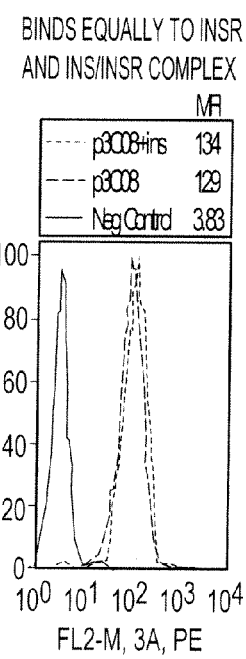

BaF3/GCSFR cells ($1 \times 10^6$ cells/sample) were washed 2× with PBS/2% FBS/0.1% azide, then incubated for 15 min on ice with rhGCSF diluted into the same buffer. GCSF/GCSFR test antibodies at 5 ug/mL in the presence or absence of rhGCSF (0, 1, 10 or 100 ng/mL) were added and incubated for 1 hour on ice, followed by addition of 10 ug/mL of phycoerythrin-labeled goat anti-human IgG (H+L) (Jackson Labs, Bar Harbor, Me.) and another 1 hour incubation on ice. If the test antibodies bound to the GCSF/GCSFR complex, the secondary antibody then bound to the test antibody and stained the cells. Several test antibodies were observed to bind to BaF3/GCSFR cells in the presence, but not in the absence of GCSF. These antibodies were shown not to bind to GCSFR or to GCSF, and therefore bound only to the GCSF/GCSFR signaling complex, suggesting that they may positively modulate signaling of the GCSF/GCSFR complex. Example data for antibody A10(B6) (see example 2) is shown in FIG. 10. Treatment of cells with increasing concentrations of rhGCSF and a fixed concentration of A10(B6) led to a dose dependent increase in mean fluorescence index (MFI) readout in the assay as compared to cells stained with rhGCSF and an irrelevant antibody (KLH8-G2).

Example 4

Identification of Kinetic Modulators of INS-INSR Binding Using a Cell-Based Antibody Affinity Measurement Method This example describes the use of flow cytometric (FACS) based assays to measure differential antibody binding to cells in the presence or absence of human insulin (hINS). Anti-insulin receptor (INSR) antibodies from phage display libraries were screened in the assays to identify modulators of INS-INSR binding.

IM-9 cells were obtained from the American Type Culture Collection (ATCC) and maintained in RPMI 1640+10% FBS. Prior to use in assays cells were washed in serum-free RPMI 1640, counted and the concentration adjusted to $2 \times 10^6$ cells/ml in RPMI 1640+0.5% BSA (Sigma-Aldrich). The cells were cultured overnight in this media and as such were designated as "serum-starved." These cells were washed once and resuspended at $2 \times 10^6$ cells/ml in PBS containing 0.5% BSA and 0.01% sodium azide (FACS buffer).

Cells exposed to insulin were resuspended in FACS buffer supplemented with 70 nM human insulin (Sigma-Aldrich, St. Louis, Mo.). Both cell populations (+hINS) or (−hINS) were incubated at 4° C. for 30 minutes, washed once with FACS buffer and resuspended at $2 \times 10^6$ cells/ml in FACS buffer. Twenty five microliter aliquots of cells were plated into 96 well plates, mixed with 25 ul of antibody or PPE and incubated on ice for 1 h.

The cells were then washed once with FACS buffer and the binding of the antibody was detected by the addition of 25 ul of an appropriate fluorochrome-conjugated secondary antibody. If the initial incubation had been with PPE containing a myc-tagged antibody, 25 ul of a 1/1000 dilution of an anti-c-myc antibody (Roche) was added to the wells and the cells incubated on ice for 30 mins. The cells were then washed once with FACS buffer and the binding of the anti-c-myc revealed by the addition of a phycoerythrin-conjugated anti-mouse IgG. After a final 15 min incubation on ice the cells were washed and the pellets resuspended in FACS buffer. The cells were analyzed on a FACScan™ (Becton-Dickinson, Milipitas, Calif.) and the data analysed in both FlowJo™ (Treestar, Ashland, Oreg.) and Microsoft Excel™.

This assay allowed the detection of four types of antibody, examples of which are shown in FIG. 11:
1. Antibodies that only bind to IM-9 cells if they have been exposed to human insulin (bind exclusively to INS/INSR complex)
2. Antibodies that bind more strongly to IM-9 cells if they have been exposed to human insulin (bind preferentially to INS/INSR complex)
3. Antibodies that bind less strongly to IM-9 cells if they have been exposed to human insulin (bind preferentially to uncomplexed INSR)
4. Antibodies that bind to IM-9 cells independent of the exposure of the IM9 cells to human insulin (bind equally to uncomplexed INSR and INS/INSR complex)

Antibodies were scored as predicted positive modulators if the ratio of antibody binding to INS/INSR complex: antibody binding to uncomplexed INSR was greater than 1.3. Antibodies were scored as predicted negative modulators if the ratio of antibody binding to INS/INSR complex: antibody binding to uncomplexed INSR was less than 0.6. Antibodies were scored as predicted non-modulators if the ratio of antibody binding to INS/INSR complex: antibody binding to uncomplexed INSR was greater than 0.9 but less than 1.1.

Experiments were performed as described above except that suspension adapted CHO-K1 transfected with either hINSR or muINSR were used instead of IM-9 cells, and cells exposed to insulin were resuspended in FACS buffer supplemented with 150 nM rather than 70 nM human insulin.

FACS binding data for a number of anti-INSR antibodies having positive or negative modulating activity in functional assays was reviewed. Negative modulators were found to have a binding ratio +insulin/−insulin of approximately 0.7 or less, with the majority having a ratio of 0.5 or less. Positive modulators were found to have a binding ratio +insulin/−insulin of approximately 1.0 or more, with the majority having a ratio of 1.3 or more. The binding ratios are shown in Table 3 below. Thus the ratio of differential receptor binding activity by a modulating antibody in the presence of absence of ligand is generally predictive of its modulating function (positive or negative).

TABLE 3

| Antibody | Functional Activity (by pAKT and/or pIRS-1 assay) | FACS area under log transformed data MFI ratio of clones binding to human INSR CHO-K1 with insulin and without insulin (+insulin/−insulin) |
|---|---|---|
| Ab050 | Negative modulator | 0.32 |
| Ab052 | Negative modulator | 0.30 |
| Ab055 | Negative modulator | 0.64 |
| Ab057 | Negative modulator | 0.56 |
| Ab061 | Negative modulator | 0.29 |
| Ab063 | Weak Negative modulator | 0.71 |
| Ab065 | Negative modulator | 0.28 |
| Ab070 | Negative modulator | 0.53 |
| Ab072 | Negative modulator | 0.37 |
| Ab074 | Negative modulator | 0.44 |
| Ab081 | Negative modulator | 0.42 |
| Ab059 | Positive modulator | 34.25 |
| Ab076 | Positive modulator | 0.98 |
| Ab077 | Positive modulator | 2.12 |
| Ab078 | Positive modulator | 66 |
| Ab079 | Positive modulator | 1.30 |
| Ab080 | Positive modulator | 1.37 |
| Ab083 | Positive modulator | 3.03 |

Example 5

Identification of Kinetic Modulators Using a Cell-Based Ligand Affinity Measurement Method This example describes the use of FACS based assays to measure differential ligand (human insulin) binding to cells in the presence or absence of test compounds (antibodies against the INSR). INSR antibodies from phage display libraries were screened in the assays to identify modulators of the INS-INSR complex.

IM 9 cells were obtained from the American Type Culture Collection (ATCC) and maintained in RPMI 1640+10% FBS. Prior to use in assays cells were washed in serum-free RPMI 1640, counted and the concentration adjusted to $2\times10^6$ cells/ml in RPMI 1640+0.5% BSA (Sigma-Aldrich). The cells were cultured overnight in this media and as such were designated as "serum-starved." These cells were washed once and resuspended at $2\times10^6$ cells/ml in PBS containing 0.5% BSA (binding buffer).

Serum-starved cells were pre-exposed to INSR antibodies at room temperature for 15 minutes and then incubated with various concentrations of biotinylated human insulin purchased from R&D Systems for a further 30 minutes at room temperature. The binding of the biotinylated insulin was revealed by the addition of a 1/100 dilution of streptavidin-phycoerythrin to this mixture for a further 15 minutes at room temperature. The cells were then washed once with binding buffer and resuspended in equal volumes of PBS containing 0.5% BSA, 0.1% sodium azide and 2% para-formaldehyde. The cells were analyzed on a FACScan™ (Becton-Dickinson, Milipitas, Calif.) and the data analyzed in both FlowJo™ (Treestar, Ashland, Oreg.) and Microsoft Excel™.

FIG. 12 shows the binding of biotinylated insulin to IM9 cells in the presence or absence of anti-INSR antibodies at different insulin concentrations. Antibody 83-7 enhanced binding of biotinylated insulin; antibody MA-20 diminished binding of biotinylated insulin; control mouse IgG had no effect on binding of biotinylated insulin.

Example 6

Confirmation of Kinetic Modulation Using a Phosphorylation Assay

The substrate proteins which are phosphorylated by the INSR include a protein called insulin receptor substrate 1 (IRS-1). IRS-1 phosphorylation to form pIRS-1 eventually leads to an increase in the high affinity glucose transporter (Glut4) molecules on the outer membrane of insulin-responsive tissues, and therefore to an increase in the uptake of glucose from blood into these tissues. A pIRS-1 assay was developed using the Luminex® technology platform (Luminex Corp., Austin, Tex.). Two modes of assay were developed: (a) titration of test antibody at a fixed concentration of insulin, and (b) titration of insulin at a fixed concentration of antibody. Anti-insulin receptor (INSR) antibodies selected on the basis of their differential binding to complexed and uncomplexed INSR (see examples 4 and 5) were tested in the assays to identify modulators of the INS-INSR complex.

Cell Treatment and Lysis

IM-9 cells were serum starved for 16-20 hours by counting, centrifuging, washing once with PBS and re-suspending at about $2\times10^6$ cells/ml in RPMI+0.5% Sigma Cohn V BSA (10% stock in RPMI, filter sterilized, stored 4° C.).

2× concentrated solutions of insulin (Sigma I-9278 (10 mg/ml) 1.77 mM liquid stock stored at 4' C) dilutions were prepared in RPMI+0.5% BSA. A standard insulin titration may include 4-fold serial dilutions of for example: 6.25 nM, 1.56 nM, 0.39 nM, 0.097 nM, 0.024 nM, 0.006 nM, 0.0015 nM, 0 nM.

Milliplex MAP Cell Signalling Buffer and Detection Kit (Millipore catalog #48-602) and Phospho-IRS-1 MAP Mates (Millipore catalog #46-627) were employed for the detection of pIRS-1 levels, according to the manufacturer's instructions. Briefly, V-bottomed plates containing 50 ul/well of 2× treatment media (RPMI containing 0.5% BSA+/−test antibody) were prepared and $1\times10^6$ cells serum-starved IM-9 cells resuspended in 50 ul RPMI+0.5% BSA were added per well. Antibody pretreatment was performed for 15 minutes prior to insulin treatment, either (a) as a bulk antibody/cell mixture at a single antibody concentration that was then applied to wells containing serial dilutions of insulin, or (b) by adding cells directly to wells containing serial dilutions of antibody and spiking in insulin at 0.1 nM. Plates were placed in a 37° C. incubator and centrifuged at 1500 rpm at RT for the last 3 minutes of treatment time (total of 15 minutes). Supernatant was removed by inversion and gentle blotting and treated cell pellets were lysed by triturating 3 times using a multi channel pipette with 100 ul Lysis Buffer prepared according to Table 1 below (labile components, i.e. protease inhibitors and benzonase, were added just prior to use). Plates were placed on a shaker at RT for 30 minutes and centrifuged at 3000 rpm for 10 minutes to clarify the lysate and remove any air bubbles that may have occurred during trituration. 50 ul of cleared lysate was removed and diluted 1:1 in 50 uL Assay Buffer-1 (AB-1) from the Detection Kit, triturated 2-3 times to mix and 50 ul was loaded onto a filter plate membrane on top of the 25 ul/well of diluted beads (see below).

TABLE 1

| Lysis Buffer | 10 wells 1 ml | 20 wells 2 mls | 25 wells 2.5 mls | 30 wells 3 mls | 40 wells 4 mls | 50 wells 5 mls | 60 wells 6 mls | 100 wells 10 mls |
|---|---|---|---|---|---|---|---|---|
| Lysis Buffer (Millipore cat. #43-040) | 1 | 2 | 2.5 | 3 | 4 | 5 | 6 | 10 |
| SDS 20% stock | 0.045 | 0.09 | 0.1125 | 0.135 | 0.18 | 0.225 | 0.27 | 0.45 |
| MgCl 50 mM (Invitrogen cat. #Y02016) | 0.02 | 0.04 | 0.05 | 0.06 | 0.08 | 0.1 | 0.12 | 0.2 |
| Protease inhibitors (50X) (Millipore cat. #20-201) | 0.02 | 0.04 | 0.05 | 0.06 | 0.08 | 0.1 | 0.12 | 0.2 |
| Benzonase EMD 1.01697.0002 @ 250 ug/ml | 0.004 | 0.008 | 0.01 | 0.012 | 0.016 | 0.02 | 0.024 | 0.04 |

Filter plate membranes (Millipore Catalog# MABVN1250) were pre-wet with 25 ul AB-1/well. Pre-wetting buffer was aspirated from the filter plate using a Millipore vacuum manifold, being careful not to dry the membranes, and any remaining liquid was blotted from the bottom of the filter plate. 25 ul of 1× bead suspension was added per well (pIRS-1 beads (Millipore catalog #46-627) were pre-prepared by diluting from 20× concentrate into AB-1 buffer and alternately vortexing and sonicating for 5 seconds 3 times each).

Filter plate wells were covered with a plate sealer, covered in aluminum foil to prevent light exposure, and incubated on a plate shaker (setting 7-8 on a Labline, Bella) plate shaker or similar model) at either RT for 2 hours or alternatively at 4° C. overnight.

Luminex Detection

The filter plates were aspirated and their bottoms blotted. The beads remained in the well and were washed with 100 µl of AB-1 and placed on shaker for 1-2 minutes. Plates were aspirated, and the wash step was repeated.

25 ul per well 1× biotinylated detection antibody, diluted from a 20× stock into AB-1 buffer, was added and plates were incubated on a shaker at RT for 1 hour. Plates were aspirated and their bottoms blotted. 25 ul per well 1× streptavidin phycoerythrin diluted from a 25× stock into AB-1 buffer, was added and plates were incubated on a shaker at RT for 15 minutes. 25 ul of Amplification Buffer (Millipore catalog #48-602) was added to each well, and plates were incubated on a shaker at RT for further 15 minutes. The plates were aspirated and the beads were resuspended in 150 uL AB-1 and read on the Luminex® instrument.

Results

FIG. 13 shows pIRS-1 assay results from titrations of insulin in the presence of fixed concentrations of representative test antibodies. MFIs were normalized such that the curve fit maximum was adjusted to 100%. Some antibodies (positive modulators) shifted the insulin titration curve to the left. Other antibodies (negative modulators) shifted the insulin titration curve to the right. Varying magnitudes of modulation were observed. The data in FIG. 13 shows antibodies producing up to a 9-fold increase, or up to a 24-fold decrease, in insulin sensitivity.

FIG. 14 is a table showing insulin EC50 values from the pIRS-1 assay in the presence or absence of fixed concentrations of various test antibodies. The results are ranked according to EC50 ratio +Ab/−Ab.

Example 7

Identification of Kinetic Modulators of TNF-α/TNFR Binding

A desired property of TNFα modulators would be to attenuate signal transduction of pathologic levels of TNFα while allowing sufficient signaling to support the innate immune response. Identification of such TNFα modulators is accomplished through the selection of polypeptide binding agents (e.g. antibodies) that reduce the affinity of TNFα for one or both of its receptor(s). The reduced affinity of TNFα for its receptor(s) is reflected in a number of standard analytical measurements such as faster off-rate, slower on-rate, lower association constant and higher dissociation constant. Alternatively, this can be detected by preferential binding (e.g. higher binding signal) of the polypeptide binding agents to TNFα alone compared to the TNFα-TNFR complex. Absence of binding signal for the TNFα-TNFR complex is indicative of a complete blocker and is not selected.

This example describes the use of assays to measure differential ligand (human TNFα) binding to TNFR1 or TNFR2 in the presence or absence of test compounds (TNFα-binding polypeptides). Because TNFR1 and TNFR2 are believed to play different roles in biological pathways it may be desirable to selectively modulate the activity of these two receptors (e.g. TNFα induces inflammatory responses primarily through interaction with TNFR1, while TNFR2 expression provides protection in an inflammatory colitis model; upregulation of TNFR1 provides neuroprotection in an ischemic preconditioning model). Selective modulation of the binding of TNFα to the two receptors could provide benefits in different diseases (Schneider et al Eur. J. Immunol. 39 (7):1743-53 (2009); Mukai et al, J. Biochem. 146 (2):167-72 (2009); Pradillo et al J. Cereb. Flow Metab. 25 (2):193-203 (2005)). TNFα-binding polypeptides are obtained de novo from sources such as naive phage display libraries and hybridomas, or are generated as variants of known of TNFα-binding polypeptides, such as infliximab, adalimumab, certolizumab pegol, HUMICADE™, golimumab, atacicept, and etanercept.

Antibody modulators of the TNFα-TNFR binding interaction can be identified using the assay described below.

Purified TNF (cat #210-TA-010, R&D Systems Minneapolis, Minn.) is biotinylated through activated NHS chemistry using $PEG_4$ Biotin (Pierce Protein Research Products cat#21329, Rockford, Ill.). TNFR1 or TNFR2 (cat #636-R1-025 or 1089-R2-025, R&D Systems Minneapolis, Minn.) is coated on an EIA plate (Nunc, Rochester, N.Y.) in PBS at 2 ug/mL, 100 uL/well at 37° C. for 1 hour on a shaker. The plate is then blocked with a bovine serum albumin (BSA) and ChemiBlock™ (Millipore Billerica, Mass.) blocking solution for at least ½ hour at room temperature on a shaker. Any blocking solution that does not interfere with the reactants and sufficiently blocks nonspecific binding on the EIA plate can be used for the assay.

Samples are prepared on a dilution plate. TNFα-binding scFv or Fab can be screened as periplasmic extracts (PPE) or hybridoma supernatants. For a single point assay, PPE samples are mixed 1:1 with biotinylated TNF prepared at 0.15 ug/mL in blocking buffer and 50 uL of this solution is loaded onto the EIA plate. Potential hits from the single point assay are purified and further tested using titrations of ligand, or tested at various titrations at a fixed ligand concentration. 50 uL/well of this antibody-TNF-biotin solution is added to the blocked EIA plate and incubated at room temperature for >1 hour on a shaker. Negative controls of PBS and blocking buffer alone are included in the single point assay to establish a background signal level. The biotinylated analyte and antibody mixture remains in the well and is not removed or washed out. The plate is then incubated at room temperature on a shaker for an additional >1 hour (total reaction time of 3-4 hours is used in most assays; however longer incubations allow slower interactions to achieve equilibrium). The plate is then thoroughly washed and the developed with 100 uL/well p-NitroPhenyl Phosphate (PNPP; Pierce Protein Research Products Rockford, Ill.). After allowing the plate to develop for 5 to 15 minutes the reaction is stopped, using 100 μL/well of 1M NaOH. The absorbance is read on a microplate reader at 405 nm.

Functional assays are performed to confirm that the reduction in the affinities of signal complex components will cause as shift in the cellular dose-response to TNFα. A variety of cell-based assays may be used for this purpose, including for example, assays described in U.S. Pat. Nos. 7,524,502 and 7,179,893 and U.S. application 2009/0155205.

Neutralization of TNFα-Induced Cytotoxicity in L929 Cells

TNFα-sensitive L929 mouse fibroblasts cells are seeded into 96-well tissue culture plates at a density of $5\times10^4$ cells in RPMI medium containing 10% fetal bovine serum (FBS). An antibody potency assay is performed by adding to the L929 cells RPMI+FBS media containing recombinant TNFα (500 pg/mL), pre-incubated for 1 hour at 37° C. with either anti-TNFα antibody or anti-KLH (Keyhole limpet hemocyanin) isotype control antibody at desired test concentrations. An TNFα dose-response assay is performed using increasing amounts of TNFα pre-incubated overnight at room temperature with 100-fold molar excess of antibody prior to addition to the L929 cells. The plates are then incubated overnight (18-24 hours) at 37° C. in 5% $CO_2$.

To determine the effect on TNFα-induced cell cytotoxicity, 100 uL of medium is removed from each well and 50 uL of 5 mg/mL 3,(4,4-dimethylthiazol-2-yl)2,5-diphenyl-tetrazolium bromide (MTT; Sigma Chemical Co., St. Louis, Mo.) in PBS is added. The plates are then incubated for 4 hours at 37° C. Fifty uL of 20% sodium dodecyl sulfate (SDS) is then added to each well and the plates are incubated overnight at 37° C. The optical density at 570/630 nm is measured, curves are plotted for each sample and $IC_{50}$ are determined by standard methods. All samples are set up and assayed in duplicate or triplicate.

Inhibition of ELAM-1 and/or ICAM-1 Expression on HUVEC

TNFα induces surface expression of endothelial cell adhesion molecules such as ELAM-1 and ICAM-1. The ability of anti-TNFα antibodies to neutralize TNFα stimulated production in human umbilical vein endothelial cells (HUVEC) of membrane bound ICAM-1 and or ELAM-1, is tested in an in vitro assay Briefly, HUVEC (ATCC No. CRL 1730) are grown in a 96-well plate in the presence of TNFα and varying concentrations of test or control antibody. The quantitative relative expression of membrane bound ICAM-1 and/or ELAM-1 is subsequently assessed by cell lysis and an enzyme linked immunoabsorbance assay (ELISA) using a commercially available detection reagents. HUVEC are seeded in 96-well plates at a density of $5\times10^4$ cells per well and allowed to adhere to the plate by incubation at 37° C., 5% $CO_2$ for at least 2 hours.

An antibody potency assay is performed by adding to the HUVEC media containing recombinant TNFα, pre-incubated for 1 hour at 37° C. with either anti-TNFα antibody or anti-KLH (Keyhole limpet hemocyanin) isotype control antibody at desired test concentrations. A TNFα dose-response assay is performed using increasing amounts of TNFα pre-incubated overnight at room temperature with 100-fold molar excess of antibody prior to addition to the HUVEC. The plates are then incubated for 24 hours at 37° C. in 5% $CO_2$. Following incubation, the medium is removed and the cells washed with PBS. The cells are lysed and the lysate assayed for the presence of ICAM-1 and/or ELAM-1. For assay, cleared lysate is analyzed for the presence of solubilized ICAM-1 or ELAM-1 by standard ELISA using commercially available reagents (e.g., sICAM-1 Module set; Bender Medsystems, Towcester, UK). All samples are set up and assayed in duplicate or triplicate.

Inhibition TNFα Induced Up-Regulation of IL-6 in Hs 27 Cells

Human foreskin fibroblast cells can be induced to produce IL-6 by exposure to TNFα. The ability of anti-TNFα antibodies to inhibit this up-regulation of expression is assessed by co-incubation of the cells with recombinant TNFα and the test antibodies, followed by a determination of the subsequent IL-6 levels secreted into the medium using a commercially available IL-6 detection system.

TNFα-sensitive human foreskin fibroblast cells Hs 27 (e.g., from the European Collection of Animal Cell Cultures (ECACC no. 94041901)), are seeded into 96-well tissue culture plates at a density of $2\times10^4$ cells in DMEM+Glutamax containing 10% fetal calf serum medium and allowed to adhere to the plate by overnight incubation at 37° C. An antibody potency assay is performed by adding to the Hs 27 cells media containing recombinant TNFα, pre-incubated for 1 hour at 37° C. with either anti-TNFα antibody or anti-KLH (Keyhole limpet hemocyanin) isotype control antibody at desired test concentrations. A TNFα dose-response assay is performed using increasing amounts of TNFα pre-incubated overnight at room temperature with 100-fold molar excess of antibody prior to addition to the Hs 27 cells. The plates are then incubated overnight (18-24 hours) at 37° C. in 5% $CO_2$. Following incubation, the medium is removed from and transferred to a U-bottomed 96 well plate for assay. The medium is analyzed for the presence of IL-6 using a commercial ELISA system (e.g., R&D Systems, as described above). All samples are set up and assayed in duplicate or triplicate.

Example 8

Effects of Partial Agonist Anti-INSR Antibodies on Glycemic Control in DIO Mice

In the diet-induced obesity (DIO) model, C57BL/6 mice can become insulin resistant after approximately 12-14 weeks on a high-fat diet (HFD). Anti-INSR antibodies demonstrated to behave as partial agonists or positive modulators in vitro were evaluated in this model to determine if these antibodies improved insulin sensitivity and/or glycemic control in vivo.

Figure 15A:
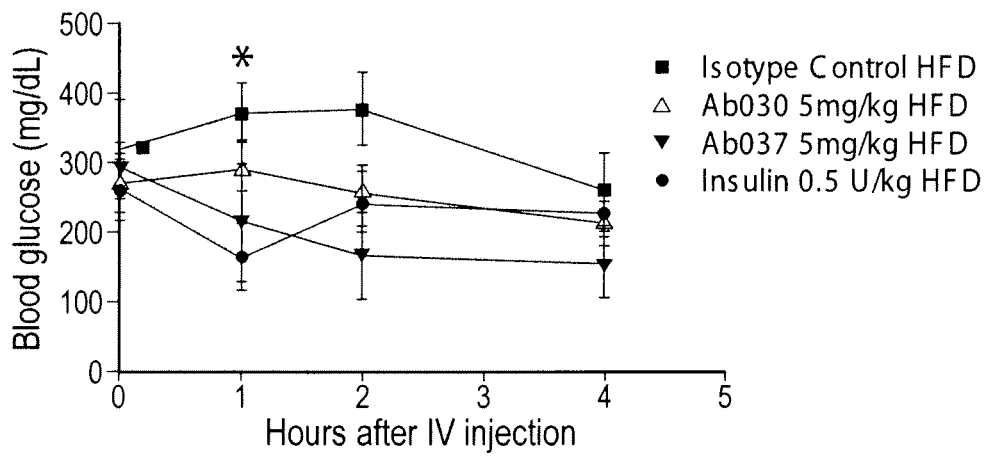
FIGS. 15A-B show blood glucose levels in 20 week old DIO mice fed a high fat diet and treated with partial agonist anti-INSR antibodies.
Figure 15B:
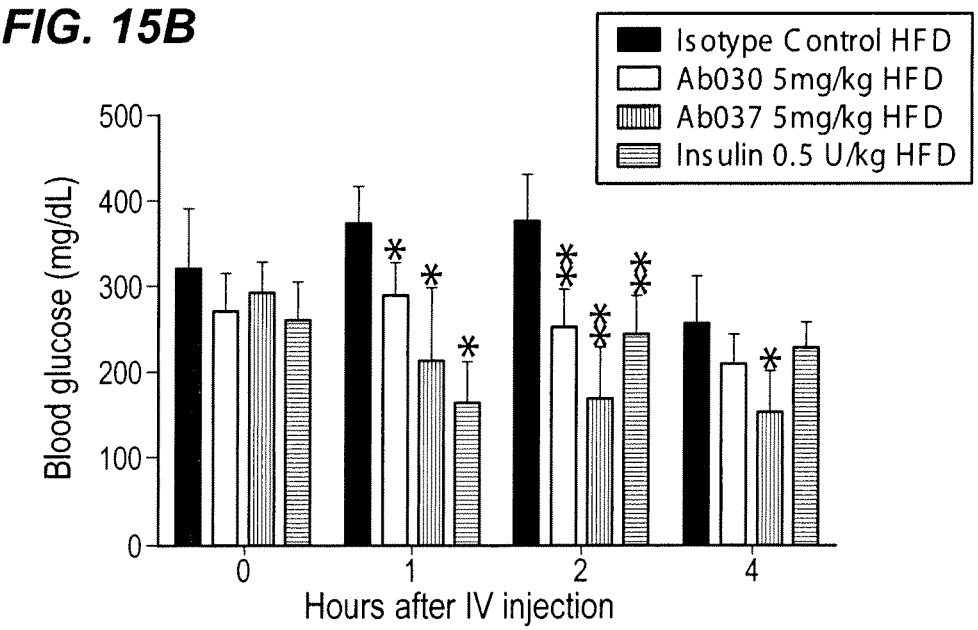

To determine whether partial agonist anti-INSR antibodies reduce fasted blood glucose, 20 week-old DIO mice (14 weeks on HFD; n=8/group) were fasted for 5 hours and challenged intravenously with partial agonist antibodies Ab030 and Ab037, or an isotype control (5 mg/kg). In additional control studies, DIO mice were treated with insulin (0.5 U/kg), or age-matched mice fed a normal diet (ND) were dosed with isotype control (5 mg/kg). Blood glucose was sampled prior to injection (time=0) and 1, 2 and 4 hours post-administration. Compared to age-matched controls, increased blood glucose was observed in DIO mice (HFD-fed/isotype control) at the 1-hour time point, consistent with insulin resistance in animals fed HFD (FIG. 15A). Administration of insulin or either of the partial agonist antibodies resulted in a statistically significant reduction (p<0.05; one-tailed t-test) in blood glucose (FIG. 15B). Neither antibody induced hypoglycemia at any time point (defined as blood glucose <36 mg/dL). These results suggest that anti-INSR partial agonist antibodies safely and effectively reduce fasting blood glucose.

To further evaluate the effect of a partial agonist anti-INSR antibody on glycemic control, 18-week old DIO mice (12 weeks on HFD; n=8/group) were injected intraperitoneally (IP) with Ab037 (0.1, 1.0 or 9 mg/kg) or isotype control (1.0 mg/kg). As additional controls, age-matched control mice were dosed with isotype control (1.0 mg/kg) or DIO animals were given insulin (0.75 U/kg; IP). A glucose tolerance test (GTT) was performed 24 hours after antibody administration (30 min after insulin) by fasting the animals for 16 hours (beginning approximately 8 hours after antibody administration), injecting glucose (1.0 U/kg) and following blood glucose over 2 hours. In this experiment, HFD did not have a significant impact on fasting glucose (FIG. 16B) or post-bolus peak glucose (FIG. 16A). Nevertheless, in DIO mice, partial agonist antibody significantly reduced fasting blood glucose relative to isotype control when dosed at or above 1.0 mg/kg (FIG. 16B) and reduced GTT area under the curve (AUC) at 9.0 mg/kg (FIG. 16C).

This outcome demonstrates that an anti-INSR partial agonist antibody can reduce fasting glucose and improve glycemic control in vivo.

Example 9

Figure 17A:
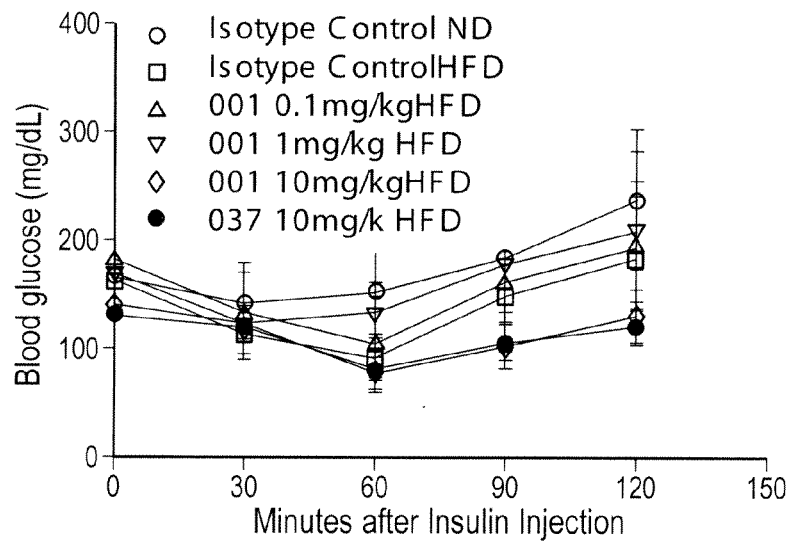
FIGS. 17A-C show that a positive modulator anti-INSR antibody improves insulin sensitivity in DIO mice.
Figure 17B:
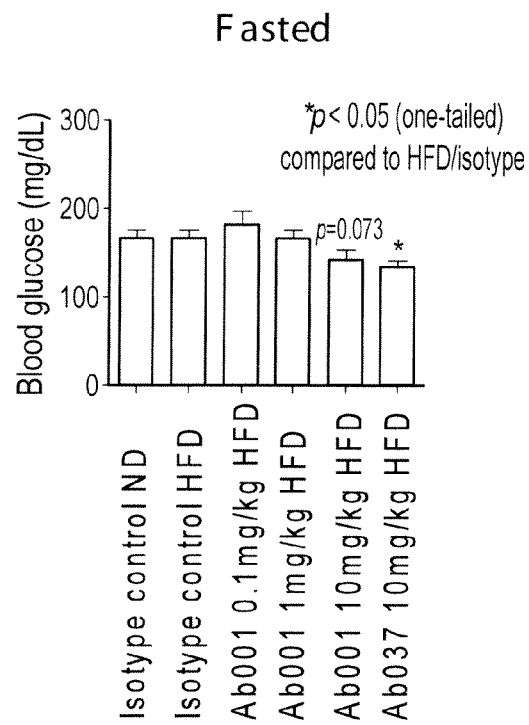
Figure 17C:
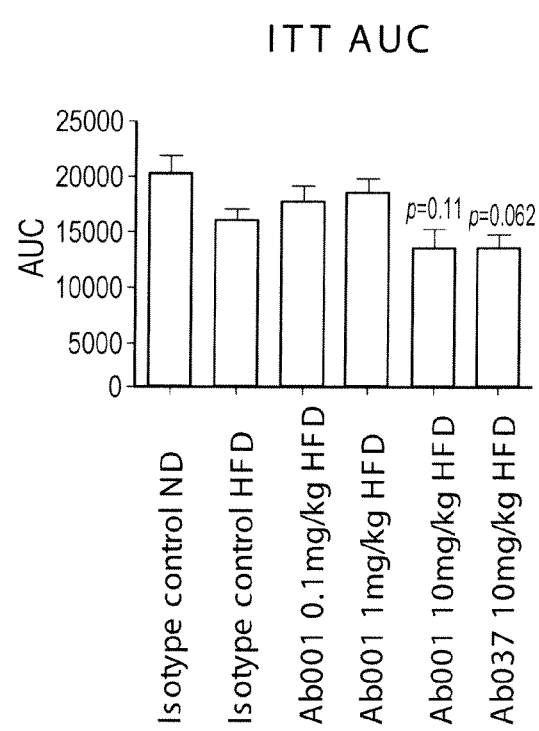

Effects of Positive Modulator Anti-INSR Antibodies on Glycemic Control in DIO Mice To determine if a positive modulator anti-INSR antibody improves insulin sensitivity in vivo, 18-week old DIO mice (n=8/group) were given IP injections of Ab001 (positive modulator) (0.1, 1.0 or 10 mg/kg), partial agonist antibody (Ab037) (10 mg/kg) or isotype control (1.0 mg/kg). Age-matched mice fed ND dosed with isotype control (1.0 mg/kg) served as an additional control (FIG. 17A). Twenty-four hours later, an insulin tolerance test (ITT) was carried out by administering insulin (0.5 U/kg) after a 5 hour fast and monitoring blood glucose levels over 2 hours. A HFD did not have a significant impact on fasting glucose (FIG. 17B) or ITT AUC (FIG. 17C) relative to regular diet, and neither partial agonist antibody (Ab037) nor positive modulator antibody (Ab001) administration resulted in a statistically significant lower AUC ITT, relative to isotype control treated DIO animals (FIG. 17C). Partial agonist antibody Ab037 significantly reduced fasting glucose, while positive modulator antibody Ab001 induced a non-statistically significant, dose-dependent trend towards reduced fasting glucose.

Figure 18A:
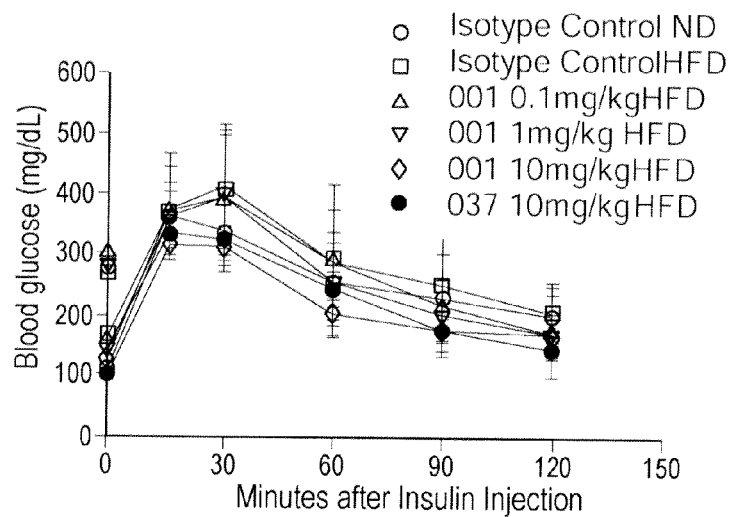
FIGS. 18A-C show that a positive modulator anti-INSR antibody improves glycemic control in DIO mice.
Figure 18B:
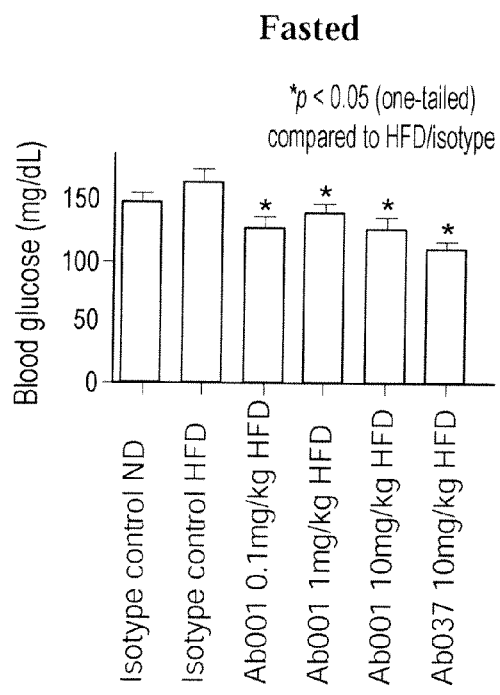
Figure 18C:
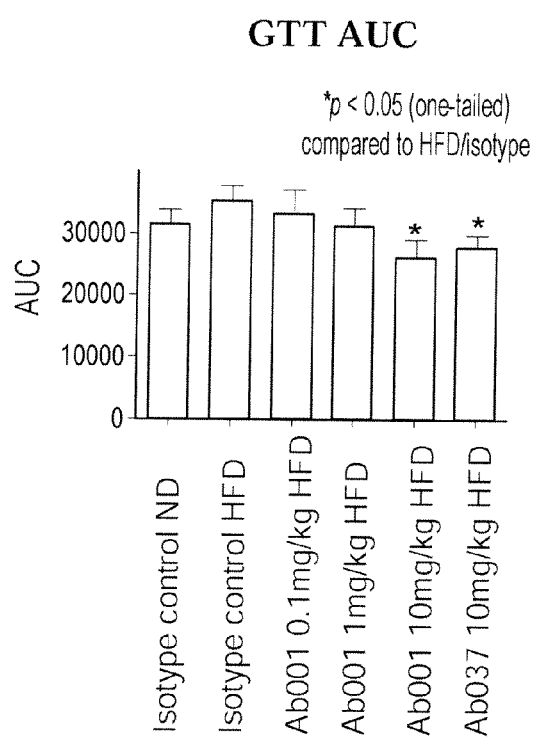

The following week, a GTT was carried out on the same animals after an additional dose of antibody (FIG. 18A). In this study, HFD resulted in a non-statistical increase in fasting glucose (FIG. 18B) and GTT AUC (FIG. 18C) compared to control fed animals. Compared to isotype control-treated DIO mice, partial agonist antibody and positive modulator antibody significantly reduced fasting glucose at all doses tested. In addition, both partial agonist antibody and positive modulator antibody significantly reduced GTT AUC at 10 mg/kg relative to isotype control.

These results suggest that partial agonist and positive modulator antibodies specific for the INSR improve glycemic control in diabetic subjects.

Example 10

Panning for Allosteric Agonist Antibodies Against a Receptor

Selection of agonist antibodies that exhibit greater binding to the complex of receptor/ligand than to the free receptor enhances the probability of identifying antibodies that are noncompetitive with the ligand and do not block or diminish binding of the ligand to the orthosteric site of the receptor. An antibody of this type, that binds to a site on the target receptor distinct from the endogenous binding site, is known as an allosteric agonist (Kenakin et al., J Receptors and Signal Transduction, 27:247-259, 2007; Jahns et al., J Am Coll Cardiol. 36:1280-87, 2000; May et al., Ann Rev Toxicol. 47: 1-51, 2007).

Methods described above to screen for agonist antibodies are also useful to screen for allosteric agonists. Preferential binding of the test antibody to the receptor ligand complex is consistent with allosteric activity whereas preferential binding of the test antibody to the free receptor is consistent with an antibody that competes with insulin for the orthosteric site. The screen is useful to enrich the pool of candidate clones for allosteric agonists by eliminating the some if not all competitive agonists.

Allosteric antibodies are less likely to interfere with the binding affinity and efficacy of the ligand and therefore, are less likely to interfere with the maximum ligand signaling or maximum sensitivity to ligand. Allosteric antibodies can exhibit a range of agonism from weak partial agonists to agonism levels similar to the endogenous ligand. A partial allosteric agonist will elicit a maximum signaling response that is of significantly lower in magnitude than the maximum response of the endogenous ligand. In some applications, where sustained sub maximal signal activation is preferred over maximum signal activation, a partial agonist antibody is preferable to a full agonist antibody. The distinguishing characteristics between a partial allosteric agonist and a positive allosteric modulator are evident from a comparison of the dose response curves shown in FIGS. 19 and 20, which show the different binding curves for a partial allosteric agonist (FIG. 19) and a positive allosteric modulator (sensitizer) antibody (FIG. 20), as exemplified using an antibody specific for INSR.

Figure 19A:
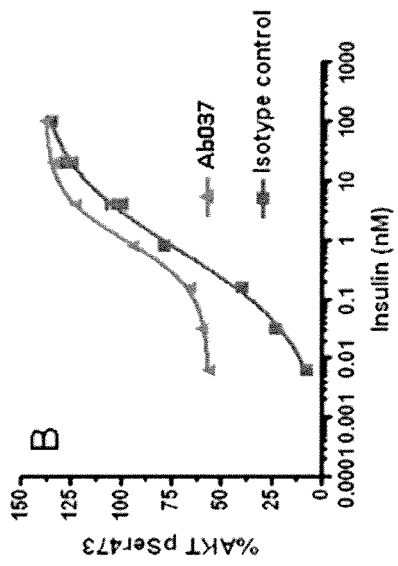
FIGS. 19A-B illustrate the dose response from a partial allosteric agonist in comparison to the dose response to the endogenous ligand (FIG. 19A) or activation by ligand in the presence or absence of the allosteric agonist (FIG. 19B).
Figure 20A:
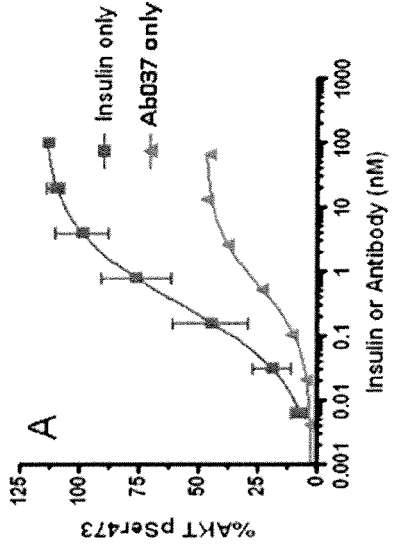
FIGS. 20A-B show the dose response from a positive allosteric modulator antibody in comparison to the dose response to the endogenous ligand (FIG. 20A) or the dose response of an endogenous ligand in the presence and absence of a positive allosteric modulator antibody (FIG. 20B).
Figure 19B:
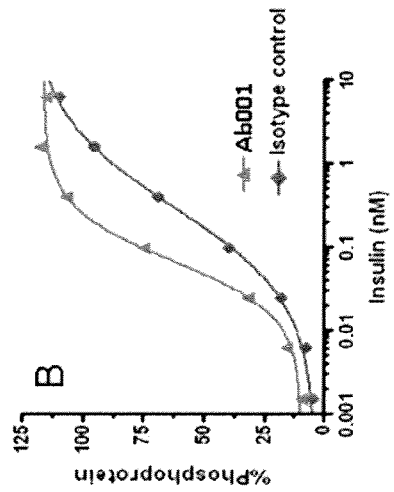
Figure 20B:
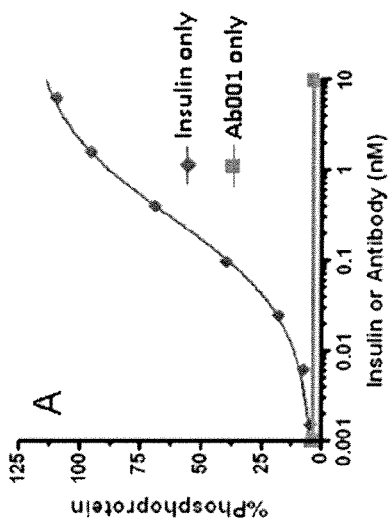

FIG. 19A illustrates an example of the dose response from a partial allosteric agonist in comparison to the dose response to the endogenous ligand (insulin) and FIG. 19B demonstrates activation by ligand in the presence or absence of the allosteric agonist. FIG. 20A shows the dose response from a positive allosteric modulator antibody in comparison to the dose response to the endogenous ligand while FIG. 20B shows a dose response curve of an endogenous ligand (insulin) in the presence and absence of a positive allosteric modulator antibody that binds INSR. FIG. 21 provides the activation parameters for a set of partial allosteric agonists relative to the endogenous ligand. The nature of signal activation by the partial allosteric agonists is distinct from that of an allosteric modulator obtained from the same primary screening approach.

A non-competitive partial allosteric agonist antibody may offer a therapeutic advantage over a competitive agonist where it is beneficial to have independent signal activation by both the partial agonist and an endogenous ligand simultaneously. For example, and not to be bound by theory, a partial allosteric agonist can be used to elevate the basal activation of a signaling pathway while still allowing response from transient fluctuations in endogenous ligand levels. In certain instances, under conditions where a partial allosteric agonist of this sort is present, the endogenous ligand dose response will exhibit an increase in the baseline (constitutive or basal) signaling level and will achieve the same or greater maximal response to the endogenous ligand with little or no significant change in the ligand EC50. For example, FIG. 19B shows the dose response of an endogenous ligand in the presence and absence of a partial allosteric agonist and FIG. 22 shows the maximal activation of insulin in the presence partial allosteric agonist antibodies relative to the maximal response to the endogenous ligand in the presence of a negative control antibody. FIG. 22 demonstrates that the partial allosteric agonist antibodies Ab037 and Ab040 have little or no significant impact on the EC50 of the dose response and maximum phosphorylation of Akt at Ser473 by insulin when compared to a negative control antibody within the same assay.

Example 21

Assay to Measure Modulation of Insulin Binding Affinity for INSR by Anti-INSR Antibodies To determine the ability of the modulating antibodies to affect the binding of insulin to the insulin receptor, the affinity of unmodified insulin binding to human INSR expressed on the surface of serum starved CHOK1 cells (hINSR8-CHOK1) was measured in the presence and absence of monoclonal antibodies to INSR. A KinExA assay was developed to measure very low levels of insulin in cell culture media. This assay allowed the binding of insulin to cells expressing INSR to be measured by determining the level of insulin depletion from the cell culture media. As insulin became bound to the cells, the concentration of insulin in the cell culture media dropped. By using a titration of cells expressing INSR and measuring the percent free insulin, the affinity of the INS-INSR interaction could be estimated using KinExA software. This assay was used to measure the degree of modulation of insulin binding activity shown by various anti-INSR antibodies.

hINSR8-CHOK1 cells were serum starved overnight and then prepared for assay by pelleting cells and resuspending at a concentration of 2× the final assay concentration for the highest dilutions (between $3.5 \times 10^7$ and $2.0 \times 10^7$ cells/mL in assay dilution buffer of PBS (Teknova, Hollister Calif.) with 500 μg/mL BSA and 0.1% sodium azide (Sigma Aldrich, St. Louis, Mo.)). A two-fold serial dilution of cells was prepared creating a ten-point dilutions series and a no-cells control was also used. Cell suspensions were aliquoted into polypropylene assay tubes in 2 mL volume each. To these cell suspensions 1 mL of 40 ug/mL test antibody (or 100 ug/mL for Ab078) was added to each tube, gently mixed and incubated for 30-45 minutes on ice. The antibodies used were tested in comparison to the negative control human IgG2 anti-KLH antibody. 1 mL of 200 pM insulin was added to each tube to establish a final insulin concentration of 50 pM (300 pg/mL) (Sigma-Aldrich, St. Louis, Mo.). Samples were incubated overnight at 4° C. for 18 hours then centrifuged to pellet cells and supernatants were removed for testing.

KinExA 3000 analysis was performed using beads coated with an anti-insulin monoclonal antibody. 2 grams of poly (methyl methacrylate) (PMMA) beads (Sapidyne, Boise, Id.) was suspended in 9 mL of assay buffer PBS containing 65 ug/mL of clone D6C4 mouse anti-insulin monoclonal antibody (Fitzgerald Industries, Acton Mass.). Beads were rotated at room temperature for 6 hours then allowed to settle. Supernatant was replaced with PBS with 50 mg/mL BSA Fraction V (Sigma-Aldrich, St. Louis, Mo.) and rotated overnight at 4° C. Detection solution used was biotinylated mouse anti-insulin clone D3E7 (Fitzgerald Industries, Acton Mass.) at 0.15 μg/mL in assay dilution buffer with Streptavidin-PE at 1 ug/mL (Invitrogen, Carlsbad, Calif.). On the KinExA 3000 the sample was injected at 0.25 mL/minute for 240 seconds, then rinsed for 60 seconds in running buffer (PBS with 0.05% sodium azide), then 240 seconds of the detection solution was injected, followed by a final 90 second wash at 1 mL/minute. The difference in voltage from an early initial time-point and a time point near the end of the run was measured and used to calculate affinities. The INSR concentration on the cells was estimated at $2.5 \times 10^5$ receptors/cell. Affinity was determined using the KinExA software (Sapidyne, Boise Id.) and EC50's were calculated by non-linear fit in Prism (GraphPad Software, La Jolla Calif.).

A number of anti-INSR antibodies enhanced the affinity of insulin for the cells, as shown in Table 4 below. One of the tested antibodies decreased the affinity of insulin for the cells by approximately three-fold.

TABLE 4

Insulin Affinity and IC50 Table

| Antibody | $K_D$ (pM) | EC50 (pM) | Fold Shift in Affinity |
|---|---|---|---|
| IgG2-KLH | 272 | 365 | 1.0 |
| Ab037 | 271 | 471 | 1.0 |
| Ab001 | 49 | 104 | +5.6 |
| Ab053 | 228 | 33 | +1.2 |
| Ab062 | 762 | 760 | −2.8 |
| Ab078 | 41 | 80 | +6.6 |
| Ab079 | 12.1 | 40 | +22.5 |
| Ab080 | 11.2 | 34 | +24.3 |
| Ab083 | 13.7 | 39 | +19.9 |
| Ab085 | 34 | 70 | +8.0 |

These data illustrate that the screening methods described herein produce positive modulator antibodies that strengthen the binding affinity of insulin for insulin receptor.

From the foregoing it will be appreciated that, although specific embodiments of the invention have been described herein for purposes of illustration, various modifications, variations and combinations of embodiments may be made without deviating from the spirit and scope of the invention. Such modifications, variations and combinations are intended to be encompassed by the following claims.

Q8NFU4
Follicular dendritic cell secreted peptide (FDC secreted protein) (FDC-SP)
85
Q6E0U4
Dermokine (Epidermis-specific secreted protein SK30/SK89)
476
Q8N474
Secreted frizzled-related protein 1 (sFRP-1) (Frizzled-related protein 1) (FRP-1) (Secreted apoptosis-related protein 2) (SARP-2)
314
Q92838
Ectodysplasin-A (Ectodermal dysplasia protein) (EDA protein) [Cleaved into: Ectodysplasin-A, membrane form; Ectodysplasin-A, secreted form]
391
Q96HF1
Secreted frizzled-related protein 2 (sFRP-2) (Secreted apoptosis-related protein 1) (SARP-1) (Frizzled-related protein 2) (FRP-2)
295
Q9HD89

-continued

Resistin (Cysteine-rich secreted protein FIZZ3) (Adipose tissue-specific secretory factor) (ADSF) (C/EBP-epsilon-regulated myeloid-specific secreted cysteine-rich protein) (Cysteine-rich secreted protein A12-alpha-like 2)
108
P10451
Osteopontin (Bone sialoprotein 1) (Secreted phosphoprotein 1) (SPP-1) (Urinary stone protein) (Nephropontin) (Uropontin)
314
Q5T4F7
Secreted frizzled-related protein 5 (sFRP-5) (Secreted apoptosis-related protein 3) (SARP-3) (Frizzled-related protein 1b) (FRP-1b)
317
Q6FHJ7
Secreted frizzled-related protein 4 (sFRP-4) (Frizzled protein, human endometrium) (FrpHE)
346
Q13103
Secreted phosphoprotein 24 (Spp-24) (Secreted phosphoprotein 2)
211
Q9Y625
Glypican-6 [Cleaved into: Secreted glypican-6]
555
Q92765
Secreted frizzled-related protein 3 (sFRP-3) (Frizzled-related protein 1) (FrzB-1) (Frezzled) (Fritz)
325
P13236
C-C motif chemokine 4 (Small-inducible cytokine A4) (Macrophage inflammatory protein 1-beta) (MIP-1-beta) (MIP-1-beta(1-69))
(T-cell activation protein 2) (ACT-2) (PAT 744) (Protein H400) (SIS-gamma) (Lymphocyte activation gene 1 protein) (LAG-1) (HC21)
(G-26 T-lymphocyte-secreted protein) [Cleaved into: MIP-1-beta(3-69)]
92
P40967
Melanocyte protein Pmel 17 (Silver locus protein homolog) (Melanocyte lineage-specific antigen GP100) (Melanoma-associated ME20 antigen)
(ME20-M) (ME20M) [Cleaved into: ME20-S (Secreted melanoma-associated ME20 antigen) (ME20S) (95 kDa melanocyte-specific secreted glycoprotein)]
661
P55000
Secreted Ly-6/uPAR-related protein 1 (SLURP-1) (ARS component B) (ARS(component B)-81/S) (Anti-neoplastic urinary protein) (ANUP)
103
P08118
Beta-microseminoprotein (Prostate secreted seminal plasma protein) (Prostate secretory protein PSP94) (PSP-94) (Seminal plasma beta-inhibin) (Immunoglobulin-binding factor) (IGBF) (PN44)
114
O75487
Glypican-4 (K-glypican) [Cleaved into: Secreted glypican-4]
556
O95150
Tumor necrosis factor ligand superfamily member 15 (Vascular endothelial cell growth inhibitor) (TNF ligand-related molecule 1)
[Cleaved into: Tumor necrosis factor ligand superfamily member 15, membrane form; Tumor necrosis factor ligand superfamily member 15, secreted form]
251
Q9BQ08
Resistin-like beta (RELMbeta) (Cysteine-rich secreted protein FIZZ2) (Colon and small intestine-specific cysteine-rich protein)
(Cysteine-rich secreted protein A12-alpha-like 1) (Colon carcinoma-related gene protein)
111
O43508
Tumor necrosis factor ligand superfamily member 12 (TNF-related weak inducer of apoptosis) (TWEAK) (APO3 ligand)
[Cleaved into: Tumor necrosis factor ligand superfamily member 12, membrane form; Tumor necrosis factor ligand superfamily member 12, secreted form]
249
P09486
SPARC (Secreted protein acidic and rich in cysteine) (Osteonectin) (ON) (Basement-membrane protein 40) (BM-40)
303
P78333
Glypican-5 [Cleaved into: Secreted glypican-5]
572
O95994
Anterior gradient protein 2 homolog (hAG-2) (AG-2) (Secreted cement gland protein XAG-2 homolog) (HPC8)
175
Q9Y2B0
Protein canopy homolog 2 (MIR-interacting saposin-like protein) (Transmembrane protein 4) (Putative secreted protein ZSIG9)
182
P35052
Glypican-1 [Cleaved into: Secreted glypican-1]
558
Q5GFL6
von Willebrand factor A domain-containing protein 2 (A domain-containing protein similar to matrilin and collagen) (AMACO)
(Colon cancer secreted protein 2) (CCSP-2)
755
O95388
WNT1-inducible-signaling pathway protein 1 (WISP-1) (Wnt-1-induced secreted protein)
367
P22362
C-C motif chemokine 1 (Small-inducible cytokine A1) (T lymphocyte-secreted protein I-309)

96
Q9H3U7
SPARC-related modular calcium-binding protein 2 (Secreted modular calcium-binding protein 2) (SMOC-2)
(Smooth muscle-associated protein 2) (SMAP-2)
446
Q9Y240
C-type lectin domain family 11 member A (Stem cell growth factor) (Lymphocyte secreted C-type lectin) (p47)
(C-type lectin superfamily member 3)
323
Q86SR0
Secreted Ly-6/uPAR-related protein 2 (SLURP-2)
97
P51654
Glypican-3 (Intestinal protein OCI-5) (GTR2-2) (MXR7) [Cleaved into: Secreted glypican-3]
580
Q8WVN6
Secreted and transmembrane protein 1 (Protein K12)
248
Q9Y6I9
Testis-expressed sequence 264 protein (Putative secreted protein ZSIG11)
313
Q8N158
Glypican-2 [Cleaved into: Secreted glypican-2]
579
O95084
Serine protease 23 (EC 3.4.21.-) (Putative secreted protein ZSIG13)
383
Q7Z7F7
39S ribosomal protein L55, mitochondrial (L55mt) (MRP-L55)
128
Q9UFN0
Protein NipSnap homolog 3A (NipSnap3A) (NipSnap4) (Target for Salmonella secreted protein C) (TassC)
247
P02751
Fibronectin (FN) (Cold-insoluble globulin) (CIG) [Cleaved into: Ugl-Y1; Ugl-Y2; Ugl-Y3]
2,386
Q9UMX5
Neudesin (Neuron-derived neurotrophic factor) (Secreted protein of unknown function) (SPUF protein) (Cell immortalization-related protein 2)
172
P21802
Fibroblast growth factor receptor 2 (FGFR-2) (EC 2.7.10.1) (Keratinocyte growth factor receptor 2) (CD antigen CD332)
821
P23280
Carbonic anhydrase 6 (EC 4.2.1.1) (Carbonic anhydrase VI) (CA-VI) (Carbonate dehydratase VI) (Secreted carbonic anhydrase)
(Salivary carbonic anhydrase)
308
Q9UGM3
Deleted in malignant brain tumors 1 protein (Glycoprotein 340) (Gp-340) (Surfactant pulmonary-associated D-binding protein) (Hensin)
(Salivary agglutinin) (SAG)
2,413
Q9H4F8
SPARC-related modular calcium-binding protein 1 (Secreted modular calcium-binding protein 1) (SMOC-1)
434
P05067
Amyloid beta A4 protein (Alzheimer disease amyloid protein) (ABPP) (APPI) (APP) (PreA4) (Cerebral vascular amyloid peptide) (CVAP)
(Protease nexin-II) (PN-II) [Cleaved into: N-APP; Soluble APP-alpha (S-APP-alpha); Soluble APP-beta (S-APP-beta); C99; Beta-amyloid protein 42
(Beta-APP42); Beta-amyloid protein 40 (Beta-APP40); C83; P3(42); P3(40); Gamma-secretase C-terminal fragment 59 (Gamma-CTF(59))
(Amyloid intracellular domain 59) (AICD-59) (AID(59)); Gamma-secretase C-terminal fragment 57 (Gamma-CTF(57)) (Amyloid intracellular
domain 57) (AICD-57) (AID(57)); Gamma-secretase C-terminal fragment 50 (Gamma-CTF(50)) (Amyloid intracellular domain 50) (AICD-50)
(AID(50)); C31]
770
P25445
Tumor necrosis factor receptor superfamily member 6 (FASLG receptor) (Apoptosis-mediating surface antigen FAS) (Apo-1 antigen) (CD
antigen CD95)
335
Q9UBS5
Gamma-aminobutyric acid type B receptor subunit 1 (GABA-B receptor 1) (GABA-B-R1) (Gb1)
961
Q02297
Pro-neuregulin-1, membrane-bound isoform (Pro-NRG1) [Cleaved into: Neuregulin-1 (Neu differentiation factor) (Heregulin) (HRG)
(Breast cancer cell differentiation factor p45) (Acetylcholine receptor-inducing activity) (ARIA) (Sensory and motor neuron-derived factor)
(Glial growth factor)]
640
Q96T91
Glycoprotein hormone alpha-2 (Thyrostimulin subunit alpha) (Putative secreted protein ZSIG51)
129
Q495T6
Membrane metallo-endopeptidase-like 1 (EC 3.4.24.11) (Membrane metallo-endopeptidase-like 2) (Neprilysin-2) (Neprilysin II) (NL2) (NEPII)
(NEP2(m)) [Cleaved into: Membrane metallo-endopeptidase-like 1, soluble form (Neprilysin-2 secreted) (NEP2(s))]

779
Q7L513
Fc receptor-like A (Fc receptor-like and mucin-like protein 1) (Fc receptor homolog expressed in B-cells) (Fc receptor-related protein X) (FcRX) (Fc receptor-like protein)
359
Q8NHW4
C-C motif chemokine 4-like (Small-inducible cytokine A4-like) (Lymphocyte activation gene 1 protein) (LAG-1) (Macrophage inflammatory protein 1-beta) (MIP-1-beta) (Monocyte adherence-induced protein 5-alpha)
92
Q08345
Epithelial discoidin domain-containing receptor 1 (Epithelial discoidin domain receptor 1) (EC 2.7.10.1) (Tyrosine kinase DDR) (Discoidin receptor tyrosine kinase )(Tyrosine-protein kinase CAK) (Cell adhesion kinase) (TRK E) (Protein-tyrosine kinase RTK 6) (HGK2) (CD167 antigen-like family member A) (CD antigen CD167a)
913
P15941
Mucin-1 (MUC-1) (Polymorphic epithelial mucin) (PEM) (PEMT) (Episialin) (Tumor-associated mucin) (Carcinoma-associated mucin) (Tumor-associated epithelial membrane antigen) (EMA) (H23AG) (Peanut-reactive urinary mucin) (PUM) (Breast carcinoma-associated antigen DF3) (CD antigen CD227) [Cleaved into: Mucin-1 subunit alpha (MUC1-alpha) (MUC1-NT); Mucin-1 subunit beta (MUC1-beta) (MUC1-CT)]
1,255
P15692
Vascular endothelial growth factor A (VEGF-A) (Vascular permeability factor) (VPF)
232
P23142
Fibulin-1 (FIBL-1)
703
P16471
Prolactin receptor (PRL-R)
622
P29122
Proprotein convertase subtilisin/kexin type 6 (EC 3.4.21.-) (Paired basic amino acid cleaving enzyme 4) (Subtilisin/kexin-like protease PACE4) (Subtilisin-like proprotein convertase 4) (SPC4)
969
Q9NNX6
CD209 antigen (Dendritic cell-specific ICAM-3-grabbing non-integrin 1) (DC-SIGN1) (DC-SIGN) (C-type lectin domain family 4 member L) (CD antigen CD209)
404
P13942
Collagen alpha-2(XI) chain
1,736
P15509
Granulocyte-macrophage colony-stimulating factor receptor subunit alpha (GM-CSF-R-alpha) (GMR) (CDw116) (CD antigen CD116)
400
P15502
Elastin (Tropoelastin)
786
Q13261
Interleukin-15 receptor subunit alpha (IL-15R-alpha) (IL-15RA) [Cleaved into: Soluble interleukin-15 receptor subunit alpha (sIL-15R-alpha) (sIL-15RA)]
267
P21741
Midkine (MK) (Neurite outgrowth-promoting protein) (Midgestation and kidney protein) (Amphiregulin-associated protein) (ARAP) (Neurite outgrowth-promoting factor 2)
143
Q13683
Integrin alpha-7 [Cleaved into: Integrin alpha-7 heavy chain; Integrin alpha-7 light chain]
1,181
Q99102
Mucin-4 (MUC-4) (Pancreatic adenocarcinoma mucin) (Testis mucin) (Ascites sialoglycoprotein) (ASGP) (Tracheobronchial mucin) [Cleaved into: Mucin-4 alpha chain (Ascites sialoglycoprotein 1) (ASGP-1); Mucin-4 beta chain (Ascites sialoglycoprotein 2) (ASGP-2)]
2,169
P19021
Peptidyl-glycine alpha-amidating monooxygenase (PAM) [Includes: Peptidylglycine alpha-hydroxylating monooxygenase (PHM) (EC 1.14.17.3); Peptidyl-alpha-hydroxyglycine alpha-amidating lyase (EC 4.3.2.5) (Peptidylamidoglycolate lyase) (PAL)]
973
P02647
Apolipoprotein A-I (Apo-AI) (ApoA-I) [Cleaved into: Apolipoprotein A-I(1-242)]
267
Q92954
Proteoglycan 4 (Lubricin) (Megakaryocyte-stimulating factor) (Superficial zone proteoglycan) [Cleaved into: Proteoglycan 4 C-terminal part]
1,404
Q93038
Tumor necrosis factor receptor superfamily member 25 (WSL-1 protein) (Apoptosis-mediating receptor DR3) (Apoptosis-mediating receptor TRAMP) (Death domain receptor 3) (WSL protein) (Apoptosis-inducing receptor AIR) (Apo-3) (Lymphocyte-associated receptor of death) (LARD)
417
O75882
Attractin (Mahogany homolog) (DPPT-L)
1,429
Q1L6U9
Prostate-associated microseminoprotein (PC3-secreted microprotein)

-continued

139
P04745
Alpha-amylase 1 (EC 3.2.1.1) (1,4-alpha-D-glucan glucanohydrolase 1) (Salivary alpha-amylase)
511
P23560
Brain-derived neurotrophic factor (BDNF) (Abrineurin)
247
Q9H2X3
C-type lectin domain family 4 member M (CD209 antigen-like protein 1) (Dendritic cell-specific ICAM-3-grabbing non-integrin 2) (DC-SIGN2)
(DC-SIGN-related protein) (DC-SIGNR) (Liver/lymph node-specific ICAM-3-grabbing non-integrin) (L-SIGN) (CD antigen CD299)
399
Q99062
Granulocyte colony-stimulating factor receptor (G-CSF-R) (CD antigen CD114)
836
P01344
Insulin-like growth factor II (IGF-II) (Somatomedin-A) [Cleaved into: Insulin-like growth factor II Ala-25 Del; Preptin]
180
P13688
Carcinoembryonic antigen-related cell adhesion molecule 1 (Biliary glycoprotein 1) (BGP-1) (CD antigen CD66a)
526
Q9BXN2
C-type lectin domain family 7 member A (Dendritic cell-associated C-type lectin 1) (DC-associated C-type lectin 1) (Dectin-1) (Beta-glucan receptor)
(C-type lectin superfamily member 12)
247
Q8TDQ1
CMRF35-like molecule 1 (CLM-1) (CD300 antigen-like family member F) (Immune receptor expressed on myeloid cells 1) (IREM-1)
(Immunoglobulin superfamily member 13) (IgSF13) (NK inhibitory receptor) (CD antigen CD300f)
290
Q53GD3
Choline transporter-like protein 4 (Solute carrier family 44 member 4)
710
Q8IWL2
Pulmonary surfactant-associated protein A1 (SP-A1) (SP-A) (PSP-A) (PSPA) (Alveolar proteinosis protein) (35 kDa pulmonary surfactant-associated
protein)
248
Q9NWM0
Spermine oxidase (EC 1.5.3.n1) (EC 1.5.3.n2) (Polyamine oxidase 1) (PAO-1) (PAOh1)
555
Q11203
CMP-N-acetylneuraminate-beta-1,4-galactoside alpha-2,3-sialyltransferase (EC 2.4.99.6) (N-acetyllactosaminide alpha-2,3-sialyltransferase)
(Gal beta-1,3(4) GlcNAc alpha-2,3 sialyltransferase) (ST3GalIII) (ST3N) (Sialyltransferase 6)
375
O60259
Kallikrein-8 (hK8) (EC 3.4.21.118) (Neuropsin) (NP) (Ovasin) (Serine protease TADG-14) (Tumor-associated differentially expressed gene 14 protein)
(Serine protease 19)
260
P00750
Tissue-type plasminogen activator (t-plasminogen activator) (t-PA) (tPA) (EC 3.4.21.68) (Alteplase) (Reteplase) [Cleaved into: Tissue-type plasminogen
activator chain A; Tissue-type plasminogen activator chain B]
562
Q6QHF9
Peroxisomal N(1)-acetyl-spermine/spermidine oxidase (EC 1.5.3.n3) (EC 1.5.3.n4) (EC 1.5.3.n10) (Polyamine oxidase)
649
Q9NPG8
Probable palmitoyltransferase ZDHHC4 (EC 2.3.1.-) (Zinc finger DHHC domain-containing protein 4) (DHHC-4) (Zinc finger protein 374)
344
P11597
Cholesteryl ester transfer protein (Lipid transfer protein I)
493
P01892
HLA class I histocompatibility antigen, A-2 alpha chain (MHC class I antigen A*2)
365
P02458
Collagen alpha-1(II) chain (Alpha-1 type II collagen) [Cleaved into: Chondrocalcin]
1,487
Q14005
Pro-interleukin-16 [Cleaved into: Interleukin-16 (IL-16) (Lymphocyte chemoattractant factor) (LCF)]
1,332
P48357
Leptin receptor (LEP-R) (OB receptor) (OB-R) (HuB219) (CD antigen CD295)
1,165
P07585
Decorin (Bone proteoglycan II) (PG-S2) (PG40)
359
P48061
Stromal cell-derived factor 1 (SDF-1) (hSDF-1) (C-X-C motif chemokine 12) (Pre-B cell growth-stimulating factor) (PBSF) (hIRH) [Cleaved into:
SDF-1-beta(3-72); SDF-1-alpha(3-67)]
93
P24821

-continued

Tenascin (TN) (Tenascin-C) (TN-C) (Hexabrachion) (Cytotactin) (Neuronectin) (GMEM) (JI) (Myotendinous antigen) (Glioma-associated-extracellular matrix antigen) (GP 150-225)
2,201
O43184
Disintegrin and metalloproteinase domain-containing protein 12 (ADAM 12) (EC 3.4.24.-) (Meltrin-alpha)
909
Q76LX8
A disintegrin and metalloproteinase with thrombospondin motifs 13 (ADAMTS-13) (ADAM-TS 13) (ADAM-TS13) (EC 3.4.24.-) (von Willebrand factor-cleaving protease) (vWF-cleaving protease) (vWF-CP)
1,427
P01732
T-cell surface glycoprotein CD8 alpha chain (T-lymphocyte differentiation antigen T8/Leu-2) (CD antigen CD8a)
235
Q96AW1
EGFR-coamplified and overexpressed protein (ECop) (Glioblastoma-amplified secreted protein) (Putative NF-kappa-B-activating protein 055N)
172
Q676U5
Autophagy-related protein 16-1 (APG16-like 1)
607
O75815
Breast cancer anti-estrogen resistance protein 3 (SH2 domain-containing protein 3B) (Novel SH2-containing protein 2)
825
Q9H251
Cadherin-23 (Otocadherin)
3,354
P09603
Macrophage colony-stimulating factor 1 (CSF-1) (MCSF) (M-CSF) (Lanimostim) [Cleaved into: Processed macrophage colony-stimulating factor 1]
554
P15328
Folate receptor alpha (FR-alpha) (Folate receptor 1) (Folate receptor, adult) (Adult folate-binding protein) (FBP) (Ovarian tumor-associated antigen MOv18) (KB cells FBP)
257
Q14114
Low-density lipoprotein receptor-related protein 8 (Apolipoprotein E receptor 2)
963
Q6UWE0
E3 ubiquitin-protein ligase LRSAM1 (EC 6.3.2.-) (Leucine-rich repeat and sterile alpha motif-containing protein 1) (Tsg101-associated ligase) (hTAL)
723
P13591
Neural cell adhesion molecule 1 (NCAM-1) (N-CAM-1) (CD antigen CD56)
858
Q8N0W4
Neuroligin-4, X-linked (Neuroligin X) (HNLX)
816
Q9Y2I2
Netrin-G1 (Laminet-1)
539
Q969N2
GPI transamidase component PIG-T (Phosphatidylinositol-glycan biosynthesis class T protein)
578
P21583
Kit ligand (C-kit ligand) (Stem cell factor) (SCF) (Mast cell growth factor) (MGF)
273
Q9BYH1
Seizure 6-like protein
1,024
Q9NQ25
SLAM family member 7 (CD2-like receptor-activating cytotoxic cells) (CRACC) (Protein 19A) (CD2 subset 1) (Novel Ly9) (Membrane protein FOAP-12) (CD antigen CD319)
335
P01375
Tumor necrosis factor (TNF-alpha) (Tumor necrosis factor ligand superfamily member 2) (TNF-a) (Cachectin) [Cleaved into: Tumor necrosis factor, membrane form; Tumor necrosis factor, soluble form]
233
P07911
Uromodulin (Tamm-Horsfall urinary glycoprotein) (THP)
640
O75888
Tumor necrosis factor ligand superfamily member 13 (A proliferation-inducing ligand) (APRIL) (TNF- and APOL-related leukocyte expressed ligand 2) (TALL-2) (TNF-related death ligand 1) (TRDL-1) (CD antigen CD256)
250
O75629
Protein CREG1 (Cellular repressor of E1A-stimulated genes 1)
220
Q99944
EGF-like domain-containing protein 8 (Epidermal growth factor-like protein 8) (Multiple EGF-like domain protein 8) (Vascular endothelial-statin 2) (VE-statin-2)
293
Q12904

-continued

Aminoacyl tRNA synthetase complex-interacting multifunctional protein 1 (Multisynthetase complex auxiliary component p43) [Cleaved into Endothelial monocyte-activating polypeptide 2 (EMAP-II) (Small inducible cytokine subfamily E member 1)]
312
Q6UY14
ADAMTS-like protein 4 (ADAMTSL-4) (Thrombospondin repeat-containing protein 1)
1,074
P03951
Coagulation factor XI (FXI) (EC 3.4.21.27) (Plasma thromboplastin antecedent) (PTA) [Cleaved into: Coagulation factor XIa heavy chain; Coagulation factor XIa light chain]
625
Q969J5
Interleukin-22 receptor subunit alpha-2 (IL-22R-alpha-2) (Interleukin-22-binding protein) (IL22BP) (Cytokine receptor family class II member 10) (CRF2-10) (Cytokine receptor family type 2, soluble 1) (CRF2-S1)
263
O75398
Deformed epidermal autoregulatory factor 1 homolog (Nuclear DEAF-1-related transcriptional regulator) (NUDR) (Suppressin) (Zinc finger MYND domain-containing protein 5)
565
P41222
Prostaglandin-H2 D-isomerase (EC 5.3.99.2) (Lipocalin-type prostaglandin-D synthase) (Glutathione-independent PGD synthetase) (Prostaglandin-D2 synthase) (PGD2 synthase) (PGDS2) (PGDS) (Beta-trace protein) (Cerebrin-28)
190
P01009
Alpha-1-antitrypsin (Alpha-1 protease inhibitor) (Alpha-1-antiproteinase) [Cleaved into: Short peptide from AAT (SPAAT)]
418
P01011
Alpha-1-antichymotrypsin (ACT) (Cell growth-inhibiting gene 24/25 protein) [Cleaved into: Alpha-1-antichymotrypsin His-Pro-less]
423
P07108
Acyl-CoA-binding protein (ACBP) (Diazepam-binding inhibitor) (DBI) (Endozepine) (EP)
87
P00751
Complement factor B (EC 3.4.21.47) (C3/C5 convertase) (Properdin factor B) (Glycine-rich beta glycoprotein) (GBG) (PBF2) [Cleaved into: Complement factor B Ba fragment; Complement factor B Bb fragment]
764
P01233
Choriogonadotropin subunit beta (CG-beta) (Chorionic gonadotrophin chain beta)
165
P13611
Versican core protein (Large fibroblast proteoglycan) (Chondroitin sulfate proteoglycan core protein 2) (PG-M) (Glial hyaluronate-binding protein) (GHAP)
3,396
P00533
Epidermal growth factor receptor (EC 2.7.10.1) (Receptor tyrosine-protein kinase ErbB-1)
1,210
Q16206
Ecto-NOX disulfide-thiol exchanger 2 (Tumor-associated hydroquinone oxidase) (tNOX) (Cytosolic ovarian carcinoma antigen 1) (APK1 antigen) [Includes: Hydroquinone [NADH]oxidase (EC 1.-.-.-); Protein disulfide-thiol oxidoreductase (EC 1.-.-.-)]
610
Q12794
Hyaluronidase-1 (Hyal-1) (EC 3.2.1.35) (Hyaluronoglucosaminidase-1) (LUCA-1)
435
P18510
Interleukin-1 receptor antagonist protein (IL-1ra) (IL-1RN) (IRAP) (IL1 inhibitor) (ICIL-1RA) (Anakinra)
177
P40189
Interleukin-6 receptor subunit beta (IL-6R-beta) (Interleukin-6 signal transducer) (Membrane glycoprotein 130) (gp130) (CDw130) (Oncostatin-M receptor subunit alpha) (CD antigen CD130)
918
Q01638
Interleukin-1 receptor-like 1 (Protein ST2)
556
P01308
Insulin [Cleaved into: Insulin B chain; Insulin A chain]
110
P09466
Glycodelin (GD) (Pregnancy-associated endometrial alpha-2 globulin) (PAEG) (PEG) (Placental protein 14) (PP14) (Progesterone-associated endometrial protein) (Progestagen-associated endometrial protein)
180
P12272
Parathyroid hormone-related protein (PTH-rP) (PTHrP) [Cleaved into: PTHrP[1-36]; PTHrP[38-94]; Osteostatin (PTHrP[107-139])]
177
Q8IXM6
Nurim (Nuclear rim protein) (Nuclear envelope membrane protein)
262
O15460
Prolyl 4-hydroxylase subunit alpha-2 (EC 1.14.11.2) (4-PH alpha-2) (Procollagen-proline,2-oxoglutarate-4-dioxygenase subunit alpha-2)
535
Q5ZPR3

CD276 antigen (Costimulatory molecule) (B7 homolog 3) (B7-H3) (4Ig-B7-H3) (CD antigen CD276)
534
Q96HD1
Cysteine-rich with EGF-like domain protein 1
420
Q96PZ7
CUB and sushi domain-containing protein 1 (CUB and sushi multiple domains protein 1)
3,565
Q15485
Ficolin-2 (Ficolin-B) (Ficolin-beta) (L-ficolin) (Collagen/fibrinogen domain-containing protein 2) (Serum lectin p35) (37 kDa elastin-binding protein) (EBP-37) (Hucolin)
313
Q96RD9
Fc receptor-like protein 5 (FcR-like protein 5) (FcRL5) (Fc receptor homolog 5) (FcRH5) (Immunoglobulin receptor translocation-associated protein 2) (BXMAS1) (CD antigen CD307)
977
Q9Y302
Protein GPR89 (Putative MAPK-activating protein PM01) (Putative NF-kappa-B-activating protein 90)
455
Q9Y624
Junctional adhesion molecule A (JAM-A) (Junctional adhesion molecule 1) (JAM-1) (Platelet adhesion molecule 1) (PAM-1) (Platelet F11 receptor) (CD antigen CD321)
299
Q8IWT6
Leucine-rich repeat-containing protein 8A
810
Q9UNW1
Multiple inositol polyphosphate phosphatase 1 (EC 3.1.3.62) (Inositol (1,3,4,5)-tetrakisphosphate 3-phosphatase) (Ins(1,3,4,5)P(4) 3-phosphatase)
487
O14786
Neuropilin-1 (Vascular endothelial cell growth factor 165 receptor) (CD antigen CD304)
923
Q9HCM2
Plexin-A4
1,894
O43157
Plexin-B1 (Semaphorin receptor SEP)
2,135
Q15063
Periostin (PN) (Osteoblast-specific factor 2) (OSF-2)
836
Q7Z5B4
Protein RIC-3
369
Q9H156
SLIT and NTRK-like protein 2
845
Q8NBK3
Sulfatase-modifying factor 1 (EC 1.8.99.-) (C-alpha-formylglycine-generating enzyme 1)
374
Q8NBJ7
Sulfatase-modifying factor 2 (C-alpha-formylglycine-generating enzyme 2)
301
Q8IU80
Transmembrane protease, serine 6 (EC 3.4.21.-) (Matriptase-2)
811
P01374
Lymphotoxin-alpha (LT-alpha) (TNF-beta) (Tumor necrosis factor ligand superfamily member 1)
205
O14763
Tumor necrosis factor receptor superfamily member 10B (Death receptor 5) (TNF-related apoptosis-inducing ligand receptor 2) (TRAIL receptor 2) (TRAIL-R2) (CD antigen CD262)
440
Q03405
Urokinase plasminogen activator surface receptor (uPAR) (U-PAR) (Monocyte activation antigen Mo3) (CD antigen CD87)
335
Q7Z7D3
V-set domain-containing T-cell activation inhibitor 1 (Immune costimulatory protein B7-H4) (B7h.5) (T-cell costimulatory molecule B7x) (Protein B7S1)
282
P01275
Glucagon [Cleaved into: Glicentin; Glicentin-related polypeptide (GRPP); Oxyntomodulin (OXY) (OXM); Glucagon; Glucagon-like peptide 1 (GLP-1); Glucagon-like peptide 1(7-37) (GLP-1(7-37)); Glucagon-like peptide 1(7-36) (GLP-1(7-36)); Glucagon-like peptide 2 (GLP-2)]
180
Q96PD5
N-acetylmuramoyl-L-alanine amidase (EC 3.5.1.28) (Peptidoglycan recognition protein long) (PGRP-L) (Peptidoglycan recognition protein 2)
576
O00391
Sulfhydryl oxidase 1 (hQSOX) (EC 1.8.3.2) (Quiescin Q6)

747
Q9BTZ2
Dehydrogenase/reductase SDR family member 4 (EC 1.1.1.184) (Short-chain dehydrogenase/reductase family member 4) (NADPH-dependent carbonyl reductase/NADP-retinol dehydrogenase) (PHCR) (CR) (Peroxisomal short-chain alcohol dehydrogenase) (PSCD) (NADPH-dependent retinol dehydrogenase/reductase) (NRDR) (humNRDR) (SCAD-SRL)
260
O95998
Interleukin-18-binding protein (IL-18BP) (Tadekinig-alfa)
194
Q6UWL6
Kin of IRRE-like protein 2 (Kin of irregular chiasm-like protein 2) (Nephrin-like protein 3)
708
Q96S97
Myeloid-associated differentiation marker (SB135)
322
Q9NPP4
NLR family CARD domain-containing protein 4 (Caspase recruitment domain-containing protein 12) (Ice protease-activating factor) (Ipaf) (CARD, LRR, and NACHT-containing protein) (Clan protein)
1,024
Q9NRZ7
1-acyl-sn-glycerol-3-phosphate acyltransferase gamma (EC 2.3.1.51) (1-acylglycerol-3-phosphate O-acyltransferase 3) (1-AGP acyltransferase 3) (1-AGPAT 3) (Lysophosphatidic acid acyltransferase gamma) (LPAAT-gamma)
376
Q15109
Advanced glycosylation end product-specific receptor (Receptor for advanced glycosylation end products)
404
Q9H2X0
Chordin
955
O14511
Pro-neuregulin-2, membrane-bound isoform (Pro-NRG2) [Cleaved into: Neuregulin-2 (NRG-2) (Neural- and thymus-derived activator for ERBB kinases) (NTAK) (Divergent of neuregulin-1) (DON-1)]
850
Q6PDA7
Sperm-associated antigen 11A (Protein EP2) (Sperm antigen HE2)
123
A8MZH6
Oocyte-secreted protein 1 homolog
123
P02768
Serum albumin
609
O43405
Cochlin (COCH-5B2)
550
P05155
Plasma protease C1 inhibitor (C1 Inh) (C1Inh) (C1 esterase inhibitor) (C1-inhibiting factor)
500
P16871
Interleukin-7 receptor subunit alpha (IL-7R-alpha) (CDw127) (CD antigen CD127)
459
Q86UX2
Inter-alpha-trypsin inhibitor heavy chain H5 (Inter-alpha-inhibitor heavy chain 5) (ITI heavy chain H5)
942
Q9GZP0
Platelet-derived growth factor D (PDGF-D) (Iris-expressed growth factor) (Spinal cord-derived growth factor B) (SCDGF-B) [Cleaved into: Platelet-derived growth factor D, latent form (PDGFD latent form); Platelet-derived growth factor D, receptor-binding form (PDGFD receptor-binding form)]
370
P31151
Protein S100-A7 (S100 calcium-binding protein A7) (Psoriasin)
101
Q96LC7
Sialic acid-binding Ig-like lectin 10 (Siglec-10) (Siglec-like protein 2)
697
Q9GZM7
Tubulointerstitial nephritis antigen-like (Tubulointerstitial nephritis antigen-related protein) (TIN Ag-related protein) (TIN-Ag-RP) (Glucocorticoid-inducible protein 5) (Oxidized LDL-responsive gene 2 protein) (OLRG-2)
467
Q9Y275
Tumor necrosis factor ligand superfamily member 13B (TNF- and APOL-related leukocyte expressed ligand 1) (TALL-1) (B lymphocyte stimulator) (BLyS) (B cell-activating factor) (BAFF) (Dendritic cell-derived TNF-like molecule) (CD antigen CD257) [Cleaved into: Tumor necrosis factor ligand superfamily member 13b, membrane form; Tumor necrosis factor ligand superfamily member 13b, soluble form]
285
Q9ULC5
Long-chain-fatty-acid--CoA ligase 5 (EC 6.2.1.3) (Long-chain acyl-CoA synthetase 5) (LACS 5)
683
O95500
Claudin-14

-continued

239
Q8TCA0
Leucine-rich repeat-containing protein 20
184
Q9NZH6
Interleukin-1 family member 7 (IL-1F7) (Interleukin-1 zeta) (IL-1 zeta) (FIL1 zeta) (Interleukin-1 homolog 4) (IL-1H4) (Interleukin-1-related protein) (IL-1RP1) (IL-1X protein)
218
Q8NDX9
Lymphocyte antigen 6 complex locus protein G5b
201
P22303
Acetylcholinesterase (AChE) (EC 3.1.1.7)
614
Q99217
Amelogenin, X isoform
191
P03950
Angiogenin (EC 3.1.27.-) (Ribonuclease 5) (RNase 5)
147
P58335
Anthrax toxin receptor 2 (Capillary morphogenesis gene 2 protein) (CMG-2)
489
P07355
Annexin A2 (Annexin-2) (Annexin II) (Lipocortin II) (Calpactin I heavy chain) (Chromobindin-8) (p36) (Protein I) (Placental anticoagulant protein IV) (PAP-IV)
339
P02656
Apolipoprotein C-III (Apo-CIII) (ApoC-III)
99
O14791
Apolipoprotein L1 (Apolipoprotein L-I) (ApoL-I) (Apolipoprotein L) (Apo-L) (ApoL)
398
P02745
Complement C1q subcomponent subunit A
245
P02747
Complement C1q subcomponent subunit C
245
P01258
Calcitonin [Cleaved into: Calcitonin; Katacalcin (Calcitonin carboxyl-terminal peptide) (CCP) (PDN-21)]
141
Q8WVQ1
Soluble calcium-activated nucleotidase 1 (SCAN-1) (EC 3.6.1.6) (Apyrase homolog) (Putative MAPK-activating protein PM09) (Putative NF-kappa-B-activating protein 107)
401
Q16663
C-C motif chemokine 15 (Small-inducible cytokine A15) (Macrophage inflammatory protein 5) (MIP-5) (Chemokine CC-2) (HCC-2) (NCC-3) (MIP-1 delta) (Leukotactin-1) (LKN-1) (Mrp-2b) [Cleaved into: CCL15(22-92); CCL15(25-92); CCL15(29-92)]
113
P48960
CD97 antigen (Leukocyte antigen CD97) (CD antigen CD97) [Cleaved into: CD97 antigen subunit alpha; CD97 antigen subunit beta]
835
Q8IWV2
Contactin-4 (Brain-derived immunoglobulin superfamily protein 2) (BIG-2)
1,026
P06681
Complement C2 (EC 3.4.21.43) (C3/C5 convertase) [Cleaved into: Complement C2b fragment; Complement C2a fragment]
752
Q14031
Collagen alpha-6(IV) chain
1,691
P12110
Collagen alpha-2(VI) chain
1,019
P12107
Collagen alpha-1(XI) chain
1,806
P82279
Crumbs homolog 1
1,406
P01034
Cystatin-C (Cystatin-3) (Neuroendocrine basic polypeptide) (Gamma-trace) (Post-gamma-globulin)
146
P59665
Neutrophil defensin 1 (HNP-1) (HP-1) (HP1) (Defensin, alpha 1) [Cleaved into: HP 1-56; Neutrophil defensin 2 (HNP-2) (HP-2) (HP2)]
94
P14138
Endothelin-3 (ET-3) (Preproendothelin-3) (PPET3)

238
P06734
Low affinity immunoglobulin epsilon Fc receptor (Lymphocyte IgE receptor) (Fc-epsilon-RII) (BLAST-2) (Immunoglobulin E-binding factor) (CD antigen CD23) [Cleaved into: Low affinity immunoglobulin epsilon Fc receptor membrane-bound form; Low affinity immunoglobulin epsilon Fc receptor soluble form]
321
P22607
Fibroblast growth factor receptor 3 (FGFR-3) (EC 2.7.10.1) (CD antigen CD333)
806
P22455
Fibroblast growth factor receptor 4 (FGFR-4) (EC 2.7.10.1) (CD antigen CD334)
802
Q14393
Growth arrest-specific protein 6 (GAS-6) (AXL receptor tyrosine kinase ligand)
721
P10912
Growth hormone receptor (GH receptor) (Somatotropin receptor) [Cleaved into: Growth hormone-binding protein (GH-binding protein) (GHBP) (Serum-binding protein)]
638
Q9Y223
Bifunctional UDP-N-acetylglucosamine 2-epimerase/N-acetylmannosamine kinase (UDP-GlcNAc-2-epimerase/ManAc kinase) [Includes: UDP-N-acetylglucosamine 2-epimerase (EC 5.1.3.14) (Uridine diphosphate-N-acetylglucosamine-2-epimerase) (UDP-GlcNAc-2-epimerase); N-acetylmannosamine kinase (EC 2.7.1.60) (ManAc kinase)]
7
Q969P0
Immunoglobulin superfamily member 8 (CD81 partner 3) (Glu-Trp-Ile EWI motif-containing protein 2) (EWI-2) (Keratinocytes-associated transmembrane protein 4) (KCT-4) (LIR-D1) (CD antigen CD316)
613
P24394
Interleukin-4 receptor alpha chain (IL-4R-alpha) (CD antigen CD124) [Cleaved into: Soluble interleukin-4 receptor alpha chain (sIL4Ralpha/prot) (IL-4-binding protein) (IL4-BP)]
825
Q9P0G3
Kallikrein-14 (hK14) (EC 3.4.21.-) (Kallikrein-like protein 6) (KLK-L6)
267
Q92876
Kallikrein-6 (EC 3.4.21.-) (Protease M) (Neurosin) (Zyme) (SP59) (Serine protease 9) (Serine protease 18)
244
Q13751
Laminin subunit beta-3 (Laminin 5 beta 3) (Laminin B1k chain) (Kalinin B1 chain)
1,172
Q9UIQ6
Leucyl-cystinyl aminopeptidase (Cystinyl aminopeptidase) (EC 3.4.11.3) (Oxytocinase) (OTase) (Insulin-regulated membrane aminopeptidase) (Insulin-responsive aminopeptidase) (IRAP) (Placental leucine aminopeptidase) (P-LAP) [Cleaved into: Leucyl-cystinyl aminopeptidase, pregnancy serum form]
1,025
P48740
Mannan-binding lectin serine protease 1 (EC 3.4.21.-) (Mannose-binding lectin-associated serine protease-1) (MASP-1) (Mannose-binding protein-associated serine protease) (Complement factor MASP-3) (Serine protease 5) (Complement-activating component of Ra-reactive factor) (Ra-reactive factor serine protease p100) (RaRF) [Cleaved into: Mannan-binding lectin serine protease 1 heavy chain; Mannan-binding lectin serine protease 1 light chain]
699
O00187
Mannan-binding lectin serine protease 2 (EC 3.4.21.104) (Mannose-binding protein-associated serine protease 2) (MASP-2) (MBL-associated serine protease 2) [Cleaved into: Mannan-binding lectin serine protease 2 A chain; Mannan-binding lectin serine protease 2 B chain]
686
P80188
Neutrophil gelatinase-associated lipocalin (NGAL) (p25) (25 kDa alpha-2-microglobulin-related subunit of MMP-9) (Lipocalin-2) (Oncogene 24p3)
198
P01303
Neuropeptide Y [Cleaved into: Neuropeptide Y (Neuropeptide tyrosine) (NPY); C-flanking peptide of NPY (CPON)]
97
P16112
Aggrecan core protein (Cartilage-specific proteoglycan core protein) (CSPCP) (Chondroitin sulfate proteoglycan core protein 1) [Cleaved into: Aggrecan core protein 2]
2,415
P07988
Pulmonary surfactant-associated protein B (SP-B) (Pulmonary surfactant-associated proteolipid SPL(Phe)) (18 kDa pulmonary-surfactant protein) (6 kDa protein)
381
Q15223
Poliovirus receptor-related protein 1 (Herpes virus entry mediator C) (HveC) (Nectin-1) (Herpesvirus Ig-like receptor) (HIgR) (CD antigen CD111)
517
P00797
Renin (EC 3.4.23.15) (Angiotensinogenase)
406
P07998
Ribonuclease pancreatic (EC 3.1.27.5) (RNase 1) (RNase A) (RNase UpI-1) (RIB-1) (HP-RNase)
156

P04279
Semenogelin-1 (Semenogelin I) (SGI) [Cleaved into: Alpha-inhibin-92; Alpha-inhibin-31; Seminal basic protein]
462
Q13291
Signaling lymphocytic activation molecule (IPO-3) (CDw150) (CD antigen CD150)
335
P10646
Tissue factor pathway inhibitor (TFPI) (Lipoprotein-associated coagulation inhibitor) (LACI) (Extrinsic pathway inhibitor) (EPI)
304
O75445
Usherin (Usher syndrome type-2A protein) (Usher syndrome type IIa protein)
5,202
Q9GZV9
Fibroblast growth factor 23 (FGF-23) (Tumor-derived hypophosphatemia-inducing factor) (Phosphatonin) [Cleaved into: Fibroblast growth factor 23 N-terminal peptide; Fibroblast growth factor 23 C-terminal peptide]
251
Q9NPF7
Interleukin-23 subunit alpha (IL-23 subunit alpha) (Interleukin-23 subunit p19) (IL-23p19)
189
P61916
Epididymal secretory protein E1 (Niemann-Pick disease type C2 protein) (hE1)
151
Q8N6G6
ADAMTS-like protein 1 (ADAMTSL-1) (Punctin-1)
525
Q9UBR5
Chemokine-like factor (C32)
152
Q9UHF1
EGF-like domain-containing protein 7 (Multiple EGF-like domain protein 7) (Multiple epidermal growth factor-like domain protein 7) (Vascular endothelial statin) (VE-statin) (NOTCH4-like protein) (ZNEU1)
273
Q2MV58
Tectonic-1
587
Q86YD3
Transmembrane protein 25
366
O75752
UDP-GalNAc:beta-1,3-N-acetylgalactosaminyltransferase 1 (EC 2.4.1.79) (Beta-3-GalNAc-T1) (Beta-1,3-galactosyltransferase 3) (Beta-1,3-GalTase 3) (Beta3Gal-T3) (b3Gal-T3) (Beta-3-Gx-T3) (Galactosylgalactosylglucosylceramide beta-D-acetyl-galactosaminyltransferase) (UDP-N-acetylgalactosamine:globotriaosylceramide beta-1,3-N-acetylgalactosaminyltransferase) (Globoside synthase)
331
P40933
Interleukin-15 (IL-15)
162
A6BM72
Multiple epidermal growth factor-like domains 11 (Multiple EGF-like-domains 11)
1,044
Q9HBB8
Mucin and cadherin-like protein (Mu-protocadherin)
845
P34096
Ribonuclease 4 (RNase 4) (EC 3.1.27.-)
147
Q8N5H7
SH2 domain-containing protein 3C (Novel SH2-containing protein 3)
860
Q11206
CMP-N-acetylneuraminate-beta-galactosamide-alpha-2,3-sialyltransferase (Beta-galactoside alpha-2,3-sialyltransferase) (EC 2.4.99.-) (Alpha 2,3-sialyltransferase IV) (Alpha 2,3-ST) (Gal-NAc6S) (STZ) (SIAT4-C) (ST3Gal III) (SAT-3) (ST-4)
333
Q9P0T7
Transmembrane protein 9 (Dermal papilla-derived protein 4)
183
Q14508
WAP four-disulfide core domain protein 2 (Major epididymis-specific protein E4) (Epididymal secretory protein E4) (Putative protease inhibitor WAP5)
124
P33765
Adenosine A3 receptor
318
Q96BI3
Gamma-secretase subunit APH-1A (APH-1a) (Aph-1alpha) (Presenilin-stabilization factor)
265
P35613
Basigin (Leukocyte activation antigen M6) (Collagenase stimulatory factor) (Extracellular matrix metalloproteinase inducer) (EMMPRIN) (5F7) (Tumor cell-derived collagenase stimulatory factor) (TCSF) (OK blood group antigen) (CD antigen CD147)
385
Q96CA5

-continued

Baculoviral IAP repeat-containing protein 7 (Kidney inhibitor of apoptosis protein) (KIAP) (Melanoma inhibitor of apoptosis protein) (ML-IAP) (Livin) (RING finger protein 50)
298
O43852
Calumenin (Crocalbin) (IEF SSP 9302)
315
P47710
Alpha-S1-casein [Cleaved into: Casoxin-D]
185
Q9UK58
Cyclin-L1 (Cyclin-L)
526
P08603
Complement factor H (H factor 1)
1,231
P01243
Chorionic somatomammotropin hormone (Choriomammotropin) (Lactogen)
217
P78310
Coxsackievirus and adenovirus receptor (Coxsackievirus B-adenovirus receptor) (HCVADR) (hCAR) (CVB3-binding protein)
365
Q13822
Ectonucleotide pyrophosphatase/phosphodiesterase family member 2 (E-NPP 2) (EC 3.1.4.39) (Extracellular lysophospholipase D) (LysoPLD) (Autotaxin)
863
Q96HE7
ERO1-like protein alpha (ERO1-L-alpha) (ERO1-L) (EC 1.8.4.-) (Oxidoreductin-1-L-alpha) (Endoplasmic oxidoreductin-1-like protein)
468
P00740
Coagulation factor IX (EC 3.4.21.22) (Christmas factor) (Plasma thromboplastin component) (PTC) [Cleaved into: Coagulation factor IXa light chain; Coagulation factor IXa heavy chain]
461
O75015
Low affinity immunoglobulin gamma Fc region receptor III-B (IgG Fc receptor III-1) (Fc-gamma RIII-beta) (Fc-gamma RIIIb) (FcRIIIb) (Fc-gamma RIII) (FcRIII) (FcR-10) (CD antigen CD16b)
233
O75636
Ficolin-3 (Collagen/fibrinogen domain-containing protein 3) (Collagen/fibrinogen domain-containing lectin 3 p35) (Hakata antigen)
299
Q96LA5
Fc receptor-like protein 2 (FcR-like protein 2) (FcRL2) (Fc receptor homolog 2) (FcRH2) (Immunoglobulin receptor translocation-associated protein 4) (IFGP family protein 4) (SH2 domain-containing phosphatase anchor protein 1)
508
Q9NZU0
Leucine-rich repeat transmembrane protein FLRT3 (Fibronectin-like domain-containing leucine-rich transmembrane protein 3)
649
P06396
Gelsolin (Actin-depolymerizing factor) (ADF) (Brevin) (AGEL)
782
P22749
Granulysin (Protein NKG5) (Lymphokine LAG-2) (T-cell activation protein 519)
145
Q14956
Transmembrane glycoprotein NMB (Transmembrane glycoprotein HGFIN)
572
P28799
Granulins (Proepithelin) (PEPI) [Cleaved into: Acrogranin; Paragranulin; Granulin-1 (Granulin G); Granulin-2 (Granulin F); Granulin-3 (Granulin B); Granulin-4 (Granulin A); Granulin-5 (Granulin C); Granulin-6 (Granulin D); Granulin-7 (Granulin E)]
593
Q9Y251
Heparanase (EC 3.2.-.-) (Heparanase-1) (Hpa1) (Endo-glucoronidase) [Cleaved into: Heparanase 8 kDa subunit; Heparanase 50 kDa subunit]
543
P01871
Ig mu chain C region
452
P01583
Interleukin-1 alpha (IL-1 alpha) (Hematopoietin-1)
271
Q8NI17
Interleukin-31 receptor A (IL-31RA) (Cytokine receptor-like 3) (Gp130-like monocyte receptor) (HGLM-R) (GLM-R) (Gp130-like receptor)
732
P57087
Junctional adhesion molecule B (JAM-B) (Junctional adhesion molecule 2) (Vascular endothelial junction-associated molecule) (VE-JAM) (CD antigen CD322)
298
P31025
Lipocalin-1 (Von Ebner gland protein) (VEG protein) (Tear prealbumin) (TP) (Tear lipocalin) (Tlc)
176
Q9HBX8

-continued

Leucine-rich repeat-containing G-protein coupled receptor 6
967
Q14766
Latent-transforming growth factor beta-binding protein 1 (LTBP-1) (Transforming growth factor beta-1-binding protein 1) (TGF-beta1-BP-1)
1,721
O15232
Matrilin-3
486
O95297
Myelin protein zero-like protein 1 (Protein zero-related)
269
Q6ZNJ1
Neurobeachin-like protein 2
2,754
Q92542
Nicastrin
709
Q9BW91
ADP-ribose pyrophosphatase, mitochondrial (EC 3.6.1.13) (ADP-ribose diphosphatase) (Adenosine diphosphoribose pyrophosphatase) (ADPR-PPase) (ADP-ribose phosphohydrolase) (Nucleoside diphosphate-linked moiety X motif 9) (Nudix motif 9)
350
Q96QU1
Protocadherin-15
1,955
P49763
Placenta growth factor (PlGF)
221
Q8WZA1
Protein O-linked-mannose beta-1,2-N-acetylglucosaminyltransferase 1 (POMGnT1) (EC 2.4.1.-) (UDP-GlcNAc:alpha-D-mannoside beta-1,2-N-acetylglucosaminyltransferase I.2) (GnT I.2)
660
Q8N490
Probable hydrolase PNKD (EC 3.-.-.-) (Paroxysmal nonkinesiogenic dyskinesia protein) (Myofibrillogenesis regulator 1) (MR-1) (Trans-activated by hepatitis C virus core protein 2)
385
P21246
Pleiotrophin (PTN) (Heparin-binding growth-associated molecule) (HB-GAM) (Heparin-binding growth factor 8) (HBGF-8) (Osteoblast-specific factor 1) (OSF-10) (Heparin-binding neurite outgrowth-promoting factor 1) (HBNF-1) (Heparin-binding brain mitogen) (HBBM)
168
P15151
Poliovirus receptor (Nectin-like protein 5) (Necl-5) (CD antigen CD155)
417
Q9BZR6
Reticulon-4 receptor (Nogo receptor) (NgR) (Nogo-66 receptor)
473
P02735
Serum amyloid A protein (SAA) [Cleaved into: Amyloid protein A (Amyloid fibril protein AA); Serum amyloid protein A(2-104); Serum amyloid protein A(3-104); Serum amyloid protein A(2-103); Serum amyloid protein A(2-102); Serum amyloid protein A(4-101)]
122
P04278
Sex hormone-binding globulin (SHBG) (Sex steroid-binding protein) (SBP) (Testis-specific androgen-binding protein) (ABP) (Testosterone-estrogen-binding globulin) (Testosterone-estradiol-binding globulin) (TeBG)
402
Q96DU3
SLAM family member 6 (NK-T-B-antigen) (NTB-A) (Activating NK receptor)
332
Q14BN4
Sarcolemmal membrane-associated protein (Sarcolemmal-associated protein)
828
Q4LDE5
Sushi, von Willebrand factor type A, EGF and pentraxin domain-containing protein 1 (Polydom) (Selectin-like osteoblast-derived protein) (SEL-OB) (CCP module-containing protein 22) (Serologically defined breast cancer antigen NY-BR-38)
3,574
P05543
Thyroxine-binding globulin (T4-binding globulin) (Serpin A7)
415
Q9UM00
Transmembrane and coiled-coil domain-containing protein 1 (Xenogeneic cross-immune protein PCIA3) (Transmembrane and coiled-coil domains protein 4)
188
P57727
Transmembrane protease, serine 3 (EC 3.4.21.-) (Tumor-associated differentially-expressed gene 12 protein) (Serine protease TADG-12)
454
O14798
Tumor necrosis factor receptor superfamily member 10C (Decoy receptor 1) (DcR1) (Decoy TRAIL receptor without death domain) (TNF-related apoptosis-inducing ligand receptor 3) (TRAIL receptor 3) (TRAIL-R3) (Trail receptor without an intracellular domain) (Lymphocyte inhibitor of TRAIL) (Antagonist decoy receptor for TRAIL/Apo-2L) (CD antigen CD263)
259
O00300

Tumor necrosis factor receptor superfamily member 11B (Osteoprotegerin) (Osteoclastogenesis inhibitory factor)
401
P02787
Serotransferrin (Transferrin) (Siderophilin) (Beta-1 metal-binding globulin)
698
P20231
Tryptase beta-2 (Tryptase-2) (EC 3.4.21.59) (Tryptase II)
275
O95292
Vesicle-associated membrane protein-associated protein B/C (VAMP-associated protein B/C) (VAMP-B/VAMP-C) (VAP-B/VAP-C)
243
Q969M3
Protein YIPF5 (YIP1 family member 5) (YPT-interacting protein 1 A) (Five-pass transmembrane protein localizing in the Golgi apparatus and the endoplasmic reticulum 5) (Smooth muscle cell-associated protein 5) (SMAP-5)
257
B2RDL6
cDNA, FLJ96669, highly similar to Homo sapiens secreted protein, acidic, cysteine-rich (osteonectin)(SPARC), mRNA
303
A8KAM5
cDNA FLJ77519, highly similar to Homo sapiens secreted frizzled related protein mRNA
313
P30203
T-cell differentiation antigen CD6 (T12) (TP120) (CD antigen CD6)
668
Q63HQ2
Pikachurin (EGF-like, fibronectin type-III and laminin G-like domain-containing protein)
1,017
Q08830
Fibrinogen-like protein 1 (Hepatocyte-derived fibrinogen-related protein 1) (HFREP-1) (Hepassocin) (Liver fibrinogen-related protein 1) (LFIRE-1) (HP-041)
312
P24001
Interleukin-32 (IL-32) (Natural killer cells protein 4) (Tumor necrosis factor alpha-inducing factor)
234
O95460
Matrilin-4
622
Q08648
Sperm-associated antigen 11B (Protein EP2) (Sperm antigen HE2)
103
P00748
Coagulation factor XII (EC 3.4.21.38) (Hageman factor) (HAF) [Cleaved into: Coagulation factor XIIa heavy chain; Beta-factor XIIa part 1; Beta-factor XIIa part 2; Coagulation factor XIIa light chain]
615
P81172
Hepcidin (Liver-expressed antimicrobial peptide) (LEAP-1) (Putative liver tumor regressor) (PLTR) [Cleaved into: Hepcidin-25 (Hepc25); Hepcidin-20 (Hepc20)]
84
Q9UEF7
Klotho (EC 3.2.1.31) [Cleaved into: Klotho peptide]
1,012
P10124
Serglycin (Secretory granule proteoglycan core protein) (Platelet proteoglycan core protein) (P.PG) (Hematopoetic proteoglycan core protein)
158
Q9UIK5
Tomoregulin-2 (Transmembrane protein with EGF-like and two follistatin-like domains) (TR-2) (Hyperplastic polyposis protein 1)
374
Q6WN34
Chordin-like protein 2 (Chordin-related protein 2) (Breast tumor novel factor 1) (BNF-1)
429
Q8WWZ1
Interleukin-1 family member 10 (IL-1F10) (Interleukin-1 receptor antagonist-like FIL1 theta) (Interleukin-1 theta) (IL-1 theta) (FIL1 theta) (Interleukin-1 HY2) (IL-1HY2)
152
Q9UBX7
Kallikrein-11 (hK11) (EC 3.4.21.-) (Hippostasin) (Trypsin-like protease) (Serine protease 20) [Cleaved into: Kallikrein-11 inactive chain 1; Kallikrein-11 inactive chain 2]
282
Q9NP55
Protein Plunc (Palate lung and nasal epithelium clone protein) (Lung-specific protein X) (Nasopharyngeal carcinoma-related protein) (Tracheal epithelium-enriched protein) (Secretory protein in upper respiratory tracts) (Von Ebner protein Hl)
256
Q7Z5L7
Podocan
613
O95407
Tumor necrosis factor receptor superfamily member 6B (Decoy receptor for Fas ligand) (Decoy receptor 3) (DcR3) (M68)
300
Q96A57

UPF0414 transmembrane protein C20orf30
120
Q8WTT0
C-type lectin domain family 4 member C (C-type lectin superfamily member 7) (Blood dendritic cell antigen 2 protein) (BDCA-2) (Dendritic lectin) (CD antigen CD303)
213
Q7Z3D6
UPF0317 protein C14orf159, mitochondrial
616
Q96CW9
Netrin-G2 (Laminet-2)
530
Q8NFT2
Metalloreductase STEAP2 (EC 1.16.1.-) (Six-transmembrane epithelial antigen of prostate 2) (SixTransMembrane protein of prostate 1) (Prostate cancer-associated protein 1) (Protein upregulated in metastatic prostate cancer) (PUMPCn)
490
Q5VX71
Sushi domain-containing protein 4
490
Q5BJH7
Protein YIF1B (YIP1-interacting factor homolog B)
314
Q9NRN5
Olfactomedin-like protein 3 (HNOEL-iso) (hOLF44)
406
O95445
Apolipoprotein M (Apo-M) (ApoM) (Protein G3a)
188
P20851
C4b-binding protein beta chain
252
P10966
T-cell surface glycoprotein CD8 beta chain (CD antigen CD8b)
210
P16619
C-C motif chemokine 3-like 1 (Small-inducible cytokine A3-like 1) (Tonsillar lymphocyte LD78 beta protein) (LD78-beta(1-70)) (G0/G1 switch regulatory protein 19-2) (G0S19-2 protein) (PAT 464.2) [Cleaved into: LD78-beta(3-70); LD78-beta(5-70)]
93
P55075
Fibroblast growth factor 8 (FGF-8) (Heparin-binding growth factor 8) (HBGF-8) (Androgen-induced growth factor) (AIGF)
233
Q04900
Sialomucin core protein 24 (MUC-24) (Multi-glycosylated core protein 24) (MGC-24) (Endolyn) (CD antigen CD164)
197
Q9BQ51
Programmed cell death 1 ligand 2 (Programmed death ligand 2) (PD-L2) (PD-1-ligand 2) (PDCD1 ligand 2) (Butyrophilin B7-DC) (B7-DC) (CD antigen CD273)
273
B2R7H0
Secreted and transmembrane 1 (cDNA, FLJ93441, Homo sapiens secreted and transmembrane 1 (SECTM1), mRNA)
248
Q9BXI9
Complement C1q tumor necrosis factor-related protein 6
259
Q9BY15
EGF-like module-containing mucin-like hormone receptor-like 3 (EGF-like module-containing mucin-like receptor EMR3) [Cleaved into: EGF-like module-containing mucin-like hormone receptor-like 3 subunit alpha; EGF-like module-containingmucin-like hormone receptor-like 3 subunit beta]
652
Q96PB7
Noelin-3 (Olfactomedin-3) (Optimedin)
478
Q9NPH6
Odorant-binding protein 2b (OBPIIb)
170
O95399
Urotensin-2 (Urotensin-II) (U-II) (UII)
124
Q6UXI7
Vitrin
678
O95389
WNT1-inducible-signaling pathway protein 3 (WISP-3)
354
A8K7E3
cDNA FLJ75759, highly similar to Homo sapiens follistatin-like 3 (secreted glycoprotein) (FSTL3), mRNA (Follistatin-like 3 (Secreted glycoprotein), isoform CRA_a)
263
Q9BYF1

-continued

Angiotensin-converting enzyme 2 (EC 3.4.17.-) (ACE-related carboxypeptidase) (Angiotensin-converting enzyme homolog) (ACEH) (Metalloprotease MPROT15) [Cleaved into: Processed angiotensin-converting enzyme 2]
805
Q15848
Adiponectin (Adipocyte, C1q and collagen domain-containing protein) (30 kDa adipocyte complement-related protein) (Adipocyte complement-related 30 kDa protein) (ACRP30) (Adipose most abundant gene transcript 1 protein) (apM-1) (Gelatin-binding protein)
244
Q9BY76
Angiopoietin-related protein 4 (Angiopoietin-like 4) (Hepatic fibrinogen/angiopoietin-related protein) (HFARP)
406
Q6Q788
Apolipoprotein A-V (Apo-AV) (ApoA-V) (Apolipoprotein A5) (Regeneration-associated protein 3)
366
Q9BXN1
Asporin (Periodontal ligament-associated protein 1) (PLAP-1)
380
P17213
Bactericidal permeability-increasing protein (BPI) (CAP 57)
487
Q9H5V8
CUB domain-containing protein 1 (Transmembrane and associated with src kinases) (Membrane glycoprotein gp140) (Subtractive immunization M plus HEp3-associated 135 kDa protein) (SIMA135) (CD antigen CD318)
836
O75339
Cartilage intermediate layer protein 1 (CILP-1) (Cartilage intermediate-layer protein) [Cleaved into: Cartilage intermediate layer protein 1 C1; Cartilage intermediate layer protein 1 C2]
1,184
Q96KN2
Beta-Ala-His dipeptidase (EC 3.4.13.20) (Carnosine dipeptidase 1) (CNDP dipeptidase 1) (Serum carnosinase) (Glutamate carboxypeptidase-like protein 2)
507
P20908
Collagen alpha-1(V) chain
1,838
Q9BXS0
Collagen alpha-1(XXV) chain (CLAC-P) (Alzheimer disease amyloid-associated protein) (AMY) [Cleaved into: Collagen-like Alzheimer amyloid plaque component (CLAC)]
654
Q8NBQ5
Estradiol 17-beta-dehydrogenase 11 (EC 1.1.1.62) (17-beta-hydroxysteroid dehydrogenase 11) (17-beta-HSD 11) (17betaHSD11) (17bHSD11) (17-beta-HSD XI) (17betaHSDXI) (Dehydrogenase/reductase SDR family member 8) (Retinal short-chain dehydrogenase/reductase 2) (retSDR2) (Cutaneous T-cell lymphoma-associated antigen HD-CL-03) (CTCL tumor antigen HD-CL-03)
300
Q8IXB1
DnaJ homolog subfamily C member 10 (ER-resident protein ERdj5) (Macrothioredoxin) (MTHr)
793
Q8IUX8
EGF-like domain-containing protein 6 (Multiple EGF-like domain protein 6) (Multiple epidermal growth factor-like domain protein 6) (MAM and EGF domains-containing gene protein)
553
P00488
Coagulation factor XIII A chain (Coagulation factor XIIIa) (EC 2.3.2.13) (Protein-glutamine gamma-glutamyltransferase A chain) (Transglutaminase A chain)
732
P06744
Glucose-6-phosphate isomerase (GPI) (EC 5.3.1.9) (Phosphoglucose isomerase) (PGI) (Phosphohexose isomerase) (PHI) (Autocrine motility factor) (AMF) (Neuroleukin) (NLK) (Sperm antigen 36) (SA-36)
558
Q9UBU3
Appetite-regulating hormone (Growth hormone secretagogue) (Growth hormone-releasing peptide) (Motilin-related peptide) (M46 protein) [Cleaved into: Ghrelin-27; Ghrelin-28 (Ghrelin); Obestatin]
117
P29460
Interleukin-12 subunit beta (IL-12B) (IL-12 subunit p40) (Cytotoxic lymphocyte maturation factor 40 kDa subunit) (CLMF p40) (NK cell stimulatory factor chain 2) (NKSF2)
328
Q9GZX6
Interleukin-22 (IL-22) (IL-10-related T-cell-derived-inducible factor) (IL-TIF)
179
Q8WWA0
Intelectin-1 (ITLN-1) (Intestinal lactoferrin receptor) (Galactofuranose-binding lectin) (Endothelial lectin HL-1) (Omentin)
313
O95970
Leucine-rich glioma-inactivated protein 1 (Epitempin-1)
557
Q9Y6Y9
Lymphocyte antigen 96 (Protein MD-2) (ESOP-1)
160
P09237

-continued

Matrilysin (EC 3.4.24.23) (Pump-1 protease) (Uterine metalloproteinase) (Matrix metalloproteinase-7) (MMP-7) (Matrin)
267
Q8N307
Mucin-20 (MUC-20)
709
Q8NBP7
Proprotein convertase subtilisin/kexin type 9 (EC 3.4.21.-) (Proprotein convertase PC9) (Subtilisin/kexin-like protease PC9) (Neural apoptosis-regulated convertase 1) (NARC-1)
692
O75594
Peptidoglycan recognition protein (PGRP-S)
196
P05161
Interferon-induced 17 kDa protein [Cleaved into: Ubiquitin cross-reactive protein (hUCRP) (Interferon-induced 15 kDa protein)]
165
P56705
Protein Wnt-4
351
Q9BQI0
Allograft inflammatory factor 1-like (Ionized calcium-binding adapter molecule 2)
150
Q9UH62
Armadillo repeat-containing X-linked protein 3 (Protein ALEX3) (ARM protein lost in epithelial cancers on chromosome X 3)
379
Q8TDX6
Chondroitin sulfate N-acetylgalactosaminyltransferase 1 (CsGalNAcT-1) (EC 2.4.1.174) (Chondroitin beta-1,4-N-acetylgalactosaminyltransferase 1) (Beta4GalNAcT-1)
532
Q13231
Chitotriosidase-1 (EC 3.2.1.14) (Chitinase-1)
466
Q9NY35
Claudin domain-containing protein 1 (Membrane protein GENX-3745)
253
O94905
Erlin-2 (Endoplasmic reticulum lipid raft-associated protein 2) (Stomatin-prohibitin-flotillin-HflC/K domain-containing protein 2) (SPFH domain-containing protein 2)
339
Q68CQ7
Glycosyltransferase 8 domain-containing protein 1 (EC 2.4.1.-)
371
Q8NBJ4
Golgi membrane protein 1 (Golgi phosphoprotein 2) (Golgi membrane protein GP73)
401
Q8IWK6
Probable G-protein coupled receptor 125
1,321
Q9UHF4
Interleukin-20 receptor alpha chain (IL-20R-alpha) (IL-20R1) (Cytokine receptor class-II member 8) (Cytokine receptor family 2 member 8) (CRF2-8) (ZcytoR7)
553
P47929
Galectin-7 (Gal-7) (HKL-14) (PI7) (p53-induced gene 1 protein)
136
Q8TD07
NKG2D ligand 4 (NKG2DL4) (N2DL-4) (Retinoic acid early transcript 1E) (Lymphocyte effector toxicity activation ligand) (RAE-1-like transcript 4) (RL-4)
263
Q96RQ9
L-amino-acid oxidase (LAAO) (LAO) (EC 1.4.3.2) (Interleukin-4-induced protein 1) (IL4-induced protein 1) (Protein Fig-1) (hFIG1)
567
Q32P28
Prolyl 3-hydroxylase 1 (EC 1.14.11.7) (Leucine- and proline-enriched proteoglycan 1) (Leprecan-1) (Growth suppressor 1)
736
Q5H8A4
GPI ethanolamine phosphate transferase 2 (EC 2.-.-.-) (Phosphatidylinositol-glycan biosynthesis class G protein) (PIG-G) (GPI7 homolog) (hGPI7)
983
Q8TEQ8
GPI ethanolamine phosphate transferase 3 (EC 2.-.-.-) (Phosphatidylinositol-glycan biosynthesis class O protein) (PIG-O)
1,089
Q6KCM7
Calcium-binding mitochondrial carrier protein SCaMC-2 (Small calcium-binding mitochondrial carrier protein 2) (Mitochondrial ATP-Mg/Pi carrier protein 3) (Mitochondrial Ca(2+)-dependent solute carrier protein 3) (Solute carrier family 25 member 25)
469
Q8IWL1
Pulmonary surfactant-associated protein A2 (SP-A2) (SP-A) (PSP-A) (PSPA) (Alveolar proteinosis protein) (35 kDa pulmonary surfactant-associated protein)
248
Q8N2M8

-continued

Splicing factor, arginine/serine-rich 16 (Suppressor of white-apricot homolog 2)
674
Q969X2
Alpha-N-acetylgalactosaminide alpha-2,6-sialyltransferase 6 (EC 2.4.99.-) (GalNAc alpha-2,6-sialyltransferase VI) (hST6GalNAc VI) (ST6GalNAc VI) (Sialyltransferase 7F)
333
Q6IA17
Single Ig IL-1-related receptor (Single Ig IL-1R-related molecule) (Single immunoglobulin domain-containing IL1R-related protein) (Toll/interleukin-1 receptor 8) (TIR8)
410
Q6NUS6
Tectonic-3
607
O14788
Tumor necrosis factor ligand superfamily member 11 (Receptor activator of nuclear factor kappa B ligand) (RANKL) (TNF-relatedactivation-induced cytokine) (TRANCE) (Osteoprotegerin ligand) (OPGL) (Osteoclast differentiation factor) (ODF) (CD antigen CD254) [Cleaved into: Tumor necrosis factor ligand superfamily member 11, membrane form; Tumor necrosis factor ligand superfamily member 11, soluble form]
317
Q9NS68
Tumor necrosis factor receptor superfamily member 19 (Toxicity and JNK inducer) (TRADE)
423
Q9Y397
Palmitoyltransferase ZDHHC9 (EC 2.3.1.-) (Zinc finger DHHC domain-containing protein 9) (DHHC-9) (DHHC9) (Zinc finger protein 379)
364
Q9UBX5
Fibulin-5 (FIBL-5) (Developmental arteries and neural crest EGF-like protein) (Dance) (Urine p50 protein) (UP50)
448
Q9UK55
Protein Z-dependent protease inhibitor (PZ-dependent protease inhibitor) (PZI) (Serpin A10)
444
P01023
Alpha-2-macroglobulin (Alpha-2-M) (C3 and PZP-like alpha-2-macroglobulin domain-containing protein 5)
1,474
O00253
Agouti-related protein
132
P04746
Pancreatic alpha-amylase (PA) (EC 3.2.1.1) (1,4-alpha-D-glucan glucanohydrolase)
511
P16860
Natriuretic peptides B (Gamma-brain natriuretic peptide) [Cleaved into: Brain natriuretic peptide 32 (BNP-32) (BNP(1-32)); BNP(1-30); BNP(1-29); BNP(1-28); BNP(2-31); BNP(3-32); BNP(3-30); BNP(3-29); BNP(4-32); BNP(4-31); BNP(4-30); BNP(4-29); BNP(4-27); BNP(5-32); BNP(5-31); BNP(5-29)]
134
P01160
Atrial natriuretic factor (ANF) (Atrial natriuretic peptide) (ANP) (Prepronatriodilatin) (CDD-ANF) [Cleaved into: Cardiodilatin-related peptide (CDP)]
153
Q9NR71
Neutral ceramidase (N-CDase) (NCDase) (EC 3.5.1.23) (Acylsphingosine deacylase 2) (N-acylsphingosine amidohydrolase 2) (Non-lysosomal ceramidase) (BCDase) (LCDase) (hCD) [Cleaved into: Neutral ceramidase soluble form]
780
P61769
Beta-2-microglobulin [Cleaved into: Beta-2-microglobulin form pI 5.3]
119
P12644
Bone morphogenetic protein 4 (BMP-4) (BMP-2B)
408
P43251
Biotinidase (Biotinase) (EC 3.5.1.12)
543
Q86VB7
Scavenger receptor cysteine-rich type 1 protein M130 (Hemoglobin scavenger receptor) (CD antigen CD163) [Cleaved into: Soluble CD163 (sCD163)]
1,156
Q96IY4
Carboxypeptidase B2 (EC 3.4.17.20) (Carboxypeptidase U) (CPU) (Thrombin-activable fibrinolysis inhibitor) (TAFI) (Plasma carboxypeptidase B) (pCPB)
423
Q66K79
Carboxypeptidase Z (CPZ) (EC 3.4.17.-)
652
P13501
C-C motif chemokine 5 (Small-inducible cytokine A5) (T-cell-specific protein RANTES) (SIS-delta) (T cell-specific protein P228) (TCP228) (Eosinophil-chemotactic cytokine) (EoCP) [Cleaved into: RANTES(3-68); RANTES(4-68)]
91
P80098
C-C motif chemokine 7 (Small-inducible cytokine A7) (Monocyte chemoattractant protein 3) (Monocyte chemotactic protein 3) (MCP-3) (NC28)
99
P80075
C-C motif chemokine 8 (Small-inducible cytokine A8) (Monocyte chemoattractant protein 2) (Monocyte chemotactic protein 2) (MCP-2) (HC14)

[Cleaved into: MCP-2(6-76)]
99
P13987
CD59 glycoprotein (Membrane attack complex inhibition factor) (MACIF) (MAC-inhibitory protein) (MAC-IP) (Protectin) (MEM43 antigen) (Membrane inhibitor of reactive lysis) (MIRL) (20 kDa homologous restriction factor) (HRF-20) (HRF20) (1F5 antigen) (CD antigen CD59)
128
P05156
Complement factor I (EC 3.4.21.45) (C3B/C4B inactivator) [Cleaved into: Complement factor I heavy chain; Complement factor I light chain]
583
P10909
Clusterin (Complement-associated protein SP-40,40) (Complement cytolysis inhibitor) (CLI) (NA1/NA2) (Apolipoprotein J) (Apo-J) (Testosterone-repressed prostate message 2) (TRPM-2) (Ku70-binding protein 1) (Aging-associated gene 4 protein) [Cleaved into: Clusterin beta chain (ApoJalpha) (Complement cytolysis inhibitor a chain); Clusterin alpha chain (ApoJbeta) (Complement cytolysis inhibitor b chain)]
449
P08123
Collagen alpha-2(I) chain (Alpha-2 type I collagen)
1,366
P02461
Collagen alpha-1(III) chain
1,466
P02462
Collagen alpha-1(IV) chain (Arresten)
1,669
Q01955
Collagen alpha-3(IV) chain (Goodpasture antigen) [Cleaved into: Tumstatin]
1,670
P29400
Collagen alpha-5(IV) chain
1,685
P12111
Collagen alpha-3(VI) chain
3,177
P13671
Complement component C6
934
P20849
Collagen alpha-1(IX) chain
921
Q03692
Collagen alpha-1(X) chain
680
Q9UMD9
Collagen alpha-1(XVII) chain (Bullous pemphigoid antigen 2) (180 kDa bullous pemphigoid antigen 2) [Cleaved into: 120 kDa linear IgA disease antigen (120 kDa linear IgA dermatosis antigen) (Linear IgA disease antigen 1) (LAD-1); 97 kDa linear IgA disease antigen (97 kDa linear IgA bullous dermatosis antigen) (97 kDa LAD antigen) (97-LAD) (Linear IgA bullous disease antigen of 97 kDa) (LABD97)]
1,497
Q96P44
Collagen alpha-1(XXI) chain
957
P53621
Coatomer subunit alpha (Alpha-coat protein) (Alpha-COP) (HEP-COP) (HEPCOP) [Cleaved into: Xenin (Xenopsin-related peptide); Proxenin]
1,224
P17927
Complement receptor type 1 (C3b/C4b receptor) (CD antigen CD35)
2,039
P01037
Cystatin-SN (Cystatin-1) (Salivary cystatin-SA-1) (Cystain-SA-I)
141
P24855
Deoxyribonuclease-1 (EC 3.1.21.1) (Deoxyribonuclease I) (DNase I) (Dornase alfa)
282
Q16610
Extracellular matrix protein 1 (Secretory component p85)
540
P12259
Coagulation factor V (Activated protein C cofactor) (Proaccelerin, labile factor) [Cleaved into: Coagulation factor V heavy chain; Coagulation factor V light chain]
2,224
P08709
Coagulation factor VII (EC 3.4.21.21) (Serum prothrombin conversion accelerator) (SPCA) (Proconvertin) (Eptacog alfa) [Cleaved into: Factor VII light chain; Factor VII heavy chain]
466
P24071
Immunoglobulin alpha Fc receptor (IgA Fc receptor) (CD antigen CD89)
287
P08637
Low affinity immunoglobulin gamma Fc region receptor III-A (IgG Fc receptor III-2) (Fc-gamma RIII-alpha) (Fc-gamma RIIIa) (FcRIIIa) (Fc-gamma RIII) (FcRIII) (FcR-10) (CD16a antigen) (CD antigen CD16a)
254

-continued

P02771
Alpha-fetoprotein (Alpha-1-fetoprotein) (Alpha-fetoglobulin)
609
P09038
Heparin-binding growth factor 2 (HBGF-2) (Basic fibroblast growth factor) (BFGF)
210
P02679
Fibrinogen gamma chain
453
P43026
Growth/differentiation factor 5 (GDF-5) (Cartilage-derived morphogenetic protein 1) (CDMP-1) (Radotermin)
501
P39905
Glial cell line-derived neurotrophic factor (Astrocyte-derived trophic factor) (ATF) (hGDNF)
211
P17936
Insulin-like growth factor-binding protein 3 (IGF-binding protein 3) (IGFBP-3) (IBP-3)
291
P01343
Insulin-like growth factor IA (IGF-IA) (Somatomedin-C) (Mechano growth factor) (MGF)
153
P01857
Ig gamma-1 chain C region
330
P01859
Ig gamma-2 chain C region
326
P01860
Ig gamma-3 chain C region (Heavy chain disease protein) (HDC)
377
Q8N6C5
Immunoglobulin superfamily member 1 (Inhibin-binding protein) (InhBP) (Immunoglobulin-like domain-containing protein 1)
(Pituitary gland specific factor 2) (p120)
1,336
P05112
Interleukin-4 (IL-4) (B-cell stimulatory factor 1) (BSF-1) (Lymphocyte stimulatory factor 1) (Binetrakin) (Pitrakinra)
153
P08887
Interleukin-6 receptor subunit alpha (IL-6R-alpha) (IL-6R 1) (Membrane glycoprotein 80) (gp80) (CD antigen CD126)
468
P05231
Interleukin-6 (IL-6) (B-cell stimulatory factor 2) (BSF-2) (Interferon beta-2) (Hybridoma growth factor) (CTL differentiation factor) (CDF)
212
P10145
Interleukin-8 (IL-8) (C-X-C motif chemokine 8) (Monocyte-derived neutrophil chemotactic factor) (MDNCF) (T-cell chemotactic factor)
(Neutrophil-activating protein 1) (NAP-1) (Protein 3-10C) (Granulocyte chemotactic protein 1) (GCP-1) (Monocyte-derived neutrophil-activating
peptide) (MONAP) (Emoctakin) [Cleaved into: MDNCF-a (IL8/NAP1 form I) (GCP/IL-8 protein IV); Interleukin-8 (IL-8(1-77)) (MDNCF-b)
(IL8/NAP1 form II) (GCP/IL-8 protein II) ((Ala-IL-8)77); IL-8(5-77); IL-8(6-77) (Lymphocyte-derived neutrophil-activating factor) (LYNAP)
(Neutrophil-activating factor) (NAF) (MDNCF-c) (IL8/NAP1 form III) (GCP/IL-8 protein I) ((Ser-IL-8)72); IL-8(7-77) (IL8/NAP1 form IV)
(GCP/IL-8 protein V); IL-8(8-77) (IL8/NAP1 form V) (GCP/IL-8 protein VI); IL-8(9-77) (IL8/NAP1 form VI) (GCP/IL-8 protein III)]
99
P51460
Insulin-like 3 (Leydig insulin-like peptide) (Ley-I-L) (Relaxin-like factor) [Cleaved into: Insulin-like 3 B chain; Insulin-like 3 A chain]
131
Q14624
Inter-alpha-trypsin inhibitor heavy chain H4 (Inter-alpha-inhibitor heavy chain 4) (ITI heavy chain H4) (Inter-alpha-trypsin inhibitor family heavy
chain-related protein) (IHRP) (Plasma kallikrein sensitive glycoprotein 120) (PK-120) (GP120) [Cleaved into: 70 kDa inter-alpha-trypsin inhibitor
heavy chain H4; 35 kDa inter-alpha-trypsin inhibitor heavy chain H4]
930
Q14667
UPF0378 protein KIAA0100 (Breast cancer overexpressed gene 1 protein) (Antigen MLAA-22)
2,235
P01042
Kininogen-1 (High molecular weight kininogen) (HMWK) (Williams-Fitzgerald-Flaujeac factor) (Fitzgerald factor) (Alpha-2-thiol proteinase inhibitor)
[Cleaved into: Kininogen-1 heavy chain; T-kinin (Ile-Ser-Bradykinin); Bradykinin (Kallidin I); Lysyl-bradykinin (Kallidin II); Kininogen-1 light chain;
Low molecular weight growth-promoting factor]
644
P24043
Laminin subunit alpha-2 (Laminin M chain) (Merosin heavy chain)
3,122
Q16363
Laminin subunit alpha-4
1,823
P07942
Laminin subunit beta-1 (Laminin B1 chain)
1,786
P28300
Protein-lysine 6-oxidase (EC 1.4.3.13) (Lysyl oxidase)
417

-continued

P08581
Hepatocyte growth factor receptor (HGF receptor) (EC 2.7.10.1) (Scatter factor receptor) (SF receptor) (HGF/SF receptor) (Met proto-oncogene tyrosine kinase) (c-Met)
1,390
P20774
Mimecan (Osteoglycin) (Osteoinductive factor) (OIF)
298
Q99542
Matrix metalloproteinase-19 (MMP-19) (EC 3.4.24.-) (Matrix metalloproteinase RASI) (MMP-18)
508
Q13201
Multimerin-1 (Endothelial cell multimerin) (EMILIN-4) (Elastin microfibril interface located protein 4) (Elastin microfibril interfacer 4) [Cleaved into: Platelet glycoprotein Ia*; 155 kDa platelet multimerin (p-155) (p155)]
1,228
P01185
Vasopressin-neurophysin 2-copeptin (AVP-NPII) [Cleaved into: Arg-vasopressin; Neurophysin 2 (Neurophysin-II); Copeptin]
164
P14543
Nidogen-1 (NID-1) (Entactin)
1,247
P14555
Phospholipase A2, membrane associated (EC 3.1.1.4) (Phosphatidylcholine 2-acylhydrolase) (Group IIA phospholipase A2) (GIIC sPLA2) (Non-pancreatic secretory phospholipase A2) (NPS-PLA2)
144
P14222
Perforin-1 (P1) (Lymphocyte pore-forming protein) (PFP) (Cytolysin)
555
P80108
Phosphatidylinositol-glycan-specific phospholipase D (PI-G PLD) (EC 3.1.4.50) (Glycoprotein phospholipase D) (Glycosyl-phosphatidylinositol-specific phospholipase D) (GPI-specific phospholipase D) (GPI-PLD)
840
Q8TCZ9
Fibrocystin (Polycystic kidney and hepatic disease 1 protein) (Polyductin) (Tigmin)
4,074
P55058
Phospholipid transfer protein (Lipid transfer protein II)
493
P15309
Prostatic acid phosphatase (EC 3.1.3.2)
386
P01236
Prolactin (PRL)
227
P27918
Properdin (Complement factor P)
469
P07225
Vitamin K-dependent protein S
676
P22891
Vitamin K-dependent protein Z
400
P02810
Salivary acidic proline-rich phosphoprotein 1/2 (PRP-1/PRP-2) (Parotid proline-rich protein 1/2) (Pr1/Pr2) (Protein C) (Parotid acidic protein) (Pa) (Parotid isoelectric focusing variant protein) (PIF-S) (Parotid double-band protein) (Db-s) [Cleaved into: Salivary acidic proline-rich phosphoprotein 1/2; Salivary acidic proline-rich phosphoprotein 3/4 (PRP-3/PRP-4) (Protein A) (PIF-F) (Db-F); Peptide P-C]
166
P11464
Pregnancy-specific beta-1-glycoprotein 1 (PSBG-1) (Pregnancy-specific beta-1 glycoprotein C/D) (PS-beta-C/D) (Fetal liver non-specific cross-reactive antigen 1/2) (FL-NCA-1/2) (PSG95) (CD66 antigen-like family member F) (CD antigen CD66f)
419
P20742
Pregnancy zone protein (C3 and PZP-like alpha-2-macroglobulin domain-containing protein 6)
1,482
P04090
Prorelaxin H2 [Cleaved into: Relaxin B chain; Relaxin A chain]
185
P78509
Reelin (EC 3.4.21.-)
3,460
P02753
Retinol-binding protein 4 (Plasma retinol-binding protein) (PRBP) (RBP) [Cleaved into: Plasma retinol-binding protein(1-182); Plasma retinol-binding protein(1-181); Plasma retinol-binding protein(1-179); Plasma retinol-binding protein(1-176)]
201
Q92854
Semaphorin-4D (BB18) (A8) (GR3) (CD antigen CD100)
862
O94813
Slit homolog 2 protein (Slit-2) [Cleaved into: Slit homolog 2 protein N-product; Slit homolog 2 protein C-product]

-continued 1,529
O75443
Alpha-tectorin
2,155
P22105
Tenascin-X (TN-X) (Hexabrachion-like protein)
4,289
Q07654
Trefoil factor 3 (Intestinal trefoil factor) (hITF) (Polypeptide P1.B) (hP1.B)
80
P02786
Transferrin receptor protein 1 (TfR1) (TfR) (TR) (Trfr) (T9) (p90) (CD antigen CD71) [Cleaved into: Transferrin receptor protein 1, serum form (sTfR)]
760
P01135
Protransforming growth factor alpha [Cleaved into: Transforming growth factor alpha (TGF-alpha) (EGF-like TGF) (ETGF) (TGF type 1)]
160
P61812
Transforming growth factor beta-2 (TGF-beta-2) (Glioblastoma-derived T-cell suppressor factor) (G-TSF) (BSC-1 cell growth inhibitor) (Polyergin) (Cetermin)
414
Q9UJW2
Tubulointerstitial nephritis antigen (TIN-Ag)
476
P48023
Tumor necrosis factor ligand superfamily member 6 (Fas antigen ligand) (Fas ligand) (CD95L protein) (Apoptosis antigen ligand) (APTL) (CD antigen CD178) [Cleaved into: Tumor necrosis factor ligand superfamily member 6, membrane form; Tumor necrosis factor ligand superfamily member 6, soluble form]
281
P20333
Tumor necrosis factor receptor superfamily member 1B (Tumor necrosis factor receptor 2) (TNF-R2) (Tumor necrosis factor receptor type II) (p75) (p80 TNF-alpha receptor) (CD antigen CD120b) (Etanercept) [Cleaved into: Tumor necrosis factor receptor superfamily member 1b, membrane form; Tumor necrosis factor-binding protein 2 (TBPII) (TBP-2)]
461
P25942
Tumor necrosis factor receptor superfamily member 5 (CD40L receptor) (B-cell surface antigen CD40) (Bp50) (CDw40) (CD antigen CD40)
277
P40225
Thrombopoietin (Megakaryocyte colony-stimulating factor) (Myeloproliferative leukemia virus oncogene ligand) (C-mpl ligand) (ML) (Megakaryocyte growth and development factor) (MGDF)
353
Q9NP99
Triggering receptor expressed on myeloid cells 1 (Triggering receptor expressed on monocytes 1) (TREM-1)
234
P01282
VIP peptides [Cleaved into: Intestinal peptide PHV-42; Intestinal peptide PHM-27 (Peptide histidine methioninamide 27); Vasoactive intestinal peptide (VIP) (Vasoactive intestinal polypeptide)]
170
Q9BZP6
Acidic mammalian chitinase (AMCase) (EC 3.2.1.14) (TSA1902)
476
P16562
Cysteine-rich secretory protein 2 (CRISP-2) (Testis-specific protein TPX-1) (Cancer/testis antigen 36) (CT36)
243
P00739
Haptoglobin-related protein
348
Q15238
Pregnancy-specific beta-1-glycoprotein 5 (PSBG-5) (Fetal liver non-specific cross-reactive antigen 3) (FL-NCA-3)
335
Q9BXJ4
Complement C1q tumor necrosis factor-related protein 3 (Secretory protein CORS26)
246
Q9BZM5
NKG2D ligand 2 (UL16-binding protein 2) (NKG2DL2) (N2DL-2) (ALCAN-alpha) (Retinoic acid early transcript 1H)
246
Q9Y258
C-C motif chemokine 26 (Small-inducible cytokine A26) (Eotaxin-3) (Macrophage inflammatory protein 4-alpha) (MIP-4-alpha) (Thymic stroma chemokine-1) (TSC-1) (CC chemokine IMAC)
94
Q9BWP8
Collectin-11 (Collectin kidney protein 1) (CL-K1)
271
Q6UXH1
Cysteine-rich with EGF-like domain protein 2
353
O75462
Cytokine receptor-like factor 1 (Cytokine-like factor 1) (CLF-1) (ZcytoR5)
422
Q9H2A7

-continued

C-X-C motif chemokine 16 (Small-inducible cytokine B16) (Transmembrane chemokine CXCL16) (SR-PSOX) (Scavenger receptor for phosphatidylserine and oxidized low density lipoprotein)
254
Q14512
Fibroblast growth factor-binding protein 1 (FGF-binding protein 1) (FGF-BP1) (FGFBP-1) (FGF-BP) (17 kDa heparin-binding growth factor-binding protein) (17 kDa HBGF-binding protein) (HBp17)
234
Q9UBH0
Interleukin-1 family member 5 (IL-1F5) (Interleukin-1 delta) (IL-1 delta) (FIL1 delta) (Interleukin-1-like protein 1) (IL-1L1) (Interleukin-1 HY1) (IL-1HY1) (Interleukin-1 receptor antagonist homolog 1) (IL-1ra homolog 1) (IL-1-related protein 3) (IL-1RP3)
155
Q9NZH8
Interleukin-1 family member 9 (IL-1F9) (Interleukin-1 homolog 1) (IL-1H1) (Interleukin-1 epsilon) (IL-1 epsilon) (IL-1-related protein 2) (IL-1RP2)
169
Q9Y337
Kallikrein-5 (EC 3.4.21.-) (Stratum corneum tryptic enzyme) (Kallikrein-like protein 2) (KLK-L2)
293
O00339
Matrilin-2
956
Q8TD46
Cell surface glycoprotein CD200 receptor 1 (Cell surface glycoprotein OX2 receptor 1) (CD200 cell surface glycoprotein receptor)
325
Q9NPH0
Lysophosphatidic acid phosphatase type 6 (EC 3.1.3.2) (Acid phosphatase 6, lysophosphatidic) (Acid phosphatase-like protein 1) (PACPL1)
428
Q9H173
Nucleotide exchange factor SIL1 (BiP-associated protein) (BAP)
461
O75094
Slit homolog 3 protein (Slit-3) (Multiple epidermal growth factor-like domains 5)
1,523
Q6X4U4
Sclerostin domain-containing protein 1 (Ectodermal BMP inhibitor) (Ectodin) (Uterine sensitization-associated gene 1 protein) (USAG-1)
206
Q86WD7
Serpin A9 (Germinal center B-cell-expressed transcript 1 protein)
417
Q6ZMP0
Thrombospondin type-1 domain-containing protein 4
1,018
O76076
WNT1-inducible-signaling pathway protein 2 (WISP-2) (Connective tissue growth factor-like protein) (CTGF-L) (Connective tissue growth factor-related protein 58)
250
Q9H8M2
Bromodomain-containing protein 9 (Rhabdomyosarcoma antigen MU-RMS-40.8)
597
Q8TCZ2
CD99 antigen-like protein 2 (MIC2-like protein 1) (CD antigen CD99)
262
Q96HA4
Uncharacterized protein C1orf159
380
Q9NRB3
Carbohydrate sulfotransferase 12 (EC 2.8.2.5) (Chondroitin 4-O-sulfotransferase 2) (Chondroitin 4-sulfotransferase 2) (C4ST2) (C4ST-2) (Sulfotransferase Hlo)
414
Q9H3G5
Probable serine carboxypeptidase CPVL (EC 3.4.16.-) (Carboxypeptidase, vitellogenic-like) (Vitellogenic carboxypeptidase-like protein) (VCP-like protein) (HVLP)
476
Q9NQ79
Cartilage acidic protein 1 (68 kDa chondrocyte-expressed protein) (CEP-68) (ASPIC)
661
Q86UP6
CUB and zona pellucida-like domain-containing protein 1 (CUB and ZP domain-containing protein 1) (Transmembrane protein UO-44)
607
Q96FL9
Polypeptide N-acetylgalactosaminyltransferase 14 (EC 2.4.1.41) (Polypeptide GalNAc transferase 14) (pp-GaNTase 14) (GalNAc-T14) (Protein-UDP acetylgalactosaminyltransferase 14) (UDP-GalNAc:polypeptide N-acetylgalactosaminyltransferase 14)
552
Q2KHT4
Germ cell-specific gene 1 protein
349
Q9HBE5
Interleukin-21 receptor (IL-21R) (Novel interleukin receptor)
538
O00182

-continued

Galectin-9 (HOM-HD-21) (Ecalectin)
355
Q8N6Y2
Leucine-rich repeat-containing protein 17 (p37NB)
441
O75325
Leucine-rich repeat neuronal protein 2 (Leucine-rich repeat neuronal protein 5) (Glioma amplified on chromosome 1 protein)
713
O95803
Bifunctional heparan sulfate N-deacetylase/N-sulfotransferase 3 (EC 2.8.2.8) (Glucosaminyl N-deacetylase/N-sulfotransferase 3) (NDST-3) (hNDST-3)
(N-heparan sulfate sulfotransferase 3) (N-HSST 3) [Includes: Heparan sulfate N-deacetylase 3 (EC 3.-.-.-); Heparan sulfate N-sulfotransferase 3
(EC 2.8.2.-)]
873
Q9H3S1
Semaphorin-4A (Semaphorin-B) (Sema B)
761
Q9HAV5
Tumor necrosis factor receptor superfamily member 27 (X-linked ectodysplasin-A2 receptor) (EDA-A2 receptor)
297
Q9NNX1
Tuftelin
390
O95258
Brain mitochondrial carrier protein 1 (BMCP-1) (Mitochondrial uncoupling protein 5) (UCP 5) (Solute carrier family 25 member 14)
325
Q8IX30
Signal peptide, CUB and EGF-like domain-containing protein 3
993
P31947
14-3-3 protein sigma (Stratifin) (Epithelial cell marker protein 1)
248
P02763
Alpha-1-acid glycoprotein 1 (AGP 1) (Orosomucoid-1) (OMD 1)
201
P19652
Alpha-1-acid glycoprotein 2 (AGP 2) (Orosomucoid-2) (OMD 2)
201
P08697
Alpha-2-antiplasmin (Alpha-2-AP) (Alpha-2-plasmin inhibitor) (Alpha-2-PI)
491
Q13443
Disintegrin and metalloproteinase domain-containing protein 9 (ADAM 9) (EC 3.4.24.-) (Metalloprotease/disintegrin/cysteine-rich protein 9)
(Myeloma cell metalloproteinase) (Meltrin-gamma) (Cellular disintegrin-related protein)
819
P02760
Protein AMBP [Cleaved into: Alpha-1-microglobulin (Protein HC) (Complex-forming glycoprotein heterogeneous in charge)
(Alpha-1 microglycoprotein); Inter-alpha-trypsin inhibitor light chain (ITI-LC) (Bikunin) (HI-30) (Uronic-acid-rich protein) (EDC1); Trypstatin]
352
P01019
Angiotensinogen (Serpin A8) [Cleaved into: Angiotensin-1 (Angiotensin I) (Ang I); Angiotensin-2 (Angiotensin II) (Ang II); Angiotensin-3
(Angiotensin III) (Ang III) (Des-Asp[1]-angiotensin II)]
485
Q9HCJ1
Progressive ankylosis protein homolog (ANK)
492
Q9HDC9
Adipocyte plasma membrane-associated protein (Protein BSCv)
416
P02652
Apolipoprotein A-II (Apo-AII) (ApoA-II) [Cleaved into: Apolipoprotein A-II(1-76)]
100
P06727
Apolipoprotein A-IV (Apo-AIV) (ApoA-IV)
396
P02655
Apolipoprotein C-II (Apo-CII) (ApoC-II)
101
P02749
Beta-2-glycoprotein 1 (Beta-2-glycoprotein I) (Beta(2)GPI) (B2GPI) (Apolipoprotein H) (Apo-H) (Activated protein C-binding protein) (APC inhibitor)
(Anticardiolipin cofactor)
345
Q6UW56
Apoptosis-related protein 3 (APR-3) (p18)
229
Q9Y5Z0
Beta-secretase 2 (EC 3.4.23.45) (Beta-site APP-cleaving enzyme 2) (Aspartyl protease 1) (Asp 1) (ASP1) (Membrane-associated aspartic protease 1)
(Memapsin-1) (Aspartic-like protease 56 kDa) (Down region aspartic protease)
518
P16442

Histo-blood group ABO system transferase (NAGAT) (Glycoprotein-fucosylgalactoside alpha-N-acetylgalactosaminyltransferase) (EC 2.4.1.40)
(Fucosylglycoprotein alpha-N-acetylgalactosaminyltransferase) (Histo-blood group A transferase) (A transferase) (Glycoprotein-fucosylgalactoside
alpha-galactosyltransferase) (EC 2.4.1.37) (Fucosylglycoprotein 3-alpha-galactosyltransferase) (Histo-blood group B transferase) (B transferase)
[Cleaved into: Fucosylglycoprotein alpha-N-acetylgalactosaminyltransferase soluble form]
354
O60911
Cathepsin L2 (EC 3.4.22.43) (Cathepsin V) (Cathepsin U)
334
P10147
C-C motif chemokine 3 (Small-inducible cytokine A3) (Macrophage inflammatory protein 1-alpha) (MIP-1-alpha) (Tonsillar lymphocyte LD78 alpha
protein) (G0/G1 switch regulatory protein 19-1) (G0S19-1 protein) (SIS-beta) (PAT 464.1) [Cleaved into: MIP-1-alpha(4-69) (LD78-alpha(4-69))]
92
Q8N6Q3
CD177 antigen (Polycythemia rubra vera protein 1) (PRV-1) (NB1 glycoprotein) (NB1 GP) (Human neutrophil alloantigen 2a) (HNA-2a)
(CD antigen CD177)
437
P00450
Ceruloplasmin (EC 1.16.3.1) (Ferroxidase)
1,065
P36222
Chitinase-3-like protein 1 (Cartilage glycoprotein 39) (CGP-39) (GP-39) (hCGP-39) (39 kDa synovial protein) (YKL-40)
383
Q9P126
C-type lectin domain family 1 member B (C-type lectin-like receptor 2) (CLEC-2)
229
A8K7I4
Calcium-activated chloride channel regulator 1 (Calcium-activated chloride channel family member 1) (hCLCA1) (Calcium-activated chloride channel
protein 1) (CaCC-1) (hCaCC-1)
914
P23946
Chymase (EC 3.4.21.39) (Alpha-chymase) (Mast cell protease I)
247
P12109
Collagen alpha-1(VI) chain
1,028
P07357
Complement component C8 alpha chain (Complement component 8 subunit alpha)
584
P02748
Complement component C9 [Cleaved into: Complement component C9a; Complement component C9b]
559
P02775
Platelet basic protein (PBP) (C-X-C motif chemokine 7) (Small-inducible cytokine B7) (Leukocyte-derived growth factor) (LDGF) (Macrophage-
derived growth factor) (MDGF) [Cleaved into: Connective tissue-activating peptide III (CTAP-III) (Low-affinity platelet factor IV) (LA-PF4); TC-2;
Connective tissue-activating peptide III(1-81) (CTAP-III(1-81)); Beta-thromboglobulin (Beta-TG); Neutrophil-activating peptide 2(74) (NAP-2(74));
Neutrophil-activating peptide 2(73) (NAP-2(73)); Neutrophil-activating peptide 2 (NAP-2); TC-1; Neutrophil-activating peptide 2(1-66)
(NAP-2(1-66)); Neutrophil-activating peptide 2(1-63) (NAP-2(1-63))]
128
O14625
C-X-C motif chemokine 11 (Small-inducible cytokine B11) (Interferon-inducible T-cell alpha chemoattractant) (I-TAC) (Interferon-gamma-inducible
protein 9) (IP-9) (H174) (Beta-R1)
94
Q9UBS4
DnaJ homolog subfamily B member 11 (ER-associated dnaJ protein 3) (ERj3p) (ERdj3) (ER-associated Hsp40 co-chaperone) (ER-associated DNAJ)
(HEDJ) (hDj9) (PWP1-interacting protein 4) (APOBEC1-binding protein 2) (ABBP-2)
358
Q6UWV6
Ectonucleotide pyrophosphatase/phosphodiesterase family member 7 (E-NPP7) (NPP-7) (EC 3.1.4.12) (Alkaline sphingomyelin phosphodiesterase)
(Intestinal alkaline sphingomyelinase) (Alk-SMase)
458
P19235
Erythropoietin receptor (EPO-R)
508
Q9NZ08
Endoplasmic reticulum aminopeptidase 1 (EC 3.4.11.-) (Adipocyte-derived leucine aminopeptidase) (A-LAP) (ARTS-1) (Aminopeptidase PILS)
(Puromycin-insensitive leucyl-specific aminopeptidase) (PILS-AP) (Type 1 tumor necrosis factor receptor shedding aminopeptidase regulator)
941
P21860
Receptor tyrosine-protein kinase erbB-3 (c-erbB3) (EC 2.7.10.1) (Tyrosine kinase-type cell surface receptor HER3)
1,342
Q9BS26
Endoplasmic reticulum resident protein ERp44 (Thioredoxin domain-containing protein 4)
406
Q9Y6R7
IgGFc-binding protein (Fcgamma-binding protein antigen) (FcgammaBP)
5,405
Q03591
Complement factor H-related protein 1 (FHR-1) (H factor-like protein 1) (H-factor-like 1) (H36)
330

Q10471
Polypeptide N-acetylgalactosaminyltransferase 2 (EC 2.4.1.41) (Polypeptide GalNAc transferase 2) (pp-GaNTase 2) (GalNAc-T2) (Protein-UDP acetylgalactosaminyltransferase 2) (UDP-GalNAc:polypeptide N-acetylgalactosaminyltransferase 2) [Cleaved into: Polypeptide N-acetylgalactosaminyltransferase 2 soluble form]
571
P22352
Glutathione peroxidase 3 (EC 1.11.1.9) (GSHPx-3) (GPx-3) (Extracellular glutathione peroxidase) (Plasma glutathione peroxidase) (GSHPx-P) (GPx-P)
226
P02790
Hemopexin (Beta-1B-glycoprotein)
462
Q04756
Hepatocyte growth factor activator (HGF activator) (HGFA) (EC 3.4.21.-) [Cleaved into: Hepatocyte growth factor activator short chain; Hepatocyte growth factor activator long chain]
655
P15516
Histatin-3 (Histidine-rich protein 3) (PB) (Basic histidine-rich protein) (Hst) [Cleaved into: Histatin-3; Histatin-3 1/25 (Histatin-6); Histatin-3 1/24 (Histatin-5); Histatin-3 1/13; Histatin-3 1/12; Histatin-3 1/11; Histatin-3 5/13; Histatin-3 5/12 (Histatin-11); Histatin-3 5/11 (Histatin-12); Histatin-3 6/13; Histatin-3 6/11; Histatin-3 7/13; Histatin-3 7/12; Histatin-3 7/11; Histatin-3 12/32 (Histatin-4); Histatin-3 12/25 (Histatin-9); Histatin-3 12/24 (Histatin-7); Histatin-3 13/25 (Histatin-10); Histatin-3 13/24 (Histatin-8); Histatin-3 14/25; Histatin-3 14/24; Histatin-3 15/25; Histatin-3 15/24; Histatin-3 26/32; Histatin-3 28/32; Histatin-3 29/32]
51
Q95460
Major histocompatibility complex class I-related gene protein (MHC class-I related-gene protein) (Class I histocompatibility antigen-like protein)
341
P00738
Haptoglobin [Cleaved into: Haptoglobin alpha chain; Haptoglobin beta chain]
406
P24592
Insulin-like growth factor-binding protein 6 (IGF-binding protein 6) (IGFBP-6) (IBP-6)
240
P01880
Ig delta chain C region
384
P01584
Interleukin-1 beta (IL-1 beta) (Catabolin)
269
P05154
Plasma serine protease inhibitor (Serpin A5) (Protein C inhibitor) (PCI) (Plasminogen activator inhibitor 3) (PAI-3) (PAI3) (Acrosomal serine protease inhibitor)
406
Q9BX67
Junctional adhesion molecule C (JAM-C) (Junctional adhesion molecule 3) (JAM-3) (JAM-2)
310
Q5VV43
Uncharacterized protein KIAA0319
1,072
P00709
Alpha-lactalbumin (Lactose synthase B protein) (Lysozyme-like protein 7)
142
O15230
Laminin subunit alpha-5
3,695
P11047
Laminin subunit gamma-1 (Laminin B2 chain)
1,609
Q08380
Galectin-3-binding protein (Lectin galactoside-binding soluble 3-binding protein) (Mac-2-binding protein) (Mac-2 BP) (MAC2BP) (Tumor-associated antigen 90K) (Basement membrane autoantigen p105)
585
P06858
Lipoprotein lipase (LPL) (EC 3.1.1.34)
475
Q7Z4F1
Low-density lipoprotein receptor-related protein 10
713
P03956
Interstitial collagenase (EC 3.4.24.7) (Matrix metalloproteinase-1) (MMP-1) (Fibroblast collagenase) [Cleaved into: 22 kDa interstitial collagenase; 27 kDa interstitial collagenase]
469
P14780
Matrix metalloproteinase-9 (MMP-9) (EC 3.4.24.35) (92 kDa type IV collagenase) (92 kDa gelatinase) (Gelatinase B) (GELB) [Cleaved into: 67 kDa matrix metalloproteinase-9; 82 kDa matrix metalloproteinase-9]
707
Q8WXI7
Mucin-16 (MUC-16) (Ovarian carcinoma antigen CA125) (Ovarian cancer-related tumor marker CA125) (CA-125)
22,152
Q02817
Mucin-2 (MUC-2) (Intestinal mucin-2)

-continued 5,179
Q9HC84
Mucin-5B (MUC-5B) (Mucin-5 subtype B, tracheobronchial) (High molecular weight salivary mucin MG1) (Sublingual gland mucin) (Cervical mucin)
5,703
Q99972
Myocilin (Trabecular meshwork-induced glucocorticoid response protein)
504
P78380
Oxidized low-density lipoprotein receptor 1 (Ox-LDL receptor 1) (Lectin-type oxidized LDL receptor 1) (Lectin-like oxidized LDL receptor 1) (Lectin-like oxLDL receptor 1) (hLOX-1) (LOX-1) [Cleaved into: Oxidized low-density lipoprotein receptor 1, soluble form]
273
Q13093
Platelet-activating factor acetylhydrolase (PAF acetylhydrolase) (EC 3.1.1.47) (PAF 2-acylhydrolase) (LDL-associated phospholipase A2) (LDL-PLA(2)) (2-acetyl-1-alkylglycerophosphocholine esterase) (1-alkyl-2-acetylglycerophosphocholine esterase)
441
Q13219
Pappalysin-1 (EC 3.4.24.79) (Pregnancy-associated plasma protein A) (PAPP-A) (Insulin-like growth factor-dependent IGF-binding protein 4 protease) (IGF-dependent IGFBP-4 protease) (IGFBP-4ase)
1,627
P01833
Polymeric immunoglobulin receptor (Poly-Ig receptor) (PIGR) (Hepatocellular carcinoma-associated protein TB6) [Cleaved into: Secretory component]
764
Q9UKY0
Prion-like protein doppel (PrPLP) (Prion protein 2)
176
Q86YD1
Prostate tumor overexpressed gene 1 protein (PTOV-1) (Activator interaction domain-containing protein 2)
416
O43353
Receptor-interacting serine/threonine-protein kinase 2 (EC 2.7.11.1) (RIP-like-interacting CLARP kinase) (Receptor-interacting protein 2) (RIP-2) (CARD-containing interleukin-1 beta-converting enzyme-associated kinase) (CARD-containing IL-1 beta ICE-kinase)
540
Q96TC7
Regulator of microtubule dynamics protein 3 (RMD-3) (hRMD-3) (Protein FAM82A2) (Protein FAM82C) (Protein tyrosine phosphatase-interacting protein 51) (TCPTP-interacting protein 51) (Cerebral protein 10)
470
Q96S37
Solute carrier family 22 member 12 (Urate anion exchanger 1) (Renal-specific transporter) (RST) (Organic anion transporter 4-like protein)
553
Q9BZD2
Equilibrative nucleoside transporter 3 (hENT3) (Solute carrier family 29 member 3)
475
P49908
Selenoprotein P (SeP)
381
P35247
Pulmonary surfactant-associated protein D (SP-D) (PSP-D) (Lung surfactant protein D)
375
Q9BX79
Stimulated by retinoic acid gene 6 protein homolog
667
Q9UMX1
Suppressor of fused homolog (SUFUH)
484
Q8IWU5
Extracellular sulfatase Sulf-2 (EC 3.1.6.-) (HSulf-2)
870
P20062
Transcobalamin-2 (TC-2) (Transcobalamin II) (TC II) (TCII)
427
P04155
Trefoil factor 1 (Protein pS2) (Polypeptide P1.A) (hP1.A) (Breast cancer estrogen-inducible protein) (PNR-2)
84
P48307
Tissue factor pathway inhibitor 2 (TFPI-2) (Placental protein 5) (PP5)
235
P00734
Prothrombin (EC 3.4.21.5) (Coagulation factor II) [Cleaved into: Activation peptide fragment 1; Activation peptide fragment 2; Thrombin light chain; Thrombin heavy chain]
622
Q9NR96
Toll-like receptor 9 (CD antigen CD289)
1,032
Q92956
Tumor necrosis factor receptor superfamily member 14 (Herpesvirus entry mediator A) (Tumor necrosis factor receptor-like 2) (TR2)
283
O14773
Tripeptidyl-peptidase 1 (TPP-1) (EC 3.4.14.9) (Tripeptidyl-peptidase I) (TPP-I) (Tripeptidyl aminopeptidase) (Lysosomal pepstatin-insensitive protease) (LPIC) (Cell growth-inhibiting gene 1 protein)

563
Q86YW5
Trem-like transcript 1 protein (TLT-1) (Triggering receptor expressed on myeloid cells-like protein 1)
311
Q5T4W7
Artemin (Enovin) (Neublastin)
220
Q99715
Collagen alpha-1(XII) chain
3,063
Q05707
Collagen alpha-1(XIV) chain (Undulin)
1,796
O15263
Beta-defensin 2 (BD-2) (hBD-2) (Defensin, beta 2) (Skin-antimicrobial peptide 1) (SAP1)
64
Q12805
EGF-containing fibulin-like extracellular matrix protein 1 (Fibulin-3) (FIBL-3) (Fibrillin-like protein) (Extracellular protein S1-5)
493
Q14773
Intercellular adhesion molecule 4 (ICAM-4) (Landsteiner-Wiener blood group glycoprotein) (LW blood group protein) (CD antigen CD242)
271
Q9UHD0
Interleukin-19 (IL-19) (Melanoma differentiation-associated protein-like protein) (NG.1)
177
Q6H9L7
Isthmin-2 (Thrombospondin and AMOP domain-containing isthmin-like protein 1) (Thrombospondin type-1 domain-containing protein 3)
571
Q96J84
Kin of IRRE-like protein 1 (Kin of irregular chiasm-like protein 1) (Nephrin-like protein 1)
757
O43240
Kallikrein-10 (EC 3.4.21.-) (Protease serine-like 1) (Normal epithelial cell-specific 1)
276
Q8N2S1
Latent-transforming growth factor beta-binding protein 4 (LTBP-4)
1,624
O60462
Neuropilin-2 (Vascular endothelial cell growth factor 165 receptor 2)
931
Q7Z3S9
Notch homolog 2 N-terminal-like protein
236
Q9UKJ1
Paired immunoglobulin-like type 2 receptor alpha (Inhibitory receptor PILR-alpha) (Cell surface receptor FDF03)
303
Q15262
Receptor-type tyrosine-protein phosphatase kappa (Protein-tyrosine phosphatase kappa) (R-PTP-kappa) (EC 3.1.3.48)
1,439
Q06141
Regenerating islet-derived protein 3 alpha (Reg III-alpha) (Pancreatitis-associated protein 1)
175
Q9BYZ8
Regenerating islet-derived protein 4 (Reg IV) (REG-like protein) (Gastrointestinal secretory protein)
158
Q99942
E3 ubiquitin-protein ligase RNF5 (EC 6.3.2.-) (RING finger protein 5) (HsRma1) (Protein G16)
180
P20366
Protachykinin-1 (PPT) [Cleaved into: Substance P; Neurokinin A (NKA) (Substance K) (Neuromedin L); Neuropeptide K (NPK); Neuropeptide gamma; C-terminal-flanking peptide]
129
Q86UU9
Tachykinin-4 (Preprotachykinin-C) (PPT-C) [Cleaved into: Endokinin-A (EKA); Endokinin-A/B (EKA/B); Endokinin-C (EKC)]
113
Q6ZSL4
Secreted frizzled-related protein 1, isoform CRA_a (cDNA FLJ45402 fis, clone BRHIP3029409, moderately similar to Homo sapiens secreted frizzled-related protein 1 (SFRP1))
178
B2RDA1
Secreted phosphoprotein 1 (Osteopontin, bone sialoprotein I, early T-lymphocyte activation 1), isoform CRA_c (cDNA, FLJ96520, Homo sapiens secreted phosphoprotein 1 (osteopontin, bonesialoprotein I, early T-lymphocyte activation 1) (SPP1), mRNA)
300
Q02325
Plasminogen-related protein B
96
P17931
Galectin-3 (Galactose-specific lectin 3) (Mac-2 antigen) (IgE-binding protein) (35 kDa lectin) (Carbohydrate-binding protein 35) (CBP 35) (Laminin-binding protein) (Lectin L-29) (L-31) (Galactoside-binding protein) (GALBP)

-continued

250
Q969W1
Probable palmitoyltransferase ZDHHC16 (EC 2.3.1.-) (Zinc finger DHHC domain-containing protein 16) (DHHC-16)
377
P60171
Pre-small/secreted glycoprotein (pre-sGP) [Cleaved into: Small/secreted glycoprotein (sGP); Delta-peptide]
364
O95841
Angiopoietin-related protein 1 (Angiopoietin-like 1) (Angiopoietin-3) (ANG-3)
491
Q9NR16
Scavenger receptor cysteine-rich type 1 protein M160 (CD163 antigen-like 1) (CD antigen CD163b)
1,453
Q9BXJ0
Complement C1q tumor necrosis factor-related protein 5
243
Q5UCC4
UPF0510 protein C19orf63 (Hematopoietic signal peptide-containing membrane domain-containing protein 1)
262
Q6UWP2
Dehydrogenase/reductase SDR family member 11 (EC 1.-.-.-)
260
Q9UBP4
Dickkopf-related protein 3 (Dickkopf-3) (Dkk-3) (hDkk-3)
350
Q9BV94
ER degradation-enhancing alpha-mannosidase-like 2
578
Q5XG92
Carboxylesterase 8 (EC 3.1.1.-)
561
Q8IW92
Beta-galactosidase-1-like protein 2 (EC 3.2.1.-)
636
Q8NFR9
Interleukin-17 receptor E (IL-17 receptor E) (IL-17RE)
667
Q9NYY1
Interleukin-20 (IL-20) (Four alpha helix cytokine Zcyto10)
176
Q9H293
Interleukin-25 (IL-25) (Interleukin-17E) (IL-17E)
177
Q9UKR0
Kallikrein-12 (EC 3.4.21.-) (Kallikrein-like protein 5) (KLK-L5)
248
Q8N387
Mucin-15 (MUC-15)
334
Q5EBL8
PDZ domain-containing protein 11
140
Q96GW7
Brevican core protein (Brain-enriched hyaluronan-binding protein) (Protein BEHAB)
911
Q8N131
Porimin (Transmembrane protein 123) (Pro-oncosis receptor inducing membrane injury) (Keratinocytes-associated transmembrane protein 3) (KCT-3)
208
Q6UW15
Regenerating islet-derived protein 3 gamma (Reg III-gamma) (Pancreatitis-associated protein 1B) (PAP IB)
175
Q8WXF3
Relaxin-3 (Prorelaxin H3) (Insulin-like peptide INSL7) (Insulin-like peptide 7) [Cleaved into: Relaxin-3 B chain; Relaxin-3 A chain]
142
Q9HB40
Retinoid-inducible serine carboxypeptidase (EC 3.4.16.-) (Serine carboxypeptidase 1)
452
Q5VYX0
Renalase (EC 1.4.-.-)
342
Q6UXX9
R-spondin-2 (Roof plate-specific spondin-2) (hRspo2)
243
Q96DR5
Short palate, lung and nasal epithelium carcinoma-associated protein 2 (Parotid secretory protein) (PSP)
249
Q9BQ16
Testican-3 (SPARC/osteonectin, CWCV, and Kazal-like domains proteoglycan 3)
436

-continued

Q9Y5U5
Tumor necrosis factor receptor superfamily member 18 (Glucocorticoid-induced TNFR-related protein) (Activation-inducible TNFR family receptor)
241
Q8TCV5
WAP four-disulfide core domain protein 5 (Putative protease inhibitor WAP1) (p53-responsive gene 5 protein)
224
Q9NRA1
Platelet-derived growth factor C (PDGF-C) (Spinal cord-derived growth factor) (SCDGF) (Fallotein) (VEGF-E) [Cleaved into: Platelet-derived growth factor C, latent form (PDGFC latent form); Platelet-derived growth factor C, receptor-binding form (PDGFC receptor-binding form)]
345
Q9BZ11
Disintegrin and metalloproteinase domain-containing protein 33 (ADAM 33) (EC 3.4.24.-)
813
O60513
Beta-1,4-galactosyltransferase 4 (Beta-1,4-GalTase 4) (Beta4Gal-T4) (b4Gal-T4) (EC 2.4.1.-) (UDP-galactose:beta-N-acetylglucosamine beta-1,4-galactosyltransferase 4) (UDP-Gal:beta-GlcNAc beta-1,4-galactosyltransferase 4) [Includes: N-acetyllactosamine synthase (EC 2.4.1.90) (Nal synthetase); Beta-N-acetylglucosaminyl-glycolipid beta-1,4-galactosyltransferase (EC 2.4.1.-)]
344
Q9BWV1
Brother of CDO (Protein BOC)
1,114
Q9NW68
BSD domain-containing protein 1
430
Q8N126
Cell adhesion molecule 3 (Immunoglobulin superfamily member 4B) (Nectin-like protein 1) (TSLC1-like protein 1) (Synaptic cell adhesion (molecule 3) > Brain immunoglobulin receptor)
398
O75419
CDC45-related protein (Cdc45) (PORC-PI-1)
566
Q9H9P2
Chondrolectin (Transmembrane protein MT75)
273
Q96PD7
Diacylglycerol O-acyltransferase 2 (EC 2.3.1.20) (Diglyceride acyltransferase 2)
388
P56937
3-keto-steroid reductase (EC 1.1.1.270) (Estradiol 17-beta-dehydrogenase 7) (EC 1.1.1.62) (17-beta-hydroxysteroid dehydrogenase 7) (17-beta-HSD 7)
341
Q9BPW9
Dehydrogenase/reductase SDR family member 9 (EC 1.1.-.-) (3-alpha hydroxysteroid dehydrogenase) (3alpha-HSD) (Short-chain dehydrogenase/reductase retSDR8) (NADP-dependent retinol dehydrogenase/reductase) (RDH-E2) (RDHL)
319
O00548
Delta-like protein 1 (Drosophila Delta homolog 1) (Delta1) (H-Delta-1)
723
P20827
Ephrin-A1 (EPH-related receptor tyrosine kinase ligand 1) (LERK-1) (Immediate early response protein B61) (Tumor necrosis factor, alpha-induced protein 4)
205
Q8N441
Fibroblast growth factor receptor-like 1 (FGF receptor-like protein 1) (Fibroblast growth factor receptor 5) (FGFR-like protein) (FGF homologous factor receptor)
504
O60609
GDNF family receptor alpha-3 (GFR-alpha-3)
400
Q9H7M9
Platelet receptor Gi24
311
Q9BQS7
Hephaestin (EC 1.-.-.-)
1,158
Q8NAC3
Interleukin-17 receptor C (IL-17 receptor C) (IL-17RC) (Interleukin-17 receptor-like protein) (IL-17RL) (Interleukin-17 receptor homolog) (IL17Rhom)
791
Q8NFM7
Interleukin-17 receptor D (IL-17 receptor D) (IL-17RD) (IL17Rhom) (Interleukin-17 receptor-like protein) (Sef homolog) (hSef)
739
Q8N201
Integrator complex subunit 1 (Int1)
2,190
Q86YT9
Junctional adhesion molecule-like (Dendritic cell-specific protein CREA7-1) (Adhesion molecule interacting with CXADR antigen 1)
394
P49862
Kallikrein-7 (hK7) (EC 3.4.21.117) (Stratum corneum chymotryptic enzyme) (hSCCE) (Serine protease 6)
253

-continued

Q13753
Laminin subunit gamma-2 (Laminin 5 gamma 2 subunit) (Kalinin/nicein/epiligrin 100 kDa subunit) (Laminin B2t chain) (Cell-scattering factor 140 kDa subunit) (CSF 140 kDa subunit) (Large adhesive scatter factor 140 kDa subunit) (Ladsin 140 kDa subunit)
1,193
Q9H0V9
VIP36-like protein (Lectin mannose-binding 2-like) (LMAN2-like protein)
348
Q6UX01
Protein LMBR1L (Lipocalin-1-interacting membrane receptor) (Lipocalin-interacting membrane receptor) (Limb region 1 protein homolog-like)
489
Q8TBB1
E3 ubiquitin-protein ligase LNX (EC 6.3.2.-) (Numb-binding protein 1) (Ligand of Numb-protein X 1)
728
Q86VH5
Leucine-rich repeat transmembrane neuronal protein 3
581
Q9UKM7
Endoplasmic reticulum mannosyl-oligosaccharide 1,2-alpha-mannosidase (EC 3.2.1.113) (ER alpha-1,2-mannosidase) (Mannosidase alpha class 1B member 1) (Man9GlcNAc2-specific-processing alpha-mannosidase)
699
Q9H0U3
Magnesium transporter protein 1 (MagT1) (Implantation-associated protein) (IAP)
335
Q9NZL9
Methionine adenosyltransferase 2 subunit beta (Methionine adenosyltransferase II beta) (MAT II beta) (Methionine adenosyltransferase 2 beta subunit) (DTDP-4-keto-6-deoxy-D-glucose 4-reductase)
334
Q5SSG8
Mucin-21 (MUC-21) (Epiglycanin)
566
Q9NZ53
Podocalyxin-like protein 2 (Endoglycan)
605
Q8N271
Prominin-2 (PROM-2) (Prominin-like protein 2) (hPROML2)
834
Q6UX71
Plexin domain-containing protein 2 (Tumor endothelial marker 7-related protein)
529
Q8WZ75
Roundabout homolog 4 (Magic roundabout)
1,007
Q9NPR2
Semaphorin-4B
832
Q9P283
Semaphorin-5B
1,151
Q9NRX5
Serine incorporator 1 (Tumor differentially expressed protein 2) (Tumor differentially expressed 1 protein-like)
453
O43556
Epsilon-sarcoglycan (Epsilon-SG)
437
Q9UNP4
Lactosylceramide alpha-2,3-sialyltransferase (EC 2.4.99.9) (CMP-NeuAc:lactosylceramide alpha-2,3-sialyltransferase) (Ganglioside GM3 synthase) (ST3Gal V) (Sialyltransferase 9)
418
Q8NBJ9
SID1 transmembrane family member 2
832
P29508
Serpin B3 (Squamous cell carcinoma antigen 1) (SCCA-1) (Protein T4-A)
390
Q6UWL2
Sushi domain-containing protein 1
747
Q9UL54
Serine/threonine-protein kinase TAO2 (EC 2.7.11.1) (Thousand and one amino acid protein 2) (Prostate-derived STE20-like kinase 1) (PSK-1) (Kinase from chicken homolog C) (hKFC-C)
1,235
Q9BXR5
Toll-like receptor 10 (CD antigen CD290)
811
Q9NR97
Toll-like receptor 8 (CD antigen CD288)
1,041
O15393
Transmembrane protease, serine 2 (EC 3.4.21.-) (Serine protease 10) [Cleaved into: Transmembrane protease, serine 2 non-catalytic chain;

-continued

Transmembrane protease, serine 2 catalytic chain]
492
Q9BVT8
Transmembrane and ubiquitin-like domain-containing protein 1 (Hepatocyte odd protein shuttling protein) (Ubiquitin-like protein SB144) (Ubiquitin-like protein DULP)
246
Q9Y320
Thioredoxin-related transmembrane protein 2 (Thioredoxin domain-containing protein 14) (Proliferation-inducing gene 26 protein)
296
Q15661
Tryptase beta-1 (Tryptase-1) (EC 3.4.21.59) (Tryptase I)
275
Q9BZJ3
Tryptase delta (EC 3.4.21.59) (Delta-tryptase) (Mast cell mMCP-7-like) (Tryptase-3) (HmMCP-3-like tryptase III)
242
Q8IZJ1
Netrin receptor UNC5B (Protein unc-5 homolog B) (Unc-5 homolog 2) (p53-regulated receptor for death and life protein 1)
945
Q8NBZ7
UDP-glucuronic acid decarboxylase 1 (EC 4.1.1.35) (UDP-glucuronate decarboxylase 1) (UXS-1) (UGD)
420
Q9BQB6
Vitamin K epoxide reductase complex subunit 1 (EC 1.1.4.1) (Vitamin K1 2,3-epoxide reductase subunit 1)
163
Q9BXJ1
Complement C1q tumor necrosis factor-related protein 1 (G protein-coupled receptor-interacting protein) (GIP)
281
Q9BRX8
Uncharacterized protein C10orf58
229
Q9UHF0
Tachykinin-3 (ZNEUROK1) [Cleaved into: Neurokinin-B (NKB) (Neuromedin-K)]
121
Q4W597
Secreted phosphoprotein 1 (cDNA FLJ78337, highly similar to Homo sapiens secreted phosphoprotein 1 (osteopontin, bone sialoprotein I, early T-lymphocyte activation 1), transcript variant 1, mRNA) (Putative uncharacterized protein SPP1) (Secreted phosphoprotein 1 (Osteopontin, bone sialoprotein I, early T-lymphocyte activation 1), isoform CRA_b)
314
Q9BQB4
Sclerostin
213
Q86TH1
ADAMTS-like protein 2 (ADAMTSL-2)
951
P59510
A disintegrin and metalloproteinase with thrombospondin motifs 20 (ADAMTS-20) (ADAM-TS 20) (ADAM-TS20) (EC 3.4.24.-)
1,910
Q9NZK5
Cat eye syndrome critical region protein 1
511
A5D8T8
C-type lectin domain family 18 member A (Mannose receptor-like protein 2)
446
Q9P218
Collagen alpha-1(XX) chain
1,329
Q9BU40
Chordin-like protein 1 (Neuralin-1) (Ventroptin) (Neurogenesin-1)
450
P54108
Cysteine-rich secretory protein 3 (CRISP-3) (SGP28 protein)
245
Q9HC73
Cytokine receptor-like factor 2 (Thymic stromal lymphopoietin protein receptor) (TSLP receptor) (Cytokine receptor-like 2) (CRL2) (IL-XR)
371
P81534
Beta-defensin 103 (Defensin, beta 103) (Beta-defensin 3) (BD-3) (hBD-3) (HBD3) (DEFB-3) (Defensin-like protein)
67
Q8N104
Beta-defensin 106 (Defensin, beta 106) (Beta-defensin 6) (BD-6) (DEFB-6)
65
O43820
Hyaluronidase-3 (Hyal-3) (EC 3.2.1.35) (Hyaluronoglucosaminidase-3) (LUCA-3)
417
Q8IU57
Interleukin-28 receptor alpha chain (IL-28R-alpha) (IL-28RA) (Cytokine receptor class-II member 12) (Cytokine receptor family 2 member 12) (CRF2-12) (Interferon lambda receptor 1) (IFN-lambda R1) (Likely interleukin or cytokine receptor 2)
520
Q9NRE1

-continued

Matrix metalloproteinase-26 (MMP-26) (EC 3.4.24.-) (Matrilysin-2) (Endometase)
261
P41271
Neuroblastoma suppressor of tumorigenicity 1 (Zinc finger protein DAN) (N03) (DAN domain family member 1)
180
Q9NY56
Odorant-binding protein 2a (OBPIIa)
170
Q8IUK5
Plexin domain-containing protein 1 (Tumor endothelial marker 7) (Tumor endothelial marker 3)
500
Q2MKA7
R-spondin-1 (Roof plate-specific spondin-1) (hRspo1)
263
Q92824
Proprotein convertase subtilisin/kexin type 5 (EC 3.4.21.-) (Proprotein convertase PC5) (Subtilisin/kexin-like protease PC5) (hPC6) (PC6)
913
P12821
Angiotensin-converting enzyme (ACE) (EC 3.4.15.1) (EC 3.2.1.-) (Dipeptidyl carboxypeptidase I) (Kininase II) (CD antigen CD143) [Cleaved into: Angiotensin-converting enzyme, soluble form]
1,306
P01008
Antithrombin-III (ATIII)
464
P04114
Apolipoprotein B-100 (Apo B-100) [Cleaved into: Apolipoprotein B-48 (Apo B-48)]
4,563
P05090
Apolipoprotein D (Apo-D) (ApoD)
189
P02649
Apolipoprotein E (Apo-E)
317
P15291
Beta-1,4-galactosyltransferase 1 (Beta-1,4-GalTase 1) (Beta4Gal-T1) (b4Gal-T1) (EC 2.4.1.-) (UDP-galactose:beta-N-acetylglucosamine beta-1,4-galactosyltransferase 1) (UDP-Gal:beta-GlcNAc beta-1,4-galactosyltransferase 1) [Cleaved into: Processed beta-1,4-galactosyltransferase 1] [Includes: Lactose synthase A protein (EC 2.4.1.22); N-acetyllactosamine synthase (EC 2.4.1.90) (Nal synthetase); Beta-N-acetylglucosaminylglycopeptide beta-1,4-galactosyltransferase (EC 2.4.1.38); Beta-N-acetylglucosaminyl-glycolipid beta-1,4-galactosyltransferase (EC 2.4.1.-)]
398
Q15582
Transforming growth factor-beta-induced protein ig-h3 (Beta ig-h3) (Kerato-epithelin) (RGD-containing collagen-associated protein) (RGD-CAP)
683
P18075
Bone morphogenetic protein 7 (BMP-7) (Osteogenic protein 1) (OP-1) (Eptotermin alfa)
431
P02746
Complement C1q subcomponent subunit B
251
P04003
C4b-binding protein alpha chain (C4bp) (Proline-rich protein) (PRP)
597
P27797
Calreticulin (CRP55) (Calregulin) (HACBP) (ERp60) (grp60)
417
P08185
Corticosteroid-binding globulin (CBG) (Transcortin) (Serpin A6)
405
P15085
Carboxypeptidase A1 (EC 3.4.17.1)
419
P48052
Carboxypeptidase A2 (EC 3.4.17.15)
417
P51671
Eotaxin (C-C motif chemokine 11) (Small-inducible cytokine A11) (Eosinophil chemotactic protein)
97
Q99616
C-C motif chemokine 13 (Small-inducible cytokine A13) (Monocyte chemoattractant protein 4) (Monocyte chemotactic protein 4) (MCP-4) (CK-beta-10) (NCC-1) [Cleaved into: C-C motif chemokine 13, long chain; C-C motif chemokine 13, medium chain; C-C motif chemokine 13, short chain]
98
P55774
C-C motif chemokine 18 (Small-inducible cytokine A18) (Macrophage inflammatory protein 4) (MIP-4) (Pulmonary and activation-regulated chemokine) (CC chemokine PARC) (Alternative macrophage activation-associated CC chemokine 1) (AMAC-1) (Dendritic cell chemokine 1) (DC-CK1) [Cleaved into: CCL18(1-68); CCL18(3-69); CCL18(4-69)]
89
P78556
C-C motif chemokine 20 (Small-inducible cytokine A20) (Macrophage inflammatory protein 3 alpha) (MIP-3-alpha) (Liver and activation-regulated chemokine) (CC chemokine LARC) (Beta chemokine exodus-1) [Cleaved into: CCL20(1-67); CCL20(1-64); CCL20(2-70)]
96
P55773
C-C motif chemokine 23 (Small-inducible cytokine A23) (Macrophage inflammatory protein 3) (MIP-3) (Myeloid progenitor inhibitory factor 1) (MPIF-1) (CK-beta-8) (CKB-8) [Cleaved into: CCL23(19-99); CCL23(22-99); CCL23(27-99); CCL23(30-99)]
120
P13500
C-C motif chemokine 2 (Small-inducible cytokine A2) (Monocyte chemoattractant protein 1) (Monocyte chemotactic protein 1) (MCP-1) (Monocyte chemotactic and activating factor) (MCAF) (Monocyte secretory protein JE) (HC11)
99
P29965
CD40 ligand (CD40-L) (Tumor necrosis factor ligand superfamily member 5) (TNF-related activation protein) (TRAP) (T-cell antigen Gp39) (CD antigen CD154) [Cleaved into: CD40 ligand, membrane form; CD40 ligand, soluble form]
261
Q15517
Corneodesmosin (S protein)
529
P00746
Complement factor D (EC 3.4.21.46) (C3 convertase activator) (Properdin factor D) (Adipsin)
253
P10645
Chromogranin-A (CgA) (Pituitary secretory protein I) (SP-I) [Cleaved into: Vasostatin-1 (Vasostatin I); Vasostatin-2 (Vasostatin II); EA-92; ES-43; Pancreastatin; SS-18; WA-8; WE-14; LF-19; AL-11; GV-19; GR-44; ER-37]
457
P02452
Collagen alpha-1(I) chain (Alpha-1 type I collagen)
1,464
P01024
Complement C3 (C3 and PZP-like alpha-2-macroglobulin domain-containing protein 1) [Cleaved into: Complement C3 beta chain; Complement C3 alpha chain; C3a anaphylatoxin; Complement C3b alpha' chain; Complement C3c alpha' chain fragment 1; Complement C3dg fragment; Complement C3g fragment; Complement C3d fragment; Complement C3f fragment; Complement C3c alpha' chain fragment 2]
1,663
P08572
Collagen alpha-2(IV) chain [Cleaved into: Canstatin]
1,712
P53420
Collagen alpha-4(IV) chain
1,690
P0C0L4
Complement C4-A (Acidic complement C4) (C3 and PZP-like alpha-2-macroglobulin domain-containing protein 2) [Cleaved into: Complement C4 beta chain; Complement C4-A alpha chain; C4a anaphylatoxin; C4b-A; C4d-A; Complement C4 gamma chain]
1,744
P0C0L5
Complement C4-B (Basic complement C4) (C3 and PZP-like alpha-2-macroglobulin domain-containing protein 3) [Cleaved into: Complement C4 beta chain; Complement C4-B alpha chain; C4a anaphylatoxin; C4b-B; C4d-B; Complement C4 gamma chain]
1,744
P05997
Collagen alpha-2(V) chain
1,499
P01031
Complement C5 (C3 and PZP-like alpha-2-macroglobulin domain-containing protein 4) [Cleaved into: Complement C5 beta chain; Complement C5 alpha chain; C5a anaphylatoxin; Complement C5 alpha' chain]
1,676
Q02388
Collagen alpha-1(VII) chain (Long-chain collagen) (LC collagen)
2,944
P10643
Complement component C7
843
P07358
Complement component C8 beta chain (Complement component 8 subunit beta)
591
P07360
Complement component C8 gamma chain
202
P39059
Collagen alpha-1(XV) chain [Cleaved into: Endostatin (Endostatin-XV) (Restin) (Related to endostatin)]
1,388
Q07092
Collagen alpha-1(XVI) chain
1,604
P39060
Collagen alpha-1(XVIII) chain [Cleaved into: Endostatin]
1,754
Q14993
Collagen alpha-1(XIX) chain (Collagen alpha-1(Y) chain)
1,142
P49747
Cartilage oligomeric matrix protein (COMP)

757
P02741
C-reactive protein [Cleaved into: C-reactive protein(1-205)]
224
P04141
Granulocyte-macrophage colony-stimulating factor (GM-CSF) (Colony-stimulating factor) (CSF) (Sargramostim) (Molgramostin)
144
P09919
Granulocyte colony-stimulating factor (G-CSF) (Pluripoietin) (Filgrastim) (Lenograstim)
207
O00622
Protein CYR61 (Cysteine-rich angiogenic inducer 61) (Insulin-like growth factor-binding protein 10) (Protein GIG1)
381
P01040
Cystatin-A (Cystatin-AS) (Stefin-A)
98
P01036
Cystatin-S (Cystatin-4) (Salivary acidic protein 1) (Cystatin-SA-III)
141
P59666
Neutrophil defensin 3 (HNP-3) (HP-3) (HP3) (Defensin, alpha 3) [Cleaved into: HP 3-56; Neutrophil defensin 2 (HNP-2) (HP-2) (HP2)]
94
P27487
Dipeptidyl peptidase 4 (EC 3.4.14.5) (Dipeptidyl peptidase IV) (DPP IV) (T-cell activation antigen CD26) (TP103) (Adenosine deaminase complexing protein 2) (ADABP)(CD antigen CD26) [Cleaved into: Dipeptidyl peptidase 4 membrane form (Dipeptidyl peptidase IV membrane form); Dipeptidyl peptidase 4 soluble form (Dipeptidyl peptidase IV soluble form)]
766
Q9NZW4
Dentin sialophosphoprotein [Cleaved into: Dentin phosphoprotein (Dentin phosphophoryn) (DPP); Dentin sialoprotein (DSP)]
1,301
P05305
Endothelin-1 (Preproendothelin-1) (PPET1) [Cleaved into: Endothelin-1 (ET-1); Big endothelin-1]
212
P98172
Ephrin-B1 (EPH-related receptor tyrosine kinase ligand 2) (LERK-2) (ELK ligand) (ELK-L) (EFL-3)
346
P19957
Elafin (Elastase-specific inhibitor) (ESI) (Skin-derived antileukoproteinase) (SKALP) (Peptidase inhibitor 3) (WAP four-disulfide core domain protein 14) (Protease inhibitor WAP3)
117
Q9Y6C2
EMILIN-1 (Elastin microfibril interface-located protein 1) (Elastin microfibril interfacer 1)
1,016
P14625
Endoplasmin (Heat shock protein 90 kDa beta member 1) (94 kDa glucose-regulated protein) (GRP94) (gp96 homolog) (Tumor rejection antigen 1)
803
P29320
Ephrin type-A receptor 3 (EC 2.7.10.1) (Tyrosine-protein kinase receptor ETK1) (HEK) (HEK4) (Tyrosine-protein kinase TYRO4)
983
O15197
Ephrin type-B receptor 6 (Tyrosine-protein kinase-defective receptor EPH-6) (HEP)
1,006
P01588
Erythropoietin (Epoetin)
193
P00742
Coagulation factor X (EC 3.4.21.6) (Stuart factor) (Stuart-Prower factor) [Cleaved into: Factor X light chain; Factor X heavy chain; Activated factor Xa heavy chain]
488
P00451
Coagulation factor VIII (Procoagulant component) (Antihemophilic factor) (AHF) [Cleaved into: Factor VIIIa heavy chain, 200 kDa isoform; Factor VIIIa heavy chain, 92 kDa isoform; Factor VIII B chain; Factor VIIIa light chain]
2,351
P35555
Fibrillin-1
2,871
P35556
Fibrillin-2
2,912
P02765
Alpha-2-HS-glycoprotein (Ba-alpha-2-glycoprotein) (Alpha-2-Z-globulin) (Fetuin-A) [Cleaved into: Alpha-2-HS-glycoprotein chain A; Alpha-2-HS-glycoprotein chain B]
367
O15520
Fibroblast growth factor 10 (FGF-10) (Keratinocyte growth factor 2)
208
P02671
Fibrinogen alpha chain [Cleaved into: Fibrinopeptide A]
866

-continued

P02675
Fibrinogen beta chain [Cleaved into: Fibrinopeptide B]
491
P01225
Follitropin subunit beta (Follicle-stimulating hormone beta subunit) (FSH-beta) (FSH-B) (Follitropin beta chain)
129
P01350
Gastrin [Cleaved into: Gastrin-71 (Gastrin component I); Gastrin-52 (G52); Big gastrin (Gastrin-34) (G34) (Gastrin component II); Gastrin (Gastrin-17) (G17) (Gastrin component III); Gastrin-14 (G14); Gastrin-6 (G6)]
101
P01215
Glycoprotein hormones alpha chain (Anterior pituitary glycoprotein hormones common subunit alpha) (Follitropin alpha chain) (Follicle-stimulating hormone alpha chain) (FSH-alpha) (Lutropin alpha chain) (Luteinizing hormone alpha chain) (LSH-alpha) (Thyrotropin alpha chain) (Thyroid-stimulating hormone alpha chain) (TSH-alpha) (Choriogonadotropin alpha chain) (Chorionic gonadotrophin subunit alpha) (CG-alpha)
116
Q3T906
N-acetylglucosamine-1-phosphotransferase subunits alpha/beta (EC 2.7.8.17) (GlcNAc-1-phosphotransferase subunits alpha/beta) (Stealth protein GNPTAB) (UDP-N-acetylglucosamine-1-phosphotransferase subunits alpha/beta) [Cleaved into: N-acetylglucosamine-1-phosphotransferase subunit alpha; N-acetylglucosamine-1-phosphotransferase subunit beta]
1,256
P12544
Granzyme A (EC 3.4.21.78) (Granzyme-1) (Cytotoxic T-lymphocyte proteinase 1) (Hanukkah factor) (H factor) (HF) (CTL tryptase) (Fragmentin-1)
262
P26927
Hepatocyte growth factor-like protein (Macrophage stimulatory protein) (Macrophage-stimulating protein) (MSP) [Cleaved into: Hepatocyte growth factor-like protein alpha chain; Hepatocyte growth factor-like protein beta chain]
711
P10997
Islet amyloid polypeptide (Amylin) (Diabetes-associated peptide) (DAP) (Insulinoma amyloid peptide)
89
P08833
Insulin-like growth factor-binding protein 1 (IGF-binding protein 1) (IGFBP-1) (IBP-1) (Placental protein 12) (PP12)
259
P18065
Insulin-like growth factor-binding protein 2 (IGF-binding protein 2) (IGFBP-2) (IBP-2)
328
P22692
Insulin-like growth factor-binding protein 4 (IGF-binding protein 4) (IGFBP-4) (IBP-4)
258
Q9BYX4
Interferon-induced helicase C domain-containing protein 1 (EC 3.6.1.-) (Interferon-induced with helicase C domain protein 1) (Helicase with 2 CARD domains) (Helicard) (Melanoma differentiation-associated protein 5) (MDA-5) (RNA helicase-DEAD box protein 116) (Murabutide down-regulated protein)
1,025
P01562
Interferon alpha-1/13 (Interferon alpha-D) (LeIF D)
189
P01563
Interferon alpha-2 (Interferon alpha-A) (LeIF A)
188
P01574
Interferon beta (IFN-beta) (Fibroblast interferon)
187
P01579
Interferon gamma (IFN-gamma) (Immune interferon)
166
P05019
Insulin-like growth factor IB (IGF-IB) (Somatomedin-C) (Mechano growth factor) (MGF)
195
Q14623
Indian hedgehog protein (IHH) (HHG-2) [Cleaved into: Indian hedgehog protein N-product; Indian hedgehog protein C-product]
411
P22301
Interleukin-10 (IL-10) (Cytokine synthesis inhibitory factor) (CSIF)
178
P35225
Interleukin-13 (IL-13)
146
P60568
Interleukin-2 (IL-2) (T-cell growth factor) (TCGF) (Aldesleukin)
153
P05113
Interleukin-5 (IL-5) (T-cell replacing factor) (TRF) (Eosinophil differentiation factor) (B-cell differentiation factor I)
134
P08476
Inhibin beta A chain (Activin beta-A chain) (Erythroid differentiation protein) (EDF)
426
P00995
Pancreatic secretory trypsin inhibitor (Serine protease inhibitor Kazal-type 1) (Tumor-associated trypsin inhibitor) (TATI)

-continued

79
P19827
Inter-alpha-trypsin inhibitor heavy chain H1 (Inter-alpha-inhibitor heavy chain 1) (ITI heavy chain H1) (Inter-alpha-trypsin inhibitor complex component III) (Serum-derived hyaluronan-associated protein) (SHAP)
911
P19823
Inter-alpha-trypsin inhibitor heavy chain H2 (Inter-alpha-inhibitor heavy chain 2) (ITI heavy chain H2) (Inter-alpha-trypsin inhibitor complex component II) (Serum-derived hyaluronan-associated protein) (SHAP)
946
Q06033
Inter-alpha-trypsin inhibitor heavy chain H3 (Inter-alpha-inhibitor heavy chain 3) (ITI heavy chain H3) (ITI-HC3) (Serum-derived hyaluronan-associated protein) (SHAP)
890
Q15726
Metastasis-suppressor KiSS-1 (Kisspeptin-1) [Cleaved into: Metastin (Kisspeptin-54); Kisspeptin-14; Kisspeptin-13; Kisspeptin-10]
145
P07288
Prostate-specific antigen (PSA) (EC 3.4.21.77) (Kallikrein-3) (Semenogelase) (Gamma-seminoprotein) (Seminin) (P-30 antigen)
261
Q9Y5K2
Kallikrein-4 (EC 3.4.21.-) (Prostase) (Kallikrein-like protein 1) (KLK-L1) (Enamel matrix serine proteinase 1) (Serine protease 17)
254
P03952
Plasma kallikrein (EC 3.4.21.34) (Plasma prekallikrein) (Kininogenin) (Fletcher factor) [Cleaved into: Plasma kallikrein heavy chain; Plasma kallikrein light chain]
638
P18428
Lipopolysaccharide-binding protein (LBP)
481
P09382
Galectin-1 (Lectin galactoside-binding soluble 1) (Beta-galactoside-binding lectin L-14-I) (Lactose-binding lectin 1) (S-Lac lectin 1) (Galaptin) (14 kDa lectin) (HPL) (HBL) (Putative MAPK-activating protein PM12)
135
P41159
Leptin (Obesity factor) (Obese protein)
167
P15018
Leukemia inhibitory factor (LIF) (Differentiation-stimulating factor) (D factor) (Melanoma-derived LPL inhibitor) (MLPLI) (Emfilermin)
202
P11150
Hepatic triacylglycerol lipase (Hepatic lipase) (HL) (EC 3.1.1.3) (Lipase member C)
499
P16233
Pancreatic triacylglycerol lipase (Pancreatic lipase) (PL) (EC 3.1.1.3)
465
Q05315
Eosinophil lysophospholipase (EC 3.1.1.5) (Charcot-Leyden crystal protein) (Lysolecithin acylhydrolase) (CLC) (Galectin-10)
142
P01229
Lutropin subunit beta (Lutropin beta chain) (Luteinizing hormone subunit beta) (LSH-beta) (LSH-B) (LH-B)
141
P55145
Mesencephalic astrocyte-derived neurotrophic factor (Protein ARMET) (Arginine-rich protein)
179
P55081
Microfibrillar-associated protein 1
439
P08493
Matrix Gla protein (MGP) (Cell growth-inhibiting gene 36 protein)
103
P08253
72 kDa type IV collagenase (EC 3.4.24.24) (72 kDa gelatinase) (Matrix metalloproteinase-2) (MMP-2) (Gelatinase A) (TBE-1)
660
P08254
Stromelysin-1 (SL-1) (EC 3.4.24.17) (Matrix metalloproteinase-3) (MMP-3) (Transin-1)
477
P22894
Neutrophil collagenase (EC 3.4.24.34) (Matrix metalloproteinase-8) (MMP-8) (PMNL collagenase) (PMNL-CL)
467
Q13421
Mesothelin (Pre-pro-megakaryocyte-potentiating factor) (CAK1 antigen) [Cleaved into: Megakaryocyte-potentiating factor (MPF); Mesothelin, cleaved form]
630
P98088
Mucin-5AC (Mucin-5 subtype AC, tracheobronchial) (Tracheobronchial mucin) (TBM) (Major airway glycoprotein) (Gastric mucin) (Lewis B blood group antigen) (LeB) (Fragments)
5,030
Q6W4X9
Mucin-6 (MUC-6) (Gastric mucin-6)

-continued 2,392
Q00604
Norrin (Norrie disease protein) (X-linked exudative vitreoretinopathy 2 protein)
133
P01178
Oxytocin-neurophysin 1 (OT-NPI) [Cleaved into: Oxytocin (Ocytocin); Neurophysin 1]
125
P01138
Beta-nerve growth factor (Beta-NGF)
241
Q13253
Noggin
232
P20783
Neurotrophin-3 (NT-3) (Neurotrophic factor) (HDNF) (Nerve growth factor 2) (NGF-2)
257
P13725
Oncostatin-M (OSM)
252
P05121
Plasminogen activator inhibitor 1 (PAI-1) (PAI) (Endothelial plasminogen activator inhibitor)
402
P05120
Plasminogen activator inhibitor 2 (PAI-2) (Placental plasminogen activator inhibitor) (Monocyte Arg-serpin) (Urokinase inhibitor)
415
Q15113
Procollagen C-endopeptidase enhancer 1 (Procollagen COOH-terminal proteinase enhancer 1) (Procollagen C-proteinase enhancer 1) (PCPE-1) (Type I procollagen COOH-terminal proteinase enhancer) (Type 1 procollagen C-proteinase enhancer protein)
449
P04085
Platelet-derived growth factor subunit A (PDGF subunit A) (Platelet-derived growth factor A chain) (Platelet-derived growth factor alpha polypeptide) (PDGF-1)
211
P01127
Platelet-derived growth factor subunit B (PDGF subunit B) (Platelet-derived growth factor B chain) (Platelet-derived growth factor beta polypeptide) (PDGF-2) (c-sis) (Becaplermin)
241
P07237
Protein disulfide-isomerase (PDI) (EC 5.3.4.1) (Prolyl 4-hydroxylase subunit beta) (Cellular thyroid hormone-binding protein) (p55)
508
P36955
Pigment epithelium-derived factor (PEDF) (Serpin-F1) (EPC-1)
418
P00790
Pepsin A (EC 3.4.23.1)
388
P20142
Gastricsin (EC 3.4.23.3) (Pepsinogen C)
388
P98160
Basement membrane-specific heparan sulfate proteoglycan core protein (HSPG) (Perlecan) (PLC)
4,391
Q96LB9
Peptidoglycan recognition protein I-alpha (PGRP-I-alpha) (Peptidoglycan recognition protein intermediate alpha) (PGLYRPIalpha) (Peptidoglycan recognition protein 3)
341
P21810
Biglycan (Bone/cartilage proteoglycan I) (PG-S1)
368
P12273
Prolactin-inducible protein (Prolactin-induced protein) (Secretory actin-binding protein) (SABP) (Gross cystic disease fluid protein 15) (GCDFP-15) (gp17)
146
P02776
Platelet factor 4 (PF-4) (C-X-C motif chemokine 4) (Oncostatin-A) (Iroplact) [Cleaved into: Platelet factor 4, short form]
101
P00747
Plasminogen (EC 3.4.21.7) [Cleaved into: Plasmin heavy chain A; Activation peptide; Angiostatin; Plasmin heavy chain A, short form; Plasmin light chain B]
810
P27169
Serum paraoxonase/arylesterase 1 (PON 1) (EC 3.1.1.2) (EC 3.1.8.1) (Serum aryldialkylphosphatase 1) (A-esterase 1) (Aromatic esterase 1) (K-45)
355
P05187
Alkaline phosphatase, placental type (EC 3.1.3.1) (PLAP-1) (Alkaline phosphatase Regan isozyme)
535
P23284
Peptidyl-prolyl cis-trans isomerase B (PPIase) (Rotamase) (EC 5.2.1.8) (Cyclophilin B) (S-cyclophilin) (SCYLP) (CYP-S1)
216

-continued

P13727
Bone marrow proteoglycan (BMPG) (Proteoglycan 2) [Cleaved into: Eosinophil granule major basic protein (EMBP) (MBP) (Pregnancy-associated major basic protein)]
222
P04280
Basic salivary proline-rich protein 1 (Salivary proline-rich protein) [Cleaved into: Proline-rich peptide II-2; Basic peptide IB-6; Peptide P-H]
392
P11686
Pulmonary surfactant-associated protein C (SP-C) (SP5) (Pulmonary surfactant-associated proteolipid SPL(Val))
197
P01270
Parathyroid hormone (PTH) (Parathyrin) (Parathormone)
115
P02743
Serum amyloid P-component (SAP) (9.5S alpha-1-glycoprotein) [Cleaved into: Serum amyloid P-component(1-203)]
223
P05060
Secretogranin-1 (Secretogranin I) (SgI) (Chromogranin-B) (CgB) [Cleaved into: GAWK peptide; CCB peptide]
677
Q15465
Sonic hedgehog protein (SHH) (HHG-1) [Cleaved into: Sonic hedgehog protein N-product; Sonic hedgehog protein C-product]
462
P03973
Antileukoproteinase (ALP) (Secretory leukocyte protease inhibitor) (HUSI-1) (Seminal proteinase inhibitor) (BLPI) (Mucus proteinase inhibitor) (MPI) (WAP four-disulfide core domain protein 4) (Protease inhibitor WAP4)
132
Q9UQE7
Structural maintenance of chromosomes protein 3 (Chondroitin sulfate proteoglycan 6) (Chromosome-associated polypeptide) (hCAP) (Basement membrane-associatedchondroitin proteoglycan) (Bamacan)
1,217
P08294
Extracellular superoxide dismutase [Cu-Zn](EC-SOD) (EC 1.15.1.1)
240
P01241
Somatotropin (Growth hormone) (GH) (GH-N) (Pituitary growth hormone) (Growth hormone 1)
217
P36952
Serpin B5 (Protease inhibitor 5) (Maspin)
375
Q9HCB6
Spondin-1 (F-spondin) (Vascular smooth muscle cell growth-promoting factor)
807
Q9NY15
Stabilin-1 (Fasciclin, EGF-like, laminin-type EGF-like and link domain-containing scavenger receptor 1) (FEEL-1) (MS-1 antigen)
2,570
Q16623
Syntaxin-1A (Neuron-specific antigen HPC-1)
288
P05452
Tetranectin (TN) (C-type lectin domain family 3 member B) (Plasminogen kringle 4-binding protein)
202
P01137
Transforming growth factor beta-1 (TGF-beta-1) [Cleaved into: Latency-associated peptide (LAP)]
390
P01266
Thyroglobulin (Tg)
2,768
P01033
Metalloproteinase inhibitor 1 (Tissue inhibitor of metalloproteinases) (TIMP-1) (Erythroid-potentiating activity) (EPA) (Fibroblast collagenase inhibitor) (Collagenase inhibitor)
207
P16035
Metalloproteinase inhibitor 2 (Tissue inhibitor of metalloproteinases 2) (TIMP-2) (CSC-21K)
220
P35625
Metalloproteinase inhibitor 3 (Tissue inhibitor of metalloproteinases 3) (TIMP-3) (Protein MIG-5)
211
P19438
Tumor necrosis factor receptor superfamily member 1A (p60) (TNF-R1) (TNF-RI) (TNFR-I) (p55) (CD antigen CD120a) [Cleaved into: Tumor necrosis factor receptor superfamily member 1A, membrane form; Tumor necrosis factor-binding protein 1 (TBPI)]
455
P02788
Lactotransferrin (Lactoferrin) (EC 3.4.21.-) (Talalactoferrin) [Cleaved into: Kaliocin-1; Lactoferroxin-A; Lactoferroxin-B; Lactoferroxin-C]
710
P07477
Trypsin-1 (EC 3.4.21.4) (Trypsin I) (Cationic trypsinogen) (Serine protease 1) (Beta-trypsin) [Cleaved into: Alpha-trypsin chain 1; Alpha-trypsin chain 2]
247
P02766
Transthyretin (Prealbumin) (TBPA) (TTR) (ATTR)

-continued

147
P00749
Urokinase-type plasminogen activator (U-plasminogen activator) (uPA) (EC 3.4.21.73) [Cleaved into: Urokinase-type plasminogen activator long chain A; Urokinase-type plasminogen activator short chain A; Urokinase-type plasminogen activator chain B]
431
P17948
Vascular endothelial growth factor receptor 1 (VEGFR-1) (EC 2.7.10.1) (Vascular permeability factor receptor) (Tyrosine-protein kinase receptor FLT) (Flt-1) (Tyrosine-protein kinase FRT) (Fms-like tyrosine kinase 1)
1,338
P02774
Vitamin D-binding protein (DBP) (VDB) (Group-specific component) (Gc-globulin)
474
P04004
Vitronectin (Serum-spreading factor) (S-protein) (V75) [Cleaved into: Vitronectin V65 subunit; Vitronectin V10 subunit; Somatomedin-B]
478
P04275
von Willebrand factor (vWF) [Cleaved into: von Willebrand antigen 2 (von Willebrand antigen II)]
2,813
O15537
Retinoschisin (X-linked juvenile retinoschisis protein)
224
P25311
Zinc-alpha-2-glycoprotein (Zn-alpha-2-glycoprotein) (Zn-alpha-2-GP)
295
Q9H972
Uncharacterized protein C14orf93
538
Q5SRR4
Lymphocyte antigen 6 complex locus protein G5c
150
P11465
Pregnancy-specific beta-1-glycoprotein 2 (PSBG-2) (Pregnancy-specific beta-1 glycoprotein E) (PS-beta-E)
335
B2RAD4
C-type lectin domain family 11, member A, isoform CRA_b (cDNA, FLJ94843, Homo sapiens stem cell growth factor; lymphocyte secreted C-type lectin (SCGF), mRNA)
323
P14174
Macrophage migration inhibitory factor (MIF) (EC 5.3.2.1) (Phenylpyruvate tautomerase) (L-dopachrome tautomerase) (EC 5.3.3.12) (L-dopachrome isomerase) (Glycosylation-inhibiting factor) (GIF)
115
Q9H553
Alpha-1,3-mannosyltransferase ALG2 (EC 2.4.1.-) (GDP-Man:Man(1)GlcNAc(2)-PP-dolichol mannosyltransferase) (Asparagine-linked glycosylation protein 2)
416
Q9BWW8
Apolipoprotein L6 (Apolipoprotein L-VI) (ApoL-VI)
343
Q8WY98
UPF0546 membrane protein C1orf91
164
Q9NS85
Carbonic anhydrase-related protein 10 (Carbonic anhydrase-related protein X) (CA-RP X) (CARP X) (Cerebral protein 15)
328
P06307
Cholecystokinin (CCK) [Cleaved into: Cholecystokinin-58 (CCK58); Cholecystokinin-58 desnonopeptide ((1-49)-CCK58); Cholecystokinin-39 (CCK39); Cholecystokinin-33 (CCK33); Cholecystokinin-25 (CCK25); Cholecystokinin-18 (CCK18); Cholecystokinin-12 (CCK12); Cholecystokinin-8 (CCK8); Cholecystokinin-7 (CCK7); Cholecystokinin-5 (CCK5)]
115
Q8IWY9
Codanin-1
1,227
Q6UWU4
Uncharacterized protein C6orf89
347
Q9P2E5
Chondroitin sulfate glucuronyltransferase (EC 2.4.1.226) (N-acetylgalactosaminyl-proteoglycan 3-beta-glucuronosyltransferase) (Chondroitin glucuronyltransferase II) (CSGlcA-T)
772
Q9BWS9
Chitinase domain-containing protein 1 (Stabilin-1-interacting chitinase-like protein) (SI-CLP)
393
Q9UGQ2
Transmembrane protein C9orf7
172
Q6UXG3
CMRF35-like molecule 9 (CLM-9) (Triggering receptor expressed on myeloid cells 4) (TREM-4) (CD300 antigen-like family member G) (CD antigen CD300g)
332

Q96SQ9
Cytochrome P450 2S1 (EC 1.14.14.1) (CYPIIS1)
504
Q9BUF7
Crumbs protein homolog 3
120
Q9Y394
Dehydrogenase/reductase SDR family member 7 (EC 1.1.-.-) (Retinal short-chain dehydrogenase/reductase 4) (retSDR4)
339
Q6UWH4
Protein ENED (Expressed in nerve and epithelium during development)
519
Q92496
Complement factor H-related protein 4 (FHR-4)
331
Q96DB9
FXYD domain-containing ion transport regulator 5 (Dysadherin)
178
Q8WTR4
Glycerophosphodiester phosphodiesterase domain-containing protein 5 (EC 3.1.-.-) (Glycerophosphodiester phosphodiesterase 2)
605
Q6ZMI3
Gliomedin
551
Q8IZF5
Probable G-protein coupled receptor 113 (G-protein coupled receptor PGR23)
1,079
Q8IZF4
Probable G-protein coupled receptor 114 (G-protein coupled receptor PGR27)
528
Q86UL3
Glycerol-3-phosphate acyltransferase 4 (GPAT4) (EC 2.3.1.15) (Acyl-CoA:glycerol-3-phosphate acyltransferase 4) (1-acylglycerol-3-phosphate O-acyltransferase 6) (1-AGP acyltransferase 6) (1-AGPAT 6) (Lysophosphatidic acid acyltransferase zeta) (LPAAT-zeta)
456
O60565
Gremlin-1 (Cysteine knot superfamily 1, BMP antagonist 1) (Increased in high glucose protein 2) (IHG-2) (Down-regulated in Mos-transformed cells protein) (DAN domain family member 2) (Cell proliferation-inducing gene 2 protein)
184
Q96T54
Potassium channel subfamily K member 17 (TWIK-related alkaline pH-activated K(+) channel 2) (2P domain potassium channel Talk-2) (TWIK-related acid-sensitive K(+) channel 4) (TASK-4)
332
Q7Z4H8
KDEL motif-containing protein 2
507
Q6UX15
Layilin
382
Q6P9F7
Leucine-rich repeat-containing protein 8B (T-cell activation leucine repeat-rich protein)
803
Q7L1W4
Leucine-rich repeat-containing protein 8D
858
Q6UXM1
Leucine-rich repeats and immunoglobulin-like domains protein 3 (LIG-3)
1,119
Q86UE6
Leucine-rich repeat transmembrane neuronal protein 1
522
Q8N2G4
Ly6/PLAUR domain-containing protein 1 (Putative HeLa tumor suppressor) (PHTS)
141
Q6UWN5
Ly6/PLAUR domain-containing protein 5
251
O95772
MLN64 N-terminal domain homolog (STARD3 N-terminal-like protein)
234
Q6UXD7
Major facilitator superfamily domain-containing protein 7 (Myosin light polypeptide 5 regulatory protein) (MYL5)
560
Q86VF5
2-acylglycerol O-acyltransferase 3 (EC 2.3.1.22) (EC 2.3.1.20) (Monoacylglycerol O-acyltransferase 3) (Acyl CoA:monoacylglycerol acyltransferase 3) (MGAT3) (Diacylglycerol acyltransferase 2-like protein 7) (Diacylglycerol O-acyltransferase candidate 7) (hDC7)
341
Q9NZJ7
Mitochondrial carrier homolog 1 (Presenilin-associated protein)
389

-continued

Q9NX14
NADH dehydrogenase [ubiquinone]1 beta subcomplex subunit 11, mitochondrial (NADH-ubiquinone oxidoreductase ESSS subunit) (Complex I-ESSS) (CI-ESSS) (Neuronal protein 17.3) (Np17.3) (p17.3)
153
Q9UN73
Protocadherin alpha-6 (PCDH-alpha-6)
950
O60330
Protocadherin gamma-A12 (PCDH-gamma-A12) (Cadherin-21) (Fibroblast cadherin-3)
932
Q9H490
Phosphatidylinositol glycan anchor biosynthesis class U protein (GPI transamidase component PIG-U) (Cell division cycle protein 91-like 1) (Protein CDC91-like 1)
435
Q6NUM9
All-trans-retinol 13,14-reductase (EC 1.3.99.23) (All-trans-13,14-dihydroretinol saturase) (RetSat)
610
Q96LZ7
Regulator of microtubule dynamics protein 2 (RMD-2) (hRMD-2) (Protein FAM82A1)
410
Q2I0M5
R-spondin-4 (Roof plate-specific spondin-4) (hRspo4)
234
Q5K4L6
Long-chain fatty acid transport protein 3 (Fatty acid transport protein 3) (FATP-3) (EC 6.2.1.-) (Very long-chain acyl-CoA synthetase homolog 3) (VLCS-3) (Solute carrier family 27 member 3)
730
Q9BRL7
Vesicle-trafficking protein SEC22c (SEC22 vesicle-trafficking protein homolog C) (SEC22 vesicle-trafficking protein-like 3)
303
Q11201
CMP-N-acetylneuraminate-beta-galactosamide-alpha-2,3-sialyltransferase (Beta-galactoside alpha-2,3-sialyltransferase) (Alpha 2,3-ST) (EC 2.4.99.4) (Gal-NAc6S) (Gal-beta-1,3-GalNAc-alpha-2,3-sialyltransferase) (ST3GalA.1) (ST3GalIA) (ST3Gal I) (ST3O) (SIAT4-A) (SIATFL)
340
O43699
Sialic acid-binding Ig-like lectin 6 (Siglec-6) (Obesity-binding protein 1) (OB-BP1) (CD33 antigen-like 1) (CDw327) (CD antigen CD327)
453
Q96A28
SLAM family member 9 (CD2 family member 10) (CD2F-10) (CD84 homolog 1) (CD84-H1)
289
P02814
Submaxillary gland androgen-regulated protein 3B (Proline-rich protein 3) (Proline-rich peptide P-B) [Cleaved into: Peptide P-A; Peptide D1A]
79
Q9NY57
Serine/threonine-protein kinase 32B (EC 2.7.11.1) (YANK2)
414
Q71RG4
Transmembrane and ubiquitin-like domain-containing protein 2
321
Q9UNG2
Tumor necrosis factor ligand superfamily member 18 (Glucocorticoid-induced TNF-related ligand) (hGITRL) (Activation-inducible TNF-related ligand) (AITRL)
177
P15157
Tryptase alpha-1 (Tryptase-1) (EC 3.4.21.59)
275
Q96N46
Tetratricopeptide repeat protein 14 (TPR repeat protein 14)
770
Q96DZ1
XTP3-transactivated gene B protein (ER lectin) (Erlectin)
483
Q96MV8
Palmitoyltransferase ZDHHC15 (EC 2.3.1.-) (Zinc finger DHHC domain-containing protein 15) (DHHC-15)
337
P21754
Zona pellucida sperm-binding protein 3 (Zona pellucida glycoprotein ZP3) (Zona pellucida protein C) (Sperm receptor) (ZP3A/ZP3B) [Cleaved into: Processed zona pellucida sperm-binding protein 3]
424
Q96DD0
Leucine-rich repeat-containing protein 39 (Densin hlg)
335
O95867
Lymphocyte antigen 6 complex locus protein G6c
125
Q8IV31
Transmembrane protein 139
216
O75173
A disintegrin and metalloproteinase with thrombospondin motifs 4 (ADAMTS-4) (ADAM-TS 4) (ADAM-TS4) (EC 3.4.24.82) (Aggrecanase-1)

(ADMP-1)
837
Q8N4F0
Bactericidal/permeability-increasing protein-like 1 (Long palate, lung and nasal epithelium carcinoma-associated protein 2) (RYSR)
458
O00585
C-C motif chemokine 21 (Small-inducible cytokine A21) (Beta chemokine exodus-2) (6Ckine) (Secondary lymphoid-tissue chemokine) (SLC)
134
O43866
CD5 antigen-like (SP-alpha) (CT-2) (IgM-associated peptide)
347
Q7L1S5
Carbohydrate sulfotransferase 9 (EC 2.8.2.-) (N-acetylgalactosamine-4-O-sulfotransferase 2) (GalNAc-4-O-sulfotransferase 2) (GalNAc-4-ST2)
443
Q14CN2
Calcium-activated chloride channel regulator 4 (Calcium-activated chloride channel family member 4) (hCLCA4) (Calcium-activated chloride channel protein 2) (CaCC-2) (hCaCC-2) [Cleaved into: Calcium-activated chloride channel regulator 4, 110 kDa form; Calcium-activated chloride channel regulator 4, 30 kDa form]
919
Q9NZV1
Cysteine-rich motor neuron 1 protein (CRIM-1) (Cysteine-rich repeat-containing protein S52) [Cleaved into: Processed cysteine-rich motor neuron 1 protein]
1,036
P29279
Connective tissue growth factor (Hypertrophic chondrocyte-specific protein 24)
349
Q5T1H1
Protein eyes shut homolog (Protein spacemaker homolog) (EGF-like domain-containing protein 10) (EGF-like domain-containing protein 11)
3,165
O95967
EGF-containing fibulin-like extracellular matrix protein 2 (Fibulin-4) (FIBL-4) (Protein UPH1)
443
O95750
Fibroblast growth factor 19 (FGF-19)
216
O95633
Follistatin-related protein 3 (Follistatin-like 3) (Follistatin-related gene protein)
263
Q96QV1
Hedgehog-interacting protein (HHIP) (HIP)
700
Q9NRM6
Interleukin-17 receptor B (IL-17 receptor B) (IL-17RB) (Interleukin-17B receptor) (IL-17B receptor) (IL-17 receptor homolog 1) (IL-17Rh1) (IL17Rh1) (Cytokine receptor CRL4)
502
Q8N145
Leucine-rich repeat LGI family member 3 (Leucine-rich glioma-inactivated protein 3) (LGI1-like protein 4)
548
Q9Y5X9
Endothelial lipase (EC 3.1.1.3) (Endothelial cell-derived lipase) (EDL) (EL)
500
Q96DR8
Mucin-like protein 1 (Small breast epithelial mucin) (Protein BS106)
90
Q9NRC9
Otoraplin (Fibrocyte-derived protein) (Melanoma inhibitory activity-like protein)
128
Q9NZ20
Group 3 secretory phospholipase A2 (EC 3.1.1.4) (Group III secretory phospholipase A2) (GIII sPLA2) (Phosphatidylcholine 2-acylhydrolase GIII) (sPLA2-III)
509
Q8NCC3
Group XV phospholipase A2 (EC 2.3.1.-) (1-O-acylceramide synthase) (ACS) (Lysosomal phospholipase A2) (Lysophospholipase 3) (LPLA2) (LCAT-like lysophospholipase) (LLPL)
412
Q6UXH9
Inactive serine protease PAMR1 (Peptidase domain-containing protein associated with muscle regeneration 1) (Regeneration-associated muscle protease homolog)
720
O75051
Plexin-A2 (Semaphorin receptor OCT)
1,894
O95428
Papilin
1,278
P58294
Prokineticin-1 (Endocrine-gland-derived vascular endothelial growth factor) (EG-VEGF) (Mambakine)
105
Q9H1E1

-continued

Ribonuclease 7 (RNase 7) (EC 3.1.27.-) (Skin-derived antimicrobial protein 2) (SAP-2)
156
O43278
Kunitz-type protease inhibitor 1 (Hepatocyte growth factor activator inhibitor type 1) (HAI-1)
529
Q9BUD6
Spondin-2 (Mindin) (Differentially expressed in cancerous and non-cancerous lung cells 1) (DIL-1)
331
Q92563
Testican-2 (SPARC/osteonectin, CWCV, and Kazal-like domains proteoglycan 2)
424
O43557
Tumor necrosis factor ligand superfamily member 14 (Herpesvirus entry mediator-ligand) (HVEM-L) (CD antigen CD258) [Cleaved into: Tumor necrosis factor ligand superfamily member 14, membrane form; Tumor necrosis factor ligand superfamily member 14, soluble form]
240
Q5JU69
Torsin-2A (Torsin family 2 member A) (Torsin-related protein 1)
321
Q7L8A9
Vasohibin-1
365
Q6EMK4
Vasorin (Protein slit-like 2)
673
Q86Y38
Xylosyltransferase 1 (EC 2.4.2.26) (Xylosyltransferase I) (XylT-I) (XT-I) (Peptide O-xylosyltransferase 1)
959
O95832
Claudin-1 (Senescence-associated epithelial membrane protein)
211
Q96CD2
Phosphopantothenoylcysteine decarboxylase (PPC-DC) (EC 4.1.1.36) (CoaC)
204
Q9BUN8
Derlin-1 (Der1-like protein 1) (Degradation in endoplasmic reticulum protein 1) (DERtrin-1)
251
Q9Y287
Integral membrane protein 2B (Transmembrane protein BRI) [Cleaved into: ABri/ADan amyloid peptide]
266
Q16651
Prostasin (EC 3.4.21.-) (Serine protease 8) [Cleaved into: Prostasin light chain; Prostasin heavy chain]
343
Q9UL52
Transmembrane protease, serine 11E (EC 3.4.21.-) (Serine protease DESC1) [Cleaved into: Transmembrane protease, serine 11E non-catalytic chain; Transmembrane protease, serine 11E catalytic chain]
423
Q9Y5W5
Wnt inhibitory factor 1 (WIF-1)
379
Q29960
HLA class I histocompatibility antigen, Cw-16 alpha chain (MHC class I antigen Cw*16)
366
P23582
C-type natriuretic peptide [Cleaved into: CNP-22; CNP-29; CNP-53]
126
O15123
Angiopoietin-2 (ANG-2)
496
Q9UKP5
A disintegrin and metalloproteinase with thrombospondin motifs 6 (ADAMTS-6) (ADAM-TS 6) (ADAM-TS6) (EC 3.4.24.-)
1,117
Q8WXQ8
Carboxypeptidase A5 (EC 3.4.17.1)
436
Q16627
C-C motif chemokine 14 (Small-inducible cytokine A14) (Chemokine CC-1/CC-3) (HCC-1/HCC-3) (HCC-1(1-74)) (NCC-2) [Cleaved into: HCC-1(3-74); HCC-1(4-74); HCC-1(9-74)]
93
P08217
Chymotrypsin-like elastase family member 2A (EC 3.4.21.71) (Elastase-2A)
269
O00533
Neural cell adhesion molecule L1-like protein (Close homolog of L1) [Cleaved into: Processed neural cell adhesion molecule L1-like protein]
1,208
P19875
C-X-C motif chemokine 2 (Macrophage inflammatory protein 2-alpha) (MIP2-alpha) (Growth-regulated protein beta) (Gro-beta) [Cleaved into: GRO-beta(5-73) (GRO-beta-T) (SB-251353) (Hematopoietic synergistic factor) (HSF)]
107
P42830

-continued

C-X-C motif chemokine 5 (Small-inducible cytokine B5) (Epithelial-derived neutrophil-activating protein 78) (Neutrophil-activating peptide ENA-78) (ENA-78(1-78)) [Cleaved into: ENA-78(8-78); ENA-78(9-78)]
114
Q13609
Deoxyribonuclease gamma (DNase gamma) (EC 3.1.21.-) (Deoxyribonuclease I-like 3) (DNase I-like 3) (DNase I homolog protein DHP2) (Liver and spleen DNase) (LS-DNase) (LSD)
305
Q9NRM1
Enamelin
1,142
P98095
Fibulin-2 (FIBL-2)
1,184
O00602
Ficolin-1 (Ficolin-A) (Ficolin-alpha) (M-ficolin) (Collagen/fibrinogen domain-containing protein 1)
326
P49771
SL cytokine (Fms-related tyrosine kinase 3 ligand) (Flt3 ligand) (Flt3L)
235
Q5H8C1
FRAS1-related extracellular matrix protein 1 (Protein QBRICK)
2,179
P19883
Follistatin (FS) (Activin-binding protein)
344
Q10472
Polypeptide N-acetylgalactosaminyltransferase 1 (EC 2.4.1.41) (Protein-UDP acetylgalactosaminyltransferase 1) (UDP-GalNAc:polypeptide N-acetylgalactosaminyltransferase 1) (Polypeptide GalNAc transferase 1) (pp-GaNTase 1) (GalNAc-T1) [Cleaved into: Polypeptide N-acetylgalactosaminyltransferase 1 soluble form]
559
P10915
Hyaluronan and proteoglycan link protein 1 (Proteoglycan link protein) (Cartilage link protein) (LP)
354
P01570
Interferon alpha-14 (Interferon alpha-H) (LeIF H) (Interferon lambda-2-H)
189
Q96PD4
Interleukin-17F (IL-17F) (Interleukin-24) (IL-24) (Cytokine ML-1)
163
Q9NPH3
Interleukin-1 receptor accessory protein (IL-1 receptor accessory protein) (IL-1RAcP)
570
Q9NQ38
Serine protease inhibitor Kazal-type 5 (Lympho-epithelial Kazal-type-related inhibitor) (LEKTI) [Cleaved into: Hemofiltrate peptide HF6478; Hemofiltrate peptide HF7665]
1,064
Q9H2R5
Kallikrein-15 (EC 3.4.21.-) (ACO protease)
256
Q8N6C8
Leukocyte immunoglobulin-like receptor subfamily A member 3 (Leukocyte immunoglobulin-like receptor 4) (LIR-4) (Immunoglobulin-like transcript 6) (ILT-6) (Monocyte inhibitory receptor HM43/HM31) (CD85 antigen-like family member E) (CD antigen CD85e)
439
Q9NS15
Latent-transforming growth factor beta-binding protein 3 (LTBP-3)
1,303
P45452
Collagenase 3 (EC 3.4.24.-) (Matrix metalloproteinase-13) (MMP-13)
471
P51512
Matrix metalloproteinase-16 (MMP-16) (EC 3.4.24.-) (Membrane-type matrix metalloproteinase 3) (MT-MMP 3) (MTMMP3) (Membrane-type-3 matrix metalloproteinase) (MT3-MMP) (MT3MMP) (MMP-X2)
607
P18509
Pituitary adenylate cyclase-activating polypeptide (PACAP) [Cleaved into: PACAP-related peptide (PRP-48); Pituitary adenylate cyclase-activating polypeptide 27 (PACAP-27) (PACAP27); Pituitary adenylate cyclase-activating polypeptide 38 (PACAP-38) (PACAP38)]
176
Q9HC23
Prokineticin-2 (PK2) (Protein Bv8 homolog)
129
Q00888
Pregnancy-specific beta-1-glycoprotein 4 (PSBG-4) (PSBG-9)
419
P01286
Somatoliberin (Growth hormone-releasing factor) (GRF) (Growth hormone-releasing hormone) (GHRH) (Somatocrinin) (Somatorelin) (Sermorelin)
108
O75093
Slit homolog 1 protein (Slit-1) (Multiple epidermal growth factor-like domains 4)
1,534

-continued

P01242
Growth hormone variant (GH-V) (Placenta-specific growth hormone) (Growth hormone 2)
217
Q03167
TGF-beta receptor type III (TGFR-3) (Transforming growth factor beta receptor III) (Betaglycan)
850
P01222
Thyrotropin subunit beta (Thyrotropin beta chain) (Thyroid-stimulating hormone subunit beta) (TSH-beta) (TSH-B) (Thyrotropin alfa)
138
Q9BXJ5
Complement C1q tumor necrosis factor-related protein 2
285
Q1ZYL8
Uncharacterized protein C19orf36 (Sperm 22 kDa protein c113)
232
Q96L15
Ecto-ADP-ribosyltransferase 5 (EC 2.4.2.31) (NAD(P)(+)--arginine ADP-ribosyltransferase 5) (Mono(ADP-ribosyl)transferase 5)
292
Q8TAA1
Probable ribonuclease 11 (RNase 11) (EC 3.1.27.-)
199
Q9NS62
Thrombospondin type-1 domain-containing protein 1 (Transmembrane molecule with thrombospondin module)
852
Q8N302
Angiogenic factor with G patch and FHA domains 1 (Angiogenic factor VG5Q) (Vasculogenesis gene on 5q protein) (hVG5Q) (G patch domain-containing protein 7)
714
Q9Y5C1
Angiopoietin-related protein 3 (Angiopoietin-like 3) (Angiopoietin-5) (ANG-5)
460
O43827
Angiopoietin-related protein 7 (Angiopoietin-like 7) (Angiopoietin-like factor) (Cornea-derived transcript 6 protein)
346
P58397
A disintegrin and metalloproteinase with thrombospondin motifs 12 (ADAMTS-12) (ADAM-TS 12) (ADAM-TS12) (EC 3.4.24.-)
1,593
O75493
Carbonic anhydrase-related protein 11 (CA-RP XI) (CARP XI) (CA-XI) (Carbonic anhydrase-related protein 2) (CARP-2) (CA-RP II)
328
Q6UXH8
Collagen and calcium-binding EGF domain-containing protein 1 (Full of fluid protein homolog)
406
Q96SM3
Probable carboxypeptidase X1 (EC 3.4.17.-) (Metallocarboxypeptidase CPX-1)
734
Q9H0B8
Cysteine-rich secretory protein LCCL domain-containing 2 (LCCL domain-containing cysteine-rich secretory protein 2) (Cysteine-rich secretory protein 11) (CRISP-11)
497
O95715
C-X-C motif chemokine 14 (Small-inducible cytokine B14) (Chemokine BRAK)
99
Q9H1M4
Beta-defensin 127 (Defensin, beta 127) (Beta-defensin 27) (DEFB-27)
99
Q9H1M3
Beta-defensin 129 (Defensin, beta 129) (Beta-defensin 29) (DEFB-29)
183
P81605
Dermcidin (Preproteolysin) [Cleaved into: Survival-promoting peptide; DCD-1]
110
Q7Z5P4
17-beta hydroxysteroid dehydrogenase 13 (EC 1.1.-.-) (Short-chain dehydrogenase/reductase 9)
300
O94907
Dickkopf-related protein 1 (Dickkopf-1) (Dkk-1) (hDkk-1) (SK)
266
P52798
Ephrin-A4 (EPH-related receptor tyrosine kinase ligand 4) (LERK-4)
201
Q96BQ1
Protein FAM3D
224
Q9NSA1
Fibroblast growth factor 21 (FGF-21)
209
Q9BTY2
Plasma alpha-L-fucosidase (EC 3.2.1.51) (Alpha-L-fucoside fucohydrolase 2) (Alpha-L-fucosidase 2)

467
Q9NS71
Gastrokine-1 (18 kDa antrum mucosa protein) (AMP-18) (Protein CA11)
199
Q86XP6
Gastrokine-2 (Blottin) (Trefoil factor interactions(z) 1) (Down-regulated in gastric cancer)
184
Q96SL4
Glutathione peroxidase 7 (EC 1.11.1.9) (CL683)
187
Q96JK4
HHIP-like protein 1
782
Q9P0W0
Interferon kappa (IFN-kappa)
207
Q9Y5Q6
Insulin-like peptide INSL5 (Insulin-like peptide 5) [Cleaved into: Insulin-like peptide INSL5 B chain; Insulin-like peptide INSL5 A chain]
135
O14498
Immunoglobulin superfamily containing leucine-rich repeat protein
428
Q96I82
Kazal-type serine protease inhibitor domain-containing protein 1
304
O75610
Left-right determination factor 1 (Protein lefty-1) (Left-right determination factor B) (Protein lefty-B)
366
Q8N135
Leucine-rich repeat LGI family member 4 (Leucine-rich glioma-inactivated protein 4) (LGI1-like protein 3)
537
Q8TDL5
Long palate, lung and nasal epithelium carcinoma-associated protein 1 (Von Ebner minor salivary gland protein) (VEMSGP)
484
Q86TE4
Leucine zipper protein 2
346
O95157
Neurexophilin-3
252
Q99983
Osteomodulin (Osteoadherin) (OSAD) (Keratan sulfate proteoglycan osteomodulin) (KSPG osteomodulin)
421
Q9UKZ9
Procollagen C-endopeptidase enhancer 2 (Procollagen COOH-terminal proteinase enhancer 2) (Procollagen C-proteinase enhancer 2) (PCPE-2)
415
Q8IXA5
Sperm acrosome membrane-associated protein 3 (Sperm lysozyme-like protein 1) (Lysozyme-like protein 3) (Lysozyme-like acrosomal sperm-specific secretory protein ALLP-17) (Sperm protein reactive with antisperm antibodies) (Sperm protein reactive with ASA) (Cancer/testis antigen 54) (CT54) [Cleaved into: Sperm acrosome membrane-associated protein 3, membrane form; Sperm acrosome membrane-associated protein 3, processed form]
215
Q96QR1
Secretoglobin family 3A member 1 (Uteroglobin-related protein 2) (Cytokine HIN-1) (High in normal 1) (Pneumo secretory protein 2) (PnSP-2)
104
Q8WUA8
Tsukushin (Tsukushi) (Leucine-rich repeat-containing protein 54) (E2-induced gene 4 protein)
353
P57739
Claudin-2 (SP82)
230
Q8IWY4
Signal peptide, CUB and EGF-like domain-containing protein 1
988
P02654
Apolipoprotein C-I (Apo-CI) (ApoC-I)
83
Q6UWZ7
BRCA1-A complex subunit Abraxas (Coiled-coil domain-containing protein 98) (Protein FAM175A)
409
Q53EP0
Fibronectin type III domain-containing protein 3B (Factor for adipocyte differentiation 104) (HCV NS5A-binding protein 37)
1,204
Q9UBK5
Hematopoietic cell signal transducer (Transmembrane adapter protein KAP10) (DNAX-activation protein 10) (Membrane protein DAP10)
93
Q96FE5
Leucine-rich repeat and immunoglobulin-like domain-containing nogo receptor-interacting protein 1 (Leucine-rich repeat and immunoglobilin-domain containing protein 1) (Leucine-rich repeat neuronal protein 6A) (Leucine-rich repeat neuronal protein 1)
620

Q5JRA6
Melanoma inhibitory activity protein 3 (Transport and Golgi organization protein 1) (TANGO1) (C219-reactive peptide) (D320)
1,907
Q9H3N1
Thioredoxin-related transmembrane protein 1 (Thioredoxin domain-containing protein 1) (Transmembrane Trx-related protein)
280
Q8TAD4
Zinc transporter 5 (ZnT-5) (ZnT-like transporter 1) (hZTL1) (Solute carrier family 30 member 5)
765
Q8TC27
Disintegrin and metalloproteinase domain-containing protein 32 (ADAM 32)
787
Q6UXC1
Apical endosomal glycoprotein (MAM domain-containing protein 4)
1,216
Q9BT22
Chitobiosyldiphosphodolichol beta-mannosyltransferase (EC 2.4.1.142) (GDP-mannose-dolichol diphosphochitobiose mannosyltransferase)
(GDP-Man:GlcNAc2-PP-dolichol mannosyltransferase) (Beta-1,4-mannosyltransferase) (Mannosyltransferase-1) (Hmat-1) (MT-1)
(Asparagine-linked glycosylation protein 1)
464
Q9Y2A9
UDP-GlcNAc:betaGal beta-1,3-N-acetylglucosaminyltransferase 3 (Beta3Gn-T3) (BGnT-3) (EC 2.4.1.-) (Core 1 extending
beta-1,3-N-acetylglucosaminyltransferase) (Core1-beta3GlcNAcT) (Beta-1,3-galactosyltransferase 8) (Beta-1,3-GalTase 8) (Beta3Gal-T8) (b3Gal-T8)
(Beta-3-Gx-T8) (UDP-galactose:beta-N-acetylglucosamine beta-1,3-galactosyltransferase 8) (UDP-Gal:beta-GlcNAc beta-1,3-galactosyltransferase 8)
372
Q9UBV7
Beta-1,4-galactosyltransferase 7 (Beta-1,4-GalTase 7) (Beta4Gal-T7) (b4Gal-T7) (EC 2.4.1.-) (UDP-galactose:beta-N-acetylglucosamine
beta-1,4-galactosyltransferase 7) (UDP-Gal:beta-GlcNAc beta-1,4-galactosyltransferase 7) [Includes: Xylosylprotein 4-beta-galactosyltransferase
(EC 2.4.1.133) (UDP-galactose:beta-xylose beta-1,4-galactosyltransferase) (Xylosylprotein beta-1,4-galactosyltransferase) (XGPT)
(Proteoglycan UDP-galactose:beta-xylose beta1,4-galactosyltransferase I) (XGalT-1)]
327
Q9BUT1
3-hydroxybutyrate dehydrogenase type 2 (EC 1.1.1.30) (R-beta-hydroxybutyrate dehydrogenase) (Dehydrogenase/reductase SDR family member 6)
(Oxidoreductase UCPA)
245
Q96EU7
C1GALT1-specific chaperone 1 (Core 1 beta3-galactosyltransferase-specific molecular chaperone) (Beta1,3-galactosyltransferase 2) (C1Gal-T2)
(C1GalT2) (C38H2-like protein 1) (C38H2-L1)
318
P05814
Beta-casein
226
P07498
Kappa-casein
182
Q8N357
Transmembrane protein C2orf18
371
P15169
Carboxypeptidase N catalytic chain (CPN) (EC 3.4.17.3) (Carboxypeptidase N polypeptide 1) (Carboxypeptidase N small subunit)
(Lysine carboxypeptidase) (Arginine carboxypeptidase) (Kininase-1) (Serum carboxypeptidase N) (SCPN) (Anaphylatoxin inactivator)
(Plasma carboxypeptidase B)
458
Q9NPF0
CD320 antigen (8D6 antigen) (FDC-signaling molecule 8D6) (FDC-SM-8D6) (Transcobalamin receptor) (TCblR) (CD antigen CD320)
282
Q86X52
Chondroitin sulfate synthase 1 (EC 2.4.1.175) (Glucuronosyl-N-acetylgalactosaminyl-proteoglycan 4-beta-N-acetylgalactosaminyltransferase 1)
(N-acetylgalactosaminyl-proteoglycan 3-beta-glucuronosyltransferase 1) (EC 2.4.1.226) (Chondroitin glucuronyltransferase II)
(N-acetylgalactosaminyltransferase II)
802
Q8IZ52
Chondroitin sulfate synthase 2 (EC 2.4.1.175) (Glucuronosyl-N-acetylgalactosaminyl-proteoglycan 4-beta-N-acetylgalactosaminyltransferase II)
(N-acetylgalactosaminyl-proteoglycan 3-beta-glucuronosyltransferase II) (EC 2.4.1.226) (Chondroitin glucuronyltransferase II)
(N-acetylgalactosaminyltransferase) (Chondroitin-polymerizing factor)
775
A8K4G0
CMRF35-like molecule 7 (CLM-7) (CMRF35-A2) (Immune receptor expressed on myeloid cells 3) (IREM-3) (Triggering receptor expressed on
myeloid cells 5) (TREM-5) (Leukocyte mono-Ig-like receptor 5) (CD300 antigen-like family member B) (CD antigen CD300b)
201
Q9BT09
Protein canopy homolog 3 (Trinucleotide repeat-containing gene 5 protein) (CTG repeat protein 4a) (Expanded repeat-domain protein CAG/CTG 5)
(Protein associated with TLR4)
278
O75911
Short-chain dehydrogenase/reductase 3 (EC 1.1.-.-) (Retinal short-chain dehydrogenase/reductase 1) (retSDR1) (DD83.1)
302
Q9NR61
Delta-like protein 4 (Drosophila Delta homolog 4) (Delta4)

-continued

685
Q8NFT8
Delta and Notch-like epidermal growth factor-related receptor
737
Q9UPQ8
Dolichol kinase (EC 2.7.1.108) (Transmembrane protein 15)
538
O95672
Endothelin-converting enzyme-like 1 (EC 3.4.24.-) (Xce protein)
775
P60508
HERV-FRD_6p24.1 provirus ancestral Env polyprotein (Envelope polyprotein) (HERV-FRD) (Syncytin-2) [Cleaved into: Surface protein (SU); Transmembrane protein (TM)]
538
O14638
Ectonucleotide pyrophosphatase/phosphodiesterase family member 3 (E-NPP 3) (Phosphodiesterase I/nucleotide pyrophosphatase 3) (Phosphodiesterase I beta) (PD-Ibeta) (CD antigen CD203c) [Includes: Alkaline phosphodiesterase I (EC 3.1.4.1); Nucleotide pyrophosphatase (NPPase) (EC 3.6.1.9)]
875
Q96AP7
Endothelial cell-selective adhesion molecule
390
P36980
Complement factor H-related protein 2 (FHR-2) (H factor-like protein 2) (H factor-like 3) (DDESK59)
270
Q02985
Complement factor H-related protein 3 (FHR-3) (H factor-like protein 3) (DOWN16)
330
O43155
Leucine-rich repeat transmembrane protein FLRT2 (Fibronectin-like domain-containing leucine-rich transmembrane protein 2)
660
Q12841
Follistatin-related protein 1 (Follistatin-like 1)
308
Q8N5D6
Globoside alpha-1,3-N-acetylgalactosaminyltransferase 1 (EC 2.4.1.-) (Forssman glycolipid synthetase-like protein)
347
Q92820
Gamma-glutamyl hydrolase (EC 3.4.19.9) (Gamma-Glu-X carboxypeptidase) (Conjugase) (GH)
318
Q8N3T1
Polypeptide N-acetylgalactosaminyltransferase-like protein 2 (EC 2.4.1.41) (Polypeptide GalNAc transferase-like protein 2) (pp-GaNTase-like protein 2) (GalNAc-T-like protein 2) (Protein-UDP acetylgalactosaminyltransferase-like protein 2) (UDP-GalNAc:polypeptide N-acetylgalactosaminyltransferase-like protein 2)
639
Q53EU6
Glycerol-3-phosphate acyltransferase 3 (GPAT3) (EC 2.3.1.15) (1-acylglycerol-3-phosphate O-acyltransferase 9) (1-AGP acyltransferase 9) (1-AGPAT 9) (Lysophosphatidic acid acyltransferase theta) (LPAAT-theta) (Acyl-CoA:glycerol-3-phosphate acyltransferase 3) (hGPAT3) (Lung cancer metastasis-associated protein 1) (MAG-1)
434
Q9Y653
G-protein coupled receptor 56 (Protein TM7XN1)
693
Q14520
Hyaluronan-binding protein 2 (EC 3.4.21.-) (Plasma hyaluronan-binding protein) (Hepatocyte growth factor activator-like protein) (Factor VII-activating protease) (Factor seven-activating protease) (FSAP) [Cleaved into: Hyaluronan-binding protein 2 50 kDa heavy chain; Hyaluronan-binding protein 2 50 kDa heavy chain alternate form; Hyaluronan-binding protein 2 27 kDa light chain; Hyaluronan-binding protein 2 27 kDa light chain alternate form]
560
Q99075
Proheparin-binding EGF-like growth factor [Cleaved into: Heparin-binding EGF-like growth factor (HB-EGF) (HBEGF) (Diphtheria toxin receptor)] (DT-R)
208
P04196
Histidine-rich glycoprotein (Histidine-proline-rich glycoprotein) (HPRG)
525
Q9Y663
Heparan sulfate glucosamine 3-O-sulfotransferase 3A1 (EC 2.8.2.30) (Heparan sulfate D-glucosaminyl 3-O-sulfotransferase 3A1) (Heparan sulfate 3-O-sulfotransferase 3A1) (h3-OST-3A)
406
Q6UXL0
Interleukin-20 receptor beta chain (IL-20R-beta) (IL-20R2)
311
P24593
Insulin-like growth factor-binding protein 5 (IGF-binding protein 5) (IGFBP-5) (IBP-5)
272
Q16270
Insulin-like growth factor-binding protein 7 (IGF-binding protein 7) (IGFBP-7) (IBP-7) (MAC25 protein) (Prostacyclin-stimulating factor) (PGI2-stimulating factor) (IGFBP-rP1) (Tumor-derived adhesion factor) (TAF)
282

-continued

P29622
Kallistatin (Kallikrein inhibitor) (Protease inhibitor 4) (Serpin A4)
427
Q8IZU9
Kin of IRRE-like protein 3 (Kin of irregular chiasm-like protein 3) (Nephrin-like 2)
778
P42702
Leukemia inhibitory factor receptor (LIF receptor) (LIF-R) (CD antigen CD118)
1,097
Q9HAP6
Lin-7 homolog B (Lin-7B) (hLin7B) (Mammalian lin-seven protein 2) (MALS-2) (Vertebrate lin-7 homolog 2) (Veli-2 protein) (hVeli2)
207
Q9HBW1
Leucine-rich repeat-containing protein 4 (Brain tumor-associated protein BAG) (Nasopharyngeal carcinoma-associated gene 14 protein)
653
Q6UXK5
Leucine-rich repeat neuronal protein 1 (Neuronal leucine-rich repeat protein 1) (NLRR-1)
716
O95274
Ly6/PLAUR domain-containing protein 3 (GPI-anchored metastasis-associated protein C4.4A homolog) (Matrigel-induced gene C4 protein) (MIG-C4)
346
Q9Y5Y7
Lymphatic vessel endothelial hyaluronic acid receptor 1 (LYVE-1) (Cell surface retention sequence-binding protein 1) (CRSBP-1) (Hyaluronic acid receptor) (Extracellular link domain-containing protein 1)
322
Q9UQ53
Alpha-1,3-mannosyl-glycoprotein 4-beta-N-acetylglucosaminyltransferase B (EC 2.4.1.145) (UDP-N-acetylglucosamine: alpha-1,3-D-mannoside beta-1,4-N-acetylglucosaminyltransferase IVb) (N-glycosyl-oligosaccharide-glycoprotein N-acetylglucosaminyltransferase IVb) (N-acetylglucosaminyltransferase IVb) (GlcNAc-T IVb) (GnT-IVb)
548
Q16674
Melanoma-derived growth regulatory protein (Melanoma inhibitory activity)
131
Q8IXL7
Methionine-R-sulfoxide reductase B3, mitochondrial (MsrB3) (EC 1.8.4.-)
185
Q8NC67
Neuropilin and tolloid-like protein 2 (Brain-specific transmembrane protein containing 2 CUB and 1 LDL-receptor class A domains protein 2)
525
Q86WC4
Osteopetrosis-associated transmembrane protein 1
334
Q9UHG3
Prenylcysteine oxidase 1 (EC 1.8.3.5) (Prenylcysteine lyase)
505
Q9UBV8
Peflin (PEF protein with a long N-terminal hydrophobic domain) (Penta-EF hand domain-containing protein 1)
284
Q9Y3C6
Peptidyl-prolyl cis-trans isomerase-like 1 (PPIase) (Rotamase) (EC 5.2.1.8)
166
O43653
Prostate stem cell antigen
123
Q9Y6C5
Protein patched homolog 2 (PTC2)
1,203
P35542
Serum amyloid A-4 protein (Constitutively expressed serum amyloid A protein) (C-SAA)
130
Q9UBV2
Protein sel-1 homolog 1 (Suppressor of lin-12-like protein 1) (Sel-1L)
794
P15907
Beta-galactoside alpha-2,6-sialyltransferase 1 (EC 2.4.99.1) (CMP-N-acetylneuraminate-beta-galactosamide-alpha-2,6-sialyltransferase 1) (Alpha 2,6-ST) (Sialyltransferase 1) (ST6Gal I) (B-cell antigen CD75)
406
Q9Y336
Sialic acid-binding Ig-like lectin 9 (Siglec-9) (Protein FOAP-9)
463
Q96PX8
SLIT and NTRK-like protein 1 (Leucine-rich repeat-containing protein 12)
696
P02808
Statherin
62
Q9Y6M0
Testisin (EC 3.4.21.-) (Serine protease 21) (Eosinophil serine protease 1) (ESP-1)
314

-continued

Q6UXY8
Transmembrane channel-like protein 5
1,006
Q9NRS4
Transmembrane protease, serine 4 (EC 3.4.21.-) (Membrane-type serine protease 2) (MT-SP2)
437
O75509
Tumor necrosis factor receptor superfamily member 21 (TNFR-related death receptor 6) (Death receptor 6)
655
Q9UBN6
Tumor necrosis factor receptor superfamily member 10D (Decoy receptor 2) (DcR2) (TNF-related apoptosis-inducing ligand receptor 4) (TRAIL receptor 4) (TRAIL-R4) (TRAIL receptor with a truncated death domain) (CD antigen CD264)
386
Q5T2D2
Trem-like transcript 2 protein (TLT-2) (Triggering receptor expressed on myeloid cells-like protein 2)
321
O95881
Thioredoxin domain-containing protein 12 (EC 1.8.4.2) (Thioredoxin-like protein p19) (Endoplasmic reticulum protein ERp19) (ERp18) (hTLP19)
172
P49765
Vascular endothelial growth factor B (VEGF-B) (VEGF-related factor) (VRF)
207
P49767
Vascular endothelial growth factor C (VEGF-C) (Vascular endothelial growth factor-related protein) (VRP) (Flt4 ligand) (Flt4-L)
419
Q9Y279
V-set and immunoglobulin domain-containing protein 4 (Protein Z39Ig)
399
Q9BXJ2
Complement C1q tumor necrosis factor-related protein 7
289
P98173
Protein FAM3A (2-19 protein)
230
Q9Y334
Protein G7c
891
Q8TDF5
Neuropilin and tolloid-like protein 1 (Brain-specific transmembrane protein containing 2 CUB and 1 LDL-receptor class A domains protein 1)
533
Q9UQ72
Pregnancy-specific beta-1-glycoprotein 11 (PSBG-11) (Pregnancy-specific beta-1-glycoprotein 13) (PSBG-13)
332
O75077
Disintegrin and metalloproteinase domain-containing protein 23 (ADAM 23) (Metalloproteinase-like, disintegrin-like, and cysteine-rich protein 3) (MDC-3)
832
O15204
ADAM DEC1 (EC 3.4.24.-) (A disintegrin and metalloproteinase domain-like protein decysin 1) (ADAM-like protein decysin 1)
470
Q9BRR6
ADP-dependent glucokinase (ADP-GK) (ADPGK) (EC 2.7.1.147) (RbBP-35)
497
P19961
Alpha-amylase 2B (EC 3.2.1.1) (1,4-alpha-D-glucan glucanohydrolase 2B) (Carcinoid alpha-amylase)
511
Q9H324
A disintegrin and metalloproteinase with thrombospondin motifs 10 (ADAMTS-10) (ADAM-TS 10) (ADAM-TS10) (EC 3.4.24.-)
1,103
Q8WXS8
A disintegrin and metalloproteinase with thrombospondin motifs 14 (ADAMTS-14) (ADAM-TS 14) (ADAM-TS14) (EC 3.4.24.-)
1,223
Q13410
Butyrophilin subfamily 1 member A1 (BT)
526
P35070
Probetacellulin [Cleaved into: Betacellulin (BTC)]
178
P10092
Calcitonin gene-related peptide 2 (Calcitonin gene-related peptide II) (CGRP-II) (Beta-type CGRP)
127
P16870
Carboxypeptidase E (CPE) (EC 3.4.17.10) (Carboxypeptidase H) (CPH) (Enkephalin convertase) (Prohormone-processing carboxypeptidase)
476
Q9UBD9
Cardiotrophin-like cytokine factor 1 (B cell-stimulating factor 3) (BSF-3) (Novel neurotrophin-1) (NNT-1)
225
P25067
Collagen alpha-2(VIII) chain (Endothelial collagen)

-continued

703
Q5IJ48
Crumbs homolog 2 (Crumbs-like protein 2)
1,285
Q13316
Dentin matrix acidic phosphoprotein 1 (Dentin matrix protein 1) (DMP-1)
513
O60469
Down syndrome cell adhesion molecule (CHD2)
2,012
Q9BXX0
EMILIN-2 (Elastin microfibril interface-located protein 2) (Elastin microfibril interfacer 2) (Protein FOAP-10)
1,053
Q5JZY3
Ephrin type-A receptor 10 (EC 2.7.10.1)
1,008
Q9UBQ6
Exostosin-like 2 (EC 2.4.1.223) (Glucuronyl-galactosyl-proteoglycan 4-alpha-N-acetylglucosaminyltransferase)
(Alpha-1,4-N-acetylhexosaminyltransferase EXTL2) (Alpha-GalNAcT EXTL2) (EXT-related protein 2) [Cleaved into: Processed exostosin-like 2]
330
Q6MZW2
Follistatin-related protein 4 (Follistatin-like 4)
842
Q8N475
Follistatin-related protein 5 (Follistatin-like 5)
847
Q7Z5L2
Growth inhibition and differentiation-related protein 88 (Putative mitochondrial space protein 32.1)
792
Q96RW7
Hemicentin-1 (Fibulin-6) (FIBL-6)
5,635
P01861
Ig gamma-4 chain C region
327
Q13007
Interleukin-24 (Suppression of tumorigenicity 16 protein) (Melanoma differentiation-associated gene 7 protein) (MDA-7)
206
O00515
Ladinin-1 (Lad-1) (Linear IgA disease antigen) (LADA)
517
Q6XZB0
Lipase member I (EC 3.1.1.-) (Membrane-associated phosphatidic acid-selective phospholipase A1-beta) (mPA-PLA1 beta) (LPD lipase)
(Cancer/testis antigen 17) (CT17)
460
P54315
Pancreatic lipase-related protein 1 (PL-RP1) (EC 3.1.1.3)
467
O95711
Lymphocyte antigen 86 (Protein MD-1)
162
O75095
Multiple epidermal growth factor-like domains 6 (EGF-like domain-containing protein 3) (Multiple EGF-like domain protein 3)
1,541
P55083
Microfibril-associated glycoprotein 4
255
Q9UM21
Alpha-1,3-mannosyl-glycoprotein 4-beta-N-acetylglucosaminyltransferase A (EC 2.4.1.145) (UDP-N-acetylglucosamine: alpha-1,3-D-mannoside
beta-1,4-N-acetylglucosaminyltransferase IVa) (N-glycosyl-oligosaccharide-glycoprotein N-acetylglucosaminyltransferase IVa)
(N-acetylglucosaminyltransferase IVa) (GlcNAc-T IVa) (GnT-IVa) [Cleaved into: Alpha-1,3-mannosyl-glycoprotein
4-beta-N-acetylglucosaminyltransferase A soluble form]
535
Q9NR99
Matrix-remodeling-associated protein 5 (Adhesion protein with leucine-rich repeats and immunoglobulin domains related to perlecan) (Adlican)
2,828
Q9HB63
Netrin-4 (Beta-netrin) (Hepar-derived netrin-like protein)
628
P08949
Neuromedin-B [Cleaved into: Neuromedin-B-32; Neuromedin-B]
121
P56975
Pro-neuregulin-3, membrane-bound isoform (Pro-NRG3) [Cleaved into: Neuregulin-3 (NRG-3)]
720
Q9GZU5
Nyctalopin
481
P02818

-continued

Osteocalcin (Gamma-carboxyglutamic acid-containing protein) (Bone Gla protein) (BGP)
100
Q04118
Basic salivary proline-rich protein 3 (Parotid salivary glycoprotein G1) (Proline-rich protein G1)
309
Q15235
Pregnancy-specific beta-1-glycoprotein 10 (PSBG-10) (Pregnancy-specific beta-1-glycoprotein 12) (PSBG-12)
424
P04808
Prorelaxin H1 [Cleaved into: Relaxin B chain; Relaxin A chain]
185
Q9BXY4
R-spondin-3 (Roof plate-specific spondin-3) (hRspo3) (Thrombospondin type-1 domain-containing protein 2) (Protein with TSP type-1 repeat) (hPWTSR)
272
Q9BZZ2
Sialoadhesin (Sialic acid-binding Ig-like lectin 1) (Siglec-1) (CD antigen CD169)
1,709
P35030
Trypsin-3 (EC 3.4.21.4) (Trypsin III) (Brain trypsinogen) (Mesotrypsinogen) (Trypsin IV) (Serine protease 3) (Serine protease 4)
304
Q5TIE3
von Willebrand factor A domain-containing protein 5B1
1,220
Q9UBV4
Protein Wnt-16
365
Q93097
Protein Wnt-2b (Wnt-13)
391
Q6UX41
Butyrophilin-like protein 8
500
Q86UP0
Cadherin-24
819
Q9H4A9
Dipeptidase 2 (EC 3.4.13.19)
486
Q6UXU4
Germ cell-specific gene 1-like protein (GSG1-like protein)
331
Q6UY01
Leucine-rich repeat-containing protein 31
552
Q86VH4
Leucine-rich repeat transmembrane neuronal protein 4
590
Q9BXS4
Transmembrane protein 59 (Liver membrane-bound protein)
323
Q9BUR5
Apolipoprotein O (Protein FAM121B)
198
Q96CG8
Collagen triple helix repeat-containing protein 1 (NMTC1 protein)
243
Q9UKF2
Disintegrin and metalloproteinase domain-containing protein 30 (ADAM 30) (EC 3.4.24.-)
790
Q86WK7
Amphoterin-induced protein 3 (AMIGO-3) (Alivin-3)
504
Q8WW43
Gamma-secretase subunit APH-1B (APH-1b) (Aph-1beta) (Presenilin-stabilization factor-like)
257
P55056
Apolipoprotein C-IV (Apo-CIV) (ApoC-IV)
127
Q96EG1
Arylsulfatase G (ASG) (EC 3.1.6.-)
525
Q9H0J0
Zinc finger RAD18 domain-containing protein C1orf124
489
Q9ULX7
Carbonic anhydrase 14 (EC 4.2.1.1) (Carbonic anhydrase XIV) (CA-XIV) (Carbonate dehydratase XIV)
337
P57730

Caspase recruitment domain-containing protein 18 (Caspase-1 inhibitor Iceberg)
90
Q8NCH0
Carbohydrate sulfotransferase 14 (EC 2.8.2.-) (Dermatan 4-sulfotransferase 1) (D4ST-1) (hD4ST)
376
Q86T13
C-type lectin domain family 14 member A (Epidermal growth factor receptor 5) (EGFR-5)
490
Q86VU5
Catechol-O-methyltransferase domain-containing protein 1 (EC 2.1.1.-)
262
O95406
Protein cornichon homolog (T-cell growth-associated molecule 77) (TGAM77)
144
Q8N4M1
Choline transporter-like protein 3 (Solute carrier family 44 member 3)
653
Q9BPX1
17-beta-hydroxysteroid dehydrogenase 14 (EC 1.1.1.-) (Dehydrogenase/reductase SDR family member 10) (17-beta-hydroxysteroid dehydrogenase DHRS10) (Retinal short-chain dehydrogenase/reductase retSDR3)
270
Q8N5I4
Dehydrogenase/reductase SDR family member on chromosome X (EC 1.1.-.-) (DHRSXY)
330
Q8TBM8
DnaJ homolog subfamily B member 14
379
Q9HBW9
EGF, latrophilin and seven transmembrane domain-containing protein 1 (EGF-TM7-latrophilin-related protein) (ETL protein)
690
Q8WW52
Protein FAM151A
585
Q8TC84
Fibronectin type 3 and ankyrin repeat domains protein 1
345
Q9NRD0
F-box only protein 8 (F-box/SEC7 protein FBS)
319
Q14314
Fibroleukin (Fibrinogen-like protein 2) (pT49)
439
Q9NWM8
FK506-binding protein 14 (EC 5.2.1.8) (Peptidyl-prolyl cis-trans isomerase) (PPIase) (Rotamase) (22 kDa FK506-binding protein) (FKBP-22)
211
Q9NZU1
Leucine-rich repeat transmembrane protein FLRT1 (Fibronectin-like domain-containing leucine-rich transmembrane protein 1)
646
Q9H0Q3
FXYD domain-containing ion transport regulator 6 (Phosphohippolin)
95
Q9Y3E0
Vesicle transport protein GOT1B (Golgi transport 1 homolog B) (hGOT1a) (Putative NF-kappa-B-activating protein 470)
138
Q5T9L3
Integral membrane protein GPR177 (Protein wntless homolog) (Protein evenness interrupted homolog) (EVI) (Putative NF-kappa-B-activating protein 373)
541
Q96P69
Probable G-protein coupled receptor 78
363
A8MVW5
HEPACAM family member 2
462
Q6UWB1
Interleukin-27 receptor subunit alpha (IL-27R-alpha) (WSX-1) (Type I T-cell cytokine receptor) (TCCR) (Protein CRL1)
636
Q6UXK2
Immunoglobulin superfamily containing leucine-rich repeat protein 2
745
O75578
Integrin alpha-10
1,167
Q8NBL1
KTEL motif-containing protein 1 (CAP10-like 46 kDa protein) (Myelodysplastic syndromes relative protein)
392
P83111
Serine beta-lactamase-like protein LACTB, mitochondrial (EC 3.4.-.-)
547

-continued

Q6UWP7
Lysocardiolipin acyltransferase 1 (EC 2.3.1.51) (EC 2.3.1.-) (Acyl-CoA:lysocardiolipin acyltransferase 1) (1-acylglycerol-3-phosphate
O-acyltransferase 8) (1-AGP acyltransferase 8) (1-AGPAT 8)
414
Q7L985
Leucine-rich repeat and immunoglobulin-like domain-containing nogo receptor-interacting protein 2 (Leucine-rich repeat neuronal protein 6C)
(Leucine-rich repeat neuronal protein 3)
606
A6NI73
Leukocyte immunoglobulin-like receptor subfamily A member 5 (Leukocyte immunoglobulin-like receptor 9) (LIR-9) (Immunoglobulin-like
transcript 11) (ILT-11) (CD85 antigen-like family member F) (CD antigen CD85f)
299
Q9BTN0
Leucine-rich repeat and fibronectin type-III domain-containing protein 3
628
Q8NA29
Major facilitator superfamily domain-containing protein 2
543
Q9HCJ2
Netrin-G1 ligand (NGL-1) (Leucine-rich repeat-containing protein 4C)
640
Q96RD7
Pannexin-1
426
Q9NPG4
Protocadherin-12 (Vascular cadherin-2) (Vascular endothelial cadherin-2) (VE-cadherin-2) (VE-cad-2)
1,184
Q9Y5I2
Protocadherin alpha-10 (PCDH-alpha-10)
948
Q9UN67
Protocadherin beta-10 (PCDH-beta-10)
800
Q9Y5F0
Protocadherin beta-13 (PCDH-beta-13)
798
Q9UHG2
ProSAAS (pro-SAAS) (Proprotein convertase subtilisin/kexin type 1 inhibitor) (Proprotein convertase 1 inhibitor) [Cleaved into: KEP;
Big SAAS (b-SAAS); Little SAAS (l-SAAS) (N-proSAAS); Big PEN-LEN (b-PEN-LEN) (SAAS CT(1-49)); PEN; Little LEN (l-LEN);
Big LEN (b-LEN) (SAAS CT(25-40))]
260
Q6UW60
Proprotein convertase subtilisin/kexin type 4 (EC 3.4.21.-) (Proprotein convertase PC4)
755
Q96FM1
Post-GPI attachment to proteins factor 3 (PER1-like domain-containing protein 1) (Gene coamplified with ERBB2 protein) (hCOS16)
320
Q96S52
GPI transamidase component PIG-S (Phosphatidylinositol-glycan biosynthesis class S protein)
555
Q5FWE3
Proline-rich transmembrane protein 3
981
Q6ZRP7
Sulfhydryl oxidase 2 (EC 1.8.3.2) (Quiescin Q6-like protein 1) (Neuroblastoma-derived sulfhydryl oxidase)
698
Q96D15
Reticulocalbin-3 (EF-hand calcium-binding protein RLP49)
328
O60939
Sodium channel subunit beta-2
215
Q9HCN8
Stromal cell-derived factor 2-like protein 1 (SDF2-like protein 1) (PWP1-interacting protein 8)
221
Q9BRG2
SH2 domain-containing protein 3A (Novel SH2-containing protein 1)
576
Q6S5L8
SHC-transforming protein 4 (Src homology 2 domain-containing-transforming protein C4) (SH2 domain protein C4) (Rai-like protein) (RaLP) (hShcD)
630
P48594
Serpin B4 (Squamous cell carcinoma antigen 2) (SCCA-2) (Leupin)
390
Q9Y4P3
Transducin beta-like protein 2 (WS beta-transducin repeats protein) (WS-betaTRP) (Williams-Beuren syndrome chromosomal region 13 protein)
447
Q5VZ19
Tudor domain-containing protein 10

366
Q9NYK1
Toll-like receptor 7
1,049
Q8N3G9
Transmembrane protein 130
435
Q9BSN7
Transmembrane protein 204 (Claudin-like protein 24)
226
Q9HD45
Transmembrane 9 superfamily member 3 (SM-11044-binding protein) (EP70-P-iso)
589
Q8TDI7
Transmembrane channel-like protein 2 (Transmembrane cochlear-expressed protein 2)
906
Q6UWJ1
Transmembrane and coiled-coil domain-containing protein 3 (Putative LAG1-interacting protein)
677
Q96BY9
Transmembrane protein 66 (Protein FOAP-7) (HBV X-transactivated gene 3 protein)
339
Q9H1E5
Thioredoxin-related transmembrane protein 4 (Thioredoxin domain-containing protein 13)
349
Q9H2S6
Tenomodulin (TeM) (hTeM) (Chondromodulin-I-like protein) (ChM1L) (hChM1L) (Myodulin) (Tendin)
317
O43657
Tetraspanin-6 (Tspan-6) (Transmembrane 4 superfamily member 6) (T245 protein) (Tetraspanin TM4-D) (A15 homolog) (Putative NF-kappa-B-activating protein 321)
245
Q8NBS9
Thioredoxin domain-containing protein 5 (Thioredoxin-like protein p46) (Endoplasmic reticulum protein ERp46)
432
O43915
Vascular endothelial growth factor D (VEGF-D) (c-fos-induced growth factor) (FIGF)
354
Q96IQ7
V-set and immunoglobulin domain-containing protein 2 (CT-like protein) (Cortical thymocyte-like protein)
327
Q13275
Semaphorin-3F (Semaphorin IV) (Sema IV) (Sema III/F)
785
Q8TE99
Acid phosphatase-like protein 2 (EC 3.1.3.2)
480
Q6UXV4
Apolipoprotein O-like (Protein FAM121A)
268
Q96EE4
Coiled-coil domain-containing protein 126
140
O00230
Cortistatin [Cleaved into: Cortistatin-29; Cortistatin-17]
105
Q9H7Y0
UPF0672 protein CXorf36
433
Q8N690
Beta-defensin 119 (Defensin, beta 119) (Beta-defensin 19) (DEFB-19) (Beta-defensin 120) (Defensin, beta 120) (Beta-defensin 20) (DEFB-20)
84
Q9UJA9
Ectonucleotide pyrophosphatase/phosphodiesterase family member 5 (E-NPP5) (NPP-5) (EC 3.1.-.-)
477
Q6UXB0
Protein FAM131A
335
P58499
Protein FAM3B (Cytokine-like protein 2-21)
235
O76093
Fibroblast growth factor 18 (FGF-18) (zFGF5)
207
Q6UWU2
Beta-galactosidase-1-like protein (EC 3.2.1.-)
654
Q8N1E2
Lysozyme g-like protein 1 (EC 3.2.1.-)

-continued

194
Q86Y78
Ly6/PLAUR domain-containing protein 6
171
Q96QH8
Sperm acrosome-associated protein 5 (EC 3.2.1.17) (Lysozyme-like protein 5) (Sperm-specific lysozyme-like protein X) (SLLP-X)
159
O75951
Lysozyme-like protein 6 (EC 3.2.1.17)
148
Q9NQ76
Matrix extracellular phosphoglycoprotein (Osteoblast/osteocyte factor 45) (OF45)
525
Q6UW10
Surfactant-associated protein 2 (Surfactant-associated protein G)
78
Q96A54
Adiponectin receptor protein 1 (Progestin and adipoQ receptor family member I)
375
P58166
Inhibin beta E chain (Activin beta-E chain)
350
P05408
Neuroendocrine protein 7B2 (Secretory granule endocrine protein I) (Secretogranin-5) (Secretogranin V) (Pituitary polypeptide) [Cleaved into: N-terminal peptide; C-terminal peptide]
212
P04217
Alpha-1B-glycoprotein (Alpha-1-B glycoprotein)
495
P02750
Leucine-rich alpha-2-glycoprotein (LRG)
347
P19801
Amiloride-sensitive amine oxidase [copper-containing](Diamine oxidase) (DAO) (EC 1.4.3.22) (Amiloride-binding protein) (ABP) (Histaminase) (Kidney amine oxidase) (KAO)
751
Q6PIU2
Arylacetamide deacetylase-like 1 (EC 3.1.1.-) (Neutral cholesterol ester hydrolase) (NCEH)
408
P35318
ADM [Cleaved into: Adrenomedullin (AM); Proadrenomedullin N-20 terminal peptide (ProAM N-terminal 20 peptide) (ProAM-N20) (PAMP)]
185
P43652
Afamin (Alpha-albumin) (Alpha-Alb)
599
O00468
Agrin
2,045
P35858
Insulin-like growth factor-binding protein complex acid labile chain (ALS)
605
P42127
Agouti-signaling protein (ASP) (Agouti switch protein)
132
Q9UHI8
A disintegrin and metalloproteinase with thrombospondin motifs 1 (ADAMTS-1) (ADAM-TS 1) (ADAM-TS1) (EC 3.4.24.-) (METH-1)
967
O95972
Bone morphogenetic protein 15 (BMP-15) (Growth/differentiation factor 9B) (GDF-9B)
392
P12645
Bone morphogenetic protein 3 (BMP-3) (Osteogenin) (BMP-3A)
472
Q10589
Bone marrow stromal antigen 2 (BST-2) (Tetherin) (HM1.24 antigen) (CD antigen CD317)
180
P55285
Cadherin-6 (Kidney cadherin) (K-cadherin)
790
P49913
Cathelicidin antimicrobial peptide (18 kDa cationic antimicrobial protein) (CAP-18) (hCAP-18) [Cleaved into: Antibacterial protein FALL-39 (FALL-39 peptide antibiotic); Antibacterial protein LL-37]
170
Q16568
Cocaine- and amphetamine-regulated transcript protein [Cleaved into: CART(1-39); CART(42-89)]
116
P15086
Carboxypeptidase B (EC 3.4.17.2) (Pancreas-specific protein) (PASP)
417

-continued

O15467
C-C motif chemokine 16 (Small-inducible cytokine A16) (IL-10-inducible chemokine) (Chemokine LEC) (Liver-expressed chemokine) (Monotactin-1) (MTN-1) (Chemokine CC-4) (HCC-4) (NCC-4) (Lymphocyte and monocyte chemoattractant) (LMC) (LCC-1)
120
Q92583
C-C motif chemokine 17 (Small-inducible cytokine A17) (Thymus and activation-regulated chemokine) (CC chemokine TARC)
94
O00626
C-C motif chemokine 22 (Small-inducible cytokine A22) (Macrophage-derived chemokine) (MDC(1-69)) (Stimulated T-cell chemotactic protein 1) (CC chemokine STCP-1) [Cleaved into: MDC(3-69); MDC(5-69); MDC(7-69)]
93
O00175
C-C motif chemokine 24 (Small-inducible cytokine A24) (Myeloid progenitor inhibitory factor 2) (MPIF-2) (CK-beta-6) (Eosinophil chemotactic protein 2) (Eotaxin-2)
119
Q6PJG6
HEAT repeat-containing protein C7orf27
821
Q14055
Collagen alpha-2(IX) chain
689
Q14050
Collagen alpha-3(IX) chain
684
P04118
Colipase
112
Q8IZC6
Collagen alpha-1(XXVII) chain
1,860
P22792
Carboxypeptidase N subunit 2 (Carboxypeptidase N polypeptide 2) (Carboxypeptidase N 83 kDa chain) (Carboxypeptidase N regulatory subunit) (Carboxypeptidase N large subunit)
545
P80162
C-X-C motif chemokine 6 (Small-inducible cytokine B6) (Granulocyte chemotactic protein 2) (GCP-2) (Chemokine alpha 3) (CKA-3) [Cleaved into: Small-inducible cytokine B6, N-processed variant 1; Small-inducible cytokine B6, N-processed variant 2; Small-inducible cytokine B6, N-processed variant 3]
114
P02778
C-X-C motif chemokine 10 (Small-inducible cytokine B10) (10 kDa interferon-gamma-induced protein) (Gamma-IP10) (IP-10) [Cleaved into: CXCL10(1-73)]
98
P28325
Cystatin-D (Cystatin-5)
142
O76096
Cystatin-F (Leukocystatin) (Cystatin-7) (Cystatin-like metastasis-associated protein) (CMAP)
145
P09228
Cystatin-SA (Cystatin-2) (Cystatin-S5)
141
Q14118
Dystroglycan (Dystrophin-associated glycoprotein 1) [Cleaved into: Alpha-dystroglycan (Alpha-DG); Beta-dystroglycan (Beta-DG)]
895
P12838
Neutrophil defensin 4 (HNP-4) (HP-4) (Defensin, alpha 4)
97
P60022
Beta-defensin 1 (BD-1) (hBD-1) (Defensin, beta 1)
68
P20800
Endothelin-2 (ET-2) (Preproendothelin-2) (PPET2)
178
O75354
Ectonucleoside triphosphate diphosphohydrolase 6 (NTPDase 6) (EC 3.6.1.6) (CD39 antigen-like 2)
484
Q6BAA4
Fc receptor-like B (Fc receptor-like protein 2) (Fc receptor-like and mucin-like protein 2) (Fc receptor-related protein Y) (FcRY) (Fc receptor homolog expressed in B cells protein 2) (FREB-2)
426
P31371
Glia-activating factor (GAF) (Fibroblast growth factor 9) (FGF-9) (HBGF-9)
208
Q06828
Fibromodulin (FM) (Collagen-binding 59 kDa protein) (Keratan sulfate proteoglycan fibromodulin) (KSPG fibromodulin)
376
P14207
Folate receptor beta (FR-beta) (Folate receptor 2) (Folate receptor, fetal/placental) (Placental folate-binding protein) (FBP)

255
P22466
Galanin [Cleaved into: Galanin; Galanin message-associated peptide (GMAP)]
123
Q99988
Growth/differentiation factor 15 (GDF-15) (Placental bone morphogenetic protein) (Placental TGF-beta) (Macrophage inhibitory cytokine 1) (MIC-1) (Prostate differentiation factor) (NSAID-activated gene 1 protein) (NAG-1) (NSAID-regulated gene 1 protein) (NRG-1)
308
P07093
Glia-derived nexin (GDN) (Protease nexin I) (PN-1) (Protease inhibitor 7)
398
P01148
Progonadoliberin-1 (Progonadoliberin I) [Cleaved into: Gonadoliberin-1 (Gonadoliberin I) (Luteinizing hormone-releasing hormone I) (LH-RH I) (Gonadotropin-releasing hormone I) (GnRH-I) (Luliberin I) (Gonadorelin); GnRH-associated peptide 1 (GnRH-associated peptide I)]
92
P49863
Granzyme K (EC 3.4.21.-) (Granzyme-3) (NK-tryptase-2) (NK-TRYP-2) (Fragmentin-3)
264
Q02747
Guanylin (Guanylate cyclase activator 2A) (Guanylate cyclase-activating protein 1) (Gap-I) [Cleaved into: HMW-guanylin; Guanylin]
115
Q16661
Guanylate cyclase activator 2B [Cleaved into: Guanylate cyclase C-activating peptide 2 (Guanylate cyclase C-activating peptide II) (GCAP-II); Uroguanylin (UGN)]
112
Q9Y6W8
Inducible T-cell costimulator (Activation-inducible lymphocyte immunomediatory molecule) (CD antigen CD278)
199
P01571
Interferon alpha-17 (Interferon alpha-I') (LeIF I) (Interferon alpha-T) (Interferon alpha-88)
189
P01568
Interferon alpha-21 (Interferon alpha-F) (LeIF F)
189
P32881
Interferon alpha-8 (Interferon alpha-B2) (Interferon alpha-B) (LeIF B)
189
P05000
Interferon omega-1 (Interferon alpha-II-1)
195
P15814
Immunoglobulin lambda-like polypeptide 1 (Immunoglobulin-related protein 14.1) (Immunoglobulin omega polypeptide) (Ig lambda-5) (CD179 antigen-like family member B) (CD antigen CD179b)
213
Q9HBE4
Interleukin-21 (IL-21) (Za11)
155
P08700
Interleukin-3 (IL-3) (Multipotential colony-stimulating factor) (Hematopoietic growth factor) (P-cell-stimulating factor) (Mast cell growth factor) (MCGF)
152
P13232
Interleukin-7 (IL-7)
177
P05111
Inhibin alpha chain
366
Q14641
Early placenta insulin-like peptide (EPIL) (Placentin) (Insulin-like peptide 4) [Cleaved into: Early placenta insulin-like peptide B chain; Early placenta insulin-like peptide A chain]
139
O60938
Keratocan (KTN) (Keratan sulfate proteoglycan keratocan)
352
Q16787
Laminin subunit alpha-3 (Epiligrin 170 kDa subunit) (E170) (Nicein subunit alpha)
3,333
P55268
Laminin subunit beta-2 (S-laminin) (Laminin B1s chain)
1,798
O00292
Left-right determination factor 2 (Protein lefty-2) (Left-right determination factor A) (Protein lefty-A) (Transforming growth factor beta-4) (TGF-beta-4) (Endometrial bleeding-associated factor)
366
Q8N0V4
Leucine-rich repeat LGI family member 2 (Leucine-rich glioma-inactivated protein 2) (LGI1-like protein 2)
545
Q96JB6
Lysyl oxidase homolog 4 (EC 1.4.3.-) (Lysyl oxidase-like protein 4) (Lysyl oxidase-related protein C)

-continued

756
Q14767
Latent-transforming growth factor beta-binding protein 2 (LTBP-2)
1,821
P51884
Lumican (Keratan sulfate proteoglycan lumican) (KSPG lumican)
338
Q14703
Membrane-bound transcription factor site-1 protease (EC 3.4.21.112) (S1P endopeptidase) (Site-1 protease) (Subtilisin/kexin-isozyme 1) (SKI-1)
1,052
P24347
Stromelysin-3 (SL-3) (ST3) (EC 3.4.24.-) (Matrix metalloproteinase-11) (MMP-11)
488
P39900
Macrophage metalloelastase (HME) (EC 3.4.24.65) (Matrix metalloproteinase-12) (MMP-12) (Macrophage elastase) (ME)
470
O75900
Matrix metalloproteinase-23 (MMP-23) (EC 3.4.24.-) (Matrix metallopeptidase 21) (MMP-21) (Matrix metalloprotease 22) (MMP-22) (Femalysin) (MIFR-1) [Cleaved into: Matrix metalloproteinase-23, soluble form]
390
P80303
Nucleobindin-2 (DNA-binding protein NEFA) (Gastric cancer antigen Zg4)
420
Q9UBM4
Opticin (Oculoglycan)
332
P04054
Phospholipase A2 (EC 3.1.1.4) (Phosphatidylcholine 2-acylhydrolase) (Group IB phospholipase A2)
148
P01298
Pancreatic prohormone (Pancreatic polypeptide) (PP) (Obinepitide) [Cleaved into: Pancreatic hormone (PH); Pancreatic icosapeptide (PI)]
95
P01213
Proenkephalin-B (Beta-neoendorphin-dynorphin) (Preprodynorphin) [Cleaved into: Alpha-neoendorphin; Beta-neoendorphin; Big dynorphin (Big Dyn); Dynorphin A(1-17) (Dynorphin A) (Dyn-A17); Dynorphin A(1-13); Dynorphin A(1-8); Leu-enkephalin; Rimorphin (Dynorphin B) (Dyn-B) (Dynorphin B(1-13)); Leumorphin (Dynorphin B-29)]
254
P01210
Proenkephalin-A [Cleaved into: Synenkephalin; Met-enkephalin (Opioid growth factor) (OGF); PENK(114-133); PENK(143-183); Met-enkephalin-Arg-Gly-Leu; Leu-enkephalin; PENK(237-258); Met-enkephalin-Arg-Phe]
267
Q9Y646
Plasma glutamate carboxypeptidase (EC 3.4.17.-)
472
Q96LB8
Peptidoglycan recognition protein I-beta (PGRP-I-beta) (Peptidoglycan recognition protein intermediate beta) (PGLYRPIbeta) (Peptidoglycan recognition protein 4)
373
Q16557
Pregnancy-specific beta-1-glycoprotein 3 (PSBG-3) (Carcinoembryonic antigen SG5)
428
Q00889
Pregnancy-specific beta-1-glycoprotein 6 (PSBG-6)
435
Q00887
Pregnancy-specific beta-1-glycoprotein 9 (Pregnancy-specific glycoprotein 9) (PSBG-9) (Pregnancy-specific beta-1 glycoprotein B) (PS-beta-B) (PS34) (Pregnancy-specific glycoprotein 7) (PSG7)
426
P26022
Pentraxin-related protein PTX3 (Pentaxin-related protein PTX3) (Tumor necrosis factor-inducible gene 14 protein) (TSG-14)
381
P10082
Peptide YY (PYY) (PYY-I) (Peptide tyrosine tyrosine) [Cleaved into: Peptide YY(3-36) (PYY-II)]
97
P10745
Retinol-binding protein 3 (Interphotoreceptor retinoid-binding protein) (IRBP) (Interstitial retinol-binding protein)
1,247
Q68DV7
RING finger protein 43
783
Q6SPF0
Atherin (Sterile alpha motif domain-containing protein 1)
538
Q9UGP8
Translocation protein SEC63 homolog
760
Q02383
Semenogelin-2 (Semenogelin II) (SGII)
582

-continued

P21815
Bone sialoprotein 2 (Bone sialoprotein II) (BSP II) (Cell-binding sialoprotein) (Integrin-binding sialoprotein)
317
P10600
Transforming growth factor beta-3 (TGF-beta-3)
412
O14656
Torsin-1A (Torsin family 1 member A) (Dystonia 1 protein)
332
P11684
Uteroglobin (Secretoglobin family 1A member 1) (Clara cell phospholipid-binding protein) (CCPBP) (Clara cells 10 kDa secretory protein) (CC10) (Urinary protein 1) (Urine protein 1) (UP1)
91
O00744
Protein Wnt-10b (Wnt-12)
389
P47992
Lymphotactin (C motif chemokine 1) (Cytokine SCM-1) (ATAC) (Lymphotaxin) (SCM-1-alpha) (Small-inducible cytokine C1) (XC chemokine ligand 1)
114
Q9UQC9
Calcium-activated chloride channel regulator 2 (Calcium-activated chloride channel family member 2) (hCLCA2) (Calcium-activated chloride channel protein 3) (CaCC-3) (hCaCC-3) [Cleaved into: Calcium-activated chloride channel regulator 2, 109 kDa form; Calcium-activated chloride channel regulator 2, 35 kDa form]
943
P09341
Growth-regulated alpha protein (C-X-C motif chemokine 1) (Melanoma growth stimulatory activity) (MGSA) (Neutrophil-activating protein 3) (NAP-3) (GRO-alpha(1-73)) [Cleaved into: GRO-alpha(4-73); GRO-alpha(5-73); GRO-alpha(6-73)]
107
Q02505
Mucin-3A (MUC-3A) (Intestinal mucin-3A)
2,541
P10163
Basic salivary proline-rich protein 4 (Salivary proline-rich protein Po) (Parotid o protein) (Salivary proline-rich protein II-1) [Cleaved into: Protein N1; Glycosylated protein A; Peptide P-D (Proline-rich peptide IB-5)]
310
Q92626
Peroxidasin homolog (EC 1.11.1.7) (Vascular peroxidase 1) (Melanoma-associated antigen MG50) (p53-responsive gene 2 protein)
1,479
Q9UI42
Carboxypeptidase A4 (EC 3.4.17.-) (Carboxypeptidase A3)
421
Q6UX06
Olfactomedin-4 (OLM4) (G-CSF-stimulated clone 1 protein) (hGC-1) (hOLfD) (Antiapoptotic protein GW112)
510
Q13018
Secretory phospholipase A2 receptor (PLA2-R) (PLA2R) (180 kDa secretory phospholipase A2 receptor) (M-type receptor) [Cleaved into: Soluble secretory phospholipase A2 receptor (Soluble PLA2-R) (Soluble PLA2R)]
1,463
Q6UXB2
VEGF co-regulated chemokine 1 (C-X-C motif chemokine 17) (Dendritic cell and monocyte chemokine-like protein) (DMC)
119
Q7Z4H4
ADM2 (Intermedin) [Cleaved into: Adrenomedullin-2 (Intermedin-long) (IMDL); Intermedin-short (IMDS)]
148
Q99218
Amelogenin, Y isoform
206
P54793
Arylsulfatase F (ASF) (EC 3.1.6.-)
590
Q6NT52
Choriogonadotropin subunit beta variant 2
195
Q8WTQ1
Beta-defensin 104 (Defensin, beta 104) (Beta-defensin 4) (BD-4) (hBD-4) (DEFB-4)
72
Q8NG35
Beta-defensin 105 (Defensin, beta 105) (Beta-defensin 5) (BD-5) (DEFB-5)
78
Q8IZN7
Beta-defensin 107 (Defensin, beta 107) (Beta-defensin 7) (BD-7) (DEFB-7)
70
Q7Z5J1
Hydroxysteroid 11-beta-dehydrogenase 1-like protein (EC 1.1.1.-) (Short-chain dehydrogenase/reductase 10) (11-beta-hydroxysteroid dehydrogenase type 3) (11-beta-HSD3)
315
O95925
Eppin (Epididymal protease inhibitor) (Serine protease inhibitor-like with Kunitz and WAP domains 1) (WAP four-disulfide core domain protein 7)

-continued (Protease inhibitor WAP7) (Cancer/testis antigen 71) (CT71)
133
O43555
Progonadoliberin-2 (Progonadoliberin II) [Cleaved into: Gonadoliberin-2 (Gonadoliberin II) (Luteinizing hormone-releasing hormone II) (LH-RH II) (Gonadotropin-releasing hormone II) (GnRH II) (Luliberin II); GnRH-associated peptide 2 (GnRH-associated peptide II)]
120
Q7RTW8
Otoancorin
1,153
Q92752
Tenascin-R (TN-R) (Restrictin) (Janusin)
1,358
Q9NZC2
Triggering receptor expressed on myeloid cells 2 (Triggering receptor expressed on monocytes 2) (TREM-2)
230
Q8WU66
Protein TSPEAR (TSP-EAR)
669
Q8NEX6
Protein WFDC11
87
Q9BQY6
WAP four-disulfide core domain protein 6 (Putative protease inhibitor WAP6)
131
Q6UW88
Epigen (Epithelial mitogen) (EPG)
154
Q7Z5A7
Protein FAM19A5 (Chemokine-like protein TAFA-5)
132
Q9Y3Q7
Disintegrin and metalloproteinase domain-containing protein 18 (ADAM 18) (Transmembrane metalloproteinase-like, disintegrin-like, and cysteine-rich protein III) (tMDC III)
739
Q13790
Apolipoprotein F (Apo-F) (Lipid transfer inhibitor protein) (LTIP)
308
Q6UXE8
Butyrophilin-like protein 3 (Butyrophilin-like receptor)
466
Q6UXG8
Butyrophilin-like protein 9
535
Q6P4E1
Protein CASC4 (Cancer susceptibility candidate gene 4 protein)
433
Q7Z692
Carcinoembryonic antigen-related cell adhesion molecule 19 (Carcinoembryonic antigen-like 1)
300
P56856
Claudin-18
261
P56747
Claudin-6 (Skullin 2)
220
P56748
Claudin-8
225
Q6UWF3
Transmembrane protein C17orf87
145
Q96MF6
Protein COQ10 A, mitochondrial
247
Q6UXV1
Uncharacterized protein C19orf41
221
P58658
Uncharacterized protein C21orf63 (SUE21)
441
Q6UY11
Protein delta homolog 2 (DLK-2) (EGF-like domain-containing protein 9) (Multiple EGF-like domain protein 9)
383
Q6UX65
DNA damage-regulated autophagy modulator protein 2 (Transmembrane protein 77)
266
Q9BXR6
Complement factor H-related protein 5 (FHR-5)
569

-continued

Q9Y680
FK506-binding protein 7 (EC 5.2.1.8) (Peptidyl-prolyl cis-trans isomerase) (PPIase) (Rotamase) (FKBP-23)
259
Q96PP8
Guanylate-binding protein 5 (Guanine nucleotide-binding protein 5) (GTP-binding protein 5) (GBP-5) (GBP-TA antigen)
586
P55259
Pancreatic secretory granule membrane major glycoprotein GP2 (Pancreatic zymogen granule membrane protein GP-2) (ZAP75)
537
Q86WI0
Lipoma HMGIC fusion partner-like 1 protein
220
Q9HAT1
Protein ERGIC-53-like (ERGIC53-like protein) (Lectin mannose-binding 1-like) (LMAN1-like protein)
526
Q8N456
Leucine-rich repeat-containing protein 18
261
Q8N386
Leucine-rich repeat-containing protein 25 (Monocyte and plasmacytoid-activated protein)
305
Q96PB8
Leucine-rich repeat-containing protein 3B (Leucine-rich repeat protein LRP15)
259
Q9BY71
Leucine-rich repeat-containing protein 3
257
Q6UWN0
Ly6/PLAUR domain-containing protein 4
246
Q9BZM2
Group IIF secretory phospholipase A2 (GIIF sPLA2) (EC 3.1.1.4) (Phosphatidylcholine 2-acylhydrolase GIIF) (sPLA(2)-IIF)
168
Q9HBH5
Retinol dehydrogenase 14 (EC 1.1.1.-) (Alcohol dehydrogenase PAN2)
336
Q96G75
Protein RMD5 homolog B
393
Q6ZMJ2
Scavenger receptor class A member 5 (Scavenger receptor hlg)
495
P62341
Selenoprotein T (SelT)
195
Q9H3T3
Semaphorin-6B (Semaphorin-Z) (Sema Z)
888
Q96SA4
Serine incorporator 2 (Tumor differentially expressed 2-like)
456
Q16842
CMP-N-acetylneuraminate-beta-galactosamide-alpha-2,3-sialyltransferase (Beta-galactoside alpha-2,3-sialyltransferase) (Alpha 2,3-ST) (EC 2.4.99.-) (Gal-NAc6S) (Gal-beta-1,3-GalNAc-alpha-2,3-sialyltransferase) (ST3GalA.2) (SIAT4-B) (ST3Gal II)
350
Q96RL6
Sialic acid-binding Ig-like lectin 11 (Sialic acid-binding lectin 11) (Siglec-11)
686
Q9Y343
Sorting nexin-24
169
Q96L08
Sushi domain-containing protein 3
255
Q6UXF1
Transmembrane protein 108
575
Q4V9L6
Transmembrane protein 119
283
Q6UXZ0
Transmembrane and immunoglobulin domain-containing protein 1
262
Q9Y2Y6
Transmembrane protein 98 (Protein TADA1)
226
Q9BY14
Testis-expressed protein 101 (Scleroderma-associated autoantigen) (Cell surface receptor NYD-SP8) (Spermatogenesis-related gene protein)
249

-continued

Q6UXZ4
Netrin receptor UNC5D (Protein unc-5 homolog D) (Unc-5 homolog 4)
953
Q9UKI3
Pre-B lymphocyte protein 3 (Protein VPreB3) (N27C7-2)
123
Q9H1B5
Xylosyltransferase 2 (EC 2.4.2.26) (Xylosyltransferase II) (XylT-II) (XT-II) (Peptide O-xylosyltransferase 1)
865
Q96TA2
ATP-dependent metalloprotease YME1L1 (EC 3.4.24.-) (YME1-like protein 1) (ATP-dependent metalloprotease FtsH1) (Meg-4) (Presenilin-associated metalloprotease) (PAMP)
773
Q9H3R2
Mucin-13 (MUC-13) (Down-regulated in colon cancer 1)
512
O57166
Growth factor (Secreted epidermal growth factor-like) (Vaccinia growth factor)
140
P20494
Growth factor (Secreted epidermal growth factor-like) (Vaccinia growth factor)
142
Q86607
Growth factor (Secreted epidermal growth factor-like) (Vaccinia growth factor)
140
Q9H336
Cysteine-rich secretory protein LCCL domain-containing 1 (LCCL domain-containing cysteine-rich secretory protein 1) (Cysteine-rich secretory protein 10) (CRISP-10) (Trypsin inhibitor Hl) (CocoaCrisp)
500
Q6UWT2
Adropin (Energy homeostasis-associated protein)
76
Q6UWR7
Ectonucleotide pyrophosphatase/phosphodiesterase family member 6 (E-NPP6) (NPP-6) (EC 3.1.-.-) [Cleaved into: Ectonucleotide pyrophosphatase/phosphodiesterase family member 6 soluble form]
440
Q96MK3
Protein FAM20A
541
P60985
Keratinocyte differentiation-associated protein
99
Q9BSG0
Protease-associated domain-containing protein of 21 kDa (hPAP21)
188
Q6UY27
Prostate and testis expressed protein 2 (PATE-like protein M) (PATE-M)
113
Q9BZM1
Group XIIA secretory phospholipase A2 (GXII sPLA2) (EC 3.1.1.4) (Phosphatidylcholine 2-acylhydrolase GXII) (sPLA2-XII)
189
Q9BX93
Group XIIB secretory phospholipase A2-like protein (Group XIII secretory phospholipase A2-like protein) (GXIII sPLA2-like) (sPLA2-GXIIB) (GXIIB)
195
A8K2U0
Alpha-2-macroglobulin-like protein 1 (C3 and PZP-like alpha-2-macroglobulin domain-containing protein 9)
1,454
Q8TE60
A disintegrin and metalloproteinase with thrombospondin motifs 18 (ADAMTS-18) (ADAM-TS 18) (ADAM-TS18) (EC 3.4.24.-)
1,221
Q8TE59
A disintegrin and metalloproteinase with thrombospondin motifs 19 (ADAMTS-19) (ADAM-TS 19) (ADAM-TS19) (EC 3.4.24.-)
1,207
O15072
A disintegrin and metalloproteinase with thrombospondin motifs 3 (ADAMTS-3) (ADAM-TS 3) (ADAM-TS3) (EC 3.4.24.-) (Procollagen II amino propeptide-processing enzyme) (Procollagen II N-proteinase) (PC II-NP)
1,205
Q9UNA0
A disintegrin and metalloproteinase with thrombospondin motifs 5 (ADAMTS-5) (ADAM-TS 5) (ADAM-TS5) (EC 3.4.24.-) (Aggrecanase-2) (ADMP-2) (A disintegrin and metalloproteinase with thrombospondin motifs 11) (ADAMTS-11) (ADAM-TS 11)
930
Q9UKP4
A disintegrin and metalloproteinase with thrombospondin motifs 7 (ADAMTS-7) (ADAM-TS 7) (ADAM-TS7) (EC 3.4.24.-) (COMPase)
1,686
Q9P2N4
A disintegrin and metalloproteinase with thrombospondin motifs 9 (ADAMTS-9) (ADAM-TS 9) (ADAM-TS9) (EC 3.4.24.-)
1,935
P12643

-continued

Bone morphogenetic protein 2 (BMP-2) (BMP-2A)
396
P22004
Bone morphogenetic protein 6 (BMP-6)
513
Q8N8U9
BMP-binding endothelial regulator protein (Bone morphogenetic protein-binding endothelial cell precursor-derived regulator) (Protein crossveinless-2) (hCV2)
685
O95813
Cerberus (Cerberus-related protein) (DAN domain family member 4)
267
Q9H2A9
Carbohydrate sulfotransferase 8 (EC 2.8.2.-) (N-acetylgalactosamine-4-O-sulfotransferase 1) (GalNAc-4-O-sulfotransferase 1) (GalNAc-4-ST1) (GalNAc4ST-1)
424
Q9BZ76
Contactin-associated protein-like 3 (Cell recognition molecule Caspr3)
1,288
P25940
Collagen alpha-3(V) chain
1,745
P06850
Corticoliberin (Corticotropin-releasing hormone) (Corticotropin-releasing factor) (CRF)
196
O75718
Cartilage-associated protein
401
Q969H8
UPF0556 protein C19orf10 (Stromal cell-derived growth factor SF20) (Interleukin-25) (IL-25)
173
P19876
C-X-C motif chemokine 3 (Macrophage inflammatory protein 2-beta) (MIP2-beta) (Growth-regulated protein gamma) (GRO-gamma) (GRO-gamma(1-73)) [Cleaved into: GRO-gamma(5-73)]
107
Q15828
Cystatin-M (Cystatin-6) (Cystatin-E)
149
Q01523
Defensin-5 (Defensin, alpha 5)
94
Q01524
Defensin-6 (Defensin, alpha 6)
100
Q07507
Dermatopontin (Tyrosine-rich acidic matrix protein) (TRAMP)
201
O43323
Desert hedgehog protein (DHH) (HHG-3) [Cleaved into: Desert hedgehog protein N-product; Desert hedgehog protein C-product]
396
Q9UBT3
Dickkopf-related protein 4 (Dickkopf-4) (Dkk-4) (hDkk-4) [Cleaved into: Dickkopf-related protein 4 short form]
224
O94769
Extracellular matrix protein 2 (Matrix glycoprotein SC1/ECM2)
699
Q9UM22
Mammalian ependymin-related protein 1 (MERP-1) (Upregulated in colorectal cancer gene 1 protein)
224
Q75N90
Fibrillin-3
2,809
Q9UGM5
Fetuin-B (Gugu) (IRL685) (16G2)
382
P10767
Fibroblast growth factor 6 (FGF-6) (Heparin-binding growth factor 6) (HBGF-6) (HST-2)
208
P21781
Keratinocyte growth factor (KGF) (Fibroblast growth factor 7) (FGF-7) (Heparin-binding growth factor 7) (HBGF-7)
194
O14793
Growth/differentiation factor 8 (GDF-8) (Myostatin)
375
P09681
Gastric inhibitory polypeptide (GIP) (Glucose-dependent insulinotropic polypeptide)
153
Q86YW7
Glycoprotein hormone beta-5 (Thyrostimulin subunit beta)

```
130
P51124
Granzyme M (EC 3.4.21.-) (Met-ase) (Natural killer cell granular protease) (HU-Met-1) (Met-1 serine protease)
257
P07492
Gastrin-releasing peptide (GRP) [Cleaved into: Neuromedin-C (GRP-10)]
148
Q92743
Serine protease HTRA1 (EC 3.4.21.-) (L56) (Serine protease 11)
480
P05014
Interferon alpha-4 (Interferon alpha-4B) (Interferon alpha-M1) (Interferon alpha-76)
189
P01569
Interferon alpha-5 (Interferon alpha-G) (LeIF G) (Interferon alpha-61)
189
P01567
Interferon alpha-7 (Interferon alpha-J1) (IFN-alpha-J1) (Interferon alpha-J) (LeIF J)
189
P27352
Gastric intrinsic factor (Intrinsic factor) (INF) (IF)
417
Q6WRI0
Immunoglobulin superfamily member 10 (Calvaria mechanical force protein 608) (CMF608)
2,623
Q9UHA7
Interleukin-1 family member 6 (IL-1F6) (Interleukin-1 epsilon) (IL-1 epsilon) (FIL1 epsilon)
158
Q14213
Interleukin-27 subunit beta (IL-27 subunit beta) (IL-27B) (Epstein-Barr virus-induced gene 3 protein) (EBV-induced gene 3 protein)
229
O95760
Interleukin-33 (IL-33) (Interleukin-1 family member 11) (IL-1F11) (Nuclear factor from high endothelial venules) (NF-HEV)
270
Q01113
Interleukin-9 receptor (IL-9R) (CD antigen CD129)
521
P15248
Interleukin-9 (IL-9) (T-cell growth factor P40) (P40 cytokine)
144
P09529
Inhibin beta B chain (Activin beta-B chain)
407
P20155
Serine protease inhibitor Kazal-type 2 (Acrosin-trypsin inhibitor) (HUSI-II)
84
A3KMH1
Uncharacterized protein KIAA0564
1,905
Q8N6L1
Keratinocyte-associated protein 2 (KCP-2)
162
P25391
Laminin subunit alpha-1 (Laminin A chain)
3,075
O14960
Leukocyte cell-derived chemotaxin-2 (hLECT2)
151
P07098
Gastric triacylglycerol lipase (Gastric lipase) (GL) (EC 3.1.1.3)
398
P54317
Pancreatic lipase-related protein 2 (PL-RP2) (EC 3.1.1.3)
469
Q96II8
Leucine-rich repeat and calponin homology domain-containing protein 3
777
Q9Y2E5
Epididymis-specific alpha-mannosidase (EC 3.2.1.24) (Mannosidase alpha class 2B member 2)
1,009
P20382
Pro-MCH [Cleaved into: Neuropeptide-glycine-glutamic acid (Neuropeptide G-E) (NGE); Neuropeptide-glutamic acid-isoleucine (Neuropeptide E-I) (NEI); Melanin-concentrating hormone (MCH)]
165
Q13361
Microfibrillar-associated protein 5 (MFAP-5) (Microfibril-associated glycoprotein 2) (MAGP-2) (MP25)
173
P03971
Muellerian-inhibiting factor (MIS) (Anti-Muellerian hormone) (AMH) (Muellerian-inhibiting substance)
```

560
P09238
Stromelysin-2 (SL-2) (EC 3.4.24.22) (Matrix metalloproteinase-10) (MMP-10) (Transin-2)
476
Q9ULZ9
Matrix metalloproteinase-17 (MMP-17) (EC 3.4.24.-) (Membrane-type matrix metalloproteinase 4) (MT-MMP 4) (Membrane-type-4 matrix metalloproteinase) (MT4-MMP)
606
O60882
Matrix metalloproteinase-20 (MMP-20) (EC 3.4.24.-) (Enamel metalloproteinase) (Enamelysin)
483
Q8N119
Matrix metalloproteinase-21 (MMP-21) (EC 3.4.24.-)
569
Q9H8L6
Multimerin-2 (EMILIN-3) (Elastin microfibril interface located protein 3) (Elastin microfibril interfacer 3) (EndoGlyx-1 p125/p140 subunit)
949
P12872
Promotilin [Cleaved into: Motilin; Motilin-associated peptide (MAP)]
115
Q8TAX7
Mucin-7 (MUC-7) (Salivary mucin-7) (Apo-MG2)
377
Q92832
Protein kinase C-binding protein NELL1 (NEL-like protein 1) (Nel-related protein 1)
810
Q99435
Protein kinase C-binding protein NELL2 (NEL-like protein 2) (Nel-related protein 2)
816
P56730
Neurotrypsin (EC 3.4.21.-) (Serine protease 12) (Motopsin) (Leydin)
875
Q99574
Neuroserpin (Serpin I1) (Protease inhibitor 12)
410
Q14112
Nidogen-2 (NID-2) (Osteonidogen)
1,375
P48745
Protein NOV homolog (NovH) (Nephroblastoma overexpressed gene protein homolog)
357
P34130
Neurotrophin-4 (NT-4) (Neurotrophic factor 4) (Neurotrophin-5) (NT-5)
210
Q9UNK4
Group IID secretory phospholipase A2 (GIID sPLA2) (EC 3.1.1.4) (Phosphatidylcholine 2-acylhydrolase GIID) (PLA2IID) (sPLA(2)-IID) (Secretory-type PLA, stroma-associated homolog)
145
O15496
Group 10 secretory phospholipase A2 (EC 3.1.1.4) (Group X secretory phospholipase A2) (GX sPLA2) (Phosphatidylcholine 2-acylhydrolase GX) (sPLA2-X)
165
Q9BXP8
Pappalysin-2 (EC 3.4.24.-) (Pregnancy-associated plasma protein A2) (PAPP-A2) (Pregnancy-associated plasma protein E1) (PAPP-E)
1,791
P22079
Lactoperoxidase (LPO) (EC 1.11.1.7) (Salivary peroxidase) (SPO)
712
Q96FX8
p53 apoptosis effector related to PMP-22 (Keratinocyte-associated protein 1) (KCP-1) (P53-induced protein PIGPC1) (Transmembrane protein THW)
193
Q9HBJ0
Placenta-specific protein 1
212
Q15166
Serum paraoxonase/lactonase 3 (EC 3.1.1.-)
354
P51888
Prolargin (Proline-arginine-rich end leucine-rich repeat protein)
382
P13521
Secretogranin-2 (Secretogranin II) (SgII) (Chromogranin-C) [Cleaved into: Secretoneurin (SN)]
617
O76038
Secretagogin
276
Q13214
Semaphorin-3B (Semaphorin V) (Sema V) (Sema A(V))
749

-continued

P61278
Somatostatin (Growth hormone release-inhibiting factor) [Cleaved into: Somatostatin-28; Somatostatin-14]
116
O76061
Stanniocalcin-2 (STC-2) (Stanniocalcin-related protein) (STCRP) (STC-related protein)
302
P20061
Transcobalamin-1 (TC-1) (Transcobalamin I) (TC I) (TCI)
433
Q03403
Trefoil factor 2 (Spasmolytic polypeptide) (SP) (Spasmolysin)
129
Q08629
Testican-1 (Protein SPOCK)
439
Q96A98
Tuberoinfundibular peptide of 39 residues (TIP39) (Parathyroid hormone 2)
100
Q9Y6L7
Tolloid-like protein 2 (EC 3.4.24.-)
1,015
P07478
Trypsin-2 (EC 3.4.21.4) (Trypsin II) (Anionic trypsinogen) (Serine protease 2)
247
P55089
Urocortin
124
O96014
Protein Wnt-11
354
P09544
Protein Wnt-2 (Int-1-related protein) (IRP protein)
360
O00755
Protein Wnt-7a
349
Q93098
Protein Wnt-8b
351
P78423
Fractalkine (C-X3-C motif chemokine 1) (Neurotactin) (CX3C membrane-anchored chemokine) (Small-inducible cytokine D1) [Cleaved into: Processed fractalkine]
397
Q96A84
EMI domain-containing protein 1 (Emilin and multimerin domain-containing protein 1) (Emu1)
441
Q6UXA7
Uncharacterized protein C6orf15 (Protein STG)
325
Q9Y6Z7
Collectin-10 (Collectin liver protein 1) (CL-L1) (Collectin-34)
277
Q6UWX4
HHIP-like protein 2
724
Q8WWZ8
Oncoprotein-induced transcript 3 protein (Liver-specific zona pellucida domain-containing protein)
545
O43692
Peptidase inhibitor 15 (Cysteine-rich secretory protein 8) (CRISP-8) (25 kDa trypsin inhibitor) (p25TI) (SugarCrisp)
258
Q96NZ9
Proline-rich acidic protein 1 (Uterine-specific proline-rich acidic protein)
151
Q96DX4
RING finger and SPRY domain-containing protein 1
576
Q8IYP2
Trypsin-X3 (EC 3.4.21.4)
241
Q5FVE4
Long-chain-fatty-acid--CoA ligase ACSBG2 (EC 6.2.1.3) (Acyl-CoA synthetase bubblegum family member 2) (Bubblegum-related protein) (PRTD-NY3)
666
Q9C0J1
UDP-GlcNAc:betaGal beta-1,3-N-acetylglucosaminyltransferase 4 (Beta-1,3-N-acetylglucosaminyltransferase-4) (Beta3Gn-T4) (BGnT-4) (EC 2.4.1.-)
378
Q9P1Z2
Calcium-binding and coiled-coil domain-containing protein 1 (Calphoglin) (Sarcoma antigen NY-SAR-3) (Coiled-coil coactivator protein)

-continued

691
Q5MY95
Ectonucleoside triphosphate diphosphohydrolase 8 (E-NTPDase 8) (NTPDase 8) (NTPDase8) (EC 3.6.1.5)
495
Q86WN1
FCH and double SH3 domains protein 1
690
Q7Z4V5
Hepatoma-derived growth factor-related protein 2 (HRP-2) (Hepatoma-derived growth factor 2)
671
P29459
Interleukin-12 subunit alpha (IL-12A) (IL-12 subunit p35) (Cytotoxic lymphocyte maturation factor 35 kDa subunit) (CLMF p35) (NK cell stimulatory factor chain 1) (NKSF1)
219
Q6UXG2
UPF0577 protein KIAA1324 (Estrogen-induced gene 121 protein)
1,013
Q6UVY6
DBH-like monooxygenase protein 1 (EC 1.14.17.-) (Monooxygenase X)
613
Q685J3
Mucin-17 (MUC-17) (Small intestinal mucin-3) (MUC-3)
4,493
Q8WWB7
Lysosomal protein NCU-G1
406
Q7Z4N8
Prolyl 4-hydroxylase subunit alpha-3 (EC 1.14.11.2) (4-PH alpha-3) (Procollagen-proline,2-oxoglutarate-4-dioxygenase subunit alpha-3)
544
Q75T13
GPI inositol-deacylase (EC 3.1.-.-) (Post-GPI attachment to proteins factor 1) (hPGAP1)
922
Q6UXB8
Peptidase inhibitor 16 (Cysteine-rich secretory protein 9) (CRISP-9) (PSP94-binding protein)
463
Q96NY8
Poliovirus receptor-related protein 4 (Nectin-4) (Ig superfamily receptor LNIR) [Cleaved into: Processed poliovirus receptor-related protein 4]
510
Q8IZD6
Solute carrier family 22 member 15 (Fly-like putative transporter 1) (Flipt 1)
547
Q6UX04
Peptidyl-prolyl cis-trans isomerase SDCCAG10 (EC 5.2.1.8) (Serologically defined colon cancer antigen 10) (Antigen NY-CO-10)
472
Q9BTV4
Transmembrane protein 43 (Protein LUMA)
400
Q9UKU9
Angiopoietin-related protein 2 (Angiopoietin-like 2)
493
Q8NI99
Angiopoietin-related protein 6 (Angiopoietin-like 6) (Angiopoietin-related growth factor) (Angiopoietin-related protein 5)
470
Q6UWY0
Arylsulfatase K (ASK) (EC 3.1.6.-) (Telethon sulfatase)
536
Q9H1Z8
Augurin (Esophageal cancer-related gene 4 protein)
148
Q9GZN4
Brain-specific serine protease 4 (BSSP-4) (EC 3.4.21.-) (Serine protease 22) (Serine protease 26) (Tryptase epsilon)
317
P0C862
Complement C1q tumor necrosis factor-related protein 9
333
Q9BUN1
Uncharacterized protein C1orf56
341
Q6UW01
Cerebellin-3
205
Q9NTU7
Cerebellin-4 (Cerebellin-like glycoprotein 1)
201
Q6UWE3
Colipase-like protein C6orf126
100
Q6UW78
Uncharacterized protein C11orf83

93
Q6UX73
Uncharacterized protein C16orf89
402
Q8N436
Carboxypeptidase-like protein X2
756
Q9H4G1
Cystatin-9-like
147
Q9NRR1
Cytokine-like protein 1 (Protein C17)
136
Q8N688
Beta-defensin 123 (Defensin, beta 123) (Beta-defensin 23) (DEFB-23)
67
Q7Z7B7
Beta-defensin 132 (Defensin, beta 132) (Beta-defensin 32) (BD-32) (Defensin HEL-75) (DEFB-32)
95
Q6UX07
Dehydrogenase/reductase SDR family member 13 (EC 1.1.-.-)
377
Q9UBU2
Dickkopf-related protein 2 (Dickkopf-2) (Dkk-2) (hDkk-2)
259
Q9UK85
Dickkopf-like protein 1 (Protein soggy-1) (SGY-1) (Cancer/testis antigen 34) (CT34)
242
P56851
Epididymal secretory protein E3-beta (Human epididymis-specific protein 3-beta) (HE3 beta)
147
Q969Y0
Protein FAM55C
559
Q6UWF7
Protein FAM55D
544
O60258
Fibroblast growth factor 17 (FGF-17)
216
Q9HCT0
Fibroblast growth factor 22 (FGF-22)
170
Q9BYJ0
Fibroblast growth factor-binding protein 2 (FGF-binding protein 2) (FGF-BP2) (FGFBP-2) (37 kDa killer-specific secretory protein) (Ksp37) (HBp17-related protein) (HBp17-RP)
223
Q9NR23
Growth/differentiation factor 3 (GDF-3)
364
Q6UWM5
GLIPR1-like protein 1
242
Q96S86
Hyaluronan and proteoglycan link protein 3
360
Q9UHF5
Interleukin-17B (IL-17B) (Cytokine-like protein Zcyto7) (Neuronal interleukin-17-related factor) (Interleukin-20) (IL-20)
180
Q9P0M4
Interleukin-17C (IL-17C) (Cytokine CX2)
197
Q8TAD2
Interleukin-17D (IL-17D) (Interleukin-27) (IL-27)
202
Q6UWN8
Serine protease inhibitor Kazal-type 6
80
P58062
Serine protease inhibitor Kazal-type 7 (Esophagus cancer-related gene 2 protein) (ECRG-2)
85
Q53RY4
Keratinocyte-associated protein 3 (KCP-3)
240
Q6UWQ5
Lysozyme-like protein 1 (EC 3.2.1.17)
148
Q9H239
Matrix metalloproteinase-28 (MMP-28) (EC 3.4.24.-) (Epilysin)

520
Q6UXI9
Nephronectin (Preosteoblast EGF-like repeat protein with MAM domain) (Protein EGFL6-like)
565
O95158
Neurexophilin-4
308
Q6UWY5
Olfactomedin-like protein 1
402
Q68BL7
Olfactomedin-like protein 2A (Photomedin-1)
652
Q9BQR3
Serine protease 27 (EC 3.4.21.-) (Marapsin) (Pancreasin) (Channel-activating protease 2) (CAPH2)
290
Q8WXD2
Secretogranin-3 (Secretogranin III) (SgIII)
468
O75711
Scrapie-responsive protein 1 (ScRG-1)
98
O95025
Semaphorin-3D
777
Q96PL1
Secretoglobin family 3A member 2 (Uteroglobin-related protein 1) (Pneumo secretory protein 1) (PnSP-1)
93
O60235
Transmembrane protease, serine 11D (EC 3.4.21.-) (Airway trypsin-like protease) [Cleaved into: Transmembrane protease, serine 11D non-catalytic chain; Transmembrane protease, serine 11D catalytic chain]
418
Q7Z5L0
Vitelline membrane outer layer protein 1 homolog
202
Q8WWY7
WAP four-disulfide core domain protein 12 (Putative protease inhibitor WAP12) (Whey acidic protein 2)
111
O14905
Protein Wnt-9b (Wnt-15) (Wnt-14b)
357
Q96DA0
Zymogen granule protein 16 homolog B
208
Q9UKQ2
Disintegrin and metalloproteinase domain-containing protein 28 (ADAM 28) (EC 3.4.24.-) (Metalloproteinase-like, disintegrin-like, and cysteine-rich protein L) (MDC-L) (Epididymial metalloproteinase-like, disintegrin-like, and cysteine-rich protein II) (eMDC II)
775
Q9BPW4
Apolipoprotein L4 (Apolipoprotein L-IV) (ApoL-IV)
351
Q92485
Acid sphingomyelinase-like phosphodiesterase 3b (ASM-like phosphodiesterase 3b) (EC 3.1.4.-)
455
O95450
A disintegrin and metalloproteinase with thrombospondin motifs 2 (ADAMTS-2) (ADAM-TS 2) (ADAM-TS2) (EC 3.4.24.14) (Procollagen I/II amino propeptide-processing enzyme) (Procollagen I N-proteinase) (PC I-NP) (Procollagen N-endopeptidase) (pNPI)
1,211
A6NMY6
Putative annexin A2-like protein (Annexin A2 pseudogene 2) (Lipocortin II pseudogene)
339
O95393
Bone morphogenetic protein 10 (BMP-10)
424
Q8NFQ6
Bactericidal/permeability-increasing protein-like 2
507
Q9BXJ3
Complement C1q tumor necrosis factor-related protein 4
329
Q8WWF1
Uncharacterized protein C1orf54
131
Q8N4T0
Carboxypeptidase A6 (EC 3.4.17.1) (Carboxypeptidase B)
437
Q99731
C-C motif chemokine 19 (Small-inducible cytokine A19) (Macrophage inflammatory protein 3 beta) (MIP-3-beta) (EBI1-ligand chemokine) (ELC) (Beta chemokine exodus-3) (CK beta-11)

-continued

98
O15444
C-C motif chemokine 25 (Small-inducible cytokine A25) (Thymus-expressed chemokine) (Chemokine TECK)
150
Q86SI9
Protein CEI (Coordinated expression to IRXA2 protein)
138
P08218
Chymotrypsin-like elastase family member 2B (EC 3.4.21.71) (Elastase-2B)
269
Q86T20
Uncharacterized protein C6orf1 (Protein LBH)
159
Q96L11
Uncharacterized protein C7orf34 (MSSP-binding protein CTM-1)
122
A6NKQ9
Choriogonadotropin subunit beta variant 1
187
Q6ZRZ4
Uncharacterized protein C9orf47
202
P27658
Collagen alpha-1(VIII) chain (Endothelial collagen)
744
Q8IYD9
Uncharacterized protein C18orf54
372
Q9H114
Cystatin-like 1 (RCET11)
145
Q9Y426
C2 domain-containing protein 2
696
Q96HY6
DDRGK domain-containing protein 1
314
O43854
EGF-like repeat and discoidin I-like domain-containing protein 3 (Developmentally-regulated endothelial cell locus 1 protein) (Integrin-binding protein DEL1)
480
Q96A83
Collagen alpha-1(XXVI) chain (EMI domain-containing protein 2) (Emilin and multimerin domain-containing protein 2) (Emu2)
441
Q8N3H0
Protein FAM19A2 (Chemokine-like protein TAFA-2)
131
Q9C0B6
Protein FAM5B (BMP/retinoic acid-inducible neural-specific protein 2) (DBCCR1-like protein 2)
783
P12034
Fibroblast growth factor 5 (FGF-5) (Heparin-binding growth factor 5) (HBGF-5) (Smag-82)
268
P83110
Probable serine protease HTRA3 (EC 3.4.21.-) (High-temperature requirement factor A3) (Pregnancy-related serine protease)
453
Q9NZH7
Interleukin-1 family member 8 (IL-1F8) (Interleukin-1 eta) (IL-1 eta) (FIL1 eta) (Interleukin-1 homolog 2) (IL-1H2)
164
O60575
Serine protease inhibitor Kazal-type 4 (Peptide PEC-60 homolog)
86
Q6ISS4
Leukocyte-associated immunoglobulin-like receptor 2 (LAIR-2) (CD antigen CD306)
152
Q969E1
Liver-expressed antimicrobial peptide 2 (LEAP-2)
77
Q08397
Lysyl oxidase homolog 1 (EC 1.4.3.-) (Lysyl oxidase-like protein 1) (LOL)
574
Q9Y4K0
Lysyl oxidase homolog 2 (EC 1.4.3.-) (Lysyl oxidase-like protein 2) (Lysyl oxidase-related protein 2) (Lysyl oxidase-related protein WS9-14)
774
P59827
Long palate, lung and nasal epithelium carcinoma-associated protein 4 (Ligand-binding protein RY2G5)
614
Q86SG7
Lysozyme g-like protein 2 (EC 3.2.1.-)

212
Q9ULC0
Endomucin (Endomucin-2) (Mucin-14) (MUC-14) (Gastric cancer antigen Ga34)
261
Q8NG41
Neuropeptide B (Preproprotein L7) (hPPL7) [Cleaved into: Neuropeptide B-23 (NPB23) (hL7); Neuropeptide B-29 (NPB29) (hL7C)]
125
Q8WWG1
Pro-neuregulin-4, membrane-bound isoform (Pro-NRG4) [Cleaved into: Neuregulin-4 (NRG-4)]
115
Q8NHW6
Otospiralin
89
P39877
Calcium-dependent phospholipase A2 (EC 3.1.1.4) (Phosphatidylcholine 2-acylhydrolase) (PLA2-10) (Group V phospholipase A2)
138
Q8NB37
Parkinson disease 7 domain-containing protein 1
220
Q15198
Platelet-derived growth factor receptor-like protein (PDGF receptor beta-like tumor suppressor)
375
Q9UIG4
Psoriasis susceptibility 1 candidate gene 2 protein (SPR1 protein)
136
P49223
Kunitz-type protease inhibitor 3 (HKIB9)
89
Q4W5P6
Protein TMEM155
130
Q8N2E6
Prosalusin (Torsin-2A) (Torsin family 2 member A) [Cleaved into: Salusin-alpha; Salusin-beta]
242
A6NCI4
von Willebrand factor A domain-containing protein 3A
1,184
Q8IUB3
Protein WFDC10B
73
Q8IUA0
WAP four-disulfide core domain protein 8 (Putative protease inhibitor WAP8)
241
Q9H1J7
Protein Wnt-5b
359
P56706
Protein Wnt-7b
349
Q6X784
Zona pellucida-binding protein 2 (ZPBP-like protein)
338
Q7L8J4
SH3 domain-binding protein 5-like
393
Q9H6B4
Adipocyte adhesion molecule (Coxsackie- and adenovirus receptor-like membrane protein) (CAR-like membrane protein)
373
Q96CM8
Acyl-CoA synthetase family member 2, mitochondrial (EC 6.2.1.-)
615
Q8NCW5
Apolipoprotein A-I-binding protein (AI-BP) (YjeF N-terminal domain-containing protein 1)
288
Q4VNC1
Probable cation-transporting ATPase 13A4 (EC 3.6.3.-) (P5-ATPase isoform 4)
1,196
Q6UXS9
Inactive caspase-12 (CASP-12)
341
A4D0V7
Uncharacterized protein C7orf58
1,026
Q2UY09
Collagen alpha-1(XXVIII) chain
1,125
Q8IXL6
Dentin matrix protein 4 (DMP-4) (Protein FAM20C)
570

-continued

Q96DN0
Endoplasmic reticulum resident protein ERp27
273
Q6UWW8
Carboxylesterase 3 (EC 3.1.1.1) (Liver carboxylesterase 31 homolog)
571
Q9BVA6
Adenosine monophosphate-protein transferase FICD (EC 2.7.7.n1) (AMPylator FICD) (FIC domain-containing protein) (Huntingtin-interacting protein E) (Huntingtin yeast partner E) (Huntingtin-interacting protein 13)
458
Q9UHW5
GPN-loop GTPase 3 (ATP-binding domain 1 family member C)
284
Q3KR37
GRAM domain-containing protein 1B
738
Q96D96
Voltage-gated hydrogen channel 1 (Hydrogen voltage-gated channel 1) (HV1) (Voltage sensor domain-only protein)
273
Q8NEV9
Interleukin-27 subunit alpha (IL-27 subunit alpha) (IL27-A) (p28)
243
Q2M1P5
Kinesin-like protein KIF7
1,343
Q9H3W5
Leucine-rich repeat neuronal protein 3 (Neuronal leucine-rich repeat protein 3) (NLRR-3)
708
Q659A1
NMDA receptor-regulated protein 2
982
Q9UHQ9
NADH-cytochrome b5 reductase 1 (b5R.1) (EC 1.6.2.2) (NAD(P)H:quinone oxidoreductase type 3 polypeptide A2) (Humb5R2)
305
Q8WU39
Proapoptotic caspase adapter protein (PACAP)
189
Q96FC7
Phytanoyl-CoA hydroxylase-interacting protein-like
376
Q9BS91
Probable UDP-sugar transporter protein SLC35A5 (Solute carrier family 35 member A5)
424
Q8WV83
Solute carrier family 35 member F5 (Hepatitis C virus NS5A-transactivated protein 3) (HCV NS5A-transactivated protein 3)
523
Q96PQ1
Sialic acid-binding Ig-like lectin 12 (Siglec-12) (Sialic acid-binding Ig-like lectin-like 1) (Siglec-L1)
595
Q96J42
Thioredoxin domain-containing protein 15
360
Q6UXN9
WD repeat-containing protein 82 (Swd2)
313
Q8IUX7
Adipocyte enhancer-binding protein 1 (AE-binding protein 1) (Aortic carboxypeptidase-like protein)
1,158
P82987
ADAMTS-like protein 3 (ADAMTSL-3) (Punctin-2)
1,691
Q76M96
Coiled-coil domain-containing protein 80 (Down-regulated by oncogenes protein 1)
950
Q8TC92
Ecto-NOX disulfide-thiol exchanger 1 (Constitutive Ecto-NOX) (cNOX) (Candidate growth-related and time keeping constitutive hydroquinone [NADH]oxidase) (cCNOX) (Cell proliferation-inducing gene 38 protein) [Includes: Hydroquinone [NADH]oxidase (EC 1.-.-.-); Protein disulfide-thiol oxidoreductase (EC 1.-.-.-)]
643
Q4ZHG4
Fibronectin type III domain-containing protein 1 (Expressed in synovial lining protein) (Activation-associated cDNA protein)
1,888
Q17R60
Interphotoreceptor matrix proteoglycan 1 (Interphotoreceptor matrix proteoglycan of 150 kDa) (IPM-150) (Sialoprotein associated with cones and rods)
797
O95965
Integrin beta-like protein 1 (Ten integrin EGF-like repeat domain-containing protein) (Osteoblast-specific cysteine-rich protein)
494
Q8WWY8

-continued

Lipase member H (EC 3.1.1.-) (Membrane-associated phosphatidic acid-selective phospholipase A1-alpha) (mPA-PLA1 alpha) (LPD lipase-related protein) (Phospholipase A1 member B)
451
Q7Z5P9
Mucin-19 (MUC-19)
6,254
O43897
Tolloid-like protein 1 (EC 3.4.24.-)
1,013
Q96NZ8
WAP, kazal, immunoglobulin, kunitz and NTR domain-containing protein 1 (WAP, follistatin, immunoglobulin, kunitz and NTR domain-containing protein) (Growth and differentiation factor-associated serum protein 2) (GASP-2) (hGASP-2)
548
Q9BUJ0
Abhydrolase domain-containing protein 14A (EC 3.-.-.-)
271
Q9BXJ7
Protein amnionless
453
Q6UX02
Ankyrin repeat domain-containing protein 36
163
Q6UXY1
Brain-specific angiogenesis inhibitor 1-associated protein 2-like protein 2 (BAI1-associated protein 2-like protein 2)
529
Q6UWJ8
CD164 sialomucin-like 2 protein
174
O75309
Cadherin-16 (Kidney-specific cadherin) (Ksp-cadherin)
829
Q9H159
Cadherin-19
772
Q8IUK8
Cerebellin-2
224
Q9NPL8
Transmembrane protein C3orf1 (Protein M5-14)
285
Q96G28
Coiled-coil domain-containing protein 104
342
Q9NU53
Uncharacterized protein C6orf72
330
Q96F05
Uncharacterized protein C11orf24 (Protein DM4E3)
449
Q4KMG9
Uncharacterized protein C12orf59
183
Q2HXU8
C-type lectin domain family 12 member B (Macrophage antigen H)
276
Q8NC01
C-type lectin domain family 1 member A (C-type lectin-like receptor 1) (CLEC-1)
280
O75596
C-type lectin domain family 3 member A (C-type lectin superfamily member 1) (Cartilage-derived C-type lectin)
197
Q9ULY5
C-type lectin domain family 4 member E (C-type lectin superfamily member 9) (Macrophage-inducible C-type lectin)
219
Q6UXB4
C-type lectin domain family 4 member G
293
P56750
Claudin-17
224
Q9NPA0
UPF0480 protein C15orf24
242
P83436
Conserved oligomeric Golgi complex subunit 7 (COG complex subunit 7) (Component of oligomeric Golgi complex 7)
770
Q9H0I2
Uncharacterized protein C16orf48
346

Q6UWD8
Transmembrane protein C16orf54
224
Q9HCS2
Cytochrome P450 4F12 (EC 1.14.14.1) (CYPIVF12)
524
Q8N118
Cytochrome P450 4X1 (EC 1.14.14.1) (CYPIVX1)
509
Q86W10
Cytochrome P450 4Z1 (EC 1.14.14.1) (CYPIVZ1)
505
Q8IUH2
Protein CREG2
290
Q9UBS3
DnaJ homolog subfamily B member 9 (Microvascular endothelial differentiation gene 1 protein) (Mdg-1)
223
Q9H4B8
Dipeptidase 3 (EC 3.4.13.19)
488
Q8TBP5
Membrane protein FAM174A (Transmembrane protein 157) (Hepatitis C virus NS5A-transactivated protein 6) (HCV NS5A-transactivated protein 6)
190
Q7Z5A8
Protein FAM19A3 (Chemokine-like protein TAFA-3)
133
Q96LR4
Protein FAM19A4 (Chemokine-like protein TAFA-4)
140
O75063
Protein FAM20B
409
Q8N539
Fibrinogen C domain-containing protein 1
461
Q9NYL4
FK506-binding protein 11 (EC 5.2.1.8) (Peptidyl-prolyl cis-trans isomerase) (PPIase) (Rotamase) (19 kDa FK506-binding protein) (FKBP-19)
201
P59646
FXYD domain-containing ion transport regulator 4
89
O95390
Growth/differentiation factor 11 (GDF-11) (Bone morphogenetic protein 11)
407
Q9HCC8
Glycerophosphodiester phosphodiesterase domain-containing protein 2 (EC 3.1.-.-) (Glycerophosphodiester phosphodiesterase 3)
(Osteoblast differentiation promoting factor)
539
Q9H3K2
Growth hormone-inducible transmembrane protein (Dermal papilla-derived protein 2) (Transmembrane BAX inhibitor motif-containing protein 5)
345
Q9H9Y4
GPN-loop GTPase 2 (ATP-binding domain 1 family member B)
310
Q9Y278
Heparan sulfate glucosamine 3-O-sulfotransferase 2 (EC 2.8.2.29) (Heparan sulfate D-glucosaminyl 3-O-sulfotransferase 2) (Heparan sulfate
3-O-sulfotransferase 2) (h3-OST-2)
367
O43736
Integral membrane protein 2A (E25 protein)
263
Q6UW63
KDEL motif-containing protein 1 (Endoplasmic reticulum resident protein 58) (ER protein 58)
502
Q15012
Lysosomal-associated transmembrane protein 4A (Golgi 4-transmembrane spanning transporter MTP)
233
Q6UWM7
Lactase-like protein (Klotho/lactase-phlorizin hydrolase-related protein)
567
O75829
Chondromodulin-1 (Chondromodulin-I) (ChM-I) (Leukocyte cell-derived chemotaxin 1) [Cleaved into: Chondrosurfactant protein (CH-SP)]
334
O95214
Leptin receptor overlapping transcript-like 1
131
Q86YC3
Leucine-rich repeat-containing protein 33

-continued

692
Q9H8J5
MANSC domain-containing protein 1 (Loss of heterozygosity 12 chromosomal region 3 protein)
431
Q7Z553
MAM domain-containing glycosylphosphatidylinositol anchor protein 2 (MAM domain-containing protein 1)
956
Q9H1U4
Multiple epidermal growth factor-like domains 9 (EGF-like domain-containing protein 5) (Multiple EGF-like domain protein 5)
602
Q14696
Mesoderm development candidate 2 (Renal carcinoma antigen NY-REN-61)
234
Q9H8H3
Methyltransferase-like protein 7A (EC 2.1.1.-) (Protein AAM-B)
244
Q9UJH8
Meteorin
293
Q6N075
Major facilitator superfamily domain-containing protein 5
450
O60487
Myelin protein zero-like protein 2 (Epithelial V-like antigen 1)
215
Q9BV20
Methylthioribose-1-phosphate isomerase (MTR-1-P isomerase) (M1Pi) (EC 5.3.1.23) (S-methyl-5-thioribose-1-phosphate isomerase) (Translation initiation factor eIF-2B subunit alpha/beta/delta-like protein)
369
Q9H7X0
N-acetyltransferase 15 (EC 2.3.1.-)
242
Q7Z3B1
Neuronal growth regulator 1
354
Q9P121
Neurotrimin (hNT)
344
Q8NGF6
Olfactory receptor 10W1 (Olfactory receptor OR11-236)
305
Q6UWI2
Protein PARM-1
310
O15018
PDZ domain-containing protein 2 (PDZ domain-containing protein 3) (Activated in prostate cancer protein) [Cleaved into: Processed PDZ domain-containing protein 2]
2,839
Q96S96
Phosphatidylethanolamine-binding protein 4 (PEBP-4) (hPEBP4) (Protein cousin-of-RKIP 1)
227
Q8TDX9
Polycystic kidney disease protein 1-like 1 (Polycystin-1L1) (PC1-like 1 protein)
2,849
Q9NRZ5
1-acyl-sn-glycerol-3-phosphate acyltransferase delta (EC 2.3.1.51) (1-acylglycerol-3-phosphate O-acyltransferase 4) (1-AGP acyltransferase 4) (1-AGPAT 4) (Lysophosphatidic acid acyltransferase delta) (LPAAT-delta)
378
Q9Y2Y8
Proteoglycan 3 (Eosinophil major basic protein homolog) (Prepro-major basic protein homolog) (Prepro-MBPH)
225
Q8NBN7
Retinol dehydrogenase 13 (EC 1.1.1.-)
331
Q8NC24
RELT-like protein 2
303
Q7Z769
Solute carrier family 35 member E3 (Bladder cancer overexpressed gene 1 protein)
313
Q9NUM3
Zinc transporter ZIP9 (Zrt- and Irt-like protein 9) (ZIP-9) (Solute carrier family 39 member 9)
307
Q8TDM5
Sperm acrosome membrane-associated protein 4 (Sperm acrosomal membrane-associated protein 14)
124
Q6UXD5
Seizure 6-like protein 2
910

-continued

Q14563
Semaphorin-3A (Semaphorin III) (Sema III)
771
Q9C0C4
Semaphorin-4C
833
O95562
Vesicle transport protein SFT2B (SFT2 domain-containing protein 2)
160
Q6UWI4
Protein shisa-2 homolog (Transmembrane protein 46)
295
Q96DD7
Protein shisa-4 (Transmembrane protein 58)
197
Q9NSC7
Alpha-N-acetylgalactosaminide alpha-2,6-sialyltransferase 1 (EC 2.4.99.3) (GalNAc alpha-2,6-sialyltransferase I) (ST6GalNAc I) (Sialyltransferase 7A)
600
Q8NDV1
Alpha-N-acetylgalactosaminide alpha-2,6-sialyltransferase 3 (EC 2.4.99.-) (GalNAc alpha-2,6-sialyltransferase III) (ST6GalNAc III) (Sialyltransferase 7C) (STY)
305
O43760
Synaptogyrin-2 (Cellugyrin)
224
P61009
Signal peptidase complex subunit 3 (EC 3.4.-.-) (Microsomal signal peptidase 23 kDa subunit) (SPase 22 kDa subunit) (SPC22/23)
180
Q6UW49
Sperm equatorial segment protein 1 (SP-ESP) (Equatorial segment protein) (ESP) (Glycosylated 38 kDa sperm protein C-7/8)
350
Q53R12
Transmembrane 4 L6 family member 20
229
Q6UX40
Transmembrane protein 107
140
Q96AN5
Transmembrane protein 143
459
Q8NBL3
Transmembrane protein 178
297
Q6UW68
Transmembrane protein 205
189
Q96HV5
Transmembrane protein 41A
264
O95807
Transmembrane protein 50A (Small membrane protein 1)
157
P56557
Transmembrane protein 50B (HCV p7-trans-regulated protein 3)
158
Q9Y3Q3
Transmembrane emp24 domain-containing protein 3 (Membrane protein p24B)
217
Q9Y3A6
Transmembrane emp24 domain-containing protein 5
229
Q9HBJ8
Collectrin (Transmembrane protein 27)
222
Q6UXU6
Transmembrane protein 92
159
Q3KNT9
Transmembrane protein 95
176
Q9NQ34
Transmembrane protein 9B
198
Q9UKU6
Thyrotropin-releasing hormone-degrading ectoenzyme (TRH-degrading ectoenzyme) (TRH-DE) (EC 3.4.19.6) (TRH-specific aminopeptidase) (Thyroliberinase) (Pyroglutamyl-peptidase II) (PAP-II)
1,024
O95859

-continued

Tetraspanin-12 (Tspan-12) (Transmembrane 4 superfamily member 12) (Tetraspan NET-2)
305
O95857
Tetraspanin-13 (Tspan-13) (Transmembrane 4 superfamily member 13) (Tetraspan NET-6)
204
O95858
Tetraspanin-15 (Tspan-15) (Transmembrane 4 superfamily member 15) (Tetraspan NET-7)
294
Q9H6L2
UPF0513 transmembrane protein
316
O95847
Mitochondrial uncoupling protein 4 (UCP 4) (Solute carrier family 25 member 27)
323
Q6UX27
V-set and transmembrane domain-containing protein 1
236
Q6UX98
Probable palmitoyltransferase ZDHHC24 (EC 2.3.1.-) (Zinc finger DHHC domain-containing protein 24) (DHHC-24)
284
P60852
Zona pellucida sperm-binding protein 1 (Zona pellucida glycoprotein 1) (Zp-1) [Cleaved into: Processed zona pellucida sperm-binding protein 1]
638
Q05996
Zona pellucida sperm-binding protein 2 (Zona pellucida glycoprotein ZP2) (Zona pellucida protein A) [Cleaved into: Processed zona pellucida sperm-binding protein 2]
745
Q12836
Zona pellucida sperm-binding protein 4 (Zona pellucida protein B) [Cleaved into: Processed zona pellucida sperm-binding protein 4]
540
Q86V24
Adiponectin receptor protein 2 (Progestin and adipoQ receptor family member II)
386
P55103
Inhibin beta C chain (Activin beta-C chain)
352
Q2TAL6
Brorin (Brain-specific chordin-like protein) (von Willebrand factor C domain-containing protein 2)
325
Q9NZP8
Complement C1r subcomponent-like protein (C1r-like protein) (C1r-LP) (EC 3.4.21.-) (C1r-like serine protease analog protein) (CLSPa)
487
Q49AH0
Cerebral dopamine neurotrophic factor (Conserved dopamine neurotrophic factor) (ARMET-like protein 1)
187
A6NMZ7
Collagen alpha-6(VI) chain
2,263
Q8IZJ3
C3 and PZP-like alpha-2-macroglobulin domain-containing protein 8
1,885
Q53RD9
Fibulin-7 (FIBL-7)
439
Q9ULI3
Protein HEG homolog 1
1,381
Q8NBM8
Prenylcysteine oxidase-like (EC 1.8.3.-)
494
Q53H76
Phospholipase A1 member A (EC 3.1.1.-) (Phosphatidylserine-specific phospholipase A1) (PS-PLA1)
456
P02812
Basic salivary proline-rich protein 2 (Salivary proline-rich protein) (Con1 glycoprotein) [Cleaved into: Basic proline-rich peptide IB-7; Basic proline-rich peptide IB-8c (Basic peptide P-F); Basic proline-rich peptide IB-4]
416
Q9NWH7
Spermatogenesis-associated protein 6
488
O60687
Sushi repeat-containing protein SRPX2
465
Q9GZX9
Twisted gastrulation protein homolog 1
223
Q96DN2
von Willebrand factor C and EGF domain-containing protein (HBV X protein up-regulated gene 11 protein) (HBxAg up-regulated gene 11 protein)
955

-continued

P41221
Protein Wnt-5a
380
Q8NEB7
Acrosin-binding protein (Proacrosin-binding protein sp32) (Cancer/testis antigen OY-TES-1) (Cancer/testis antigen 23) (CT23)
543
Q86TW2
Uncharacterized aarF domain-containing protein kinase 1 (EC 2.7.11.-)
530
Q99541
Adipophilin (Adipose differentiation-related protein) (ADRP)
437
Q5NDL2
Uncharacterized glycosyltransferase AER61 (EC 2.4.-.-)
527
Q9NP70
Ameloblastin
447
Q9H4A4
Aminopeptidase B (Ap-B) (EC 3.4.11.6) (Arginine aminopeptidase) (Arginyl aminopeptidase)
650
Q15389
Angiopoietin-1 (ANG-1)
498
Q9Y264
Angiopoietin-4 (ANG-4) (ANG-3)
503
Q5FYB1
Arylsulfatase I (ASI) (EC 3.1.6.-)
569
Q92484
Acid sphingomyelinase-like phosphodiesterase 3a (ASM-like phosphodiesterase 3a) (EC 3.1.4.-)
453
Q6ZMM2
ADAMTS-like protein 5 (ADAMTSL-5) (Thrombospondin type-1 domain-containing protein 6)
471
Q8TE58
A disintegrin and metalloproteinase with thrombospondin motifs 15 (ADAMTS-15) (ADAM-TS 15) (ADAM-TS15) (EC 3.4.24.-)
950
Q8TE57
A disintegrin and metalloproteinase with thrombospondin motifs 16 (ADAMTS-16) (ADAM-TS 16) (ADAM-TS16) (EC 3.4.24.-)
1,224
Q8TE56
A disintegrin and metalloproteinase with thrombospondin motifs 17 (ADAMTS-17) (ADAM-TS 17) (ADAM-TS17) (EC 3.4.24.-)
1,095
P55107
Bone morphogenetic protein 3b (BMP-3b) (Growth/differentiation factor 10) (GDF-10) (Bone-inducing protein) (BIP)
478
P22003
Bone morphogenetic protein 5 (BMP-5)
454
P34820
Bone morphogenetic protein 8B (BMP-8B) (BMP-8) (Osteogenic protein 2) (OP-2)
402
Q8NFQ5
Bactericidal/permeability-increasing protein-like 3
453
O75973
C1q-related factor (Complement component 1 Q subcomponent-like 1)
258
B2RNN3
Complement C1q tumor necrosis factor-related protein 9-like
333
P23435
Cerebellin-1 (Precerebellin) [Cleaved into: Cerebellin (CER); [des-Ser1]-cerebellin]
193
Q8IVL8
Carboxypeptidase O (CPO) (EC 3.4.17.-)
374
Q8NDZ4
UPF0672 protein C3orf58
430
Q9H6E4
Coiled-coil domain-containing protein 134
229
Q6NSX1
Coiled-coil domain-containing protein 70
233
Q9NRJ3

C-C motif chemokine 28 (Small-inducible cytokine A28) (Mucosae-associated epithelial chemokine) (MEC) (Protein CCK1)
127
Q0P651
Uncharacterized protein C4orf29
414
Q5VXM1
CUB domain-containing protein 2
449
Q9UNI1
Chymotrypsin-like elastase family member 1 (EC 3.4.21.36) (Elastase-1)
258
Q6P5S2
Uncharacterized protein C6orf58
330
O15335
Chondroadherin (Cartilage leucine-rich protein)
359
Q8IUL8
Cartilage intermediate layer protein 2 (CILP-2) [Cleaved into: Cartilage intermediate layer protein 2 C1; Cartilage intermediate layer protein 2 C2]
1,156
Q5T742
Uncharacterized protein C10orf25
122
Q14406
Chorionic somatomammotropin hormone-like 1 (Chorionic somatomammotropin-like) (Lactogen-like)
199
O60676
Cystatin-8 (Cystatin-related epididymal spermatogenic protein)
142
Q16619
Cardiotrophin-1 (CT-1)
201
P17538
Chymotrypsinogen B (EC 3.4.21.1) [Cleaved into: Chymotrypsin B chain A; Chymotrypsin B chain B; Chymotrypsin B chain C]
263
Q07325
C-X-C motif chemokine 9 (Small-inducible cytokine B9) (Gamma-interferon-induced monokine) (MIG)
125
O43927
C-X-C motif chemokine 13 (Small-inducible cytokine B13) (B lymphocyte chemoattractant) (CXC chemokine BLC) (B cell-attracting chemokine 1) (BCA-1) (ANGIE)
109
Q8NET1
Beta-defensin 108B (Defensin, beta 108B) (Defensin, beta 108) (Beta-defensin 8) (BD-8) (hBD-8) (DEFB-8)
73
Q96PH6
Beta-defensin 118 (Defensin, beta 118) (Beta-defensin 18) (DEFB-18) (Epididymal secretory protein 13.6) (ESP13.6)
123
Q8NES8
Beta-defensin 124 (Defensin, beta 124) (Beta-defensin 24) (DEFB-24)
71
Q8N687
Beta-defensin 125 (Defensin, beta 125) (Beta-defensin 25) (DEFB-25)
156
Q9BYW3
Beta-defensin 126 (Beta-defensin 26) (DEFB-26) (Epididymal secretory protein 13.2) (ESP13.2)
111
Q92874
Deoxyribonuclease-1-like 2 (EC 3.1.21.-) (Deoxyribonuclease I-like 2) (DNase I-like 2) (DNase I homolog protein DHP1)
299
Q6PKH6
Dehydrogenase/reductase SDR family member 4-like 2 (EC 1.1.-.-)
230
Q9NT22
EMILIN-3 (Elastin microfibril interface-located protein 3) (Elastin microfibril interfacer 3) (EMILIN-5) (Elastin microfibril interface-located protein 5) (Elastin microfibril interfacer 5)
766
O94919
Endonuclease domain-containing 1 protein (EC 3.1.30.-)
500
Q14507
Epididymal secretory protein E3-alpha (Human epididymis-specific protein 3-alpha) (HE3 alpha)
147
Q99645
Epiphycan (Dermatan sulfate proteoglycan 3) (Small chondroitin/dermatan sulfate proteoglycan) (Proteoglycan-Lb) (PG-Lb)
322
O14944
Proepiregulin [Cleaved into: Epiregulin (EPR)]
169

Q9NQ30
Endothelial cell-specific molecule 1 (ESM-1 secretory protein) (ESM-1)
184
Q6NT32
Carboxylesterase 7 (EC 3.1.1.1) (Carboxylesterase-like urinary excreted protein homolog) (Cauxin)
575
Q5VST6
Abhydrolase domain-containing protein FAM108B1 (EC 3.-.-.-)
288
Q8WUF8
UPF0528 protein FAM172A
416
Q96GS6
Abhydrolase domain-containing protein FAM108A1 (EC 3.-.-.-)
310
Q92520
Protein FAM3C
227
Q76B58
Protein FAM5C (DBCCR1-like protein 1)
766
Q9NP95
Fibroblast growth factor 20 (FGF-20)
211
Q8TAT2
Fibroblast growth factor-binding protein 3 (FGF-binding protein 3) (FGF-BP3) (FGFBP-3)
258
Q5VTL7
Fibronectin type III domain-containing protein 7
734P41439
Folate receptor gamma (FR-gamma) (Folate receptor 3)
243
P0C091
FRAS1-related extracellular matrix protein 3
2,135
Q9UBC7
Galanin-like peptide
116
P27539
Embryonic growth/differentiation factor 1 (GDF-1)
372
Q9UK05
Growth/differentiation factor 2 (GDF-2) (Bone morphogenetic protein 9) (BMP-9)
429
Q9GZZ7
GDNF family receptor alpha-4 (GFR-alpha-4) (Persephin receptor)
299
Q9UJJ9
N-acetylglucosamine-1-phosphotransferase subunit gamma (GlcNAc-1-phosphotransferase subunit gamma) (UDP-N-acetylglucosamine-1-phosphotransferase subunit gamma)
305
O14626
Probable G-protein coupled receptor 171 (G-protein coupled receptor H963)
319
O75715
Epididymal secretory glutathione peroxidase (EC 1.11.1.9) (Epididymis-specific glutathione peroxidase-like protein) (EGLP)
221
Q9H772
Gremlin-2 (Cysteine knot superfamily 1, BMP antagonist 2) (Protein related to DAN and cerberus) (DAN domain family member 3)
168
Q9GZV7
Hyaluronan and proteoglycan link protein 2 (Brain link protein 1)
340
Q86UW8
Hyaluronan and proteoglycan link protein 4 (Brain link protein 2)
402
P01566
Interferon alpha-10 (Interferon alpha-C) (LeIF C) (Interferon alpha-6L)
189
P05015
Interferon alpha-16 (Interferon alpha-WA)
189
P05013
Interferon alpha-6 (Interferon alpha-K) (LeIF K) (Interferon alpha-54)
189
Q96ID5
Immunoglobulin superfamily member 21
467
P20809

Interleukin-11 (IL-11) (Adipogenesis inhibitory factor) (AGIF) (Oprelvekin)
199
Q16552
Interleukin-17A (IL-17A) (IL-17) (Cytotoxic T-lymphocyte-associated antigen 8) (CTLA-8)
155
Q14116
Interleukin-18 (IL-18) (Interferon-gamma-inducing factor) (IFN-gamma-inducing factor) (Interleukin-1 gamma) (IL-1 gamma) (Iboctadekin)
193
Q9NPH9
Interleukin-26 (AK155 protein)
171
Q8IZJ0
Interleukin-28A (IL-28A) (Interferon lambda-2) (IFN-lambda-2) (Cytokine ZCYTO20)
200
Q8IZI9
Interleukin-28B (IL-28B) (IL-28C) (Interferon lambda-3) (IFN-lambda-3) (Interferon lambda-4) (IFN-lambda-4) (Cytokine ZCYTO22)
200
Q8IU54
Interleukin-29 (IL-29) (Interferon lambda-1) (IFN-lambda-1) (Cytokine ZCYTO21)
200
Q9Y581
Insulin-like peptide INSL6 (Insulin-like peptide 6) (Relaxin/insulin-like factor 1) [Cleaved into: Insulin-like peptide INSL6 B chain; Insulin-like peptide INSL6 A chain]
213
Q8NC54
Keratinocyte-associated transmembrane protein 2
265
Q9H7L2
Putative killer cell immunoglobulin-like receptor-like protein KIR3DX1 (Leukocyte receptor cluster member 12)
352
Q9NVR0
Kelch-like protein 11
708
Q9UKR3
Kallikrein-13 (EC 3.4.21.-) (Kallikrein-like protein 4) (KLK-L4)
277
Q9UKQ9
Kallikrein-9 (EC 3.4.21.-) (Kallikrein-like protein 3) (KLK-L3)
250
Q9GZZ8
Extracellular glycoprotein lacritin
138
A4D0S4
Laminin subunit beta-4 (Laminin beta-1-related protein)
1,761
Q9Y6N6
Laminin subunit gamma-3 (Laminin 12 gamma 3 subunit)
1,587
P58215
Lysyl oxidase homolog 3 (EC 1.4.3.-) (Lysyl oxidase-like protein 3)
753
Q16609
Apolipoprotein(a)-like protein 2 (Apo(a)-like protein 2) (Lp(a)-liker protein 2) (Apolipoprotein a-related gene C protein) (Apo(a)rg-C)
132
Q7Z4W2
Lysozyme-like protein 2 (Lysozyme-2) (EC 3.2.1.17)
148
Q96KX0
Lysozyme-like protein 4
146
Q7Z304
MAM domain-containing protein 2 (MAM domain-containing proteoglycan) (Mamcan)
686
P55001
Microfibrillar-associated protein 2 (MFAP-2) (Microfibril-associated glycoprotein 1) (MAGP-1) (MAGP)
183
Q96PC5
Melanoma inhibitory activity protein 2
541
Q9Y5R2
Matrix metalloproteinase-24 (MMP-24) (EC 3.4.24.-) (Membrane-type matrix metalloproteinase 5) (MT-MMP 5) (Membrane-type-5 matrix metalloproteinase) (MT5-MMP) [Cleaved into: Processed matrix metalloproteinase-24]
645
Q9NPA2
Matrix metalloproteinase-25 (MMP-25) (EC 3.4.24.-) (Membrane-type matrix metalloproteinase 6) (MT-MMP 6) (Membrane-type-6 matrix metalloproteinase) (MT6-MMP) (Leukolysin)
562
O95631
Netrin-1

604
O00634
Netrin-3 (Netrin-2-like protein)
580
P30990
Neurotensin/neuromedin N [Cleaved into: Large neuromedin N (NmN-125); Neuromedin N (NmN) (NN); Neurotensin (NT); Tail peptide]
170
P48645
Neuromedin-U [Cleaved into: Neuromedin-U-25 (NmU-25)]
174
Q96S42
Nodal homolog
347
O95897
Noelin-2 (Olfactomedin-2)
454
O15130
FMRFamide-related peptides [Cleaved into: Neuropeptide SF (NPSF); Neuropeptide FF (NPFF); Neuropeptide AF (NPAF)]
113
P47972
Neuronal pentraxin-2 (NP2) (Neuronal pentraxin II) (NP-II)
431
Q8N729
Neuropeptide W (Preproprotein L8) (hPPL8) [Cleaved into: Neuropeptide W-23 (NPW23) (hL8); Neuropeptide W-30 (NPW30) (hL8C)]
165
Q99748
Neurturin
197
P58417
Neurexophilin-1
271
O95156
Neurexophilin-2
264
Q02509
Otoconin-90 (Oc90) (Phospholipase A2 homolog)
493
Q6GTS8
Probable carboxypeptidase PM20D1 (EC 3.4.17.-) (Peptidase M20 domain-containing protein 1)
502
Q9NZK7
Group IIE secretory phospholipase A2 (GIIE sPLA2) (EC 3.1.1.4) (Phosphatidylcholine 2-acylhydrolase GIIE) (sPLA(2)-IIE)
142
P10720
Platelet factor 4 variant (PF4var1) (PF4alt) (C-X-C motif chemokine 4 variant) (CXCL4L1) [Cleaved into: Platelet factor 4 variant(4-74); PPlatelet factor 4 variant(5-74); latelet factor 4 variant(6-74)]
104
Q13519
Nociceptin [Cleaved into: Neuropeptide 1; Nociceptin (Orphanin FQ) (PPNOC); Neuropeptide 2]
176
Q5K4E3
Polyserase-2 (EC 3.4.21.-) (Polyserine protease 2) (Serine protease 36)
855
Q6PEZ8
Podocan-like protein 1
512
Q16378
Proline-rich protein 4 (Lacrimal proline-rich protein) (Nasopharyngeal carcinoma-associated proline-rich protein 4)
134
P81277
Prolactin-releasing peptide (PrRP) (Prolactin-releasing hormone) [Cleaved into: Prolactin-releasing peptide PrRP31; Prolactin-releasing peptide PrRP20]
87
Q8NF86
Serine protease 33 (EC 3.4.21.-) (Serine protease EOS)
280
Q9UQ74
Pregnancy-specific beta-1-glycoprotein 8 (PSBG-8)
426
Q99969
Retinoic acid receptor responder protein 2 (Tazarotene-induced gene 2 protein) (RAR-responsive protein TIG2)
163
Q9HCQ7
FMRFamide-related peptides (Neuropeptide VF) [Cleaved into: Neuropeptide NPSF (Neuropeptide RFRP-1); Neuropeptide RFRP-2; Neuropeptide NPVF (Neuropeptide RFRP-3)]
196
Q93091
Ribonuclease K6 (RNase K6) (EC 3.1.27.-)
150

-continued

O00584
Ribonuclease T2 (EC 3.1.27.-) (Ribonuclease 6)
256
Q6XPR3
Repetin
784
Q9BSG5
Retbindin
229
Q99470
Stromal cell-derived factor 2 (SDF-2)
211
P09683
Secretin
121
Q99985
Semaphorin-3C (Semaphorin-E) (Sema E)
751
O15041
Semaphorin-3E
775
Q9NS98
Semaphorin-3G (Semaphorin sem2)
782
Q8TD33
Secretoglobin family 1C member 1 (Secretoglobin RYD5)
95
O95968
Secretoglobin family 1D member 1 (Lipophilin-A)
90
O95969
Secretoglobin family 1D member 2 (Lipophilin-B)
90
Q8IW75
Serpin A12 (Visceral adipose tissue-derived serine protease inhibitor) (Vaspin) (Visceral adipose-specific serpin) (OL-64)
414
O75830
Serpin I2 (Myoepithelium-derived serine protease inhibitor) (Pancpin) (Protease inhibitor 14) (TSA2004)
405
Q14515
SPARC-like protein 1 (High endothelial venule protein) (Hevin) (MAST 9)
664
Q9BT56
Spexin (NPQ)
116
Q8WTU2
Scavenger receptor cysteine-rich domain-containing group B protein (S4-SRCRB)
575
P52823
Stanniocalcin-1 (STC-1)
247
Q96PL2
Beta-tectorin
329
Q99727
Metalloproteinase inhibitor 4 (Tissue inhibitor of metalloproteinases 4) (TIMP-4)
224
Q8TB96
T-cell immunomodulatory protein (Protein TIP) (Integrin-alpha FG-GAP repeat-containing protein 1)
612
O14657
Torsin-1B (Torsin family 1 member B)
336
P20396
Prothyroliberin [Cleaved into: Thyroliberin (Thyrotropin-releasing hormone) (TRH) (Thyrotropin-releasing factor) (TRF) (TSH-releasing factor) (Protirelin)]
242
Q8NHM4
Putative trypsin-6 (EC 3.4.21.4) (Trypsinogen C)
247
Q969D9
Thymic stromal lymphopoietin
159
Q9P2K2
Thioredoxin domain-containing protein 16
825
Q8WVF2
Unique cartilage matrix-associated protein [Cleaved into: Unique cartilage matrix-associated protein C-terminal fragment (Ucma-C) (Gla-rich protein) (GRP)]

-continued

138
Q96RP3
Urocortin-2 (Urocortin II) (Ucn II) (Stresscopin-related peptide) (Urocortin-related peptide)
112
Q969E3
Urocortin-3 (Urocortin III) (Ucn III) (Stresscopin)
161
Q6PCB0
von Willebrand factor A domain-containing protein 1
445
Q8N2E2
Von Willebrand factor D and EGF domain-containing protein
1,590
Q9HC57
WAP four-disulfide core domain protein 1 (Prostate stromal protein ps20) (ps20 growth inhibitor)
220
Q8IUB2
WAP four-disulfide core domain protein 3 (Putative protease inhibitor WAP14)
231
Q8NEX5
Protein WFDC9
89
Q9GZT5
Protein Wnt-10a
417
P04628
Proto-oncogene protein Wnt-1
370
P56704
Protein Wnt-3a
352
P56703
Proto-oncogene protein Wnt-3
355
Q9Y6F9
Protein Wnt-6
365
O14904
Protein Wnt-9a (Wnt-14)
365
Q9UBD3
Cytokine SCM-1 beta (C motif chemokine 2) (XC chemokine ligand 2)
114
O60844
Zymogen granule membrane protein 16 (Zymogen granule protein 16) (Secretory lectin ZG16)
167
Q9BS86
Zona pellucida-binding protein 1 (Sp38)
351
Q8TD06
Anterior gradient protein 3 homolog (hAG-3) (AG-3) (AG3) (Breast cancer membrane protein 11)
166
Q6UX39
Amelotin
209
Q86XS5
Angiopoietin-related protein 5 (Angiopoietin-like 5)
388
Q5FYB0
Arylsulfatase J (ASJ) (EC 3.1.6.-)
599
Q8TB73
Fibronectin type-III domain-containing protein C4orf31
568
Q6UWT4
Uncharacterized protein C5orf46
87
Q6UXF7
C-type lectin domain family 18 member B (Mannose receptor-like protein 1)
455
Q8N129
Protein canopy homolog 4
248
Q8NBI3
Draxin (Dorsal repulsive axon guidance protein)
349
Q6UWF9
Protein FAM180A
173

Q3B7J2
Glucose-fructose oxidoreductase domain-containing protein 2 (EC 1.-.-.-)
385
Q86WN2
Interferon epsilon (Interferon epsilon-1)
208
Q6UXX5
Inter-alpha-trypsin inhibitor heavy chain H5-like protein (Inter-alpha inhibitor H5-like protein)
1,313
Q8WWU7
Intelectin-2 (Endothelial lectin HL-2)
325
Q6UWW0
Lipocalin-15
184
P62502
Epididymal-specific lipocalin-6 (Lipocalin-5)
163
Q9H306
Matrix metalloproteinase-27 (MMP-27) (EC 3.4.24.-)
513
Q8N3Z0
Inactive serine protease 35
413
Q6UWY2
Serine protease 1-like protein 1 (EC 3.4.21.-)
283
Q6UWP8
Suprabasin
247
Q6XE38
Secretoglobin family 1D member 4 (IFN-gamma-inducible secretoglobin) (IIS)
83
Q6UXN2
Trem-like transcript 4 protein (TLT-4) (Triggering receptor expressed on myeloid cells-like protein 4)
200
Q8TEU8
WAP, kazal, immunoglobulin, kunitz and NTR domain-containing protein 2 (WAP, follistatin, immunoglobulin, kunitz and
NTR domain-containing-related protein) (WFIKKN-related protein) (Growth and differentiation factor-associated serum protein 1) (GASP-1)
(hGASP-1)
576
Q8TAG5
V-set and transmembrane domain-containing protein 2A
243
Q6UX34
Uncharacterized protein C2orf82
121
A8MWS1
Putative killer cell immunoglobulin-like receptor like protein KIR3DP1 (CD antigen CD158c)
328
Q6UW32
Insulin growth factor-like family member 1
110
A8K3U3
cDNA FLJ77863, highly similar to Homo sapiens secreted and transmembrane 1 (SECTM1), mRNA
248
Q4VNC0
Probable cation-transporting ATPase 13A5 (EC 3.6.3.-) (P5-ATPase isoform 5)
1,218
A6H8M9
Cadherin-like protein 29
788
Q6UY09
Carcinoembryonic antigen-related cell adhesion molecule 20
585
Q3KPI0
Carcinoembryonic antigen-related cell adhesion molecule 21
293
Q9H741
UPF0454 protein C12orf49
205
Q6UW02
Cytochrome P450 20A1 (EC 1.14.-.-)
462
Q6NUT2
Protein dpy-19 homolog 2 (Dpy-19-like protein 2)
758
Q9BVC3
Sister chromatid cohesion protein DCC1 (Defective in sister chromatid cohesion protein 1 homolog)

393
Q96M86
Dynein heavy chain domain-containing protein 1
1,021
Q6IAN0
Dehydrogenase/reductase SDR family member 7B (EC 1.1.-.-)
325
Q7Z5A9
Protein FAM19A1 (Chemokine-like protein TAFA-1)
133
Q5JW98
Protein FAM26D
314
Q8WVX9
Fatty acyl-CoA reductase 1 (EC 1.2.1.n2) (Male sterility domain-containing protein 2)
515
Q8TAL6
Fin bud initiation factor homolog
211
Q9H6D8
Fibronectin type III domain-containing protein 4 (Fibronectin type III repeat-containing protein 1)
234
Q6UXV0
GDNF family receptor alpha-like
394
Q9H1C3
Glycosyltransferase 8 domain-containing protein 2 (EC 2.4.1.-)
349
Q8TED1
Probable glutathione peroxidase 8 (EC 1.11.1.9)
209
Q8IYS0
GRAM domain-containing protein 1C
662
B1AKI9
Isthmin-1
464
Q6UY18
Leucine-rich repeat and immunoglobulin-like domain-containing nogo receptor-interacting protein 4 (Leucine-rich repeat neuronal protein 6D)
593
Q86X40
Leucine-rich repeat-containing protein 28
367
Q8ND94
LRRN4 C-terminal-like protein
238
Q6UXB3
Ly6/PLAUR domain-containing protein 2
125
Q8N468
Major facilitator superfamily domain-containing protein 4
514
Q6UWV2
Myelin protein zero-like protein 3
235
Q6P988
Protein notum homolog (EC 3.-.-.-)
496
A1E959
Odontogenic ameloblast-associated protein (Apin)
279
Q9Y5I3
Protocadherin alpha-1 (PCDH-alpha-1)
950
Q96BZ4
Phospholipase D4 (PLD 4) (EC 3.1.4.4) (Choline phosphatase 4) (Phosphatidylcholine-hydrolyzing phospholipase D4)
506
Q8IZV5
Retinol dehydrogenase 10 (EC 1.1.1.n2)
341
Q08ET2
Sialic acid-binding Ig-like lectin 14 (Siglec-14)
396
Q9NX61
Transmembrane protein 161A
479
Q8NDZ6
Transmembrane protein 161B
487

-continued

Q6ZP80
Transmembrane protein 182
229
Q96BF3
Transmembrane and immunoglobulin domain-containing protein 2
282
Q8NDY8
Transmembrane protein 52
209
Q6P7N7
Transmembrane protein 81
255
Q6UWM9
UDP-glucuronosyltransferase 2A3 (UDPGT 2A3) (EC 2.4.1.17)
527
Q3SY77
UDP-glucuronosyltransferase 3A2 (UDPGT 3A2) (EC 2.4.1.17)
523
O15240
Neurosecretory protein VGF
615
A4QMV3
Secreted phosphoprotein 2, 24kDa (Fragment)
211
Q6UX46
Protein FAM150B
152
Q6UXS0
C-type lectin domain-containing protein UNQ5810/PRO19627
136
Q15846
Clusterin-like protein 1 (Retinal-specific clusterin-like protein)
466
Q8N5W8
Protein FAM24B
94
O60383
Growth/differentiation factor 9 (GDF-9)
454
Q6JVE6
Epididymal-specific lipocalin-10
187
Q6JVE5
Epididymal-specific lipocalin-12
192
Q6JVE9
Epididymal-specific lipocalin-8
175
P02811
Basic proline-rich peptide P-E (IB-9)
61
Q6UWK7
Putative uncharacterized protein C10orf99
81
Q96MU5
Uncharacterized protein C17orf77
206
Q6P093
Arylacetamide deacetylase-like 2 (EC 3.1.1.-)
401
Q9UP79
A disintegrin and metalloproteinase with thrombospondin motifs 8 (ADAMTS-8) (ADAM-TS 8) (ADAM-TS8) (EC 3.4.24.-) (METH-2) (METH-8)
890
Q86Y30
B melanoma antigen 2 (Cancer/testis antigen 2.2) (CT2.2)
109
Q86Y29
B melanoma antigen 3 (Cancer/testis antigen 2.3) (CT2.3)
109
Q075Z2
Bovine seminal plasma protein homolog 1
132
Q5VWW1
Complement C1q-like protein 3
255
Q8N8R5
UPF0565 protein C2orf69
385
Q7Z4R8

UPF0669 protein C6orf120
191
A2RUU4
Colipase-like protein C6orf127
121
Q9H7B7
Uncharacterized protein C7orf69
122
Q8WUY1
UPF0670 protein C8orf55 (Mesenchymal stem cell protein DSCD75)
208
Q6NUI6
Chondroadherin-like protein
762
Q8NCF0
C-type lectin domain family 18 member C (Mannose receptor-like protein 3)
446
Q96KW9
Putative uncharacterized protein C13orf28
195
Q8NFW1
Collagen alpha-1(XXII) chain
1,626
Q2VPA4
Complement component receptor 1-like protein (Complement C4b-binding protein CR-1-like protein)
569
Q9H3Y0
Peptidase inhibitor R3HDML (Cysteine-rich secretory protein R3HDML)
253
Q5W186
Cystatin-9 (Cystatin-like molecule)
159
Q8N907
DAN domain family member 5 (Cerberus-like protein 2) (Cerl-2) (Gremlin-3) (Cysteine knot superfamily 1, BMP antagonist 3)
189
Q7Z7B8
Beta-defensin 128 (Defensin, beta 128) (Beta-defensin 28) (DEFB-28)
93
Q96BH3
Epididymal sperm-binding protein 1 (Epididymal secretory protein 12) (hE12)
223
Q7RTY5
Epidermis-specific serine protease-like protein (EC 3.4.21.-)
336
Q8N323
Protein FAM55A
547
Q6KF10
Growth/differentiation factor 6 (GDF-6) (Growth/differentiation factor 16)
455
Q9NXC2
Glucose-fructose oxidoreductase domain-containing protein 1 (EC 1.-.-.-)
390
Q96MS3
Glycosyltransferase 1 domain-containing protein 1 (EC 2.4.-.-)
346
P59796
Glutathione peroxidase 6 (EC 1.11.1.9)
221
A8MTL9
Serpin-like protein HMSD (Minor histocompatibility protein HMSD) (Minor histocompatibility serpin domain-containing protein)
139
Q8WX77
Insulin-like growth factor-binding protein-like 1 (Insulin-like growth factor-binding-related protein 4) (IGFBP-rP4) (IGFBP-related protein 10)
278
Q6EBC2
Interleukin-31 (IL-31)
164
Q6ZMJ4
Interleukin-34 (IL-34)
242
Q6PEW0
Plasma kallikrein-like protein 4 (Cancer/testis antigen 67) (CT67)
395
Q8WX39
Epididymal-specific lipocalin-9 (MUP-like lipocalin)
190
Q5VXJ0
Lipase member K (EC 3.1.1.-) (Lipase-like abhydrolase domain-containing protein 2)

-continued

399
Q5VYY2
Lipase member M (EC 3.1.1.-) (Lipase-like abhydrolase domain-containing protein 3)
423
P59826
Long palate, lung and nasal epithelium carcinoma-associated protein 3 (Ligand-binding protein RYA3)
476
Q17RY6
Lymphocyte antigen 6K (Ly-6K)
165
A1L453
Serine protease MPN2 (EC 3.4.21.-) (Marapsin-2)
326
Q8WTR8
Netrin-5 (Netrin-1-like protein)
489
Q5JS37
NHL repeat-containing protein 3
347
Q68BL8
Olfactomedin-like protein 2B (Photomedin-2)
750
Q6ZRI0
Otogelin
2,925
Q7RTM1
Otopetrin-1
612
Q7RTY7
Ovochymase-1 (EC 3.4.21.-)
1,134
Q7RTZ1
Ovochymase-2 (EC 3.4.21.-) (Oviductin)
564
Q6IE36
Ovostatin homolog 2
1,432
P83859
Orexigenic neuropeptide QRFP (P518) [Cleaved into: QRF-amide (Pyroglutamylated arginine-phenylalanine-amide peptide) (Neuropeptide RF-amide)]
136
Q5R387
Putative inactive group IIC secretory phospholipase A2 (Phosphatidylcholine 2-acylhydrolase GIIC)
150
Q8WXA2
Prostate and testis expressed protein 1
126
Q6P4A8
Putative phospholipase B-like 1 (EC 3.1.1.-) (Phospholipase B domain-containing protein 1) (Lamina ancestor homolog 1) (LAMA-like protein 1)
552
Q86SH4
Putative testis-specific prion protein (Protein M8)
94
Q13046
Putative pregnancy-specific beta-1-glycoprotein 7 (PSBG-7)
419
Q8TDE3
Ribonuclease 8 (RNase 8) (EC 3.1.27.-)
154
Q8IVN8
RPE-spondin
264
Q6NUJ1
Proactivator polypeptide-like 1 [Cleaved into: Saposin A-like; Saposin B-Val-like; Saposin B-like; Saposin C-like; Saposin D-like]
521
Q8IVW8
Protein spinster homolog 2
549
Q76SI0
Urotensin-2B (Urotensin-IIB) (U-IIB) (UIIB) (Urotensin II-related peptide) (Urotensin 2 domain-containing protein)
119
B2RUY7
von Willebrand factor C domain-containing protein 2-like
222
Q9BT30
Alkylated DNA repair protein alkB homolog 7 (Spermatogenesis-associated protein 11) (Spermatogenesis cell proliferation-related protein)
221
Q6UWV7
UPF0514 membrane protein FAM159A
190

Q86YQ2
Latherin (Breast cancer and salivary gland-expressed protein)
179
Q6UX53
Methyltransferase-like protein 7B (EC 2.1.1.-)
244
Q8WW62
Transmembrane emp24 domain-containing protein 6
240
Q96SJ8
Tetraspanin-18 (Tspan-18)
248
Q6UWH6
Protein TEX261
196
Q6UX68
XK-related protein 5
686
Q6UWQ7
Insulin growth factor-like family member 2
119
Q6UXB1
Insulin growth factor-like family member 3
125
Q9ULZ1
Apelin (APJ endogenous ligand) [Cleaved into: Apelin-36; Apelin-31; Apelin-28; Apelin-13]
77
Q567T5
Secreted phosphoprotein 1 (cDNA FLJ52507, highly similar to Osteopontin) (cDNA FLJ77801) (Secreted phosphoprotein 1 (Osteopontin, bone sialoprotein I, early T-lymphocyte activation 1), isoform CRA_a)
287
A8TX70
Collagen alpha-5(VI) chain (Collagen alpha-1(XXIX) chain) (von Willebrand factor A domain-containing protein 4)
2,615
Q86Y27
B melanoma antigen 5 (Cancer/testis antigen 2.5) (CT2.5)
43
Q7Z5Y6
Bone morphogenetic protein 8A (BMP-8A)
402
Q5VUM1
UPF0369 protein C6orf57
108
Q8N7Q2
Putative uncharacterized protein C10orf31
184
Q8TAV5
Putative uncharacterized protein C11orf45
145
Q96LU7
Uncharacterized protein C12orf28
275
Q0P5P2
Uncharacterized protein C17orf67
114
Q5J5C9
Beta-defensin 121 (Defensin, beta 121) (Beta-defensin 21) (DEFB-21)
76
Q30KQ2
Beta-defensin 130 (Defensin, beta 130) (Beta-defensin 30) (DEFB-30)
79
Q9BX68
Histidine triad nucleotide-binding protein 2 (HINT-2) (EC 3.-.-.-) (HINT-3) (HIT-17kDa) (PKCI-1-related HIT protein)
163
O75200
Nuclear pore complex-interacting protein-like 1
221
Q5JTB6
Placenta-specific protein 9
97
Q86WS3
Placenta-specific 1-like protein
158
O60542
Persephin (PSP)
156
Q5W5W9
Regulated endocrine-specific protein 18 [Cleaved into: Regulated endocrine-specific protein 18; Triskadecapeptide]
173

P60153
Ribonuclease-like protein 9
205
Q9H1F0
WAP four-disulfide core domain protein 10A (Putative protease inhibitor WAP10A)
79
Q8IUB5
Protein WFDC13
93
Q9H1J5
Protein Wnt-8a (Wnt-8d)
355
A6NGN9
Ig-like domain-containing protein ENSP00000270642
336
Q6UXT9
Abhydrolase domain-containing protein 15 (EC 3.1.1.-)
468
P60827
Complement C1q tumor necrosis factor-related protein 8
262
Q6UXQ4
Uncharacterized protein C2orf66
117
Q6UX52
Uncharacterized protein C17orf99
265
Q6UXT8
Protein FAM150A
129
Q6UXH0
Hepatocellular carcinoma-associated protein TD26
198
Q7Z4B0
Uncharacterized protein C18orf20
112
Q30KR0
Beta-defensin 110 (Defensin, beta 110) (Beta-defensin 10) (DEFB-10)
62
Q5RGM9
Abhydrolase domain-containing protein FAM108A2/A3 (EC 3.-.-.-)
310
Q99954
Submaxillary gland androgen-regulated protein 3A (Proline-rich protein 5) (Proline-rich protein PBI)
134
Q6UVW9
C-type lectin domain family 2 member A (Proliferation-induced lymphocyte-associated receptor) (PILAR)
174
Q7Z2Q7
Leucine-rich repeat-containing protein 70 (Synleurin)
622
Q6UXR4
Serpin A13
307
Q6UXU0
Putative uncharacterized protein UNQ9165/PRO28630
137
Q8IYJ0
Uncharacterized protein C12orf53
282
Q6UXN8
C-type lectin domain family 9 member A
241
Q9Y6N3
Calcium-activated chloride channel regulator family member 3 (Calcium-activated chloride channel family member 3) (hCLCA3)
262
Q6UXZ3
CMRF35-like molecule 4 (CLM-4) (CMRF35-A4) (CD300 antigen-like family member D) (CD antigen CD300d)
194
Q6UXP7
Protein FAM151B
276
Q496H8
Neuritin-like protein
165
P61366
Osteocrin (Musclin)
133
A6NL71

-continued

Transmembrane protease, serine 11E2 (EC 3.4.21.-) [Cleaved into: Transmembrane protease, serine 11E2 non-catalytic chain; Transmembrane protease, serine 11E2 catalytic chain]
423
Q6UXP3
Transmembrane protein 14E
125
Q6UWW9
Transmembrane protein 207
146
Q6UXN7
TOMM20-like protein 1
152
Q6UWB4
Probable serine protease UNQ9391/PRO34284 (EC 3.4.21.-)
352
Q6UXD1
Histidine-rich carboxyl terminus protein 1
115
Q13072
B melanoma antigen 1 (B melanoma antigen) (Antigen MZ2-BA) (Cancer/testis antigen 2.1) (CT2.1)
43
Q9UKY3
Inactive carboxylesterase 4 (Placental carboxylesterase 3) (PCE-3)
287
Q86VR8
Four-jointed box protein 1 (Four-jointed protein homolog)
437
Q6IFS5
Protein HSN2
434
Q8IVG9
Humanin
24
Q6ZWJ8
Kielin/chordin-like protein (Kielin/chordin-like protein 1) (Cysteine-rich motor neuron 2 protein) (CRIM-2) (Cysteine-rich BMP regulator 2)
1,503
Q2TV78
Putative macrophage-stimulating protein MSTP9 (Brain rescue factor 1) (BRF-1) (Hepatocyte growth factor-like protein homolog)
715
P0C859
Putative neurofibromin 1-like protein 4/6
116
A1KZ92
Peroxidasin-like protein (EC 1.11.1.7) (Vascular peroxidase 2) (Cardiac peroxidase)
1,463
A2VEC9
SCO-spondin
5,147
A6NE02
BTB/POZ domain-containing protein 17 (Galectin-3-binding protein-like)
478
Q86Z23
Complement C1q-like protein 4
238
Q9UFP1
Uncharacterized protein C3orf41
575
Q17RF5
Uncharacterized protein C4orf26
130
Q6MZM9
Uncharacterized protein C4orf40
219
Q8N2X6
Uncharacterized protein C5orf55
119
Q5JXM2
UPF0624 protein C6orf186
366
A6NNL5
Uncharacterized protein C15orf61
157
Q6GPI1
Chymotrypsinogen B2 (EC 3.4.21.1) [Cleaved into: Chymotrypsin B2 chain A; Chymotrypsin B2 chain B; Chymotrypsin B2 chain C]
263
A8MXU0
Beta-defensin 108A (Defensin, beta 108A) (Putative beta-defensin 108B pseudogene 1)
73
Q30KQ9

Beta-defensin 111 (Defensin, beta 111) (Beta-defensin 11) (DEFB-11)
67
Q30KQ8
Beta-defensin 112 (Defensin, beta 112) (Beta-defensin 12) (DEFB-12)
113
Q30KQ6
Beta-defensin 114 (Defensin, beta 114) (Beta-defensin 14) (DEFB-14)
69
Q30KQ5
Beta-defensin 115 (Defensin, beta 115) (Beta-defensin 15) (DEFB-15)
88
Q30KQ4
Beta-defensin 116 (Defensin, beta 116) (Beta-defensin 16) (DEFB-16)
102
P59861
Beta-defensin 131 (Defensin, beta 131) (Beta-defensin 31) (DEFB-31)
70
Q4QY38
Beta-defensin 134 (Defensin, beta 134)
66
Q30KP8
Beta-defensin 136 (Defensin, beta 136)
78
A6NNS2
Dehydrogenase/reductase SDR family member 7C (EC 1.1.-.-)
312
Q5T7M4
Protein FAM132A
302
Q4G0M1
Protein FAM132B
354
Q6IE38
Putative serine protease inhibitor Kazal-type 5-like 2
97
Q1W4C9
Serine protease inhibitor Kazal-type 5-like 3 (Hepatitis B virus DNA polymerase transactivated serine protease inhibitor) (Hespintor)
94
Q5DT21
Serine protease inhibitor Kazal-type 9 (Lymphoepithelial Kazal-type-related inhibitor 2)
86
Q5VXI9
Lipase member N (EC 3.1.1.-) (Lipase-like abhydrolase domain-containing protein 4)
398
Q17RR3
Pancreatic lipase-related protein 3 (PL-RP3) (EC 3.1.1.3)
467
Q641Q3
Meteorin-like protein
311
Q5H8A3
Neuromedin-S
153
P0C0P6
Neuropeptide S
89
Q96A99
Neuronal pentraxin-like protein C16orf38
478
A6NHN0
Otolin-1
477
Q6IE37
Ovostatin homolog 1
1,185
Q6ZNF0
Iron/zinc purple acid phosphatase-like protein (EC 3.1.3.2)
438
Q15195
Plasminogen-related protein A (Plasminogen-like protein A) (Plasminogen-like protein A1)
96
Q2L4Q9
Polyserase-3 (EC 3.4.21.-) (Polyserine protease 3)
553
Q9NRI6
Putative peptide YY-2 (Putative peptide YY2)
33
Q5JQD4
Putative peptide YY-3 (Putative peptide YY3) (PYY-III)

-continued

```
70
Q5GAN6
Ribonuclease-like protein 10
216
Q5GAN4
Ribonuclease-like protein 12
147
Q5GAN3
Ribonuclease-like protein 13
156
Q86U17
Serpin A11
422
Q6UDR6
Kunitz-type protease inhibitor 4
99
Q6URK8
Testis, prostate and placenta-expressed protein
271
Q7Z5A4
Putative testis serine protease 2 (EC 3.4.21.-)
293
A6NJ16
Putative V-set and immunoglobulin domain-containing protein 6
123
Q2M2E5
Uncharacterized protein FLJ37543
130
A4D1T9
Peptidase S1 domain-containing protein LOC136242
235
Q1ZYW2
Secreted frizzled-related protein 4
346
Q7Z5L3
Complement C1q-like protein 2
287
Q96LR1
Putative uncharacterized protein C17orf69
157
Q4G179
Putative cystatin-13
69
Q30KR1
Beta-defensin 109 (Defensin, beta 109)
87
Q30KQ7
Beta-defensin 113 (Defensin, beta 113) (Beta-defensin 13) (DEFB-13)
82
Q30KP9
Beta-defensin 135 (Defensin, beta 135)
77
A6NFZ4
Protein FAM24A
105
Q7Z4P5
Growth/differentiation factor 7 (GDF-7)
450
A6NJ69
IgA-inducing protein homolog
53
Q5VSP4
Putative lipocalin 1-like protein 1
162
A6NIE9
Putative serine protease 29 (Implantation serine proteinase 2-like protein) (ISP2-like protein)
313
Q4G0G5
Secretoglobin-like protein
96
Q4G0T1
Putative scavenger receptor cysteine-rich domain-containing protein LOC619207
232
A6NGW2
Putative stereocilin-like protein
1,772
A6NDP1
Putative V-set and immunoglobulin domain-containing protein 7
120
```

A6NJS3
Putative V-set and immunoglobulin domain-containing-like protein ENSP00000303034
120
Q6ZRU5
Putative uncharacterized protein FLJ46089
148
Q6B9Z1
Insulin growth factor-like family member 4
124
Q6UX72
UDP-GlcNAc:betaGal beta-1,3-N-acetylglucosaminyltransferase 9 (Beta-1,3-N-acetylglucosaminyltransferase-9) (Beta3Gn-T9) (BGnT-9) (EC 2.4.1.-)
402
O15150
Replication initiation-like protein (Myelin transcription factor 2) (MyT2) (Cerebrin-50)
435
B3GLJ2
Prostate and testis expressed protein 3 (PATE-like protein DJ) (PATE-DJ) (Acrosomal vesicle protein HEL-127)
98
Q86Y28
B melanoma antigen 4 (Cancer/testis antigen 2.4) (CT2.4)
39
Q7Z2R9
Putative uncharacterized protein C1orf191
100
A6NNL9
Putative abhydrolase domain-containing protein FAM108A5 (EC 3.-.-.-)
308
Q6UY13
Putative uncharacterized protein UNQ5830/PRO19650/PRO19816
95
B3KQR2
Secreted frizzled-related protein 2 (cDNA PSEC0060 fis, clone NT2RP2000638, highly similar to Secreted frizzled-related protein 2)
295
Q6UXP8
Putative uncharacterized protein UNQ6975/PRO21958
91
O43320
Fibroblast growth factor 16 (FGF-16)
207
P0C7L1
Serine protease inhibitor Kazal-type 8
97
Q9UF72
Uncharacterized protein KIAA0495
201
Q13862
Platelet basic protein-like 2 (DNA-binding protein amplifying expression of surfactant protein B) (DNA-binding protein SPBPBP)
106
A8MV23
Serpin E3
424
A1L4H1
Scavenger receptor cysteine-rich domain-containing protein LOC284297
1,096
A6XMV6
Secreted phosphoprotein 1
314
A4ZYV1
Stress induced secreted protein 1
311
P0C854
Putative cat eye syndrome critical region protein 9
216
A6NG13
Glycosyltransferase 54 domain-containing protein (EC 2.4.1.-)
371
A8MTI9
Putative serine protease LOC138652 (EC 3.4.21.-)
375
A6NC86
Uncharacterized protein ENSP00000244321
204
A8MT79
Putative zinc-alpha-2-glycoprotein-like 1
204
Q5TEV5
Putative uncharacterized protein C1orf134
83

-continued

A6NCS6
Uncharacterized protein C2orf72
168
Q8N8P7
Uncharacterized protein C11orf44
122
Q69YU5
Uncharacterized protein C12orf73
71
Q5W188
Putative cystatin-9-like 2
147
A6NDD2
Beta-defensin 108B-like
73
Q30KQ1
Beta-defensin 133 (Defensin, beta 133)
61
A6NEC5
Putative abhydrolase domain-containing protein FAM108A6 (EC 3.-.-.-)
299
P62706
Fibrosin-1
177
A6ND01
Probable folate receptor delta (FR-delta) (Folate receptor 4)
244
A6NF02
NPIP-like protein ENSP00000346774
221
A6NHN6
Nuclear pore complex-interacting protein-like 2
382
Q99935
Proline-rich protein 1 (PRL1) (Basic proline-rich lacrimal protein)
201
Q71RG6
Putative uncharacterized protein FP248
208
Q6ZVS6
Putative uncharacterized protein FLJ42147
177
A8MXB1
Putative zinc-alpha-2-glycoprotein-like 2
111
Q6IBK4
SPARC protein (Secreted protein, acidic, cysteine-rich (Osteonectin), isoform CRA_b)
303
Q6UWF6
Putative uncharacterized protein UNQ3029/PRO9830
113
B4DYC1
cDNA FLJ60957, highly similar to Secreted frizzled-related protein 4
368
B4DRV4
cDNA FLJ55667, highly similar to Secreted protein acidic and rich in cysteine
212
Q6UXU1
Putative uncharacterized protein UNQ6490/PRO21339
168
Q6UXQ6
Putative uncharacterized protein UNQ6125/PRO20090
108
Q6UXR6
Putative uncharacterized protein UNQ6494/PRO21346
183
Q6UXQ8
Putative uncharacterized protein UNQ6190/PRO20217
127
Q6UXV3
Uncharacterized protein UNQ6126/PRO20091
157
B3KSM5
cDNA FLJ36603 fis, clone TRACH2015180, highly similar to Secreted frizzled-related protein 2
238
P0C8F1
Prostate and testis expressed protein 4 (PATE-like protein B) (PATE-B)
95
Q6UX82

Uncharacterized protein UNQ511/PRO1026
237
Q6UWF5
Putative uncharacterized protein UNQ5815/PRO19632
114
Q6UXR8
Putative uncharacterized protein UNQ6493/PRO21345
122
Q5U0B9
Stem cell growth factor; lymphocyte secreted C-type lectin
323
B4E1T4
cDNA FLJ53955, highly similar to Secreted frizzled-related protein 4
343
Q6UXP9
Putative uncharacterized protein UNQ9370/PRO34162
181
Q9P1C3
Putative uncharacterized protein PRO2829
46
Q96I85
Putative uncharacterized protein C14orf144
54
P0C876
Uncharacterized protein FLJ90687
127
P04281
Basic proline-rich peptide IB-1
96
A8MTW9
Putative uncharacterized protein ENSP00000380674
85
A8MUN3
Putative uncharacterized protein ENSP00000381830
132
Q53G63
Secreted and transmembrane 1 precusor variant (Fragment)
248
Q53G27
Secreted and transmembrane 1 precusor variant (Fragment)
248
Q16521
CR1 receptor (CR1 receptor SCR9) (Fragment)
33
P61109
Kidney androgen-regulated protein (KAP) (ARP)
121
P85047
Opiorphin
5
Q6ZS96
Protein Wnt
329
Q4VAJ4
Protein Wnt
191
Q9UNH2
MC51L-53L-54L homolog (Fragment)
184
O60748
COBW-like placental protein (Fragment)
106
B8A597
Protein Wnt
205
B8A595
Protein Wnt
333
Q3SY79
Protein Wnt
385
Q96H90
Protein Wnt
349
Q5TEH9
Protein Wnt
391
Q6DK41
Protein Wnt (Fragment)

381
Q05BQ6
Protein Wnt (Fragment)
379
Q5TEH8
Protein Wnt
299
A0N6Y5
Fibroblast growth factor receptor FGFR-1 secreted form protein (Fragment)
92
Q6UXM4
Ficolin (Collagen/fibrinogen domain containing) 3 (Hakata antigen) (NL3) (Ficolin (Collagen/fibrinogen domain containing) 3 (Hakata antigen), isoform CRA_b)
288
Q6UW50
TOM1
209
Q6UW36
ECE2
736
Q6UWM0
EPA6
285
Q53S44
Protein Wnt
417
Q5TEI2
Protein Wnt
372
A8K315
Protein Wnt
359
Q5IHW6
KIR2DL4 (Fragment)
367
A4D0W7
Protein Wnt
355
B8A596
Protein Wnt
349
Q53S45
Protein Wnt (Fragment)
338
Q86YL8
Putative soluble interleukin 18 receptor 1
170
Q5JYX2
Protein Wnt (Fragment)
149
Q6ZSP0
Protein Wnt
351
A6NE61
Protein Wnt (Fragment)
239
Q6UY50
NL3
218
Q5U0N2
Protein Wnt
370
A4D0V1
Protein Wnt
360
B2R7A5
Protein Wnt
389
A0FKD1
WNT1 induced secreted protein 1 splice variant x (Fragment)
43
B5MCC8
Protein Wnt
173
B7Z1Y5
Protein Wnt
153
A4D0W8
Protein Wnt

```
365
A8K0G1
Protein Wnt
353
Q5U0K5
Protein Wnt
354
Q9BTP0
Protein Wnt (Fragment)
293
Q8IUM6
Protein Wnt
351
B4DJF9
Protein Wnt
296
Q8N2E5
Protein Wnt
365
Q59G81
Protein Wnt (Fragment)
284
Q2TQ40
B cell maturation antigen transcript variant 4 (Tumor necrosis factor receptor superfamily member 17)
135
Q8IWS1
Keratinocytes associated transmembrane protein 1
178
B3KQX9
Protein Wnt
291
Q6UWZ0
WLPL514
86
Q6UWF4
GLGQ5807
153
Q6UWW7
TUFT1
199
Q6UWC1
DRLV8200
456
Q6UVX0
IDLW5808
80
Q6UWR4
UBAP2
363
B7U178
C1q/TNF-related protein 8
262
A3R3E3
KIR2DL4 (Fragment)
367
Q5I2A4
Chemokine-like factor super family 2 transcript variant 2
195
Q6UWX0
PLA2G2D
116
Q6UWT8
GKGM353
67
Q6UWM6
MATL2963
88
Q6UXV6
NINP6167
142
Q6UW61
POM121-like
428
Q6UXS7
RTFV9368 (SLE-dependent upregulation 1)
120
Q9UK79
Herstatin (V-erb-b2 erythroblastic leukemia viral oncogene homolog 2, neuro/glioblastoma derived oncogene homolog (Avian), isoform CRA_a)
419
```

Q8N2D3
Protein Wnt
253
Q6UXQ9
ELCV5929
189
Q6UWM4
KVVM3106
93
Q6UXR9
ISPF6484
88
Q6UXP6
LKHP9428
218
Q6UXT6
VNFT9373
308
Q6UY24
ACAH3104
115
Q6UXU7
RVLA1944
88
Q6UY31
Wpep3002
85
Q6UWR9
ZDHHC11
142
Q6UWV9
AGLW2560
178
Q6UWH1
TSSP3028
102
Q6UXX8
RFVG5814
206
Q6UWJ0
SHSS3124
97
Q6UWI1
MMP19
105
Q6UXW7
GSQS6193
108
Q6UW46
VGPW2523
315
Q6UXR2
LMNE6487
150
Q6UWG3
ALLA2487
243
Q6UWR0
GALI1870
121
Q6UWG4
FRSS1829
73
Q6UXQ5
MRSS6228
114
Q6UWK3
GRPR5811
159
Q6UWH2
AVLL5809
159
Q6UXV8
KCNQ2
95
Q6UY29
PIKR2786
93
Q5M770

-continued

S100 calcium binding protein A7-like 3
96
Q6Y2K9
GTWW5826 (LP5085 protein)
148
Q6UXP2
KTIS8219 (HCG2020043)
101
Q6UWC4
PPIF
128
Q6UXQ0
Micronovel
115
Q6UX30
SAMK3000
100
Q6UY40
VFLL3057
126
Q6UXY5
CVWG5837
125
Q6UWI7
VGSA5840
90
Q6UXY7
GHPS3125
140
Q6UXS6
GRTR3118
119
Q6UXQ7
PAMP6501
173
Q6UXR7
LTLL9335
104
Q6UXT5
VCEW9374
127
Q6UXP0
AHPA9419
99
Q6UWJ2
MDHV1887
108
Q6UWG9
HSAL5836
89
Q6UXS3
LHLC1946
108
Q6UWR2
CLECSF12
90
Q6UWQ9
LPPA601
120
Q6UW64
PINK1
109
Q6UY30
SERH2790
109
Q6UXP4
FLFF9364
118
Q6UWT3
APELIN
73
Q6UXV5
GLSH6409
118
Q6UWE9
SFVP2550
103
Q6UXT2
RRLF9220

| | | |
|---|---|---|
| 250 | | |
| Q6UXW0 | PTML5838 | 95 |
| Q6UWG0 | VLGN1945 | 125 |
| Q6UXS4 | AVPC1948 | 83 |
| Q6UWR5 | AWQG2491 | 83 |
| Q6UXR5 | PSVL6168 | 90 |
| Q6UY26 | LCII3035 | 78 |
| Q6UXW9 | PPRR6495 | 112 |
| Q6UWB8 | RLSC6348 | 110 |
| Q6UWS5 | CSRP2BP | 81 |
| Q6UX66 | GLLV3061 | 139 |
| Q6UXR0 | GWSI6489 | 91 |
| Q6UXU5 | C8orf2 | 86 |
| O76106 | CR1 C3b/C4b receptor SCR9 (or 16) C-term. exon SCR = short consensus repeat | 28 |
| Q6UWF8 | VSSW1971 | 120 |
| Q6UXR3 | KLIA6249 | 102 |
| Q6UWG2 | ALLW1950 | 84 |
| Q6UWS8 | GVEI466 | 52 |
| Q6UXV9 | ESFI5812 | 134 |
| Q6UWM8 | GNNC2999 | 100 |
| Q6UXR1 | AAGG6488 | 85 |
| Q6UWP5 | HHSL751 | 143 |

What is claimed is:

1. A method of screening for a candidate kinetic modulating monoclonal antibody that modulates binding between a first protein component and a second protein component of a signaling complex, comprising the steps of:
   (a) (i) measuring a binding affinity or binding rate parameter of a test antibody for said first component in the presence of said second component, and (ii) measuring a binding affinity or binding rate parameter of said test antibody for said first component in the absence of said second component; and
   (b) (i) measuring a binding affinity or binding rate parameter of a test antibody for said second component in the presence of said first component and (ii) measuring a binding affinity or binding rate parameter of said test antibody for said second component in the absence of said first component; and
   (c) identifying said test antibody as a candidate kinetic modulating antibody when said test antibody exhibits a 1.5-fold to 1000-fold difference in the binding affinity or binding rate parameter measured in steps (a) and (b),
   wherein the test antibody is identified as a candidate positive modulating antibody if the binding affinity or binding rate parameter measured in step (a)(i) or (b)(i) is about 1.5-fold to 1000-fold stronger than the binding affinity or binding rate parameter measured in step (a)(ii) or (b)(ii), and wherein at least one of the components or the test antibody is at a sub-saturating concentration relative to the other component or test antibody.

2. The method of claim 1 wherein the binding affinity or binding rate parameter measured in step (a)(i) or (b)(i) is about 2-fold to 200-fold stronger than the binding affinity or binding rate parameter measured in step (a)(ii) or (b)(ii).

3. The method of claim 1 wherein the binding affinity or binding rate parameter of the test antibody for the first component but not for the second component is measured.

4. The method of claim 3 wherein the binding affinity or binding rate parameter of the test antibody for the second component but not for the first component is measured.

5. The method of claim 4 wherein the binding affinity $K_D$ of the test antibody for a complex comprising the first and second components is about $10^{-5}$ $M^{-1}$ or less, and the test antibody does not detectably bind to either the first component alone or the second component alone.

6. The method of claim 4 wherein the test antibody (M) is identified as a candidate positive modulating antibody if a binding affinity or binding rate parameter selected from the group consisting of (A) the binding affinity or binding rate parameter of the test antibody for a complex comprising the first component (C1) and the second component (C2), optionally $K_{[C1C2]M}$, (B) the binding affinity or binding rate parameter of the first component for a complex comprising the antibody and the second component, optionally $K_{[MC2]C1}$, or (C) the binding affinity or binding rate parameter of the second component for a complex comprising the antibody and the first component, optionally $K_{[MC1]C2}$, is about 1.5-fold to 1000-fold stronger than a binding affinity or binding rate parameter selected from the group consisting of (1) the binding affinity or binding rate parameter of the test antibody for the second component alone, optionally $K_{MC2}$ or (2) the binding affinity or binding rate parameter of the test antibody for the first component alone, optionally $K_{MC1}$.

7. The method of claim 6 wherein the binding affinity or binding rate parameter of any one or more of (A), (B) or (C) is about 2-fold or 200-fold stronger than the binding affinity or binding rate parameter of any one or more of (1) or (2).

8. The method of claim 6 wherein the binding affinity or binding rate parameter of any one or more of (A), (B) or (C) is about 1.5-fold to 1000-fold stronger than the binding affinity or binding rate parameter of both (1) and (2).

9. The method of claim 6 wherein the binding affinity or binding rate parameter of any one or more of (A), (B) or (C) is about 2-fold to 200-fold stronger than the binding affinity or binding rate parameter of both (1) and (2).

10. The method of claim 6 wherein the binding affinity or binding rate parameter of (1) is stronger than the binding affinity of or binding rate parameter of (2).

11. The method of claim 6 wherein the binding affinity or binding rate parameter of (2) is stronger than the binding affinity or binding rate parameter of (1).

12. The method of claim 6 wherein the binding affinity is the equilibrium dissociation constant $K_D$, and any one or more of $K_{[C1C2]M}$, $K_{[MC2]C1}$, or $K_{[MC1]C2}$ is about 1.5-fold to 1000-fold lower than any one or more of $K_{MC2}$ or $K_{MC1}$.

13. The method of claim 12 wherein $K_{[C1C2]M}$ is about 1.5-fold to 1000-fold lower than $K_{MC2}$.

14. The method of claim 12 wherein $K_{[MC2]C1}$ is about 1.5-fold to 1000-fold lower than $K_{MC2}$.

15. The method of claim 12 wherein $K_{[MC1]C2}$ is about 1.5-fold to 1000-fold lower than $K_{MC2}$.

16. The method of claim 12 wherein $K_{[C1C2]M}$ is about 1.5-fold to 1000-fold lower than $K_{MC1}$.

17. The method of claim 12 wherein $K_{[MC2]C1}$ is about 1.5-fold to 1000-fold lower than $K_{MC1}$.

18. The method of claim 12 wherein $K_{[MC1]C2}$ is about 1.5-fold to 1000-fold lower than $K_{MC1}$.

19. The method of claim 6 wherein the binding affinity is the equilibrium association constant $K_A$, and any one or more of $K_{[C1C2]M}$, $K_{[MC2]C1}$, or $K_{[MC1]C2}$ is about 1.5-fold to 1000-fold higher than any one or more of $K_{MC2}$ or $K_{MC1}$.

20. The method of claim 1 wherein the antigen to which the test antibody binds is the first component and the test antibody is at a saturating concentration compared to the concentration of the first component.

21. The method of claim 1 wherein the antigen to which the test antibody binds is the second component and the test antibody is at a saturating concentration compared to the concentration of the second component.

22. The method of claim 20 wherein the concentration of the test antibody is greater than or equal to the $K_D$ of the test antibody for a complex comprising the first component and the second component.

23. The method of claim 22 wherein the concentration of the second component is less than the $K_D$ of the test antibody for the first component.

24. The method of claim 23 wherein the concentration of the first component is at a subsaturating concentration for the binding of first component to second component.

25. The method of claim 24 wherein the concentration of the first component is within the range of about $EC_{20}$ to $EC_{80}$ for the interaction of the first component with the second component.

26. The method of claim 1 wherein one or more concentrations of the test antibody is contacted with multiple different concentrations of the first component in the presence of one or more concentrations of the second component.

27. The method of claim 1 wherein one or more concentrations of the test antibody is contacted with multiple different concentrations of the second component in the presence of one or more concentrations of the first component.

28. The method of claim 2 wherein the test antibody is at a saturating concentration for a complex comprising the first component and the second component.

29. The method of claim 28 wherein the concentration of test antibody is greater than or equal to the $K_D$ of the test antibody for a complex comprising the first component and the second component.

30. The method of claim 29 wherein the concentration of the second component is greater than the $K_D$ of the second component for the first component.

31. The method of claim 30 wherein the concentration of the first component is a saturating concentration for the second component.

32. The method of claim 2 wherein the test antibody is at a subsaturating concentration for a complex comprising the first component and the second component.

33. The method of claim 32 wherein the concentration of the antibody is within the range of about $EC_{20}$ to $EC_{80}$ for the interaction of the first component with the second component.

34. The method of claim 33 wherein the concentration of the second component is greater than the $K_D$ of the second component for the first component.

35. The method of claim 34 wherein the concentration of the first component is a saturating concentration for the second component.

36. The method of claim 1 further comprising, prior to step (a), assaying a plurality of test antibodies for binding affinity to said first component, optionally with an equilibrium dissociation constant $K_D$ of $10^{-5}$M or stronger binding affinity.

37. The method of claim 1 further comprising, prior to step (b), assaying a plurality of test antibodies for binding affinity to said second component, optionally with an equilibrium dissociation constant $K_D$ of $10^{-5}$M or stronger binding affinity.

38. The method of claim 1 further comprising measuring a binding affinity or binding rate parameter of said first component for a binding partner wherein the binding partner is a decoy receptor, clearance receptor, or alternate signal pathway component, wherein the binding partner is not said second component, in the presence and absence of said test antibody.

39. The method of claim 38 comprising identifying a test antibody that does not significantly change the binding affinity or binding rate parameter of said first component for said binding partner.

40. The method of claim 1 wherein said test antibody is selected from the group consisting of antibody fragments, scFv, Fab, CDRs, rodent antibodies, mammalian antibodies, human antibodies, chimeric antibodies and humanized antibodies.

41. The method of claim 1 wherein said binding affinity or binding rate parameter is selected from the group consisting of equilibrium association constant $K_A$, equilibrium dissociation constant $K_D$, on-rate, off-rate and surrogate parameters for any of the foregoing.

42. The method of claim 41 wherein said surrogate parameter is the quantity or level of binding of said first component to said second component at a subsaturating concentration of either said first component or said second component.

43. The method of claim 1 wherein all of said test antibody, said first component, and said second component are in solution.

44. The method of claim 1 wherein one of said test antibody, said first component, and said second component is linked to a solid phase.

45. The method of claim 44 wherein the linkage is noncovalent.

46. The method of claim 44 wherein one of said test antibody, said first component, and said second component is coated on a bead.

47. The method of claim 1 wherein at least one of said first component or second component is expressed on a cell surface.

48. The method of claim 1 wherein said first component is expressed on a cell surface and said second component is expressed on a different cell surface.

49. The method of claim 1 wherein said first component is a soluble ligand and said second component is a membrane-bound receptor.

50. The method of claim 1 wherein said first component is a membrane-bound receptor and said second component is a soluble ligand.

51. The method of claim 1 wherein said first component is a membrane-bound ligand and said second component is a membrane-bound receptor.

52. The method of claim 50 or 51 wherein said membrane-bound receptor is selected from the group consisting of 7-transmembrane receptors, G-protein coupled receptors (GPCRs), adrenergic receptors, neurotransmitter receptors, olfactory receptors, opioid receptors, chemokine receptors, rhodopsin, receptor tyrosine kinases, growth factor receptors, integrins, and toll-like receptors.

53. The method of claim 1 wherein said first component is an enzyme and said second component is a substrate for said enzyme.

54. The method of claim 1 wherein said first component is a cytokine or chemokine and said second component is a receptor for said first component.

55. The method of claim 1 wherein said first component is a growth factor and said second component is a receptor for said first component.

56. The method of claim 1, wherein said first component is IL-1β and said second component is IL-1 receptor type I (IL-1RI).

57. The method of claim 1, wherein said first component is GCSF and said second component is GCSFR.

58. The method of claim 1, wherein said first component is GCSFR and said second component is GCSF.

59. The method of claim 1, wherein said first component is TNFα and said second component is TNFR1 or 2.

60. The method of claim 1, wherein said first component is TNFR1 or 2 and said second component is TNFα.

61. The method of claim 1 further comprising recloning the antibody identified in step (c) into an expression vector and expressing the antibody.

62. The method of claim 1 further comprising purifying the antibody identified in step (c).

63. The method of claim 1 further comprising sequencing the antibody identified in step (c).

64. The method of claim 1 further comprising adding or replacing an Fc region or fragment thereof of the test antibody.

65. The method of claim 1 further comprising formulating an antibody comprising at least six CDRs of the test antibody identified in step (c) in a sterile composition with a sterile pharmaceutically acceptable diluent.

66. The method of claim 1 further comprising administering an antibody comprising at least six CDRs of the test antibody identified in step (c) to an animal.

67. The method of claim 1 further comprising measuring the level of signaling mediated by said signaling complex in the presence and absence of the test antibody.

68. The method of claim 67 wherein the level of signaling mediated by the signaling complex is measured in a phosphorylation assay, ion flux assay, molecular transport assay, or gene expression assay.

69. The method of any of claims 67-68 wherein said test antibody increases the $EC_{50}$ of the first component of said signaling complex by about 1.5-fold to about 1000-fold.

70. The method of any of claims 67-68 wherein said test antibody does not significantly change the maximal agonist response of the signaling produced by said first component.

71. The method of any of claims 67-68 wherein said test antibody reduces the maximal agonist response of the signaling produced by said signaling complex by about 1.5-fold to 1000-fold.

72. The method of any of claims 67-68 wherein said test antibody decreases the EC50 of the signaling produced by said signaling complex by about 1.5-fold to about 1000-fold.

73. The method of any of claims 67-68 wherein said candidate antibody increases the maximal agonist response of the signaling produced by said first component by at least 10%.

74. The method of claim 1 wherein said candidate antibody does not significantly decrease clearance of said first component, said second component, or said signaling complex comprising said first and second components.

75. The method of claim 38 wherein the first component is IL-1 beta, the second component is IL-1R1, and the binding partner is either IL-1R2 or IL-1 accessory protein.

76. The method of claim 38 wherein the first component is TNF alpha, the second component is TNFR1, and the binding partner is TNFR2.

77. The method of claim 38 wherein the first component is TNF alpha, the second component is TNFR2, and the binding partner is TNFR1.

* * * * *

SEQUENCE LISTING

<160> NUMBER OF SEQ ID NOS: 88

<210> SEQ ID NO 1
<211> LENGTH: 233
<212> TYPE: PRT
<213> ORGANISM: Homo sapiens
<220> FEATURE:
<221> NAME/KEY: MISC_FEATURE

```
<223> OTHER INFORMATION: TNF-alpha
<300> PUBLICATION INFORMATION:
<308> DATABASE ACCESSION NUMBER: GenBank / NP_000585
<309> DATABASE ENTRY DATE: 2010-09-19
<313> RELEVANT RESIDUES IN SEQ ID NO: (1)..(233)

<400> SEQUENCE: 1

Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 2
<211> LENGTH: 15
<212> TYPE: PRT
<213> ORGANISM: Homo sapiens
<220> FEATURE:
<221> NAME/KEY: MISC_FEATURE
<223> OTHER INFORMATION: T cell receptor beta chain CD3 region; TCR CD3
<300> PUBLICATION INFORMATION:
<308> DATABASE ACCESSION NUMBER: GenBank / AAB27501
<309> DATABASE ENTRY DATE: 2000-07-14
<313> RELEVANT RESIDUES IN SEQ ID NO: (1)..(15)

<400> SEQUENCE: 2

Cys Ala Ser Ser Ser Asp Ser Gly Arg Leu His Asp Gln Tyr Phe
1               5                   10                  15

<210> SEQ ID NO 3
<211> LENGTH: 127
<212> TYPE: PRT
<213> ORGANISM: Homo sapiens
<220> FEATURE:
<221> NAME/KEY: MISC_FEATURE
<223> OTHER INFORMATION: CD3 antigen, delta subunit isoform B precursor
```

```
<300> PUBLICATION INFORMATION:
<308> DATABASE ACCESSION NUMBER: GenBank / NP_001035741
<309> DATABASE ENTRY DATE: 2010-09-12
<313> RELEVANT RESIDUES IN SEQ ID NO: (1)..(127)

<400> SEQUENCE: 3

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Thr Ala Asp Thr Gln
                85                  90                  95

Ala Leu Leu Arg Asn Asp Gln Val Tyr Gln Pro Leu Arg Asp Arg Asp
            100                 105                 110

Asp Ala Gln Tyr Ser His Leu Gly Gly Asn Trp Ala Arg Asn Lys
        115                 120                 125

<210> SEQ ID NO 4
<211> LENGTH: 171
<212> TYPE: PRT
<213> ORGANISM: Homo sapiens
<220> FEATURE:
<221> NAME/KEY: MISC_FEATURE
<223> OTHER INFORMATION: CD3 antigen, delta subunit isoform A precursor
<300> PUBLICATION INFORMATION:
<308> DATABASE ACCESSION NUMBER: GenBank / NP_000723
<309> DATABASE ENTRY DATE: 2010-09-12
<313> RELEVANT RESIDUES IN SEQ ID NO: (1)..(171)

<400> SEQUENCE: 4

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170
```

<210> SEQ ID NO 5
<211> LENGTH: 182
<212> TYPE: PRT
<213> ORGANISM: Homo sapiens
<220> FEATURE:
<221> NAME/KEY: MISC_FEATURE
<223> OTHER INFORMATION: T-cell surface glycoprotein CD3 gamma chain
<300> PUBLICATION INFORMATION:
<308> DATABASE ACCESSION NUMBER: Swiss-Prot / P09693
<309> DATABASE ENTRY DATE: 2010-08-10
<313> RELEVANT RESIDUES IN SEQ ID NO: (1)..(182)

<400> SEQUENCE: 5

```
Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180
```

<210> SEQ ID NO 6
<211> LENGTH: 182
<212> TYPE: PRT
<213> ORGANISM: Homo sapiens
<220> FEATURE:
<221> NAME/KEY: MISC_FEATURE
<223> OTHER INFORMATION: T-cell surface glycoprotein CD3 gamma chain precursor
<300> PUBLICATION INFORMATION:
<308> DATABASE ACCESSION NUMBER: GenBank / ACA05963
<309> DATABASE ENTRY DATE: 2008-02-22
<313> RELEVANT RESIDUES IN SEQ ID NO: (1)..(182)

<400> SEQUENCE: 6

```
Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
50                  55                  60
```

```
Leu Thr Glu Asp Lys Lys Lys Trp Asn Leu Gly Ser Asn Ala Lys Asp
 65                  70                  75                  80

Pro Arg Gly Met Tyr Gln Cys Lys Gly Ser Gln Asn Lys Ser Lys Pro
                 85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180
```

```
<210> SEQ ID NO 7
<211> LENGTH: 207
<212> TYPE: PRT
<213> ORGANISM: Homo sapiens
<220> FEATURE:
<221> NAME/KEY: MISC_FEATURE
<223> OTHER INFORMATION: T-cell surface glycoprotein CD3 epsilon chain
<300> PUBLICATION INFORMATION:
<308> DATABASE ACCESSION NUMBER: Swiss-Prot / P07766
<309> DATABASE ENTRY DATE: 2010-08-10
<313> RELEVANT RESIDUES IN SEQ ID NO: (1)..(207)

<400> SEQUENCE: 7

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
 50                  55                  60

Asn Ile Gly Gly Asp Glu Asp Lys Asn Ile Gly Ser Asp Glu Asp
 65                  70                  75                  80

His Leu Ser Leu Lys Glu Phe Ser Glu Leu Glu Gln Ser Gly Tyr Tyr
                 85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205
```

-continued

```
<210> SEQ ID NO 8
<211> LENGTH: 171
<212> TYPE: PRT
<213> ORGANISM: Homo sapiens
<300> PUBLICATION INFORMATION:
<308> DATABASE ACCESSION NUMBER: Swiss-Prot / P04234
<309> DATABASE ENTRY DATE: 2010-08-10
<313> RELEVANT RESIDUES IN SEQ ID NO: (1)..(171)

<400> SEQUENCE: 8

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 9
<211> LENGTH: 171
<212> TYPE: PRT
<213> ORGANISM: Homo sapiens
<220> FEATURE:
<221> NAME/KEY: MISC_FEATURE
<223> OTHER INFORMATION: T-cell surface glycoprotein CD3 delta chain
      precursor
<300> PUBLICATION INFORMATION:
<308> DATABASE ACCESSION NUMBER: GenBank / ACA05962
<309> DATABASE ENTRY DATE: 2008-02-20
<313> RELEVANT RESIDUES IN SEQ ID NO: (1)..(171)

<400> SEQUENCE: 9

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
```

```
                100                 105                 110
Ile Ala Thr Leu Leu Ala Leu Gly Val Phe Cys Phe Ala Gly His
            115                 120                 125

Glu Thr Gly Arg Leu Ser Gly Ala Ala Asp Thr Gln Ala Leu Leu Arg
        130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
            165                 170

<210> SEQ ID NO 10
<211> LENGTH: 164
<212> TYPE: PRT
<213> ORGANISM: Homo sapiens
<220> FEATURE:
<221> NAME/KEY: MISC_FEATURE
<223> OTHER INFORMATION: T-cell surface glycoprotein CD3 zeta chain
<300> PUBLICATION INFORMATION:
<308> DATABASE ACCESSION NUMBER: Swiss-Prot / P20963
<309> DATABASE ENTRY DATE: 2010-08-10
<313> RELEVANT RESIDUES IN SEQ ID NO: (1)..(164)

<400> SEQUENCE: 10

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 11
<211> LENGTH: 458
<212> TYPE: PRT
<213> ORGANISM: Homo sapiens
<220> FEATURE:
<221> NAME/KEY: MISC_FEATURE
<223> OTHER INFORMATION: CD4
<300> PUBLICATION INFORMATION:
<308> DATABASE ACCESSION NUMBER: Swiss-Prot / P01730
<309> DATABASE ENTRY DATE: 2010-09-07
<313> RELEVANT RESIDUES IN SEQ ID NO: (1)..(458)

<400> SEQUENCE: 11

Met Asn Arg Gly Val Pro Phe Arg His Leu Leu Leu Val Leu Gln Leu
1               5                   10                  15
```

-continued

Ala Leu Leu Pro Ala Ala Thr Gln Gly Lys Lys Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
                180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Lys Ser Trp Ile Thr Phe Asp Leu
                245                 250                 255

Lys Asn Lys Glu Val Ser Val Lys Arg Val Thr Gln Asp Pro Lys Leu
                260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
                340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
                420                 425                 430

Ser Gln Ile Lys Arg Leu Leu Ser Glu Lys Lys Thr Cys Gln Cys Pro

```
                    435                 440                 445
His Arg Phe Gln Lys Thr Cys Ser Pro Ile
    450                 455

<210> SEQ ID NO 12
<211> LENGTH: 458
<212> TYPE: PRT
<213> ORGANISM: Homo sapiens
<220> FEATURE:
<221> NAME/KEY: MISC_FEATURE
<223> OTHER INFORMATION: CD4 antigen (p55), isoform CRA_a
<300> PUBLICATION INFORMATION:
<308> DATABASE ACCESSION NUMBER: GenBank / EAW88739
<309> DATABASE ENTRY DATE: 2010-02-04
<313> RELEVANT RESIDUES IN SEQ ID NO: (1)..(458)

<400> SEQUENCE: 12

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320
```

```
Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
        435                 440                 445

His Arg Phe Gln Lys Thr Cys Ser Pro Ile
    450                 455

<210> SEQ ID NO 13
<211> LENGTH: 297
<212> TYPE: PRT
<213> ORGANISM: Homo sapiens
<220> FEATURE:
<221> NAME/KEY: MISC_FEATURE
<223> OTHER INFORMATION: CD20
<300> PUBLICATION INFORMATION:
<308> DATABASE ACCESSION NUMBER: Swiss-Prot / P11836
<309> DATABASE ENTRY DATE: 2010-09-07
<313> RELEVANT RESIDUES IN SEQ ID NO: (1)..(297)

<400> SEQUENCE: 13

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190
```

```
Ile Leu Ser Val Met Leu Ile Phe Ala Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
                260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295
```

<210> SEQ ID NO 14
<211> LENGTH: 297
<212> TYPE: PRT
<213> ORGANISM: Homo sapiens
<220> FEATURE:
<221> NAME/KEY: MISC_FEATURE
<223> OTHER INFORMATION: membrane-spanning 4-domains, subfamily A, member 1
<300> PUBLICATION INFORMATION:
<308> DATABASE ACCESSION NUMBER: NCBI / NP_690605
<309> DATABASE ENTRY DATE: 2010-08-29
<313> RELEVANT RESIDUES IN SEQ ID NO: (1)..(297)

<400> SEQUENCE: 14

```
Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Gln Glu Leu Val Ile
        195                 200                 205

Ala Gly Ile Val Glu Asn Glu Trp Lys Arg Thr Cys Ser Arg Pro Lys
    210                 215                 220
```

-continued

```
Ser Asn Ile Val Leu Leu Ser Ala Glu Glu Lys Glu Gln Thr Ile
225                 230                 235                 240

Glu Ile Lys Glu Glu Val Val Gly Leu Thr Glu Thr Ser Ser Gln Pro
            245                 250                 255

Lys Asn Glu Glu Asp Ile Glu Ile Pro Ile Gln Glu Glu Glu
            260                 265                 270

Glu Glu Thr Glu Thr Asn Phe Pro Glu Pro Pro Gln Asp Gln Glu Ser
            275                 280                 285

Ser Pro Ile Glu Asn Asp Ser Ser Pro
            290                 295

<210> SEQ ID NO 15
<211> LENGTH: 214
<212> TYPE: PRT
<213> ORGANISM: Homo sapiens
<220> FEATURE:
<221> NAME/KEY: MISC_FEATURE
<223> OTHER INFORMATION: membrane-spanning 4-domains, subfamily A,
      member 3 isoform a
<300> PUBLICATION INFORMATION:
<308> DATABASE ACCESSION NUMBER: NCBI / NP_006129
<309> DATABASE ENTRY DATE: 2010-09-12
<313> RELEVANT RESIDUES IN SEQ ID NO: (1)..(214)

<400> SEQUENCE: 15

Met Ala Ser His Glu Val Asp Asn Ala Glu Leu Gly Ser Ala Ser Ala
1               5                   10                  15

His Gly Thr Pro Gly Ser Glu Ala Gly Pro Glu Glu Leu Asn Thr Ser
            20                  25                  30

Val Tyr Gln Pro Ile Asp Gly Ser Pro Asp Tyr Gln Lys Ala Lys Leu
        35                  40                  45

Gln Val Leu Gly Ala Ile Gln Ile Leu Asn Ala Ala Met Ile Leu Ala
    50                  55                  60

Leu Gly Val Phe Leu Gly Ser Leu Gln Tyr Pro Tyr His Phe Gln Lys
65                  70                  75                  80

His Phe Phe Phe Phe Thr Phe Tyr Thr Gly Tyr Pro Ile Trp Gly Ala
                85                  90                  95

Val Phe Phe Cys Ser Ser Gly Thr Leu Ser Val Val Ala Gly Ile Lys
            100                 105                 110

Pro Thr Arg Thr Trp Ile Gln Asn Ser Phe Gly Met Asn Ile Ala Ser
        115                 120                 125

Ala Thr Ile Ala Leu Val Gly Thr Ala Phe Leu Ser Leu Asn Ile Ala
    130                 135                 140

Val Asn Ile Gln Ser Leu Arg Ser Cys His Ser Ser Ser Glu Ser Pro
145                 150                 155                 160

Asp Leu Cys Asn Tyr Met Gly Ser Ile Ser Asn Gly Met Val Ser Leu
                165                 170                 175

Leu Leu Ile Leu Thr Leu Leu Glu Leu Cys Val Thr Ile Ser Thr Ile
            180                 185                 190

Ala Met Trp Cys Asn Ala Asn Cys Cys Asn Ser Arg Glu Glu Ile Ser
        195                 200                 205

Ser Pro Pro Asn Ser Val
    210

<210> SEQ ID NO 16
<211> LENGTH: 168
<212> TYPE: PRT
<213> ORGANISM: Homo sapiens
<220> FEATURE:
```

<221> NAME/KEY: MISC_FEATURE
<223> OTHER INFORMATION: membrane-spanning 4-domains, subfamily A,
      member 3 isoform b
<300> PUBLICATION INFORMATION:
<308> DATABASE ACCESSION NUMBER: NCBI / NP_001026979
<309> DATABASE ENTRY DATE: 2010-09-20
<313> RELEVANT RESIDUES IN SEQ ID NO: (1)..(168)

<400> SEQUENCE: 16

```
Met Ala Ser His Glu Val Asp Asn Ala Glu Leu Gly Ser Ala Ser
1               5                   10                  15

His Gly Thr Pro Gly Ser Glu Ala Gly Pro Glu Leu Asn Thr Ser
            20                  25                  30

Val Tyr Gln Pro Ile Asp Gly Ser Pro Asp Tyr Gln Lys Ala Lys Leu
        35                  40                  45

Gln Val Leu Gly Phe Cys Ser Ser Gly Thr Leu Ser Val Val Ala Gly
    50                  55                  60

Ile Lys Pro Thr Arg Thr Trp Ile Gln Asn Ser Phe Gly Met Asn Ile
65                  70                  75                  80

Ala Ser Ala Thr Ile Ala Leu Val Gly Thr Ala Phe Leu Ser Leu Asn
                85                  90                  95

Ile Ala Val Asn Ile Gln Ser Leu Arg Ser Cys His Ser Ser Ser Glu
            100                 105                 110

Ser Pro Asp Leu Cys Asn Tyr Met Gly Ser Ile Ser Asn Gly Met Val
            115                 120                 125

Ser Leu Leu Leu Ile Leu Thr Leu Leu Glu Leu Cys Val Thr Ile Ser
        130                 135                 140

Thr Ile Ala Met Trp Cys Asn Ala Asn Cys Cys Asn Ser Arg Glu Glu
145                 150                 155                 160

Ile Ser Ser Pro Pro Asn Ser Val
                165
```

<210> SEQ ID NO 17
<211> LENGTH: 91
<212> TYPE: PRT
<213> ORGANISM: Homo sapiens
<220> FEATURE:
<221> NAME/KEY: MISC_FEATURE
<223> OTHER INFORMATION: membrane-spanning 4-domains, subfamily A,
      member 3 isoform c
<300> PUBLICATION INFORMATION:
<308> DATABASE ACCESSION NUMBER: NCBI / NP_001026836
<309> DATABASE ENTRY DATE: 2010-09-20
<313> RELEVANT RESIDUES IN SEQ ID NO: (1)..(91)

<400> SEQUENCE: 17

```
Met Asn Ile Ala Ser Ala Thr Ile Ala Leu Val Gly Thr Ala Phe Leu
1               5                   10                  15

Ser Leu Asn Ile Ala Val Asn Ile Gln Ser Leu Arg Ser Cys His Ser
            20                  25                  30

Ser Ser Glu Ser Pro Asp Leu Cys Asn Tyr Met Gly Ser Ile Ser Asn
        35                  40                  45

Gly Met Val Ser Leu Leu Leu Ile Leu Thr Leu Leu Glu Leu Cys Val
    50                  55                  60

Thr Ile Ser Thr Ile Ala Met Trp Cys Asn Ala Asn Cys Cys Asn Ser
65                  70                  75                  80

Arg Glu Glu Ile Ser Ser Pro Pro Asn Ser Val
                85                  90
```

<210> SEQ ID NO 18

-continued

```
<211> LENGTH: 232
<212> TYPE: PRT
<213> ORGANISM: Homo sapiens
<220> FEATURE:
<221> NAME/KEY: MISC_FEATURE
<223> OTHER INFORMATION: VEGF-A

<400> SEQUENCE: 18

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 19
<211> LENGTH: 412
<212> TYPE: PRT
<213> ORGANISM: Homo sapiens
<220> FEATURE:
<221> NAME/KEY: MISC_FEATURE
<223> OTHER INFORMATION: vascular endothelial growth factor A isoform a
      precursor
<300> PUBLICATION INFORMATION:
<308> DATABASE ACCESSION NUMBER: NCBI / NP_001020537
<309> DATABASE ENTRY DATE: 2010-09-20
<313> RELEVANT RESIDUES IN SEQ ID NO: (1)..(412)

<400> SEQUENCE: 19

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
            20                  25                  30

Gly Pro Glu Pro Ala Pro Gly Gly Val Glu Gly Val Gly Ala Arg
        35                  40                  45
```

```
Gly Val Ala Leu Lys Leu Phe Val Gln Leu Leu Gly Cys Ser Arg Phe
 50                  55                  60

Gly Gly Ala Val Val Arg Ala Gly Glu Ala Glu Pro Ser Gly Ala Ala
 65                  70                  75                  80

Arg Ser Ala Ser Ser Gly Arg Glu Glu Pro Gln Pro Glu Glu Gly Glu
                 85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
            340                 345                 350

Leu Met Pro Trp Ser Leu Pro Gly Pro His Pro Cys Gly Pro Cys Ser
        355                 360                 365

Glu Arg Arg Lys His Leu Phe Val Gln Asp Pro Gln Thr Cys Lys Cys
370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410

<210> SEQ ID NO 20
<211> LENGTH: 395
<212> TYPE: PRT
<213> ORGANISM: Homo sapiens
<220> FEATURE:
<221> NAME/KEY: MISC_FEATURE
<223> OTHER INFORMATION: vascular endothelial growth factor A isoform b
      precursor
<300> PUBLICATION INFORMATION:
```

<308> DATABASE ACCESSION NUMBER: NCBI / NP_003367
<309> DATABASE ENTRY DATE: 2010-09-20
<313> RELEVANT RESIDUES IN SEQ ID NO: (1)..(395)

<400> SEQUENCE: 20

```
Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
            35                  40                  45

Gly Val Ala Leu Lys Leu Phe Val Gln Leu Leu Gly Cys Ser Arg Phe
65              55                  60

Gly Gly Ala Val Val Arg Ala Gly Glu Ala Glu Pro Ser Gly Ala Ala
65              70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
                100                 105                 110

Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
        130                 135                 140

Arg Gly Gly Arg Val Ala Arg Arg Gly Ala Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
                180                 185                 190

Ala Leu Leu Leu Tyr Leu His His Ala Lys Trp Ser Gln Ala Ala Pro
            195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
                260                 265                 270

Glu Cys Val Pro Thr Glu Glu Ser Asn Ile Thr Met Gln Ile Met Arg
            275                 280                 285

Ile Lys Pro His Gln Gly Gln His Ile Gly Glu Met Ser Phe Leu Gln
290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Pro Cys Gly Pro Cys Ser Glu
                340                 345                 350

Arg Arg Lys His Leu Phe Val Gln Asp Pro Gln Thr Cys Lys Cys Ser
                355                 360                 365

Cys Lys Asn Thr Asp Ser Arg Cys Lys Ala Arg Gln Leu Glu Leu Asn
            370                 375                 380

Glu Arg Thr Cys Arg Cys Asp Lys Pro Arg Arg
```

```
385                 390                 395
```

<210> SEQ ID NO 21
<211> LENGTH: 389
<212> TYPE: PRT
<213> ORGANISM: Homo sapiens
<220> FEATURE:
<221> NAME/KEY: MISC_FEATURE
<223> OTHER INFORMATION: vascular endothelial growth factor A isoform c
      precursor
<300> PUBLICATION INFORMATION:
<308> DATABASE ACCESSION NUMBER: NCBI / NP_001020538
<309> DATABASE ENTRY DATE: 2010-09-12
<313> RELEVANT RESIDUES IN SEQ ID NO: (1)..(389)

<400> SEQUENCE: 21

```
Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
            195                 200                 205

Met Ala Glu Gly Gly Gly Gln Asn His His Glu Val Val Lys Phe Met
        210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
            275                 280                 285

Ile Lys Pro His Gln Gly Gln His Ile Gly Glu Met Ser Phe Leu Gln
        290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
```

```
                        325                 330                 335
Lys Ser Arg Pro Cys Gly Pro Cys Ser Glu Arg Arg Lys His Leu Phe
            340                 345                 350

Val Gln Asp Pro Gln Thr Cys Lys Cys Ser Cys Lys Asn Thr Asp Ser
            355                 360                 365

Arg Cys Lys Ala Arg Gln Leu Glu Leu Asn Glu Arg Thr Cys Arg Cys
    370                 375                 380

Asp Lys Pro Arg Arg
385

<210> SEQ ID NO 22
<211> LENGTH: 371
<212> TYPE: PRT
<213> ORGANISM: Homo sapiens
<220> FEATURE:
<221> NAME/KEY: MISC_FEATURE
<223> OTHER INFORMATION: vascular endothelial growth factor A isoform d
      precursor
<300> PUBLICATION INFORMATION:
<308> DATABASE ACCESSION NUMBER: NCBI / NP_001020539
<309> DATABASE ENTRY DATE: 2010-09-20
<313> RELEVANT RESIDUES IN SEQ ID NO: (1)..(371)

<400> SEQUENCE: 22

Met Thr Asp Arg Gln Thr Asp Thr Ala Pro Ser Pro Ser Tyr His Leu
1               5                   10                  15

Leu Pro Gly Arg Arg Thr Val Asp Ala Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Gly Arg Val Ala Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
```

-continued

```
                260                 265                 270
Glu Cys Val Pro Thr Glu Glu Ser Asn Ile Thr Met Gln Ile Met Arg
            275                 280                 285

Ile Lys Pro His Gln Gly Gln His Ile Gly Glu Met Ser Phe Leu Gln
        290                 295                 300

His Asn Lys Cys Glu Cys Arg Pro Lys Lys Asp Arg Ala Arg Gln Glu
305                 310                 315                 320

Asn Pro Cys Gly Pro Cys Ser Glu Arg Arg Lys His Leu Phe Val Gln
                325                 330                 335

Asp Pro Gln Thr Cys Lys Cys Ser Cys Lys Asn Thr Asp Ser Arg Cys
            340                 345                 350

Lys Ala Arg Gln Leu Glu Leu Asn Glu Arg Thr Cys Arg Cys Asp Lys
        355                 360                 365

Pro Arg Arg
    370

<210> SEQ ID NO 23
<211> LENGTH: 354
<212> TYPE: PRT
<213> ORGANISM: Homo sapiens
<220> FEATURE:
<221> NAME/KEY: MISC_FEATURE
<223> OTHER INFORMATION: vascular endothelial growth factor A isoform e
      precursor
<300> PUBLICATION INFORMATION:
<308> DATABASE ACCESSION NUMBER: NCBI / NP_001020540
<309> DATABASE ENTRY DATE: 2010-09-12
<313> RELEVANT RESIDUES IN SEQ ID NO: (1)..(354)

<400> SEQUENCE: 23

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
```

```
                210                 215                 220
Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
                260                 265                 270

Glu Cys Val Pro Thr Glu Glu Ser Asn Ile Thr Met Gln Ile Met Arg
                275                 280                 285

Ile Lys Pro His Gln Gly Gln His Ile Gly Glu Met Ser Phe Leu Gln
                290                 295                 300

His Asn Lys Cys Glu Cys Arg Pro Lys Lys Asp Arg Ala Arg Gln Glu
305                 310                 315                 320

Asn Pro Cys Gly Pro Cys Ser Glu Arg Arg Lys His Leu Phe Val Gln
                325                 330                 335

Asp Pro Gln Thr Cys Lys Cys Ser Cys Lys Asn Thr Asp Ser Arg Cys
                340                 345                 350

Lys Met

<210> SEQ ID NO 24
<211> LENGTH: 327
<212> TYPE: PRT
<213> ORGANISM: Homo sapiens
<220> FEATURE:
<221> NAME/KEY: MISC_FEATURE
<223> OTHER INFORMATION: vascular endothelial growth factor A isoform f
      precursor
<300> PUBLICATION INFORMATION:
<308> DATABASE ACCESSION NUMBER: NCBI / NP_001020541
<309> DATABASE ENTRY DATE: 2010-09-20
<313> RELEVANT RESIDUES IN SEQ ID NO: (1)..(327)

<400> SEQUENCE: 24

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
                20                  25                  30

Gly Pro Glu Pro Ala Pro Gly Gly Gly Val Glu Gly Val Gly Ala Arg
                35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
                100                 105                 110

Ala Arg Lys Pro Gly Ser Trp Thr Gly Glu Ala Ala Val Cys Ala Asp
                115                 120                 125

Ser Ala Pro Ala Ala Arg Ala Pro Gln Ala Leu Ala Arg Ala Ser Gly
                130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
                180                 185                 190
```

```
Ala Leu Leu Leu Tyr Leu His His Ala Lys Trp Ser Gln Ala Ala Pro
            195                 200                 205

Met Ala Glu Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
                260                 265                 270

Glu Cys Val Pro Thr Glu Glu Ser Asn Ile Thr Met Gln Ile Met Arg
            275                 280                 285

Ile Lys Pro His Gln Gly Gln His Ile Gly Glu Met Ser Phe Leu Gln
            290                 295                 300

His Asn Lys Cys Glu Cys Arg Pro Lys Lys Asp Arg Ala Arg Gln Glu
305                 310                 315                 320

Lys Cys Asp Lys Pro Arg Arg
                325

<210> SEQ ID NO 25
<211> LENGTH: 371
<212> TYPE: PRT
<213> ORGANISM: Homo sapiens
<220> FEATURE:
<221> NAME/KEY: MISC_FEATURE
<223> OTHER INFORMATION: vascular endothelial growth factor A isoform g
      precursor
<300> PUBLICATION INFORMATION:
<308> DATABASE ACCESSION NUMBER: NCBI / NP_001028928
<309> DATABASE ENTRY DATE: 2010-09-20
<313> RELEVANT RESIDUES IN SEQ ID NO: (1)..(371)

<400> SEQUENCE: 25

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
                20                  25                  30

Gly Pro Glu Pro Ala Pro Gly Gly Val Glu Gly Val Gly Ala Arg
            35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
                100                 105                 110

Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
            130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190
```

```
Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Asn Pro Cys Gly Pro Cys Ser Glu Arg Arg Lys His Leu Phe Val Gln
                325                 330                 335

Asp Pro Gln Thr Cys Lys Cys Ser Cys Lys Asn Thr Asp Ser Arg Cys
            340                 345                 350

Lys Ala Arg Gln Leu Glu Leu Asn Glu Arg Thr Cys Arg Ser Leu Thr
        355                 360                 365

Arg Lys Asp
    370

<210> SEQ ID NO 26
<211> LENGTH: 272
<212> TYPE: PRT
<213> ORGANISM: Homo sapiens
<220> FEATURE:
<221> NAME/KEY: MISC_FEATURE
<223> OTHER INFORMATION: CD25 (interleukin 2 receptor, alpha chain
      precursor)
<300> PUBLICATION INFORMATION:
<308> DATABASE ACCESSION NUMBER: NCBI / NP_000408
<309> DATABASE ENTRY DATE: 2010-09-12
<313> RELEVANT RESIDUES IN SEQ ID NO: (1)..(272)

<400> SEQUENCE: 26

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
    50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
    130                 135                 140
```

```
Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Thr Ser Gln
                180                 185                 190

Phe Pro Gly Glu Glu Lys Pro Gln Ala Ser Pro Glu Gly Arg Pro Glu
                195                 200                 205

Ser Glu Thr Ser Cys Leu Val Thr Thr Thr Asp Phe Gln Ile Gln Thr
                210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
                260                 265                 270

<210> SEQ ID NO 27
<211> LENGTH: 1255
<212> TYPE: PRT
<213> ORGANISM: Homo sapiens
<220> FEATURE:
<221> NAME/KEY: MISC_FEATURE
<223> OTHER INFORMATION: HER-2
<300> PUBLICATION INFORMATION:
<308> DATABASE ACCESSION NUMBER: GenBank / AAA75493
<309> DATABASE ENTRY DATE: 1995-09-18
<313> RELEVANT RESIDUES IN SEQ ID NO: (1)..(1255)

<400> SEQUENCE: 27

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
                35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65              70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
                100                 105                 110

Ala Leu Ala Val Leu Asp Asn Gly Asp Pro Leu Asn Asn Thr Thr Pro
                115                 120                 125

Val Thr Gly Ala Ser Pro Gly Gly Leu Arg Glu Leu Gln Leu Arg Ser
                130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
                180                 185                 190

His Pro Cys Ser Pro Met Cys Lys Gly Ser Arg Cys Trp Gly Glu Ser
                195                 200                 205
```

-continued

```
Ser Glu Asp Cys Gln Ser Leu Thr Arg Thr Val Cys Ala Gly Gly Cys
    210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
            260                 265                 270
Thr Tyr Asn Thr Asp Thr Phe Glu Ser Met Pro Asn Pro Glu Gly Arg
        275                 280                 285
Tyr Thr Phe Gly Ala Ser Cys Val Thr Ala Cys Pro Tyr Asn Tyr Leu
    290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
        355                 360                 365
Lys Ile Phe Gly Ser Leu Ala Phe Leu Pro Glu Ser Phe Asp Gly Asp
    370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
    530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
    610                 615                 620
Pro Cys Pro Ile Asn Cys Thr His Ser Cys Val Asp Leu Asp Asp Lys
```

```
               625                 630                 635                 640
Gly Cys Pro Ala Glu Gln Arg Ala Ser Pro Leu Thr Ser Ile Val Ser
                    645                 650                 655

Ala Val Val Gly Ile Leu Leu Val Val Leu Gly Val Val Phe Gly
                660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
            725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
            850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
        930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
                980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr
        1010                1015                 1020

Leu Val Pro Gln Gln Gly Phe Phe Cys Pro Asp Pro Ala Pro Gly
        1025                1030                 1035

Ala Gly Gly Met Val His His Arg His Arg Ser Ser Ser Thr Arg
        1040                1045                 1050
```

-continued

```
Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Ala Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 28
<211> LENGTH: 1091
<212> TYPE: PRT
<213> ORGANISM: Homo sapiens
<220> FEATURE:
<221> NAME/KEY: MISC_FEATURE
<223> OTHER INFORMATION: EGFR
<300> PUBLICATION INFORMATION:
<308> DATABASE ACCESSION NUMBER: GenBank / AAH94761
<309> DATABASE ENTRY DATE: 2005-07-28
<313> RELEVANT RESIDUES IN SEQ ID NO: (1)..(1091)

<400> SEQUENCE: 28

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110
```

-continued

```
Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Gly Gln Lys
130                 135                 140

Cys Asp Pro Ser Cys Pro Asn Gly Ser Cys Trp Gly Ala Gly Glu Glu
145                 150                 155                 160

Asn Cys Gln Lys Leu Thr Lys Ile Ile Cys Ala Gln Gln Cys Ser Gly
                165                 170                 175

Arg Cys Arg Gly Lys Ser Pro Ser Asp Cys Cys His Asn Gln Cys Ala
            180                 185                 190

Ala Gly Cys Thr Gly Pro Arg Glu Ser Asp Cys Leu Val Cys Arg Lys
        195                 200                 205

Phe Arg Asp Glu Ala Thr Cys Lys Asp Thr Cys Pro Pro Leu Met Leu
210                 215                 220

Tyr Asn Pro Thr Thr Tyr Gln Met Asp Val Asn Pro Glu Gly Lys Tyr
225                 230                 235                 240

Ser Phe Gly Ala Thr Cys Val Lys Lys Cys Pro Arg Asn Tyr Val Val
                245                 250                 255

Thr Asp His Gly Ser Cys Val Arg Ala Cys Gly Ala Asp Ser Tyr Glu
            260                 265                 270

Met Glu Glu Asp Gly Val Arg Lys Cys Lys Lys Cys Glu Gly Pro Cys
        275                 280                 285

Arg Lys Val Cys Asn Gly Ile Gly Ile Gly Glu Phe Lys Asp Ser Leu
290                 295                 300

Ser Ile Asn Ala Thr Asn Ile Lys His Phe Lys Asn Cys Thr Ser Ile
305                 310                 315                 320

Ser Gly Asp Leu His Ile Leu Pro Val Ala Phe Arg Gly Asp Ser Phe
                325                 330                 335

Thr His Thr Pro Pro Leu Asp Pro Gln Glu Leu Asp Ile Leu Lys Thr
            340                 345                 350

Val Lys Glu Ile Thr Gly Phe Leu Leu Ile Gln Ala Trp Pro Glu Asn
        355                 360                 365

Arg Thr Asp Leu His Ala Phe Glu Asn Leu Glu Ile Ile Arg Gly Arg
370                 375                 380

Thr Lys Gln His Gly Gln Phe Ser Leu Ala Val Val Ser Leu Asn Ile
385                 390                 395                 400

Thr Ser Leu Gly Leu Arg Ser Leu Lys Glu Ile Ser Asp Gly Asp Val
                405                 410                 415

Ile Ile Ser Gly Asn Lys Asn Leu Cys Tyr Ala Asn Thr Ile Asn Trp
            420                 425                 430

Lys Lys Leu Phe Gly Thr Ser Gly Gln Lys Thr Lys Ile Ile Ser Asn
        435                 440                 445

Arg Gly Glu Asn Ser Cys Lys Ala Thr Gly Gln Val Cys His Ala Leu
450                 455                 460

Cys Ser Pro Glu Gly Cys Trp Gly Pro Glu Pro Arg Asp Cys Val Ser
465                 470                 475                 480

Cys Arg Asn Val Ser Arg Gly Arg Glu Cys Val Asp Lys Cys Asn Leu
                485                 490                 495

Leu Glu Gly Glu Pro Arg Glu Phe Val Glu Asn Ser Glu Cys Ile Gln
            500                 505                 510

Cys His Pro Glu Cys Leu Pro Gln Ala Met Asn Ile Thr Cys Thr Gly
        515                 520                 525

Arg Gly Pro Asp Asn Cys Ile Gln Cys Ala His Tyr Ile Asp Gly Pro
```

```
                530                 535                 540
His Cys Val Lys Thr Cys Pro Ala Gly Val Met Gly Glu Asn Asn Thr
545                 550                 555                 560

Leu Val Trp Lys Tyr Ala Asp Ala Gly His Val Cys His Leu Cys His
                565                 570                 575

Pro Asn Cys Thr Tyr Gly Cys Thr Gly Pro Gly Leu Glu Gly Cys Pro
                580                 585                 590

Thr Asn Gly Pro Lys Ile Pro Ser Ile Ala Thr Gly Met Val Gly Ala
                595                 600                 605

Leu Leu Leu Leu Leu Val Val Ala Leu Gly Ile Gly Leu Phe Met Arg
                610                 615                 620

Arg Arg His Ile Val Arg Lys Arg Thr Leu Arg Arg Leu Leu Gln Glu
625                 630                 635                 640

Arg Glu Leu Val Glu Pro Leu Thr Pro Ser Gly Glu Ala Pro Asn Gln
                645                 650                 655

Ala Leu Leu Arg Ile Leu Lys Glu Thr Glu Phe Lys Lys Ile Lys Val
                660                 665                 670

Leu Gly Ser Gly Ala Phe Gly Thr Val Tyr Lys Gly Leu Trp Ile Pro
                675                 680                 685

Glu Gly Glu Lys Val Lys Ile Pro Val Ala Ile Lys Glu Leu Arg Glu
                690                 695                 700

Ala Thr Ser Pro Lys Ala Asn Lys Glu Ile Leu Asp Glu Ala Tyr Val
705                 710                 715                 720

Met Ala Ser Val Asp Asn Pro His Val Cys Arg Leu Leu Gly Ile Cys
                725                 730                 735

Leu Thr Ser Thr Val Gln Leu Ile Thr Gln Leu Met Pro Phe Gly Cys
                740                 745                 750

Leu Leu Asp Tyr Val Arg Glu His Lys Asp Asn Ile Gly Ser Gln Tyr
                755                 760                 765

Leu Leu Asn Trp Cys Val Gln Ile Ala Lys Gly Met Asn Tyr Leu Glu
                770                 775                 780

Asp Arg Arg Leu Val His Arg Asp Leu Ala Ala Arg Asn Val Leu Val
785                 790                 795                 800

Lys Thr Pro Gln His Val Lys Ile Thr Asp Phe Gly Leu Ala Lys Leu
                805                 810                 815

Leu Gly Ala Glu Glu Lys Glu Tyr His Ala Glu Gly Gly Lys Val Pro
                820                 825                 830

Ile Lys Trp Met Ala Leu Glu Ser Ile Leu His Arg Ile Tyr Thr His
                835                 840                 845

Gln Ser Asp Val Trp Ser Tyr Gly Val Thr Val Trp Glu Leu Met Thr
850                 855                 860

Phe Gly Ser Lys Pro Tyr Asp Gly Ile Pro Ala Ser Glu Ile Ser Ser
865                 870                 875                 880

Ile Leu Glu Lys Gly Glu Arg Leu Pro Gln Pro Pro Ile Cys Thr Ile
                885                 890                 895

Asp Val Tyr Met Ile Met Val Lys Cys Trp Met Ile Asp Ala Asp Ser
                900                 905                 910

Arg Pro Lys Phe Arg Glu Leu Ile Ile Glu Phe Ser Lys Met Ala Arg
                915                 920                 925

Asp Pro Gln Arg Tyr Leu Val Ile Gln Gly Asp Glu Arg Met His Leu
                930                 935                 940

Pro Ser Pro Thr Asp Ser Asn Phe Tyr Arg Ala Leu Met Asp Glu Glu
945                 950                 955                 960
```

-continued

```
Asp Met Asp Asp Val Val Asp Ala Asp Glu Tyr Leu Ile Pro Gln Gln
            965                 970                 975

Gly Phe Phe Ser Ser Pro Ser Thr Ser Arg Thr Pro Leu Leu Ser Ser
            980                 985                 990

Leu Ser Ala Thr Ser Asn Asn Ser  Thr Val Ala Cys Ile Asp Arg Asn
            995                 1000                1005

Gly Leu  Gln Ser Cys Pro Ile  Lys Glu Asp Ser Phe  Leu Gln Arg
    1010                1015                1020

Tyr Ser  Ser Asp Pro Thr Gly  Ala Leu Thr Glu Asp  Ser Ile Asp
    1025                1030                1035

Asp Thr  Phe Leu Pro Val Pro  Gly Glu Trp Leu Val  Trp Lys Gln
    1040                1045                1050

Ser Cys  Ser Ser Thr Ser Ser  Thr His Ser Ala Ala  Ala Ser Leu
    1055                1060                1065

Gln Cys  Pro Ser Gln Val Leu  Pro Pro Ala Ser Pro  Glu Gly Glu
    1070                1075                1080

Thr Val  Ala Asp Leu Gln Thr  Gln
    1085                1090

<210> SEQ ID NO 29
<211> LENGTH: 1210
<212> TYPE: PRT
<213> ORGANISM: Homo sapiens
<220> FEATURE:
<221> NAME/KEY: MISC_FEATURE
<223> OTHER INFORMATION: epidermal growth factor receptor isoform a
      precursor
<300> PUBLICATION INFORMATION:
<308> DATABASE ACCESSION NUMBER: NCBI / NP_005219
<309> DATABASE ENTRY DATE: 2010-09-12
<313> RELEVANT RESIDUES IN SEQ ID NO: (1)..(1210)

<400> SEQUENCE: 29

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
            85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
            165                 170                 175

Ser Met Asp Phe Gln Asn His Leu Gly Ser Cys Gln Lys Cys Asp Pro
            180                 185                 190
```

```
Ser Cys Pro Asn Gly Ser Cys Trp Gly Ala Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
        290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
        450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
            595                 600                 605
```

```
Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
```

-continued

```
              1025                1030                1035
Ser Ala Thr Ser Asn Asn Ser Thr Val Ala Cys Ile Asp Arg Asn
        1040                1045                1050

Gly Leu Gln Ser Cys Pro Ile Lys Glu Asp Ser Phe Leu Gln Arg
        1055                1060                1065

Tyr Ser Asp Pro Thr Gly Ala Leu Thr Glu Asp Ser Ile Asp
        1070                1075                1080

Asp Thr Phe Leu Pro Val Pro Glu Tyr Ile Asn Gln Ser Val Pro
        1085                1090                1095

Lys Arg Pro Ala Gly Ser Val Gln Asn Pro Val Tyr His Asn Gln
        1100                1105                1110

Pro Leu Asn Pro Ala Pro Ser Arg Asp Pro His Tyr Gln Asp Pro
        1115                1120                1125

His Ser Thr Ala Val Gly Asn Pro Glu Tyr Leu Asn Thr Val Gln
        1130                1135                1140

Pro Thr Cys Val Asn Ser Thr Phe Asp Ser Pro Ala His Trp Ala
        1145                1150                1155

Gln Lys Gly Ser His Gln Ile Ser Leu Asp Asn Pro Asp Tyr Gln
        1160                1165                1170

Gln Asp Phe Phe Pro Lys Glu Ala Lys Pro Asn Gly Ile Phe Lys
        1175                1180                1185

Gly Ser Thr Ala Glu Asn Ala Glu Tyr Leu Arg Val Ala Pro Gln
        1190                1195                1200

Ser Ser Glu Phe Ile Gly Ala
        1205                1210
```

<210> SEQ ID NO 30
<211> LENGTH: 628
<212> TYPE: PRT
<213> ORGANISM: Homo sapiens
<220> FEATURE:
<221> NAME/KEY: MISC_FEATURE
<223> OTHER INFORMATION: epidermal growth factor receptor isoform b precursor
<300> PUBLICATION INFORMATION:
<308> DATABASE ACCESSION NUMBER: NCBI / NP_958439
<309> DATABASE ENTRY DATE: 2010-09-12
<313> RELEVANT RESIDUES IN SEQ ID NO: (1)..(628)

<400> SEQUENCE: 30

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
```

```
            130                 135                 140
His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560
```

```
Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
        610                 615                 620

Thr Tyr Gly Ser
625

<210> SEQ ID NO 31
<211> LENGTH: 405
<212> TYPE: PRT
<213> ORGANISM: Homo sapiens
<220> FEATURE:
<221> NAME/KEY: MISC_FEATURE
<223> OTHER INFORMATION: epidermal growth factor receptor isoform c
      precursor
<300> PUBLICATION INFORMATION:
<308> DATABASE ACCESSION NUMBER: NCBI / NP_958440
<309> DATABASE ENTRY DATE: 2010-09-20
<313> RELEVANT RESIDUES IN SEQ ID NO: (1)..(405)

<400> SEQUENCE: 31

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255
```

```
Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
        290                 295                 300

Gly Ser Cys Val Arg Ala Cys Gly Ala Asp Ser Tyr Glu Met Glu Glu
305                 310                 315                 320

Asp Gly Val Arg Lys Cys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Leu Ser
            405

<210> SEQ ID NO 32
<211> LENGTH: 705
<212> TYPE: PRT
<213> ORGANISM: Homo sapiens
<220> FEATURE:
<221> NAME/KEY: MISC_FEATURE
<223> OTHER INFORMATION: epidermal growth factor receptor isoform d
      precursor
<300> PUBLICATION INFORMATION:
<308> DATABASE ACCESSION NUMBER: NCBI / NP_958441
<309> DATABASE ENTRY DATE: 2010-09-20
<313> RELEVANT RESIDUES IN SEQ ID NO: (1)..(705)

<400> SEQUENCE: 32

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175
```

-continued

```
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Glu Asn Cys Gln
            195                 200                 205
Lys Leu Thr Lys Ile Ile Cys Ala Gln Gln Cys Ser Gly Arg Cys Arg
            210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                    245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
            275                 280                 285
Ala Thr Cys Val Lys Lys Cys Pro Arg Asn Tyr Val Val Thr Asp His
            290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                    325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
            355                 360                 365
Leu His Ile Leu Pro Val Ala Phe Arg Gly Asp Ser Phe Thr His Thr
            370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                    405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                    485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
            530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                    565                 570                 575
Asp Asn Cys Ile Gln Cys Ala His Tyr Ile Asp Gly Pro His Cys Val
            580                 585                 590
```

-continued

```
Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
    610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                645                 650                 655

Gln Ser Gly Ser Pro Ala Ala Gln Glu Ser Cys Leu Gly Trp Ile Pro
            660                 665                 670

Ser Leu Leu Pro Ser Glu Phe Gln Leu Gly Trp Gly Gly Cys Ser His
            675                 680                 685

Leu His Ala Trp Pro Ser Ala Ser Val Ile Ile Thr Ala Ser Ser Cys
    690                 695                 700

His
705

<210> SEQ ID NO 33
<211> LENGTH: 364
<212> TYPE: PRT
<213> ORGANISM: Homo sapiens
<220> FEATURE:
<221> NAME/KEY: MISC_FEATURE
<223> OTHER INFORMATION: CD33 antigen isoform 1 precursor
<300> PUBLICATION INFORMATION:
<308> DATABASE ACCESSION NUMBER: NCBI / NP_001763
<309> DATABASE ENTRY DATE: 2010-08-04
<313> RELEVANT RESIDUES IN SEQ ID NO: (1)..(364)

<400> SEQUENCE: 33

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
                20                  25                  30

Glu Gly Leu Cys Val Leu Val Pro Cys Thr Phe Phe His Pro Ile Pro
            35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
```

```
                210                 215                 220
Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
                260                 265                 270

Leu Cys Leu Cys Leu Ile Phe Phe Ile Val Lys Thr His Arg Arg Lys
                275                 280                 285

Ala Ala Arg Thr Ala Val Gly Arg Asn Asp Thr His Pro Thr Thr Gly
                290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
                340                 345                 350

Asp Thr Ser Thr Glu Tyr Ser Glu Val Arg Thr Gln
                355                 360

<210> SEQ ID NO 34
<211> LENGTH: 237
<212> TYPE: PRT
<213> ORGANISM: Homo sapiens
<220> FEATURE:
<221> NAME/KEY: MISC_FEATURE
<223> OTHER INFORMATION: CD33 antigen isoform 2 precursor
<300> PUBLICATION INFORMATION:
<308> DATABASE ACCESSION NUMBER: NCBI / NP_001076087
<309> DATABASE ENTRY DATE: 2010-08-01
<313> RELEVANT RESIDUES IN SEQ ID NO: (1)..(237)

<400> SEQUENCE: 34

Met Pro Leu Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
                20                  25                  30

Asn Leu Thr Cys Ser Val Ser Trp Ala Cys Glu Gln Gly Thr Pro Pro
                35                  40                  45

Ile Phe Ser Trp Leu Ser Ala Ala Pro Thr Ser Leu Gly Pro Arg Thr
50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
                100                 105                 110

Thr Gly Ile Phe Pro Gly Asp Gly Ser Gly Lys Gln Glu Thr Arg Ala
                115                 120                 125

Gly Val Val His Gly Ala Ile Gly Gly Ala Gly Val Thr Ala Leu Leu
                130                 135                 140

Ala Leu Cys Leu Cys Leu Ile Phe Phe Ile Val Lys Thr His Arg Arg
145                 150                 155                 160

Lys Ala Ala Arg Thr Ala Val Gly Arg Asn Asp Thr His Pro Thr Thr
                165                 170                 175

Gly Ser Ala Ser Pro Lys His Gln Lys Lys Ser Lys Leu His Gly Pro
                180                 185                 190
```

```
Thr Glu Thr Ser Ser Cys Ser Gly Ala Ala Pro Thr Val Glu Met Asp
        195                 200                 205

Glu Glu Leu His Tyr Ala Ser Leu Asn Phe His Gly Met Asn Pro Ser
    210                 215                 220

Lys Asp Thr Ser Thr Glu Tyr Ser Glu Val Arg Thr Gln
225                 230                 235

<210> SEQ ID NO 35
<211> LENGTH: 221
<212> TYPE: PRT
<213> ORGANISM: Homo sapiens
<220> FEATURE:
<221> NAME/KEY: MISC_FEATURE
<223> OTHER INFORMATION: CD33 antigen (gp67), isoform CRA_a
<300> PUBLICATION INFORMATION:
<308> DATABASE ACCESSION NUMBER: GenBank / EAW71994
<309> DATABASE ENTRY DATE: 2006-12-18
<313> RELEVANT RESIDUES IN SEQ ID NO: (1)..(221)

<400> SEQUENCE: 35

Met Pro Leu Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
            20                  25                  30

Asn Leu Thr Cys Ser Val Ser Trp Ala Cys Glu Gln Gly Thr Pro Pro
        35                  40                  45

Ile Phe Ser Trp Leu Ser Ala Ala Pro Thr Ser Leu Gly Pro Arg Thr
    50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Trp Lys Gln Glu Thr Arg Ala
            100                 105                 110

Gly Val Val His Gly Ala Ile Gly Gly Ala Gly Val Thr Ala Leu Leu
        115                 120                 125

Ala Leu Cys Leu Cys Leu Ile Phe Phe Ile Val Lys Thr His Arg Arg
    130                 135                 140

Lys Ala Ala Arg Thr Ala Val Gly Arg Asn Asp Thr His Pro Thr Thr
145                 150                 155                 160

Gly Ser Ala Ser Pro Lys His Gln Lys Lys Ser Lys Leu His Gly Pro
                165                 170                 175

Thr Glu Thr Ser Ser Cys Ser Gly Ala Ala Pro Thr Val Glu Met Asp
            180                 185                 190

Glu Glu Leu His Tyr Ala Ser Leu Asn Phe His Gly Met Asn Pro Ser
        195                 200                 205

Lys Asp Thr Ser Thr Glu Tyr Ser Glu Val Arg Thr Gln
    210                 215                 220

<210> SEQ ID NO 36
<211> LENGTH: 364
<212> TYPE: PRT
<213> ORGANISM: Homo sapiens
<220> FEATURE:
<221> NAME/KEY: MISC_FEATURE
<223> OTHER INFORMATION: CD33 antigen (gp67), isoform CRA_b
<300> PUBLICATION INFORMATION:
<308> DATABASE ACCESSION NUMBER: GenBank / EAW71994
<309> DATABASE ENTRY DATE: 2006-12-18
<313> RELEVANT RESIDUES IN SEQ ID NO: (1)..(364)
```

<400> SEQUENCE: 36

```
Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
                100                 105                 110

Asn Gly Ser Tyr Phe Phe Arg Met Glu Arg Gly Ser Thr Lys Tyr Ser
            115                 120                 125

Tyr Lys Ser Pro Gln Leu Ser Val His Val Thr Asp Leu Thr His Arg
130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
            195                 200                 205

Asn Leu Thr Cys Gln Val Lys Phe Ala Gly Ala Gly Val Thr Thr Glu
210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360
```

<210> SEQ ID NO 37
<211> LENGTH: 237
<212> TYPE: PRT
<213> ORGANISM: Homo sapiens
<220> FEATURE:
<221> NAME/KEY: MISC_FEATURE
<223> OTHER INFORMATION: CD33 antigen (gp67), isoform CRA_c
<300> PUBLICATION INFORMATION:
<308> DATABASE ACCESSION NUMBER: GenBank / EAW71996
<309> DATABASE ENTRY DATE: 2006-12-18
<313> RELEVANT RESIDUES IN SEQ ID NO: (1)..(237)

<400> SEQUENCE: 37

```
Met Pro Leu Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
            20                  25                  30

Asn Leu Thr Cys Ser Val Ser Trp Ala Cys Glu Gln Gly Thr Pro Pro
        35                  40                  45

Ile Phe Ser Trp Leu Ser Ala Ala Pro Thr Ser Leu Gly Pro Arg Thr
    50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
            100                 105                 110

Thr Gly Ile Phe Pro Gly Asp Gly Ser Gly Lys Gln Glu Thr Arg Ala
        115                 120                 125

Gly Val Val His Gly Ala Ile Gly Gly Ala Gly Val Thr Ala Leu Leu
    130                 135                 140

Ala Leu Cys Leu Cys Leu Ile Phe Phe Ile Val Lys Thr His Arg Arg
145                 150                 155                 160

Lys Ala Ala Arg Thr Ala Val Gly Arg Asn Asp Thr His Pro Thr Thr
                165                 170                 175

Gly Ser Ala Ser Pro Lys His Gln Lys Lys Ser Lys Leu His Gly Pro
            180                 185                 190

Thr Glu Thr Ser Ser Cys Ser Gly Ala Ala Pro Thr Val Glu Met Asp
        195                 200                 205

Glu Glu Leu His Tyr Ala Ser Leu Asn Phe His Gly Met Asn Pro Ser
    210                 215                 220

Lys Asp Thr Ser Thr Glu Tyr Ser Glu Val Arg Thr Gln
225                 230                 235
```

<210> SEQ ID NO 38
<211> LENGTH: 61
<212> TYPE: PRT
<213> ORGANISM: Homo sapiens
<220> FEATURE:
<221> NAME/KEY: MISC_FEATURE
<223> OTHER INFORMATION: CD52 antigen precursor
<300> PUBLICATION INFORMATION:
<308> DATABASE ACCESSION NUMBER: NCBI / NP_001794
<309> DATABASE ENTRY DATE: 2010-07-04
<313> RELEVANT RESIDUES IN SEQ ID NO: (1)..(61)

<400> SEQUENCE: 38

```
Met Lys Arg Phe Leu Phe Leu Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Ala Ser Ser Asn Ile Ser Gly Gly Ile Phe Leu Phe
        35                  40                  45

Phe Val Ala Asn Ala Ile Ile His Leu Phe Cys Phe Ser
    50                  55                  60
```

```
<210> SEQ ID NO 39
<211> LENGTH: 193
<212> TYPE: PRT
<213> ORGANISM: Homo sapiens
<220> FEATURE:
<221> NAME/KEY: MISC_FEATURE
<223> OTHER INFORMATION: EPO - Erythropoietin
<300> PUBLICATION INFORMATION:
<308> DATABASE ACCESSION NUMBER: GenBank / CAA26095
<309> DATABASE ENTRY DATE: 2006-11-14
<313> RELEVANT RESIDUES IN SEQ ID NO: (1)..(193)

<400> SEQUENCE: 39

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Gln Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 40
<211> LENGTH: 110
<212> TYPE: PRT
<213> ORGANISM: Homo sapiens
<220> FEATURE:
<221> NAME/KEY: MISC_FEATURE
<223> OTHER INFORMATION: insulin
<300> PUBLICATION INFORMATION:
<308> DATABASE ACCESSION NUMBER: GenBank / AAA59172
<309> DATABASE ENTRY DATE: 2001-02-12
<313> RELEVANT RESIDUES IN SEQ ID NO: (1)..(110)

<400> SEQUENCE: 40

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
```

```
                50              55              60
Gln Val Glu Leu Gly Gly Pro Gly Ala Gly Ser Leu Gln Pro Leu
 65                  70                  75                  80

Ala Leu Glu Gly Ser Leu Gln Lys Arg Gly Ile Val Glu Gln Cys Cys
                     85                  90                  95

Thr Ser Ile Cys Ser Leu Tyr Gln Leu Glu Asn Tyr Cys Asn
                100                 105                 110

<210> SEQ ID NO 41
<211> LENGTH: 1382
<212> TYPE: PRT
<213> ORGANISM: Homo sapiens
<220> FEATURE:
<221> NAME/KEY: MISC_FEATURE
<223> OTHER INFORMATION: INSR
<300> PUBLICATION INFORMATION:
<308> DATABASE ACCESSION NUMBER: Swiss-Prot / P06213
<309> DATABASE ENTRY DATE: 2010-09-07
<313> RELEVANT RESIDUES IN SEQ ID NO: (1)..(1382)

<400> SEQUENCE: 41

Met Gly Thr Gly Gly Arg Arg Gly Ala Ala Ala Ala Pro Leu Leu Val
  1               5                  10                  15

Ala Val Ala Ala Leu Leu Leu Gly Ala Ala Gly His Leu Tyr Pro Gly
                 20                  25                  30

Glu Val Cys Pro Gly Met Asp Ile Arg Asn Asn Leu Thr Arg Leu His
                 35                  40                  45

Glu Leu Glu Asn Cys Ser Val Ile Glu Gly His Leu Gln Ile Leu Leu
                 50                  55                  60

Met Phe Lys Thr Arg Pro Glu Asp Phe Arg Asp Leu Ser Phe Pro Lys
 65                  70                  75                  80

Leu Ile Met Ile Thr Asp Tyr Leu Leu Leu Phe Arg Val Tyr Gly Leu
                 85                  90                  95

Glu Ser Leu Lys Asp Leu Phe Pro Asn Leu Thr Val Ile Arg Gly Ser
                100                 105                 110

Arg Leu Phe Phe Asn Tyr Ala Leu Val Ile Phe Glu Met Val His Leu
                115                 120                 125

Lys Glu Leu Gly Leu Tyr Asn Leu Met Asn Ile Thr Arg Gly Ser Val
                130                 135                 140

Arg Ile Glu Lys Asn Asn Glu Leu Cys Tyr Leu Ala Thr Ile Asp Trp
145                 150                 155                 160

Ser Arg Ile Leu Asp Ser Val Glu Asp Asn Tyr Ile Val Leu Asn Lys
                165                 170                 175

Asp Asp Asn Glu Glu Cys Gly Asp Ile Cys Pro Gly Thr Ala Lys Gly
                180                 185                 190

Lys Thr Asn Cys Pro Ala Thr Val Ile Asn Gly Gln Phe Val Glu Arg
                195                 200                 205

Cys Trp Thr His Ser His Cys Gln Lys Val Cys Pro Thr Ile Cys Lys
                210                 215                 220

Ser His Gly Cys Thr Ala Glu Gly Leu Cys Cys His Ser Glu Cys Leu
225                 230                 235                 240

Gly Asn Cys Ser Gln Pro Asp Asp Pro Thr Lys Cys Val Ala Cys Arg
                245                 250                 255

Asn Phe Tyr Leu Asp Gly Arg Cys Val Glu Thr Cys Pro Pro Pro Tyr
                260                 265                 270

Tyr His Phe Gln Asp Trp Arg Cys Val Asn Phe Ser Phe Cys Gln Asp
                275                 280                 285
```

-continued

```
Leu His His Lys Cys Lys Asn Ser Arg Arg Gln Gly Cys His Gln Tyr
    290                 295                 300
Val Ile His Asn Asn Lys Cys Ile Pro Glu Cys Pro Ser Gly Tyr Thr
305                 310                 315                 320
Met Asn Ser Ser Asn Leu Leu Cys Thr Pro Cys Leu Gly Pro Cys Pro
                325                 330                 335
Lys Val Cys His Leu Leu Glu Gly Glu Lys Thr Ile Asp Ser Val Thr
            340                 345                 350
Ser Ala Gln Glu Leu Arg Gly Cys Thr Val Ile Asn Gly Ser Leu Ile
        355                 360                 365
Ile Asn Ile Arg Gly Gly Asn Asn Leu Ala Ala Glu Leu Glu Ala Asn
370                 375                 380
Leu Gly Leu Ile Glu Glu Ile Ser Gly Tyr Leu Lys Ile Arg Arg Ser
385                 390                 395                 400
Tyr Ala Leu Val Ser Leu Ser Phe Phe Arg Lys Leu Arg Leu Ile Arg
                405                 410                 415
Gly Glu Thr Leu Glu Ile Gly Asn Tyr Ser Phe Tyr Ala Leu Asp Asn
            420                 425                 430
Gln Asn Leu Arg Gln Leu Trp Asp Trp Ser Lys His Asn Leu Thr Ile
        435                 440                 445
Thr Gln Gly Lys Leu Phe Phe His Tyr Asn Pro Lys Leu Cys Leu Ser
    450                 455                 460
Glu Ile His Lys Met Glu Glu Val Ser Gly Thr Lys Gly Arg Gln Glu
465                 470                 475                 480
Arg Asn Asp Ile Ala Leu Lys Thr Asn Gly Asp Gln Ala Ser Cys Glu
                485                 490                 495
Asn Glu Leu Leu Lys Phe Ser Tyr Ile Arg Thr Ser Phe Asp Lys Ile
            500                 505                 510
Leu Leu Arg Trp Glu Pro Tyr Trp Pro Pro Asp Phe Arg Asp Leu Leu
        515                 520                 525
Gly Phe Met Leu Phe Tyr Lys Glu Ala Pro Tyr Gln Asn Val Thr Glu
    530                 535                 540
Phe Asp Gly Gln Asp Ala Cys Gly Ser Asn Ser Trp Thr Val Val Asp
545                 550                 555                 560
Ile Asp Pro Pro Leu Arg Ser Asn Asp Pro Lys Ser Gln Asn His Pro
                565                 570                 575
Gly Trp Leu Met Arg Gly Leu Lys Pro Trp Thr Gln Tyr Ala Ile Phe
            580                 585                 590
Val Lys Thr Leu Val Thr Phe Ser Asp Glu Arg Arg Thr Tyr Gly Ala
        595                 600                 605
Lys Ser Asp Ile Ile Tyr Val Gln Thr Asp Ala Thr Asn Pro Ser Val
    610                 615                 620
Pro Leu Asp Pro Ile Ser Val Ser Asn Ser Ser Ser Gln Ile Ile Leu
625                 630                 635                 640
Lys Trp Lys Pro Pro Ser Asp Pro Asn Gly Asn Ile Thr His Tyr Leu
                645                 650                 655
Val Phe Trp Glu Arg Gln Ala Glu Asp Ser Glu Leu Phe Glu Leu Asp
            660                 665                 670
Tyr Cys Leu Lys Gly Leu Lys Leu Pro Ser Arg Thr Trp Ser Pro Pro
        675                 680                 685
Phe Glu Ser Glu Asp Ser Gln Lys His Asn Gln Ser Glu Tyr Glu Asp
    690                 695                 700
```

-continued

```
Ser Ala Gly Glu Cys Cys Ser Cys Pro Lys Thr Asp Ser Gln Ile Leu
705                 710                 715                 720

Lys Glu Leu Glu Glu Ser Ser Phe Arg Lys Thr Phe Glu Asp Tyr Leu
                725                 730                 735

His Asn Val Val Phe Val Pro Arg Lys Thr Ser Ser Gly Thr Gly Ala
            740                 745                 750

Glu Asp Pro Arg Pro Ser Arg Lys Arg Arg Ser Leu Gly Asp Val Gly
            755                 760                 765

Asn Val Thr Val Ala Val Pro Thr Val Ala Ala Phe Pro Asn Thr Ser
770                 775                 780

Ser Thr Ser Val Pro Thr Ser Pro Glu Glu His Arg Pro Phe Glu Lys
785                 790                 795                 800

Val Val Asn Lys Glu Ser Leu Val Ile Ser Gly Leu Arg His Phe Thr
                805                 810                 815

Gly Tyr Arg Ile Glu Leu Gln Ala Cys Asn Gln Asp Thr Pro Glu Glu
            820                 825                 830

Arg Cys Ser Val Ala Ala Tyr Val Ser Ala Arg Thr Met Pro Glu Ala
            835                 840                 845

Lys Ala Asp Asp Ile Val Gly Pro Val Thr His Glu Ile Phe Glu Asn
850                 855                 860

Asn Val His Leu Met Trp Gln Glu Pro Lys Glu Pro Asn Gly Leu
865                 870                 875                 880

Ile Val Leu Tyr Glu Val Ser Tyr Arg Arg Tyr Gly Asp Glu Glu Leu
                885                 890                 895

His Leu Cys Val Ser Arg Lys His Phe Ala Leu Glu Arg Gly Cys Arg
            900                 905                 910

Leu Arg Gly Leu Ser Pro Gly Asn Tyr Ser Val Arg Ile Arg Ala Thr
            915                 920                 925

Ser Leu Ala Gly Asn Gly Ser Trp Thr Glu Pro Thr Tyr Phe Tyr Val
930                 935                 940

Thr Asp Tyr Leu Asp Val Pro Ser Asn Ile Ala Lys Ile Ile Ile Gly
945                 950                 955                 960

Pro Leu Ile Phe Val Phe Leu Phe Ser Val Val Ile Gly Ser Ile Tyr
                965                 970                 975

Leu Phe Leu Arg Lys Arg Gln Pro Asp Gly Pro Leu Gly Pro Leu Tyr
            980                 985                 990

Ala Ser Ser Asn Pro Glu Tyr Leu Ser Ala Ser Asp Val Phe Pro Cys
            995                 1000                1005

Ser Val Tyr Val Pro Asp Glu Trp Glu Val Ser Arg Glu Lys Ile
    1010                1015                1020

Thr Leu Leu Arg Glu Leu Gly Gln Gly Ser Phe Gly Met Val Tyr
    1025                1030                1035

Glu Gly Asn Ala Arg Asp Ile Ile Lys Gly Glu Ala Glu Thr Arg
    1040                1045                1050

Val Ala Val Lys Thr Val Asn Glu Ser Ala Ser Leu Arg Glu Arg
    1055                1060                1065

Ile Glu Phe Leu Asn Glu Ala Ser Val Met Lys Gly Phe Thr Cys
    1070                1075                1080

His His Val Val Arg Leu Leu Gly Val Val Ser Lys Gly Gln Pro
    1085                1090                1095

Thr Leu Val Val Met Glu Leu Met Ala His Gly Asp Leu Lys Ser
    1100                1105                1110

Tyr Leu Arg Ser Leu Arg Pro Glu Ala Glu Asn Asn Pro Gly Arg
```

```
                1115                1120                1125

Pro Pro Pro Thr Leu Gln Glu Met Ile Gln Met Ala Ala Glu Ile
        1130                1135                1140

Ala Asp Gly Met Ala Tyr Leu Asn Ala Lys Lys Phe Val His Arg
        1145                1150                1155

Asp Leu Ala Ala Arg Asn Cys Met Val Ala His Asp Phe Thr Val
        1160                1165                1170

Lys Ile Gly Asp Phe Gly Met Thr Arg Asp Ile Tyr Glu Thr Asp
        1175                1180                1185

Tyr Tyr Arg Lys Gly Gly Lys Gly Leu Leu Pro Val Arg Trp Met
        1190                1195                1200

Ala Pro Glu Ser Leu Lys Asp Gly Val Phe Thr Thr Ser Ser Asp
        1205                1210                1215

Met Trp Ser Phe Gly Val Val Leu Trp Glu Ile Thr Ser Leu Ala
        1220                1225                1230

Glu Gln Pro Tyr Gln Gly Leu Ser Asn Glu Gln Val Leu Lys Phe
        1235                1240                1245

Val Met Asp Gly Gly Tyr Leu Asp Gln Pro Asp Asn Cys Pro Glu
        1250                1255                1260

Arg Val Thr Asp Leu Met Arg Met Cys Trp Gln Phe Asn Pro Lys
        1265                1270                1275

Met Arg Pro Thr Phe Leu Glu Ile Val Asn Leu Leu Lys Asp Asp
        1280                1285                1290

Leu His Pro Ser Phe Pro Glu Val Ser Phe Phe His Ser Glu Glu
        1295                1300                1305

Asn Lys Ala Pro Glu Ser Glu Glu Leu Glu Met Glu Phe Glu Asp
        1310                1315                1320

Met Glu Asn Val Pro Leu Asp Arg Ser Ser His Cys Gln Arg Glu
        1325                1330                1335

Glu Ala Gly Gly Arg Asp Gly Gly Ser Ser Leu Gly Phe Lys Arg
        1340                1345                1350

Ser Tyr Glu Glu His Ile Pro Tyr Thr His Met Asn Gly Gly Lys
        1355                1360                1365

Lys Asn Gly Arg Ile Leu Thr Leu Pro Arg Ser Asn Pro Ser
        1370                1375                1380

<210> SEQ ID NO 42
<211> LENGTH: 1370
<212> TYPE: PRT
<213> ORGANISM: Homo sapiens
<220> FEATURE:
<221> NAME/KEY: MISC_FEATURE
<223> OTHER INFORMATION: insulin receptor isoform Short precursor
<300> PUBLICATION INFORMATION:
<308> DATABASE ACCESSION NUMBER: NCBI / NP_001073285
<309> DATABASE ENTRY DATE: 2010-09-19
<313> RELEVANT RESIDUES IN SEQ ID NO: (1)..(1370)

<400> SEQUENCE: 42

Met Ala Thr Gly Gly Arg Arg Gly Ala Ala Ala Ala Pro Leu Leu Val
1               5                   10                  15

Ala Val Ala Ala Leu Leu Leu Gly Ala Ala Gly His Leu Tyr Pro Gly
                20                  25                  30

Glu Val Cys Pro Gly Met Asp Ile Arg Asn Asn Leu Thr Arg Leu His
            35                  40                  45

Glu Leu Glu Asn Cys Ser Val Ile Glu Gly His Leu Gln Ile Leu Leu
        50                  55                  60
```

```
Met Phe Lys Thr Arg Pro Glu Asp Phe Arg Asp Leu Ser Phe Pro Lys
 65                  70                  75                  80

Leu Ile Met Ile Thr Asp Tyr Leu Leu Leu Phe Arg Val Tyr Gly Leu
             85                  90                  95

Glu Ser Leu Lys Asp Leu Phe Pro Asn Leu Thr Val Ile Arg Gly Ser
            100                 105                 110

Arg Leu Phe Phe Asn Tyr Ala Leu Val Ile Phe Glu Met Val His Leu
        115                 120                 125

Lys Glu Leu Gly Leu Tyr Asn Leu Met Asn Ile Thr Arg Gly Ser Val
    130                 135                 140

Arg Ile Glu Lys Asn Asn Glu Leu Cys Tyr Leu Ala Thr Ile Asp Trp
145                 150                 155                 160

Ser Arg Ile Leu Asp Ser Val Glu Asp Asn Tyr Ile Val Leu Asn Lys
                165                 170                 175

Asp Asp Asn Glu Glu Cys Gly Asp Ile Cys Pro Gly Thr Ala Lys Gly
            180                 185                 190

Lys Thr Asn Cys Pro Ala Thr Val Ile Asn Gly Gln Phe Val Glu Arg
        195                 200                 205

Cys Trp Thr His Ser His Cys Gln Lys Val Cys Pro Thr Ile Cys Lys
    210                 215                 220

Ser His Gly Cys Thr Ala Glu Gly Leu Cys Cys His Ser Glu Cys Leu
225                 230                 235                 240

Gly Asn Cys Ser Gln Pro Asp Asp Pro Thr Lys Cys Val Ala Cys Arg
                245                 250                 255

Asn Phe Tyr Leu Asp Gly Arg Cys Val Glu Thr Cys Pro Pro Pro Tyr
            260                 265                 270

Tyr His Phe Gln Asp Trp Arg Cys Val Asn Phe Ser Phe Cys Gln Asp
        275                 280                 285

Leu His His Lys Cys Lys Asn Ser Arg Arg Gln Gly Cys His Gln Tyr
    290                 295                 300

Val Ile His Asn Asn Lys Cys Ile Pro Glu Cys Pro Ser Gly Tyr Thr
305                 310                 315                 320

Met Asn Ser Ser Asn Leu Leu Cys Thr Pro Cys Leu Gly Pro Cys Pro
                325                 330                 335

Lys Val Cys His Leu Leu Glu Gly Glu Lys Thr Ile Asp Ser Val Thr
            340                 345                 350

Ser Ala Gln Glu Leu Arg Gly Cys Thr Val Ile Asn Gly Ser Leu Ile
        355                 360                 365

Ile Asn Ile Arg Gly Gly Asn Asn Leu Ala Ala Glu Leu Glu Ala Asn
    370                 375                 380

Leu Gly Leu Ile Glu Glu Ile Ser Gly Tyr Leu Lys Ile Arg Arg Ser
385                 390                 395                 400

Tyr Ala Leu Val Ser Leu Ser Phe Phe Arg Lys Leu Arg Leu Ile Arg
                405                 410                 415

Gly Glu Thr Leu Glu Ile Gly Asn Tyr Ser Phe Tyr Ala Leu Asp Asn
            420                 425                 430

Gln Asn Leu Arg Gln Leu Trp Asp Trp Ser Lys His Asn Leu Thr Ile
        435                 440                 445

Thr Gln Gly Lys Leu Phe Phe His Tyr Asn Pro Lys Leu Cys Leu Ser
    450                 455                 460

Glu Ile His Lys Met Glu Glu Val Ser Gly Thr Lys Gly Arg Gln Glu
465                 470                 475                 480
```

Arg Asn Asp Ile Ala Leu Lys Thr Asn Gly Asp Gln Ala Ser Cys Glu
            485                 490                 495

Asn Glu Leu Leu Lys Phe Ser Tyr Ile Arg Thr Ser Phe Asp Lys Ile
        500                 505                 510

Leu Leu Arg Trp Glu Pro Tyr Trp Pro Asp Phe Arg Asp Leu Leu
        515                 520                 525

Gly Phe Met Leu Phe Tyr Lys Glu Ala Pro Tyr Gln Asn Val Thr Glu
        530                 535                 540

Phe Asp Gly Gln Asp Ala Cys Gly Ser Asn Ser Trp Thr Val Val Asp
545                 550                 555                 560

Ile Asp Pro Pro Leu Arg Ser Asn Asp Pro Lys Ser Gln Asn His Pro
                565                 570                 575

Gly Trp Leu Met Arg Gly Leu Lys Pro Trp Thr Gln Tyr Ala Ile Phe
            580                 585                 590

Val Lys Thr Leu Val Thr Phe Ser Asp Glu Arg Arg Thr Tyr Gly Ala
        595                 600                 605

Lys Ser Asp Ile Ile Tyr Val Gln Thr Asp Ala Thr Asn Pro Ser Val
        610                 615                 620

Pro Leu Asp Pro Ile Ser Val Ser Asn Ser Ser Ser Gln Ile Ile Leu
625                 630                 635                 640

Lys Trp Lys Pro Pro Ser Asp Pro Asn Gly Asn Ile Thr His Tyr Leu
                645                 650                 655

Val Phe Trp Glu Arg Gln Ala Glu Asp Ser Glu Leu Phe Glu Leu Asp
            660                 665                 670

Tyr Cys Leu Lys Gly Leu Lys Leu Pro Ser Arg Thr Trp Ser Pro Pro
        675                 680                 685

Phe Glu Ser Glu Asp Ser Gln Lys His Asn Gln Ser Glu Tyr Glu Asp
        690                 695                 700

Ser Ala Gly Glu Cys Cys Ser Cys Pro Lys Thr Asp Ser Gln Ile Leu
705                 710                 715                 720

Lys Glu Leu Glu Glu Ser Ser Phe Arg Lys Thr Phe Glu Asp Tyr Leu
                725                 730                 735

His Asn Val Val Phe Val Pro Arg Pro Ser Arg Lys Arg Arg Ser Leu
            740                 745                 750

Gly Asp Val Gly Asn Val Thr Val Ala Val Pro Thr Val Ala Ala Phe
        755                 760                 765

Pro Asn Thr Ser Ser Thr Ser Val Pro Thr Ser Pro Glu Glu His Arg
        770                 775                 780

Pro Phe Glu Lys Val Val Asn Lys Glu Ser Leu Val Ile Ser Gly Leu
785                 790                 795                 800

Arg His Phe Thr Gly Tyr Arg Ile Glu Leu Gln Ala Cys Asn Gln Asp
                805                 810                 815

Thr Pro Glu Glu Arg Cys Ser Val Ala Ala Tyr Val Ser Ala Arg Thr
            820                 825                 830

Met Pro Glu Ala Lys Ala Asp Asp Ile Val Gly Pro Val Thr His Glu
        835                 840                 845

Ile Phe Glu Asn Asn Val Val His Leu Met Trp Gln Glu Pro Lys Glu
        850                 855                 860

Pro Asn Gly Leu Ile Val Leu Tyr Glu Val Ser Tyr Arg Arg Tyr Gly
865                 870                 875                 880

Asp Glu Glu Leu His Leu Cys Val Ser Arg Lys His Phe Ala Leu Glu
                885                 890                 895

Arg Gly Cys Arg Leu Arg Gly Leu Ser Pro Gly Asn Tyr Ser Val Arg

-continued

```
              900                 905                 910
Ile Arg Ala Thr Ser Leu Ala Gly Asn Gly Ser Trp Thr Glu Pro Thr
            915                 920                 925

Tyr Phe Tyr Val Thr Asp Tyr Leu Asp Val Pro Ser Asn Ile Ala Lys
            930                 935                 940

Ile Ile Ile Gly Pro Leu Ile Phe Val Phe Leu Phe Ser Val Val Ile
945                 950                 955                 960

Gly Ser Ile Tyr Leu Phe Leu Arg Lys Arg Gln Pro Asp Gly Pro Leu
            965                 970                 975

Gly Pro Leu Tyr Ala Ser Ser Asn Pro Glu Tyr Leu Ser Ala Ser Asp
            980                 985                 990

Val Phe Pro Cys Ser Val Tyr Val Pro Asp Glu Trp Glu Val Ser Arg
            995                 1000                1005

Glu Lys Ile Thr Leu Leu Arg Glu Leu Gly Gln Gly Ser Phe Gly
            1010                1015                1020

Met Val Tyr Glu Gly Asn Ala Arg Asp Ile Ile Lys Gly Glu Ala
            1025                1030                1035

Glu Thr Arg Val Ala Val Lys Thr Val Asn Glu Ser Ala Ser Leu
            1040                1045                1050

Arg Glu Arg Ile Glu Phe Leu Asn Glu Ala Ser Val Met Lys Gly
            1055                1060                1065

Phe Thr Cys His His Val Val Arg Leu Leu Gly Val Val Ser Lys
            1070                1075                1080

Gly Gln Pro Thr Leu Val Val Met Glu Leu Met Ala His Gly Asp
            1085                1090                1095

Leu Lys Ser Tyr Leu Arg Ser Leu Arg Pro Glu Ala Glu Asn Asn
            1100                1105                1110

Pro Gly Arg Pro Pro Thr Leu Gln Glu Met Ile Gln Met Ala
            1115                1120                1125

Ala Glu Ile Ala Asp Gly Met Ala Tyr Leu Asn Ala Lys Lys Phe
            1130                1135                1140

Val His Arg Asp Leu Ala Ala Arg Asn Cys Met Val Ala His Asp
            1145                1150                1155

Phe Thr Val Lys Ile Gly Asp Phe Gly Met Thr Arg Asp Ile Tyr
            1160                1165                1170

Glu Thr Asp Tyr Tyr Arg Lys Gly Gly Lys Gly Leu Leu Pro Val
            1175                1180                1185

Arg Trp Met Ala Pro Glu Ser Leu Lys Asp Gly Val Phe Thr Thr
            1190                1195                1200

Ser Ser Asp Met Trp Ser Phe Gly Val Val Leu Trp Glu Ile Thr
            1205                1210                1215

Ser Leu Ala Glu Gln Pro Tyr Gln Gly Leu Ser Asn Glu Gln Val
            1220                1225                1230

Leu Lys Phe Val Met Asp Gly Gly Tyr Leu Asp Gln Pro Asp Asn
            1235                1240                1245

Cys Pro Glu Arg Val Thr Asp Leu Met Arg Met Cys Trp Gln Phe
            1250                1255                1260

Asn Pro Lys Met Arg Pro Thr Phe Leu Glu Ile Val Asn Leu Leu
            1265                1270                1275

Lys Asp Asp Leu His Pro Ser Phe Pro Glu Val Ser Phe Phe His
            1280                1285                1290

Ser Glu Glu Asn Lys Ala Pro Glu Ser Glu Glu Leu Glu Met Glu
            1295                1300                1305
```

-continued

```
Phe Glu Asp Met Glu Asn Val Pro Leu Asp Arg Ser Ser His Cys
    1310                1315                1320

Gln Arg Glu Glu Ala Gly Gly Arg Asp Gly Gly Ser Ser Leu Gly
    1325                1330                1335

Phe Lys Arg Ser Tyr Glu Glu His Ile Pro Tyr Thr His Met Asn
    1340                1345                1350

Gly Gly Lys Lys Asn Gly Arg Ile Leu Thr Leu Pro Arg Ser Asn
    1355                1360                1365

Pro Ser
    1370

<210> SEQ ID NO 43
<211> LENGTH: 1382
<212> TYPE: PRT
<213> ORGANISM: Homo sapiens
<220> FEATURE:
<221> NAME/KEY: MISC_FEATURE
<223> OTHER INFORMATION: human growth hormone
<300> PUBLICATION INFORMATION:
<308> DATABASE ACCESSION NUMBER: NCBI / NP_000199
<309> DATABASE ENTRY DATE: 2010-09-12
<313> RELEVANT RESIDUES IN SEQ ID NO: (1)..(1382)

<400> SEQUENCE: 43

Met Ala Thr Gly Gly Arg Arg Gly Ala Ala Ala Ala Pro Leu Leu Val
1               5                   10                  15

Ala Val Ala Ala Leu Leu Leu Gly Ala Ala Gly His Leu Tyr Pro Gly
                20                  25                  30

Glu Val Cys Pro Gly Met Asp Ile Arg Asn Asn Leu Thr Arg Leu His
            35                  40                  45

Glu Leu Glu Asn Cys Ser Val Ile Glu Gly His Leu Gln Ile Leu Leu
        50                  55                  60

Met Phe Lys Thr Arg Pro Glu Asp Phe Arg Asp Leu Ser Phe Pro Lys
65                  70                  75                  80

Leu Ile Met Ile Thr Asp Tyr Leu Leu Leu Phe Arg Val Tyr Gly Leu
                85                  90                  95

Glu Ser Leu Lys Asp Leu Phe Pro Asn Leu Thr Val Ile Arg Gly Ser
            100                 105                 110

Arg Leu Phe Phe Asn Tyr Ala Leu Val Ile Phe Glu Met Val His Leu
        115                 120                 125

Lys Glu Leu Gly Leu Tyr Asn Leu Met Asn Ile Thr Arg Gly Ser Val
    130                 135                 140

Arg Ile Glu Lys Asn Asn Glu Leu Cys Tyr Leu Ala Thr Ile Asp Trp
145                 150                 155                 160

Ser Arg Ile Leu Asp Ser Val Glu Asp Asn Tyr Ile Val Leu Asn Lys
                165                 170                 175

Asp Asp Asn Glu Glu Cys Gly Asp Ile Cys Pro Gly Thr Ala Lys Gly
            180                 185                 190

Lys Thr Asn Cys Pro Ala Thr Val Ile Asn Gly Gln Phe Val Glu Arg
        195                 200                 205

Cys Trp Thr His Ser His Cys Gln Lys Val Cys Pro Thr Ile Cys Lys
    210                 215                 220

Ser His Gly Cys Thr Ala Glu Gly Leu Cys Cys His Ser Glu Cys Leu
225                 230                 235                 240

Gly Asn Cys Ser Gln Pro Asp Asp Pro Thr Lys Cys Val Ala Cys Arg
                245                 250                 255
```

```
Asn Phe Tyr Leu Asp Gly Arg Cys Val Glu Thr Cys Pro Pro Tyr
            260                 265                 270

Tyr His Phe Gln Asp Trp Arg Cys Val Asn Phe Ser Phe Cys Gln Asp
        275                 280                 285

Leu His His Lys Cys Lys Asn Ser Arg Arg Gln Gly Cys His Gln Tyr
        290                 295                 300

Val Ile His Asn Asn Lys Cys Ile Pro Glu Cys Pro Ser Gly Tyr Thr
305                 310                 315                 320

Met Asn Ser Ser Asn Leu Leu Cys Thr Pro Cys Leu Gly Pro Cys Pro
                325                 330                 335

Lys Val Cys His Leu Leu Glu Gly Glu Lys Thr Ile Asp Ser Val Thr
                340                 345                 350

Ser Ala Gln Glu Leu Arg Gly Cys Thr Val Ile Asn Gly Ser Leu Ile
            355                 360                 365

Ile Asn Ile Arg Gly Gly Asn Asn Leu Ala Ala Glu Leu Glu Ala Asn
            370                 375                 380

Leu Gly Leu Ile Glu Glu Ile Ser Gly Tyr Leu Lys Ile Arg Arg Ser
385                 390                 395                 400

Tyr Ala Leu Val Ser Leu Ser Phe Phe Arg Lys Leu Arg Leu Ile Arg
                405                 410                 415

Gly Glu Thr Leu Glu Ile Gly Asn Tyr Ser Phe Tyr Ala Leu Asp Asn
            420                 425                 430

Gln Asn Leu Arg Gln Leu Trp Asp Trp Ser Lys His Asn Leu Thr Ile
            435                 440                 445

Thr Gln Gly Lys Leu Phe Phe His Tyr Asn Pro Lys Leu Cys Leu Ser
450                 455                 460

Glu Ile His Lys Met Glu Glu Val Ser Gly Thr Lys Gly Arg Gln Glu
465                 470                 475                 480

Arg Asn Asp Ile Ala Leu Lys Thr Asn Gly Asp Gln Ala Ser Cys Glu
                485                 490                 495

Asn Glu Leu Leu Lys Phe Ser Tyr Ile Arg Thr Ser Phe Asp Lys Ile
                500                 505                 510

Leu Leu Arg Trp Glu Pro Tyr Trp Pro Pro Asp Phe Arg Asp Leu Leu
                515                 520                 525

Gly Phe Met Leu Phe Tyr Lys Glu Ala Pro Tyr Gln Asn Val Thr Glu
            530                 535                 540

Phe Asp Gly Gln Asp Ala Cys Gly Ser Asn Ser Trp Thr Val Val Asp
545                 550                 555                 560

Ile Asp Pro Pro Leu Arg Ser Asn Asp Pro Lys Ser Gln Asn His Pro
                565                 570                 575

Gly Trp Leu Met Arg Gly Leu Lys Pro Trp Thr Gln Tyr Ala Ile Phe
            580                 585                 590

Val Lys Thr Leu Val Thr Phe Ser Asp Glu Arg Arg Thr Tyr Gly Ala
            595                 600                 605

Lys Ser Asp Ile Ile Tyr Val Gln Thr Asp Ala Thr Asn Pro Ser Val
            610                 615                 620

Pro Leu Asp Pro Ile Ser Val Ser Asn Ser Ser Ser Gln Ile Ile Leu
625                 630                 635                 640

Lys Trp Lys Pro Pro Ser Asp Pro Asn Gly Asn Ile Thr His Tyr Leu
                645                 650                 655

Val Phe Trp Glu Arg Gln Ala Glu Asp Ser Glu Leu Phe Glu Leu Asp
                660                 665                 670

Tyr Cys Leu Lys Gly Leu Lys Leu Pro Ser Arg Thr Trp Ser Pro Pro
```

-continued

```
            675                 680                 685
Phe Glu Ser Glu Asp Ser Gln Lys His Asn Gln Ser Glu Tyr Glu Asp
        690                 695                 700
Ser Ala Gly Glu Cys Cys Ser Cys Pro Lys Thr Asp Ser Gln Ile Leu
705                 710                 715                 720
Lys Glu Leu Glu Glu Ser Ser Phe Arg Lys Thr Phe Glu Asp Tyr Leu
                725                 730                 735
His Asn Val Val Phe Val Pro Arg Lys Thr Ser Ser Gly Thr Gly Ala
            740                 745                 750
Glu Asp Pro Arg Pro Ser Arg Lys Arg Arg Ser Leu Gly Asp Val Gly
        755                 760                 765
Asn Val Thr Val Ala Val Pro Thr Val Ala Ala Phe Pro Asn Thr Ser
770                 775                 780
Ser Thr Ser Val Pro Thr Ser Pro Glu Glu His Arg Pro Phe Glu Lys
785                 790                 795                 800
Val Val Asn Lys Glu Ser Leu Val Ile Ser Gly Leu Arg His Phe Thr
                805                 810                 815
Gly Tyr Arg Ile Glu Leu Gln Ala Cys Asn Gln Asp Thr Pro Glu Glu
            820                 825                 830
Arg Cys Ser Val Ala Ala Tyr Val Ser Ala Arg Thr Met Pro Glu Ala
        835                 840                 845
Lys Ala Asp Asp Ile Val Gly Pro Val Thr His Glu Ile Phe Glu Asn
850                 855                 860
Asn Val His Leu Met Trp Gln Glu Pro Lys Glu Pro Asn Gly Leu
865                 870                 875                 880
Ile Val Leu Tyr Glu Val Ser Tyr Arg Arg Tyr Gly Asp Glu Glu Leu
                885                 890                 895
His Leu Cys Val Ser Arg Lys His Phe Ala Leu Glu Arg Gly Cys Arg
            900                 905                 910
Leu Arg Gly Leu Ser Pro Gly Asn Tyr Ser Val Arg Ile Arg Ala Thr
        915                 920                 925
Ser Leu Ala Gly Asn Gly Ser Trp Thr Glu Pro Thr Tyr Phe Tyr Val
930                 935                 940
Thr Asp Tyr Leu Asp Val Pro Ser Asn Ile Ala Lys Ile Ile Ile Gly
945                 950                 955                 960
Pro Leu Ile Phe Val Phe Leu Phe Ser Val Val Ile Gly Ser Ile Tyr
                965                 970                 975
Leu Phe Leu Arg Lys Arg Gln Pro Asp Gly Pro Leu Gly Pro Leu Tyr
            980                 985                 990
Ala Ser Ser Asn Pro Glu Tyr Leu Ser Ala Ser Asp Val Phe Pro Cys
        995                 1000                1005
Ser Val Tyr Val Pro Asp Glu Trp Glu Val Ser Arg Glu Lys Ile
        1010                1015                1020
Thr Leu Leu Arg Glu Leu Gly Gln Gly Ser Phe Gly Met Val Tyr
        1025                1030                1035
Glu Gly Asn Ala Arg Asp Ile Ile Lys Gly Glu Ala Glu Thr Arg
        1040                1045                1050
Val Ala Val Lys Thr Val Asn Glu Ser Ala Ser Leu Arg Glu Arg
        1055                1060                1065
Ile Glu Phe Leu Asn Glu Ala Ser Val Met Lys Gly Phe Thr Cys
        1070                1075                1080
His His Val Val Arg Leu Leu Gly Val Val Ser Lys Gly Gln Pro
        1085                1090                1095
```

Thr Leu Val Val Met Glu Leu Met Ala His Gly Asp Leu Lys Ser
       1100                1105                1110

Tyr Leu Arg Ser Leu Arg Pro Glu Ala Glu Asn Asn Pro Gly Arg
       1115                1120                1125

Pro Pro Pro Thr Leu Gln Glu Met Ile Gln Met Ala Ala Glu Ile
       1130                1135                1140

Ala Asp Gly Met Ala Tyr Leu Asn Ala Lys Lys Phe Val His Arg
       1145                1150                1155

Asp Leu Ala Ala Arg Asn Cys Met Val Ala His Asp Phe Thr Val
       1160                1165                1170

Lys Ile Gly Asp Phe Gly Met Thr Arg Asp Ile Tyr Glu Thr Asp
       1175                1180                1185

Tyr Tyr Arg Lys Gly Gly Lys Gly Leu Leu Pro Val Arg Trp Met
       1190                1195                1200

Ala Pro Glu Ser Leu Lys Asp Gly Val Phe Thr Thr Ser Ser Asp
       1205                1210                1215

Met Trp Ser Phe Gly Val Val Leu Trp Glu Ile Thr Ser Leu Ala
       1220                1225                1230

Glu Gln Pro Tyr Gln Gly Leu Ser Asn Glu Gln Val Leu Lys Phe
       1235                1240                1245

Val Met Asp Gly Gly Tyr Leu Asp Gln Pro Asp Asn Cys Pro Glu
       1250                1255                1260

Arg Val Thr Asp Leu Met Arg Met Cys Trp Gln Phe Asn Pro Lys
       1265                1270                1275

Met Arg Pro Thr Phe Leu Glu Ile Val Asn Leu Leu Lys Asp Asp
       1280                1285                1290

Leu His Pro Ser Phe Pro Glu Val Ser Phe Phe His Ser Glu Glu
       1295                1300                1305

Asn Lys Ala Pro Glu Ser Glu Glu Leu Glu Met Glu Phe Glu Asp
       1310                1315                1320

Met Glu Asn Val Pro Leu Asp Arg Ser Ser His Cys Gln Arg Glu
       1325                1330                1335

Glu Ala Gly Gly Arg Asp Gly Gly Ser Ser Leu Gly Phe Lys Arg
       1340                1345                1350

Ser Tyr Glu Glu His Ile Pro Tyr Thr His Met Asn Gly Gly Lys
       1355                1360                1365

Lys Asn Gly Arg Ile Leu Thr Leu Pro Arg Ser Asn Pro Ser
       1370                1375                1380

<210> SEQ ID NO 44
<211> LENGTH: 192
<212> TYPE: PRT
<213> ORGANISM: Homo sapiens
<220> FEATURE:
<221> NAME/KEY: MISC_FEATURE
<223> OTHER INFORMATION: human growth hormone
<300> PUBLICATION INFORMATION:
<308> DATABASE ACCESSION NUMBER: GenBank / AAA72260
<309> DATABASE ENTRY DATE: 1993-04-27
<313> RELEVANT RESIDUES IN SEQ ID NO: (1)..(192)

<400> SEQUENCE: 44

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

```
Glu Glu Ala Tyr Ile Pro Lys Glu Gln Lys Tyr Ser Phe Leu Gln Asn
            35                  40                  45

Pro Gln Thr Ser Leu Cys Phe Ser Glu Ser Ile Pro Thr Pro Ser Asn
 50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                 85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
            115                 120                 125

Leu Glu Asp Gly Ser Pro Arg Thr Gly Gln Ile Phe Lys Gln Thr Tyr
            130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 45
<211> LENGTH: 144
<212> TYPE: PRT
<213> ORGANISM: Homo sapiens
<220> FEATURE:
<221> NAME/KEY: MISC_FEATURE
<223> OTHER INFORMATION: GM-CSF
<300> PUBLICATION INFORMATION:
<308> DATABASE ACCESSION NUMBER: GenBank / AAA52578
<309> DATABASE ENTRY DATE: 1994-11-08
<313> RELEVANT RESIDUES IN SEQ ID NO: (1)..(144)

<400> SEQUENCE: 45

```
Met Trp Leu Gln Ser Leu Leu Leu Leu Gly Thr Val Ala Cys Ser Ile
 1               5                  10                  15

Ser Ala Pro Ala Arg Ser Pro Ser Pro Ser Thr Gln Pro Trp Glu His
             20                  25                  30

Val Asn Ala Ile Gln Glu Ala Arg Arg Leu Leu Asn Leu Ser Arg Asp
             35                  40                  45

Thr Ala Ala Glu Met Asn Glu Thr Val Glu Val Ile Ser Glu Met Phe
 50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
            130                 135                 140
```

<210> SEQ ID NO 46
<211> LENGTH: 207
<212> TYPE: PRT
<213> ORGANISM: Homo sapiens
<300> PUBLICATION INFORMATION:
<308> DATABASE ACCESSION NUMBER: Swiss-Prot / P09919

<309> DATABASE ENTRY DATE: 2010-08-10
<313> RELEVANT RESIDUES IN SEQ ID NO: (1)..(207)

<400> SEQUENCE: 46

```
Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
                20                  25                  30

Leu Gly Pro Ala Ser Ser Leu Pro Gln Ser Phe Leu Leu Lys Cys Leu
            35                  40                  45

Glu Gln Val Arg Lys Ile Gln Gly Asp Gly Ala Ala Leu Gln Glu Lys
        50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205
```

<210> SEQ ID NO 47
<211> LENGTH: 153
<212> TYPE: PRT
<213> ORGANISM: Homo sapiens
<220> FEATURE:
<221> NAME/KEY: MISC_FEATURE
<223> OTHER INFORMATION: IL-2
<300> PUBLICATION INFORMATION:
<308> DATABASE ACCESSION NUMBER: GenBank / AAB46883
<309> DATABASE ENTRY DATE: 1997-02-11
<313> RELEVANT RESIDUES IN SEQ ID NO: (1)..(153)

<400> SEQUENCE: 47

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110
```

-continued

Val Leu Glu Leu Lys Gly Ser Glu Thr Thr Phe Met Cys Glu Tyr Ala
115                 120                 125

Asp Glu Thr Ala Thr Ile Val Glu Phe Leu Asn Arg Trp Ile Thr Phe
            130                 135                 140

Cys Gln Ser Ile Ile Ser Thr Leu Thr
145                 150

<210> SEQ ID NO 48
<211> LENGTH: 353
<212> TYPE: PRT
<213> ORGANISM: Homo sapiens
<220> FEATURE:
<221> NAME/KEY: MISC_FEATURE
<223> OTHER INFORMATION: TPO
<300> PUBLICATION INFORMATION:
<308> DATABASE ACCESSION NUMBER: GenBank / AAB33390
<309> DATABASE ENTRY DATE: 1995-07-27
<313> RELEVANT RESIDUES IN SEQ ID NO: (1)..(353)

<400> SEQUENCE: 48

Met Glu Leu Thr Glu Leu Leu Val Val Met Leu Leu Leu Thr Ala
1               5                   10                  15

Arg Leu Thr Leu Ser Ser Pro Ala Pro Pro Ala Cys Asp Leu Arg Val
            20                  25                  30

Leu Ser Lys Leu Leu Arg Asp Ser His Val Leu His Ser Arg Leu Ser
        35                  40                  45

Gln Cys Pro Glu Val His Pro Leu Pro Thr Pro Val Leu Leu Pro Ala
    50                  55                  60

Val Asp Phe Ser Leu Gly Glu Trp Lys Thr Gln Met Glu Glu Thr Lys
65                  70                  75                  80

Ala Gln Asp Ile Leu Gly Ala Val Thr Leu Leu Leu Glu Gly Val Met
                85                  90                  95

Ala Ala Arg Gly Gln Leu Gly Pro Thr Cys Leu Ser Ser Leu Leu Gly
            100                 105                 110

Gln Leu Ser Gly Gln Val Arg Leu Leu Leu Gly Ala Leu Gln Ser Leu
        115                 120                 125

Leu Gly Thr Gln Leu Pro Pro Gln Gly Arg Thr Thr Ala His Lys Asp
    130                 135                 140

Pro Asn Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg Arg Ala
                165                 170                 175

Pro Pro Thr Thr Ala Val Pro Ser Arg Thr Ser Leu Val Leu Thr Leu
            180                 185                 190

Asn Glu Leu Pro Asn Arg Thr Ser Gly Leu Leu Glu Thr Asn Phe Thr
        195                 200                 205

Ala Ser Ala Arg Thr Thr Gly Ser Gly Leu Leu Lys Trp Gln Gln Gly
    210                 215                 220

Phe Arg Ala Lys Ile Pro Gly Leu Leu Asn Gln Thr Ser Arg Ser Leu
225                 230                 235                 240

Asp Gln Ile Pro Gly Tyr Leu Asn Arg Ile His Glu Leu Leu Asn Gly
                245                 250                 255

Thr Arg Gly Leu Phe Pro Gly Pro Ser Arg Arg Thr Leu Gly Ala Pro
            260                 265                 270

Asp Ile Ser Ser Gly Thr Ser Asp Thr Gly Ser Leu Pro Pro Asn Leu
        275                 280                 285

```
Gln Pro Gly Tyr Ser Pro Ser Pro Thr His Pro Pro Thr Gly Gln Tyr
            290                 295                 300

Thr Leu Phe Pro Leu Pro Pro Thr Leu Pro Thr Pro Val Val Gln Leu
305                 310                 315                 320

His Pro Leu Leu Pro Asp Pro Ser Ala Pro Thr Pro Thr Pro Thr Ser
                325                 330                 335

Pro Leu Leu Asn Thr Ser Tyr Thr His Ser Gln Asn Leu Ser Gln Glu
                340                 345                 350

Gly

<210> SEQ ID NO 49
<211> LENGTH: 299
<212> TYPE: PRT
<213> ORGANISM: Homo sapiens
<220> FEATURE:
<221> NAME/KEY: MISC_FEATURE
<223> OTHER INFORMATION: NGF
<300> PUBLICATION INFORMATION:
<308> DATABASE ACCESSION NUMBER: GenBank / AAH32517
<309> DATABASE ENTRY DATE: 2008-06-09
<313> RELEVANT RESIDUES IN SEQ ID NO: (1)..(299)

<400> SEQUENCE: 49

Gly Arg Val Gly Ala Gly Ser Arg Arg Gly Ala Gln Arg Val Leu Ala
1               5                   10                  15

Ser Gly Arg Ala Val Gln Gly Ala Gly Trp His Ala Gly Pro Lys Leu
            20                  25                  30

Ser Ser Ala Ser Gly Pro Asn Asn Ser Phe Thr Lys Gly Ala Ala Phe
        35                  40                  45

Tyr Pro Gly His Thr Glu Val His Ser Val Met Ser Met Leu Phe Tyr
    50                  55                  60

Thr Leu Ile Thr Ala Phe Leu Ile Gly Ile Gln Ala Glu Pro His Ser
65                  70                  75                  80

Glu Ser Asn Val Pro Ala Gly His Thr Ile Pro Gln Val His Trp Thr
                85                  90                  95

Lys Leu Gln His Ser Leu Asp Thr Ala Leu Arg Arg Ala Arg Ser Ala
            100                 105                 110

Pro Ala Ala Ala Ile Ala Ala Arg Val Ala Gly Gln Thr Arg Asn Ile
        115                 120                 125

Thr Val Asp Pro Arg Leu Phe Lys Lys Arg Arg Leu Arg Ser Pro Arg
    130                 135                 140

Val Leu Phe Ser Thr Gln Pro Pro Arg Glu Ala Ala Asp Thr Gln Asp
145                 150                 155                 160

Leu Asp Phe Glu Val Gly Gly Ala Ala Pro Phe Asn Arg Thr His Arg
                165                 170                 175

Ser Lys Arg Ser Ser Ser His Pro Ile Phe His Arg Gly Glu Phe Ser
            180                 185                 190

Val Cys Asp Ser Val Ser Val Trp Val Gly Asp Lys Thr Thr Ala Thr
        195                 200                 205

Asp Ile Lys Gly Lys Glu Val Met Val Leu Gly Glu Val Asn Ile Asn
    210                 215                 220

Asn Ser Val Phe Lys Gln Tyr Phe Phe Glu Thr Lys Cys Arg Asp Pro
225                 230                 235                 240

Asn Pro Val Asp Ser Gly Cys Arg Gly Ile Asp Ser Lys His Trp Asn
                245                 250                 255

Ser Tyr Cys Thr Thr Thr His Thr Phe Val Lys Ala Leu Thr Met Asp
            260                 265                 270
```

```
Gly Lys Gln Ala Ala Trp Arg Phe Ile Arg Ile Asp Thr Ala Cys Val
            275                 280                 285

Cys Val Leu Ser Arg Lys Ala Val Arg Arg Ala
        290                 295
```

<210> SEQ ID NO 50
<211> LENGTH: 241
<212> TYPE: PRT
<213> ORGANISM: Homo sapiens
<220> FEATURE:
<221> NAME/KEY: MISC_FEATURE
<223> OTHER INFORMATION: nerve growth factor, beta polypeptide precursor
<300> PUBLICATION INFORMATION:
<308> DATABASE ACCESSION NUMBER: NCBI / NP_002497
<309> DATABASE ENTRY DATE: 2010-08-03
<313> RELEVANT RESIDUES IN SEQ ID NO: (1)..(241)

<400> SEQUENCE: 50

```
Met Ser Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
            20                  25                  30

Pro Gln Ala His Trp Thr Lys Leu Gln His Ser Leu Asp Thr Ala Leu
        35                  40                  45

Arg Arg Ala Arg Ser Ala Pro Ala Ala Ala Ile Ala Ala Arg Val Ala
    50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser Ser His Pro Ile Phe
        115                 120                 125

His Arg Gly Glu Phe Ser Val Cys Asp Ser Val Ser Val Trp Val Gly
    130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
        195                 200                 205

Lys Ala Leu Thr Met Asp Gly Lys Gln Ala Ala Trp Arg Phe Ile Arg
    210                 215                 220

Ile Asp Thr Ala Cys Val Cys Val Leu Ser Arg Lys Ala Val Arg Arg
225                 230                 235                 240

Ala
```

<210> SEQ ID NO 51
<211> LENGTH: 257
<212> TYPE: PRT
<213> ORGANISM: Homo sapiens
<220> FEATURE:
<221> NAME/KEY: MISC_FEATURE
<223> OTHER INFORMATION: NT-3
<300> PUBLICATION INFORMATION:
<308> DATABASE ACCESSION NUMBER: Swiss-Prot / P20783

<309> DATABASE ENTRY DATE: 2010-09-07
<313> RELEVANT RESIDUES IN SEQ ID NO: (1)..(257)

<400> SEQUENCE: 51

Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
50                  55                  60

Lys Ala Glu Ala Pro Arg Glu Pro Glu Arg Gly Gly Pro Ala Lys Ser
65                  70                  75                  80

Ala Phe Gln Pro Val Ile Ala Met Asp Thr Glu Leu Leu Arg Gln Gln
            85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
        115                 120                 125

Val Ala Asn Arg Thr Ser Arg Arg Lys Arg Tyr Ala Glu His Lys Ser
130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
            165                 170                 175

Gly Glu Ile Lys Thr Gly Asn Ser Pro Val Lys Gln Tyr Phe Tyr Glu
        180                 185                 190

Thr Arg Cys Lys Glu Ala Arg Pro Val Lys Asn Gly Cys Arg Gly Ile
        195                 200                 205

Asp Asp Lys His Trp Asn Ser Gln Cys Lys Thr Ser Gln Thr Tyr Val
    210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
            245                 250                 255

Thr

<210> SEQ ID NO 52
<211> LENGTH: 270
<212> TYPE: PRT
<213> ORGANISM: Homo sapiens
<220> FEATURE:
<221> NAME/KEY: MISC_FEATURE
<223> OTHER INFORMATION: neurotrophin 3 isoform 1 preproprotein
<300> PUBLICATION INFORMATION:
<308> DATABASE ACCESSION NUMBER: NCBI - NP_001096124
<309> DATABASE ENTRY DATE: 2010-07-25
<313> RELEVANT RESIDUES IN SEQ ID NO: (1)..(270)

<400> SEQUENCE: 52

Met Val Thr Phe Ala Thr Ile Leu Gln Val Asn Lys Val Met Ser Ile
1               5                   10                  15

Leu Phe Tyr Val Ile Phe Leu Ala Tyr Leu Arg Gly Ile Gln Gly Asn
            20                  25                  30

Asn Met Asp Gln Arg Ser Leu Pro Glu Asp Ser Leu Asn Ser Leu Ile
        35                  40                  45

-continued

```
Ile Lys Leu Ile Gln Ala Asp Ile Leu Lys Asn Lys Leu Ser Lys Gln
 50                  55                  60

Met Val Asp Val Lys Glu Asn Tyr Gln Ser Thr Leu Pro Lys Ala Glu
 65                  70                  75                  80

Ala Pro Arg Glu Pro Glu Arg Gly Gly Pro Ala Lys Ser Ala Phe Gln
                 85                  90                  95

Pro Val Ile Ala Met Asp Thr Glu Leu Leu Arg Gln Gln Arg Arg Tyr
            100                 105                 110

Asn Ser Pro Arg Val Leu Leu Ser Asp Ser Thr Pro Leu Glu Pro Pro
        115                 120                 125

Pro Leu Tyr Leu Met Glu Asp Tyr Val Gly Ser Pro Val Val Ala Asn
    130                 135                 140

Arg Thr Ser Arg Arg Lys Arg Tyr Ala Glu His Lys Ser His Arg Gly
145                 150                 155                 160

Glu Tyr Ser Val Cys Asp Ser Glu Ser Leu Trp Val Thr Asp Lys Ser
                165                 170                 175

Ser Ala Ile Asp Ile Arg Gly His Gln Val Thr Val Leu Gly Glu Ile
            180                 185                 190

Lys Thr Gly Asn Ser Pro Val Lys Gln Tyr Phe Tyr Glu Thr Arg Cys
        195                 200                 205

Lys Glu Ala Arg Pro Val Lys Asn Gly Cys Arg Gly Ile Asp Asp Lys
    210                 215                 220

His Trp Asn Ser Gln Cys Lys Thr Ser Gln Thr Tyr Val Arg Ala Leu
225                 230                 235                 240

Thr Ser Glu Asn Asn Lys Leu Val Gly Trp Arg Trp Ile Arg Ile Asp
                245                 250                 255

Thr Ser Cys Val Cys Ala Leu Ser Arg Lys Ile Gly Arg Thr
            260                 265                 270

<210> SEQ ID NO 53
<211> LENGTH: 257
<212> TYPE: PRT
<213> ORGANISM: Homo sapiens
<220> FEATURE:
<221> NAME/KEY: MISC_FEATURE
<223> OTHER INFORMATION: neurotrophin 3 isoform 2 preproprotein
<300> PUBLICATION INFORMATION:
<308> DATABASE ACCESSION NUMBER: NCBI / NP_002518
<309> DATABASE ENTRY DATE: 2010-09-19
<313> RELEVANT RESIDUES IN SEQ ID NO: (1)..(257)

<400> SEQUENCE: 53

Met Ser Ile Leu Phe Tyr Val Ile Phe Leu Ala Tyr Leu Arg Gly Ile
 1               5                  10                  15

Gln Gly Asn Asn Met Asp Gln Arg Ser Leu Pro Glu Asp Ser Leu Asn
                 20                  25                  30

Ser Leu Ile Ile Lys Leu Ile Gln Ala Asp Ile Leu Lys Asn Lys Leu
            35                  40                  45

Ser Lys Gln Met Val Asp Val Lys Glu Asn Tyr Gln Ser Thr Leu Pro
 50                  55                  60

Lys Ala Glu Ala Pro Arg Glu Pro Glu Arg Gly Gly Pro Ala Lys Ser
 65                  70                  75                  80

Ala Phe Gln Pro Val Ile Ala Met Asp Thr Glu Leu Leu Arg Gln Gln
                 85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
```

```
            115                 120                 125
Val Ala Asn Arg Thr Ser Arg Arg Lys Arg Tyr Ala Glu His Lys Ser
130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Arg Pro Val Lys Asn Gly Cys Arg Gly Ile
        195                 200                 205

Asp Asp Lys His Trp Asn Ser Gln Cys Lys Thr Ser Gln Thr Tyr Val
210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
                245                 250                 255

Thr
```

<210> SEQ ID NO 54
<211> LENGTH: 210
<212> TYPE: PRT
<213> ORGANISM: Homo sapiens
<220> FEATURE:
<221> NAME/KEY: MISC_FEATURE
<223> OTHER INFORMATION: NT-4
<300> PUBLICATION INFORMATION:
<308> DATABASE ACCESSION NUMBER: GenBank / AAA60154
<309> DATABASE ENTRY DATE: 1995-01-08
<313> RELEVANT RESIDUES IN SEQ ID NO: (1)..(210)

<400> SEQUENCE: 54

```
Met Leu Pro Leu Pro Ser Cys Ser Leu Pro Ile Leu Leu Leu Phe Leu
1               5                   10                  15

Leu Pro Ser Val Pro Ile Glu Ser Gln Pro Pro Pro Ser Thr Leu Pro
                20                  25                  30

Pro Phe Leu Ala Pro Glu Trp Asp Leu Leu Ser Pro Arg Val Val Leu
            35                  40                  45

Ser Arg Gly Ala Pro Ala Gly Pro Pro Leu Leu Phe Leu Leu Glu Ala
50                  55                  60

Gly Ala Phe Arg Glu Ser Ala Gly Ala Pro Ala Asn Arg Ser Arg Arg
65                  70                  75                  80

Gly Val Ser Glu Thr Ala Pro Ala Ser Arg Arg Gly Glu Leu Ala Val
                85                  90                  95

Cys Asp Ala Val Ser Gly Trp Val Thr Asp Arg Arg Thr Ala Val Asp
            100                 105                 110

Leu Arg Gly Arg Glu Val Glu Val Leu Gly Glu Val Pro Ala Ala Gly
        115                 120                 125

Gly Ser Pro Leu Arg Gln Tyr Phe Phe Glu Thr Arg Cys Lys Ala Asp
    130                 135                 140

Asn Ala Glu Glu Gly Gly Pro Gly Ala Gly Gly Gly Cys Arg Gly
145                 150                 155                 160

Val Asp Arg Arg His Trp Val Ser Glu Cys Lys Ala Lys Gln Ser Tyr
                165                 170                 175

Val Arg Ala Leu Thr Ala Asp Ala Gln Gly Arg Val Gly Trp Arg Trp
            180                 185                 190
```

-continued

```
Ile Arg Ile Asp Thr Ala Cys Val Cys Thr Leu Leu Ser Arg Thr Gly
        195                 200                 205

Arg Ala
    210

<210> SEQ ID NO 55
<211> LENGTH: 119
<212> TYPE: PRT
<213> ORGANISM: Homo sapiens
<220> FEATURE:
<221> NAME/KEY: MISC_FEATURE
<223> OTHER INFORMATION: Chain A, Brain Derived Neurotrophic Factor,
      Neurotrophin-4
<300> PUBLICATION INFORMATION:
<308> DATABASE ACCESSION NUMBER: GenPept / 1B8M_A
<309> DATABASE ENTRY DATE: 1999-04-01
<313> RELEVANT RESIDUES IN SEQ ID NO: (1)..(119)

<400> SEQUENCE: 55

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg
        115

<210> SEQ ID NO 56
<211> LENGTH: 130
<212> TYPE: PRT
<213> ORGANISM: Homo sapiens
<220> FEATURE:
<221> NAME/KEY: MISC_FEATURE
<223> OTHER INFORMATION: Chain B, Brain Derived Neurotrophic Factor,
      Neurotrophin-4
<300> PUBLICATION INFORMATION:
<308> DATABASE ACCESSION NUMBER: GenPept
<309> DATABASE ENTRY DATE: 1999-04-01
<313> RELEVANT RESIDUES IN SEQ ID NO: (1)..(130)

<400> SEQUENCE: 56

Gly Val Ser Glu Thr Ala Pro Ala Ser Arg Arg Gly Glu Leu Ala Val
1               5                   10                  15

Cys Asp Ala Val Ser Gly Trp Val Thr Asp Arg Arg Thr Ala Val Asp
            20                  25                  30

Leu Arg Gly Arg Glu Val Glu Val Leu Gly Glu Val Pro Ala Ala Gly
        35                  40                  45

Gly Ser Pro Leu Arg Gln Tyr Phe Phe Glu Thr Arg Cys Lys Ala Asp
    50                  55                  60

Asn Ala Glu Glu Gly Pro Gly Ala Gly Gly Gly Cys Arg Gly
65                  70                  75                  80

Val Asp Arg Arg His Trp Val Ser Glu Cys Lys Ala Lys Gln Ser Tyr
                85                  90                  95
```

-continued

```
Val Arg Ala Leu Thr Ala Asp Ala Gln Gly Arg Val Gly Trp Arg Trp
            100                 105                 110

Ile Arg Ile Asp Thr Ala Cys Val Cys Thr Leu Leu Ser Arg Thr Gly
            115                 120                 125

Arg Ala
    130

<210> SEQ ID NO 57
<211> LENGTH: 211
<212> TYPE: PRT
<213> ORGANISM: Homo sapiens
<220> FEATURE:
<221> NAME/KEY: MISC_FEATURE
<223> OTHER INFORMATION: GDNF
<300> PUBLICATION INFORMATION:
<308> DATABASE ACCESSION NUMBER: Swiss-Prot / P39905
<309> DATABASE ENTRY DATE: 2010-08-10
<313> RELEVANT RESIDUES IN SEQ ID NO: (1)..(211)

<400> SEQUENCE: 57

Met Lys Leu Trp Asp Val Val Ala Val Cys Leu Val Leu Leu His Thr
1               5                   10                  15

Ala Ser Ala Phe Pro Leu Pro Ala Gly Lys Arg Pro Pro Glu Ala Pro
            20                  25                  30

Ala Glu Asp Arg Ser Leu Gly Arg Arg Arg Ala Pro Phe Ala Leu Ser
        35                  40                  45

Ser Asp Ser Asn Met Pro Glu Asp Tyr Pro Asp Gln Phe Asp Asp Val
    50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
    130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Leu Ser Phe Leu Asp
            180                 185                 190

Asp Asn Leu Val Tyr His Ile Leu Arg Lys His Ser Ala Lys Arg Cys
        195                 200                 205

Gly Cys Ile
    210

<210> SEQ ID NO 58
<211> LENGTH: 211
<212> TYPE: PRT
<213> ORGANISM: Homo sapiens
<220> FEATURE:
<221> NAME/KEY: MISC_FEATURE
<223> OTHER INFORMATION: glial cell derived neurotrophic factor isoform
      1 preproprotein
<300> PUBLICATION INFORMATION:
<308> DATABASE ACCESSION NUMBER: NCBI / NP_000505
<309> DATABASE ENTRY DATE: 2010-09-20
```

```
<313> RELEVANT RESIDUES IN SEQ ID NO: (1)..(211)

<400> SEQUENCE: 58

Met Lys Leu Trp Asp Val Val Ala Val Cys Leu Val Leu Leu His Thr
1               5                   10                  15

Ala Ser Ala Phe Pro Leu Pro Ala Gly Lys Arg Pro Pro Glu Ala Pro
            20                  25                  30

Ala Glu Asp Arg Ser Leu Gly Arg Arg Ala Pro Phe Ala Leu Ser
        35                  40                  45

Ser Asp Ser Asn Met Pro Glu Asp Tyr Pro Asp Gln Phe Asp Asp Val
    50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
    130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Leu Ser Phe Leu Asp
            180                 185                 190

Asp Asn Leu Val Tyr His Ile Leu Arg Lys His Ser Ala Lys Arg Cys
        195                 200                 205

Gly Cys Ile
    210

<210> SEQ ID NO 59
<211> LENGTH: 185
<212> TYPE: PRT
<213> ORGANISM: Homo sapiens
<220> FEATURE:
<221> NAME/KEY: MISC_FEATURE
<223> OTHER INFORMATION: glial cell derived neurotrophic factor isoform
      2 precursor
<300> PUBLICATION INFORMATION:
<308> DATABASE ACCESSION NUMBER: NCBI / NP_954701
<309> DATABASE ENTRY DATE: 2010-09-20
<313> RELEVANT RESIDUES IN SEQ ID NO: (1)..(185)

<400> SEQUENCE: 59

Met Lys Leu Trp Asp Val Val Ala Val Cys Leu Val Leu Leu His Thr
1               5                   10                  15

Ala Ser Ala Phe Pro Leu Pro Ala Ala Asn Met Pro Glu Asp Tyr Pro
            20                  25                  30

Asp Gln Phe Asp Asp Val Met Asp Phe Ile Gln Ala Thr Ile Lys Arg
        35                  40                  45

Leu Lys Arg Ser Pro Asp Lys Gln Met Ala Val Leu Pro Arg Arg Glu
    50                  55                  60

Arg Asn Arg Gln Ala Ala Ala Ala Asn Pro Glu Asn Ser Arg Gly Lys
65                  70                  75                  80

Gly Arg Arg Gly Gln Arg Gly Lys Asn Arg Gly Cys Val Leu Thr Ala
                85                  90                  95
```

```
Ile His Leu Asn Val Thr Asp Leu Gly Leu Gly Tyr Glu Thr Lys Glu
            100                 105                 110

Glu Leu Ile Phe Arg Tyr Cys Ser Gly Ser Cys Asp Ala Ala Glu Thr
        115                 120                 125

Thr Tyr Asp Lys Ile Leu Lys Asn Leu Ser Arg Asn Arg Arg Leu Val
130                 135                 140

Ser Asp Lys Val Gly Gln Ala Cys Cys Arg Pro Ile Ala Phe Asp Asp
145                 150                 155                 160

Asp Leu Ser Phe Leu Asp Asp Asn Leu Val Tyr His Ile Leu Arg Lys
                165                 170                 175

His Ser Ala Lys Arg Cys Gly Cys Ile
                180                 185

<210> SEQ ID NO 60
<211> LENGTH: 133
<212> TYPE: PRT
<213> ORGANISM: Homo sapiens
<220> FEATURE:
<221> NAME/KEY: MISC_FEATURE
<223> OTHER INFORMATION: glial cell derived neurotrophic factor isoform
      3
<300> PUBLICATION INFORMATION:
<308> DATABASE ACCESSION NUMBER: NCBI / NP_954704
<309> DATABASE ENTRY DATE: 2010-03-14
<313> RELEVANT RESIDUES IN SEQ ID NO: (1)..(133)

<400> SEQUENCE: 60

Met Gly Cys Arg Gly Cys Leu Pro Gly Ala Ala Pro His Arg Val Arg
1               5                   10                  15

Leu Pro Ala Ala Asn Pro Glu Asn Ser Arg Gly Lys Gly Arg Arg Gly
            20                  25                  30

Gln Arg Gly Lys Asn Arg Gly Cys Val Leu Thr Ala Ile His Leu Asn
        35                  40                  45

Val Thr Asp Leu Gly Leu Gly Tyr Glu Thr Lys Glu Glu Leu Ile Phe
    50                  55                  60

Arg Tyr Cys Ser Gly Ser Cys Asp Ala Ala Glu Thr Thr Tyr Asp Lys
65                  70                  75                  80

Ile Leu Lys Asn Leu Ser Arg Asn Arg Arg Leu Val Ser Asp Lys Val
                85                  90                  95

Gly Gln Ala Cys Cys Arg Pro Ile Ala Phe Asp Asp Asp Leu Ser Phe
            100                 105                 110

Leu Asp Asp Asn Leu Val Tyr His Ile Leu Arg Lys His Ser Ala Lys
        115                 120                 125

Arg Cys Gly Cys Ile
    130

<210> SEQ ID NO 61
<211> LENGTH: 187
<212> TYPE: PRT
<213> ORGANISM: Homo sapiens
<220> FEATURE:
<221> NAME/KEY: MISC_FEATURE
<223> OTHER INFORMATION: IFN-beta
<300> PUBLICATION INFORMATION:
<308> DATABASE ACCESSION NUMBER: Swiss-Prot / P01574
<309> DATABASE ENTRY DATE: 2010-08-10
<313> RELEVANT RESIDUES IN SEQ ID NO: (1)..(187)

<400> SEQUENCE: 61

Met Thr Asn Lys Cys Leu Leu Gln Ile Ala Leu Leu Leu Cys Phe Ser
1               5                   10                  15
```

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
                180                 185

<210> SEQ ID NO 62
<211> LENGTH: 431
<212> TYPE: PRT
<213> ORGANISM: Homo sapiens
<220> FEATURE:
<221> NAME/KEY: MISC_FEATURE
<223> OTHER INFORMATION: TGF-beta
<300> PUBLICATION INFORMATION:
<308> DATABASE ACCESSION NUMBER: GenBank / AAA36738
<309> DATABASE ENTRY DATE: 1993-08-03
<313> RELEVANT RESIDUES IN SEQ ID NO: (1)..(431)

<400> SEQUENCE: 62

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

-continued

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 63
<211> LENGTH: 802
<212> TYPE: PRT
<213> ORGANISM: Homo sapiens
<220> FEATURE:
<221> NAME/KEY: MISC_FEATURE
<223> OTHER INFORMATION: FGFR4
<300> PUBLICATION INFORMATION:
<308> DATABASE ACCESSION NUMBER: GenBank / AAB25788
<309> DATABASE ENTRY DATE: 1993-06-28
<313> RELEVANT RESIDUES IN SEQ ID NO: (1)..(802)

<400> SEQUENCE: 63

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
                20                  25                  30

Cys Leu Ala Pro Ser Leu Glu Gln Gln Glu Gln Glu Leu Thr Val Ala
            35                  40                  45

Leu Gly Gln Pro Val Arg Leu Cys Cys Gly Arg Ala Glu Arg Gly Gly
        50                  55                  60

His Trp Tyr Lys Glu Gly Ser Arg Leu Ala Pro Ala Gly Arg Val Arg

```
                65                  70                  75                  80
Gly Trp Arg Gly Arg Leu Glu Ile Ala Ser Phe Leu Pro Glu Asp Ala
                    85                  90                  95
Gly Arg Tyr Leu Cys Leu Ala Arg Gly Ser Met Ile Val Leu Gln Asn
            100                 105                 110
Leu Thr Leu Ile Thr Gly Asp Ser Leu Thr Ser Ser Asn Asp Asp Glu
        115                 120                 125
Asp Pro Lys Ser His Arg Asp Pro Ser Asn Arg His Ser Tyr Pro Gln
    130                 135                 140
Gln Ala Pro Tyr Trp Thr His Pro Gln Arg Met Glu Lys Lys Leu His
145                 150                 155                 160
Ala Val Pro Ala Gly Asn Thr Val Lys Phe Arg Cys Pro Ala Ala Gly
                165                 170                 175
Asn Pro Thr Pro Thr Ile Arg Trp Leu Lys Asp Gly Gln Ala Phe His
            180                 185                 190
Gly Glu Asn Arg Ile Gly Gly Ile Arg Leu Arg His Gln His Trp Ser
        195                 200                 205
Leu Val Met Glu Ser Val Val Pro Ser Asp Arg Gly Thr Tyr Thr Cys
    210                 215                 220
Leu Val Glu Asn Ala Val Gly Ser Ile Arg Tyr Asn Tyr Leu Leu Asp
225                 230                 235                 240
Val Leu Glu Arg Ser Pro His Arg Pro Ile Leu Gln Ala Gly Leu Pro
                245                 250                 255
Ala Asn Thr Thr Ala Val Val Gly Ser Asp Val Glu Leu Leu Cys Lys
            260                 265                 270
Val Tyr Ser Asp Ala Gln Pro His Ile Gln Trp Leu Lys His Ile Val
        275                 280                 285
Ile Asn Gly Ser Ser Phe Gly Ala Asp Gly Phe Pro Tyr Val Gln Val
    290                 295                 300
Leu Lys Thr Ala Asp Ile Asn Ser Ser Glu Val Glu Val Leu Tyr Leu
305                 310                 315                 320
Arg Asn Val Ser Ala Glu Asp Ala Gly Glu Tyr Thr Cys Leu Ala Gly
                325                 330                 335
Asn Ser Ile Gly Leu Ser Tyr Gln Ser Ala Trp Leu Thr Val Leu Pro
            340                 345                 350
Glu Glu Asp Pro Thr Trp Thr Ala Ala Ala Pro Glu Ala Arg Tyr Thr
        355                 360                 365
Asp Ile Ile Leu Tyr Ala Ser Gly Ser Leu Ala Leu Ala Val Leu Leu
    370                 375                 380
Leu Leu Ala Gly Leu Tyr Arg Gly Gln Ala Leu His Gly Arg His Pro
385                 390                 395                 400
Arg Pro Pro Ala Thr Val Gln Lys Leu Ser Arg Phe Pro Leu Ala Arg
                405                 410                 415
Gln Phe Ser Leu Glu Ser Gly Ser Gly Lys Ser Ser Ser Ser Leu
            420                 425                 430
Val Arg Gly Val Arg Leu Ser Ser Gly Pro Ala Leu Leu Ala Gly
        435                 440                 445
Leu Val Ser Leu Asp Leu Pro Leu Asp Pro Leu Trp Glu Phe Pro Arg
    450                 455                 460
Asp Arg Leu Val Leu Gly Lys Pro Leu Gly Glu Gly Cys Phe Gly Gln
465                 470                 475                 480
Val Val Arg Ala Glu Ala Phe Gly Met Asp Pro Ala Arg Pro Asp Gln
                485                 490                 495
```

-continued

```
Ala Ser Thr Val Ala Val Lys Met Leu Lys Asp Asn Ala Ser Asp Lys
            500                 505                 510

Asp Leu Ala Asp Leu Val Ser Glu Met Glu Val Met Lys Leu Ile Gly
        515                 520                 525

Arg His Lys Asn Ile Ile Asn Leu Leu Gly Val Cys Thr Gln Glu Gly
    530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
        595                 600                 605

Ile His Arg Asp Leu Ala Ala Arg Asn Val Leu Val Thr Glu Asp Asn
    610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
        675                 680                 685

Pro Tyr Pro Gly Ile Pro Val Glu Glu Leu Phe Ser Leu Leu Arg Glu
    690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ser Gly
        755                 760                 765

Gly Asp Ala Ser Ser Thr Cys Ser Ser Asp Ser Val Phe Ser His
    770                 775                 780

Asp Pro Leu Pro Leu Gly Ser Ser Ser Phe Pro Phe Gly Ser Gly Val
785                 790                 795                 800

Gln Thr

<210> SEQ ID NO 64
<211> LENGTH: 802
<212> TYPE: PRT
<213> ORGANISM: Homo sapiens
<300> PUBLICATION INFORMATION:
<308> DATABASE ACCESSION NUMBER: NCBI / NP_998812
<309> DATABASE ENTRY DATE: 2010-09-08
<313> RELEVANT RESIDUES IN SEQ ID NO: (1)..(802)

<400> SEQUENCE: 64

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
```

-continued

```
            35                  40                  45
Leu Gly Gln Pro Val Arg Leu Cys Cys Gly Arg Ala Glu Arg Gly Gly
 50                  55                  60

His Trp Tyr Lys Glu Gly Ser Arg Leu Ala Pro Ala Gly Arg Val Arg
 65                  70                  75                  80

Gly Trp Arg Gly Arg Leu Glu Ile Ala Ser Phe Leu Pro Glu Asp Ala
                 85                  90                  95

Gly Arg Tyr Leu Cys Leu Ala Arg Gly Ser Met Ile Val Leu Gln Asn
                100                 105                 110

Leu Thr Leu Ile Thr Gly Asp Ser Leu Thr Ser Ser Asn Asp Asp Glu
                115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
                180                 185                 190

Gly Glu Asn Arg Ile Gly Gly Ile Arg Leu Arg His Gln His Trp Ser
                195                 200                 205

Leu Val Met Glu Ser Val Val Pro Ser Asp Arg Gly Thr Tyr Thr Cys
210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
                260                 265                 270

Val Tyr Ser Asp Ala Gln Pro His Ile Gln Trp Leu Lys His Ile Val
                275                 280                 285

Ile Asn Gly Ser Ser Phe Gly Ala Asp Gly Phe Pro Tyr Val Gln Val
290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
                340                 345                 350

Glu Glu Asp Pro Thr Trp Thr Ala Ala Pro Glu Ala Arg Tyr Thr
                355                 360                 365

Asp Ile Ile Leu Tyr Ala Ser Gly Ser Leu Ala Leu Ala Val Leu Leu
                370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                405                 410                 415

Gln Phe Ser Leu Glu Ser Gly Ser Gly Lys Ser Ser Ser Ser Leu
                420                 425                 430

Val Arg Gly Val Arg Leu Ser Ser Ser Gly Pro Ala Leu Leu Ala Gly
                435                 440                 445

Leu Val Ser Leu Asp Leu Pro Leu Asp Pro Leu Trp Glu Phe Pro Arg
450                 455                 460
```

```
Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
            485                 490                 495

Ala Ser Thr Val Ala Val Lys Met Leu Lys Asp Asn Ala Ser Asp Lys
        500                 505                 510

Asp Leu Ala Asp Leu Val Ser Glu Met Glu Val Met Lys Leu Ile Gly
    515                 520                 525

Arg His Lys Asn Ile Ile Asn Leu Leu Gly Val Cys Thr Gln Glu Gly
530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
        595                 600                 605

Ile His Arg Asp Leu Ala Ala Arg Asn Val Leu Val Thr Glu Asp Asn
    610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
        675                 680                 685

Pro Tyr Pro Gly Ile Pro Val Glu Glu Leu Phe Ser Leu Leu Arg Glu
    690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ser Gly
        755                 760                 765

Gly Asp Ala Ser Ser Thr Cys Ser Ser Ser Asp Ser Val Phe Ser His
    770                 775                 780

Asp Pro Leu Pro Leu Gly Ser Ser Ser Phe Pro Phe Gly Ser Gly Val
785                 790                 795                 800

Gln Thr

<210> SEQ ID NO 65
<211> LENGTH: 762
<212> TYPE: PRT
<213> ORGANISM: Homo sapiens
<220> FEATURE:
<221> NAME/KEY: MISC_FEATURE
<223> OTHER INFORMATION: fibroblast growth factor receptor 4 isoform 2
      precursor
<300> PUBLICATION INFORMATION:
<308> DATABASE ACCESSION NUMBER: NCBI / NP_075252
<309> DATABASE ENTRY DATE: 2010-09-20
<313> RELEVANT RESIDUES IN SEQ ID NO: (1)..(762)
```

```
<400> SEQUENCE: 65

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
        35                  40                  45

Leu Gly Gln Pro Val Arg Leu Cys Cys Gly Arg Ala Glu Arg Gly Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Gly Thr Gly Arg Ile Pro His Leu Thr Cys Asp Ser Leu Thr Pro Ala
        355                 360                 365

Gly Arg Thr Lys Ser Pro Thr Leu Gln Phe Ser Leu Glu Ser Gly Ser
    370                 375                 380

Ser Gly Lys Ser Ser Ser Ser Leu Val Arg Gly Val Arg Leu Ser Ser
385                 390                 395                 400

Ser Gly Pro Ala Leu Leu Ala Gly Leu Val Ser Leu Asp Leu Pro Leu
```

```
                       405                 410                 415
Asp Pro Leu Trp Glu Phe Pro Arg Asp Arg Leu Val Leu Gly Lys Pro
            420                 425                 430

Leu Gly Glu Gly Cys Phe Gly Gln Val Val Arg Ala Glu Ala Phe Gly
        435                 440                 445

Met Asp Pro Ala Arg Pro Asp Gln Ala Ser Thr Val Ala Val Lys Met
450                 455                 460

Leu Lys Asp Asn Ala Ser Asp Lys Asp Leu Ala Asp Leu Val Ser Glu
465                 470                 475                 480

Met Glu Val Met Lys Leu Ile Gly Arg His Lys Asn Ile Ile Asn Leu
                485                 490                 495

Leu Gly Val Cys Thr Gln Glu Gly Pro Leu Tyr Val Ile Val Glu Cys
            500                 505                 510

Ala Ala Lys Gly Asn Leu Arg Glu Phe Leu Arg Ala Arg Arg Pro Pro
        515                 520                 525

Gly Pro Asp Leu Ser Pro Asp Gly Pro Arg Ser Ser Glu Gly Pro Leu
    530                 535                 540

Ser Phe Pro Val Leu Val Ser Cys Ala Tyr Gln Val Ala Arg Gly Met
545                 550                 555                 560

Gln Tyr Leu Glu Ser Arg Lys Cys Ile His Arg Asp Leu Ala Ala Arg
                565                 570                 575

Asn Val Leu Val Thr Glu Asp Asn Val Met Lys Ile Ala Asp Phe Gly
            580                 585                 590

Leu Ala Arg Gly Val His His Ile Asp Tyr Tyr Lys Lys Thr Ser Asn
        595                 600                 605

Gly Arg Leu Pro Val Lys Trp Met Ala Pro Glu Ala Leu Phe Asp Arg
    610                 615                 620

Val Tyr Thr His Gln Ser Asp Val Trp Ser Phe Gly Ile Leu Leu Trp
625                 630                 635                 640

Glu Ile Phe Thr Leu Gly Gly Ser Pro Tyr Pro Gly Ile Pro Val Glu
                645                 650                 655

Glu Leu Phe Ser Leu Leu Arg Glu Gly His Arg Met Asp Arg Pro Pro
            660                 665                 670

His Cys Pro Pro Glu Leu Tyr Gly Leu Met Arg Glu Cys Trp His Ala
        675                 680                 685

Ala Pro Ser Gln Arg Pro Thr Phe Lys Gln Leu Val Glu Ala Leu Asp
    690                 695                 700

Lys Val Leu Leu Ala Val Ser Glu Glu Tyr Leu Asp Leu Arg Leu Thr
705                 710                 715                 720

Phe Gly Pro Tyr Ser Pro Ser Gly Gly Asp Ala Ser Ser Thr Cys Ser
                725                 730                 735

Ser Ser Asp Ser Val Phe Ser His Asp Pro Leu Pro Leu Gly Ser Ser
            740                 745                 750

Ser Phe Pro Phe Gly Ser Gly Val Gln Thr
        755                 760

<210> SEQ ID NO 66
<211> LENGTH: 493
<212> TYPE: PRT
<213> ORGANISM: Homo sapiens
<220> FEATURE:
<221> NAME/KEY: MISC_FEATURE
<223> OTHER INFORMATION: CETP
<300> PUBLICATION INFORMATION:
<308> DATABASE ACCESSION NUMBER: Swiss-Prot / P11597
<309> DATABASE ENTRY DATE: 2010-08-10
```

-continued

<313> RELEVANT RESIDUES IN SEQ ID NO: (1)..(493)

<400> SEQUENCE: 66

```
Met Leu Ala Ala Thr Val Leu Thr Leu Ala Leu Leu Gly Asn Ala His
1               5                   10                  15

Ala Cys Ser Lys Gly Thr Ser His Glu Ala Gly Ile Val Cys Arg Ile
            20                  25                  30

Thr Lys Pro Ala Leu Leu Val Leu Asn His Glu Thr Ala Lys Val Ile
            35                  40                  45

Gln Thr Ala Phe Gln Arg Ala Ser Tyr Pro Asp Ile Thr Gly Glu Lys
    50                  55                  60

Ala Met Met Leu Leu Gly Gln Val Lys Tyr Gly Leu His Asn Ile Gln
65                  70                  75                  80

Ile Ser His Leu Ser Ile Ala Ser Ser Gln Val Glu Leu Val Glu Ala
                85                  90                  95

Lys Ser Ile Asp Val Ser Ile Gln Asn Val Ser Val Phe Lys Gly
            100                 105                 110

Thr Leu Lys Tyr Gly Tyr Thr Thr Ala Trp Trp Leu Gly Ile Asp Gln
            115                 120                 125

Ser Ile Asp Phe Glu Ile Asp Ser Ala Ile Asp Leu Gln Ile Asn Thr
    130                 135                 140

Gln Leu Thr Cys Asp Ser Gly Arg Val Arg Thr Asp Ala Pro Asp Cys
145                 150                 155                 160

Tyr Leu Ser Phe His Lys Leu Leu His Leu Gln Gly Glu Arg Glu
                165                 170                 175

Pro Gly Trp Ile Lys Gln Leu Phe Thr Asn Phe Ile Ser Phe Thr Leu
            180                 185                 190

Lys Leu Val Leu Lys Gly Gln Ile Cys Lys Glu Ile Asn Val Ile Ser
            195                 200                 205

Asn Ile Met Ala Asp Phe Val Gln Thr Arg Ala Ala Ser Ile Leu Ser
    210                 215                 220

Asp Gly Asp Ile Gly Val Asp Ile Ser Leu Thr Gly Asp Pro Val Ile
225                 230                 235                 240

Thr Ala Ser Tyr Leu Glu Ser His His Lys Gly His Phe Ile Tyr Lys
                245                 250                 255

Asn Val Ser Glu Asp Leu Pro Leu Pro Thr Phe Ser Pro Thr Leu Leu
            260                 265                 270

Gly Asp Ser Arg Met Leu Tyr Phe Trp Phe Ser Glu Arg Val Phe His
            275                 280                 285

Ser Leu Ala Lys Val Ala Phe Gln Asp Gly Arg Leu Met Leu Ser Leu
    290                 295                 300

Met Gly Asp Glu Phe Lys Ala Val Leu Glu Thr Trp Gly Phe Asn Thr
305                 310                 315                 320

Asn Gln Glu Ile Phe Gln Glu Val Val Gly Gly Phe Pro Ser Gln Ala
                325                 330                 335

Gln Val Thr Val His Cys Leu Lys Met Pro Lys Ile Ser Cys Gln Asn
            340                 345                 350

Lys Gly Val Val Asn Ser Ser Val Met Val Lys Phe Leu Phe Pro
            355                 360                 365

Arg Pro Asp Gln Gln His Ser Val Ala Tyr Thr Phe Glu Glu Asp Ile
    370                 375                 380

Val Thr Thr Val Gln Ala Ser Tyr Ser Lys Lys Lys Leu Phe Leu Ser
385                 390                 395                 400
```

```
Leu Leu Asp Phe Gln Ile Thr Pro Lys Thr Val Ser Asn Leu Thr Glu
                405                 410                 415

Ser Ser Ser Glu Ser Val Gln Ser Phe Leu Gln Ser Met Ile Thr Ala
            420                 425                 430

Val Gly Ile Pro Glu Val Met Ser Arg Leu Glu Val Val Phe Thr Ala
            435                 440                 445

Leu Met Asn Ser Lys Gly Val Ser Leu Phe Asp Ile Ile Asn Pro Glu
450                 455                 460

Ile Ile Thr Arg Asp Gly Phe Leu Leu Gln Met Asp Phe Gly Phe
465                 470                 475                 480

Pro Glu His Leu Leu Val Asp Phe Leu Gln Ser Leu Ser
                485                 490

<210> SEQ ID NO 67
<211> LENGTH: 1165
<212> TYPE: PRT
<213> ORGANISM: Homo sapiens
<220> FEATURE:
<221> NAME/KEY: MISC_FEATURE
<223> OTHER INFORMATION: Leptin Receptor
<300> PUBLICATION INFORMATION:
<308> DATABASE ACCESSION NUMBER: Swiss-Prot / P48357
<309> DATABASE ENTRY DATE: 2010-09-07
<313> RELEVANT RESIDUES IN SEQ ID NO: (1)..(1165)

<400> SEQUENCE: 67

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
                20                  25                  30

Phe Lys Leu Ser Cys Met Pro Pro Asn Ser Thr Tyr Asp Tyr Phe Leu
            35                  40                  45

Leu Pro Ala Gly Leu Ser Lys Asn Thr Ser Asn Ser Asn Gly His Tyr
        50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
```

-continued

```
                245                 250                 255
Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

Ser Ala Thr Ser Leu Leu Val Asp Ser Ile Leu Pro Gly Ser Ser Tyr
290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
        355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
        435                 440                 445

Trp Ser Thr Ser Thr Ile Gln Ser Leu Ala Glu Ser Thr Leu Gln Leu
    450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Pro Thr Cys
        515                 520                 525

Val Leu Pro Asp Ser Val Val Lys Pro Leu Pro Pro Ser Ser Val Lys
    530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
        595                 600                 605

Val Gln Val Arg Cys Lys Arg Leu Asp Gly Leu Gly Tyr Trp Ser Asn
    610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670
```

```
Leu Cys Ser Val Gln Arg Tyr Val Ile Asn His His Thr Ser Cys Asn
        675                 680                 685

Gly Thr Trp Ser Glu Asp Val Gly Asn His Thr Lys Phe Thr Phe Leu
    690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
            725                 730                 735

Lys Val Asn Ile Val Gln Ser Leu Ser Ala Tyr Pro Leu Asn Ser Ser
                740                 745                 750

Cys Val Ile Val Ser Trp Ile Leu Ser Pro Ser Asp Tyr Lys Leu Met
                755                 760                 765

Tyr Phe Ile Ile Glu Trp Lys Asn Leu Asn Glu Asp Gly Glu Ile Lys
        770                 775                 780

Trp Leu Arg Ile Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
        835                 840                 845

Ile Ile Ser Ser Ser Ile Leu Leu Leu Gly Thr Leu Leu Ile Ser His
    850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Pro Glu Thr Phe Glu
                885                 890                 895

His Leu Phe Ile Lys His Thr Ala Ser Val Thr Cys Gly Pro Leu Leu
            900                 905                 910

Leu Glu Pro Glu Thr Ile Ser Glu Asp Ile Ser Val Asp Thr Ser Trp
        915                 920                 925

Lys Asn Lys Asp Glu Met Met Pro Thr Thr Val Ser Leu Leu Ser
    930                 935                 940

Thr Thr Asp Leu Glu Lys Gly Ser Val Cys Ile Ser Asp Gln Phe Asn
945                 950                 955                 960

Ser Val Asn Phe Ser Glu Ala Glu Gly Thr Glu Val Thr Tyr Glu Asp
                965                 970                 975

Glu Ser Gln Arg Gln Pro Phe Val Lys Tyr Ala Thr Leu Ile Ser Asn
            980                 985                 990

Ser Lys Pro Ser Glu Thr Gly Glu Glu Gln Gly Leu Ile Asn Ser Ser
        995                 1000                1005

Val Thr Lys Cys Phe Ser Ser Lys Asn Ser Pro Leu Lys Asp Ser
    1010                1015                1020

Phe Ser Asn Ser Ser Trp Glu Ile Glu Ala Gln Ala Phe Phe Ile
    1025                1030                1035

Leu Ser Asp Gln His Pro Asn Ile Ile Ser Pro His Leu Thr Phe
    1040                1045                1050

Ser Glu Gly Leu Asp Glu Leu Leu Lys Leu Glu Gly Asn Phe Pro
    1055                1060                1065

Glu Glu Asn Asn Asp Lys Lys Ser Ile Tyr Tyr Leu Gly Val Thr
    1070                1075                1080
```

-continued

```
Ser Ile Lys Lys Arg Glu Ser Gly Val Leu Leu Thr Asp Lys Ser
    1085                1090                1095

Arg Val Ser Cys Pro Phe Pro Ala Pro Cys Leu Phe Thr Asp Ile
    1100                1105                1110

Arg Val Leu Gln Asp Ser Cys Ser His Phe Val Glu Asn Asn Ile
    1115                1120                1125

Asn Leu Gly Thr Ser Ser Lys Lys Thr Phe Ala Ser Tyr Met Pro
    1130                1135                1140

Gln Phe Gln Thr Cys Ser Thr Gln Thr His Lys Ile Met Glu Asn
    1145                1150                1155

Lys Met Cys Asp Leu Thr Val
    1160                1165

<210> SEQ ID NO 68
<211> LENGTH: 178
<212> TYPE: PRT
<213> ORGANISM: Homo sapiens
<220> FEATURE:
<221> NAME/KEY: MISC_FEATURE
<223> OTHER INFORMATION: IL-10
<300> PUBLICATION INFORMATION:
<308> DATABASE ACCESSION NUMBER: Swiss-Prot / P22301
<309> DATABASE ENTRY DATE: 2010-09-10
<313> RELEVANT RESIDUES IN SEQ ID NO: (1)..(178)

<400> SEQUENCE: 68

Met His Ser Ser Ala Leu Leu Cys Cys Leu Val Leu Thr Gly Val
1               5                   10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
                35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
                100                 105                 110

Gly Glu Asn Leu Lys Thr Leu Arg Leu Arg Leu Arg Arg Cys His Arg
                115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 69
<211> LENGTH: 578
<212> TYPE: PRT
<213> ORGANISM: Homo sapiens
<220> FEATURE:
<221> NAME/KEY: MISC_FEATURE
<223> OTHER INFORMATION: IL-10 Receptor alpha
<300> PUBLICATION INFORMATION:
<308> DATABASE ACCESSION NUMBER: GenBank / AAA17896
<309> DATABASE ENTRY DATE: 1994-05-04
```

<313> RELEVANT RESIDUES IN SEQ ID NO: (1)..(578)

<400> SEQUENCE: 69

```
Met Leu Pro Cys Leu Val Val Leu Leu Ala Leu Leu Ser Leu Arg
1               5                   10                  15

Leu Gly Ser Asp Ala His Gly Thr Glu Leu Pro Ser Pro Pro Ser Val
            20                  25                  30

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
    50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
        115                 120                 125

Ser Val Asn Leu Glu Ile His Asn Gly Phe Ile Leu Gly Lys Ile Gln
    130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
        195                 200                 205

Val Ala Ser Arg Ser Asn Lys Gly Met Trp Ser Lys Glu Glu Cys Ile
    210                 215                 220

Ser Leu Thr Arg Gln Tyr Phe Thr Val Thr Asn Val Ile Ile Phe Phe
225                 230                 235                 240

Ala Phe Val Leu Leu Leu Ser Gly Ala Leu Ala Tyr Cys Leu Ala Leu
                245                 250                 255

Gln Leu Tyr Val Arg Arg Arg Lys Lys Leu Pro Ser Val Leu Leu Phe
            260                 265                 270

Lys Lys Pro Ser Pro Phe Ile Phe Ile Ser Gln Arg Pro Ser Pro Glu
        275                 280                 285

Thr Gln Asp Thr Ile His Pro Leu Asp Glu Glu Ala Phe Leu Lys Val
    290                 295                 300

Ser Pro Glu Leu Lys Asn Leu Asp Leu His Gly Ser Thr Asp Ser Gly
305                 310                 315                 320

Phe Gly Ser Thr Lys Pro Ser Leu Gln Thr Glu Glu Pro Gln Phe Leu
                325                 330                 335

Leu Pro Asp Pro His Pro Gln Ala Asp Arg Thr Leu Gly Asn Gly Glu
            340                 345                 350

Pro Pro Val Leu Gly Asp Ser Cys Ser Ser Gly Ser Ser Asn Ser Thr
        355                 360                 365

Asp Ser Gly Ile Cys Leu Gln Glu Pro Ser Leu Ser Pro Ser Thr Gly
    370                 375                 380

Pro Thr Trp Glu Gln Gln Val Gly Ser Asn Ser Arg Gly Gln Asp Asp
385                 390                 395                 400
```

```
Ser Gly Ile Asp Leu Val Gln Asn Ser Glu Gly Arg Ala Gly Asp Thr
            405                 410                 415

Gln Gly Gly Ser Ala Leu Gly His His Ser Pro Pro Glu Pro Glu Val
        420                 425                 430

Pro Gly Glu Glu Asp Pro Ala Ala Val Ala Phe Gln Gly Tyr Leu Arg
            435                 440                 445

Gln Thr Arg Cys Ala Glu Lys Ala Thr Lys Thr Gly Cys Leu Glu
    450                 455                 460

Glu Glu Ser Pro Leu Thr Asp Gly Leu Gly Pro Lys Phe Gly Arg Cys
465                 470                 475                 480

Leu Val Asp Glu Ala Gly Leu His Pro Pro Ala Leu Ala Lys Gly Tyr
                485                 490                 495

Leu Lys Gln Asp Pro Leu Glu Met Thr Leu Ala Ser Ser Gly Ala Pro
                500                 505                 510

Thr Gly Gln Trp Asn Gln Pro Thr Glu Glu Trp Ser Leu Leu Ala Leu
            515                 520                 525

Ser Ser Cys Ser Asp Leu Gly Ile Ser Asp Trp Ser Phe Ala His Asp
530                 535                 540

Leu Ala Pro Leu Gly Cys Val Ala Ala Pro Gly Gly Leu Leu Gly Ser
545                 550                 555                 560

Phe Asn Ser Asp Leu Val Thr Leu Pro Leu Ile Ser Ser Leu Gln Ser
                565                 570                 575

Ser Glu

<210> SEQ ID NO 70
<211> LENGTH: 325
<212> TYPE: PRT
<213> ORGANISM: Homo sapiens
<220> FEATURE:
<221> NAME/KEY: MISC_FEATURE
<223> OTHER INFORMATION: IL-10 Receptor beta
<300> PUBLICATION INFORMATION:
<308> DATABASE ACCESSION NUMBER: GenBank / AAH01903
<309> DATABASE ENTRY DATE: 2006-07-15
<313> RELEVANT RESIDUES IN SEQ ID NO: (1)..(325)

<400> SEQUENCE: 70

Met Ala Trp Ser Leu Gly Ser Trp Leu Gly Gly Cys Leu Leu Val Ser
1               5                   10                  15

Ala Leu Gly Met Val Pro Pro Glu Asn Val Arg Met Asn Ser Val
            20                  25                  30

Asn Phe Lys Asn Ile Leu Gln Trp Glu Ser Pro Ala Phe Ala Lys Gly
                35                  40                  45

Asn Leu Thr Phe Thr Ala Gln Tyr Leu Ser Tyr Arg Ile Phe Gln Asp
    50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95

His Ser Asp Trp Val Asn Ile Thr Phe Cys Pro Val Asp Asp Thr Ile
            100                 105                 110

Ile Gly Pro Pro Gly Met Gln Val Glu Val Leu Ala Asp Ser Leu His
        115                 120                 125

Met Arg Phe Leu Ala Pro Lys Ile Glu Asn Glu Tyr Glu Thr Trp Thr
    130                 135                 140

Met Lys Asn Val Tyr Asn Ser Trp Thr Tyr Asn Val Gln Tyr Trp Lys
145                 150                 155                 160
```

```
Asn Gly Thr Asp Glu Lys Phe Gln Ile Thr Pro Gln Tyr Asp Phe Glu
                165                 170                 175

Val Leu Arg Asn Leu Glu Pro Trp Thr Thr Tyr Cys Val Gln Val Arg
            180                 185                 190

Gly Phe Leu Pro Asp Arg Asn Lys Ala Gly Glu Trp Ser Glu Pro Val
        195                 200                 205

Cys Glu Gln Thr Thr His Asp Glu Thr Val Pro Ser Trp Met Val Ala
    210                 215                 220

Val Ile Leu Met Ala Ser Val Phe Met Val Cys Leu Ala Leu Leu Gly
225                 230                 235                 240

Cys Phe Ala Leu Leu Trp Cys Val Tyr Lys Lys Thr Lys Tyr Ala Phe
                245                 250                 255

Ser Pro Arg Asn Ser Leu Pro Gln His Leu Lys Glu Phe Leu Gly His
            260                 265                 270

Pro His His Asn Thr Leu Leu Phe Phe Ser Phe Pro Leu Ser Asp Glu
        275                 280                 285

Asn Asp Val Phe Asp Lys Leu Ser Val Ile Ala Glu Asp Ser Glu Ser
    290                 295                 300

Gly Lys Gln Asn Pro Gly Asp Ser Cys Ser Leu Gly Thr Pro Pro Gly
305                 310                 315                 320

Gln Gly Pro Gln Ser
                325
```

<210> SEQ ID NO 71
<211> LENGTH: 638
<212> TYPE: PRT
<213> ORGANISM: Homo sapiens
<220> FEATURE:
<221> NAME/KEY: MISC_FEATURE
<223> OTHER INFORMATION: Growth hormone receptor
<300> PUBLICATION INFORMATION:
<308> DATABASE ACCESSION NUMBER: Swiss-Prot / P10912
<309> DATABASE ENTRY DATE: 2010-08-10
<313> RELEVANT RESIDUES IN SEQ ID NO: (1)..(638)

<400> SEQUENCE: 71

```
Met Asp Leu Trp Gln Leu Leu Leu Thr Leu Ala Leu Ala Gly Ser Ser
1               5                   10                  15

Asp Ala Phe Ser Gly Ser Glu Ala Thr Ala Ala Ile Leu Ser Arg Ala
            20                  25                  30

Pro Trp Ser Leu Gln Ser Val Asn Pro Gly Leu Lys Thr Asn Ser Ser
        35                  40                  45

Lys Glu Pro Lys Phe Thr Lys Cys Arg Ser Pro Glu Arg Glu Thr Phe
    50                  55                  60

Ser Cys His Trp Thr Asp Glu Val His His Gly Thr Lys Asn Leu Gly
65                  70                  75                  80

Pro Ile Gln Leu Phe Tyr Thr Arg Arg Asn Thr Gln Glu Trp Thr Gln
                85                  90                  95

Glu Trp Lys Glu Cys Pro Asp Tyr Val Ser Ala Gly Glu Asn Ser Cys
            100                 105                 110

Tyr Phe Asn Ser Ser Phe Thr Ser Ile Trp Ile Pro Tyr Cys Ile Lys
        115                 120                 125

Leu Thr Ser Asn Gly Gly Thr Val Asp Glu Lys Cys Phe Ser Val Asp
    130                 135                 140

Glu Ile Val Gln Pro Asp Pro Pro Ile Ala Leu Asn Trp Thr Leu Leu
145                 150                 155                 160
```

-continued

Asn Val Ser Leu Thr Gly Ile His Ala Asp Ile Gln Val Arg Trp Glu
            165                 170                 175

Ala Pro Arg Asn Ala Asp Ile Gln Lys Gly Trp Met Val Leu Glu Tyr
        180                 185                 190

Glu Leu Gln Tyr Lys Glu Val Asn Glu Thr Lys Trp Lys Met Met Asp
        195                 200                 205

Pro Ile Leu Thr Thr Ser Val Pro Val Tyr Ser Leu Lys Val Asp Lys
        210                 215                 220

Glu Tyr Glu Val Arg Val Arg Ser Lys Gln Arg Asn Ser Gly Asn Tyr
225                 230                 235                 240

Gly Glu Phe Ser Glu Val Leu Tyr Val Thr Leu Pro Gln Met Ser Gln
            245                 250                 255

Phe Thr Cys Glu Glu Asp Phe Tyr Phe Pro Trp Leu Leu Ile Ile Ile
            260                 265                 270

Phe Gly Ile Phe Gly Leu Thr Val Met Leu Phe Val Phe Leu Phe Ser
            275                 280                 285

Lys Gln Gln Arg Ile Lys Met Leu Ile Leu Pro Pro Val Pro Val Pro
            290                 295                 300

Lys Ile Lys Gly Ile Asp Pro Asp Leu Leu Lys Glu Gly Lys Leu Glu
305                 310                 315                 320

Glu Val Asn Thr Ile Leu Ala Ile His Asp Ser Tyr Lys Pro Glu Phe
            325                 330                 335

His Ser Asp Asp Ser Trp Val Glu Phe Ile Glu Leu Asp Ile Asp Glu
            340                 345                 350

Pro Asp Glu Lys Thr Glu Glu Ser Asp Thr Asp Arg Leu Leu Ser Ser
            355                 360                 365

Asp His Glu Lys Ser His Ser Asn Leu Gly Val Lys Asp Gly Asp Ser
        370                 375                 380

Gly Arg Thr Ser Cys Cys Glu Pro Asp Ile Leu Glu Thr Asp Phe Asn
385                 390                 395                 400

Ala Asn Asp Ile His Glu Gly Thr Ser Glu Val Ala Gln Pro Gln Arg
            405                 410                 415

Leu Lys Gly Glu Ala Asp Leu Leu Cys Leu Asp Gln Lys Asn Gln Asn
            420                 425                 430

Asn Ser Pro Tyr His Asp Ala Cys Pro Ala Thr Gln Gln Pro Ser Val
            435                 440                 445

Ile Gln Ala Glu Lys Asn Lys Pro Gln Pro Leu Pro Thr Glu Gly Ala
        450                 455                 460

Glu Ser Thr His Gln Ala Ala His Ile Gln Leu Ser Asn Pro Ser Ser
465                 470                 475                 480

Leu Ser Asn Ile Asp Phe Tyr Ala Gln Val Ser Asp Ile Thr Pro Ala
            485                 490                 495

Gly Ser Val Val Leu Ser Pro Gly Gln Lys Asn Lys Ala Gly Met Ser
            500                 505                 510

Gln Cys Asp Met His Pro Glu Met Val Ser Leu Cys Gln Glu Asn Phe
            515                 520                 525

Leu Met Asp Asn Ala Tyr Phe Cys Glu Ala Asp Ala Lys Lys Cys Ile
            530                 535                 540

Pro Val Ala Pro His Ile Lys Val Glu Ser His Ile Gln Pro Ser Leu
545                 550                 555                 560

Asn Gln Glu Asp Ile Tyr Ile Thr Thr Glu Ser Leu Thr Thr Ala Ala
            565                 570                 575

Gly Arg Pro Gly Thr Gly Glu His Val Pro Gly Ser Glu Met Pro Val

```
                          580                 585                 590
Pro Asp Tyr Thr Ser Ile His Ile Val Gln Ser Pro Gln Gly Leu Ile
            595                 600                 605

Leu Asn Ala Thr Ala Leu Pro Leu Pro Asp Lys Glu Phe Leu Ser Ser
            610                 615                 620

Cys Gly Tyr Val Ser Thr Asp Gln Leu Asn Lys Ile Met Pro
625                 630                 635

<210> SEQ ID NO 72
<211> LENGTH: 380
<212> TYPE: PRT
<213> ORGANISM: Homo sapiens
<220> FEATURE:
<221> NAME/KEY: MISC_FEATURE
<223> OTHER INFORMATION: IL-13 receptor
<300> PUBLICATION INFORMATION:
<308> DATABASE ACCESSION NUMBER: GenBank / CAA70021
<309> DATABASE ENTRY DATE: 2008-10-07
<313> RELEVANT RESIDUES IN SEQ ID NO: (1)..(380)

<400> SEQUENCE: 72

Met Ala Phe Val Cys Leu Ala Ile Gly Cys Leu Tyr Thr Phe Leu Ile
1               5                  10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285
```

```
Glu Asn Glu Thr Tyr Thr Leu Lys Thr Thr Asn Glu Thr Arg Gln Leu
        290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
                340                 345                 350

Ile Leu Val Ile Phe Val Thr Gly Leu Leu Leu Arg Lys Pro Asn Thr
            355                 360                 365

Tyr Pro Lys Met Ile Pro Glu Phe Phe Cys Asp Thr
370                 375                 380

<210> SEQ ID NO 73
<211> LENGTH: 541
<212> TYPE: PRT
<213> ORGANISM: Homo sapiens
<220> FEATURE:
<221> NAME/KEY: MISC_FEATURE
<223> OTHER INFORMATION: IL-18 receptor
<300> PUBLICATION INFORMATION:
<308> DATABASE ACCESSION NUMBER: GenBank / AAH93977
<309> DATABASE ENTRY DATE: 2006-07-17
<313> RELEVANT RESIDUES IN SEQ ID NO: (1)..(541)

<400> SEQUENCE: 73

Met Asn Cys Arg Glu Leu Pro Leu Thr Leu Trp Val Leu Ile Ser Val
1               5                   10                  15

Ser Thr Ala Glu Ser Cys Thr Ser Arg Pro His Ile Thr Val Val Glu
            20                  25                  30

Gly Glu Pro Phe Tyr Leu Lys His Cys Ser Cys Ser Leu Ala His Glu
        35                  40                  45

Ile Glu Thr Thr Thr Lys Ser Trp Tyr Lys Ser Ser Gly Ser Gln Glu
    50                  55                  60

His Val Glu Leu Asn Pro Arg Ser Ser Ser Arg Ile Ala Leu His Asp
65                  70                  75                  80

Cys Val Leu Glu Phe Trp Pro Val Glu Leu Asn Asp Thr Gly Ser Tyr
                85                  90                  95

Phe Phe Gln Met Lys Asn Tyr Thr Gln Lys Trp Lys Leu Asn Val Ile
            100                 105                 110

Arg Arg Asn Lys His Ser Cys Phe Thr Glu Arg Gln Val Thr Ser Lys
        115                 120                 125

Ile Val Glu Val Lys Lys Phe Phe Gln Ile Thr Cys Glu Asn Ser Tyr
    130                 135                 140

Tyr Gln Thr Leu Val Asn Ser Thr Ser Leu Tyr Lys Asn Cys Lys Lys
145                 150                 155                 160

Leu Leu Leu Glu Asn Asn Lys Asn Pro Thr Ile Lys Lys Asn Ala Glu
                165                 170                 175

Phe Glu Asp Gln Gly Tyr Tyr Ser Cys Val His Phe Leu His His Asn
            180                 185                 190

Gly Lys Leu Phe Asn Ile Thr Lys Thr Phe Asn Ile Thr Ile Val Glu
        195                 200                 205

Asp Arg Ser Asn Ile Val Pro Val Leu Leu Gly Pro Lys Leu Asn His
    210                 215                 220

Val Ala Val Glu Leu Gly Lys Asn Val Arg Leu Asn Cys Ser Ala Leu
225                 230                 235                 240
```

Leu Asn Glu Glu Asp Val Ile Tyr Trp Met Phe Gly Glu Glu Asn Gly
            245                 250                 255

Ser Asp Pro Asn Ile His Glu Glu Lys Glu Met Arg Ile Met Thr Pro
        260                 265                 270

Glu Gly Lys Trp His Ala Ser Lys Val Leu Arg Ile Glu Asn Ile Gly
            275                 280                 285

Glu Ser Asn Leu Asn Val Leu Tyr Asn Cys Thr Val Ala Ser Thr Gly
        290                 295                 300

Gly Thr Asp Thr Lys Ser Phe Ile Leu Val Arg Lys Ala Asp Met Ala
305                 310                 315                 320

Asp Ile Pro Gly His Val Phe Thr Arg Gly Met Ile Ile Ala Val Leu
                325                 330                 335

Ile Leu Val Ala Val Val Cys Leu Val Thr Val Cys Val Ile Tyr Arg
            340                 345                 350

Val Asp Leu Val Leu Phe Tyr Arg His Leu Thr Arg Arg Asp Glu Thr
        355                 360                 365

Leu Thr Asp Gly Lys Thr Tyr Asp Ala Phe Val Ser Tyr Leu Lys Glu
    370                 375                 380

Cys Arg Pro Glu Asn Gly Glu Glu His Thr Phe Ala Val Glu Ile Leu
385                 390                 395                 400

Pro Arg Val Leu Glu Lys His Phe Gly Tyr Lys Leu Cys Ile Phe Glu
                405                 410                 415

Arg Asp Val Val Pro Gly Gly Ala Val Val Asp Glu Ile His Ser Leu
            420                 425                 430

Ile Glu Lys Ser Arg Arg Leu Ile Ile Val Leu Ser Lys Ser Tyr Met
        435                 440                 445

Ser Asn Glu Val Arg Tyr Glu Leu Glu Ser Gly Leu His Glu Ala Leu
    450                 455                 460

Val Glu Arg Lys Ile Lys Ile Ile Leu Ile Glu Phe Thr Pro Val Thr
465                 470                 475                 480

Asp Phe Thr Phe Leu Pro Gln Ser Leu Lys Leu Lys Ser His Arg
                485                 490                 495

Val Leu Lys Trp Lys Ala Asp Lys Ser Leu Ser Tyr Asn Ser Arg Phe
            500                 505                 510

Trp Lys Asn Leu Leu Tyr Leu Met Pro Ala Lys Thr Val Lys Pro Gly
        515                 520                 525

Arg Asp Glu Pro Glu Val Leu Pro Val Leu Ser Glu Ser
    530                 535                 540

<210> SEQ ID NO 74
<211> LENGTH: 272
<212> TYPE: PRT
<213> ORGANISM: Homo sapiens
<220> FEATURE:
<221> NAME/KEY: MISC_FEATURE
<223> OTHER INFORMATION: IL-2 receptor alpha subunit
<300> PUBLICATION INFORMATION:
<308> DATABASE ACCESSION NUMBER: Swiss-Prot / P01589
<309> DATABASE ENTRY DATE: 2010-09-07
<313> RELEVANT RESIDUES IN SEQ ID NO: (1)..(272)

<400> SEQUENCE: 74

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn

```
            35                  40                  45
Cys Glu Cys Lys Arg Gly Phe Arg Arg Ile Lys Ser Gly Ser Leu Tyr
 50                      55                  60

Met Leu Cys Thr Gly Asn Ser Ser His Ser Ser Trp Asp Asn Gln Cys
 65                  70                  75                  80

Gln Cys Thr Ser Ser Ala Thr Arg Asn Thr Lys Gln Val Thr Pro
                 85                  90                  95

Gln Pro Glu Glu Gln Lys Glu Arg Lys Thr Thr Glu Met Gln Ser Pro
                100                 105                 110

Met Gln Pro Val Asp Gln Ala Ser Leu Pro Gly His Cys Arg Glu Pro
            115                 120                 125

Pro Pro Trp Glu Asn Glu Ala Thr Glu Arg Ile Tyr His Phe Val Val
        130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
        195                 200                 205

Ser Glu Thr Ser Cys Leu Val Thr Thr Thr Asp Phe Gln Ile Gln Thr
210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270

<210> SEQ ID NO 75
<211> LENGTH: 1676
<212> TYPE: PRT
<213> ORGANISM: Homo sapiens
<220> FEATURE:
<221> NAME/KEY: MISC_FEATURE
<223> OTHER INFORMATION: complement factor C5a
<300> PUBLICATION INFORMATION:
<308> DATABASE ACCESSION NUMBER: NCBI / NP_001726
<309> DATABASE ENTRY DATE: 2010-09-20
<313> RELEVANT RESIDUES IN SEQ ID NO: (1)..(1676)

<400> SEQUENCE: 75

Met Gly Leu Leu Gly Ile Leu Cys Phe Leu Ile Phe Leu Gly Lys Thr
 1               5                  10                  15

Trp Gly Gln Glu Gln Thr Tyr Val Ile Ser Ala Pro Lys Ile Phe Arg
                20                  25                  30

Val Gly Ala Ser Glu Asn Ile Val Ile Gln Val Tyr Gly Tyr Thr Glu
            35                  40                  45

Ala Phe Asp Ala Thr Ile Ser Ile Lys Ser Tyr Pro Asp Lys Lys Phe
 50                  55                  60

Ser Tyr Ser Ser Gly His Val His Leu Ser Ser Glu Asn Lys Phe Gln
 65                  70                  75                  80

Asn Ser Ala Ile Leu Thr Ile Gln Pro Lys Gln Leu Pro Gly Gly Gln
                 85                  90                  95

Asn Pro Val Ser Tyr Val Tyr Leu Glu Val Val Ser Lys His Phe Ser
                100                 105                 110
```

```
Lys Ser Lys Arg Met Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
        195                 200                 205

Phe Ser Thr Thr Gly Thr Ala Tyr Phe Glu Val Lys Glu Tyr Val Leu
    210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
            260                 265                 270

Glu Asp Leu Lys Asp Asp Gln Lys Glu Met Met Gln Thr Ala Met Gln
        275                 280                 285

Asn Thr Met Leu Ile Asn Gly Ile Ala Gln Val Thr Phe Asp Ser Glu
    290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
            340                 345                 350

Lys Leu Asn Leu Val Ala Thr Pro Leu Phe Leu Lys Pro Gly Ile Pro
        355                 360                 365

Tyr Pro Ile Lys Val Gln Val Lys Asp Ser Leu Asp Gln Leu Val Gly
    370                 375                 380

Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
                405                 410                 415

Val Ala Ser Phe Val Leu Asn Leu Pro Ser Gly Val Thr Val Leu Glu
            420                 425                 430

Phe Asn Val Lys Thr Asp Ala Pro Asp Leu Pro Glu Glu Asn Gln Ala
        435                 440                 445

Arg Glu Gly Tyr Arg Ala Ile Ala Tyr Ser Ser Leu Ser Gln Ser Tyr
    450                 455                 460

Leu Tyr Ile Asp Trp Thr Asp Asn His Lys Ala Leu Leu Val Gly Glu
465                 470                 475                 480

His Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
            500                 505                 510

Gly Thr Arg Glu Lys Phe Ser Asp Ala Ser Tyr Gln Ser Ile Asn Ile
        515                 520                 525
```

-continued

Pro Val Thr Gln Asn Met Val Pro Ser Ser Arg Leu Leu Val Tyr Tyr
    530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Ala Tyr Ser Pro Gly Gln Thr Val Ser Leu Asn Met
            580                 585                 590

Ala Thr Gly Met Asp Ser Trp Val Ala Leu Ala Ala Val Asp Ser Ala
        595                 600                 605

Val Tyr Gly Val Gln Arg Gly Ala Lys Lys Pro Leu Glu Arg Val Phe
    610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
            660                 665                 670

Leu Arg Pro Arg Arg Thr Leu Gln Lys Lys Ile Glu Glu Ile Ala Ala
        675                 680                 685

Lys Tyr Lys His Ser Val Val Lys Cys Cys Tyr Asp Gly Ala Cys
    690                 695                 700

Val Asn Asn Asp Glu Thr Cys Glu Gln Arg Ala Ala Arg Ile Ser Leu
705                 710                 715                 720

Gly Pro Arg Cys Ile Lys Ala Phe Thr Glu Cys Cys Val Val Ala Ser
                725                 730                 735

Gln Leu Arg Ala Asn Ile Ser His Lys Asp Met Gln Leu Gly Arg Leu
            740                 745                 750

His Met Lys Thr Leu Leu Pro Val Ser Lys Pro Glu Ile Arg Ser Tyr
        755                 760                 765

Phe Pro Glu Ser Trp Leu Trp Glu Val His Leu Val Pro Arg Arg Lys
    770                 775                 780

Gln Leu Gln Phe Ala Leu Pro Asp Ser Leu Thr Thr Trp Glu Ile Gln
785                 790                 795                 800

Gly Val Gly Ile Ser Asn Thr Gly Ile Cys Val Ala Asp Thr Val Lys
                805                 810                 815

Ala Lys Val Phe Lys Asp Val Phe Leu Glu Met Asn Ile Pro Tyr Ser
            820                 825                 830

Val Val Arg Gly Glu Gln Ile Gln Leu Lys Gly Thr Val Tyr Asn Tyr
        835                 840                 845

Arg Thr Ser Gly Met Gln Phe Cys Val Lys Met Ser Ala Val Glu Gly
    850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser His Leu Val
                885                 890                 895

Thr Phe Thr Val Leu Pro Leu Glu Ile Gly Leu His Asn Ile Asn Phe
            900                 905                 910

Ser Leu Glu Thr Trp Phe Gly Lys Glu Ile Leu Val Lys Thr Leu Arg
        915                 920                 925

Val Val Pro Glu Gly Val Lys Arg Glu Ser Tyr Ser Gly Val Thr Leu
    930                 935                 940

Asp Pro Arg Gly Ile Tyr Gly Thr Ile Ser Arg Arg Lys Glu Phe Pro

-continued

```
945                 950                 955                 960
Tyr Arg Ile Pro Leu Asp Leu Val Pro Lys Thr Glu Ile Lys Arg Ile
                965                 970                 975
Leu Ser Val Lys Gly Leu Leu Val Gly Glu Ile Leu Ser Ala Val Leu
                980                 985                 990
Ser Gln Glu Gly Ile Asn Ile Leu Thr His Leu Pro Lys Gly Ser Ala
                995                 1000                1005
Glu Ala Glu Leu Met Ser Val Val Pro Val Phe Tyr Val Phe His
        1010                1015                1020
Tyr Leu Glu Thr Gly Asn His Trp Asn Ile Phe His Ser Asp Pro
        1025                1030                1035
Leu Ile Glu Lys Gln Lys Leu Lys Lys Lys Leu Lys Glu Gly Met
        1040                1045                1050
Leu Ser Ile Met Ser Tyr Arg Asn Ala Asp Tyr Ser Tyr Ser Val
        1055                1060                1065
Trp Lys Gly Gly Ser Ala Ser Thr Trp Leu Thr Ala Phe Ala Leu
        1070                1075                1080
Arg Val Leu Gly Gln Val Asn Lys Tyr Val Glu Gln Asn Gln Asn
        1085                1090                1095
Ser Ile Cys Asn Ser Leu Leu Trp Leu Val Glu Asn Tyr Gln Leu
        1100                1105                1110
Asp Asn Gly Ser Phe Lys Glu Asn Ser Gln Tyr Gln Pro Ile Lys
        1115                1120                1125
Leu Gln Gly Thr Leu Pro Val Glu Ala Arg Glu Asn Ser Leu Tyr
        1130                1135                1140
Leu Thr Ala Phe Thr Val Ile Gly Ile Arg Lys Ala Phe Asp Ile
        1145                1150                1155
Cys Pro Leu Val Lys Ile Asp Thr Ala Leu Ile Lys Ala Asp Asn
        1160                1165                1170
Phe Leu Leu Glu Asn Thr Leu Pro Ala Gln Ser Thr Phe Thr Leu
        1175                1180                1185
Ala Ile Ser Ala Tyr Ala Leu Ser Leu Gly Asp Lys Thr His Pro
        1190                1195                1200
Gln Phe Arg Ser Ile Val Ser Ala Leu Lys Arg Glu Ala Leu Val
        1205                1210                1215
Lys Gly Asn Pro Pro Ile Tyr Arg Phe Trp Lys Asp Asn Leu Gln
        1220                1225                1230
His Lys Asp Ser Ser Val Pro Asn Thr Gly Thr Ala Arg Met Val
        1235                1240                1245
Glu Thr Thr Ala Tyr Ala Leu Leu Thr Ser Leu Asn Leu Lys Asp
        1250                1255                1260
Ile Asn Tyr Val Asn Pro Val Ile Lys Trp Leu Ser Glu Glu Gln
        1265                1270                1275
Arg Tyr Gly Gly Gly Phe Tyr Ser Thr Gln Asp Thr Ile Asn Ala
        1280                1285                1290
Ile Glu Gly Leu Thr Glu Tyr Ser Leu Leu Val Lys Gln Leu Arg
        1295                1300                1305
Leu Ser Met Asp Ile Asp Val Ser Tyr Lys His Lys Gly Ala Leu
        1310                1315                1320
His Asn Tyr Lys Met Thr Asp Lys Asn Phe Leu Gly Arg Pro Val
        1325                1330                1335
Glu Val Leu Leu Asn Asp Asp Leu Ile Val Ser Thr Gly Phe Gly
        1340                1345                1350
```

```
Ser Gly Leu Ala Thr Val His Val Thr Val Val His Lys Thr
    1355                1360                1365

Ser Thr Ser Glu Glu Val Cys Ser Phe Tyr Leu Lys Ile Asp Thr
    1370                1375                1380

Gln Asp Ile Glu Ala Ser His Tyr Arg Gly Tyr Gly Asn Ser Asp
    1385                1390                1395

Tyr Lys Arg Ile Val Ala Cys Ala Ser Tyr Lys Pro Ser Arg Glu
    1400                1405                1410

Glu Ser Ser Ser Gly Ser Ser His Ala Val Met Asp Ile Ser Leu
    1415                1420                1425

Pro Thr Gly Ile Ser Ala Asn Glu Glu Asp Leu Lys Ala Leu Val
    1430                1435                1440

Glu Gly Val Asp Gln Leu Phe Thr Asp Tyr Gln Ile Lys Asp Gly
    1445                1450                1455

His Val Ile Leu Gln Leu Asn Ser Ile Pro Ser Ser Asp Phe Leu
    1460                1465                1470

Cys Val Arg Phe Arg Ile Phe Glu Leu Phe Glu Val Gly Phe Leu
    1475                1480                1485

Ser Pro Ala Thr Phe Thr Val Tyr Glu Tyr His Arg Pro Asp Lys
    1490                1495                1500

Gln Cys Thr Met Phe Tyr Ser Thr Ser Asn Ile Lys Ile Gln Lys
    1505                1510                1515

Val Cys Glu Gly Ala Ala Cys Lys Cys Val Glu Ala Asp Cys Gly
    1520                1525                1530

Gln Met Gln Glu Glu Leu Asp Leu Thr Ile Ser Ala Glu Thr Arg
    1535                1540                1545

Lys Gln Thr Ala Cys Lys Pro Glu Ile Ala Tyr Ala Tyr Lys Val
    1550                1555                1560

Ser Ile Thr Ser Ile Thr Val Glu Asn Val Phe Val Lys Tyr Lys
    1565                1570                1575

Ala Thr Leu Leu Asp Ile Tyr Lys Thr Gly Glu Ala Val Ala Glu
    1580                1585                1590

Lys Asp Ser Glu Ile Thr Phe Ile Lys Lys Val Thr Cys Thr Asn
    1595                1600                1605

Ala Glu Leu Val Lys Gly Arg Gln Tyr Leu Ile Met Gly Lys Glu
    1610                1615                1620

Ala Leu Gln Ile Lys Tyr Asn Phe Ser Phe Arg Tyr Ile Tyr Pro
    1625                1630                1635

Leu Asp Ser Leu Thr Trp Ile Glu Tyr Trp Pro Arg Asp Thr Thr
    1640                1645                1650

Cys Ser Ser Cys Gln Ala Phe Leu Ala Asn Leu Asp Glu Phe Ala
    1655                1660                1665

Glu Asp Ile Phe Leu Asn Gly Cys
    1670                1675

<210> SEQ ID NO 76
<211> LENGTH: 866
<212> TYPE: PRT
<213> ORGANISM: Homo sapiens
<220> FEATURE:
<221> NAME/KEY: MISC_FEATURE
<223> OTHER INFORMATION: IL-17 receptor
<300> PUBLICATION INFORMATION:
<308> DATABASE ACCESSION NUMBER: GenBank / AAB99730
<309> DATABASE ENTRY DATE: 1998-01-30
<313> RELEVANT RESIDUES IN SEQ ID NO: (1)..(866)
```

<400> SEQUENCE: 76

| | | | | | | | | | | | | | | |
|---|---|---|---|---|---|---|---|---|---|---|---|---|---|---|
| Met | Gly | Ala | Ala | Arg | Ser | Pro | Pro | Ser | Ala | Val | Pro | Gly | Pro | Leu | Leu |
| 1 | | | | 5 | | | | | 10 | | | | | 15 | |
| Gly | Leu | Leu | Leu | Leu | Leu | Leu | Gly | Val | Leu | Ala | Pro | Gly | Gly | Ala | Ser |
| | | | 20 | | | | | 25 | | | | | 30 | | |
| Leu | Arg | Leu | Leu | Asp | His | Arg | Ala | Leu | Val | Cys | Ser | Gln | Pro | Gly | Leu |
| | | 35 | | | | | 40 | | | | | 45 | | | |
| Asn | Cys | Thr | Val | Lys | Asn | Ser | Thr | Cys | Leu | Asp | Asp | Ser | Trp | Ile | His |
| | 50 | | | | | 55 | | | | | 60 | | | | |
| Pro | Arg | Asn | Leu | Thr | Pro | Ser | Ser | Pro | Lys | Asp | Leu | Gln | Ile | Gln | Leu |
| 65 | | | | | 70 | | | | | 75 | | | | | 80 |
| His | Phe | Ala | His | Thr | Gln | Gln | Gly | Asp | Leu | Phe | Pro | Val | Ala | His | Ile |
| | | | | 85 | | | | | 90 | | | | | 95 | |
| Glu | Trp | Thr | Leu | Gln | Thr | Asp | Ala | Ser | Ile | Leu | Tyr | Leu | Glu | Gly | Ala |
| | | | 100 | | | | | 105 | | | | | 110 | | |
| Glu | Leu | Ser | Val | Leu | Gln | Leu | Asn | Thr | Asn | Glu | Arg | Leu | Cys | Val | Arg |
| | | 115 | | | | | 120 | | | | | 125 | | | |
| Phe | Glu | Phe | Leu | Ser | Lys | Leu | Arg | His | His | Arg | Arg | Trp | Arg | Phe |
| | 130 | | | | | 135 | | | | | 140 | | | | |
| Thr | Phe | Ser | His | Phe | Val | Val | Asp | Pro | Asp | Gln | Glu | Tyr | Glu | Val | Thr |
| 145 | | | | | 150 | | | | | 155 | | | | | 160 |
| Val | His | His | Leu | Pro | Lys | Pro | Ile | Pro | Asp | Gly | Asp | Pro | Asn | His | Gln |
| | | | | 165 | | | | | 170 | | | | | 175 | |
| Ser | Lys | Asn | Phe | Leu | Val | Pro | Asp | Cys | Glu | His | Ala | Arg | Met | Lys | Val |
| | | | 180 | | | | | 185 | | | | | 190 | | |
| Thr | Thr | Pro | Cys | Met | Ser | Ser | Gly | Ser | Leu | Trp | Asp | Pro | Asn | Ile | Thr |
| | | 195 | | | | | 200 | | | | | 205 | | | |
| Val | Glu | Thr | Leu | Glu | Ala | His | Gln | Leu | Arg | Val | Ser | Phe | Thr | Leu | Trp |
| | 210 | | | | | 215 | | | | | 220 | | | | |
| Asn | Glu | Ser | Thr | His | Tyr | Gln | Ile | Leu | Leu | Thr | Ser | Phe | Pro | His | Met |
| 225 | | | | | 230 | | | | | 235 | | | | | 240 |
| Glu | Asn | His | Ser | Cys | Phe | Glu | His | Met | His | His | Ile | Pro | Ala | Pro | Arg |
| | | | | 245 | | | | | 250 | | | | | 255 | |
| Pro | Glu | Glu | Phe | His | Gln | Arg | Ser | Asn | Val | Thr | Leu | Thr | Leu | Arg | Asn |
| | | | 260 | | | | | 265 | | | | | 270 | | |
| Leu | Lys | Gly | Cys | Cys | Arg | His | Gln | Val | Gln | Ile | Gln | Pro | Phe | Phe | Ser |
| | | 275 | | | | | 280 | | | | | 285 | | | |
| Ser | Cys | Leu | Asn | Asp | Cys | Leu | Arg | His | Ser | Ala | Thr | Val | Ser | Cys | Pro |
| | 290 | | | | | 295 | | | | | 300 | | | | |
| Glu | Met | Pro | Asp | Thr | Pro | Glu | Pro | Ile | Pro | Asp | Tyr | Met | Pro | Leu | Trp |
| 305 | | | | | 310 | | | | | 315 | | | | | 320 |
| Val | Tyr | Trp | Phe | Ile | Thr | Gly | Ile | Ser | Ile | Leu | Leu | Val | Gly | Ser | Val |
| | | | | 325 | | | | | 330 | | | | | 335 | |
| Ile | Leu | Leu | Ile | Val | Cys | Met | Thr | Trp | Arg | Leu | Ala | Gly | Pro | Gly | Ser |
| | | | 340 | | | | | 345 | | | | | 350 | | |
| Glu | Lys | Tyr | Ser | Asp | Asp | Thr | Lys | Tyr | Thr | Asp | Gly | Leu | Pro | Ala | Ala |
| | | 355 | | | | | 360 | | | | | 365 | | | |
| Asp | Leu | Ile | Pro | Pro | Pro | Leu | Lys | Pro | Arg | Lys | Val | Trp | Ile | Ile | Tyr |
| | 370 | | | | | 375 | | | | | 380 | | | | |
| Ser | Ala | Asp | His | Pro | Leu | Tyr | Val | Asp | Val | Val | Leu | Lys | Phe | Ala | Gln |
| 385 | | | | | 390 | | | | | 395 | | | | | 400 |
| Phe | Leu | Leu | Thr | Ala | Cys | Gly | Thr | Glu | Val | Ala | Leu | Asp | Leu | Leu | Glu |

-continued

```
                405                 410                 415
Glu Gln Ala Ile Ser Glu Ala Gly Val Met Thr Trp Val Gly Arg Gln
            420                 425                 430

Lys Gln Glu Met Val Glu Ser Asn Ser Lys Ile Ile Val Leu Cys Ser
            435                 440                 445

Arg Gly Thr Arg Ala Lys Trp Gln Ala Leu Leu Gly Arg Gly Ala Pro
            450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
                485                 490                 495

Gly Thr Tyr Val Val Cys Tyr Phe Ser Glu Val Ser Cys Asp Gly Asp
            500                 505                 510

Val Pro Asp Leu Phe Gly Ala Ala Pro Arg Tyr Pro Leu Met Asp Arg
            515                 520                 525

Phe Glu Glu Val Tyr Phe Arg Ile Gln Asp Leu Glu Met Phe Gln Pro
            530                 535                 540

Gly Arg Met His Arg Val Gly Glu Leu Ser Gly Asp Asn Tyr Leu Arg
545                 550                 555                 560

Ser Pro Gly Gly Arg Gln Leu Arg Ala Ala Leu Asp Arg Phe Arg Asp
                565                 570                 575

Trp Gln Val Arg Cys Pro Asp Trp Phe Glu Cys Glu Asn Leu Tyr Ser
            580                 585                 590

Ala Asp Asp Gln Asp Ala Pro Ser Leu Asp Glu Glu Val Phe Glu Glu
            595                 600                 605

Pro Leu Leu Pro Pro Gly Thr Gly Ile Val Lys Arg Ala Pro Leu Val
            610                 615                 620

Arg Glu Pro Gly Ser Gln Ala Cys Leu Ala Ile Asp Pro Leu Val Gly
625                 630                 635                 640

Glu Glu Gly Gly Ala Ala Val Ala Lys Leu Glu Pro His Leu Gln Pro
                645                 650                 655

Arg Gly Gln Pro Ala Pro Gln Pro Leu His Thr Leu Val Leu Ala Ala
            660                 665                 670

Glu Glu Gly Ala Leu Val Ala Ala Val Glu Pro Gly Pro Leu Ala Asp
            675                 680                 685

Gly Ala Ala Val Arg Leu Ala Leu Ala Gly Gly Glu Ala Cys Pro
690                 695                 700

Leu Leu Gly Ser Pro Gly Ala Gly Arg Asn Ser Val Leu Phe Leu Pro
705                 710                 715                 720

Val Asp Pro Glu Asp Ser Pro Leu Gly Ser Ser Thr Pro Met Ala Ser
                725                 730                 735

Pro Asp Leu Leu Pro Glu Asp Val Arg Glu His Leu Glu Gly Leu Met
            740                 745                 750

Leu Ser Leu Phe Glu Gln Ser Leu Ser Cys Gln Ala Gln Gly Gly Cys
            755                 760                 765

Ser Arg Pro Ala Met Val Leu Thr Asp Pro His Thr Pro Tyr Glu Glu
            770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu Glu
                805                 810                 815

Glu Glu Gln Asp Pro Gly Lys Pro Ala Leu Pro Leu Ser Pro Glu Asp
            820                 825                 830
```

-continued

```
Leu Glu Ser Leu Arg Ser Leu Gln Arg Gln Leu Leu Phe Arg Gln Leu
            835                 840                 845

Gln Lys Asn Ser Gly Trp Asp Thr Met Gly Ser Glu Ser Glu Gly Pro
        850                 855                 860

Ser Ala
865

<210> SEQ ID NO 77
<211> LENGTH: 553
<212> TYPE: PRT
<213> ORGANISM: Homo sapiens
<220> FEATURE:
<221> NAME/KEY: MISC_FEATURE
<223> OTHER INFORMATION: IL-20 receptor
<300> PUBLICATION INFORMATION:
<308> DATABASE ACCESSION NUMBER: Swiss-Prot / Q9UHF4
<309> DATABASE ENTRY DATE: 2010-09-07
<313> RELEVANT RESIDUES IN SEQ ID NO: (1)..(553)

<400> SEQUENCE: 77

Met Arg Ala Pro Gly Arg Pro Ala Leu Arg Pro Leu Pro Leu Pro Pro
1               5                   10                  15

Leu Leu Leu Leu Leu Ala Ala Pro Trp Gly Arg Ala Val Pro Cys
            20                  25                  30

Val Ser Gly Gly Leu Pro Lys Pro Ala Asn Ile Thr Phe Leu Ser Ile
            35                  40                  45

Asn Met Lys Asn Val Leu Gln Trp Thr Pro Pro Glu Gly Leu Gln Gly
        50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
            100                 105                 110

Lys Ala Ile Trp Gly Thr Lys Cys Ser Lys Trp Ala Glu Ser Gly Arg
        115                 120                 125

Phe Tyr Pro Phe Leu Glu Thr Gln Ile Gly Pro Pro Glu Val Ala Leu
    130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
        195                 200                 205

Glu Pro Asn Thr Leu Tyr Cys Val His Val Glu Ser Phe Val Pro Gly
    210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                245                 250                 255

Leu Pro Val Ser Ile Thr Val Phe Leu Phe Ser Val Met Gly Tyr Ser
            260                 265                 270

Ile Tyr Arg Tyr Ile His Val Gly Lys Glu Lys His Pro Ala Asn Leu
        275                 280                 285
```

```
Ile Leu Ile Tyr Gly Asn Glu Phe Asp Lys Arg Phe Val Pro Ala
    290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
            340                 345                 350

Glu Glu Glu Glu Val Lys His Leu Gly Tyr Ala Ser His Leu Met Glu
                355                 360                 365

Ile Phe Cys Asp Ser Glu Glu Asn Thr Glu Gly Thr Ser Leu Thr Gln
    370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Glu Val Ser Thr Gln Gly Thr Leu Leu
            420                 425                 430

Glu Ser Gln Ala Ala Leu Ala Val Leu Gly Pro Gln Thr Leu Gln Tyr
        435                 440                 445

Ser Tyr Thr Pro Gln Leu Gln Asp Leu Asp Pro Leu Ala Gln Glu His
    450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
            500                 505                 510

Gly Glu Glu Gly Leu Leu Ser Arg Leu Tyr Glu Glu Pro Ala Pro Asp
        515                 520                 525

Arg Pro Pro Gly Glu Asn Glu Thr Tyr Leu Met Gln Phe Met Glu Glu
    530                 535                 540

Trp Gly Leu Tyr Val Gln Met Glu Asn
545                 550

<210> SEQ ID NO 78
<211> LENGTH: 378
<212> TYPE: PRT
<213> ORGANISM: Homo sapiens
<220> FEATURE:
<221> NAME/KEY: MISC_FEATURE
<223> OTHER INFORMATION: IL-3 receptor
<300> PUBLICATION INFORMATION:
<308> DATABASE ACCESSION NUMBER: GenBank / AAA59148
<309> DATABASE ENTRY DATE: 1995-01-06
<313> RELEVANT RESIDUES IN SEQ ID NO: (1)..(378)

<400> SEQUENCE: 78

Met Val Leu Leu Trp Leu Thr Leu Leu Ile Ala Leu Pro Cys Leu
1               5                   10                  15

Leu Gln Thr Lys Glu Asp Pro Asn Pro Pro Ile Thr Asn Leu Arg Met
            20                  25                  30

Lys Ala Lys Ala Gln Gln Leu Thr Trp Asp Leu Asn Arg Asn Val Thr
        35                  40                  45

Asp Ile Glu Cys Val Lys Asp Ala Asp Tyr Ser Met Pro Ala Val Asn
    50                  55                  60

Asn Ser Tyr Cys Gln Phe Gly Ala Ile Ser Leu Cys Glu Val Thr Asn
```

-continued

```
                65                  70                  75                  80
Tyr Thr Val Arg Val Ala Asn Pro Pro Phe Ser Thr Trp Ile Leu Phe
                    85                  90                  95

Pro Glu Asn Ser Gly Lys Pro Trp Ala Gly Ala Glu Asn Leu Thr Cys
                100                 105                 110

Trp Ile His Asp Val Asp Phe Leu Ser Cys Ser Trp Ala Val Gly Pro
            115                 120                 125

Gly Ala Pro Ala Asp Val Gln Tyr Asp Leu Tyr Leu Asn Val Ala Asn
        130                 135                 140

Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
                180                 185                 190

Ile Pro Cys Thr Asp Lys Phe Val Val Phe Ser Gln Ile Glu Ile Leu
            195                 200                 205

Thr Pro Pro Asn Met Thr Ala Lys Cys Asn Lys Thr His Ser Phe Met
        210                 215                 220

His Trp Lys Met Arg Ser His Phe Asn Arg Lys Phe Arg Tyr Glu Leu
225                 230                 235                 240

Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
                260                 265                 270

Arg Ala Arg Glu Arg Val Tyr Glu Phe Leu Ser Ala Trp Ser Thr Pro
            275                 280                 285

Gln Arg Phe Glu Cys Asp Gln Glu Glu Gly Ala Asn Thr Arg Ala Trp
        290                 295                 300

Arg Thr Ser Leu Leu Ile Ala Leu Gly Thr Leu Leu Ala Leu Val Cys
305                 310                 315                 320

Val Phe Val Ile Cys Arg Arg Tyr Leu Val Met Gln Arg Leu Phe Pro
                325                 330                 335

Arg Ile Pro His Met Lys Asp Pro Ile Gly Asp Ser Phe Gln Asn Asp
                340                 345                 350

Lys Leu Val Val Trp Glu Ala Gly Lys Ala Gly Leu Glu Glu Cys Leu
            355                 360                 365

Val Thr Glu Val Gln Val Gln Lys Thr
        370                 375
```

<210> SEQ ID NO 79
<211> LENGTH: 825
<212> TYPE: PRT
<213> ORGANISM: Homo sapiens
<220> FEATURE:
<221> NAME/KEY: MISC_FEATURE
<223> OTHER INFORMATION: IL-1 receptor
<300> PUBLICATION INFORMATION:
<308> DATABASE ACCESSION NUMBER: GenBank / CAA36672
<309> DATABASE ENTRY DATE: 2008-10-07
<313> RELEVANT RESIDUES IN SEQ ID NO: (1)..(825)

<400> SEQUENCE: 79

```
Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30
```

-continued

```
Thr Cys Val Ser Asp Tyr Met Ser Ile Ser Thr Cys Glu Trp Lys Met
         35                  40                  45

Asn Gly Pro Thr Asn Cys Ser Thr Glu Leu Arg Leu Leu Tyr Gln Leu
 50                  55                  60

Val Phe Leu Leu Ser Glu Ala His Thr Cys Ile Pro Glu Asn Asn Gly
 65                  70                  75                  80

Gly Ala Gly Cys Val Cys His Leu Leu Met Asp Asp Val Val Ser Ala
                 85                  90                  95

Asp Asn Tyr Thr Leu Asp Leu Trp Ala Gly Gln Gln Leu Leu Trp Lys
             100                 105                 110

Gly Ser Phe Lys Pro Ser Glu His Val Lys Pro Arg Ala Pro Gly Asn
             115                 120                 125

Leu Thr Val His Thr Asn Val Ser Asp Thr Leu Leu Leu Thr Trp Ser
130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                 165                 170                 175

Val Thr Tyr Leu Glu Pro Ser Leu Arg Ile Ala Ala Ser Thr Leu Lys
             180                 185                 190

Ser Gly Ile Ser Tyr Arg Ala Arg Val Arg Ala Trp Ala Gln Cys Tyr
             195                 200                 205

Asn Thr Thr Trp Ser Glu Trp Ser Pro Ser Thr Lys Trp His Asn Ser
210                 215                 220

Tyr Arg Glu Pro Phe Glu Gln His Leu Leu Leu Gly Val Ser Val Ser
225                 230                 235                 240

Cys Ile Val Ile Leu Ala Val Cys Leu Leu Cys Tyr Val Ser Ile Thr
                 245                 250                 255

Lys Ile Lys Lys Glu Trp Trp Asp Gln Ile Pro Asn Pro Ala Arg Ser
             260                 265                 270

Arg Leu Val Ala Ile Ile Ile Gln Asp Ala Gln Gly Ser Gln Trp Glu
             275                 280                 285

Lys Arg Ser Arg Gly Gln Glu Pro Ala Lys Cys Pro His Trp Lys Asn
290                 295                 300

Cys Leu Thr Lys Leu Leu Pro Cys Phe Leu Glu His Asn Met Lys Arg
305                 310                 315                 320

Asp Glu Asp Pro His Lys Ala Ala Lys Glu Met Pro Phe Gln Gly Ser
                 325                 330                 335

Gly Lys Ser Ala Trp Cys Pro Val Glu Ile Ser Lys Thr Val Leu Trp
             340                 345                 350

Pro Glu Ser Ile Ser Val Val Arg Cys Val Glu Leu Phe Glu Ala Pro
             355                 360                 365

Val Glu Cys Glu Glu Glu Glu Val Glu Glu Glu Lys Gly Ser Phe
370                 375                 380

Cys Ala Ser Pro Glu Ser Ser Arg Asp Asp Phe Gln Glu Gly Arg Glu
385                 390                 395                 400

Gly Ile Val Ala Arg Leu Thr Glu Ser Leu Phe Leu Asp Leu Leu Gly
                 405                 410                 415

Glu Glu Asn Gly Gly Phe Cys Gln Gln Asp Met Gly Glu Ser Cys Leu
             420                 425                 430

Leu Pro Pro Ser Gly Ser Thr Ser Ala His Met Pro Trp Asp Glu Phe
             435                 440                 445
```

```
Pro Ser Ala Gly Pro Lys Glu Ala Pro Pro Trp Gly Lys Glu Gln Pro
    450                 455                 460

Leu His Leu Glu Pro Ser Pro Pro Ala Ser Pro Thr Gln Ser Pro Asp
465                 470                 475                 480

Asn Leu Thr Cys Thr Glu Thr Pro Leu Val Ile Ala Gly Asn Pro Ala
                485                 490                 495

Tyr Arg Ser Phe Ser Asn Ser Leu Ser Gln Ser Pro Cys Pro Arg Glu
                500                 505                 510

Leu Gly Pro Asp Pro Leu Leu Ala Arg His Leu Glu Glu Val Glu Pro
            515                 520                 525

Glu Met Pro Cys Val Pro Gln Leu Ser Glu Pro Thr Thr Val Pro Gln
530                 535                 540

Pro Glu Pro Glu Thr Trp Glu Gln Ile Leu Arg Arg Asn Val Leu Gln
545                 550                 555                 560

His Gly Ala Ala Ala Pro Val Ser Ala Pro Thr Ser Gly Tyr Gln
                565                 570                 575

Glu Phe Val His Ala Val Glu Gln Gly Gly Thr Gln Ala Ser Ala Val
            580                 585                 590

Val Gly Leu Gly Pro Pro Gly Glu Ala Gly Tyr Lys Ala Phe Ser Ser
    595                 600                 605

Leu Leu Ala Ser Ser Ala Val Ser Pro Glu Lys Cys Gly Phe Gly Ala
    610                 615                 620

Ser Ser Gly Glu Glu Gly Tyr Lys Pro Phe Gln Asp Leu Ile Pro Gly
625                 630                 635                 640

Cys Pro Gly Asp Pro Ala Pro Val Pro Val Pro Leu Phe Thr Phe Gly
                645                 650                 655

Leu Asp Arg Glu Pro Pro Arg Ser Pro Gln Ser Ser His Leu Pro Ser
            660                 665                 670

Ser Ser Pro Glu His Leu Gly Leu Glu Pro Gly Glu Lys Val Glu Asp
                675                 680                 685

Met Pro Lys Pro Pro Leu Pro Gln Glu Gln Ala Thr Asp Pro Leu Val
    690                 695                 700

Asp Ser Leu Gly Ser Gly Ile Val Tyr Ser Ala Leu Thr Cys His Leu
705                 710                 715                 720

Cys Gly His Leu Lys Gln Cys His Gly Gln Glu Asp Gly Gly Gln Thr
                725                 730                 735

Pro Val Met Ala Ser Pro Cys Cys Gly Cys Cys Cys Gly Asp Arg Ser
            740                 745                 750

Ser Pro Pro Thr Thr Pro Leu Arg Ala Pro Asp Pro Ser Pro Gly Gly
                755                 760                 765

Val Pro Leu Glu Ala Ser Leu Cys Pro Ala Ser Leu Ala Pro Ser Gly
770                 775                 780

Ile Ser Glu Lys Ser Lys Ser Ser Ser Phe His Pro Ala Pro Gly
785                 790                 795                 800

Asn Ala Gln Ser Ser Ser Gln Thr Pro Lys Ile Val Asn Phe Val Ser
                805                 810                 815

Val Gly Pro Thr Tyr Met Arg Val Ser
            820                 825

<210> SEQ ID NO 80
<211> LENGTH: 420
<212> TYPE: PRT
<213> ORGANISM: Homo sapiens
<220> FEATURE:
<221> NAME/KEY: MISC_FEATURE
```

```
<223> OTHER INFORMATION: IL-5 receptor
<300> PUBLICATION INFORMATION:
<308> DATABASE ACCESSION NUMBER: GenBank / CAA01794
<309> DATABASE ENTRY DATE: 1995-09-28
<313> RELEVANT RESIDUES IN SEQ ID NO: (1)..(420)

<400> SEQUENCE: 80
```

Met Ile Ile Val Ala His Val Leu Leu Ile Leu Leu Gly Ala Thr Glu
1               5                   10                  15

Ile Leu Gln Ala Asp Leu Leu Pro Asp Glu Lys Ile Ser Leu Leu Pro
            20                  25                  30

Pro Val Asn Phe Thr Ile Lys Val Thr Gly Leu Ala Gln Val Leu Leu
        35                  40                  45

Gln Trp Lys Pro Asn Pro Asp Gln Glu Gln Arg Asn Val Asn Leu Glu
    50                  55                  60

Tyr Gln Val Lys Ile Asn Ala Pro Lys Glu Asp Asp Tyr Glu Thr Arg
65                  70                  75                  80

Ile Thr Glu Ser Lys Cys Val Thr Ile Leu His Lys Gly Phe Ser Ala
                85                  90                  95

Ser Val Arg Thr Ile Leu Gln Asn Asp His Ser Leu Leu Ala Ser Ser
            100                 105                 110

Trp Ala Ser Ala Glu Leu His Ala Pro Pro Gly Ser Pro Gly Thr Ser
        115                 120                 125

Ile Val Asn Leu Thr Cys Thr Thr Asn Thr Thr Glu Asp Asn Tyr Ser
    130                 135                 140

Arg Leu Arg Ser Tyr Gln Val Ser Leu His Cys Thr Trp Leu Val Gly
145                 150                 155                 160

Thr Asp Ala Pro Glu Asp Thr Gln Tyr Phe Leu Tyr Tyr Arg Tyr Gly
                165                 170                 175

Ser Trp Thr Glu Glu Cys Gln Glu Tyr Ser Lys Asp Thr Leu Gly Arg
            180                 185                 190

Asn Ile Ala Cys Trp Phe Pro Arg Thr Phe Ile Leu Ser Lys Gly Arg
        195                 200                 205

Asp Trp Leu Ser Val Leu Val Asn Gly Ser Ser Lys His Ser Ala Ile
    210                 215                 220

Arg Pro Phe Asp Gln Leu Phe Ala Leu His Ala Ile Asp Gln Ile Asn
225                 230                 235                 240

Pro Pro Leu Asn Val Thr Ala Glu Ile Glu Gly Thr Arg Leu Ser Ile
                245                 250                 255

Gln Trp Glu Lys Pro Val Ser Ala Phe Pro Ile His Cys Phe Asp Tyr
            260                 265                 270

Glu Val Lys Ile His Asn Thr Arg Asn Gly Tyr Leu Gln Ile Glu Lys
        275                 280                 285

Leu Met Thr Asn Ala Phe Ile Ser Ile Ile Asp Asp Leu Ser Lys Tyr
    290                 295                 300

Asp Val Gln Val Arg Ala Ala Val Ser Ser Met Cys Arg Glu Ala Gly
305                 310                 315                 320

Leu Trp Ser Glu Trp Ser Gln Pro Ile Tyr Val Gly Asn Asp Glu His
                325                 330                 335

Lys Pro Leu Arg Glu Trp Phe Val Ile Met Ala Thr Ile Cys
            340                 345                 350

Phe Ile Leu Leu Ile Leu Ser Leu Ile Cys Lys Ile Cys His Leu Trp
        355                 360                 365

Ile Lys Leu Phe Pro Pro Ile Pro Ala Pro Lys Ser Asn Ile Lys Asp
    370                 375                 380

-continued

Leu Phe Val Thr Thr Asn Tyr Glu Lys Ala Gly Ser Ser Glu Thr Glu
385                 390                 395                 400

Ile Glu Val Ile Cys Tyr Ile Glu Lys Pro Gly Val Glu Thr Leu Glu
            405                 410                 415

Asp Ser Val Phe
            420

<210> SEQ ID NO 81
<211> LENGTH: 31
<212> TYPE: PRT
<213> ORGANISM: Homo sapiens
<300> PUBLICATION INFORMATION:
<308> DATABASE ACCESSION NUMBER: GenBank / AAB30844
<309> DATABASE ENTRY DATE: 2001-03-06
<313> RELEVANT RESIDUES IN SEQ ID NO: (1)..(31)

<400> SEQUENCE: 81

Gln Ala Ala Arg Ser Ile Leu Gly Lys Gly Trp Thr Leu Glu Ser Glu
1               5                   10                  15

Ala Leu Arg Arg Asp Met Gly Thr Trp Leu Leu Ala Cys Ile Cys
            20                  25                  30

<210> SEQ ID NO 82
<211> LENGTH: 557
<212> TYPE: PRT
<213> ORGANISM: Homo sapiens
<220> FEATURE:
<221> NAME/KEY: MISC_FEATURE
<223> OTHER INFORMATION: Interferon type I receptor
<300> PUBLICATION INFORMATION:
<308> DATABASE ACCESSION NUMBER: Swiss-Prot / P17181
<309> DATABASE ENTRY DATE: 2010-09-07
<313> RELEVANT RESIDUES IN SEQ ID NO: (1)..(557)

<400> SEQUENCE: 82

Met Met Val Val Leu Leu Gly Ala Thr Thr Leu Val Leu Val Ala Val
1               5                   10                  15

Ala Pro Trp Val Leu Ser Ala Ala Gly Gly Lys Asn Leu Lys Ser
            20                  25                  30

Pro Gln Lys Val Glu Val Asp Ile Ile Asp Asp Asn Phe Ile Leu Arg
        35                  40                  45

Trp Asn Arg Ser Asp Glu Ser Val Gly Asn Val Thr Phe Ser Phe Asp
    50                  55                  60

Tyr Gln Lys Thr Gly Met Asp Asn Trp Ile Lys Leu Ser Gly Cys Gln
65                  70                  75                  80

Asn Ile Thr Ser Thr Lys Cys Asn Phe Ser Ser Leu Lys Leu Asn Val
                85                  90                  95

Tyr Glu Glu Ile Lys Leu Arg Ile Arg Ala Glu Lys Glu Asn Thr Ser
            100                 105                 110

Ser Trp Tyr Glu Val Asp Ser Phe Thr Pro Phe Arg Lys Ala Gln Ile
        115                 120                 125

Gly Pro Pro Glu Val His Leu Glu Ala Glu Asp Lys Ala Ile Val Ile
    130                 135                 140

His Ile Ser Pro Gly Thr Lys Asp Ser Val Met Trp Ala Leu Asp Gly
145                 150                 155                 160

Leu Ser Phe Thr Tyr Ser Leu Val Ile Trp Lys Asn Ser Ser Gly Val
                165                 170                 175

Glu Glu Arg Ile Glu Asn Ile Tyr Ser Arg His Lys Ile Tyr Lys Leu
            180                 185                 190

```
Ser Pro Glu Thr Thr Tyr Cys Leu Lys Val Lys Ala Ala Leu Leu Thr
    195                 200                 205
Ser Trp Lys Ile Gly Val Tyr Ser Pro Val His Cys Ile Lys Thr Thr
210                 215                 220
Val Glu Asn Glu Leu Pro Pro Glu Asn Ile Glu Val Ser Val Gln
225                 230                 235                 240
Asn Gln Asn Tyr Val Leu Lys Trp Asp Tyr Thr Tyr Ala Asn Met Thr
                245                 250                 255
Phe Gln Val Gln Trp Leu His Ala Phe Leu Lys Arg Asn Pro Gly Asn
            260                 265                 270
His Leu Tyr Lys Trp Lys Gln Ile Pro Asp Cys Glu Asn Val Lys Thr
        275                 280                 285
Thr Gln Cys Val Phe Pro Gln Asn Val Phe Gln Lys Gly Ile Tyr Leu
    290                 295                 300
Leu Arg Val Gln Ala Ser Asp Gly Asn Asn Thr Ser Phe Trp Ser Glu
305                 310                 315                 320
Glu Ile Lys Phe Asp Thr Glu Ile Gln Ala Phe Leu Leu Pro Pro Val
                325                 330                 335
Phe Asn Ile Arg Ser Leu Ser Asp Ser Phe His Ile Tyr Ile Gly Ala
            340                 345                 350
Pro Lys Gln Ser Gly Asn Thr Pro Val Ile Gln Asp Tyr Pro Leu Ile
        355                 360                 365
Tyr Glu Ile Ile Phe Trp Glu Asn Thr Ser Asn Ala Glu Arg Lys Ile
    370                 375                 380
Ile Glu Lys Lys Thr Asp Val Thr Val Pro Asn Leu Lys Pro Leu Thr
385                 390                 395                 400
Val Tyr Cys Val Lys Ala Arg Ala His Thr Met Asp Glu Lys Leu Asn
                405                 410                 415
Lys Ser Ser Val Phe Ser Asp Ala Val Cys Glu Lys Thr Lys Pro Gly
            420                 425                 430
Asn Thr Ser Lys Ile Trp Leu Ile Val Gly Ile Cys Ile Ala Leu Phe
        435                 440                 445
Ala Leu Pro Phe Val Ile Tyr Ala Ala Lys Val Phe Leu Arg Cys Ile
    450                 455                 460
Asn Tyr Val Phe Phe Pro Ser Leu Lys Pro Ser Ser Ser Ile Asp Glu
465                 470                 475                 480
Tyr Phe Ser Glu Gln Pro Leu Lys Asn Leu Leu Ser Thr Ser Glu
                485                 490                 495
Glu Gln Ile Glu Lys Cys Phe Ile Ile Glu Asn Ile Ser Thr Ile Ala
            500                 505                 510
Thr Val Glu Glu Thr Asn Gln Thr Asp Glu Asp His Lys Lys Tyr Ser
        515                 520                 525
Ser Gln Thr Ser Gln Asp Ser Gly Asn Tyr Ser Asn Glu Asp Glu Ser
    530                 535                 540
Glu Ser Lys Thr Ser Glu Glu Leu Gln Gln Asp Phe Val
545                 550                 555

<210> SEQ ID NO 83
<211> LENGTH: 515
<212> TYPE: PRT
<213> ORGANISM: Homo sapiens
<300> PUBLICATION INFORMATION:
<308> DATABASE ACCESSION NUMBER: Swiss-Prot / P48551
<309> DATABASE ENTRY DATE: 2010-09-07
<313> RELEVANT RESIDUES IN SEQ ID NO: (1)..(515)
```

```
<400> SEQUENCE: 83

Met Leu Leu Ser Gln Asn Ala Phe Ile Phe Arg Ser Leu Asn Leu Val
1               5                   10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
        35                  40                  45

Arg Ser Ile Leu Ser Trp Glu Leu Lys Asn His Ser Ile Val Pro Thr
    50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
        115                 120                 125

Ala Ile Asp Met Ser Phe Glu Pro Pro Glu Phe Glu Ile Val Gly Phe
    130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Glu Gln Ser Glu Gly
            165                 170                 175

Ile Val Lys Lys His Lys Pro Glu Ile Lys Gly Asn Met Ser Gly Asn
        180                 185                 190

Phe Thr Tyr Ile Ile Asp Lys Leu Ile Pro Asn Thr Asn Tyr Cys Val
    195                 200                 205

Ser Val Tyr Leu Glu His Ser Asp Glu Gln Ala Val Ile Lys Ser Pro
210                 215                 220

Leu Lys Cys Thr Leu Leu Pro Pro Gly Gln Glu Ser Glu Ser Ala Glu
225                 230                 235                 240

Ser Ala Lys Ile Gly Gly Ile Ile Thr Val Phe Leu Ile Ala Leu Val
            245                 250                 255

Leu Thr Ser Thr Ile Val Thr Leu Lys Trp Ile Gly Tyr Ile Cys Leu
        260                 265                 270

Arg Asn Ser Leu Pro Lys Val Leu Asn Phe His Asn Phe Leu Ala Trp
    275                 280                 285

Pro Phe Pro Asn Leu Pro Pro Leu Glu Ala Met Asp Met Val Glu Val
290                 295                 300

Ile Tyr Ile Asn Arg Lys Lys Lys Val Trp Asp Tyr Asn Tyr Asp Asp
305                 310                 315                 320

Glu Ser Asp Ser Asp Thr Glu Ala Ala Pro Arg Thr Ser Gly Gly Gly
            325                 330                 335

Tyr Thr Met His Gly Leu Thr Val Arg Pro Leu Gly Gln Ala Ser Ala
        340                 345                 350

Thr Ser Thr Glu Ser Gln Leu Ile Asp Pro Glu Ser Glu Glu Glu Pro
    355                 360                 365

Asp Leu Pro Glu Val Asp Val Glu Leu Pro Thr Met Pro Lys Asp Ser
370                 375                 380

Pro Gln Gln Leu Glu Leu Leu Ser Gly Pro Cys Glu Arg Arg Lys Ser
385                 390                 395                 400

Pro Leu Gln Asp Pro Phe Pro Glu Glu Asp Tyr Ser Ser Thr Glu Gly
            405                 410                 415
```

```
Ser Gly Gly Arg Ile Thr Phe Asn Val Asp Leu Asn Ser Val Phe Leu
            420                 425                 430

Arg Val Leu Asp Asp Glu Asp Ser Asp Asp Leu Glu Ala Pro Leu Met
            435                 440                 445

Leu Ser Ser His Leu Glu Glu Met Val Asp Pro Glu Asp Pro Asp Asn
    450                 455                 460

Val Gln Ser Asn His Leu Leu Ala Ser Gly Glu Gly Thr Gln Pro Thr
465                 470                 475                 480

Phe Pro Ser Pro Ser Glu Gly Leu Trp Ser Glu Asp Ala Pro Ser
                485                 490                 495

Asp Gln Ser Asp Thr Ser Glu Ser Asp Val Asp Leu Gly Asp Gly Tyr
                500                 505                 510

Ile Met Arg
        515

<210> SEQ ID NO 84
<211> LENGTH: 250
<212> TYPE: PRT
<213> ORGANISM: Homo sapiens
<220> FEATURE:
<221> NAME/KEY: MISC_FEATURE
<223> OTHER INFORMATION: Lymphocyte function antigen-3 receptor
<300> PUBLICATION INFORMATION:
<308> DATABASE ACCESSION NUMBER: Swiss-Prot / P19256
<309> DATABASE ENTRY DATE: 2010-09-10
<313> RELEVANT RESIDUES IN SEQ ID NO: (1)..(250)

<400> SEQUENCE: 84

Met Val Ala Gly Ser Asp Ala Gly Arg Ala Leu Gly Val Leu Ser Val
1               5                   10                  15

Val Cys Leu Leu His Cys Phe Gly Phe Ile Ser Cys Phe Ser Gln Gln
            20                  25                  30

Ile Tyr Gly Val Val Tyr Gly Asn Val Thr Phe His Val Pro Ser Asn
            35                  40                  45

Val Pro Leu Lys Glu Val Leu Trp Lys Lys Gln Lys Asp Lys Val Ala
    50                  55                  60

Glu Leu Glu Asn Ser Glu Phe Arg Ala Phe Ser Ser Phe Lys Asn Arg
65                  70                  75                  80

Val Tyr Leu Asp Thr Val Ser Gly Ser Leu Thr Ile Tyr Asn Leu Thr
                85                  90                  95

Ser Ser Asp Glu Asp Glu Tyr Glu Met Glu Ser Pro Asn Ile Thr Asp
            100                 105                 110

Thr Met Lys Phe Phe Leu Tyr Val Leu Glu Ser Leu Pro Ser Pro Thr
            115                 120                 125

Leu Thr Cys Ala Leu Thr Asn Gly Ser Ile Glu Val Gln Cys Met Ile
    130                 135                 140

Pro Glu His Tyr Asn Ser His Arg Gly Leu Ile Met Tyr Ser Trp Asp
145                 150                 155                 160

Cys Pro Met Glu Gln Cys Lys Arg Asn Ser Thr Ser Ile Tyr Phe Lys
                165                 170                 175

Met Glu Asn Asp Leu Pro Gln Lys Ile Gln Cys Thr Leu Ser Asn Pro
            180                 185                 190

Leu Phe Asn Thr Thr Ser Ser Ile Ile Leu Thr Thr Cys Ile Pro Ser
            195                 200                 205

Ser Gly His Ser Arg His Arg Tyr Ala Leu Ile Pro Ile Pro Leu Ala
    210                 215                 220
```

```
Val Ile Thr Thr Cys Ile Val Leu Tyr Met Asn Gly Ile Leu Lys Cys
225                 230                 235                 240

Asp Arg Lys Pro Asp Arg Thr Asn Ser Asn
                245                 250

<210> SEQ ID NO 85
<211> LENGTH: 99
<212> TYPE: PRT
<213> ORGANISM: Homo sapiens
<220> FEATURE:
<221> NAME/KEY: MISC_FEATURE
<223> OTHER INFORMATION: Monocyte chemotactic protein 1 ligand
<300> PUBLICATION INFORMATION:
<308> DATABASE ACCESSION NUMBER: Swiss-Prot / P13500
<309> DATABASE ENTRY DATE: 2010-09-07
<313> RELEVANT RESIDUES IN SEQ ID NO: (1)..(99)

<400> SEQUENCE: 85

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 86
<211> LENGTH: 427
<212> TYPE: PRT
<213> ORGANISM: Homo sapiens
<220> FEATURE:
<221> NAME/KEY: MISC_FEATURE
<223> OTHER INFORMATION: NGF receptor
<300> PUBLICATION INFORMATION:
<308> DATABASE ACCESSION NUMBER: GenBank / AAB59544
<309> DATABASE ENTRY DATE: 1995-08-11
<313> RELEVANT RESIDUES IN SEQ ID NO: (1)..(427)

<400> SEQUENCE: 86

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
            35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
            115                 120                 125
```

-continued

Glu Ala Gly Ser Gly Leu Val Phe Ser Cys Gln Asp Lys Gln Asn Thr
        130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg Trp Asn Ser Cys Lys Gln Asn Lys Gln Gly Ala Asn Ser Arg
        275                 280                 285

Pro Val Asn Gln Thr Pro Pro Pro Glu Gly Glu Lys Leu His Ser Asp
    290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
            340                 345                 350

Gly Ser Ala Gly Asp Thr Trp Arg His Leu Ala Gly Glu Leu Gly Tyr
        355                 360                 365

Gln Pro Glu His Ile Asp Ser Phe Thr His Glu Ala Cys Pro Val Arg
    370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
            420                 425

<210> SEQ ID NO 87
<211> LENGTH: 212
<212> TYPE: PRT
<213> ORGANISM: Homo sapiens
<220> FEATURE:
<221> NAME/KEY: MISC_FEATURE
<223> OTHER INFORMATION: IL-6
<300> PUBLICATION INFORMATION:
<308> DATABASE ACCESSION NUMBER: NCBI / NP_000591
<309> DATABASE ENTRY DATE: 2010-09-19
<313> RELEVANT RESIDUES IN SEQ ID NO: (1)..(212)

<400> SEQUENCE: 87

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

-continued

```
Gly Glu Asp Ser Lys Asp Val Ala Pro His Arg Gln Pro Leu Thr
            35                  40                  45

Ser Ser Glu Arg Ile Asp Lys Gln Ile Arg Tyr Ile Leu Asp Gly Ile
 50                  55                  60

Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                 85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 88
<211> LENGTH: 468
<212> TYPE: PRT
<213> ORGANISM: Homo sapiens
<220> FEATURE:
<221> NAME/KEY: MISC_FEATURE
<223> OTHER INFORMATION: IL-6 receptor
<300> PUBLICATION INFORMATION:
<308> DATABASE ACCESSION NUMBER: NCBI / NP_000556
<309> DATABASE ENTRY DATE: 2010-09-19
<313> RELEVANT RESIDUES IN SEQ ID NO: (1)..(468)

<400> SEQUENCE: 88

Met Leu Ala Val Gly Cys Ala Leu Leu Ala Ala Leu Leu Ala Ala Pro
 1               5                  10                  15

Gly Ala Ala Leu Ala Pro Arg Arg Cys Pro Ala Gln Glu Val Ala Arg
                20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
 50                  55                  60

Pro Ala Ala Gly Ser His Pro Ser Arg Trp Ala Gly Met Gly Arg Arg
 65                  70                  75                  80

Leu Leu Leu Arg Ser Val Gln Leu His Asp Ser Gly Asn Tyr Ser Cys
                 85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
```

-continued

```
145                 150                 155                 160
Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
                180                 185                 190

Cys Val Ala Ser Ser Val Gly Ser Lys Phe Ser Lys Thr Gln Thr Phe
                195                 200                 205

Gln Gly Cys Gly Ile Leu Gln Pro Asp Pro Pro Ala Asn Ile Thr Val
        210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
                260                 265                 270

Leu Gln His His Cys Val Ile His Asp Ala Trp Ser Gly Leu Arg His
                275                 280                 285

Val Val Gln Leu Arg Ala Gln Glu Glu Phe Gly Gln Gly Glu Trp Ser
        290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Val Gln Asp Ser Ser Val Pro Leu Pro Thr Phe Leu
                355                 360                 365

Val Ala Gly Gly Ser Leu Ala Phe Gly Thr Leu Leu Cys Ile Ala Ile
        370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
                420                 425                 430

Ser Pro Ser Ser Leu Gly Ser Asp Asn Thr Ser Ser His Asn Arg Pro
        435                 440                 445

Asp Ala Arg Asp Pro Arg Ser Pro Tyr Asp Ile Ser Asn Thr Asp Tyr
450                 455                 460

Phe Phe Pro Arg
465
```